US012635408B2

(12) United States Patent
Uno

(10) Patent No.: US 12,635,408 B2
(45) Date of Patent: May 19, 2026

(54) ORGANIC ELECTROLUMINESCENCE DEVICE AND AMINE COMPOUND FOR ORGANIC ELECTROLUMINESCENCE DEVICE

(71) Applicant: Samsung Display Co., Ltd., Yongin-si (KR)

(72) Inventor: Takuya Uno, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 533 days.

(21) Appl. No.: 16/935,082

(22) Filed: Jul. 21, 2020

(65) Prior Publication Data

US 2021/0126197 A1 Apr. 29, 2021

(30) Foreign Application Priority Data

Oct. 24, 2019 (KR) ........................ 10-2019-0133193

(51) Int. Cl.
*H10K 85/60* (2023.01)
*C07D 307/91* (2006.01)
(Continued)

(52) U.S. Cl.
CPC ......... *H10K 85/636* (2023.02); *C07D 307/91* (2013.01); *C07D 333/76* (2013.01);
(Continued)

(58) Field of Classification Search
CPC ............... H01L 51/0061; H01L 51/006; H01L 51/0073; H01L 51/0074; H01L 51/0071;
(Continued)

(56) References Cited

U.S. PATENT DOCUMENTS 8,890,126 B2 11/2014 Ryu et al.
9,278,926 B2 3/2016 Kato
(Continued)

FOREIGN PATENT DOCUMENTS

CN 102596907 A 7/2012
CN 109326731 A 2/2019
(Continued)

OTHER PUBLICATIONS

Machine Translation of WO2020130528 (Year: 2020).*
(Continued)

*Primary Examiner* — Jenna N Chandhok
(74) *Attorney, Agent, or Firm* — Womble Bond Dickinson (US) LLP

(57) ABSTRACT

An organic electroluminescence device of an embodiment includes a first electrode, a second electrode, and a plurality of functional layers between the first electrode and the second electrode, wherein at least one functional layer selected from the plurality of functional layers includes an amine compound represented by Formula 1 below, thereby
(Continued)

showing high emission efficiency and improved life characteristics:

Formula 1

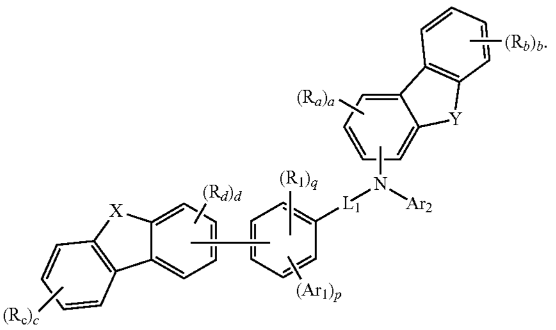

16 Claims, 2 Drawing Sheets

(51) Int. Cl.

| | |
|---|---|
| ***C07D 333/76*** | (2006.01) |
| ***C07D 409/12*** | (2006.01) |
| ***C07D 409/14*** | (2006.01) |
| ***C07F 7/08*** | (2006.01) |
| ***C09K 11/06*** | (2006.01) |
| ***H10K 50/15*** | (2023.01) |
| ***H10K 85/40*** | (2023.01) |

(52) U.S. Cl.

CPC ......... *C07D 409/12* (2013.01); *C07D 409/14* (2013.01); *C07F 7/0812* (2013.01); *C09K 11/06* (2013.01); *H10K 85/40* (2023.02); *H10K 85/633* (2023.02); *H10K 85/6574* (2023.02); *C09K 2211/1022* (2013.01); *H10K 50/15* (2023.02); *H10K 85/615* (2023.02); *H10K 85/6576* (2023.02)

(58) Field of Classification Search

CPC .. C07D 307/91; C07D 333/76; C07D 409/12; C07D 409/14; C09K 2211/1022; C09K 2211/1088; C09K 2211/1092; H10K 85/636; H10K 85/633; H10K 85/6574; H10K 85/615; H10K 85/6576; H10K 50/15; H10K 50/11; H10K 85/626; H10K 85/657

See application file for complete search history.

(56) References Cited

U.S. PATENT DOCUMENTS

| | | | |
|---|---|---|---|
| 9,972,786 | B2 | 5/2018 | Yabunouchi et al. |
| 10,256,413 | B2 | 4/2019 | Sakamoto |
| 10,326,092 | B2 | 6/2019 | Lee et al. |
| 10,424,741 | B2 | 9/2019 | Lee et al. |
| 2016/0126469 | A1 | 5/2016 | Nakano |
| 2017/0133590 | A1 | 5/2017 | Cho et al. |
| 2017/0133599 | A1 | 5/2017 | Cho et al. |
| 2017/0179398 | A1 | 6/2017 | Yokoyama et al. |
| 2017/0288147 | A1 | 10/2017 | Fujita et al. |
| 2018/0248130 | A1 | 8/2018 | Shin et al. |
| 2019/0044085 | A1 | 2/2019 | Jeong et al. |
| 2019/0131544 | A1 | 5/2019 | Park et al. |
| 2019/0165285 | A1 | 5/2019 | Uno |
| 2019/0181353 | A1 | 6/2019 | Ihn et al. |
| 2020/0365814 | A1 | 11/2020 | Ha et al. |

FOREIGN PATENT DOCUMENTS

| | | | | | |
|---|---|---|---|---|---|
| CN | 110317139 | A | * | 10/2019 | ........... C07C 211/54 |
| CN | 110577509 | A | * | 12/2019 | ........... C07D 307/91 |
| CN | 113056460 | A | | 6/2021 | |
| EP | 2 502 908 | A1 | | 9/2012 | |
| KR | 10-1516960 | B1 | | 5/2015 | |
| KR | 10-1571986 | B1 | | 11/2015 | |
| KR | 10-2015-0145033 | A | | 12/2015 | |
| KR | 10-1580074 | B1 | | 12/2015 | |
| KR | 1020160053757 | A | | 5/2016 | |
| KR | 10-2016-0079545 | A | | 7/2016 | |
| KR | 10-2017-0049115 | A | | 5/2017 | |
| KR | 10-2017-0138614 | A | | 12/2017 | |
| KR | 10-1879415 | B1 | | 7/2018 | |
| KR | 10-2018-0099965 | A | | 9/2018 | |
| KR | 10-2019-0047752 | A | | 5/2019 | |
| KR | 10-2019-0060914 | A | | 6/2019 | |
| KR | 10-2019-0067694 | A | | 6/2019 | |
| KR | 1020200061304 | A | | 6/2020 | |
| KR | 1020200075760 | A | | 6/2020 | |
| WO | WO 2011/059099 | A1 | | 5/2011 | |
| WO | WO 2016/006629 | A1 | | 1/2016 | |
| WO | WO 2018/157981 | A1 | | 9/2018 | |
| WO | WO 2019/164327 | A1 | | 8/2019 | |
| WO | WO-2020106102 | A1 | * | 5/2020 | ........... C07D 307/91 |
| WO | WO-2020130528 | A1 | * | 6/2020 | ........... C07D 307/91 |

OTHER PUBLICATIONS

Machine Translation of WO2020106102 (Year: 2020).*
Machine Translation of CN110317139 (Year: 2019).*
Machine Translation of CN110577509A (Year: 2019).*

* cited by examiner

ORGANIC ELECTROLUMINESCENCE DEVICE AND AMINE COMPOUND FOR ORGANIC ELECTROLUMINESCENCE DEVICE

CROSS-REFERENCE TO RELATED APPLICATION

This application claims priority to and the benefit of Korean Patent Application No. 10-2019-0133193, filed on Oct. 24, 2019, the entire content of which is hereby incorporated by reference.

BACKGROUND

1. Field

One or more aspects of embodiments of the present disclosure herein relate to an organic electroluminescence device and an amine compound used therein, and more particularly, to an amine compound used in a hole transport region and an organic electroluminescence device including the same.

2. Description of the Related Art

Recently, the development of an organic electroluminescence display as an image display is being actively conducted. Different from a liquid crystal display, the organic electroluminescence display is a self-luminescent display in which holes and electrons injected from a first electrode and a second electrode recombine in an emission layer, and a light-emitting material including an organic compound in the emission layer emits light to attain display of images.

In the application of an organic electroluminescence device to a display, the decrease of the driving voltage and the increase of the emission efficiency and the life of the organic electroluminescence device are required (or desired), and developments of materials for an organic electroluminescence device capable of stably (or suitably) attaining the requirements (or desired characteristics) are being continuously required.

In addition, in order to accomplish an organic electroluminescence device with high efficiency, development of a material for a hole transport layer that can restrain (or reduce) the diffusion of the exciton energy of an emission layer is being conducted.

SUMMARY

One or more aspects of embodiments of the present disclosure are directed toward an organic electroluminescence device having excellent (or suitable) emission efficiency and long-life characteristics.

The present disclosure also provides an amine compound, which is a material of an organic electroluminescence device having high efficiency and long-life characteristics.

An embodiment of the present disclosure provides an amine compound represented by the following Formula 1:

Formula 1

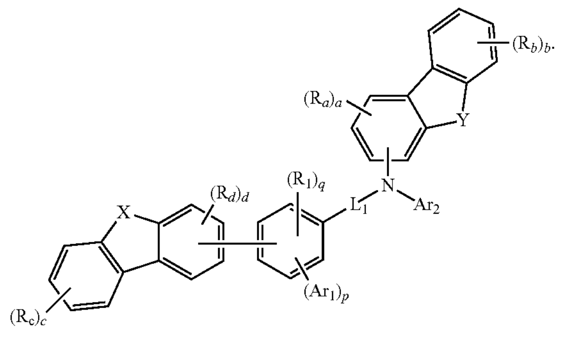

In Formula 1, X and Y may each independently be O or S, $Ar_1$ may be a substituted or unsubstituted aryl group of 6 to 40 carbon atoms for forming a ring, Are may be a substituted or unsubstituted aryl group of 6 to 40 carbon atoms for forming a ring, or a substituted or unsubstituted heteroaryl group of 2 to 40 carbon atoms for forming a ring, wherein Are is not a substituted or unsubstituted fluorene group or a substituted or unsubstituted carbazole group. $R_1$ may be a hydrogen atom or a deuterium atom, $R_a$ to $R_d$ may each independently be a hydrogen atom, a deuterium atom, a substituted or unsubstituted alkyl group of 1 to 20 carbon atoms, or a substituted or unsubstituted aryl group of 6 to 40 carbon atoms for forming a ring, $L_1$ may be a direct linkage, or a substituted or unsubstituted arylene group of 6 to 30 carbon atoms for forming a ring. "a" and "d" may be each independently be an integer of 0 to 3, "b" and "c" may each independently be an integer of 0 to 4, "p" may be 1 or 2, and "q" may be an integer of 0 to 3.

In an embodiment, Formula 1 may be represented by the following Formula 1-1 or Formula 1-2:

Formula 1-1

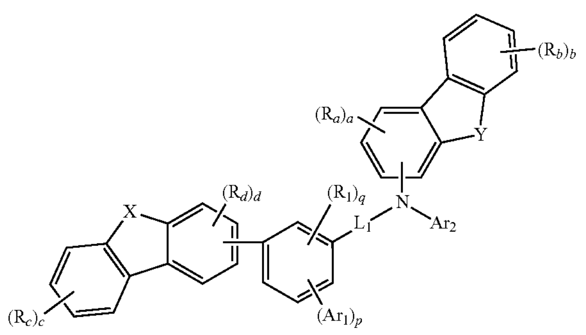

-continued

Formula 1-2

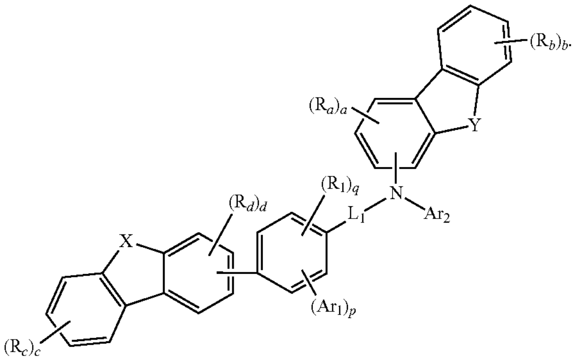

In Formula 1-1 and Formula 1-2, X, Y, $Ar_1$, $Ar_2$, $R_1$, $R_a$ to $R_d$, $L_1$, "a" to "d", "p" and "q" are the same as defined in Formula 1.

In an embodiment, Formula 1-1 may be represented by any one selected from the following Formula 1-1A to Formula 1-1C:

Formula 1-1A

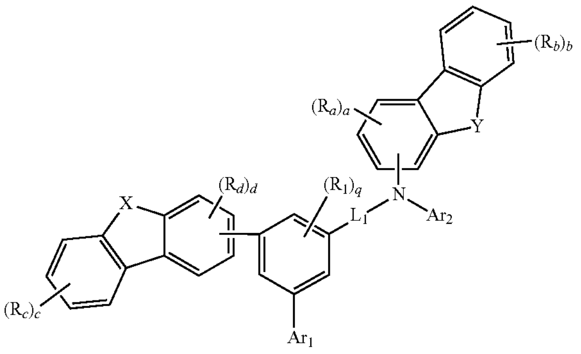

Formula 1-1B

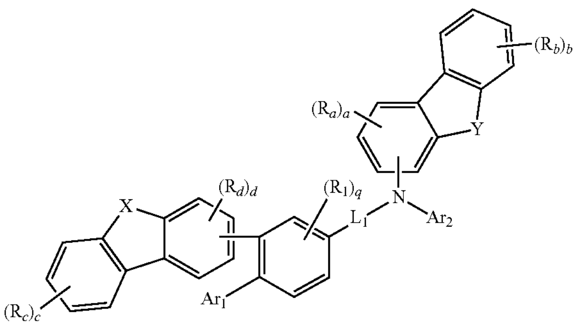

-continued

Formula 1-1C

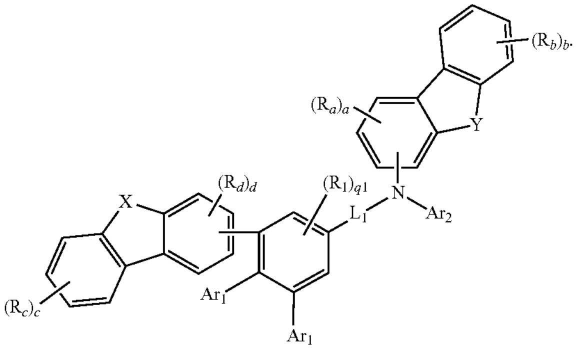

In Formula 1-1C, q1 is an integer of 0 to 2, and in Formula 1-1A to Formula 1-1C, X, Y, $Ar_1$, $Ar_2$, $R_1$, $R_a$ to $R_d$, $L_1$, "a" to "d", and "q" are the same as defined in Formula 1.

In an embodiment, Formula 1-2 may be represented by the following Formula 1-2A or Formula 1-2B:

Formula 1-2A

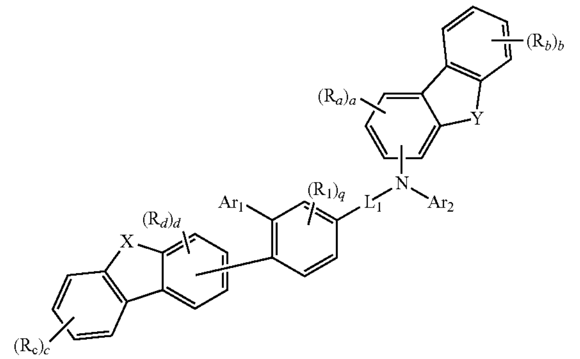

Formula 1-2B

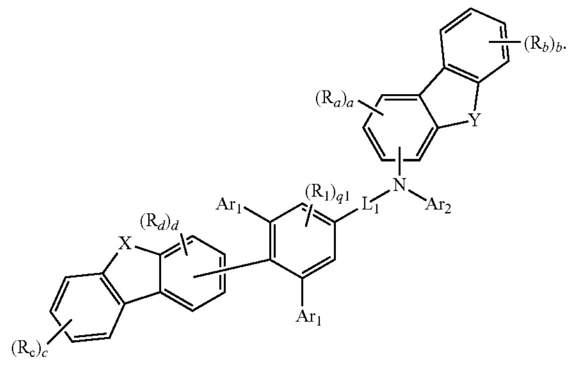

In Formula 1-2B, q1 is an integer of 0 to 2, and in Formula 1-2A and Formula 1-2B, X, Y, $Ar_1$, $Ar_2$, $R_1$, $R_a$ to $R_d$, $L_1$, "a" to "d", and "q" are the same as defined in Formula 1.

In an embodiment, Formula 1 may be represented by any one selected from the following Formula 1A to Formula 1D:

Formula 1A

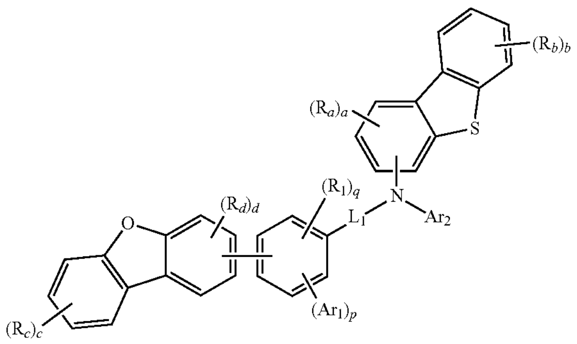

Formula 1B

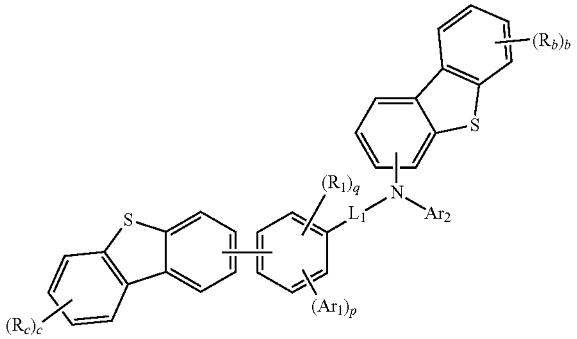

Formula 1C

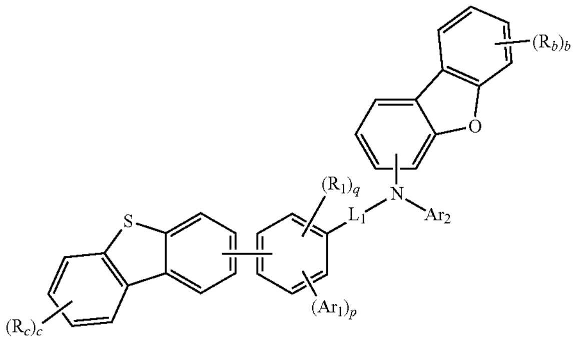

Formula 1D

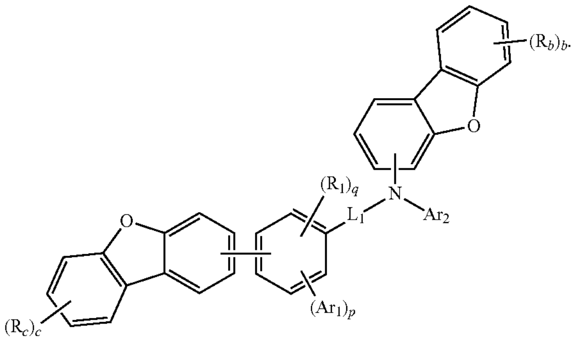

In Formula 1A to Formula 1D, $Ar_1$, $Ar_2$, $R_1$, $R_a$ to $R_d$, $L_1$, "a" to "d", "p", and "q" are the same as defined in Formula 1.

In an embodiment, $Ar_1$ may be a substituted or unsubstituted phenyl group, or a substituted or unsubstituted naphthyl group.

In an embodiment, $Ar_2$ may be represented by any one selected from the following Ar2-1 to Ar2-12:

Ar2-1

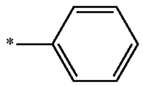

Ar2-2

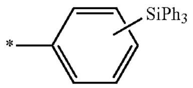

Ar2-3

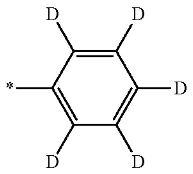

Ar2-4

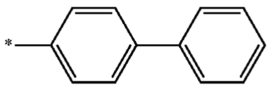

Ar2-5

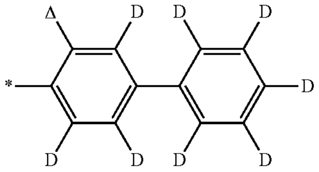

Ar2-6

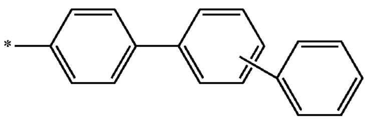

Ar2-7

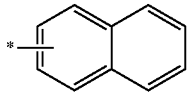

Ar2-8

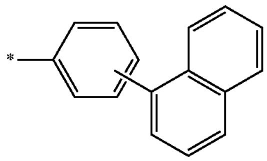

Ar2-9

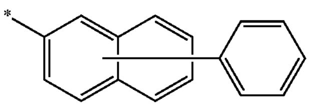

Ar2-10

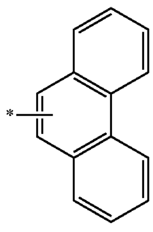

-continued

Ar2-11

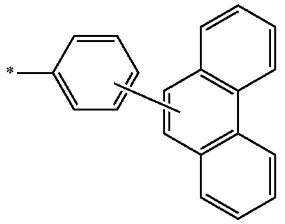

Ar2-12

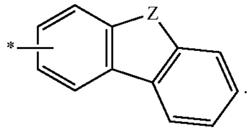

In Ar2-2, $SiPh_3$ is a triphenylsilyl group, and in Ar2-12, Z is O or S.

In an embodiment, $L_1$ may be a direct linkage, a substituted or unsubstituted phenylene group, or a substituted or unsubstituted naphthalene group.

In an embodiment of the present disclosure, there is provided an organic electroluminescence device including a first electrode; a second electrode on the first electrode; and a plurality of functional layers between the first electrode and the second electrode, wherein at least one functional layer among the plurality of functional layers includes the amine compound according to an embodiment.

In an embodiment, the plurality of functional layers may include an emission layer; a hole transport region between the first electrode and the emission layer; and an electron transport region between the emission layer and the second electrode, and the hole transport region may include the amine compound represented by Formula 1.

In an embodiment, the emission layer may include an anthracene derivative represented by the following Formula 2:

Formula 2

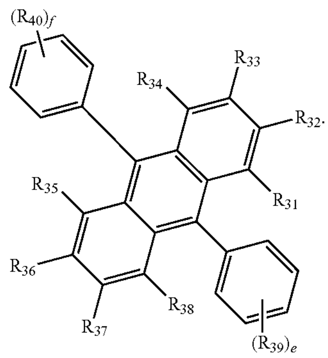

In Formula 2, $R_{31}$ to $R_{40}$ may each independently be a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 carbon atoms for forming a ring, or a substituted or unsubstituted heteroaryl group of 2 to 30 carbon atoms for forming a ring, and any of $R_{31}$ to $R_{40}$ may be combined with an adjacent group to form a ring, and "e" and "f" are each independently an integer of 0 to 5.

BRIEF DESCRIPTION OF THE DRAWINGS

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
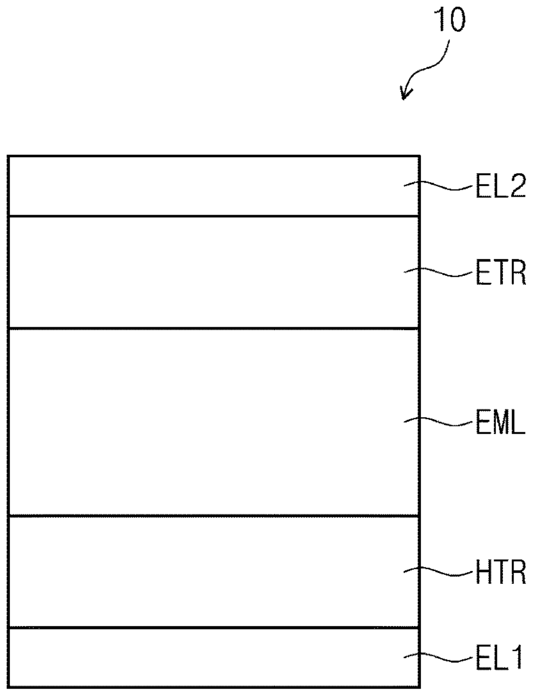
FIG. 1 is a cross-sectional view schematically illustrating an organic electroluminescence device according to an embodiment of the present disclosure.

The present disclosure may have various modifications and may be embodied in different forms, and example embodiments will be explained in more detail with reference to the accompanying drawings. The present disclosure may, however, be embodied in different forms and should not be construed as limited to the embodiments set forth herein. Rather, all modifications, equivalents, and substituents which are included in the spirit and technical scope of the present disclosure should be included in the present disclosure.

It will be understood that when an element is referred to as being "on", "connected to" or "coupled to" another element, it can be directly on, connected or coupled to the other element (without any intervening element(s) present) or intervening element(s) may be present.

Like reference numerals refer to like elements throughout. In addition, in the drawings, the thickness, the ratio, and the dimensions of constituent elements are exaggerated for effective explanation of technical contents.

The term "and/or" includes one or more combinations which may be defined by relevant elements. Expressions such as "at least one of," "one of," and "selected from," when preceding a list of elements, modify the entire list of elements and do not modify the individual elements of the list. Further, the use of "may" when describing embodiments of the present disclosure refers to "one or more embodiments of the present disclosure."

It will be understood that, although the terms first, second, etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

In addition, the terms "below", "beneath", "on" and "above" are used for explaining the relation of elements shown in the drawings. The terms are relative concept and are explained on the basis of the direction shown in the drawing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be further understood that the terms “comprises” and/or “comprising,” when used in this specification, specify the presence of stated features, numerals, steps, operations, elements, parts, or the combination thereof, but do not preclude the presence or addition of one or more other features, numerals, steps, operations, elements, parts, or the combination thereof.

Hereinafter, the organic electroluminescence device according to an embodiment of the present disclosure and a compound of an embodiment included therein will be explained with reference to attached drawings.

FIG. 1 to FIG. 4 are cross-sectional views schematically showing organic electroluminescence devices according to example embodiments of the present disclosure. Referring to FIGS. 1 to 4, in an organic electroluminescence device 10 according to an embodiment, a first electrode EL1 and a second electrode EL2 are oppositely placed (e.g., a first electrode EL1 and a second electrode EL2 face each other), and between the first electrode EL1 and the second electrode EL2, an emission layer EML may be provided.

In addition, the organic electroluminescence device 10 of an embodiment may further include a plurality of functional layers between the first electrode EL1 and the second electrode EL2, in addition to the emission layer EML. The plurality of the functional layers may include a hole transport region HTR and an electron transport region ETR. For example, the organic electroluminescence device 10 of an embodiment may include a first electrode EL1, a hole transport region HTR, an emission layer EML, an electron transport region ETR, and a second electrode, stacked one by one. In some embodiments, the organic electroluminescence device 10 of an embodiment may include a capping layer CPL disposed on the second electrode EL2.

The organic electroluminescence device 10 of an embodiment may include a compound of an embodiment, which will be explained later in more detail, in the emission layer EML between the first electrode EL1 and the second electrode EL2. However, an embodiment of the present disclosure is not limited thereto, and the organic electroluminescence device 10 of an embodiment may include the compound of an embodiment in the hole transport region HTR or the electron transport region ETR, which are in the plurality of functional layers provided between the first electrode EL1 and the second electrode EL2 in addition to the emission layer EML.

Figure 2:
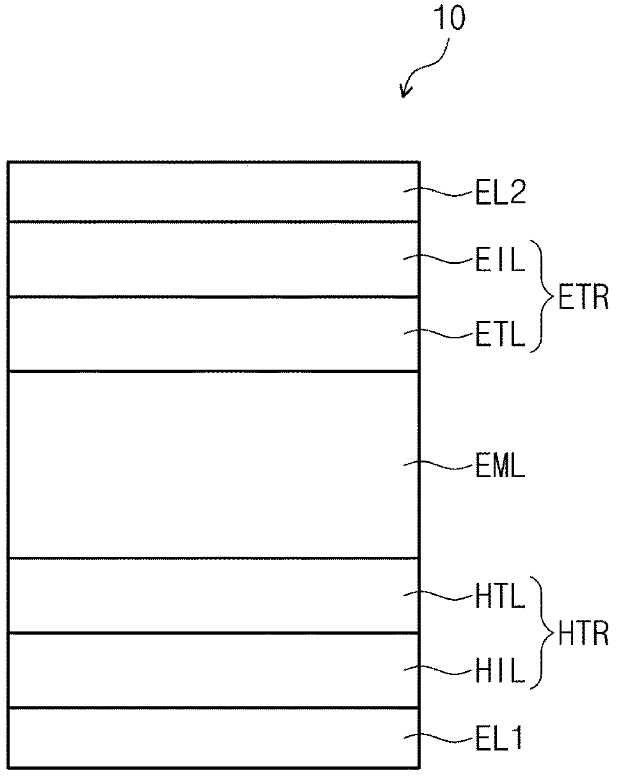
FIG. 2 is a cross-sectional view schematically illustrating an organic electroluminescence device according to an embodiment of the present disclosure.
Figure 3:
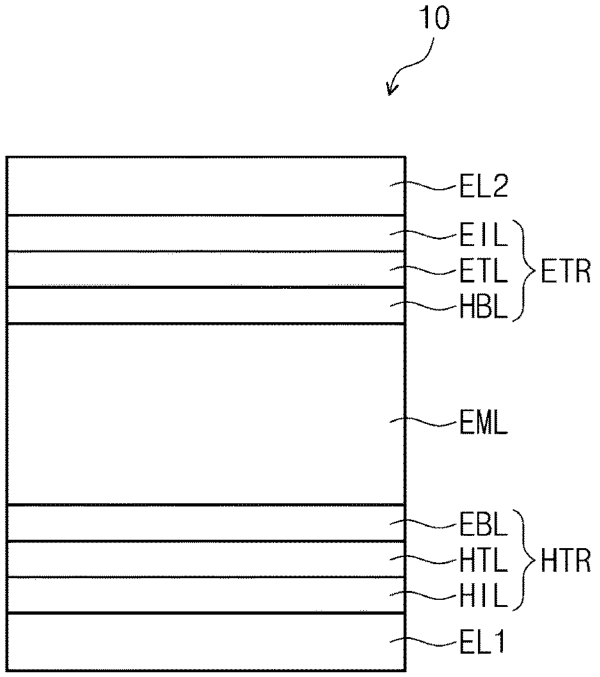
FIG. 3 is a cross-sectional view schematically illustrating an organic electroluminescence device according to an embodiment of the present disclosure.
Figure 4:
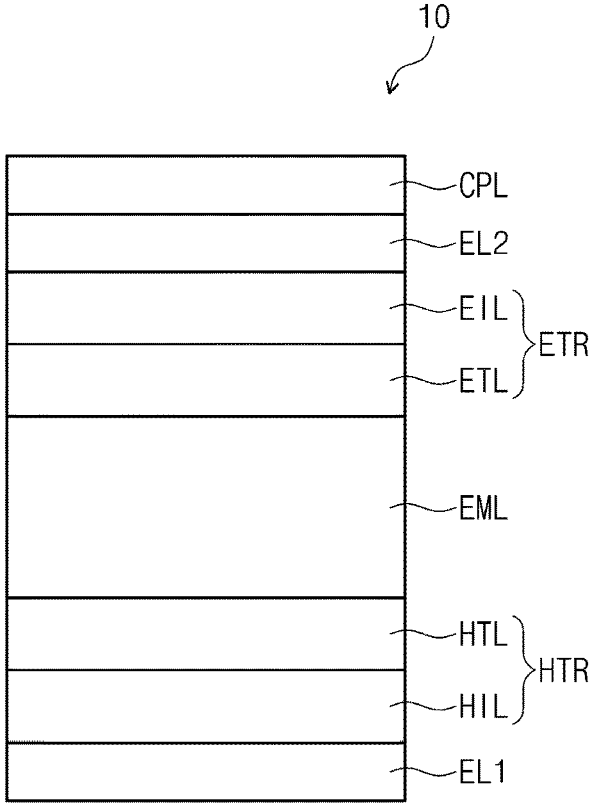
FIG. 4 is a cross-sectional view schematically illustrating an organic electroluminescence device according to an embodiment of the present disclosure.

When compared with FIG. 1, FIG. 2 shows the cross-sectional view of an organic electroluminescence device 10 of an embodiment, wherein a hole transport region HTR includes a hole injection layer HIL and a hole transport layer HTL, and an electron transport region ETR includes an electron injection layer EIL and an electron transport layer ETL. In addition, when compared with FIG. 1, FIG. 3 shows the cross-sectional view of an organic electroluminescence device 10 of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. When compared with FIG. 2, FIG. 4 shows the cross-sectional view of an organic electroluminescence device 10 of an embodiment including a capping layer CPL on the second electrode EL2.

The first electrode EL1 has conductivity. The first electrode EU may be formed using a metal alloy or any suitable conductive compound. The first electrode EL1 may be an anode. In some embodiments, the first electrode EL1 may be a pixel electrode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), and/or indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or a transflective layer formed using any of the above materials, and a transmissive conductive layer formed using ITO, IZO, ZnO, and/or ITZO. For example, the first electrode EL1 may include a three-layer structure of ITO/Ag/ITO. However, an embodiment of the present disclosure is not limited thereto. The thickness of the first electrode EU may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer EBL. The thickness of the hole transport region HTR may be from about 50 Å to about 15,000 Å

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer of a hole injection layer HIL, or a hole transport layer HTL, and may have a structure of a single layer formed using a hole injection material and a hole transport material. In some embodiments, the hole transport region HTR may have a structure of a single layer formed using a plurality of different materials, or a structure stacked from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

The hole transport region HTR may be formed using one or more suitable methods such as a vacuum deposition method, a spin coating method, a cast method, a Langmuir-Blodgett (LB) method, an inkjet printing method, a laser printing method, and/or a laser induced thermal imaging (LITI) method.

In the organic electroluminescence device 10 of an embodiment, the hole transport region HTR may include the amine compound of an embodiment.

Meanwhile, in the description, the term “substituted or unsubstituted” corresponds to a group that is unsubstituted or that is substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the exemplified substituents may itself be substituted or unsubstituted. For example, a biphenyl group may be interpreted as an aryl group or a phenyl group substituted with a phenyl group.

In the description, the halogen atom may be a fluorine atom, a chlorine atom, a bromine atom, and/or an iodine atom.

In the description, the alkyl may be a linear chain, a branched chain or a cyclic alkyl group. The carbon number of the alkyl may be 1 to 50, 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the aryl group may refer to a functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexaphenyl, triphenylenyl, pyrenyl, benzofluoranthenyl, chrysenyl, etc., without limitation.

In the description, the heterocyclic group may refer to a functional group or substituent derived from a ring including one or more selected from B, O, N, P, Si and S as ring-forming heteroatoms. The heterocyclic group may include an aliphatic heterocyclic group and an aromatic heterocyclic group. The aromatic heterocyclic group may be a heteroaryl group. The aliphatic heterocyclic group and the aromatic heterocyclic group may each independently be monocyclic or polycyclic.

In the description, the heterocycle may include one or more selected from B, O, N, P, Si and S as ring-forming heteroatoms. If the heterocycle includes two or more heteroatoms, two or more heteroatoms may be the same or different. The heterocycle may be monocyclic heterocycle or polycyclic heterocycle and has a concept including heteroaryl. The carbon number for forming a ring of the heterocycle may be 2 to 30, 2 to 20, or 2 to 10.

In the description, the aliphatic heterocyclic group may include one or more selected from B, O, N, P, Si and S as ring-forming heteroatoms. The carbon number for forming a ring of the aliphatic heterocyclic group may be 2 to 30, 2 to 20, or 2 to 10. Examples of the aliphatic heterocyclic group include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the description, the heteroaryl group may include one or more selected from B, O, N, P, Si and S as ring-forming heteroatoms. If the heteroaryl group includes two or more heteroatoms, two or more heteroatoms may be the same or different. The heteroaryl group may be a monocyclic heterocyclic group or a polycyclic heterocyclic group. The carbon number for forming a ring of the heteroaryl group may be 2 to 30, 2 to 20, or 2 to 10. Examples of the heteroaryl group may include thiophenyl, furanyl, pyrrolyl, imidazolyl, thiazolyl, oxazolyl, oxadiazolyl, triazolyl, pyridinyl, bipyridinyl, pyrimidinyl, triazinyl, acridyl, pyridazinyl, pyrazinyl, quinolinyl, quinazolinyl, quinoxalinyl, phenoxazinyl, phthalazinyl, pyrido pyrimidinyl, pyrido pyrazinyl, pyrazino pyrazinyl, isoquinolinyl, indolyl, carbazolyl, N-arylcarbazolyl, N-heteroarylcarbazolyl, N-alkylcarbazolyl, benzoxazolyl, benzoimidazolyl, benzothiazolyl, benzocarbazolyl, benzothiophenyl, dibenzothiophenyl, thienothiophenyl, benzofuranyl, phenanthrolinyl, isooxazolyl, thiadiazolyl, phenothiazinyl, dibenzosilolyl, dibenzofuranyl, etc., without limitation.

In the description, a direct linkage may mean a single bond.

In the description, "—*" means a connected position (e.g., a binding site).

In the description, "atoms for forming a ring" may refer to ring-forming atoms.

In the organic electroluminescence device 10 of an embodiment, the hole transport region HTR may include an amine compound represented by the following Formula 1:

Formula 1

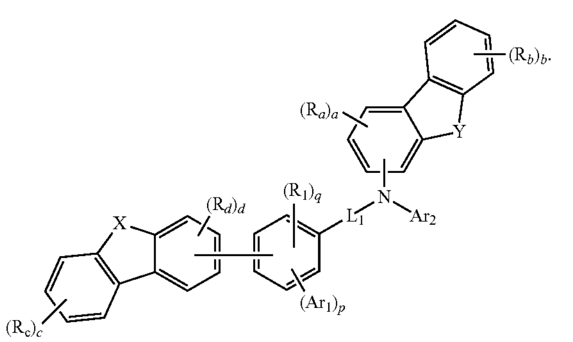

In Formula 1, X and Y may each independently be O or S. For example, the amine compound of an embodiment may be a monoamine compound including two dibenzoheterocyclic groups. In the amine compound of an embodiment, one of the two dibenzoheterocyclic groups may be directly bonded to the nitrogen atom of an amine group, and the other dibenzoheterocyclic group may be bonded to the nitrogen atom of the amine group through a substituted phenylene ring.

In Formula 1, both X and Y may be O, or both X and Y may be S. In some embodiments, one among X and Y may be O, and the other one may be S.

In Formula 1, $Ar_1$ may be a substituted or unsubstituted aryl group of 6 to 40 carbon atoms for forming a ring. In Formula 1, "p" is 1 or 2. The amine compound of an embodiment may include one or two $Ar_1$ groups, which are substituted at the phenylene group. For example, in the amine compound of an embodiment, the phenylene group, which is a linker connecting two dibenzoheterocyclic groups, may be a branched linker including at least one $Ar_1$ as a substituent.

In the amine compound of an embodiment, represented by Formula 1, $Ar_1$ may be a substituted or unsubstituted phenyl group, or a substituted or unsubstituted naphthyl group. For example, $Ar_1$ may be an unsubstituted phenyl group, a deuterium-substituted phenyl group, an unsubstituted naphthyl group, or a deuterium-substituted naphthyl group. However, an embodiment of the present disclosure is not limited thereto.

Meanwhile, if “p” is 2 in Formula 1, two $Ar_1$ groups may be the same or different. For example, if “p” is 2, two $Ar_1$ groups may be all unsubstituted phenyl groups.

In Formula 1, $Ar_2$ may be a substituted or unsubstituted aryl group of 6 to 40 carbon atoms for forming a ring, or a substituted or unsubstituted heteroaryl group of 2 to 40 carbon atoms for forming a ring. In addition, a case where $Ar_2$ is a substituted or unsubstituted fluorene group or a substituted or unsubstituted carbazole group is excluded from the amine compound represented by Formula 1.

In the amine compound of an embodiment, $Ar_2$ may be a substituted or unsubstituted phenyl group, a substituted or unsubstituted biphenyl group, a substituted or unsubstituted naphthyl group, a substituted or unsubstituted phenanthryl group, a substituted or unsubstituted dibenzofuran group, or a substituted or unsubstituted dibenzothiophene group. However, an embodiment of the present disclosure is not limited thereto.

In the amine compound of an embodiment, $Ar_2$ may be represented by any one selected from the following Ar2-1 to Ar2-12:

Ar2-1

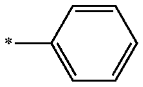

Ar2-2

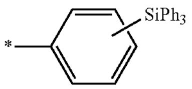

Ar2-3

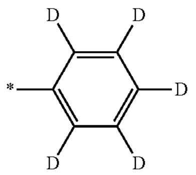

Ar2-4

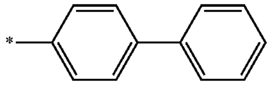

Ar2-5

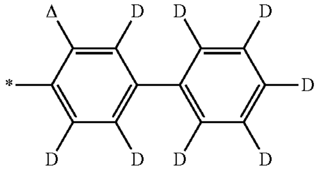

Ar2-6

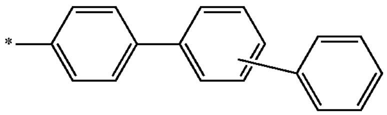

-continued

Ar2-7

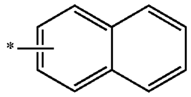

Ar2-8

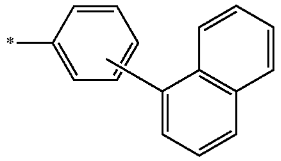

Ar2-9

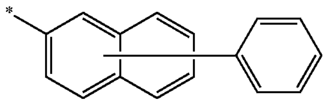

Ar2-10

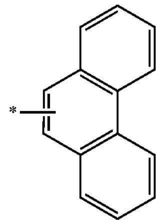

Ar2-11

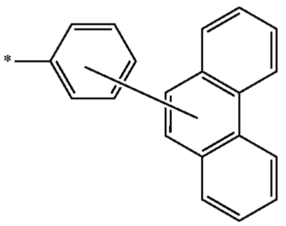

Ar2-12

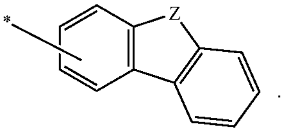

In Ar2-2, $SiPh_3$ is a triphenylsilyl group, and in Ar2-12, Z is O or S.

In the amine compound represented by Formula 1, $L_1$ may be a direct linkage, or a substituted or unsubstituted arylene group of 6 to 30 carbon atoms for forming a ring. For example, in the amine compound of an embodiment, $L_1$ may be a direct linkage, a substituted or unsubstituted phenylene group, or a substituted or unsubstituted naphthylene group. However, an embodiment of the present disclosure is not limited thereto.

In Formula 1, $R_1$ may be a hydrogen atom or a deuterium atom. In Formula 1, “q” is an integer of 0 to 3. If “q” is an integer of 2 or more, a plurality of $R_1$ groups may be the same, or at least one may be different from the remainder.

In Formula 1, $R_a$ to $R_d$ may each independently be a hydrogen atom, a deuterium atom, a substituted or unsubstituted alkyl group of 1 to 20 carbon atoms, or a substituted or unsubstituted aryl group of 6 to 40 carbon atoms for forming a ring. In Formula 1, “a” and “d” may each independently be an integer of 0 to 3, and “b” and “c” may each independently be an integer of 0 to 4.

In Formula 1, if “a” is an integer of 2 or more, a plurality of $R_a$ groups may be the same, or at least one may be different from the remainder. Meanwhile, if each of “b” to "d" is an integer of 2 or more, the same explanation as for the plurality of $R_a$ groups may be applied to each of the plurality of $R_b$ to $R_d$ groups.

For example, in the amine compound of an embodiment represented by Formula 1, $R_a$ to $R_d$ may each independently be a hydrogen atom, a deuterium atom, or a substituted or unsubstituted phenyl group. However, an embodiment of the present disclosure is not limited thereto.

The amine compound of an embodiment, represented by Formula 1 may be represented by any one selected from the following Formula 1A to Formula 1 D:

Formula 1A

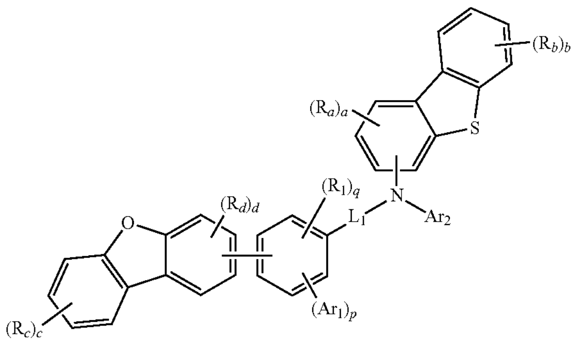

Formula 1B

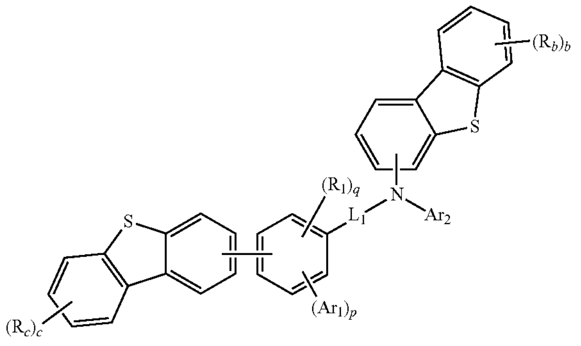

Formula 1C

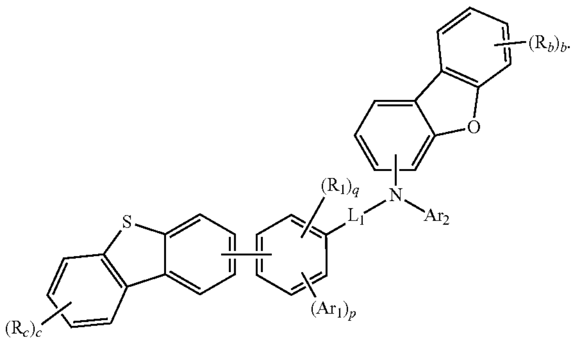

-continued

Formula 1D

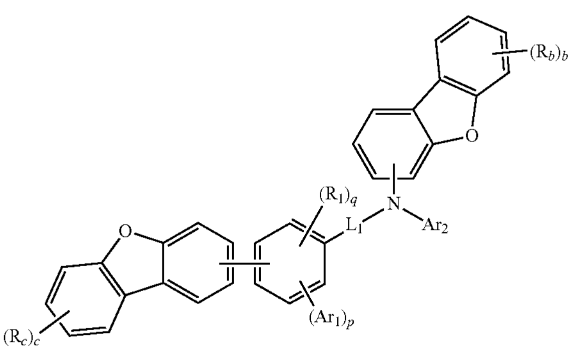

Formula 1A and Formula 1C represent cases where the amine compound of an embodiment includes one dibenzofuran group and one dibenzothiophene group. The amine compound represented by Formula 1B corresponds to a case of including two dibenzothiophene groups, and the amine compound represented by Formula 1D corresponds to a case of including two dibenzofuran groups.

Meanwhile, in Formula 1A to Formula 1D, the same explanations for $Ar_1$, $Ar_2$, $R_1$, $R_a$ to $R_d$, $L_1$, "a" to "d", "p", and "q" as those provided in Formula 1 may be applied.

The amine compound of an embodiment represented by Formula 1 may be represented by the following Formula 1-1 or Formula 1-2:

Formula 1-1

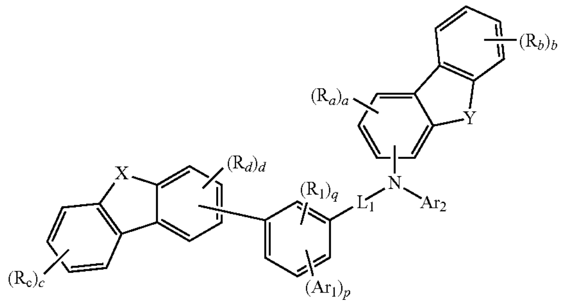

Formula 1-2

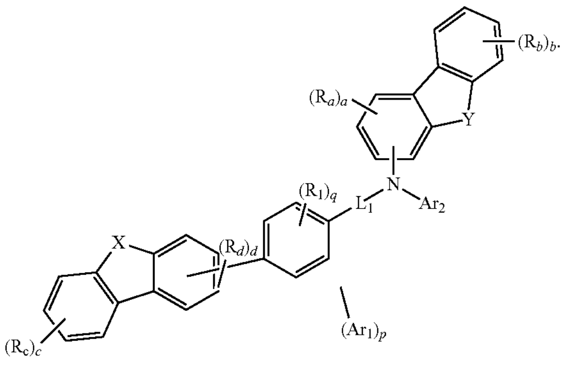

In the amine compound of an embodiment, the nitrogen atom of an amine group may be combined with a dibenzoheterocyclic group and a phenylene group, to which the other dibenzoheterocyclic group may be combined at a meta position. Formula 1-1 represents a case where the nitrogen atom of an amine group and a dibenzoheterocyclic group are combined at meta positions on a phenylene group.

In some embodiments, in the amine compound of an embodiment, the nitrogen atom of an amine group and the other dibenzoheterocyclic group may be combined at para positions on a phenylene group. Formula 1-2 represents a case where the nitrogen atom of an amine group and a dibenzoheterocyclic group are combined at para positions on a phenylene group.

In Formula 1-1 and Formula 1-2, the same explanations for X, Y, $Ar_1$, $Ar_2$, $R_1$, $R_a$ to $R_d$, $L_1$, "a" to "d", "p" and "q" as those provided in Formula 1 may be applied.

Formula 1-1 may be represented by any one selected from the following Formula 1-1A to Formula 1-1C:

Formula 1-1A

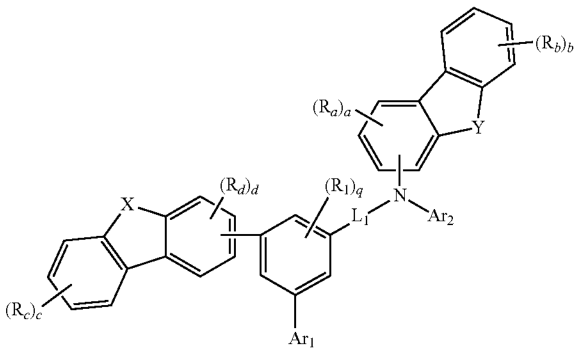

Formula 1-1B

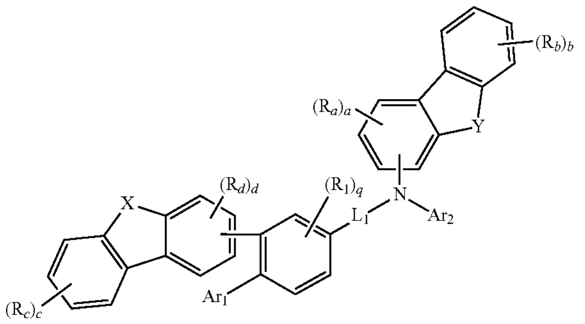

Formula 1-1C

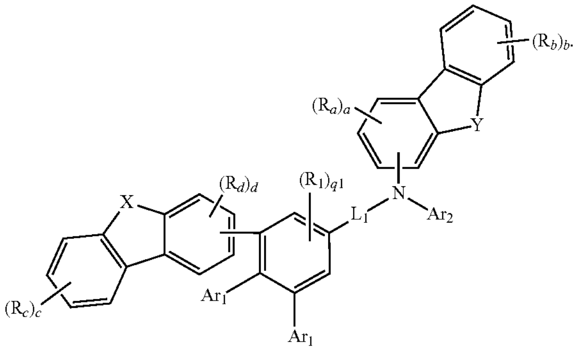

In Formula 1-1C, q1 may be an integer of 0 to 2. In addition, in Formula 1-1A to Formula 1-1C, the same explanations for X, Y, $Ar_1$, $Ar_2$, $R_1$, $R_a$ to $R_d$, $L_1$, "a" to "d", and "q" as those provided in Formula 1 may be applied.

Referring to Formula 1-1A to Formula 1-1C, in the amine compound of an embodiment, $Ar_1$ substituted at the phenylene group, which is a linker, may be combined in at least one position selected from a meta position and a para position with respect to the nitrogen atom of the amine group.

Formula 1-2 may be represented by the following Formula 1-2A or Formula 1-2B:

Formula 1-2A

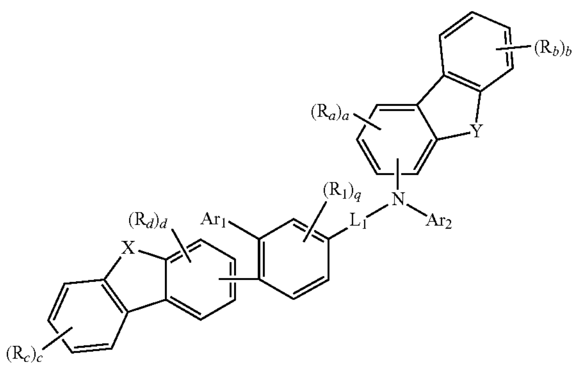

Formula 1-2B

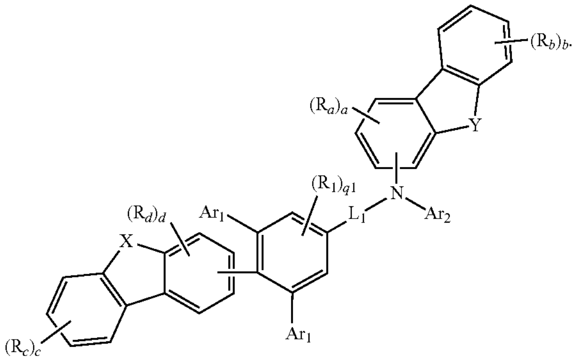

In Formula 1-2B, q1 may be an integer of 0 to 2. In addition, in Formula 1-2A and Formula 1-2B, the same explanations for X, Y, $Ar_1$, $Ar_2$, $R_1$, $R_a$ to $R_d$, $L_1$, "a" to "d", and "q" as those provided in Formula 1 may be applied.

Referring to Formula 1-2A and Formula 1-2B, in the amine compound of an embodiment, $Ar_1$ substituted at the phenylene group, which is a linker, may be combined at a meta position with respect to the nitrogen atom of the amine group.

The amine compound of an embodiment includes two dibenzoheterocyclic groups, where one of the two dibenzoheterocyclic groups may be directly combined with the nitrogen atom of an amine group, and the other dibenzoheterocyclic group may be combined with the nitrogen atom of the amine group through a substituted or unsubstituted phenylene ring. In addition, in the amine compound of an embodiment, on the phenylene ring corresponding to the linker, at least one aryl group may be substituted to form a branched linker structure. The amine compound of an embodiment includes two dibenzoheterocyclic groups and has a structure in which an aryl group is substituted at a linker (e.g., a phenylene group) connecting two dibenzoheterocycles, and if used as a material for an organic electroluminescence device, high efficiency and long-life characteristics of the device may be achieved. For example, the amine compound of an embodiment may be used as a hole transport material, and the organic electroluminescence device 10 of an embodiment includes the amine compound of an embodiment in a hole transport region HTR, thereby showing improved efficiency properties and increased life characteristics at the same time.

The amine compound of an embodiment, represented by Formula 1 may be represented by any one selected from the compounds in Compound Group 1 to Compound Group 3. For example, the organic electroluminescence device 10 of an embodiment may include at least one selected from the amine compounds represented in the following Compound Group 1 to Compound Group 3:

Compound Group 1

A1

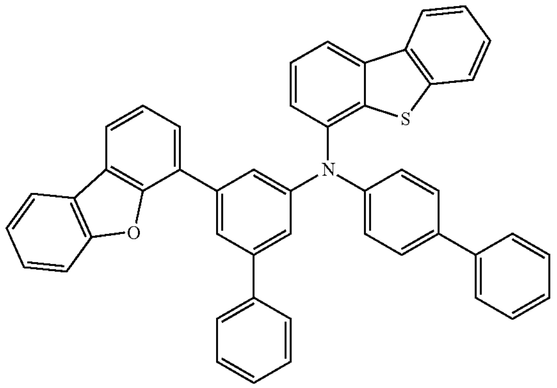

A2

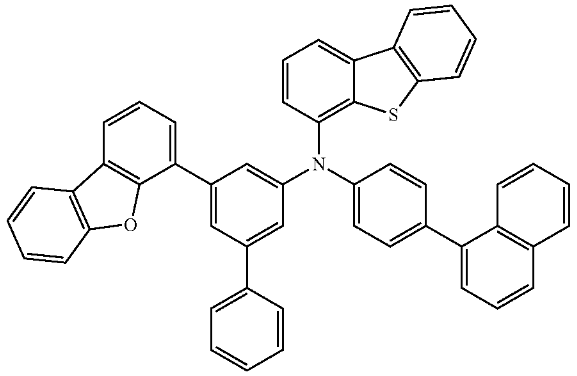

A3

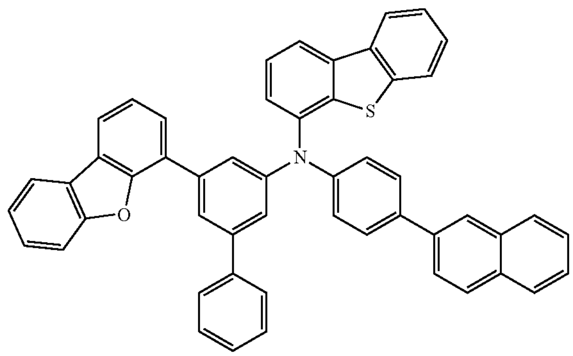

-continued

A4

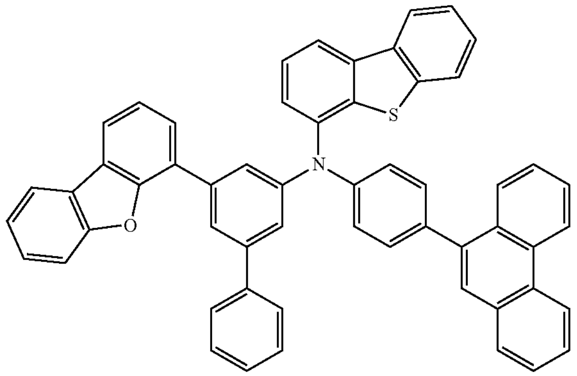

A5

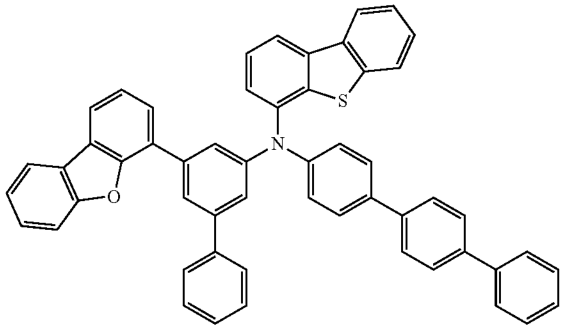

A6

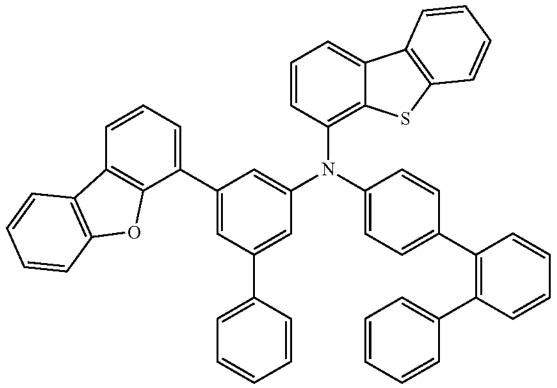

A7

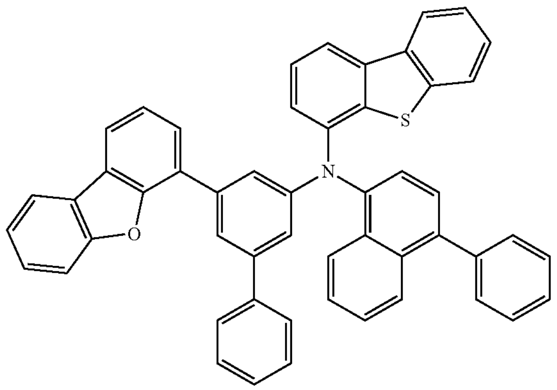

-continued
A8
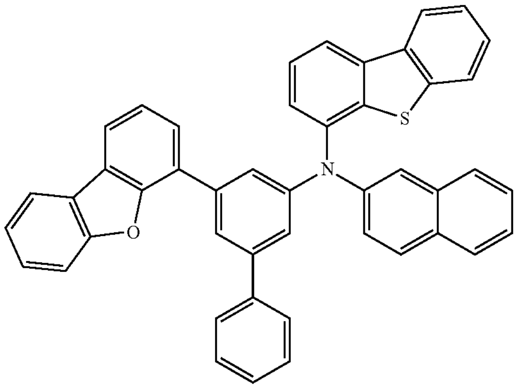
A9
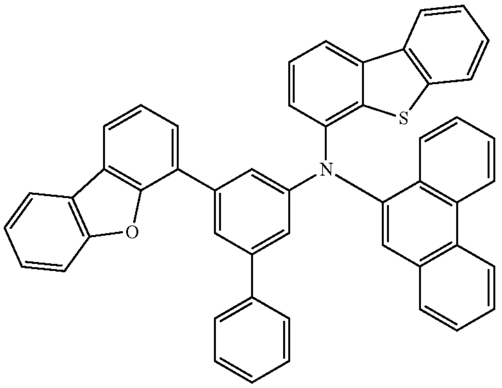
A10
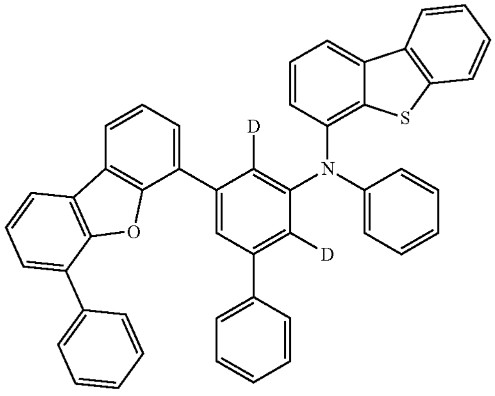
A11
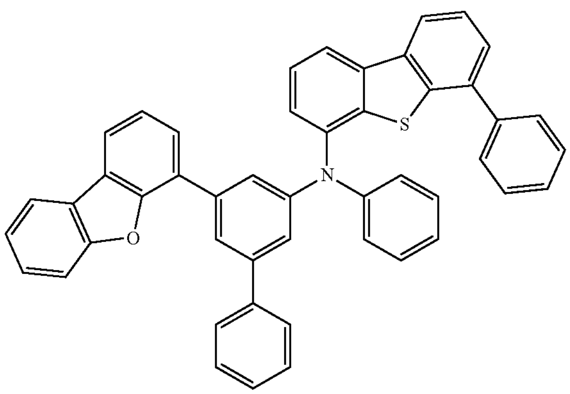
-continued
A12
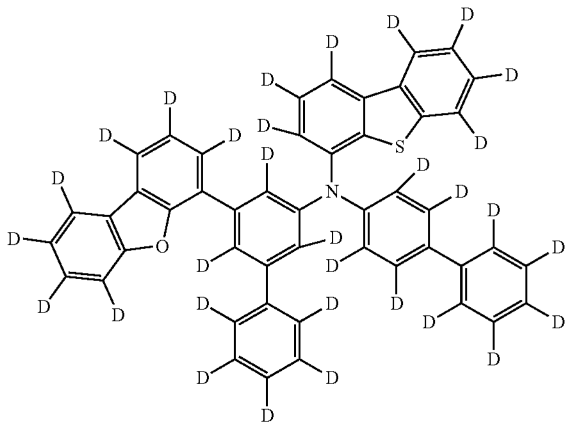
A13
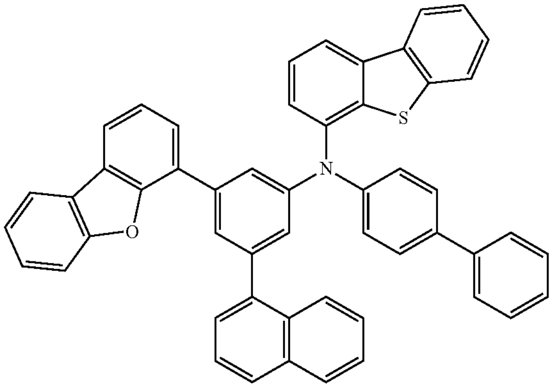
A14
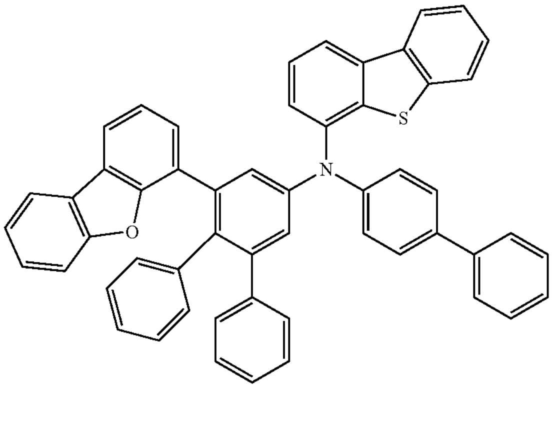

-continued
A15
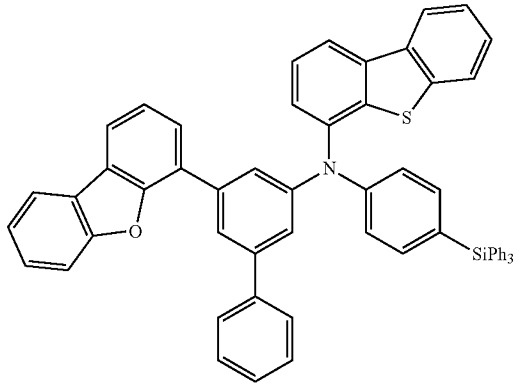
A16
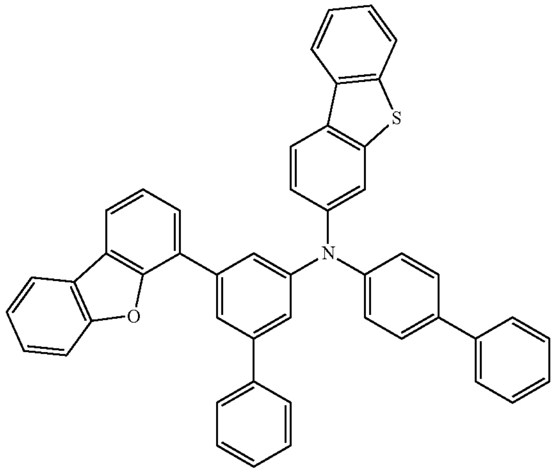
A17
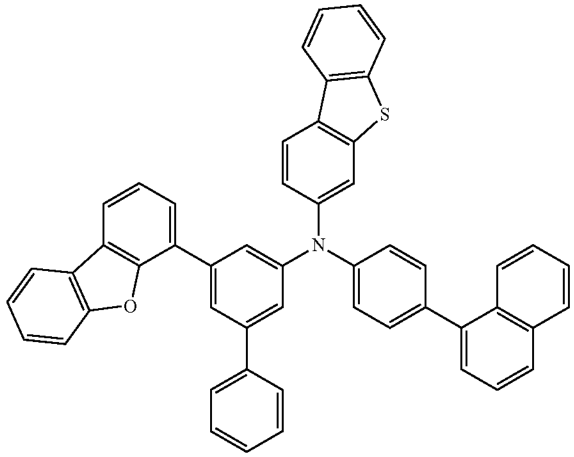
-continued
A18
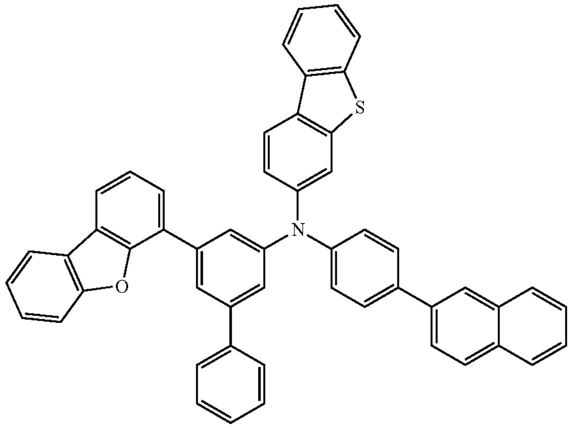
A19
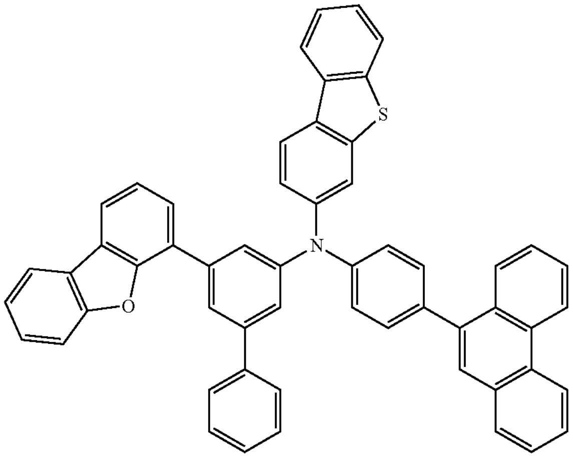
A20
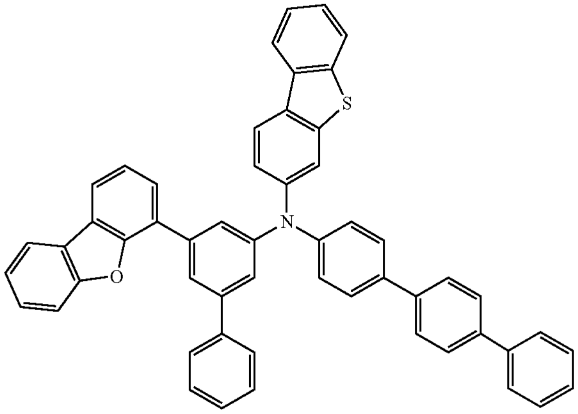

-continued
A21
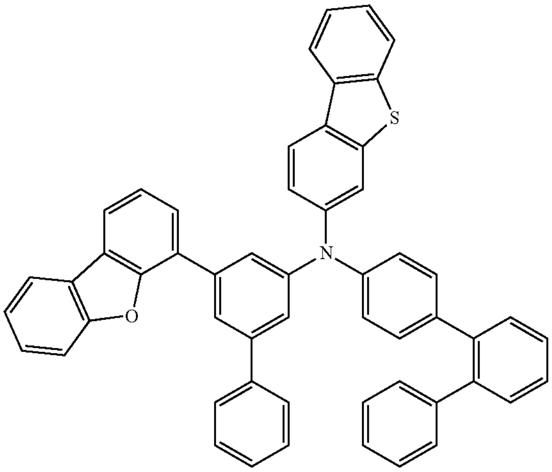
A22
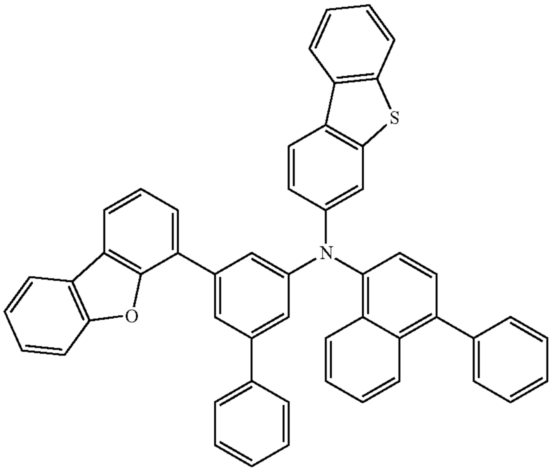
A23
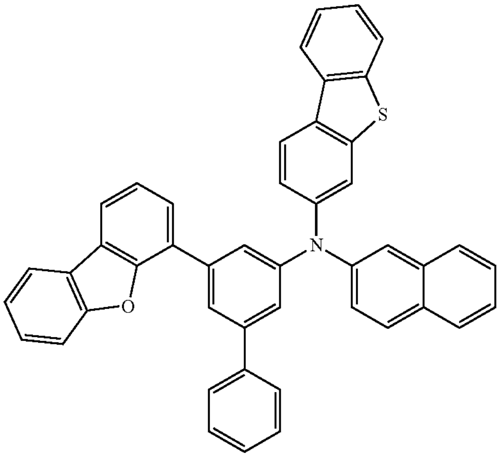
-continued
A24
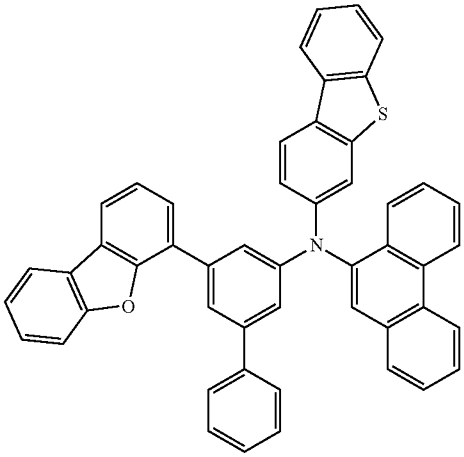
A25
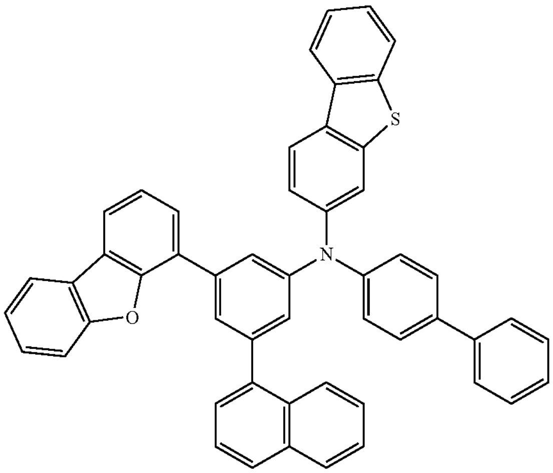
A26
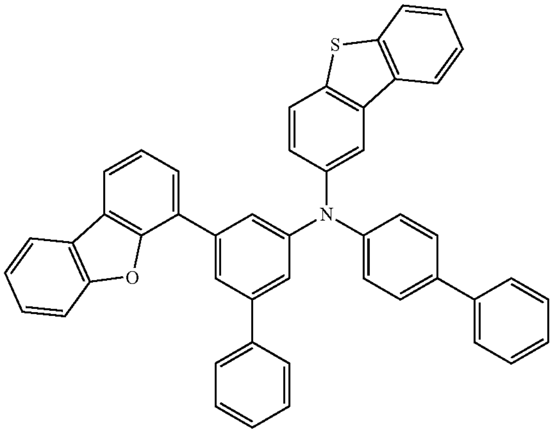

-continued
A27
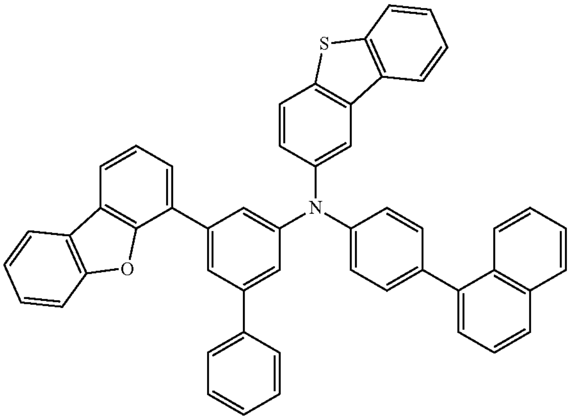
A28
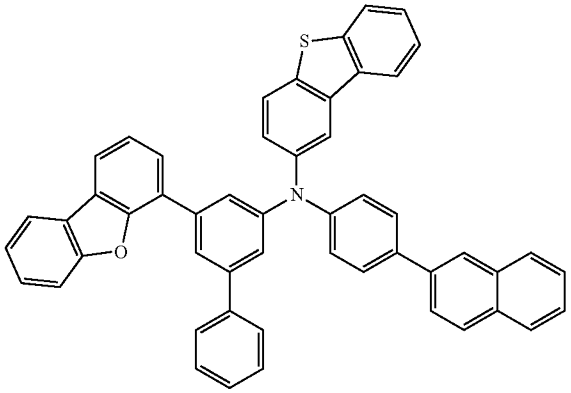
A29
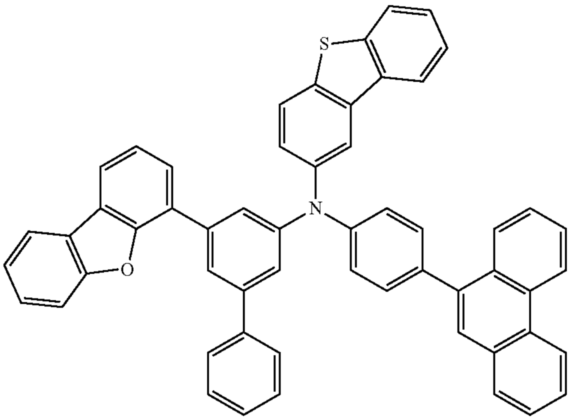
-continued
A30
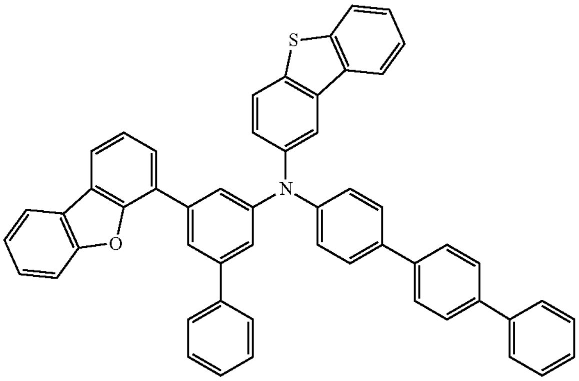
A31
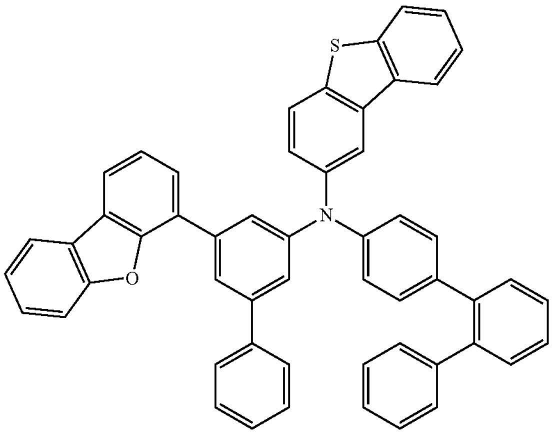
A32
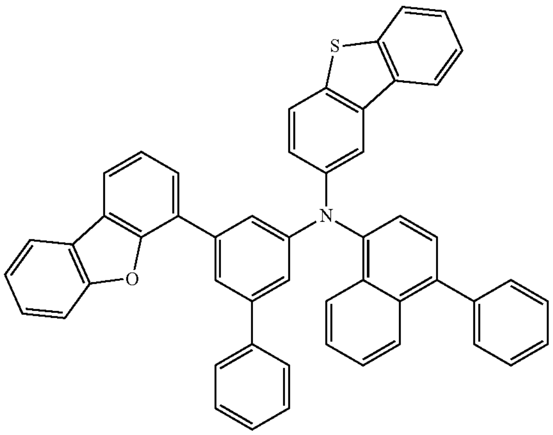

-continued
A33
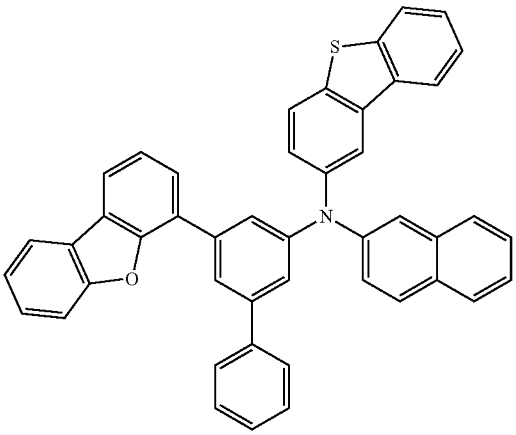
A34
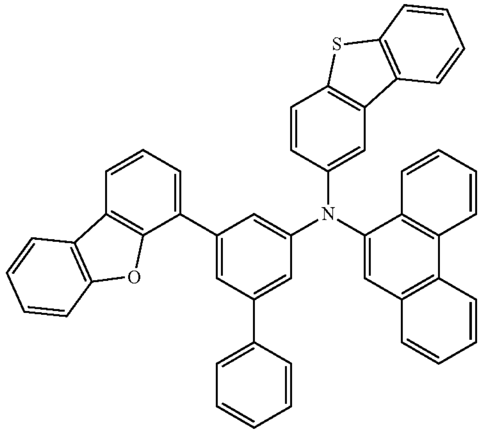
A35
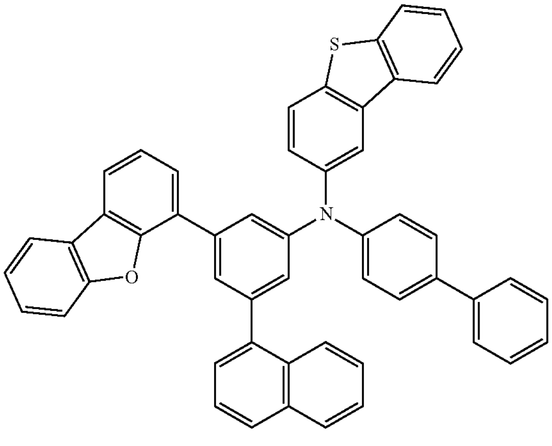
-continued
A36
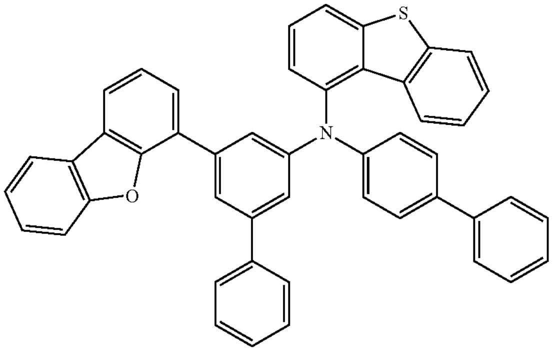
A37
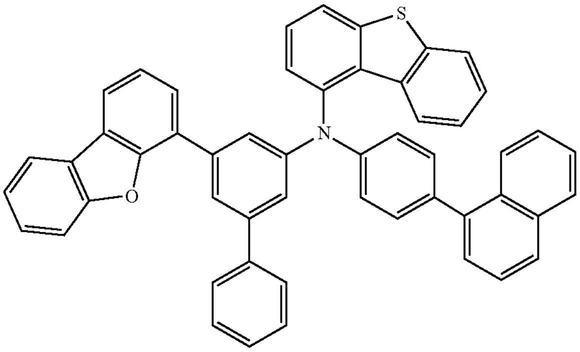
A38
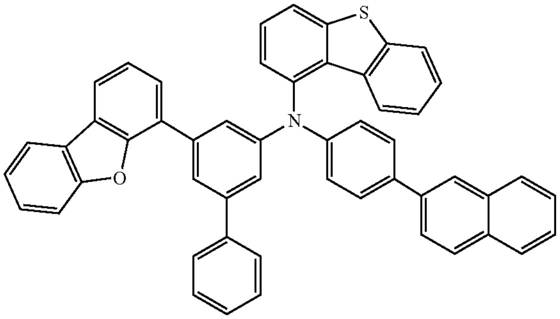
A39
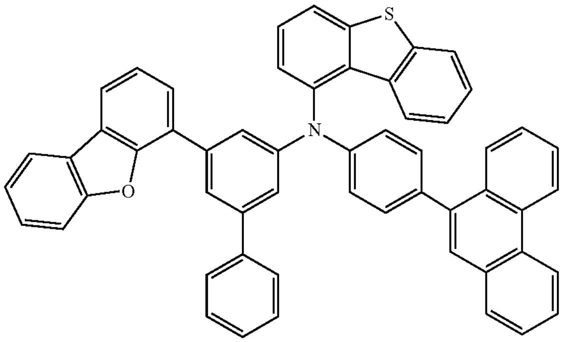

-continued
A40
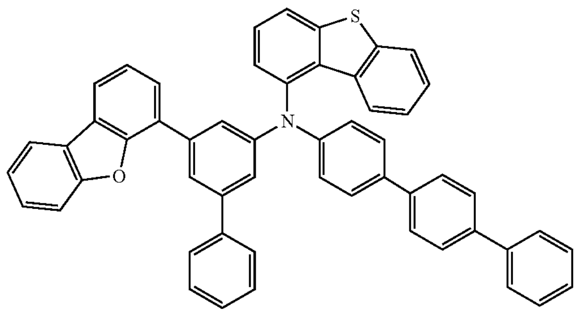
A41
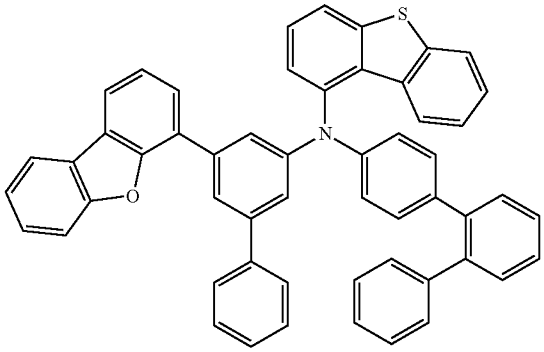
A42
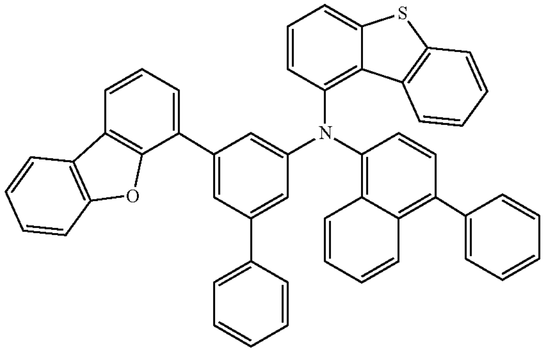
A43
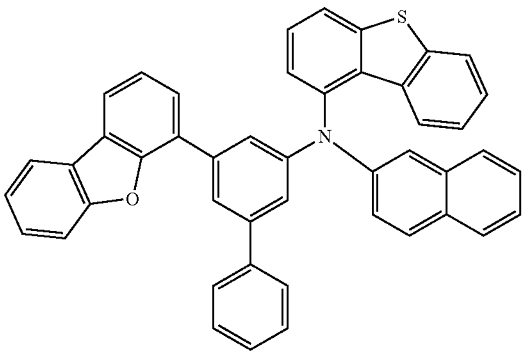
-continued
A44
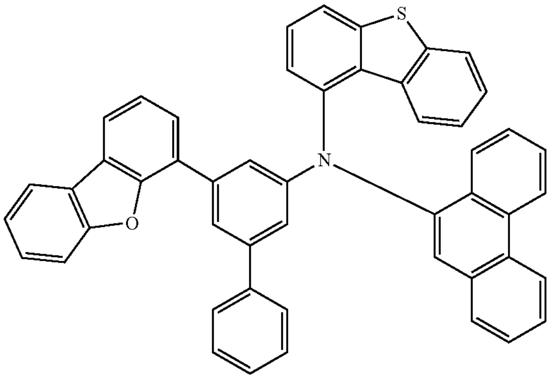
A45
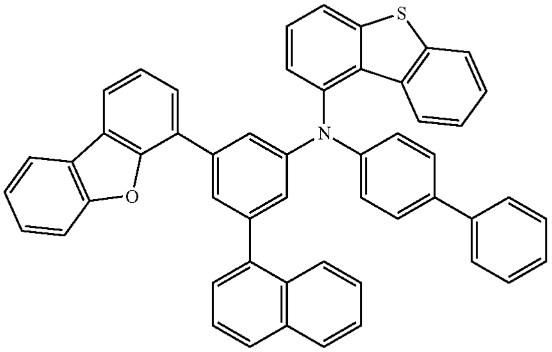
A46
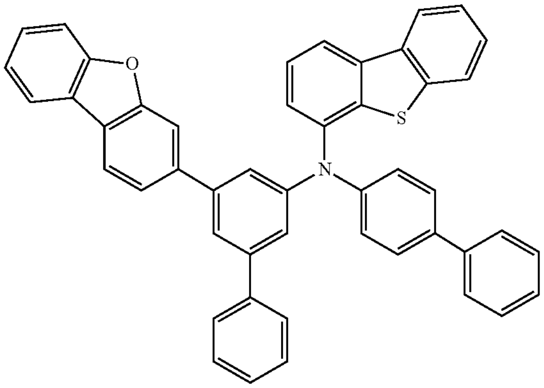
A47
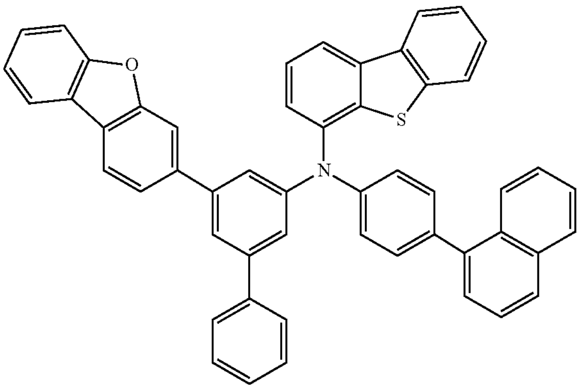

-continued
A48
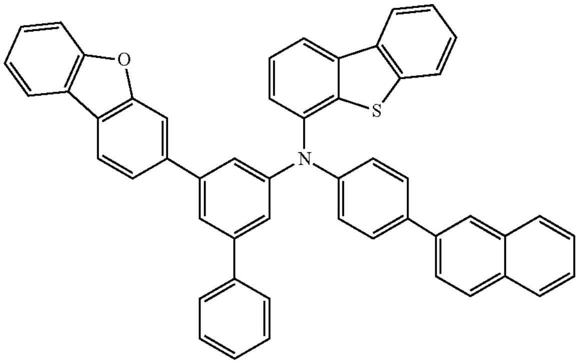
A49
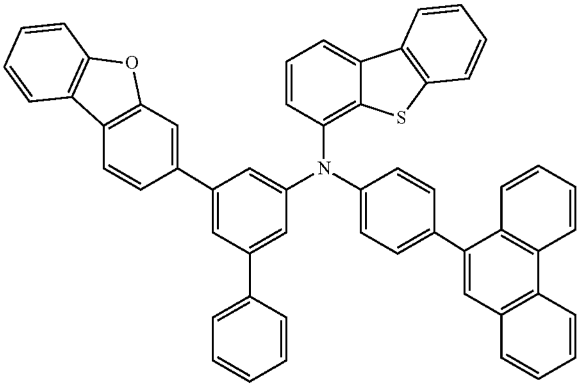
A50
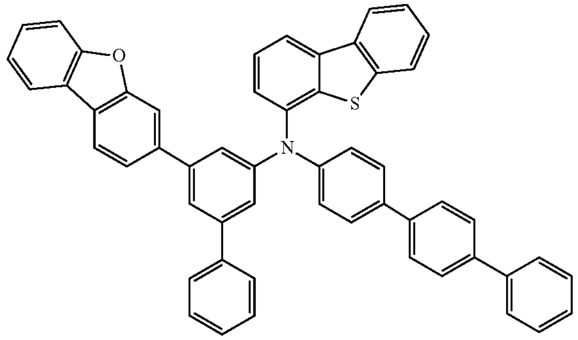
A51
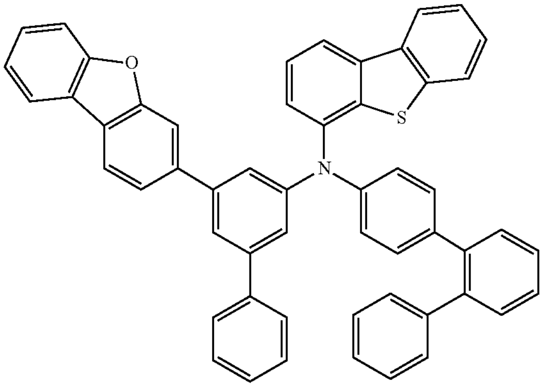
-continued
A52
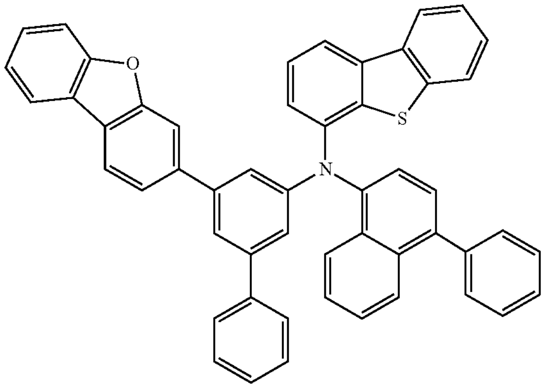
A53
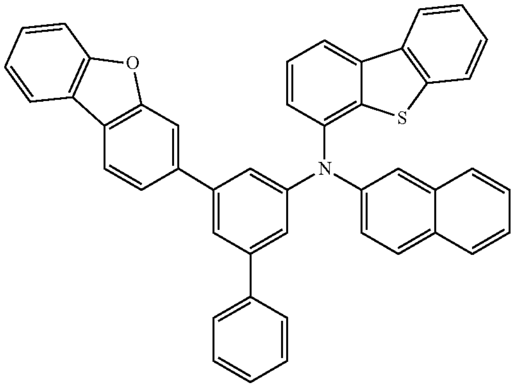
A54
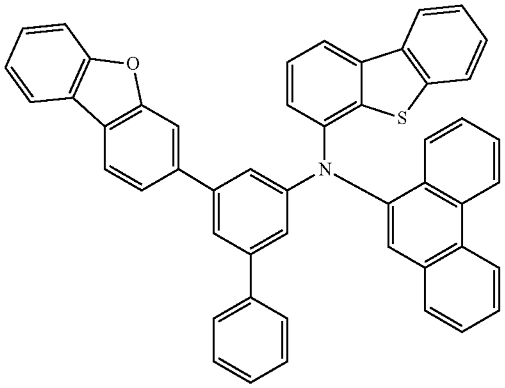
A55
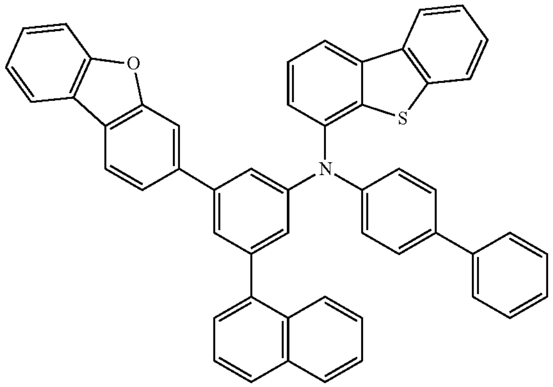

-continued
A56
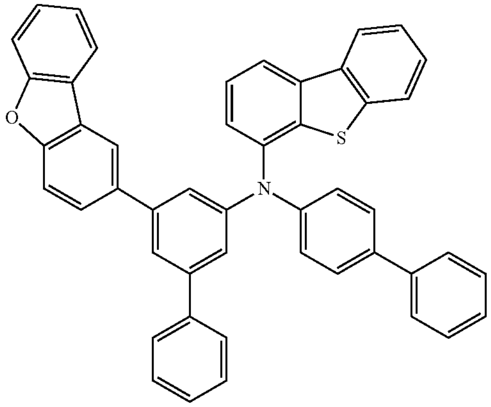
A57
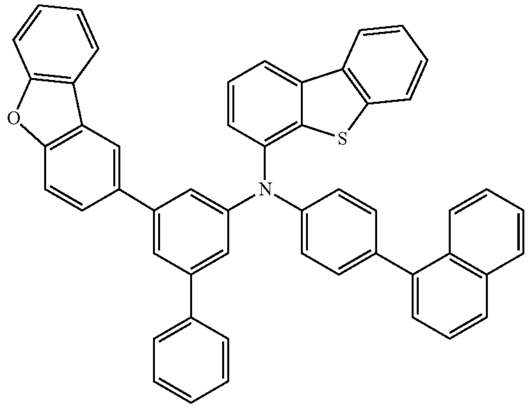
A58
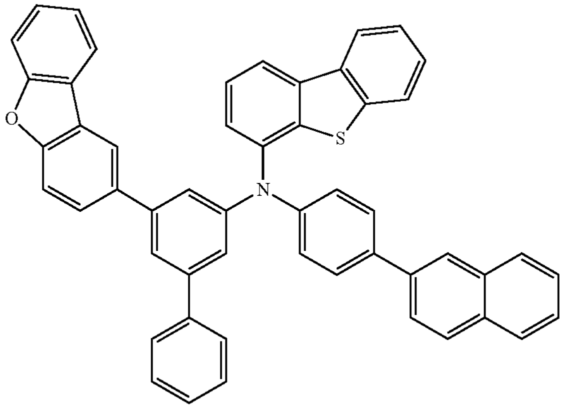
-continued
A59
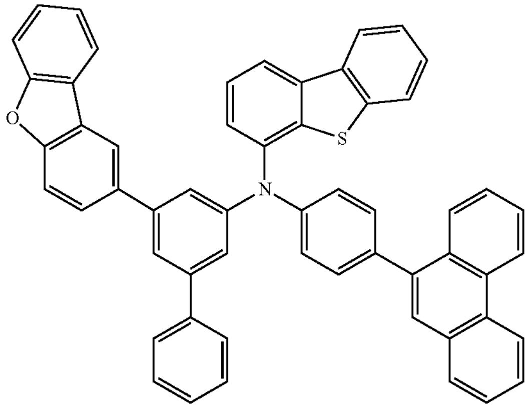
A60
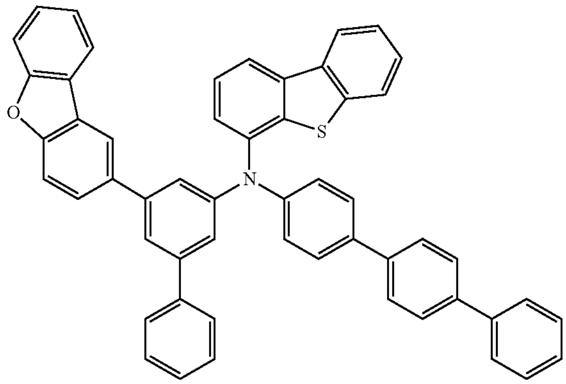
A61
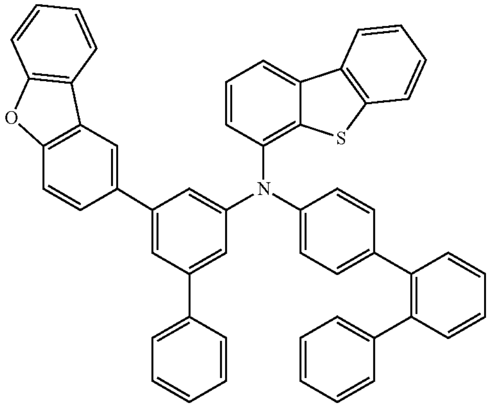
A62
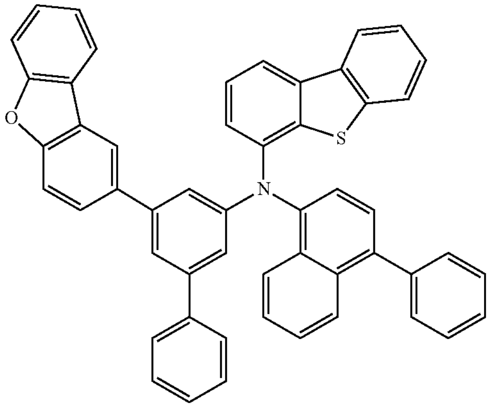

-continued
A63
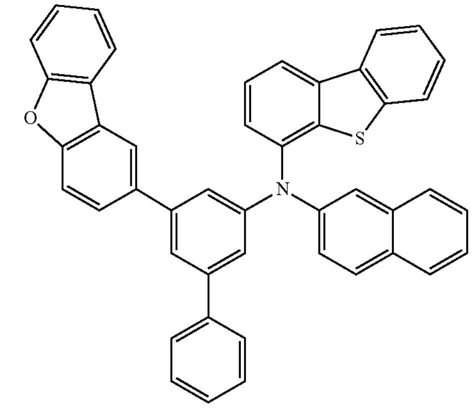
A64
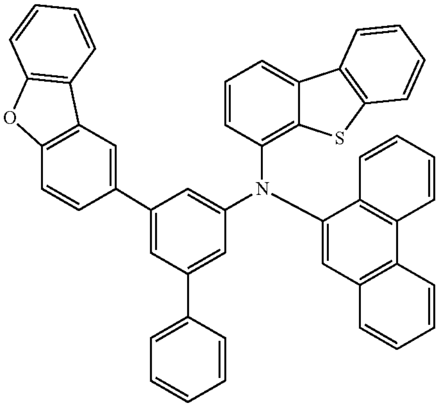
A65
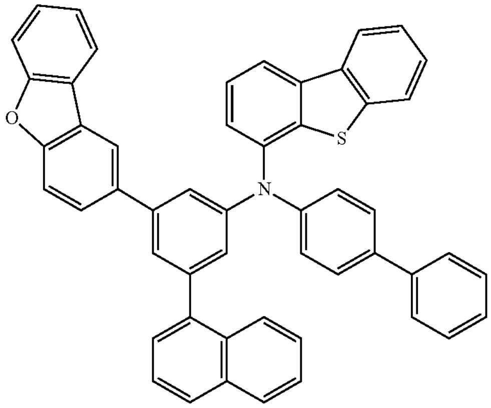
A66
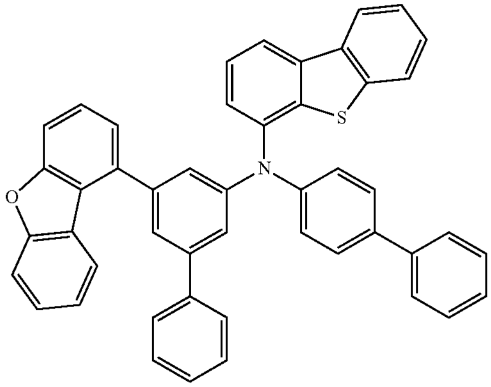
-continued
A67
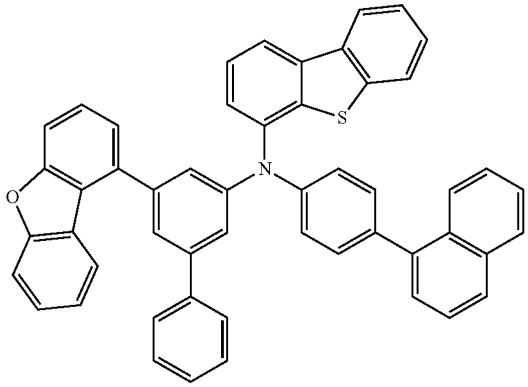
A68
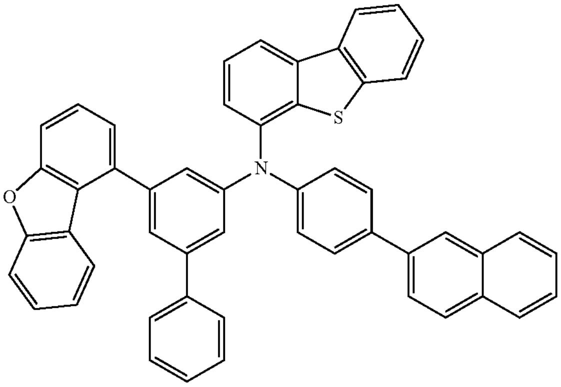
A69
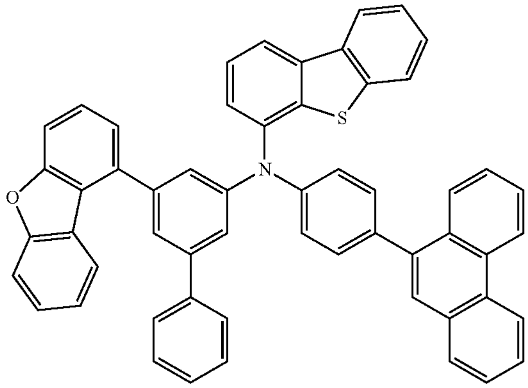
A70
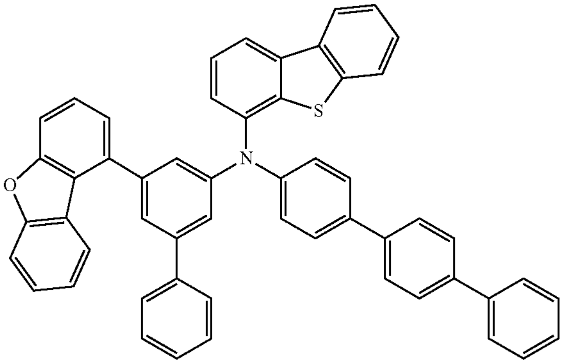

-continued
A71
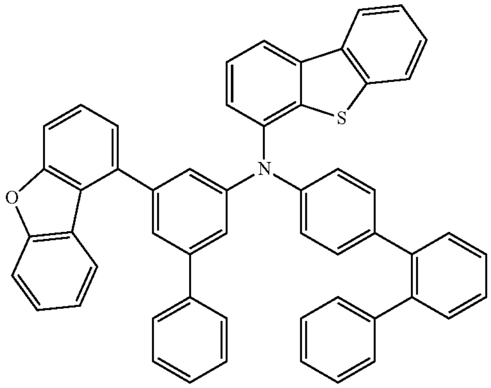
A72
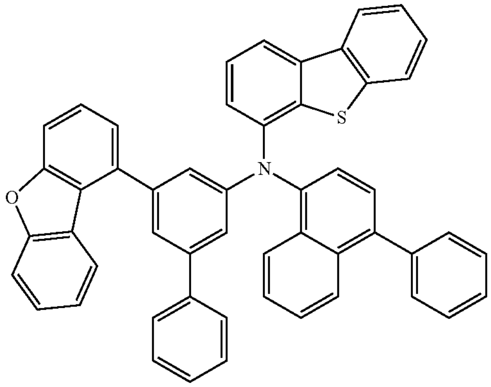
A73
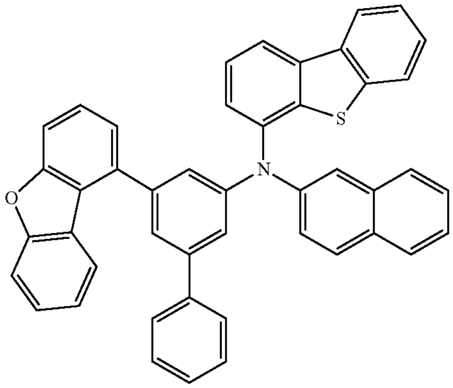
A74
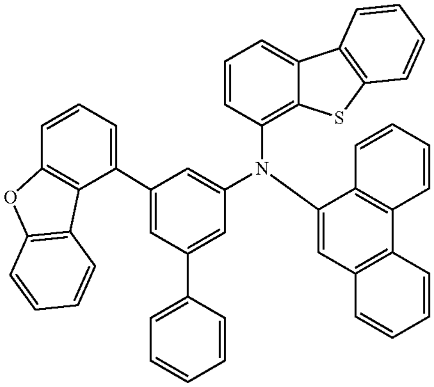
-continued
A75
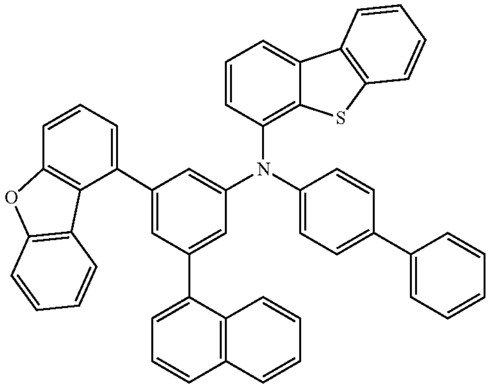
A76
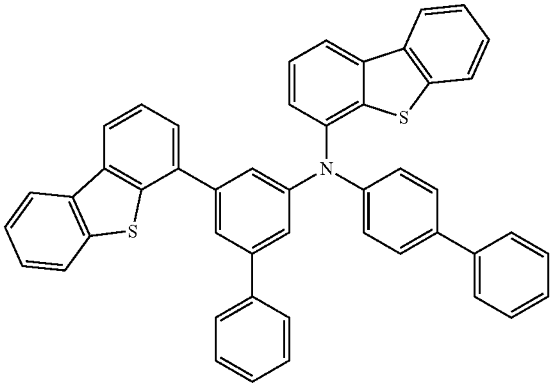
A77
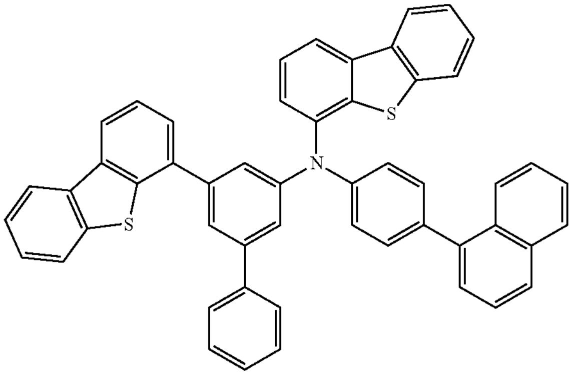
A78
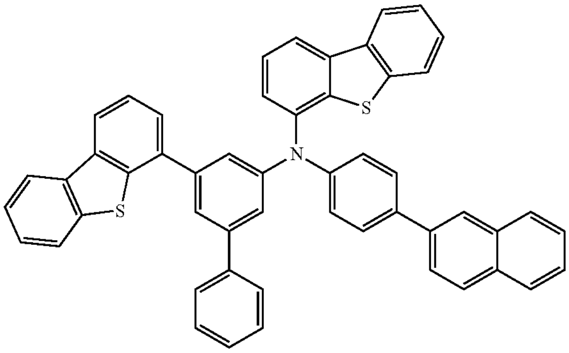

-continued
A79
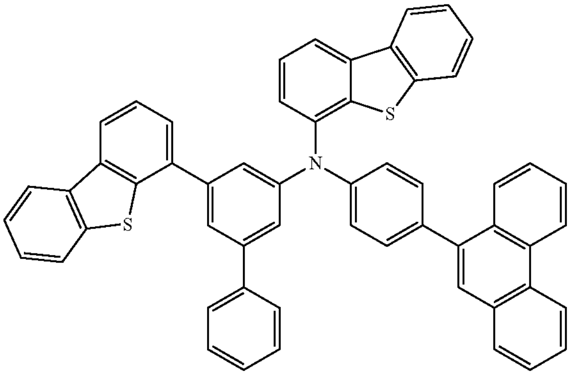
A80
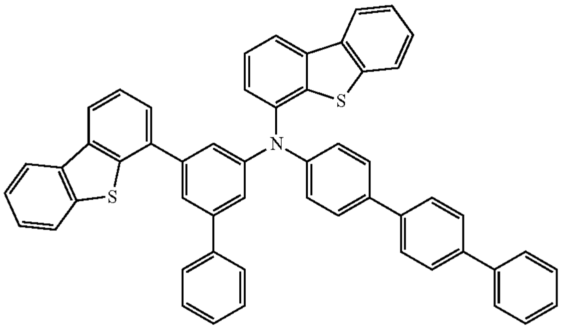
A81
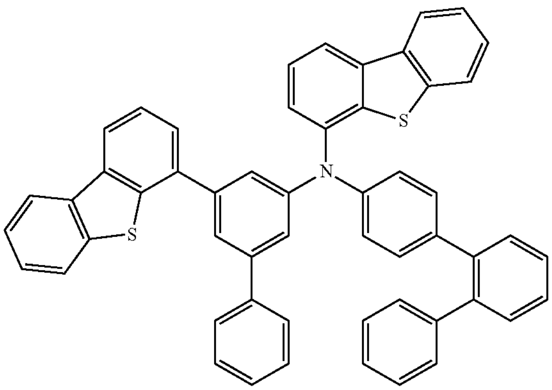
A82
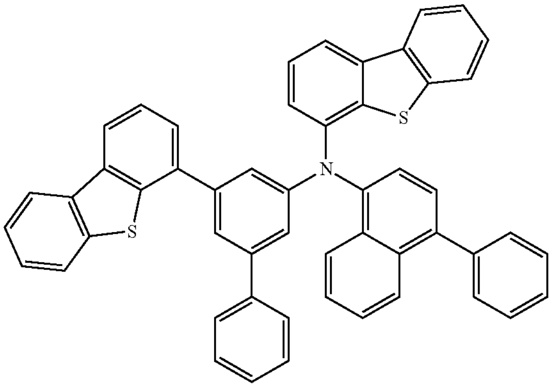
-continued
A83
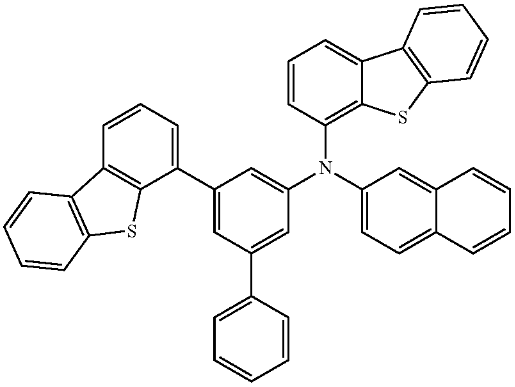
A84
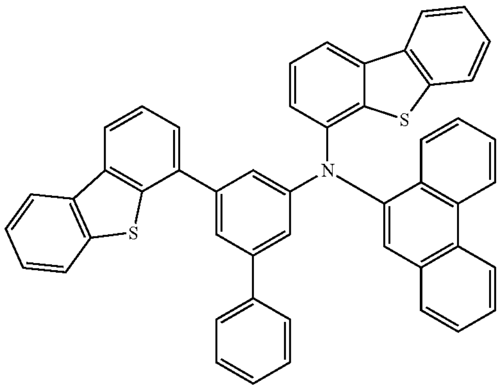
A85
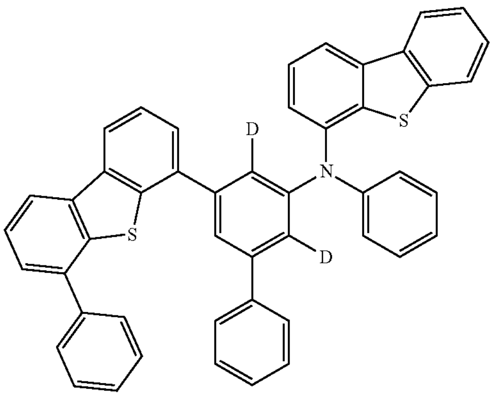
A86
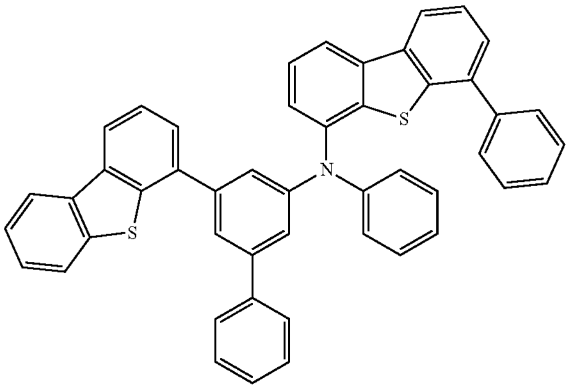

-continued
A87
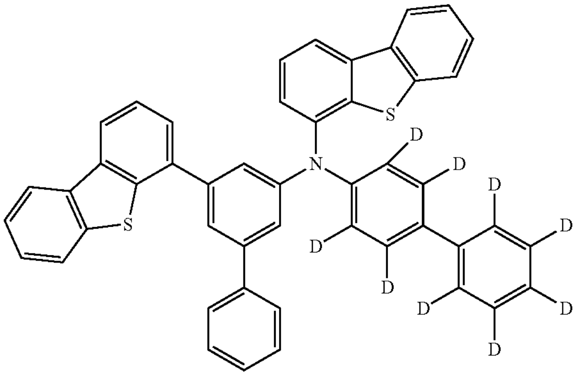
A88
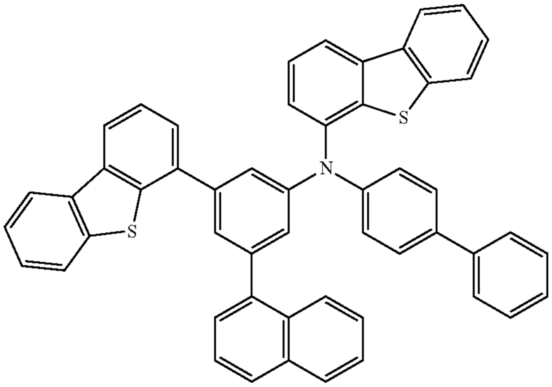
A89
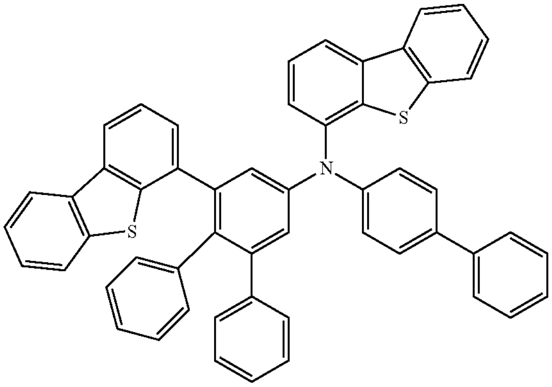
A90
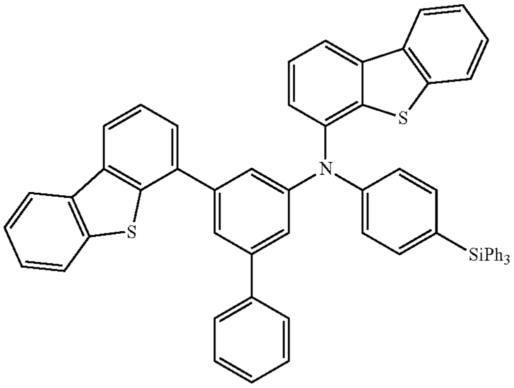
-continued
A91
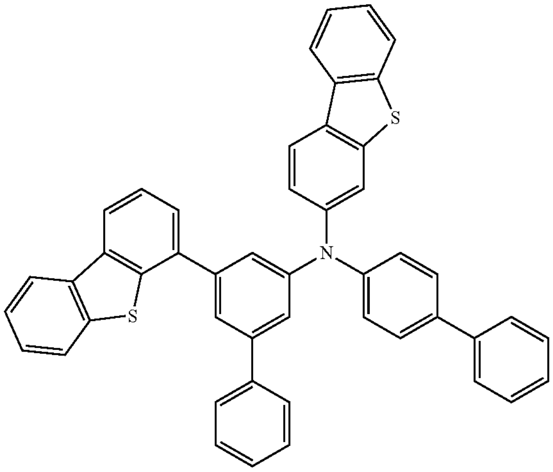
A92
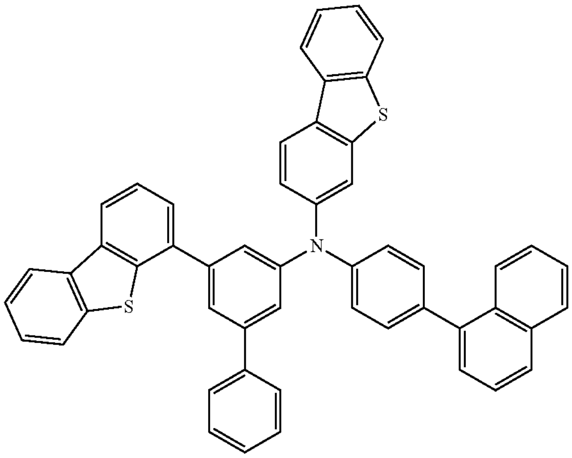
A93
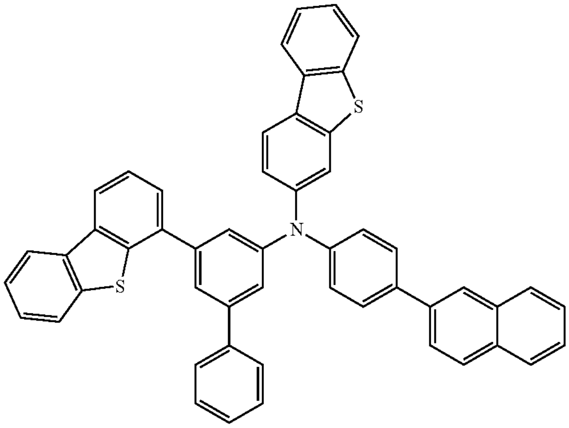

-continued
A94
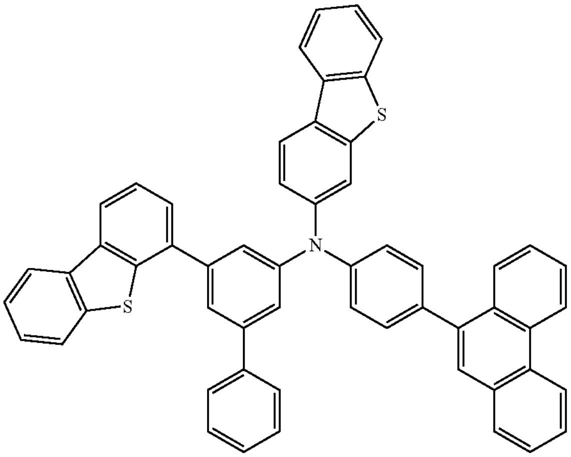
A95
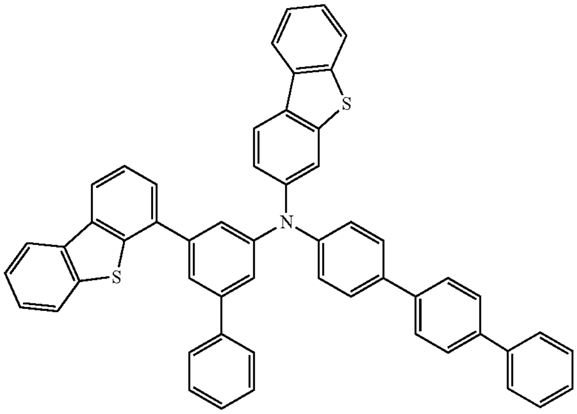
A96
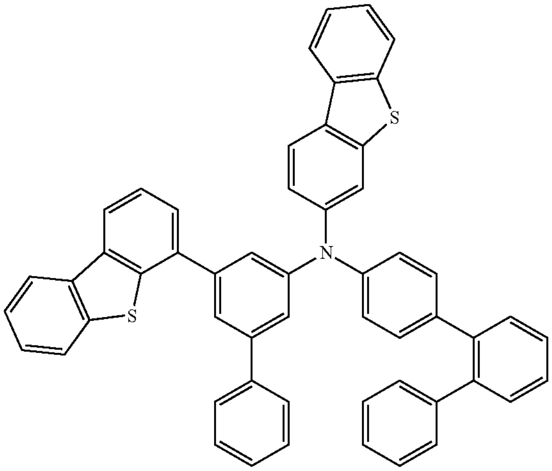
-continued
A97
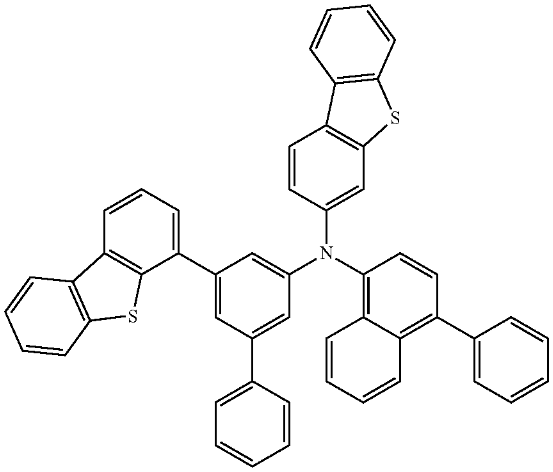
A98
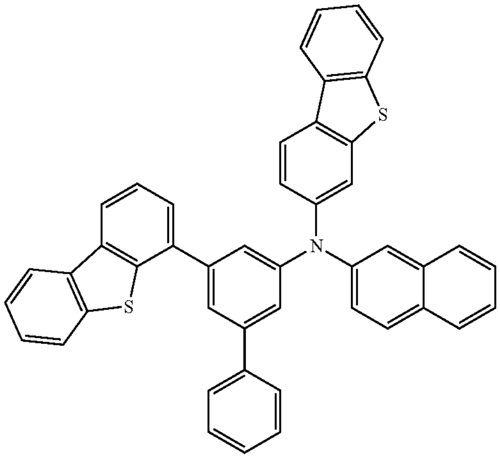
A99
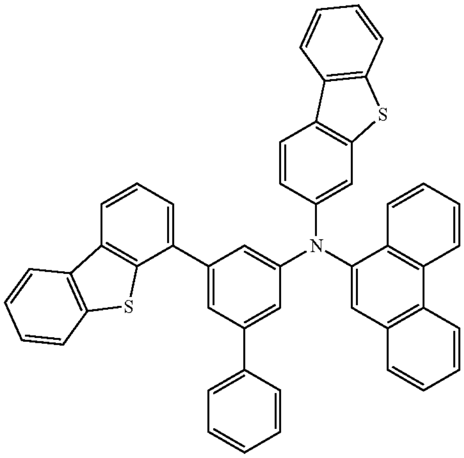

-continued
A100
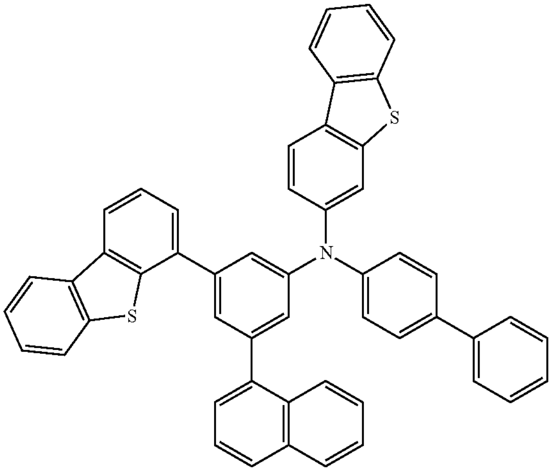
A101
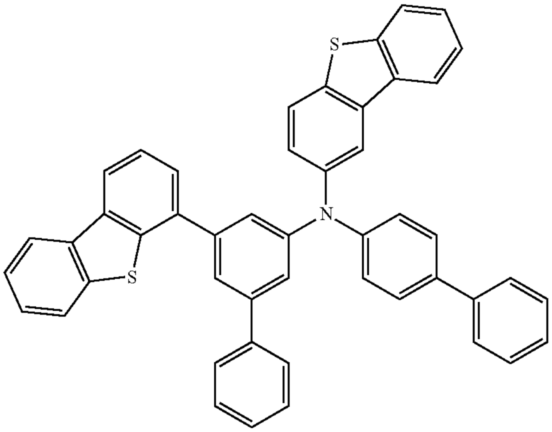
A102
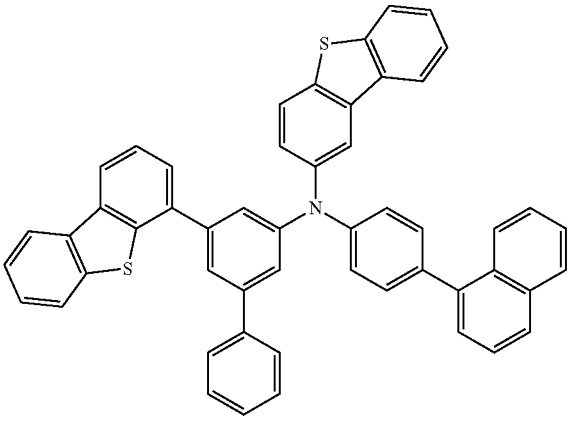
-continued
A103
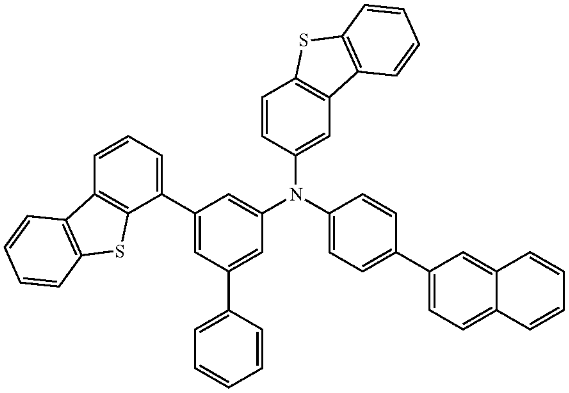
A104
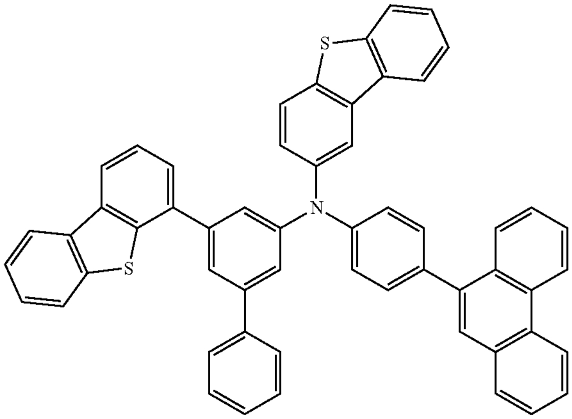
A105
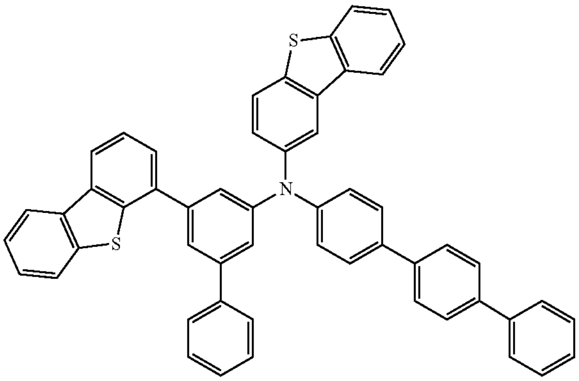

-continued
A106
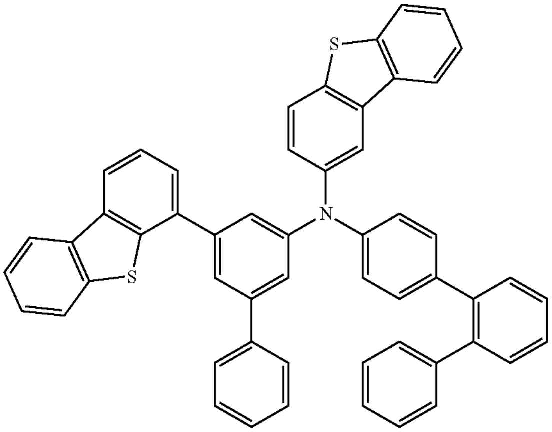
A107
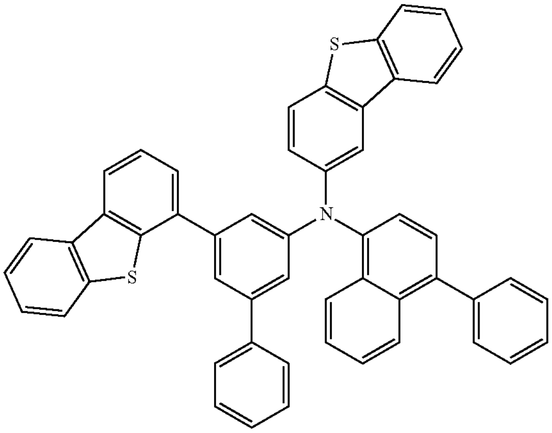
A108
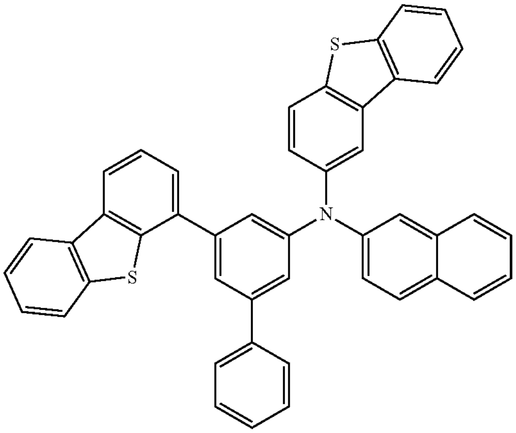
-continued
A109
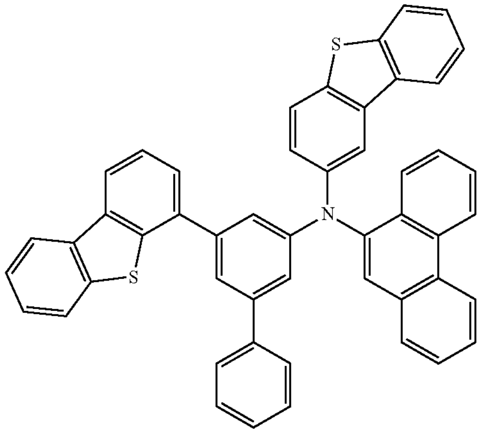
A110
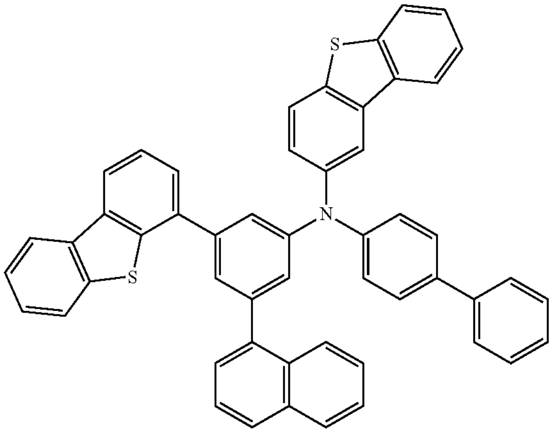
A111
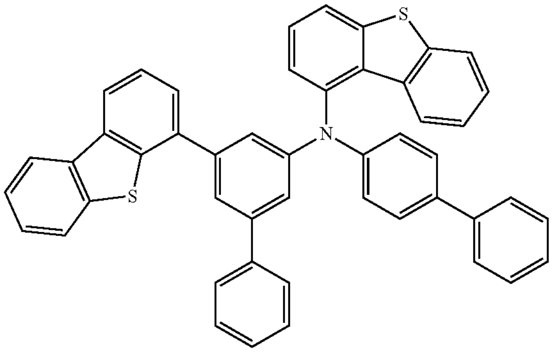
A112
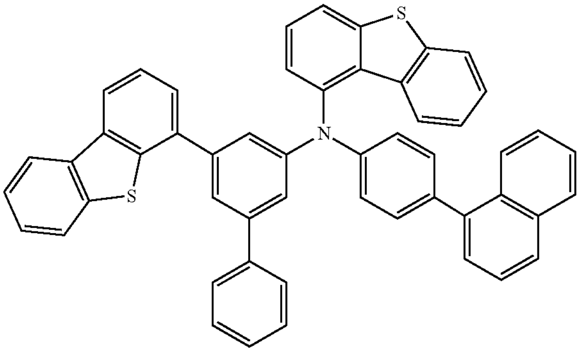

A113
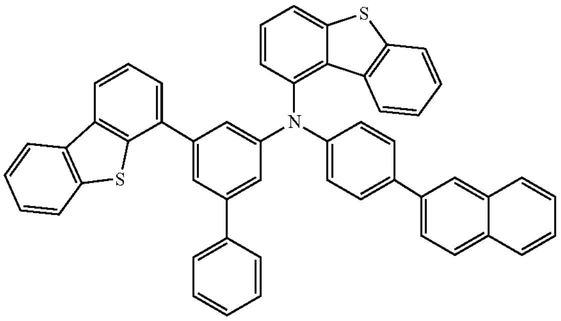
A114
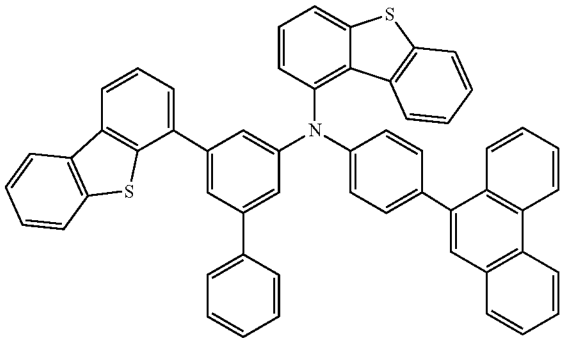
A115
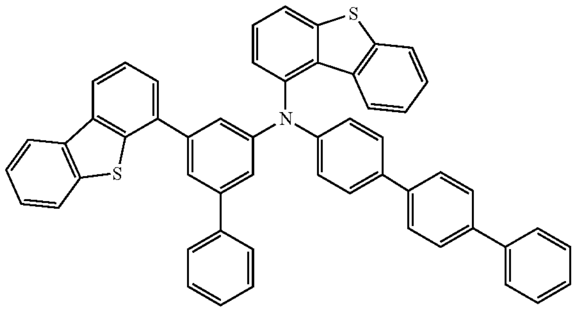
A116
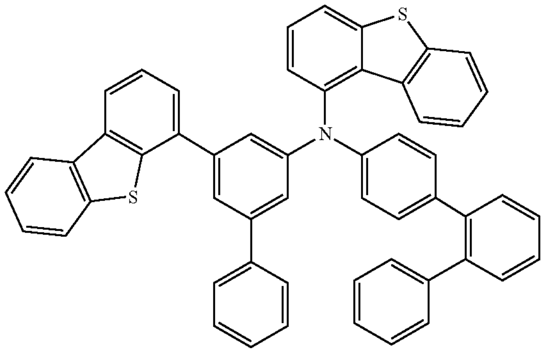
A117
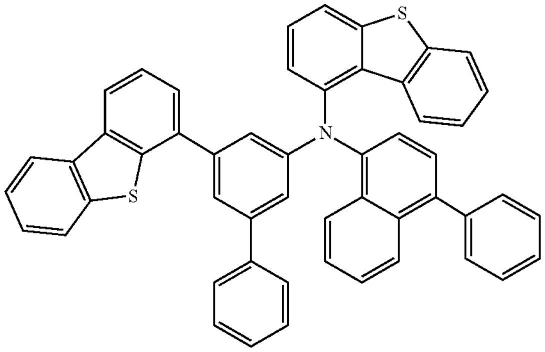
A118
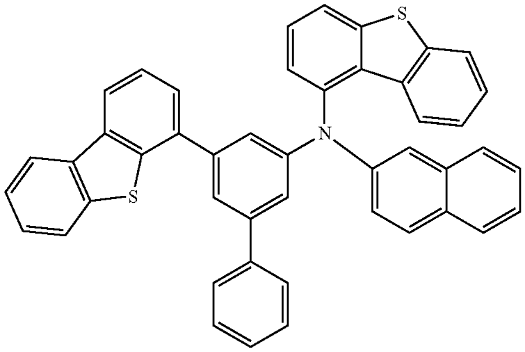
A119
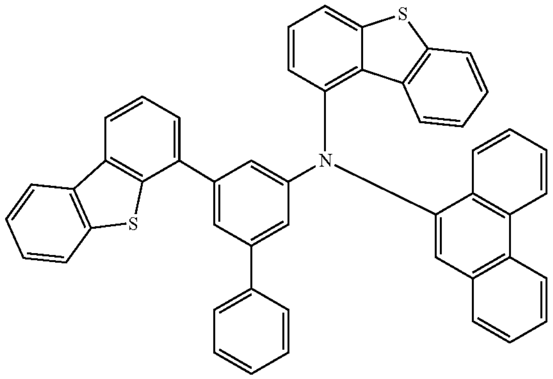
A120
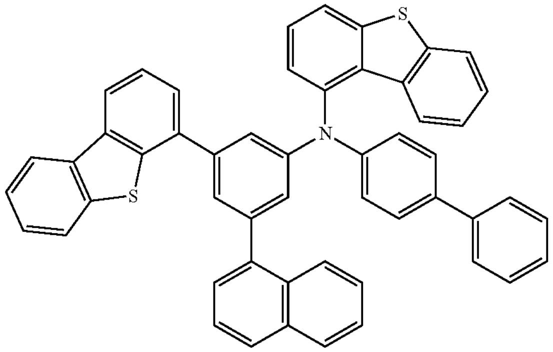

-continued
A121
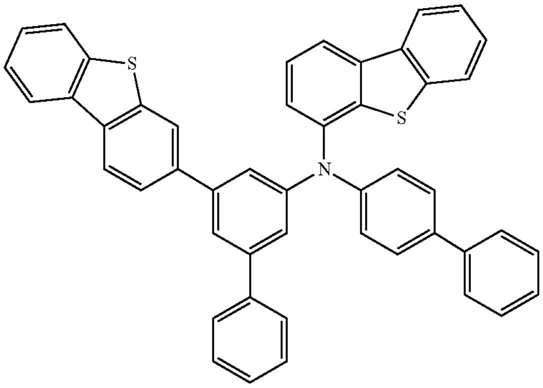
A122
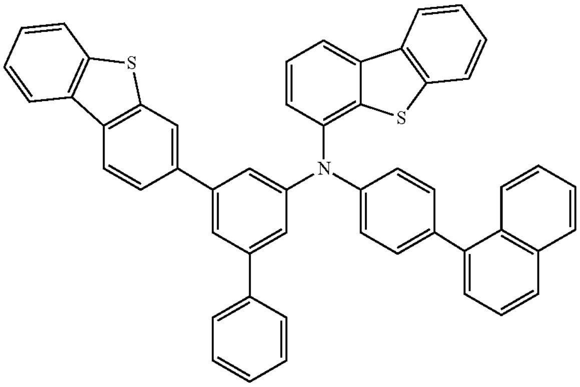
A123
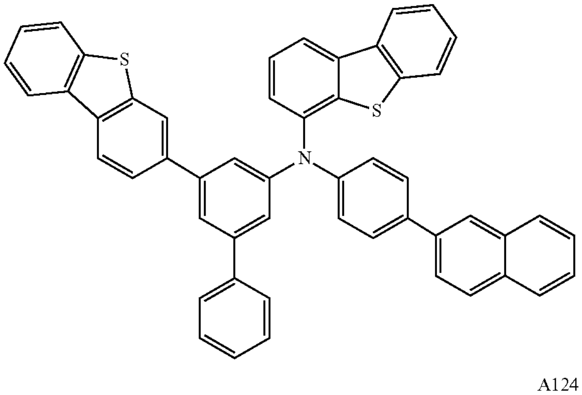
A124
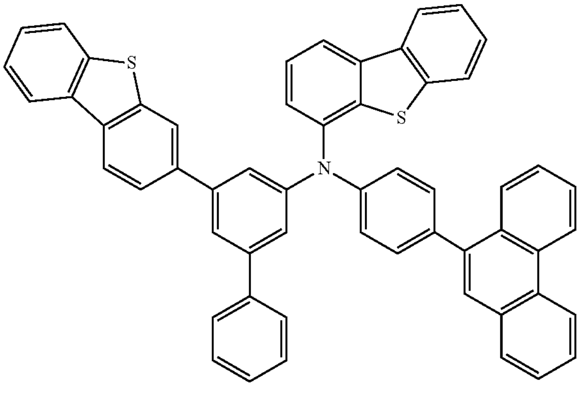
-continued
A125
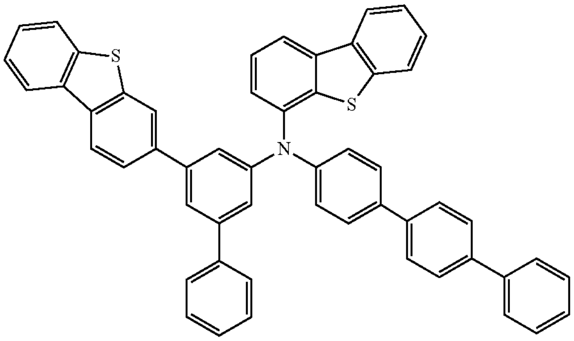
A126
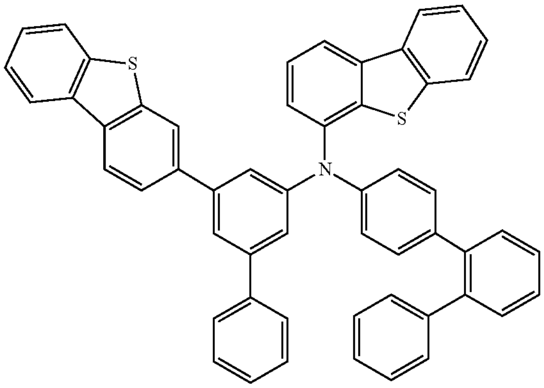
A127
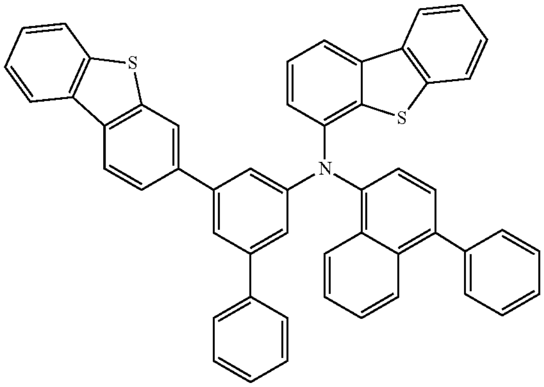
A128
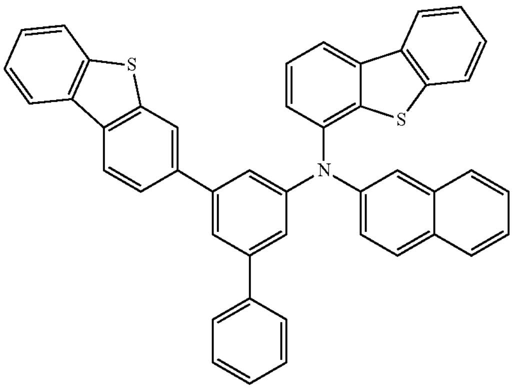

-continued
A129
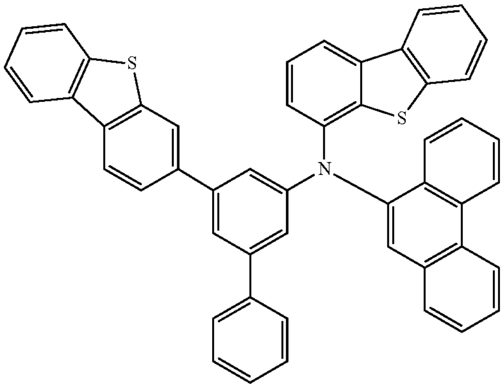
A130
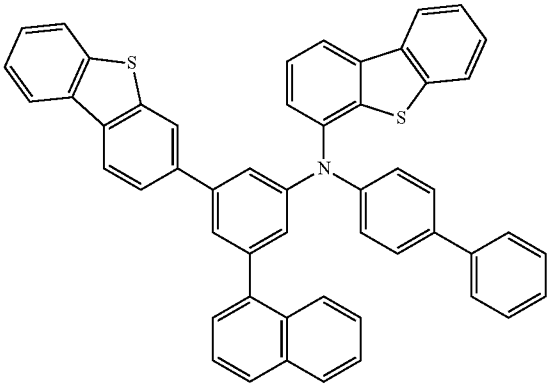
A131
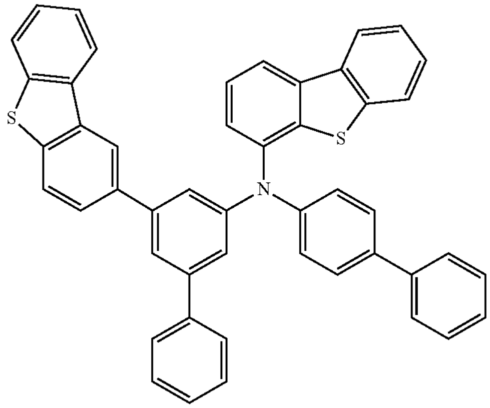
-continued
A132
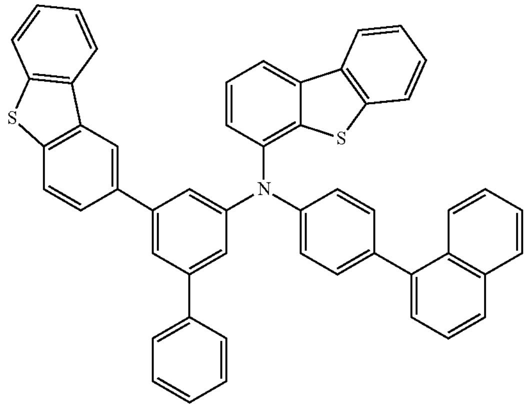
A133
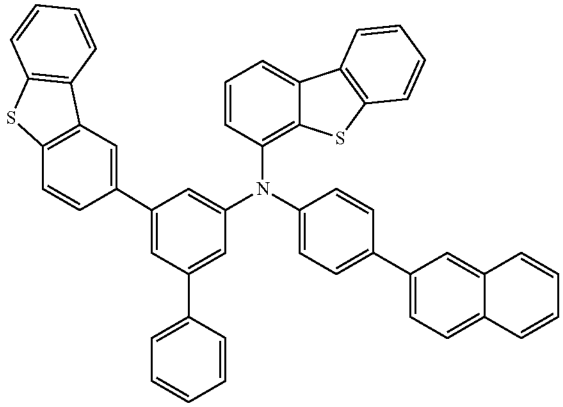
A134
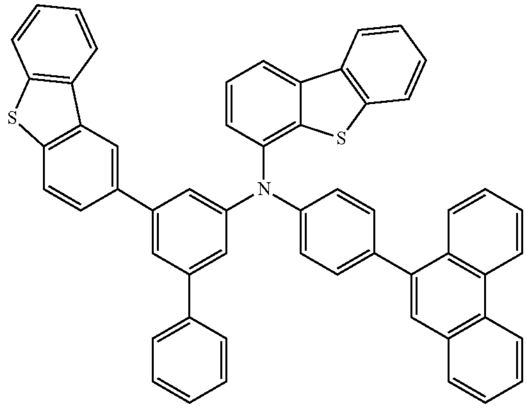

-continued
A135
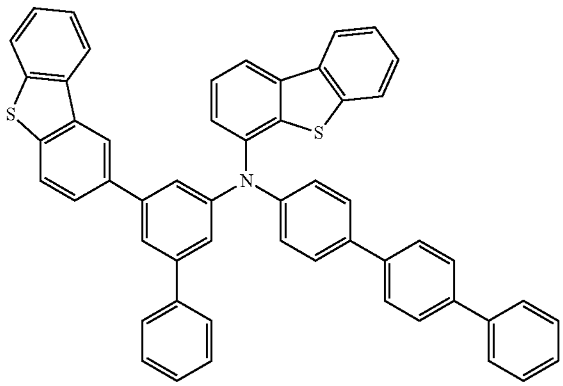
A136
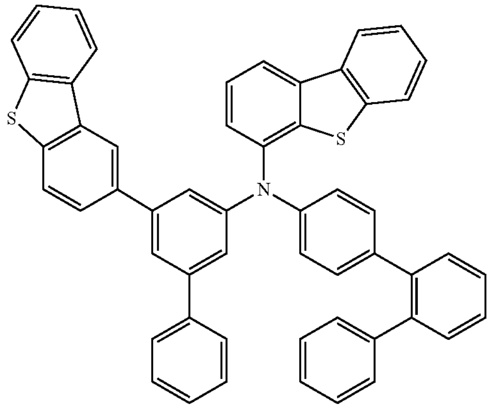
A137
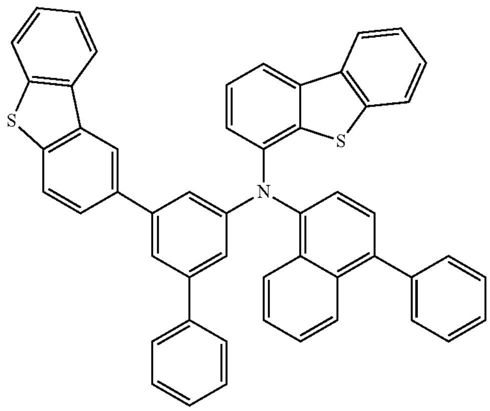
A138
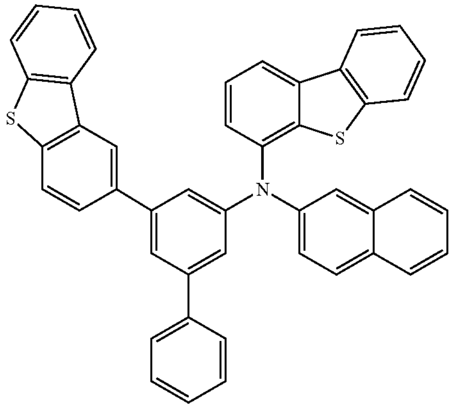
-continued
A139
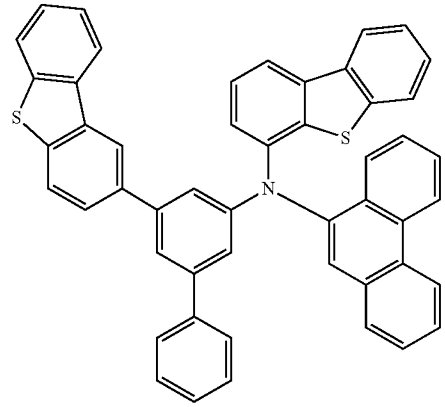
A140
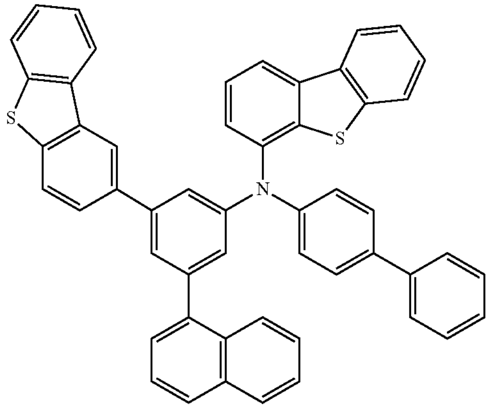
A141
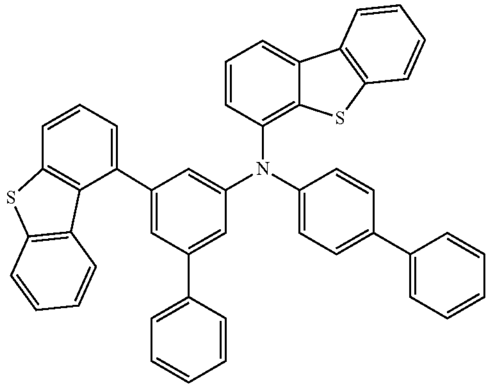
A142
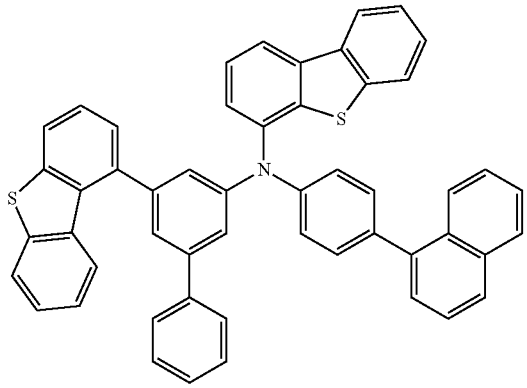

A143
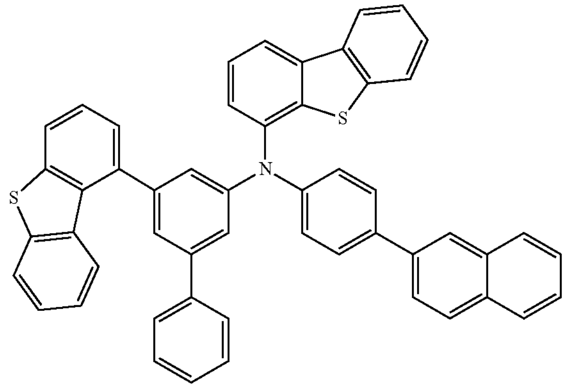
A144
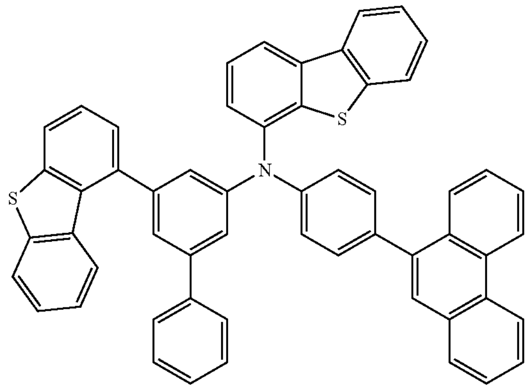
A145
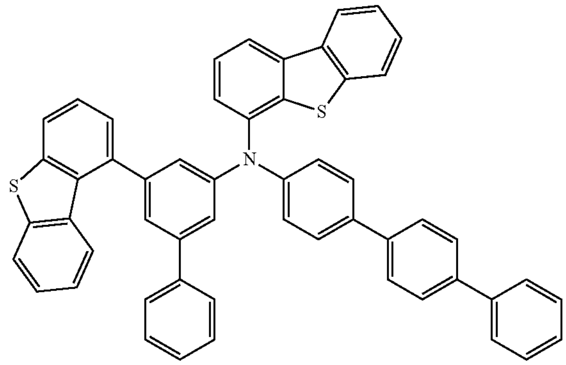
A146
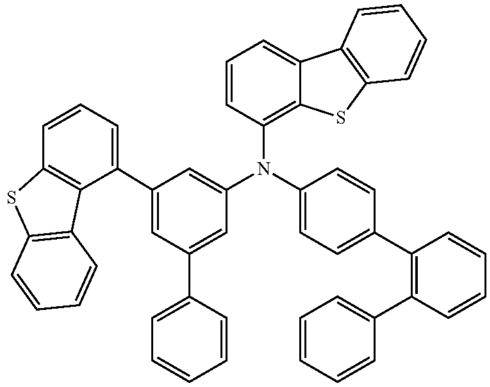
A147
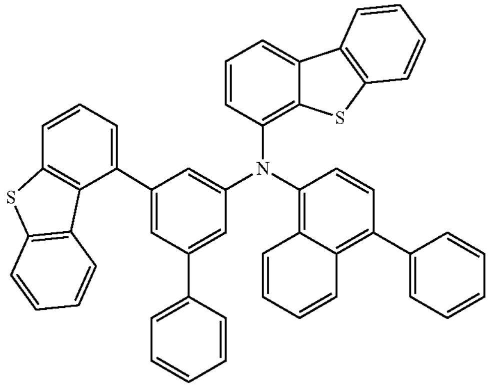
A148
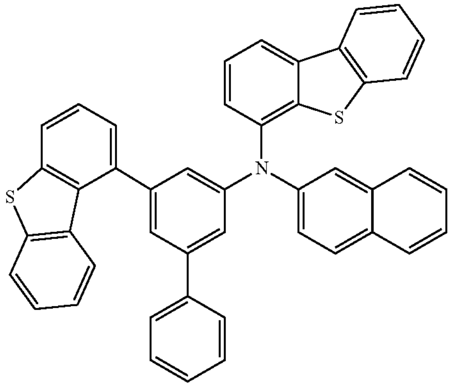
A149
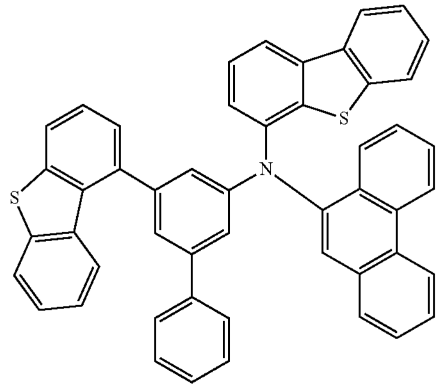
A150
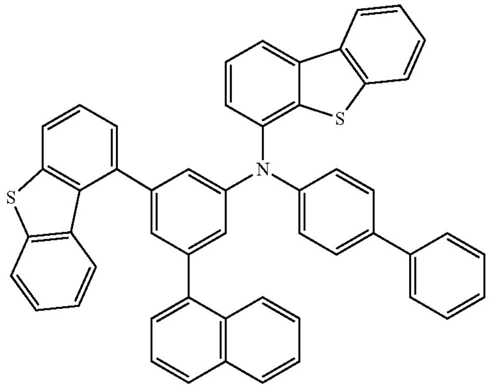

-continued
A151
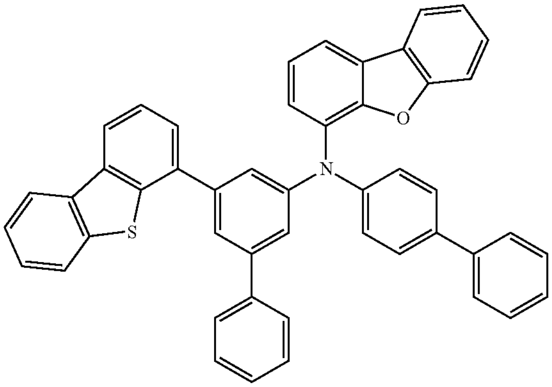
A152
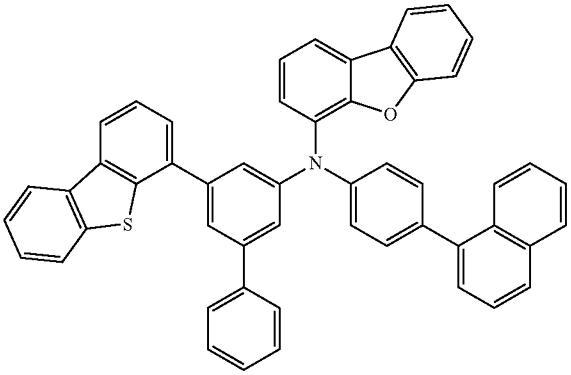
A153
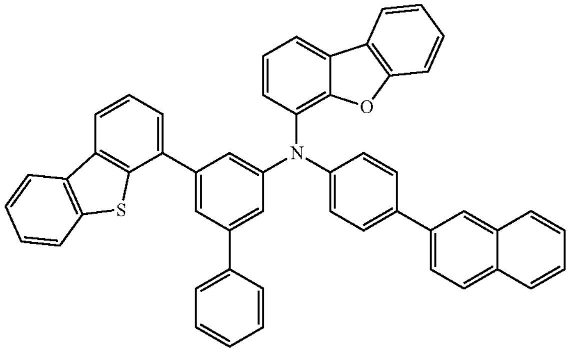
A154
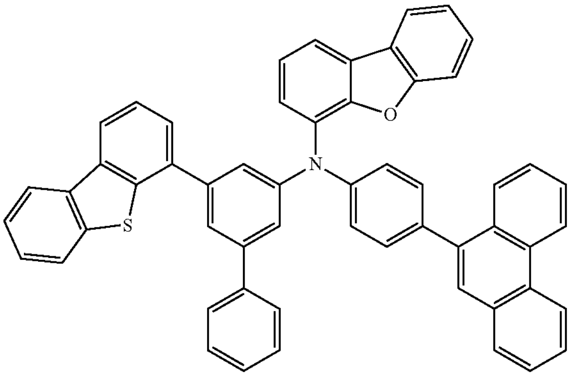
-continued
A155
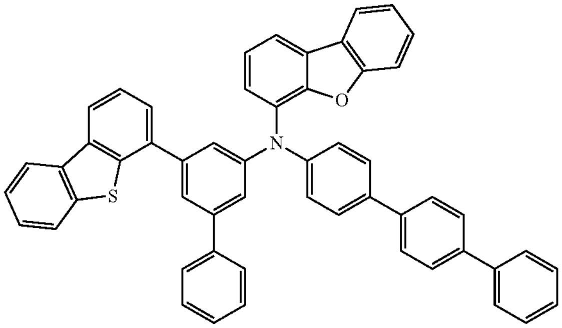
A156
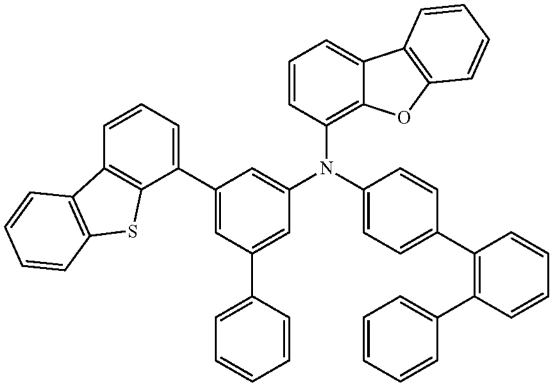
A157
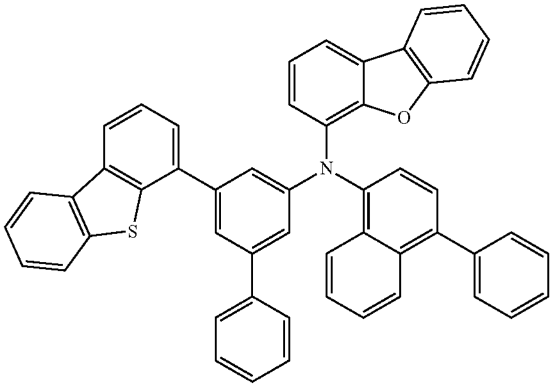
A158
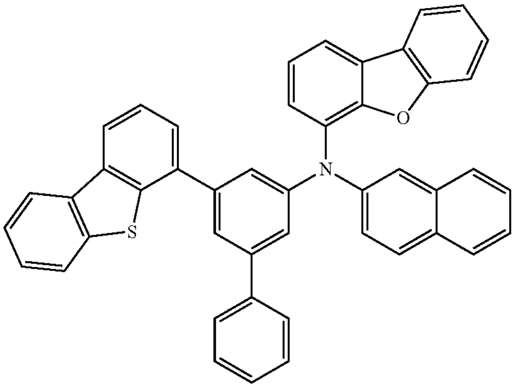

-continued
A159
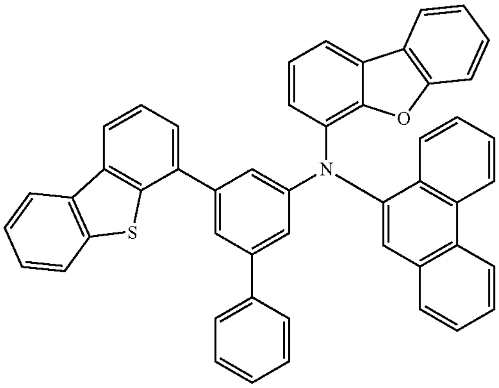
A160
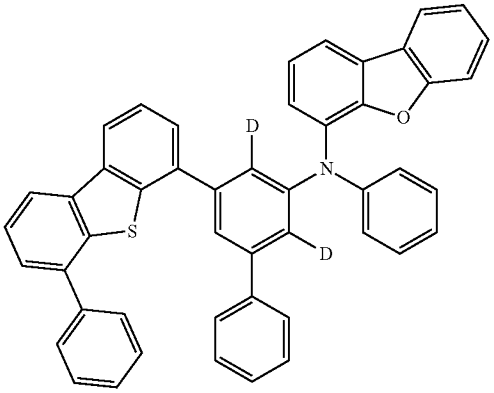
A161
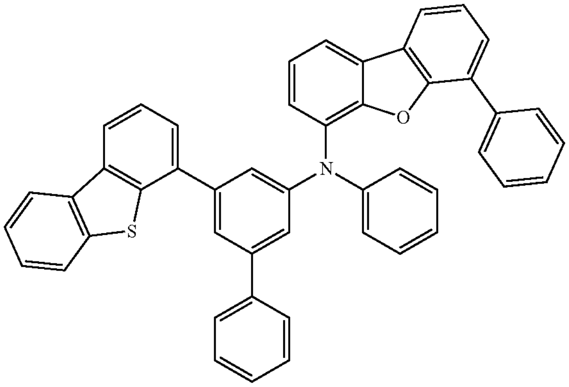
A162
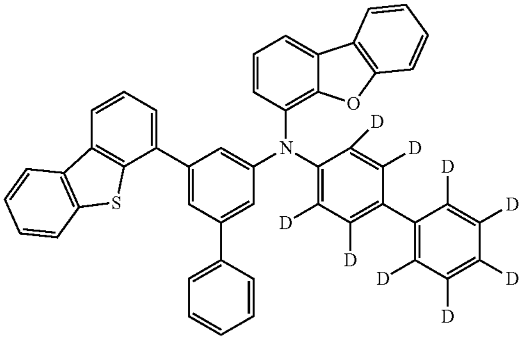
-continued
A163
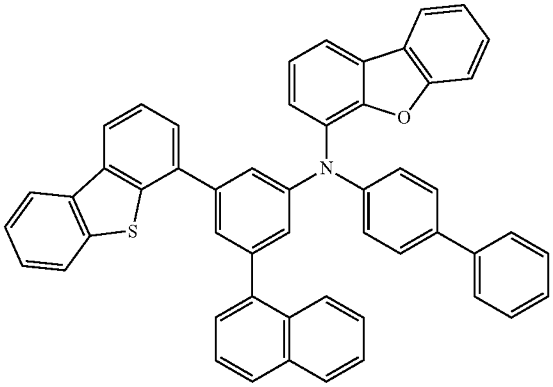
A164
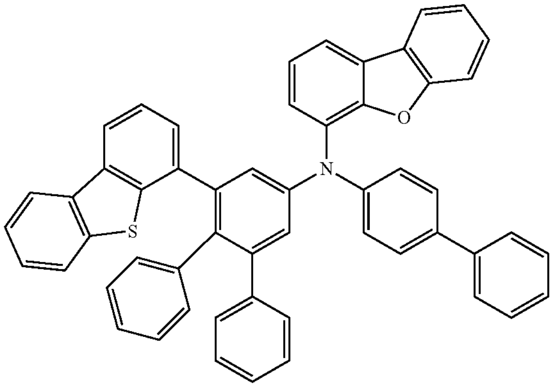
A165
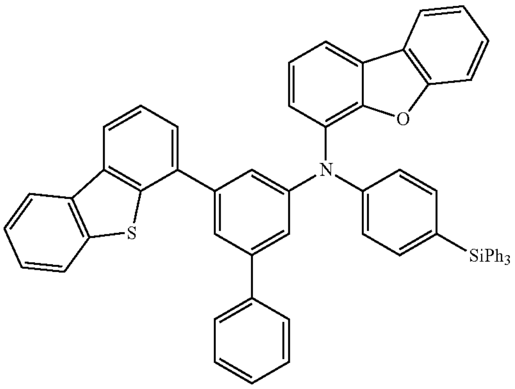

-continued
A166
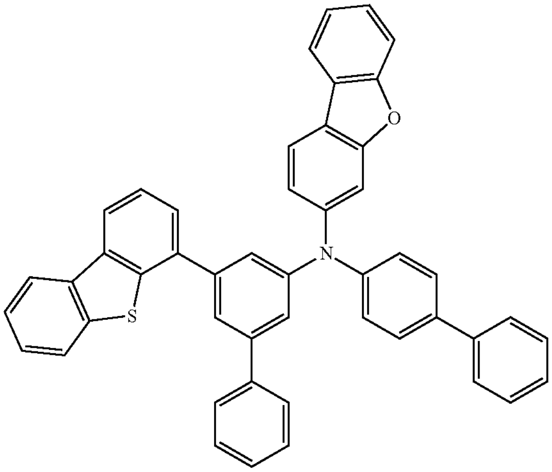
A167
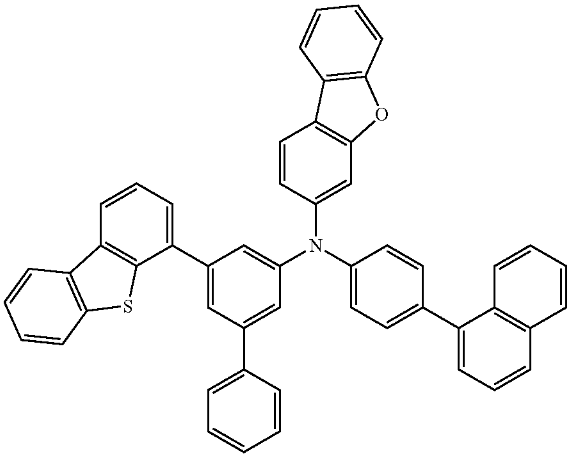
A168
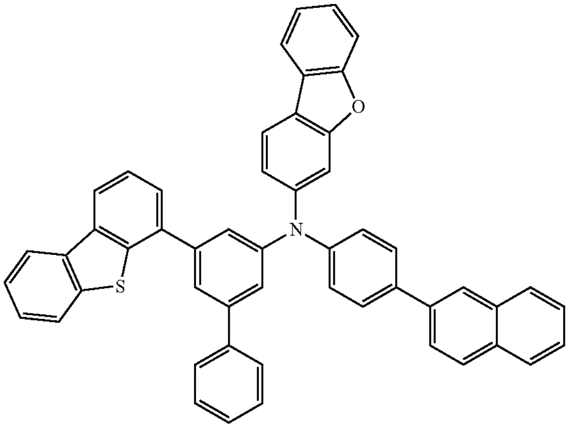
-continued
A169
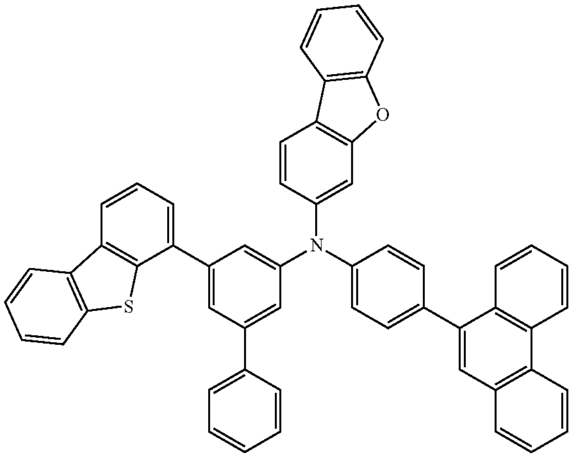
A170
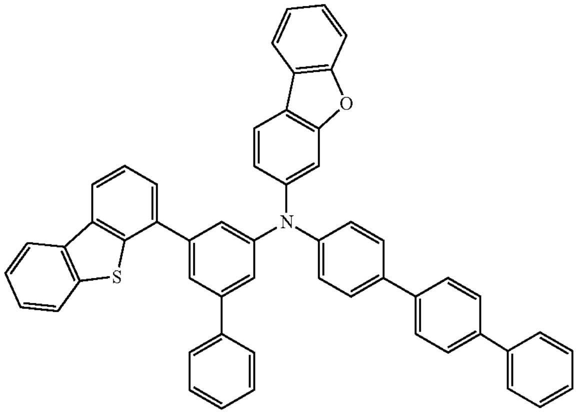
A171
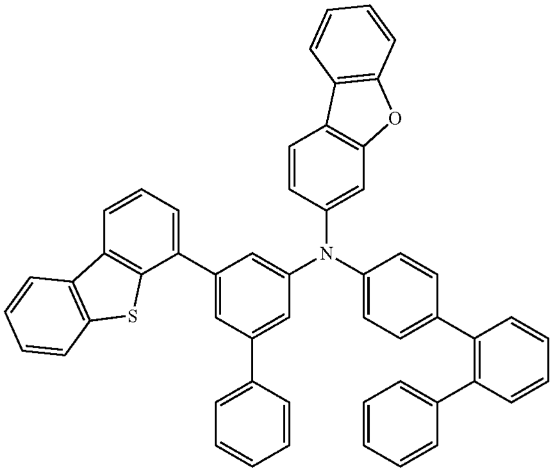

-continued
A172
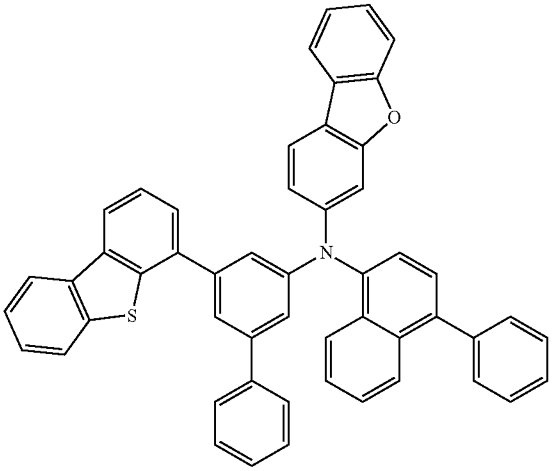
A173
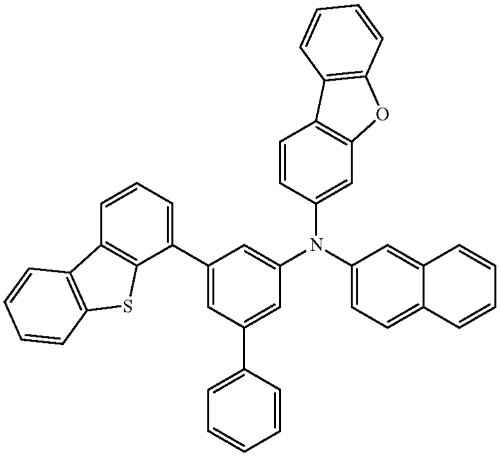
A174
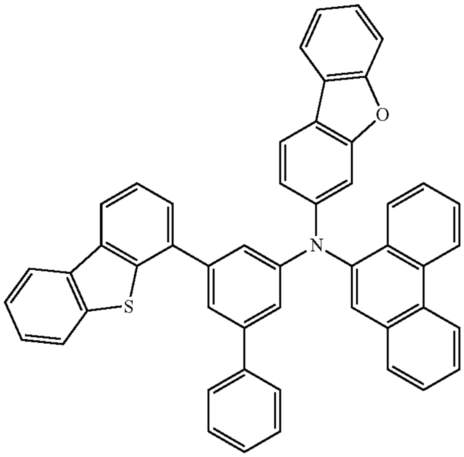
-continued
A175
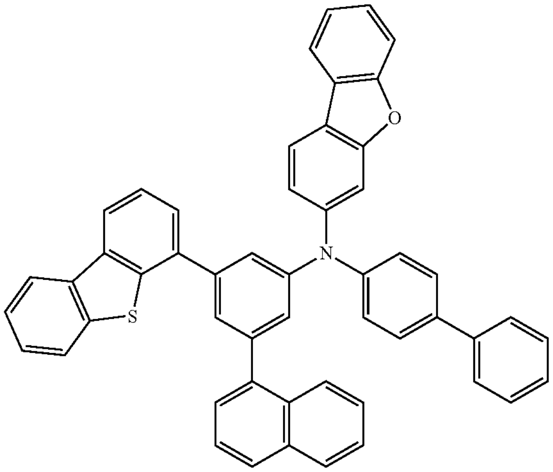
A176
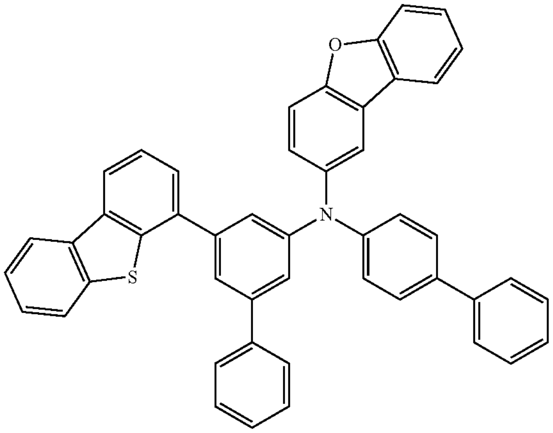
A177
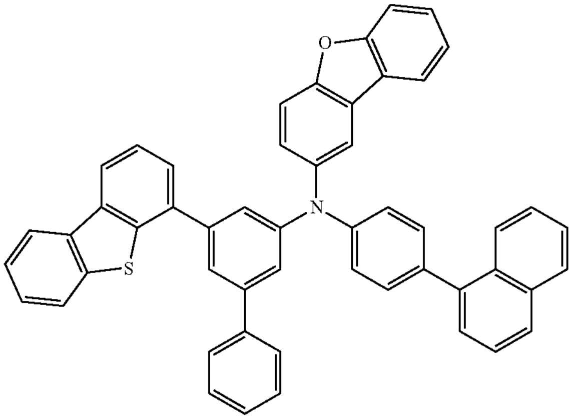

-continued
A178
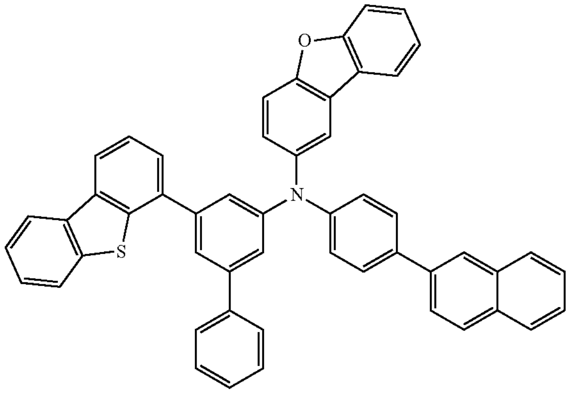
A179
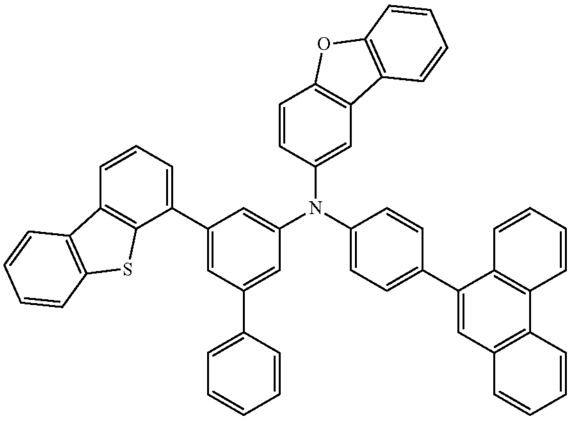
A180
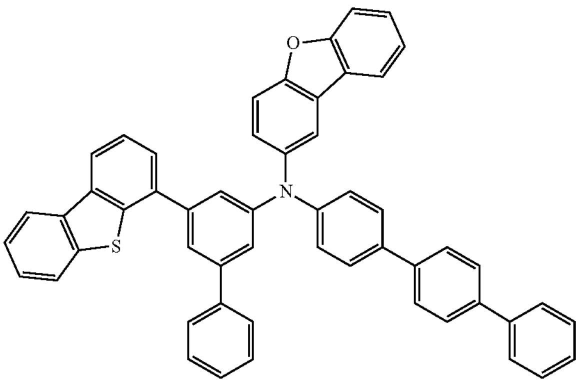
-continued
A181
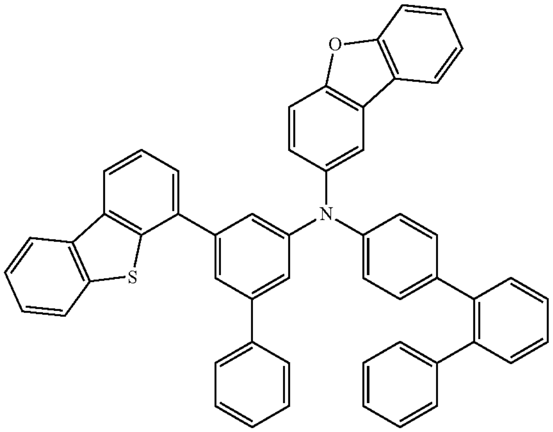
A182
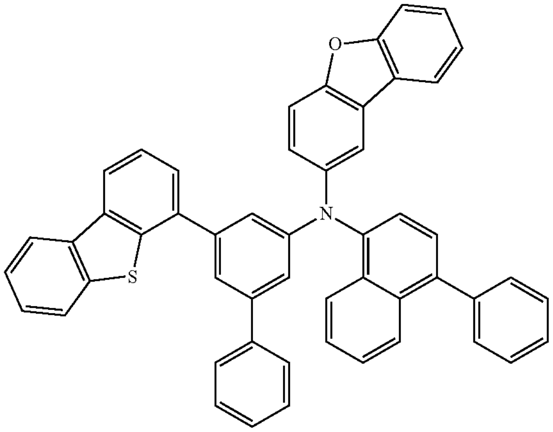
A183
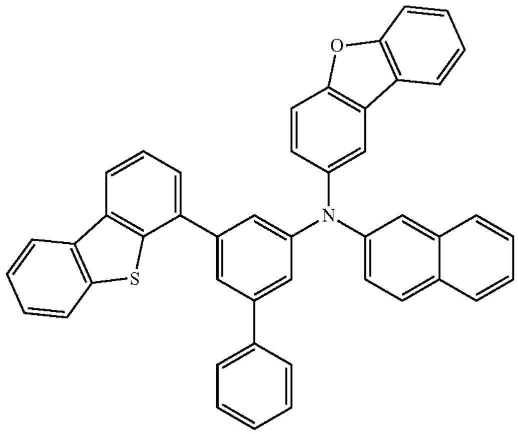

-continued
A184
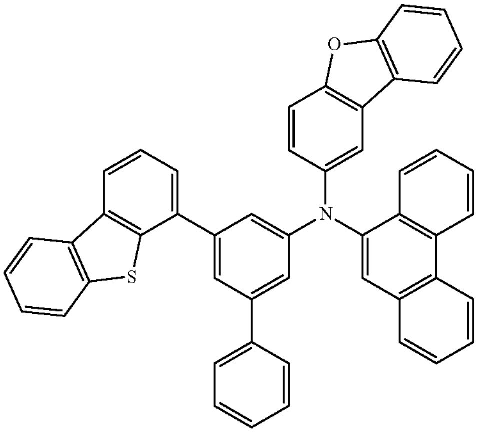
A185
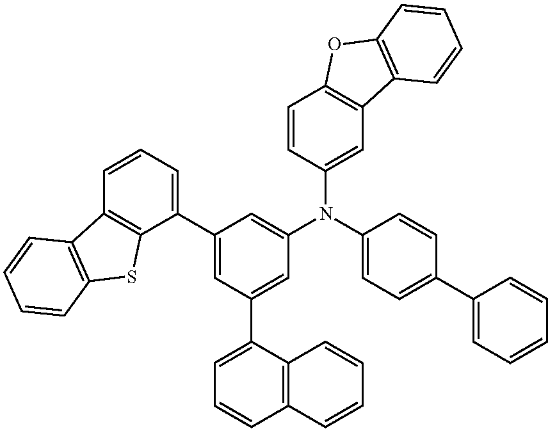
A186
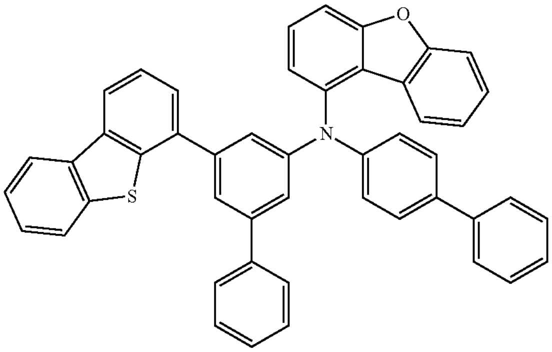
A187
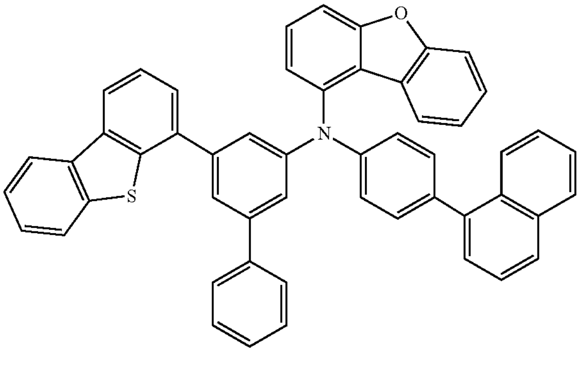
-continued
A188
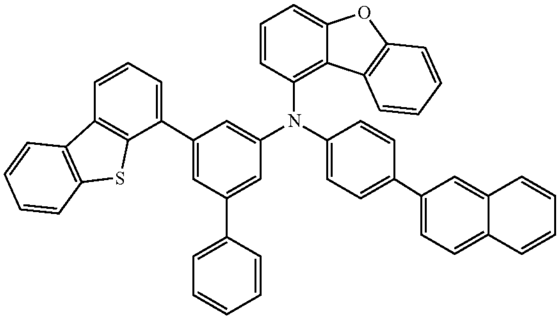
A189
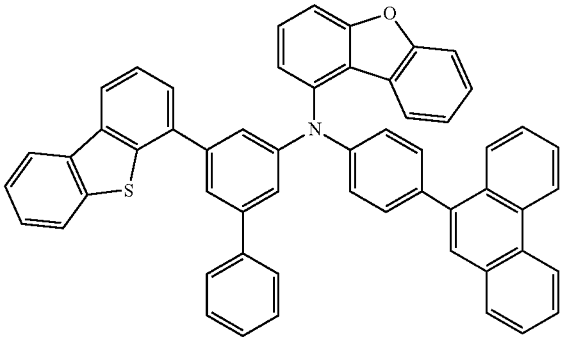
A190
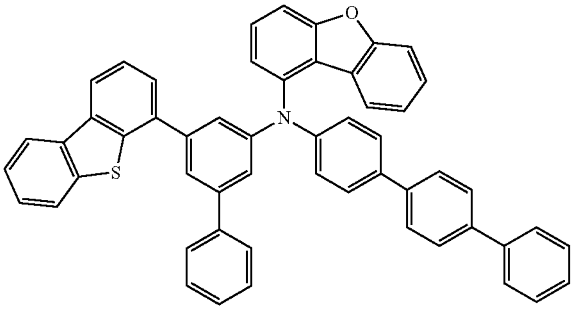
A191
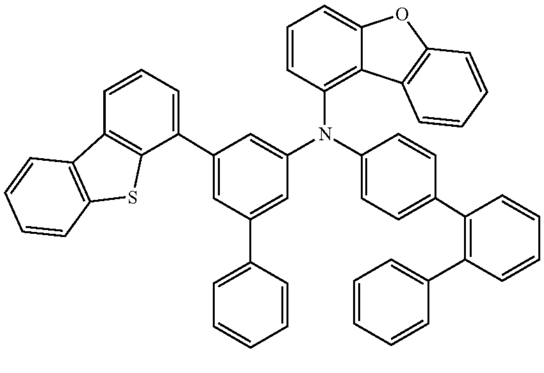

-continued
A192
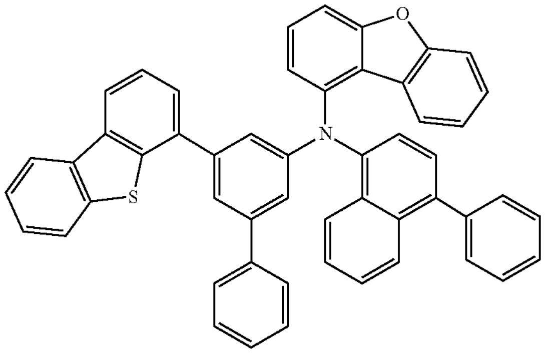
A193
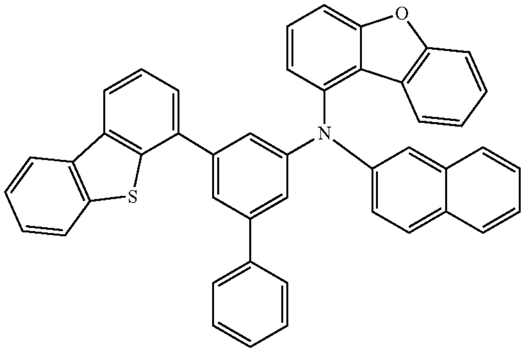
A194
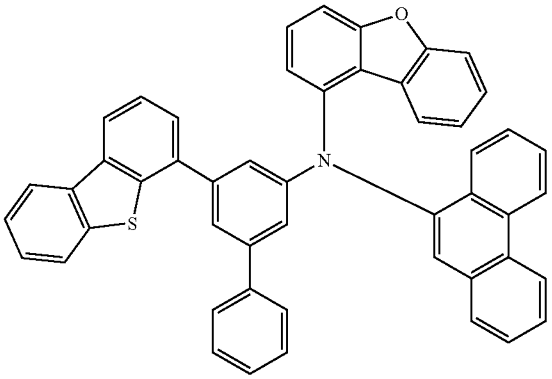
A195
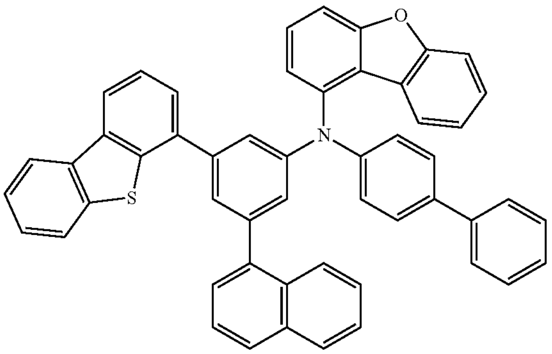
-continued
A196
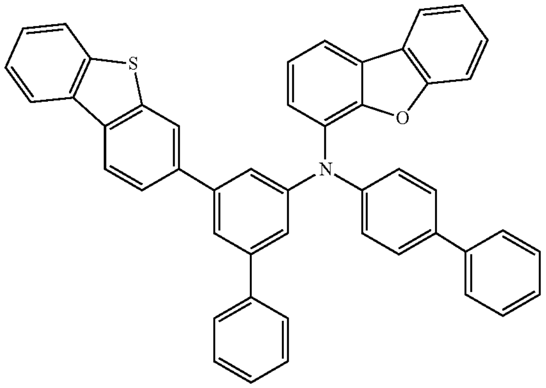
A197
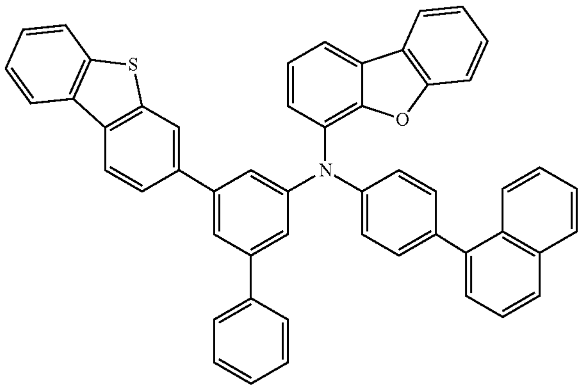
A198
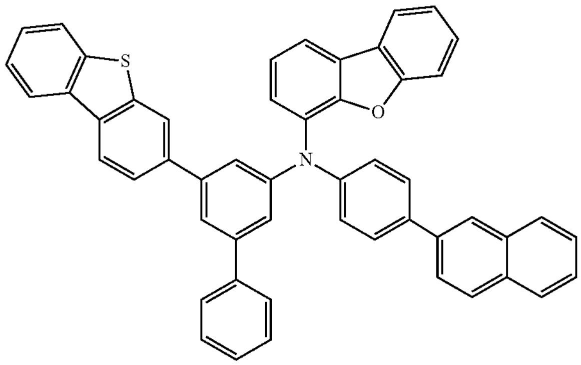
A199
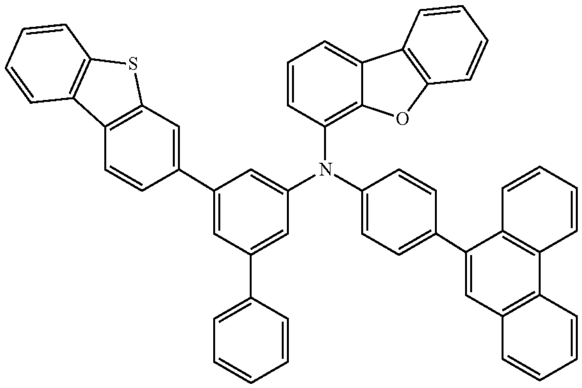

-continued
A200
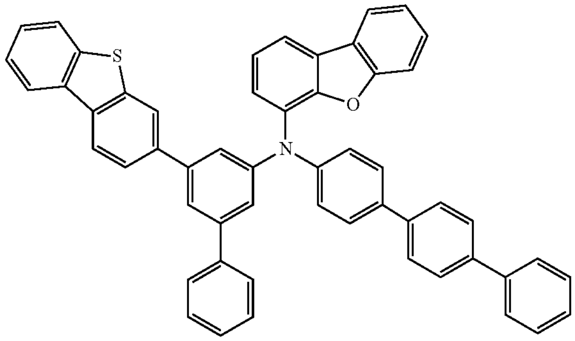
A201
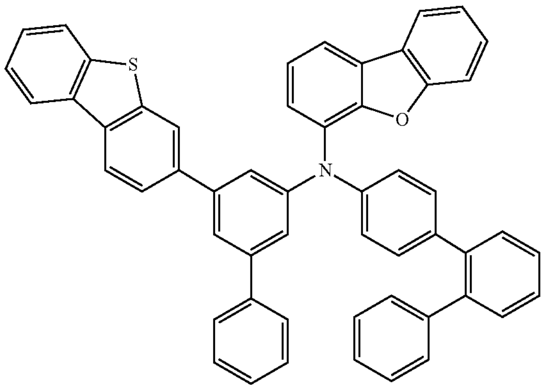
A202
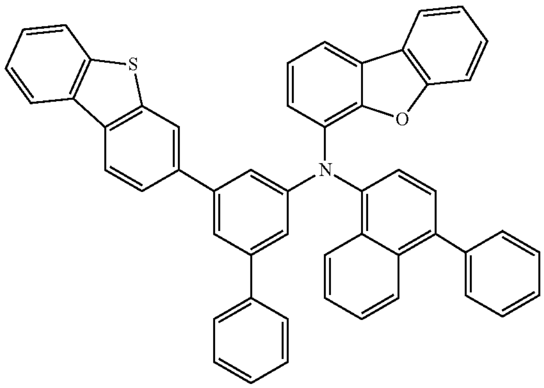
A203
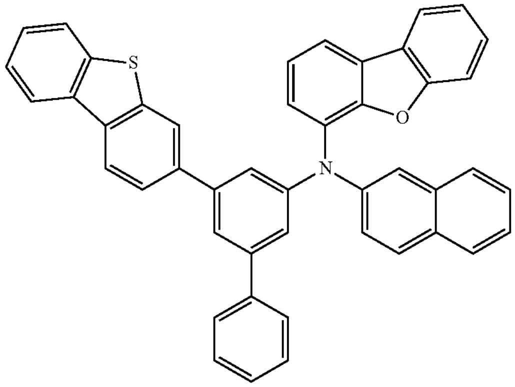
-continued
A204
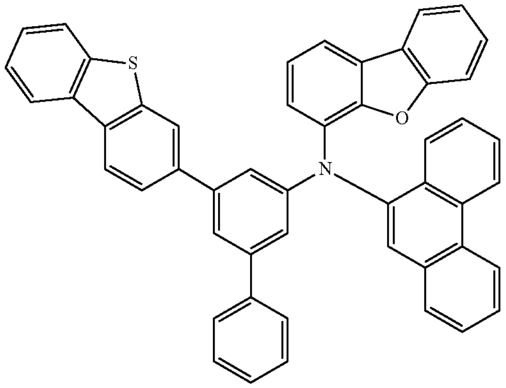
A205
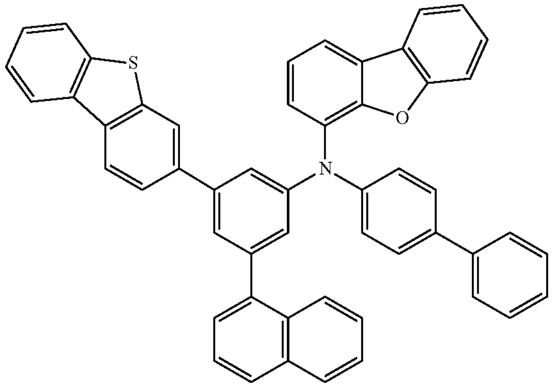
A206
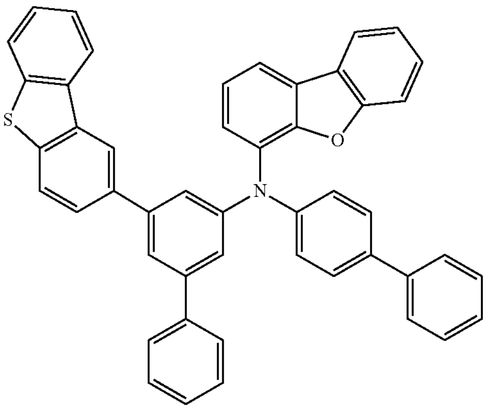

-continued
A207
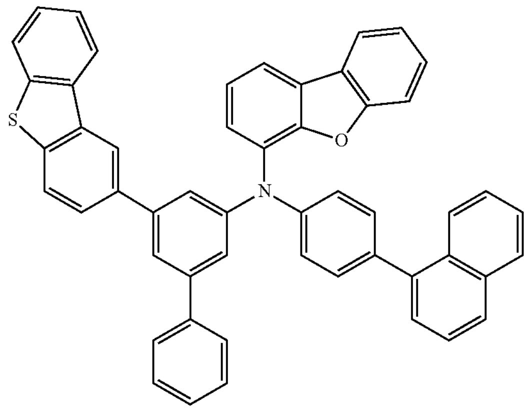
A208
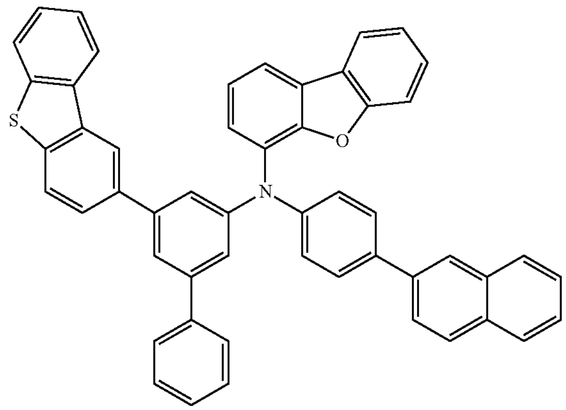
A209
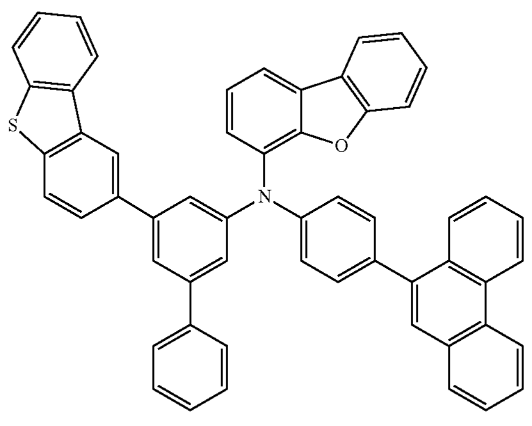
-continued
A210
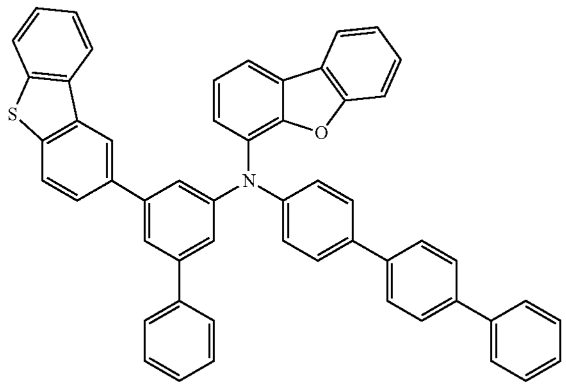
A211
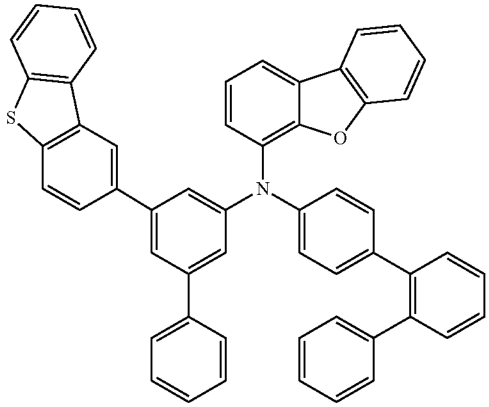
A212
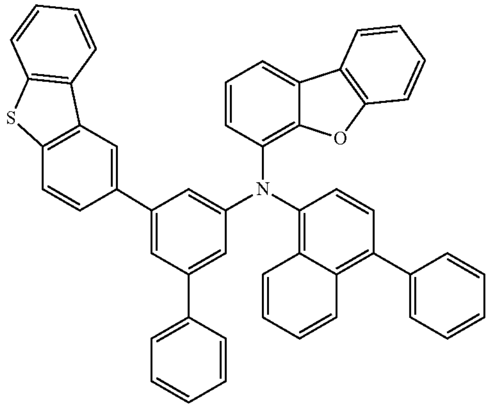
A213
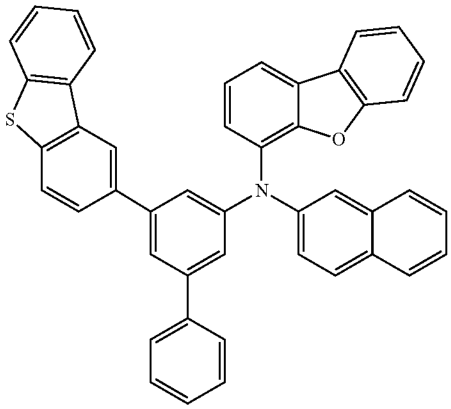

-continued
A214
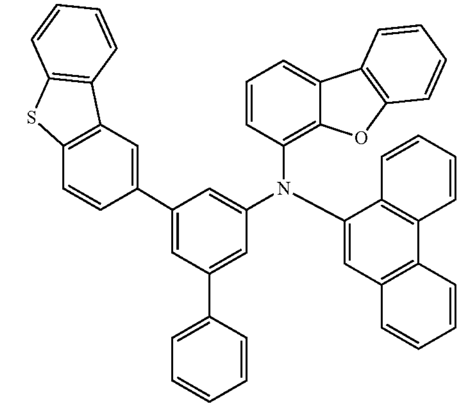
A215
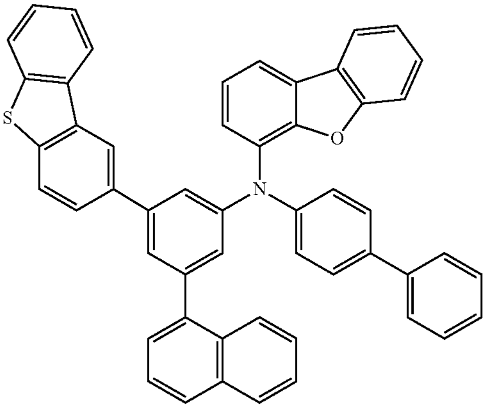
A216
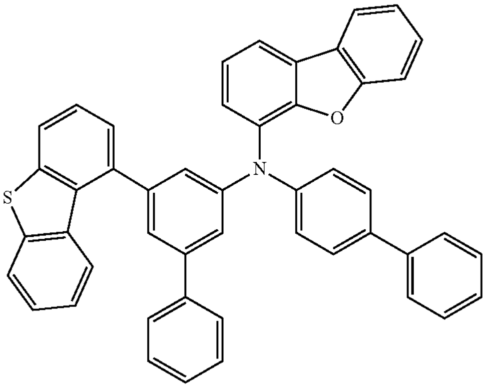
A217
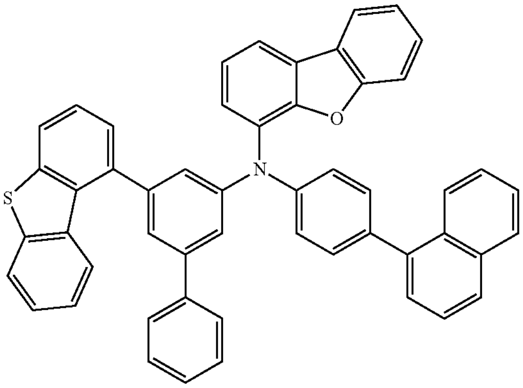
-continued
A218
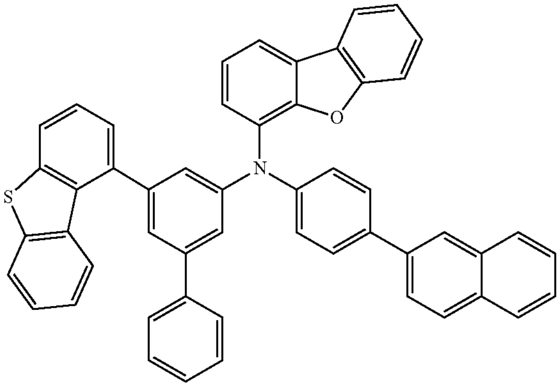
A219
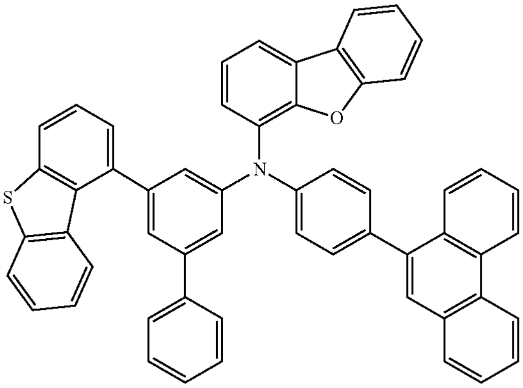
A220
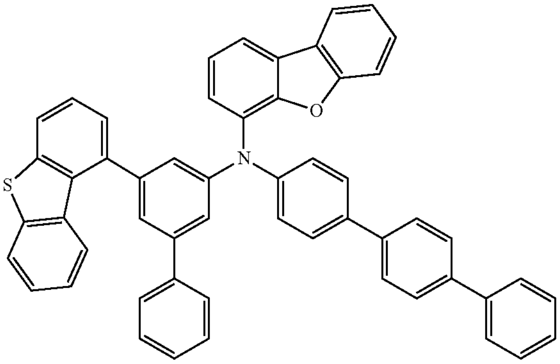
A221
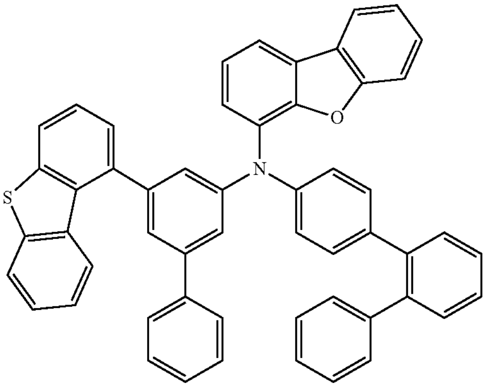

-continued
A222
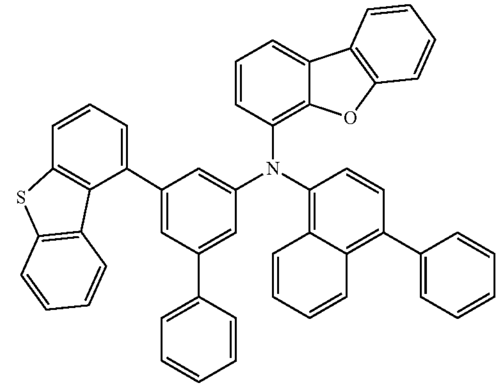
A223
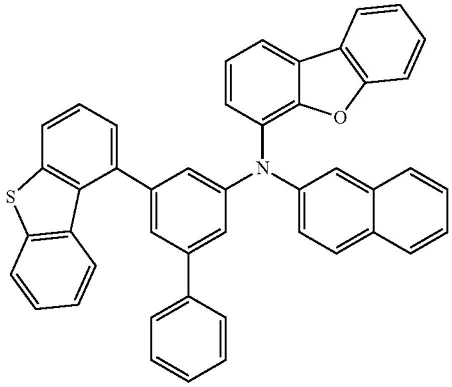
A224
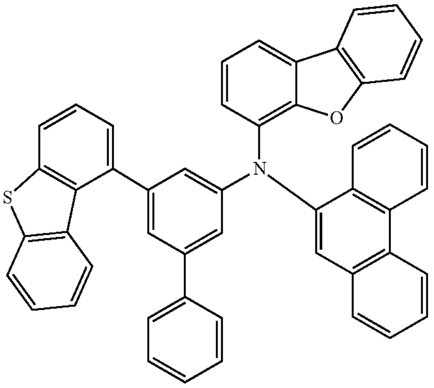
A225
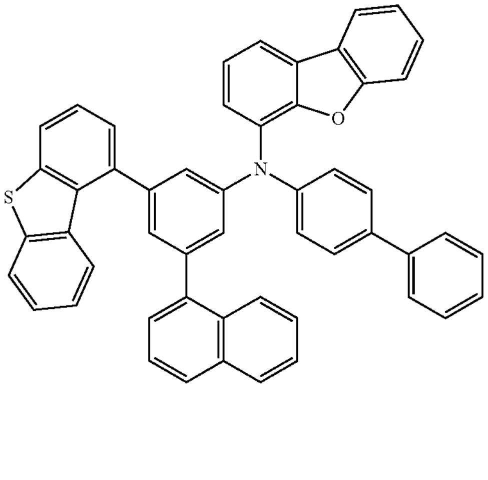
-continued
A226
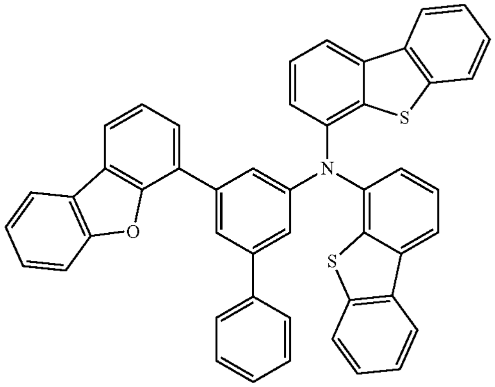
A227
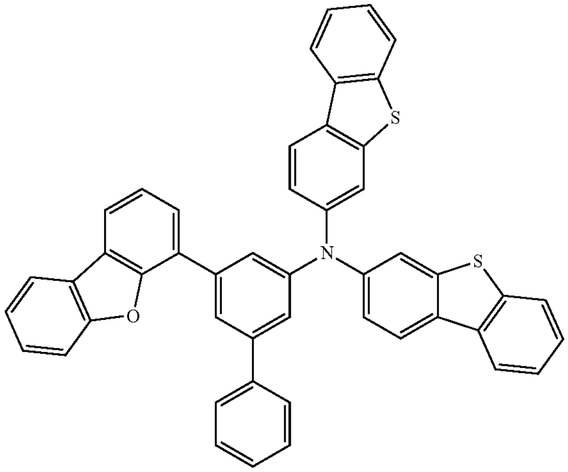
A228
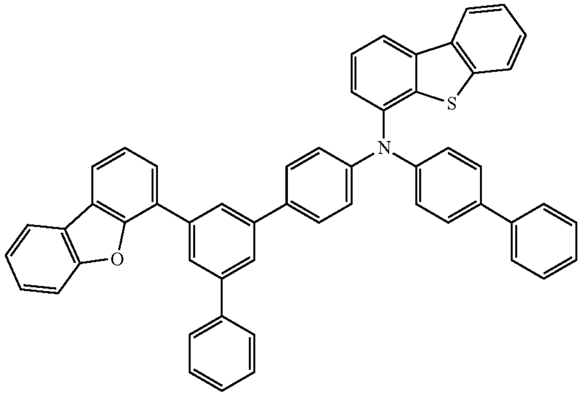

-continued
A229
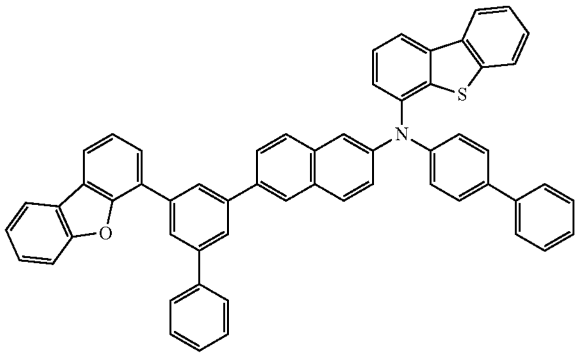
A230
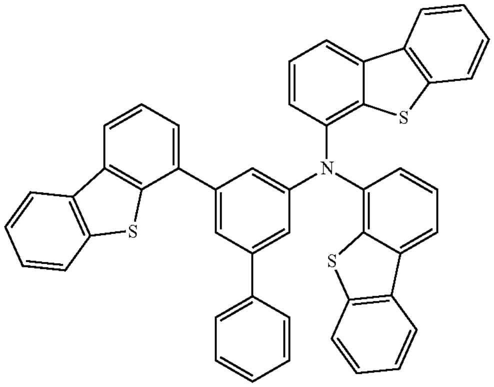
A231
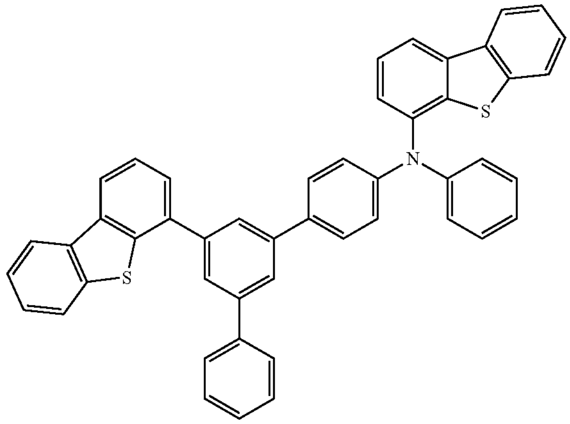
A232
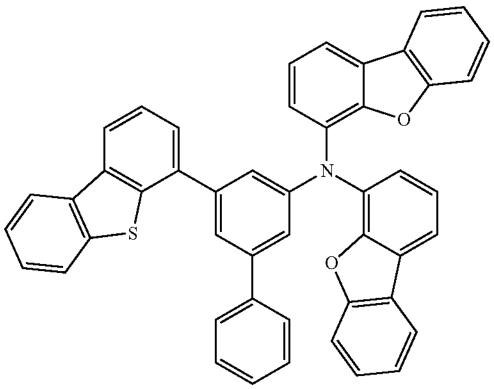
-continued
A233
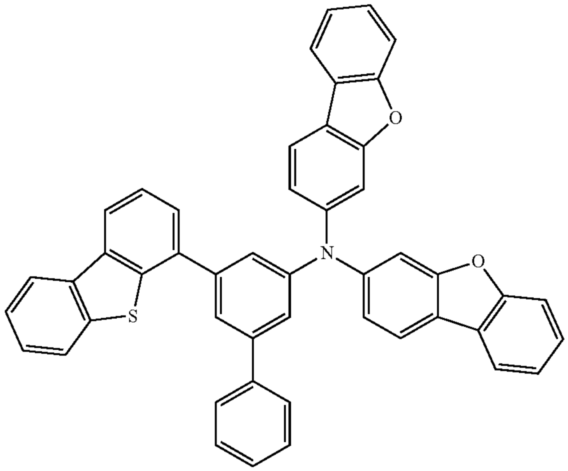
A234
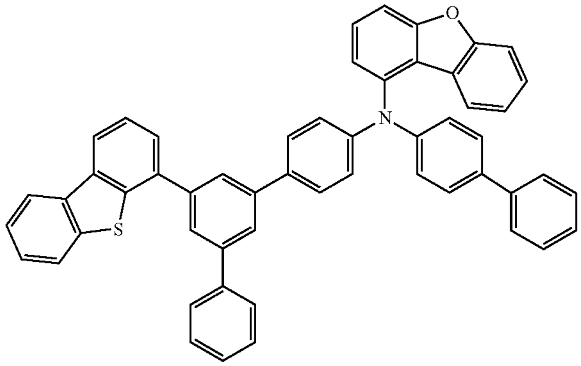
A235
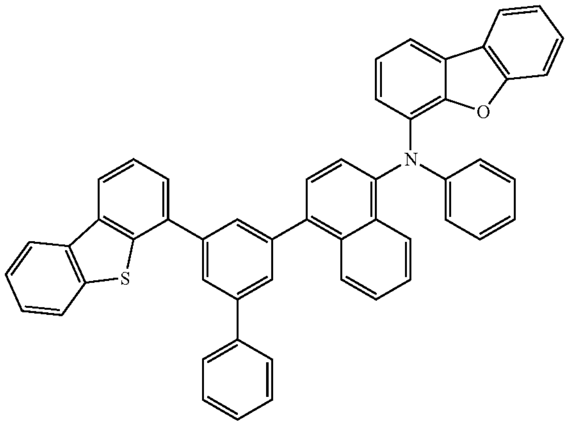

-continued
A236
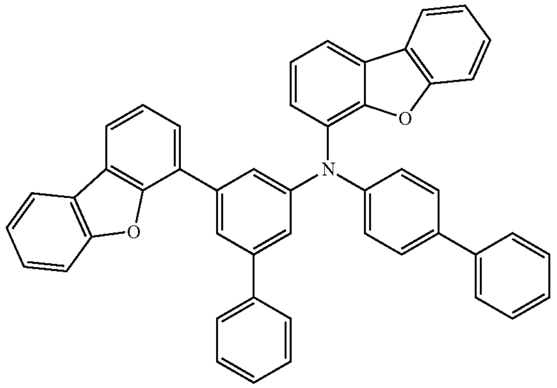
A237
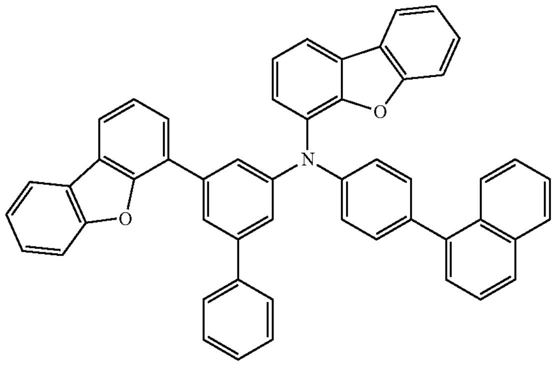
A238
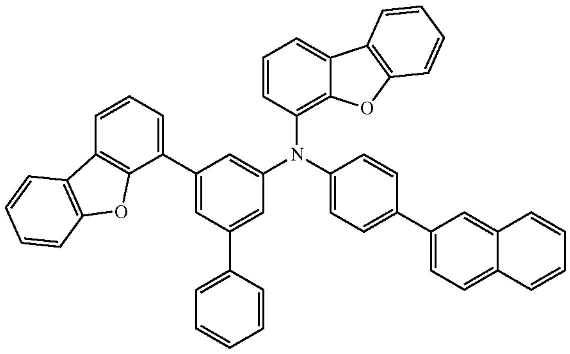
A239
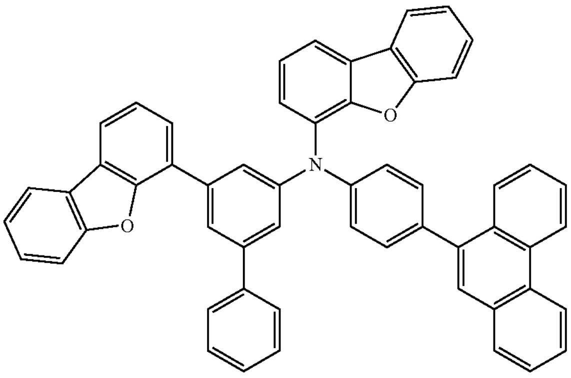
-continued
A240
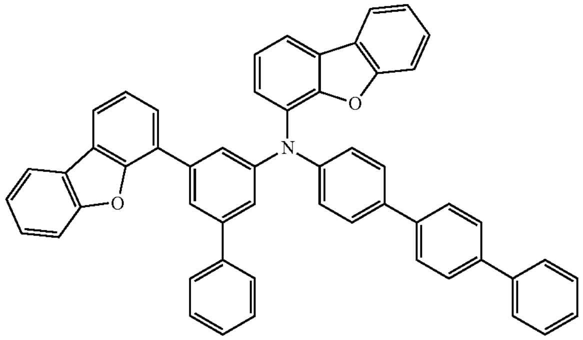
A241
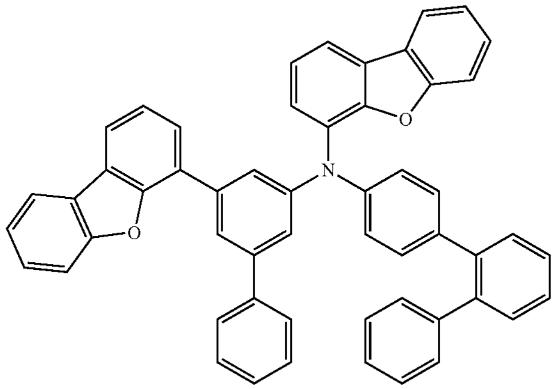
A242
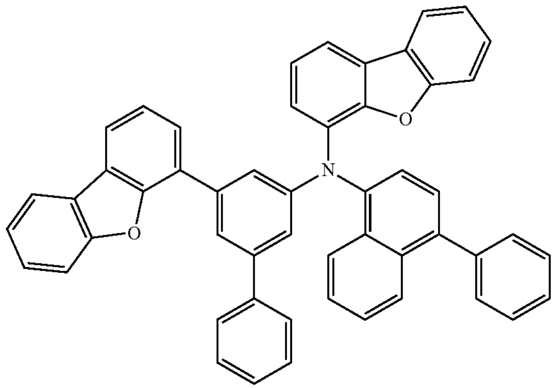
A243
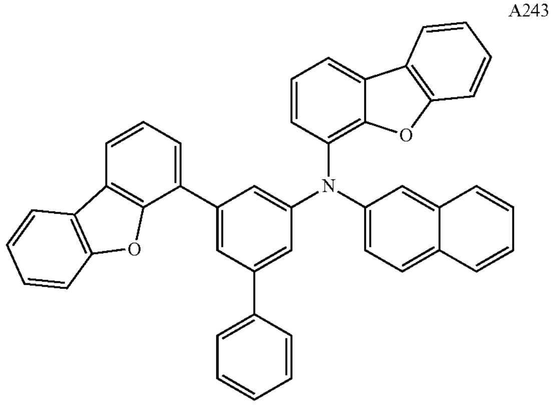

-continued
A244
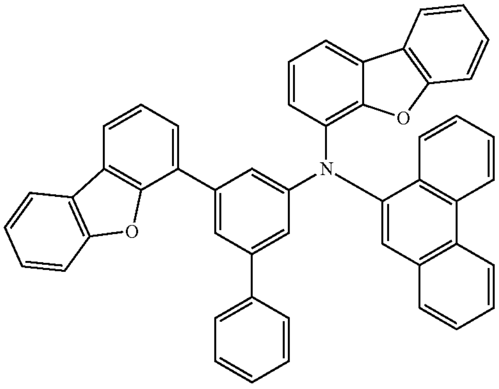
A245
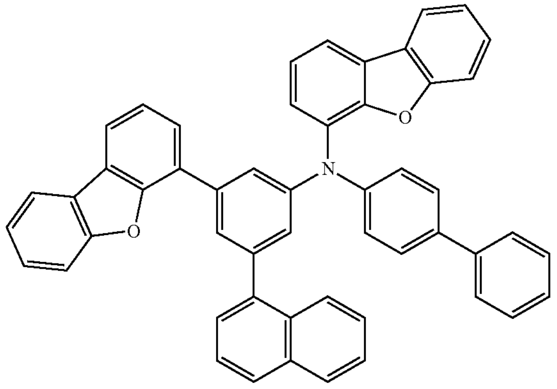
Compound Group 2
B1
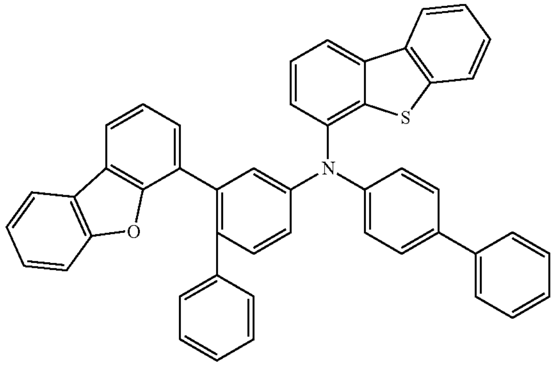
B2
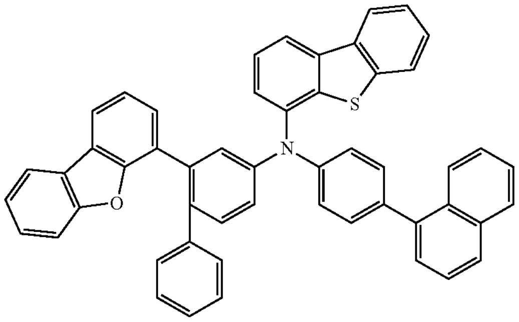
-continued
B3
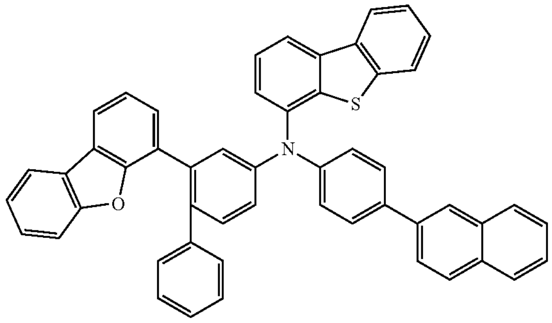
B4
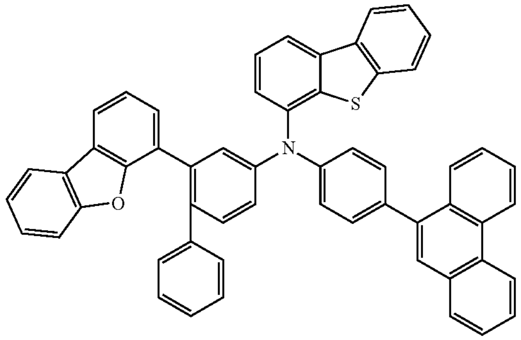
B5
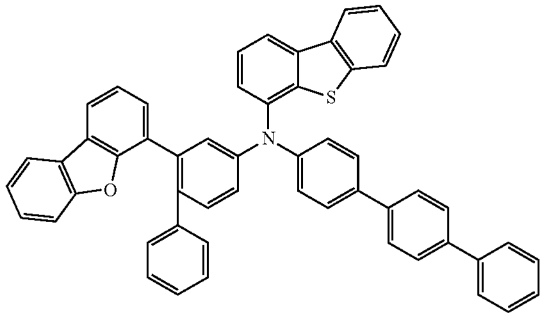
B6
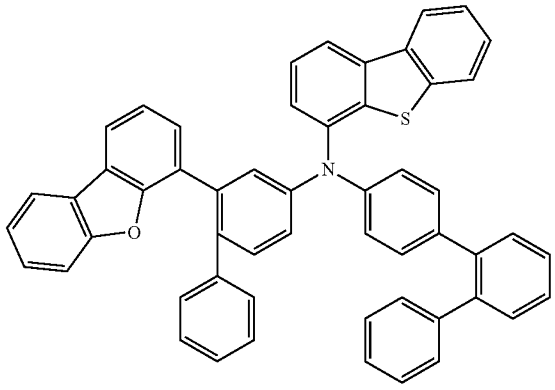

-continued
B7
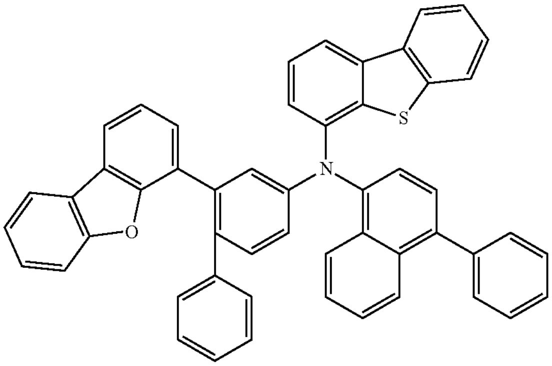
B8
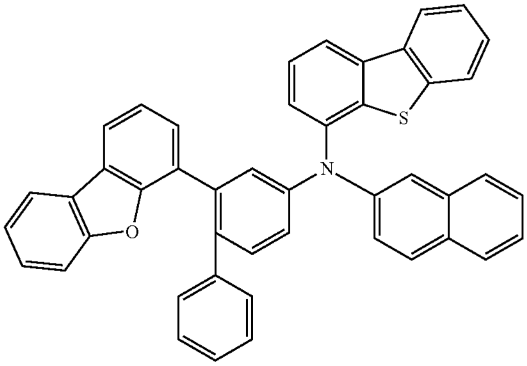
B9
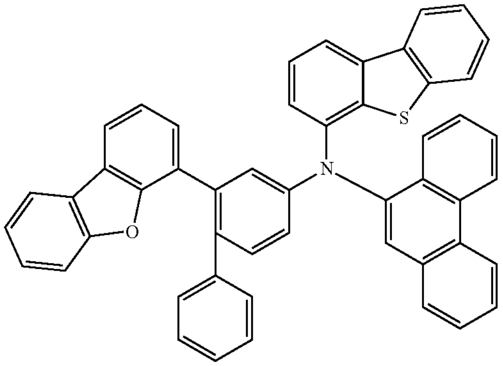
B10
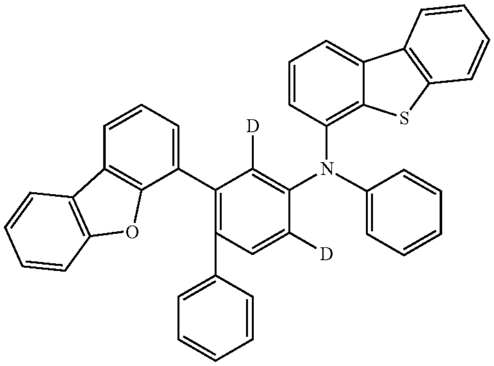
-continued
B11
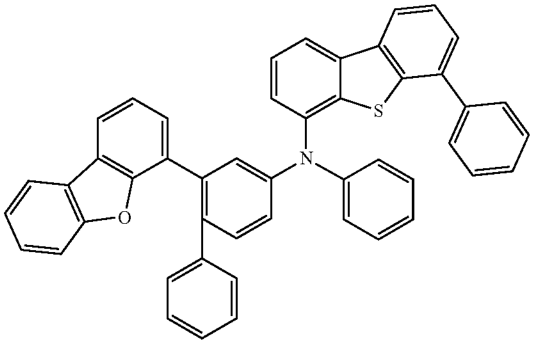
B12
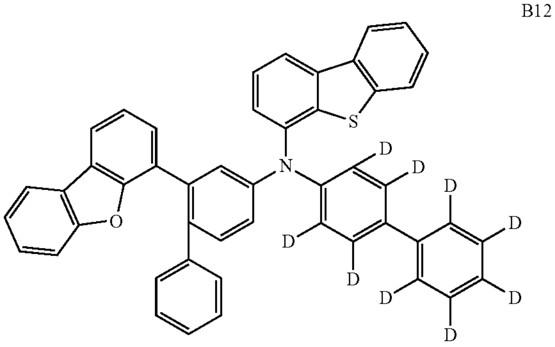
B13
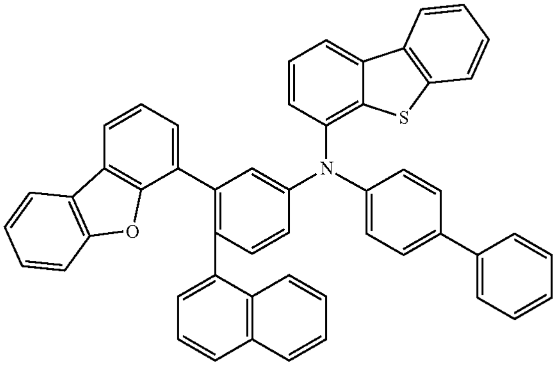
B14
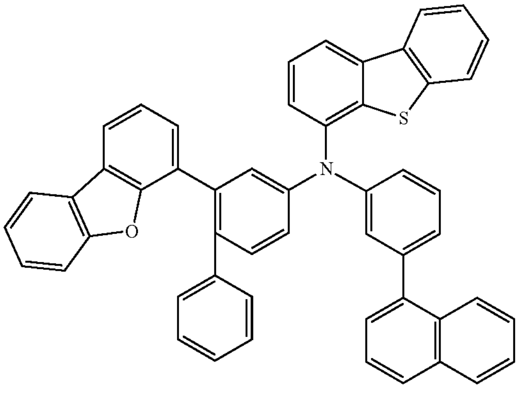

-continued
B15
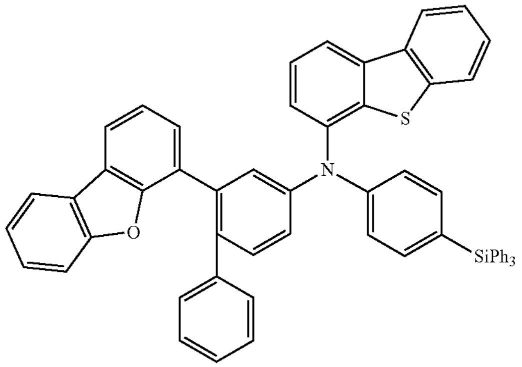
B16
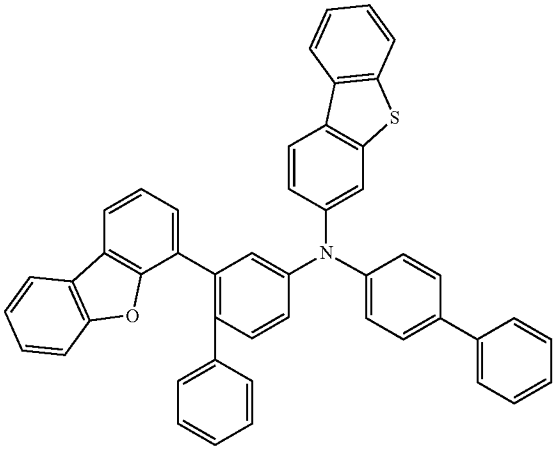
B17
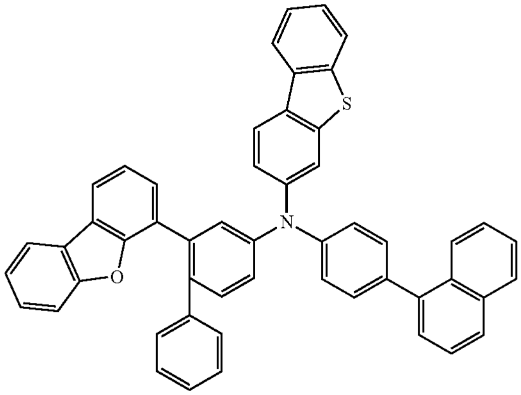
B18
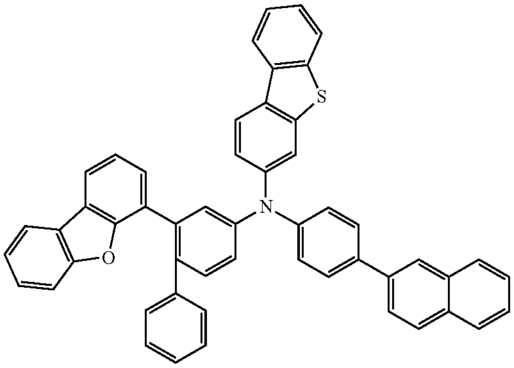
-continued
B19
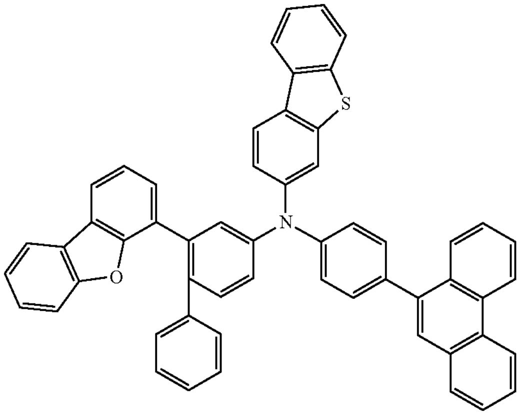
B20
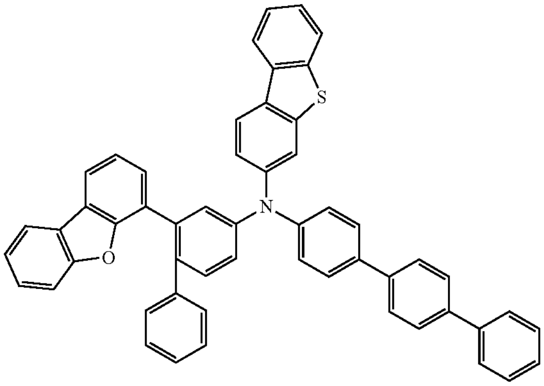
B21
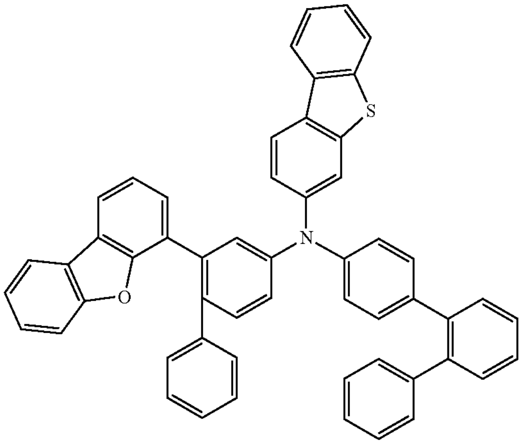

-continued
B22
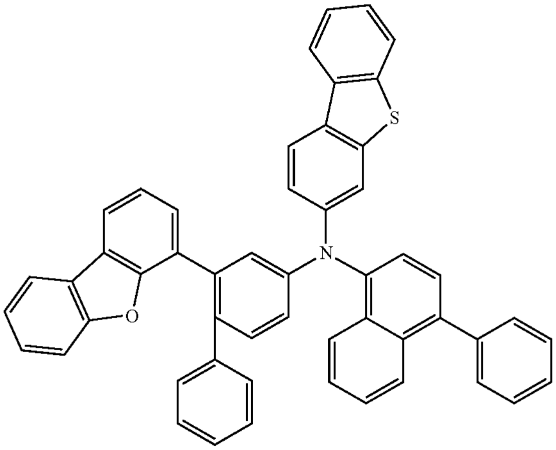
B23
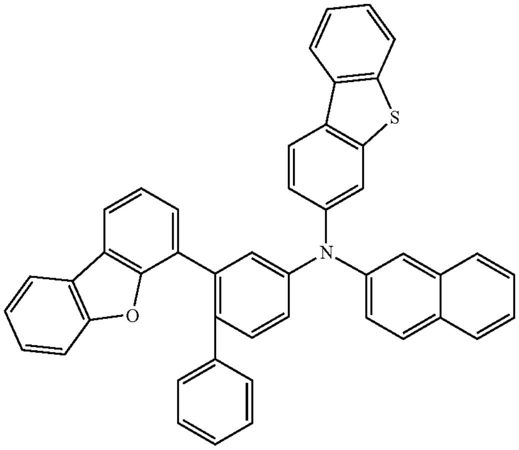
B24
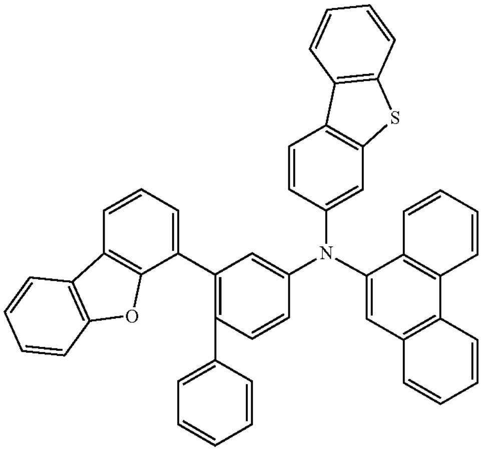
-continued
B25
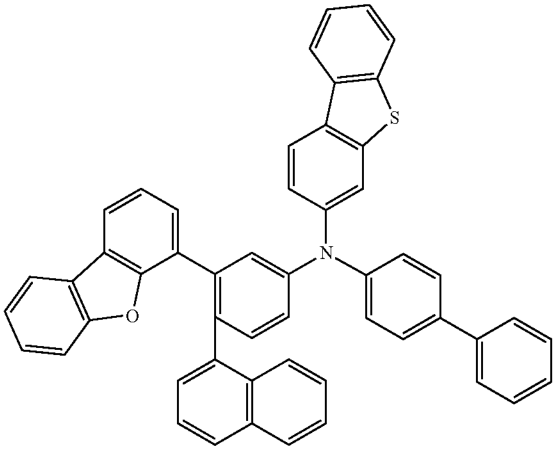
B26
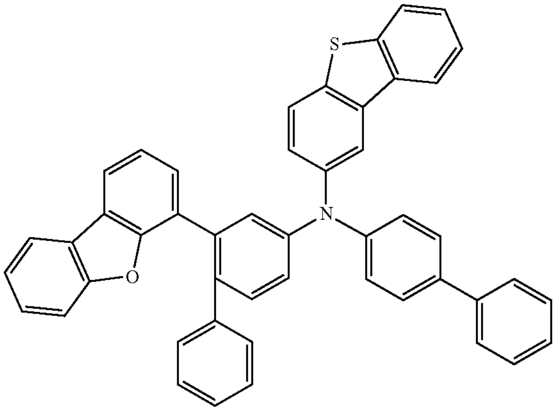
B27
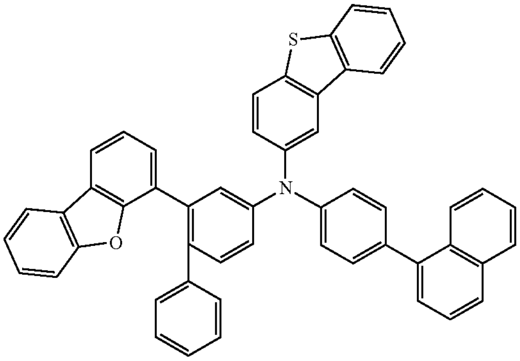
B28
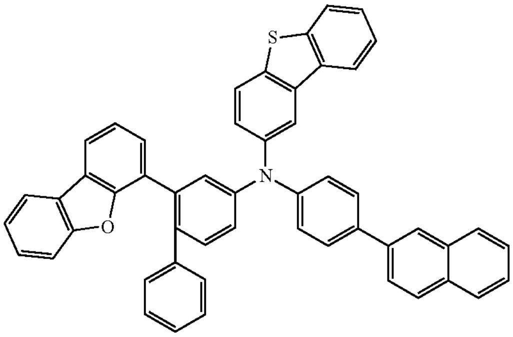

B29
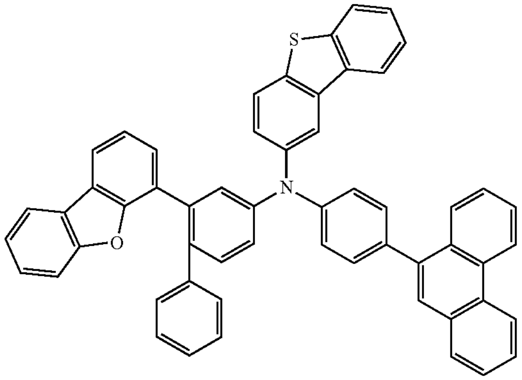
B30
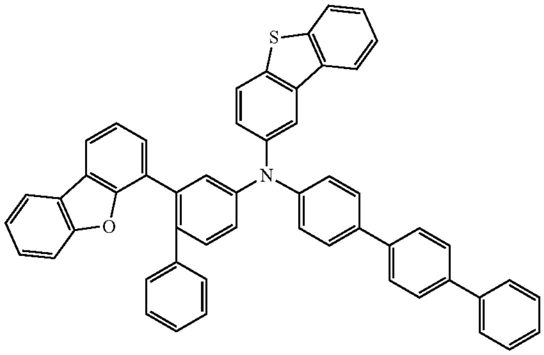
B31
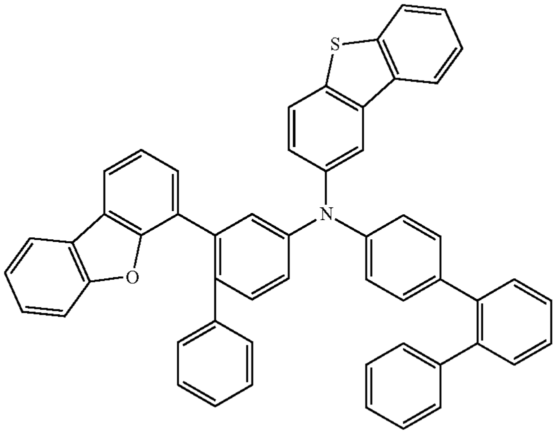
B32
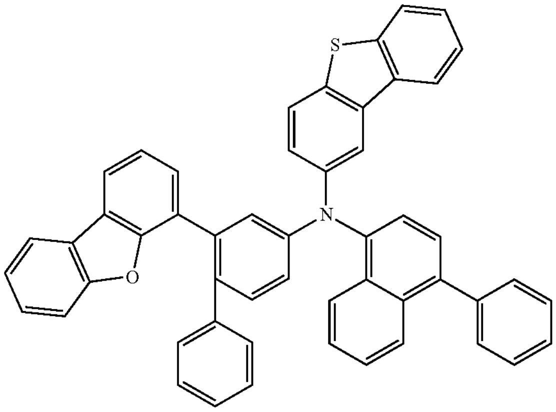
B33
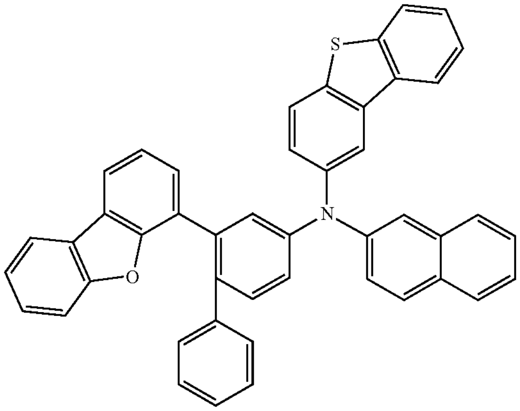
B34
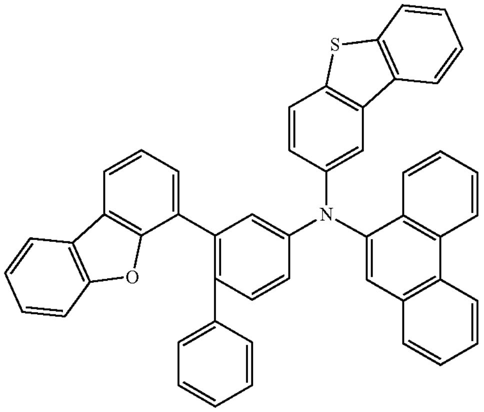
B35
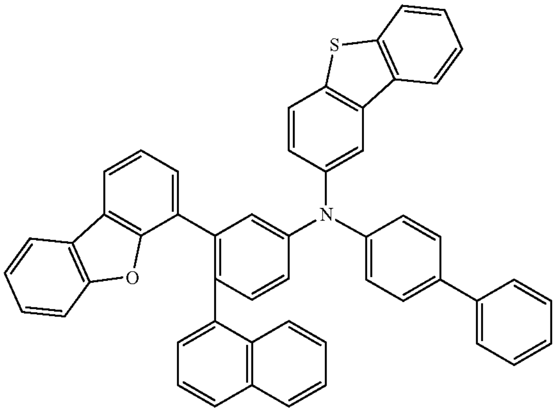
B36
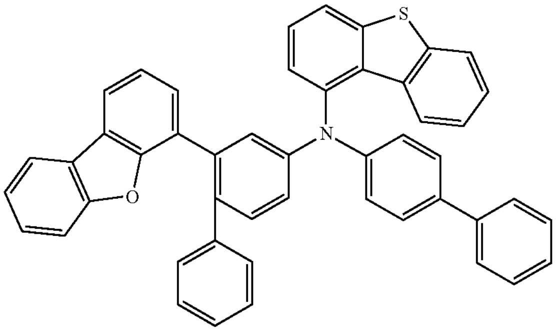

-continued
B37
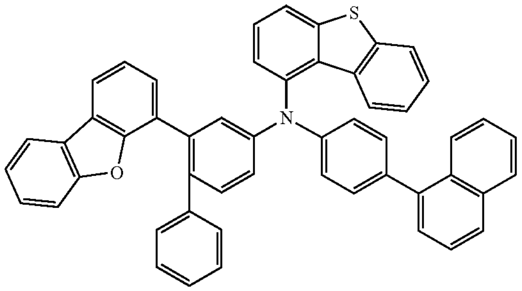
B38
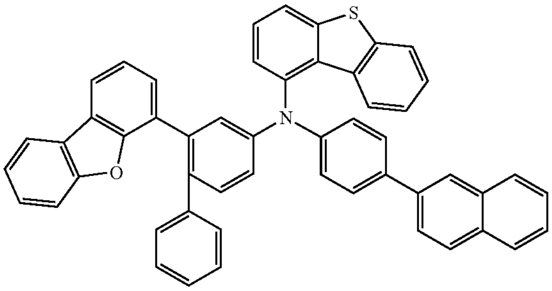
B39
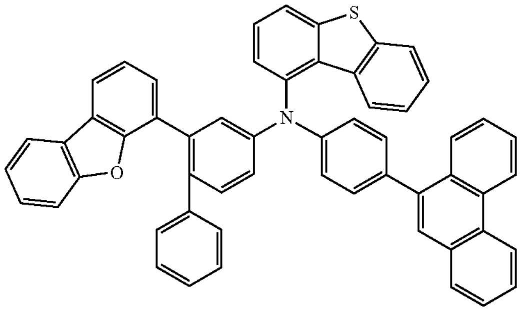
B40
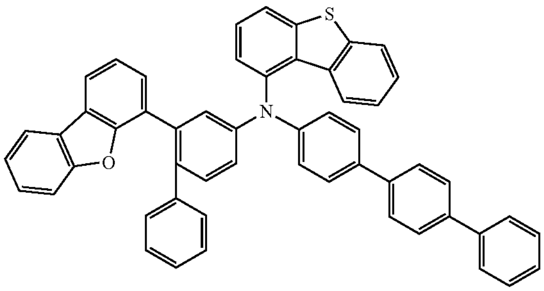
B41
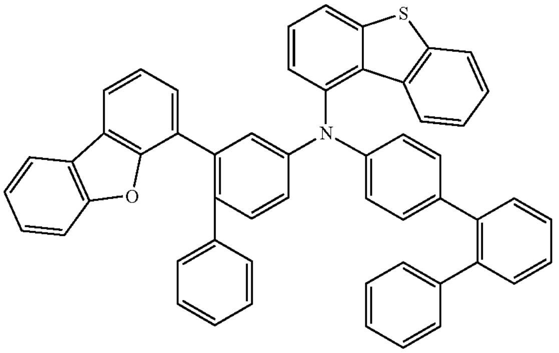
-continued
B42
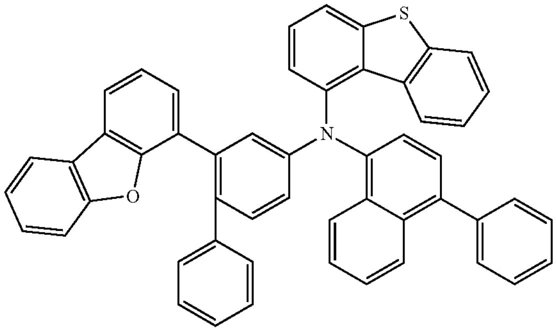
B43
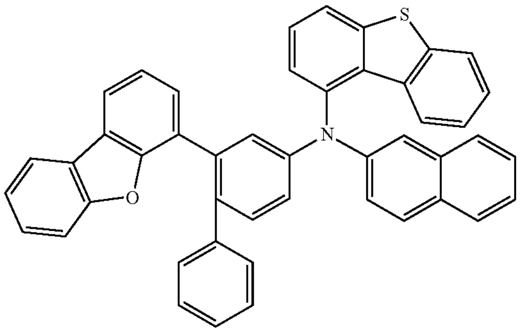
B44
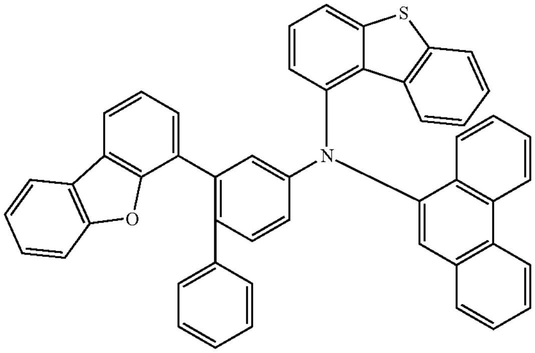
B45
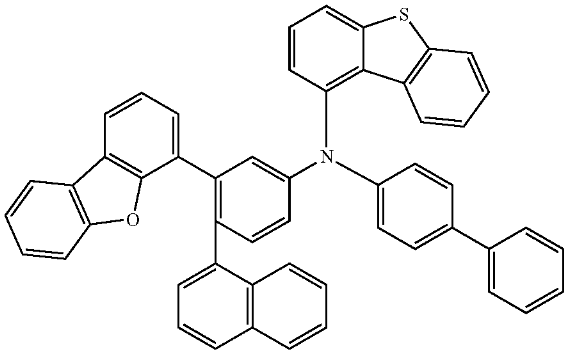

-continued
B46
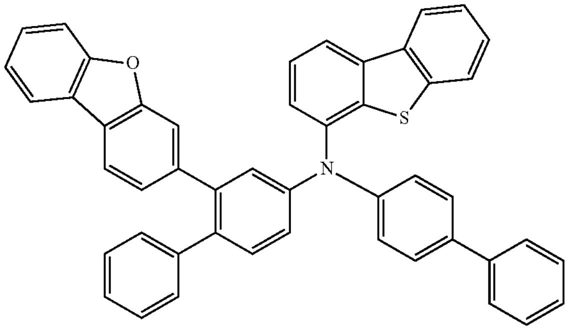
B47
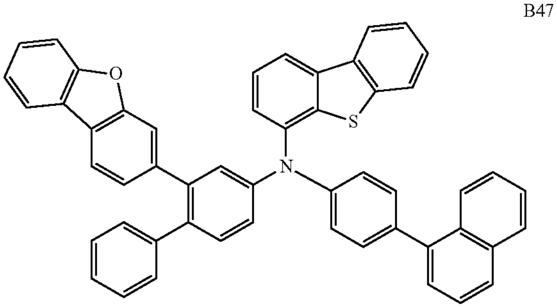
B48
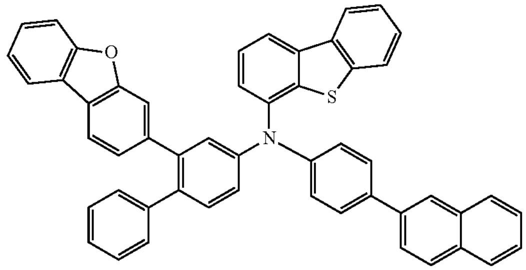
B49
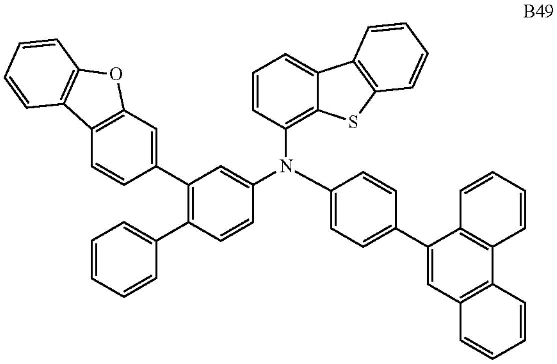
B50
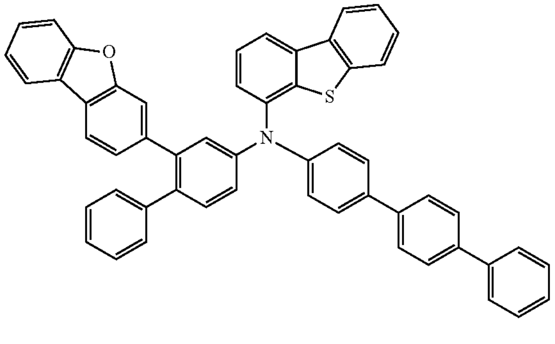
-continued
B51
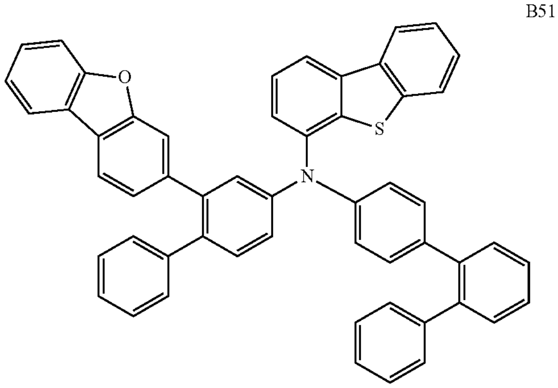
B52
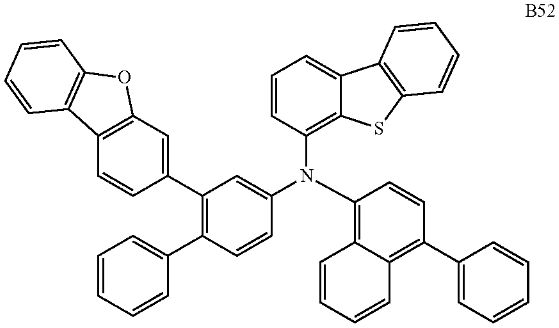
B53
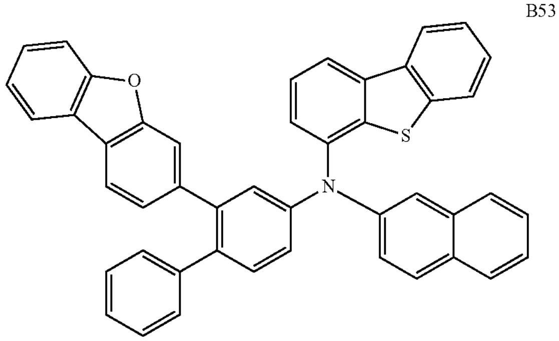
B54
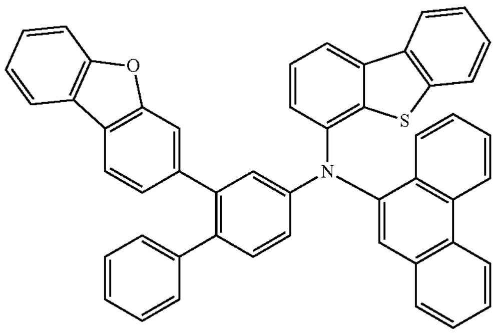

-continued
B55
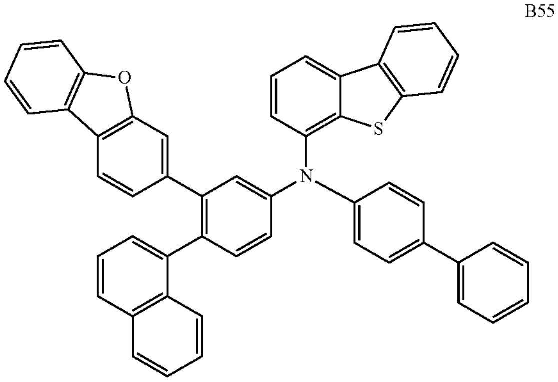
B56
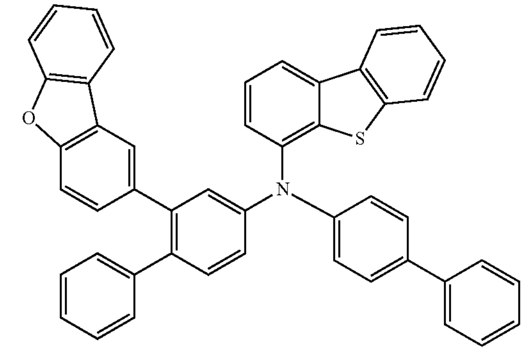
B57
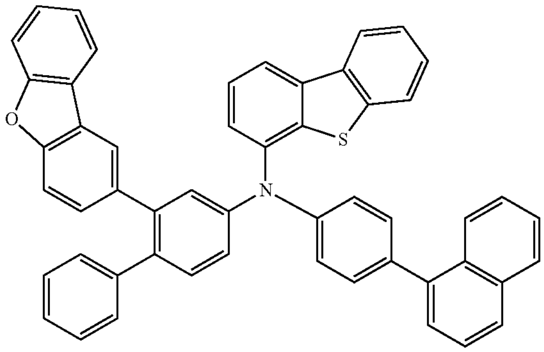
B58
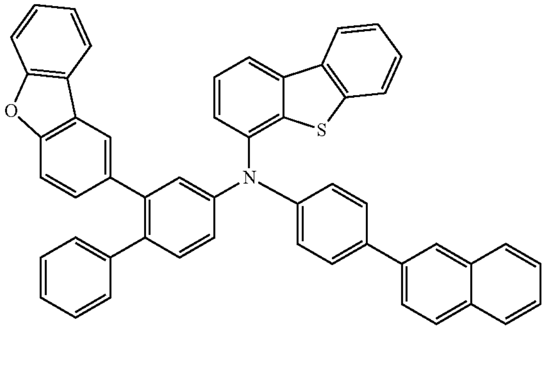
-continued
B59
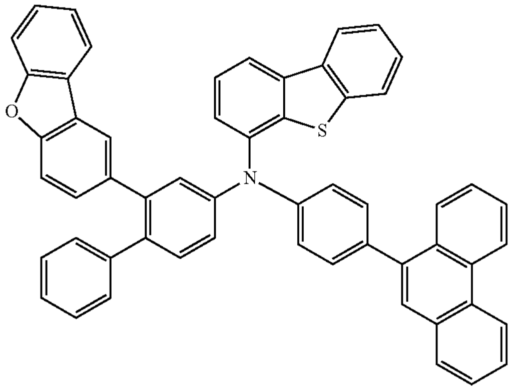
B60
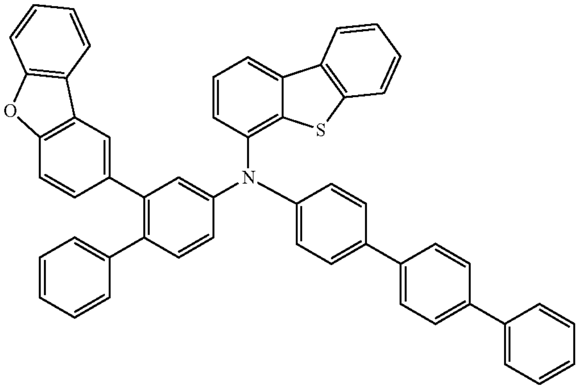
B61
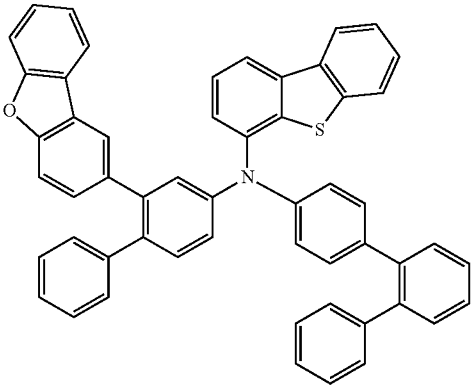
B62
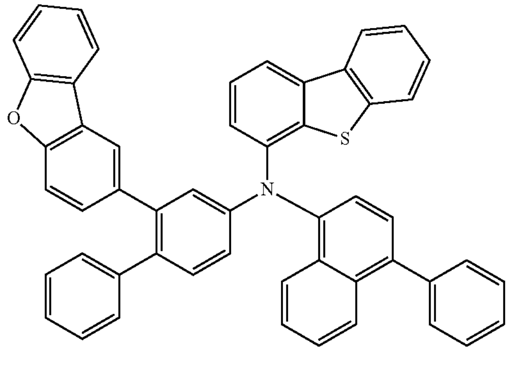

-continued
B63
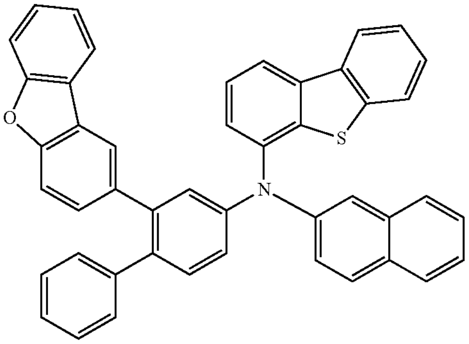
B64
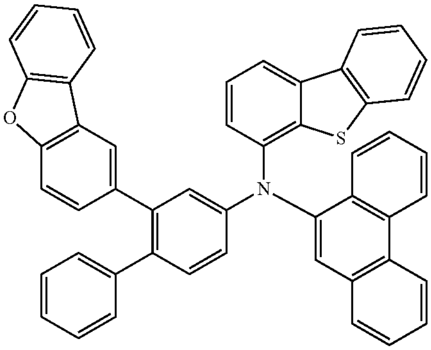
B65
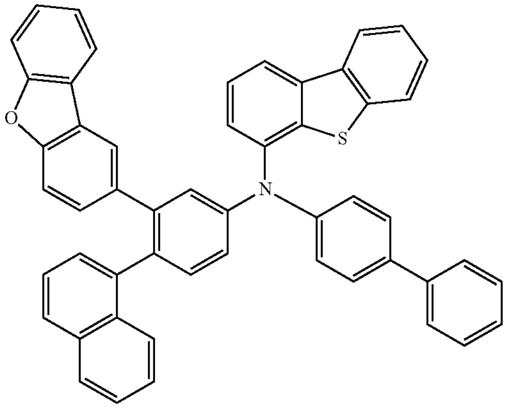
B66
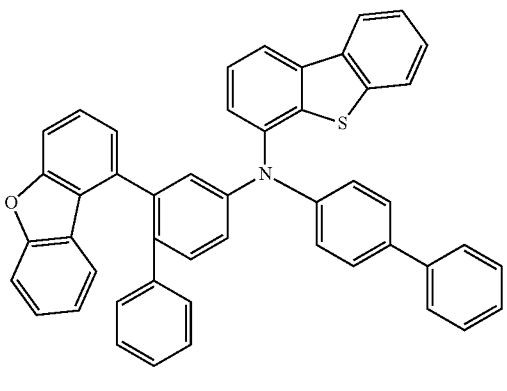
-continued
B67
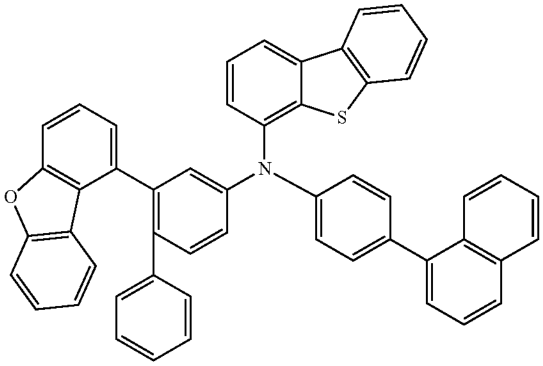
B68
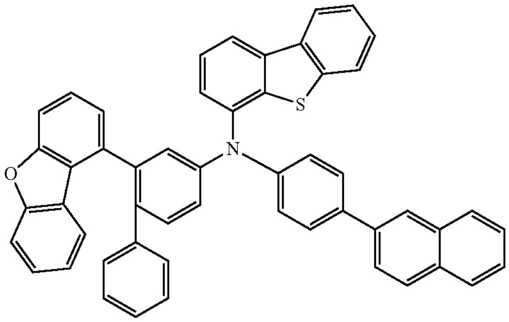
B69
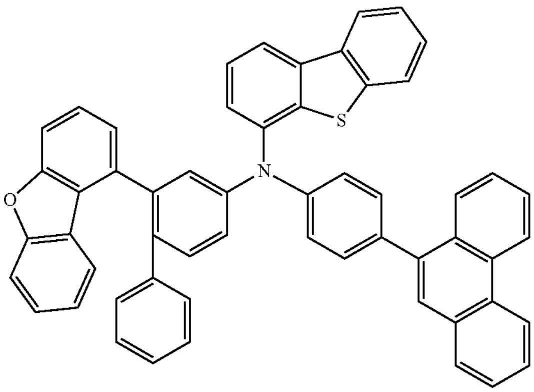
B70
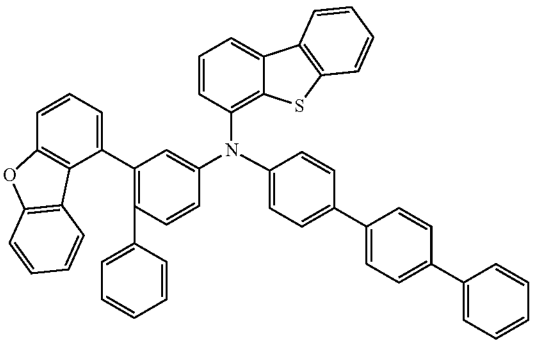

-continued
B71
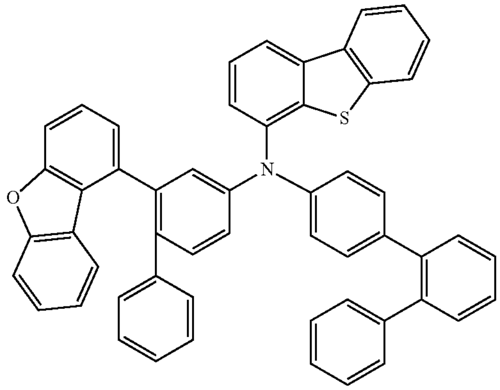
B72
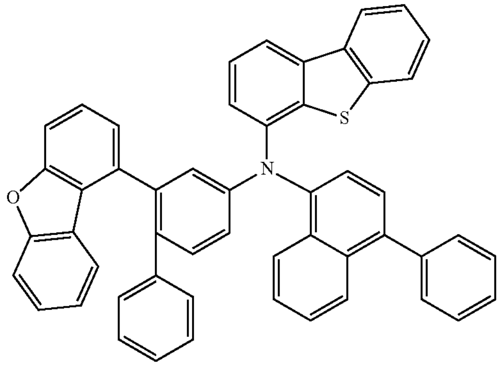
B73
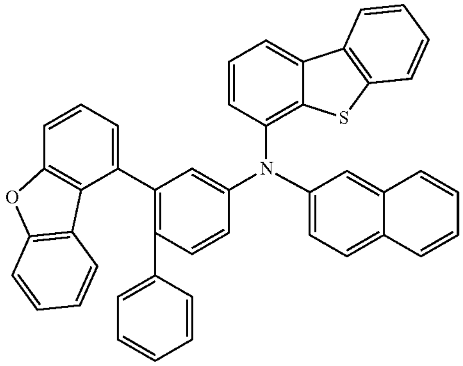
B74
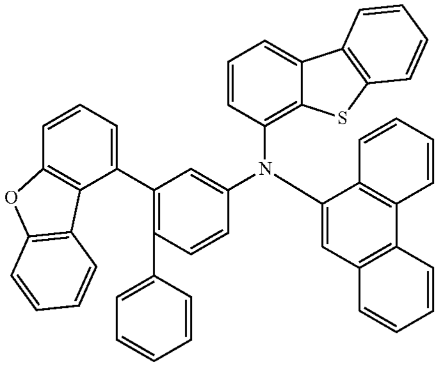
-continued
B75
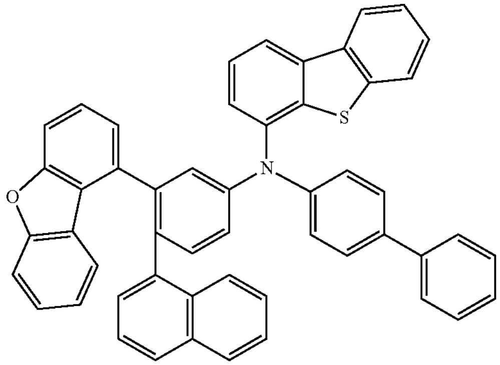
B76
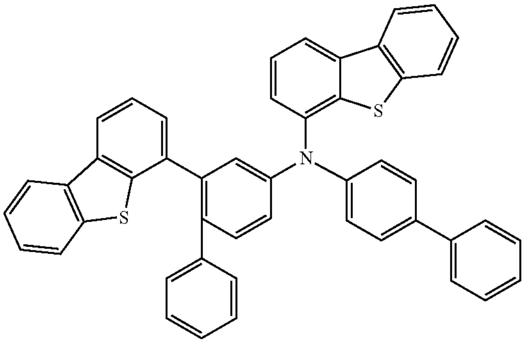
B77
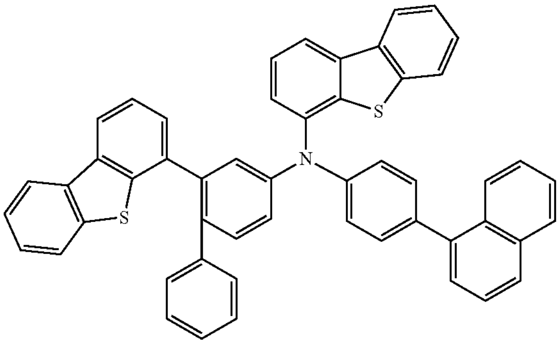
B78
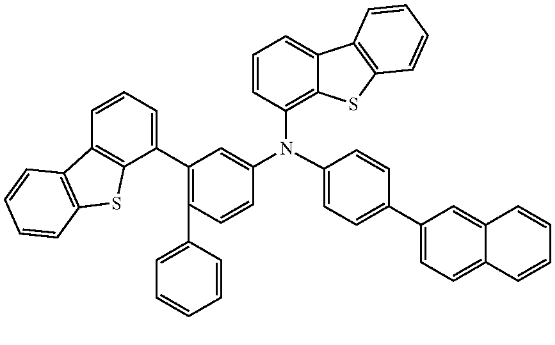

-continued
B79
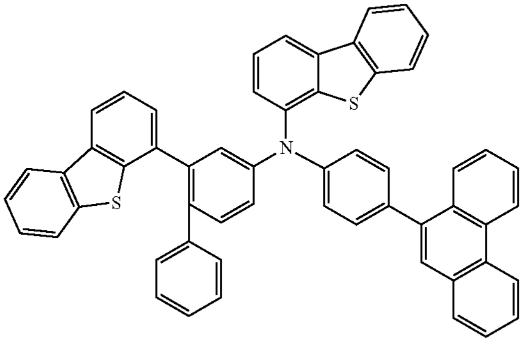
B80
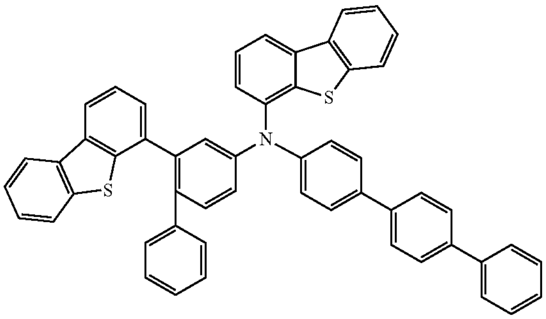
B81
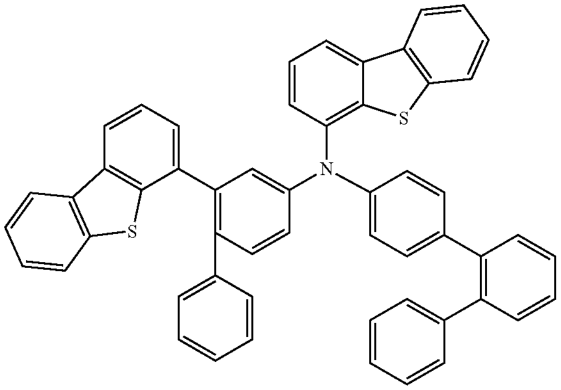
B82
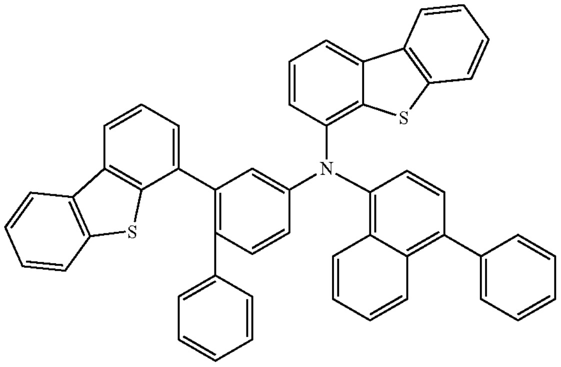
-continued
B83
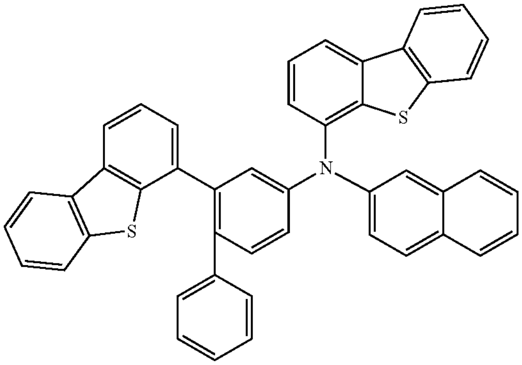
B84
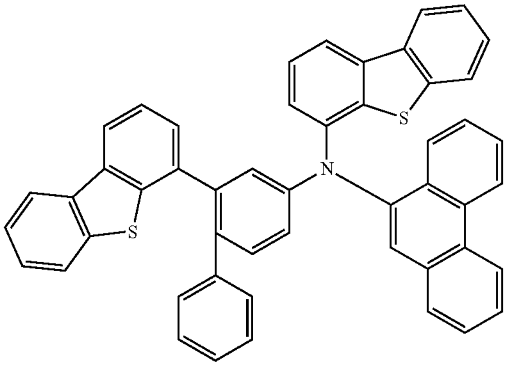
B85
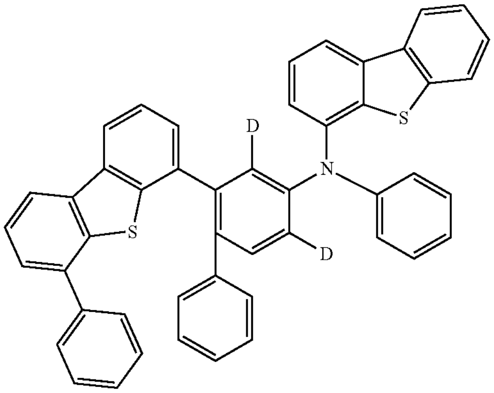
B86
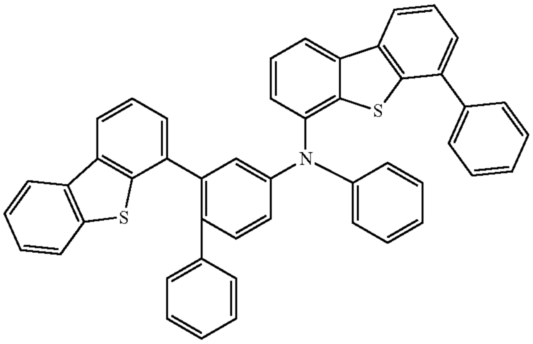

-continued
B87
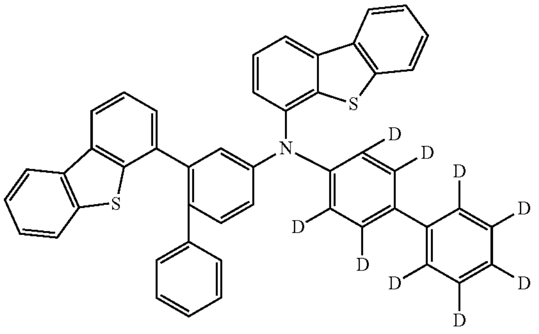
B88
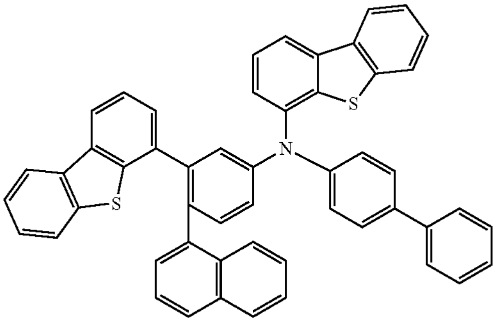
B89
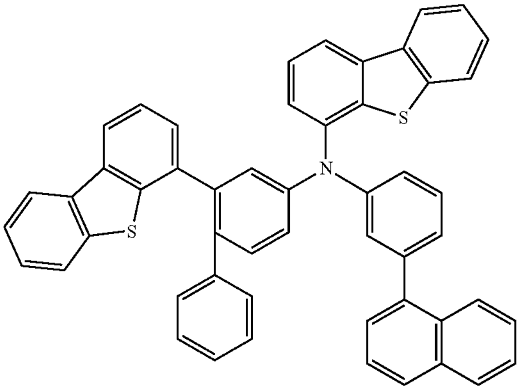
B90
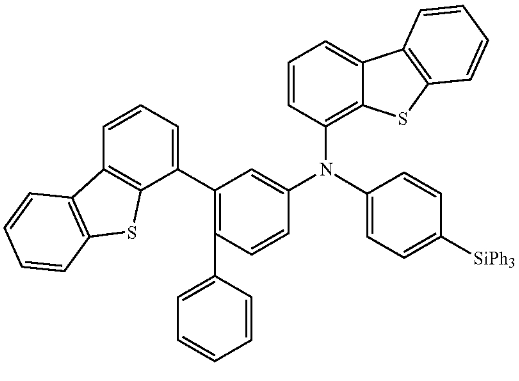
-continued
B91
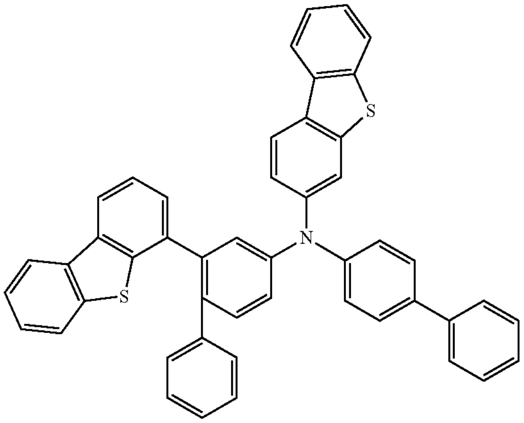
B92
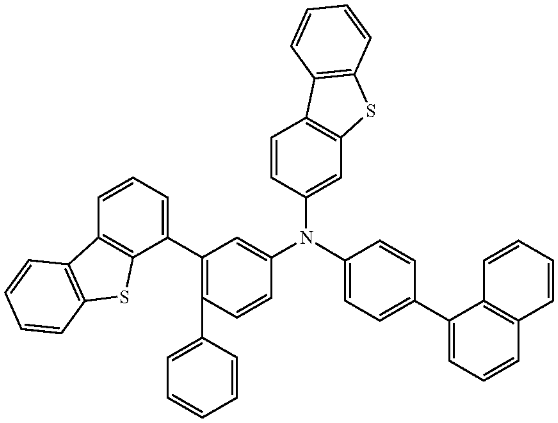
B93
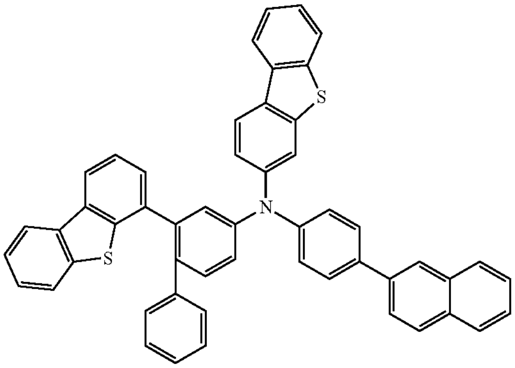

-continued
B94
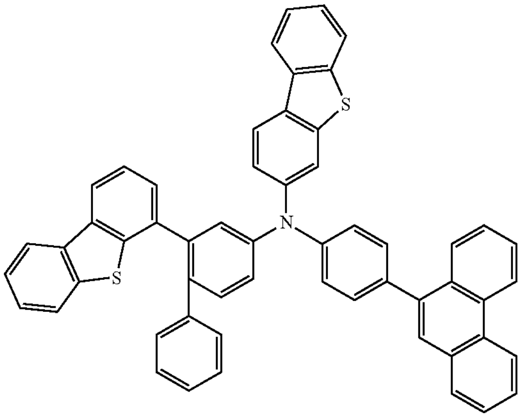
B95
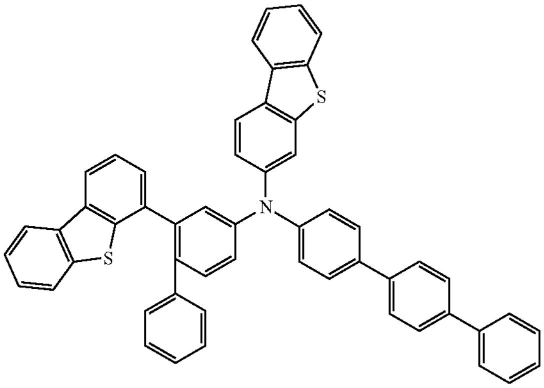
B96
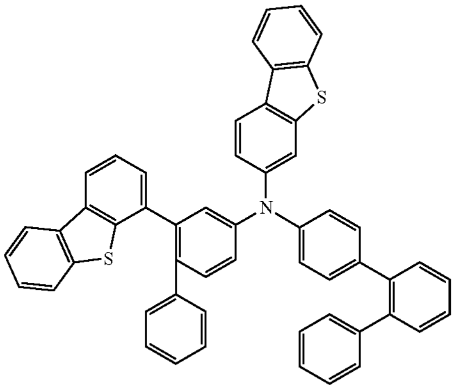
B97
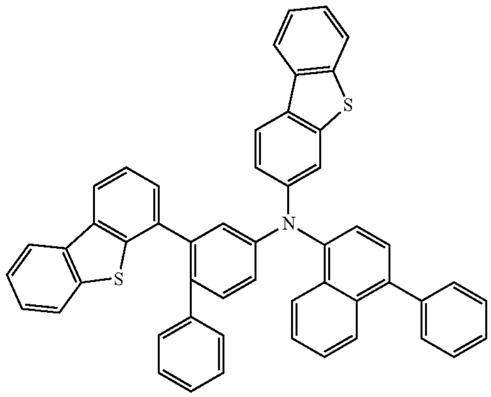
-continued
B98
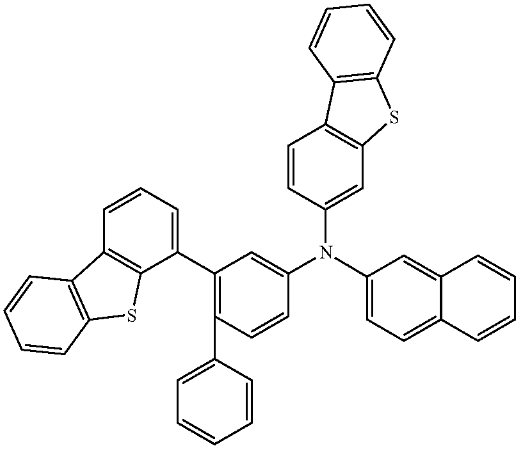
B99
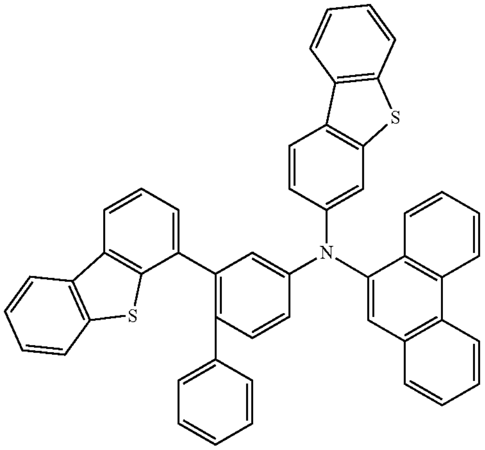
B100
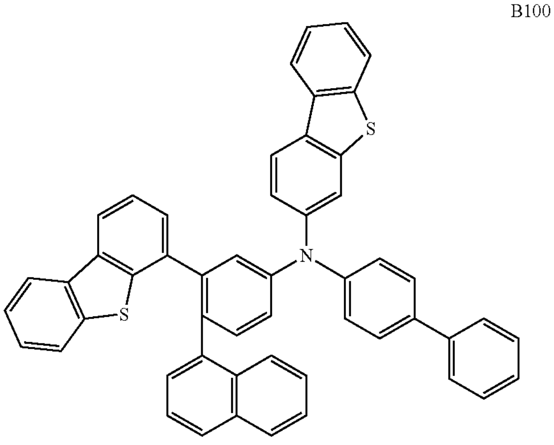

-continued
B101
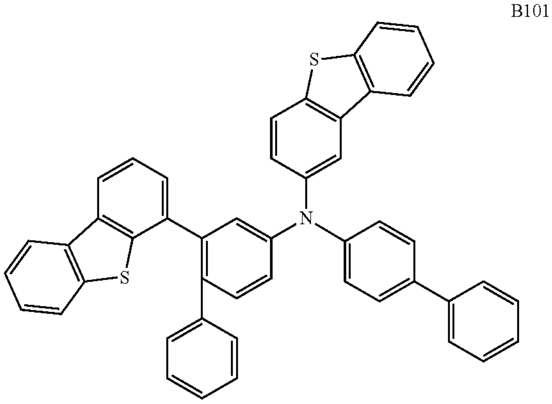
B102
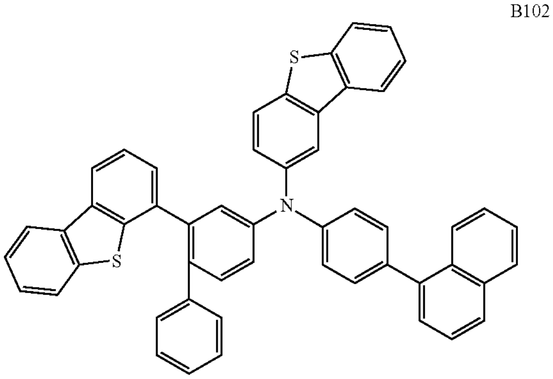
B103
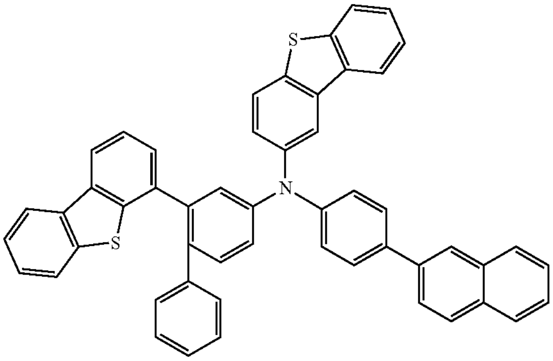
B104
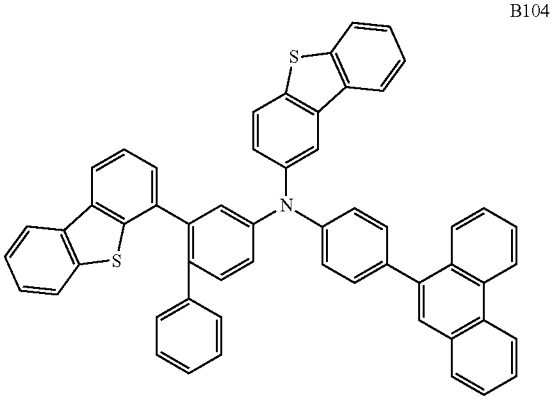
-continued
B105
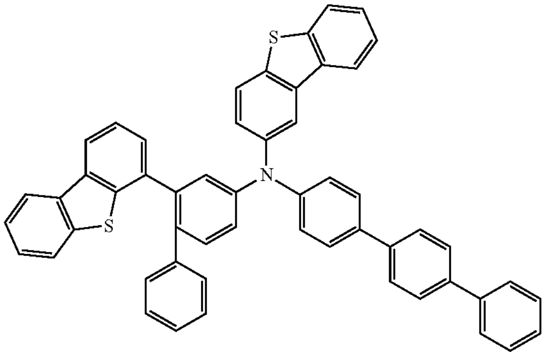
B106
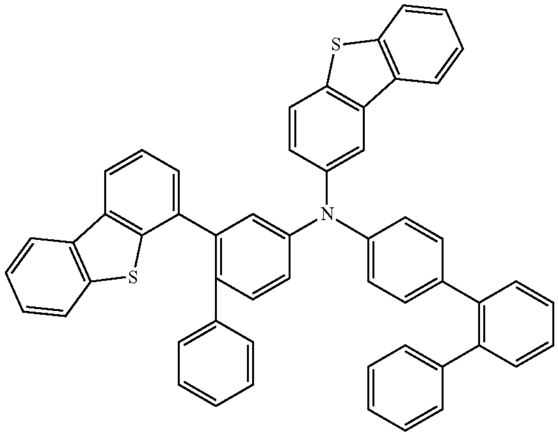
B107
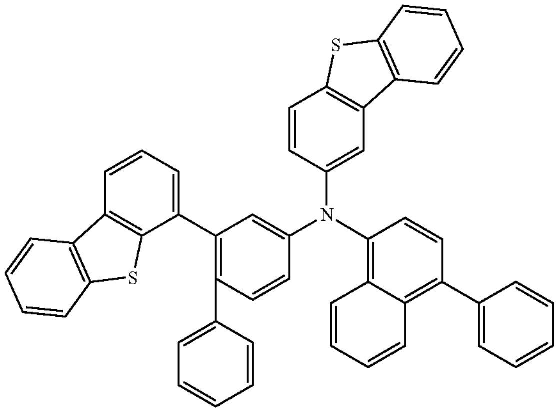

-continued
B108
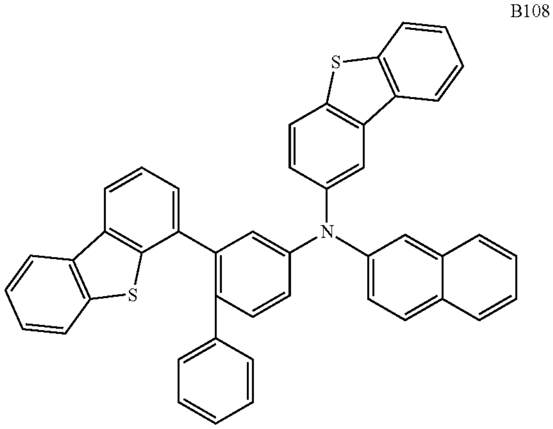
B109
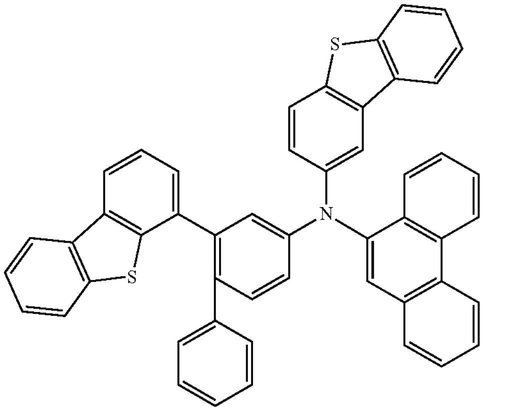
B110
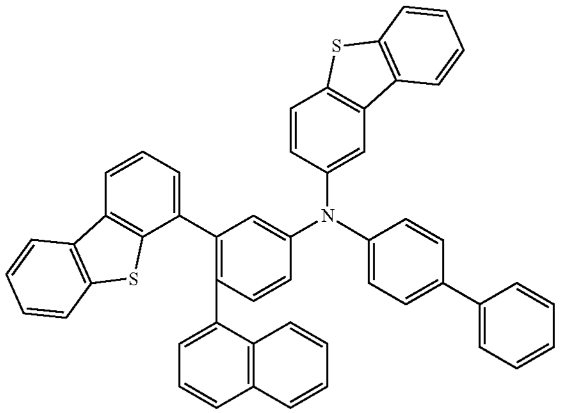
B111
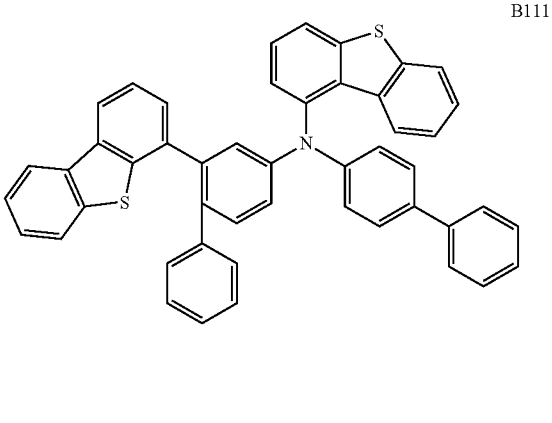
-continued
B112
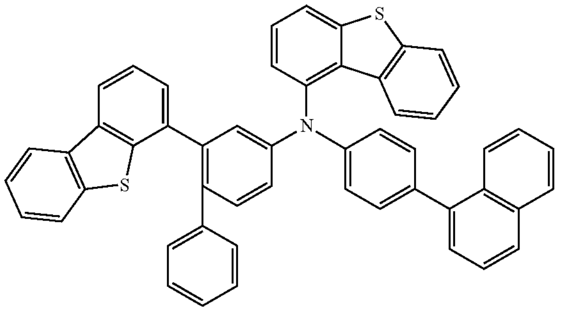
B113
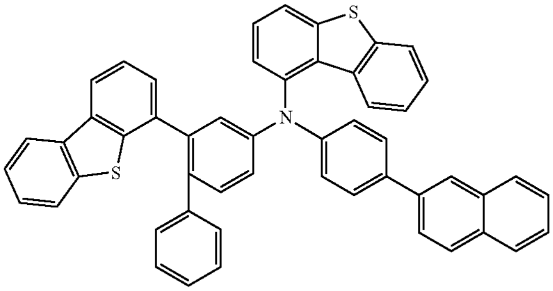
B114
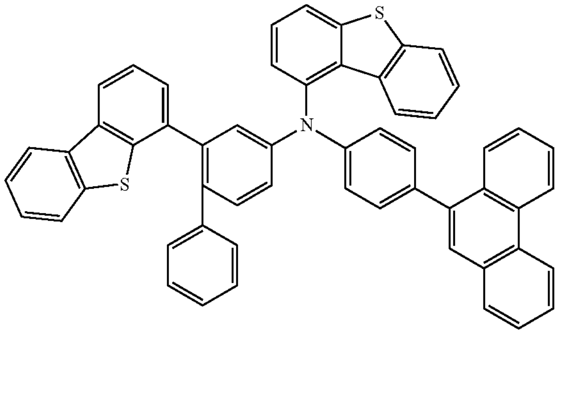
B115
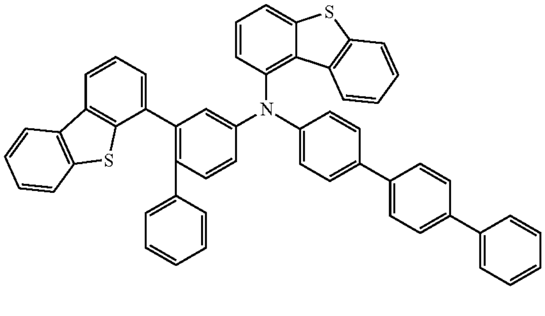

-continued
B116
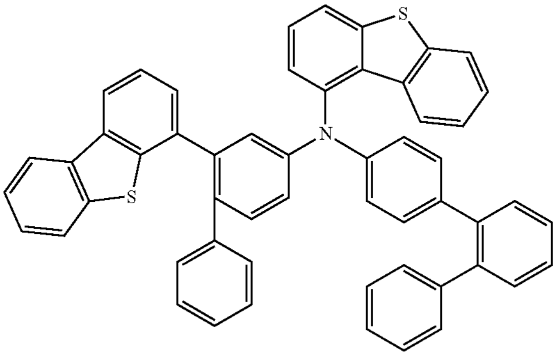
B117
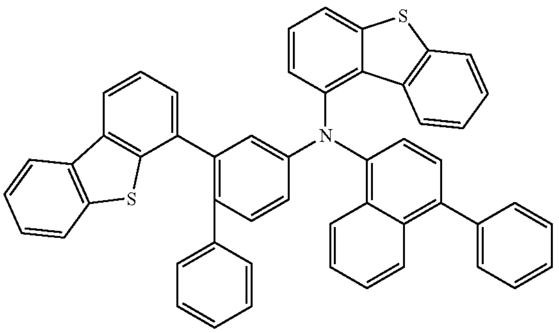
B118
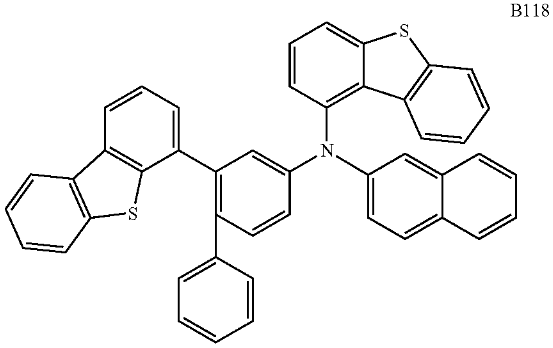
B119
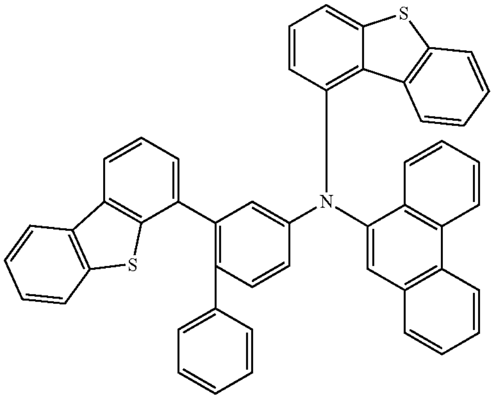
-continued
B120
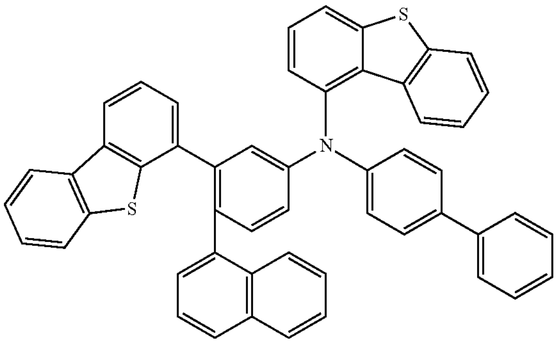
B121
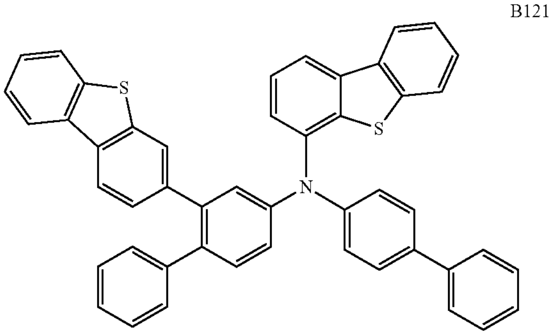
B122
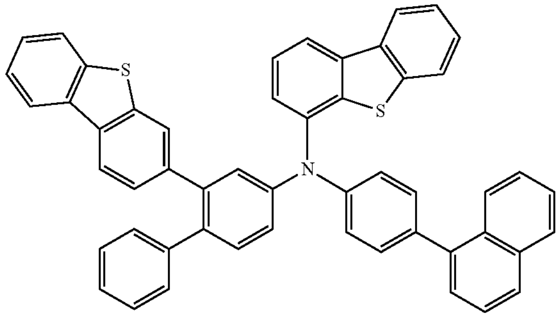
B123
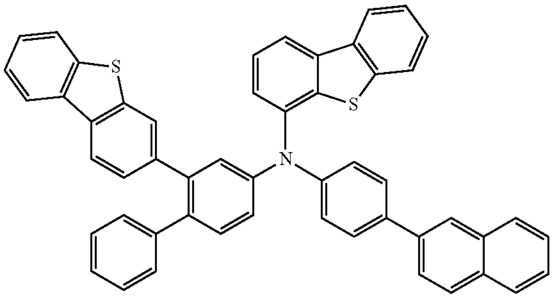

-continued
B124
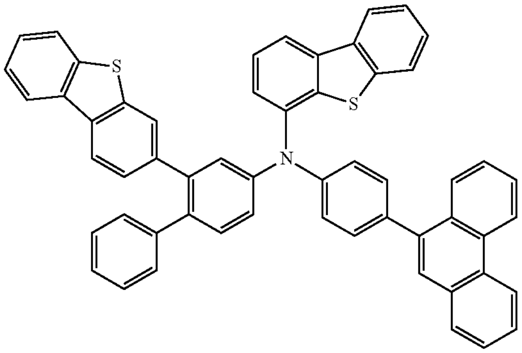
B125
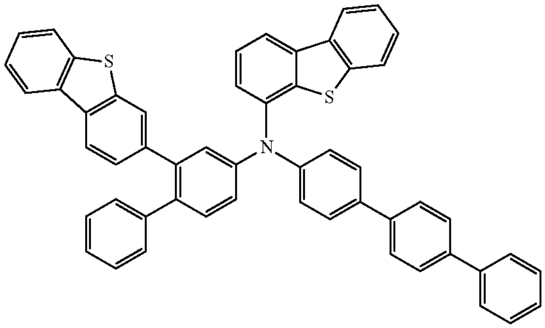
B126
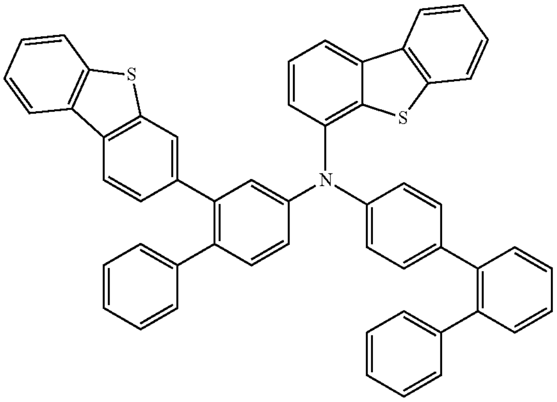
B127
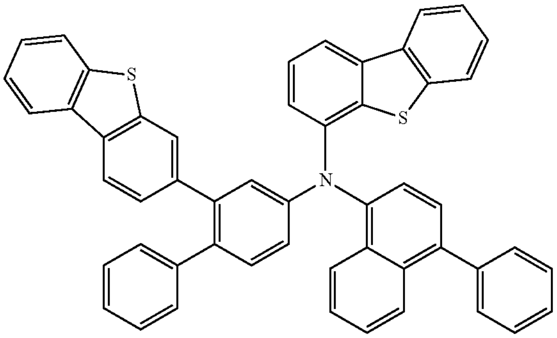
-continued
B128
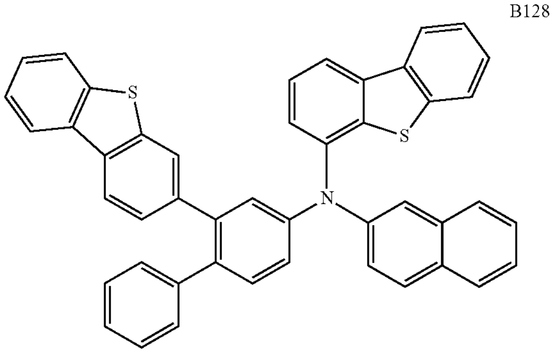
B129
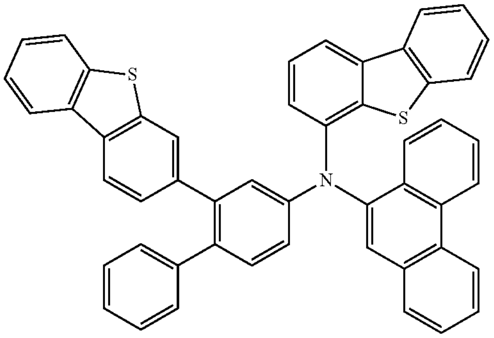
B130
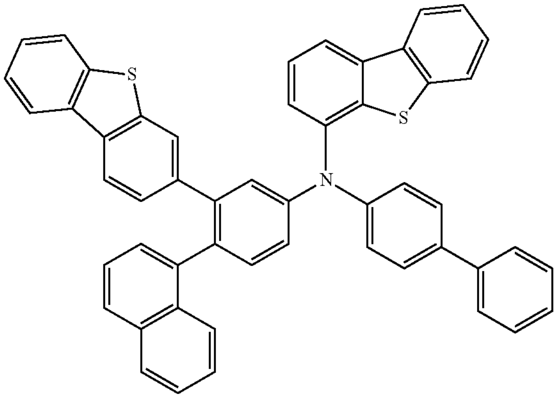
B131
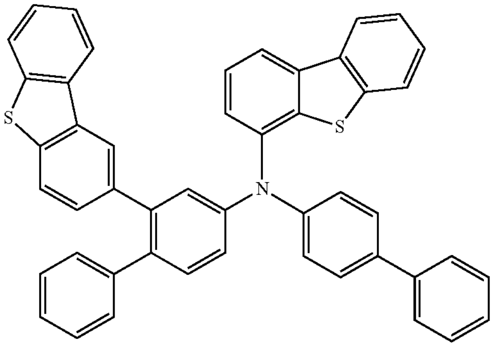

-continued
B132
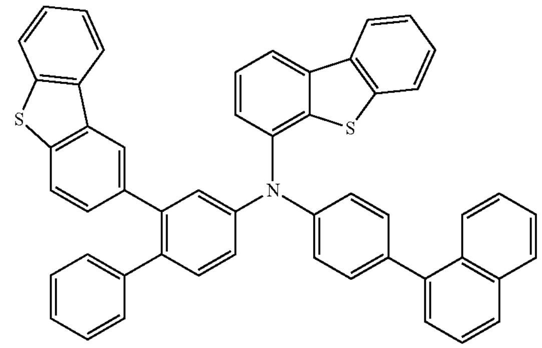
B133
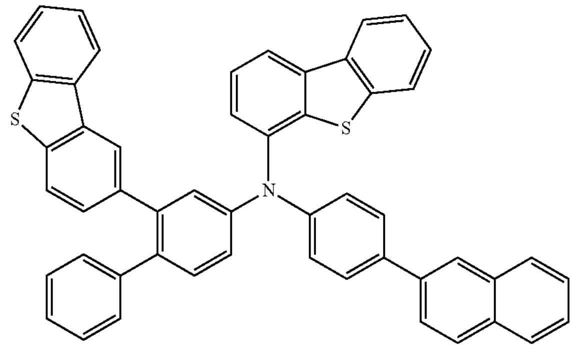
B134
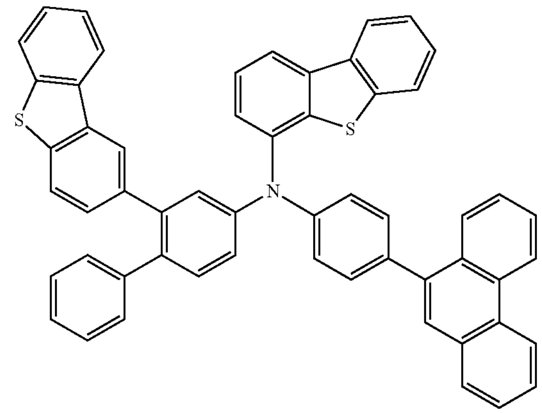
B135
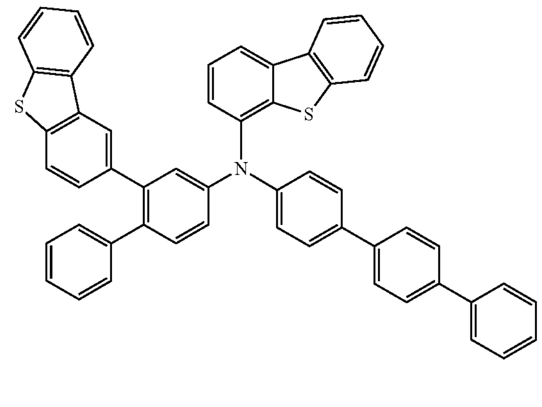
-continued
B136
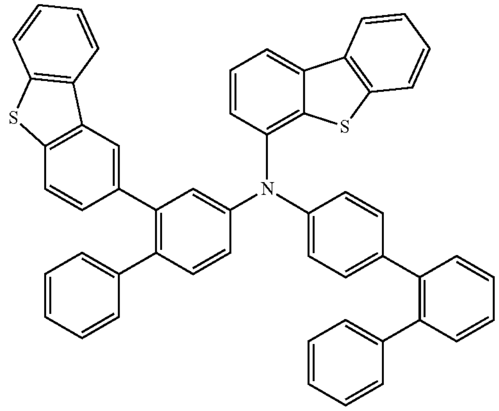
B137
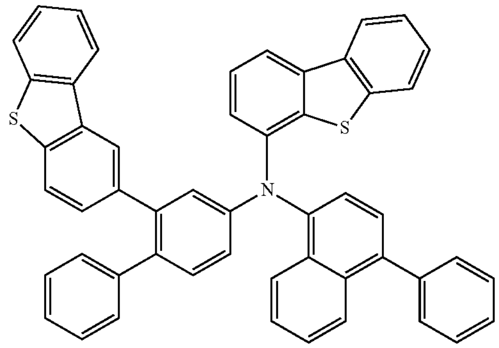
B138
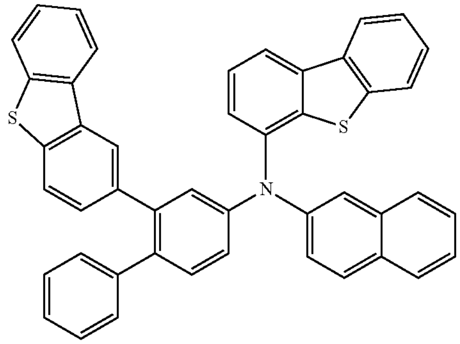
B139
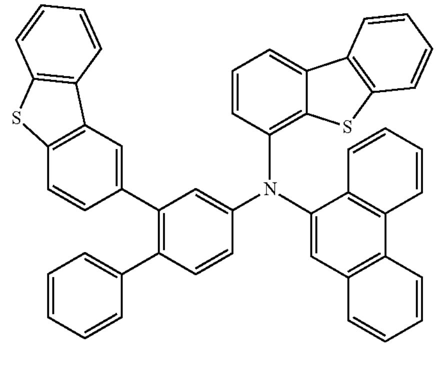

-continued
B140
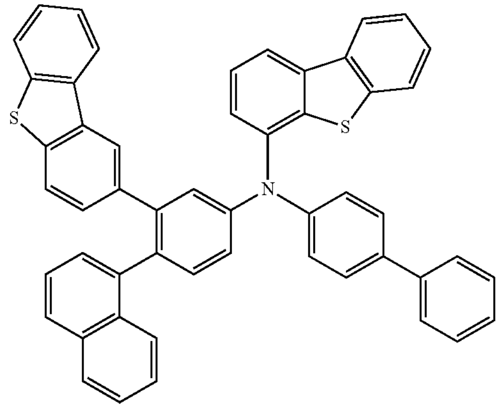
B141
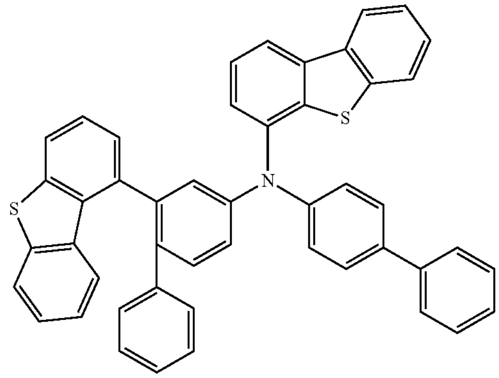
B142
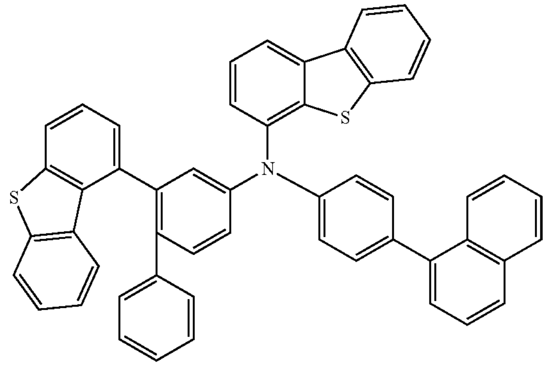
B143
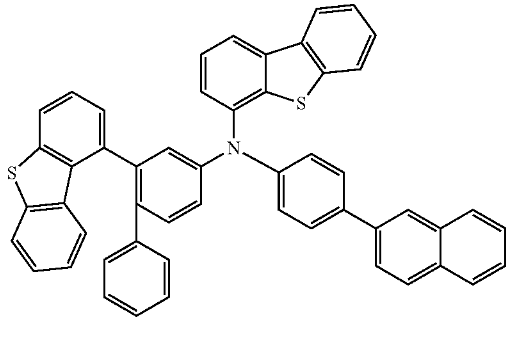
-continued
B144
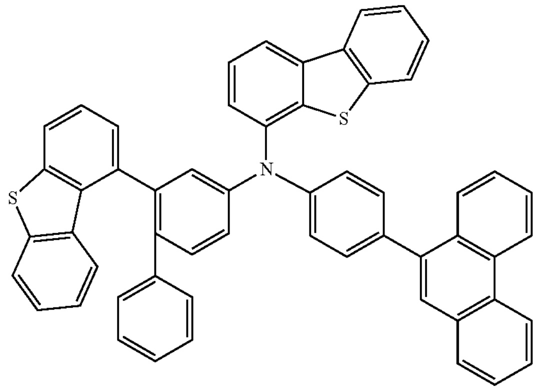
B145
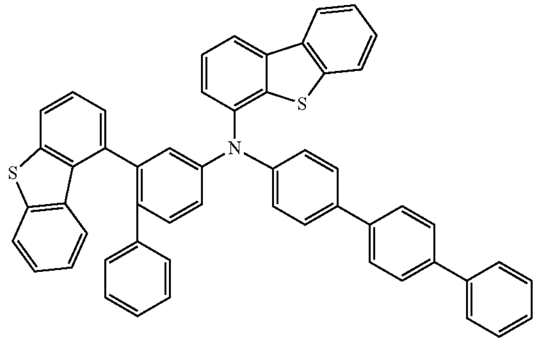
B146
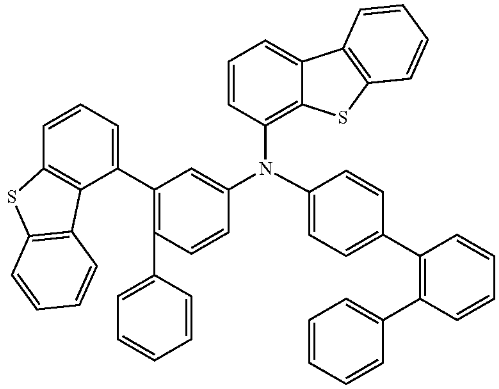
B147
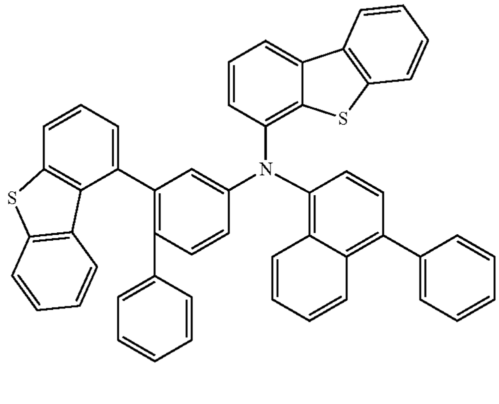

-continued
B148
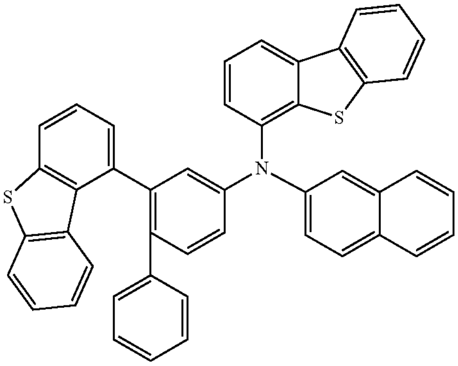
B149
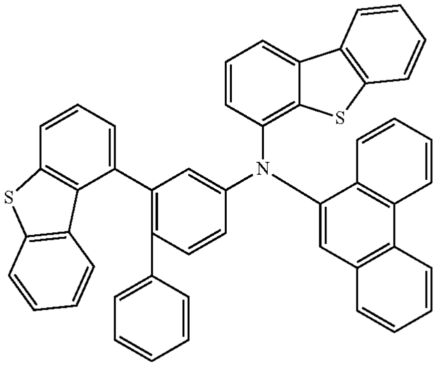
B150
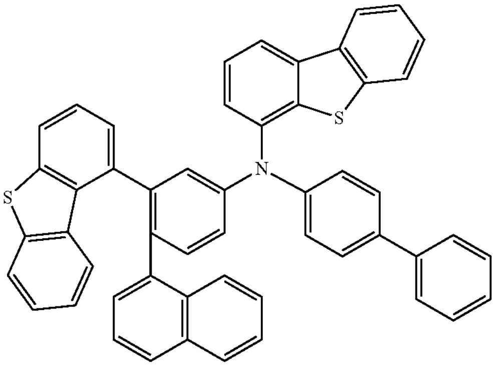
B151
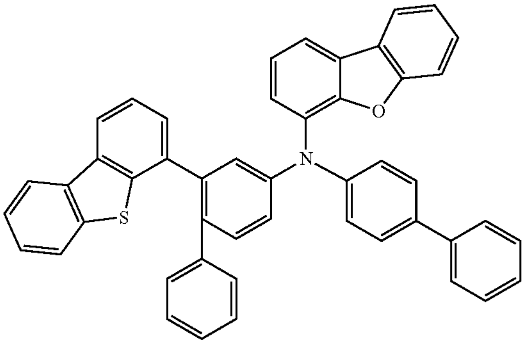
-continued
B152
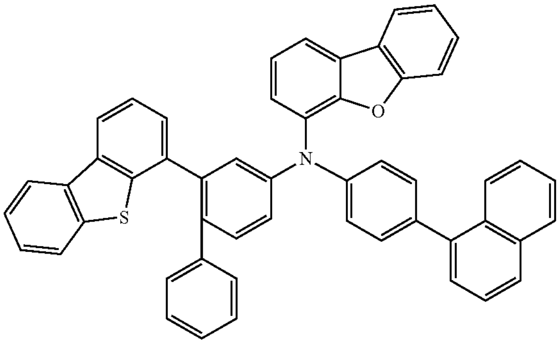
B153
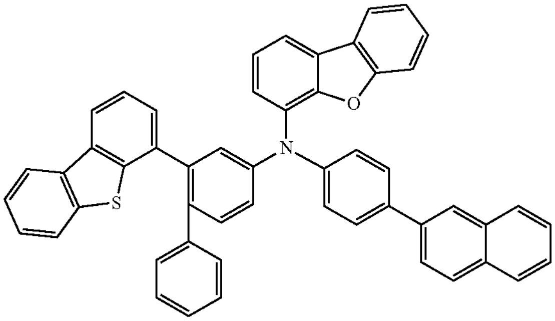
B154
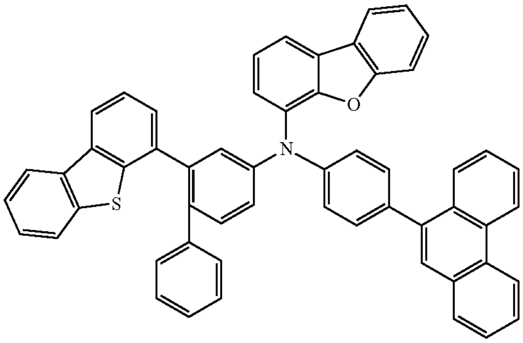
B155
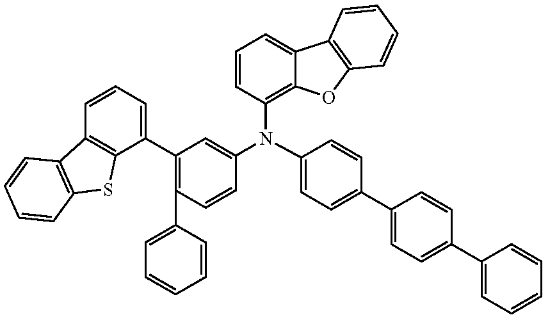

B156
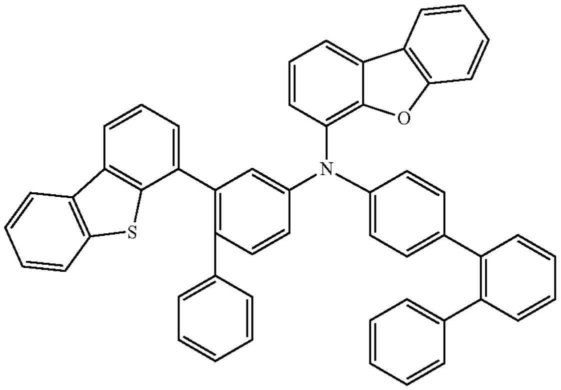
B157
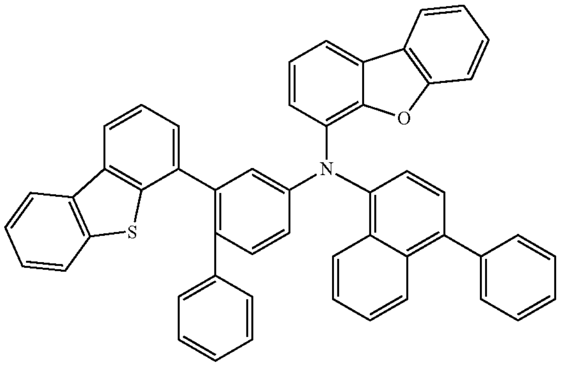
B158
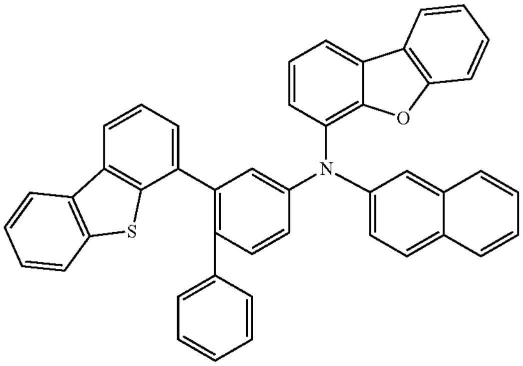
B159
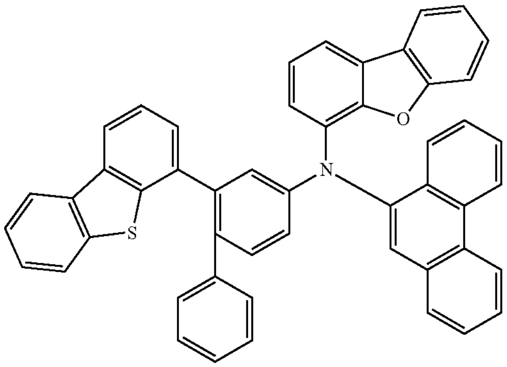
B160
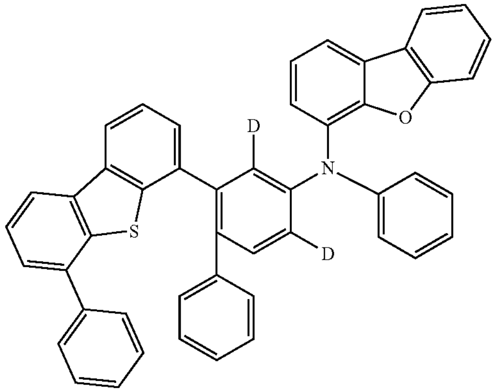
B161
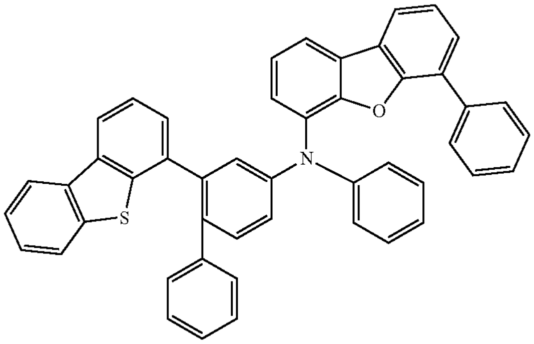
B162
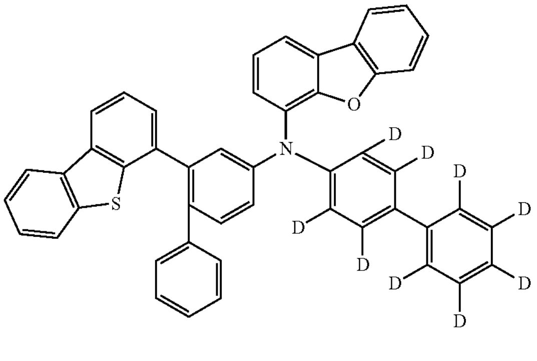
B163
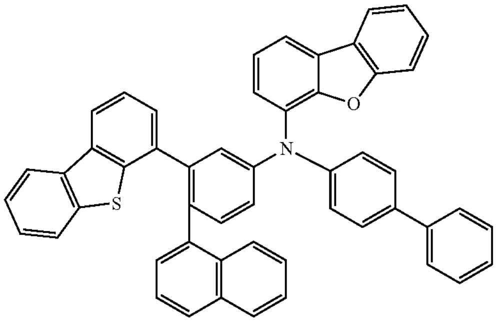

-continued
B164
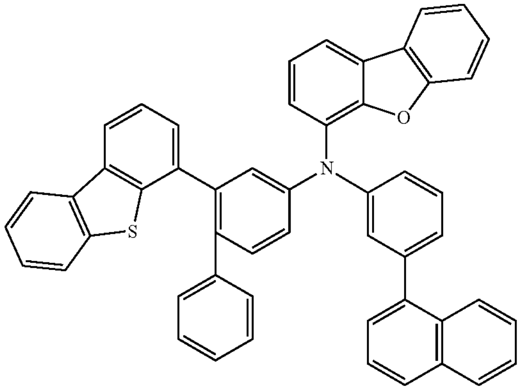
B165
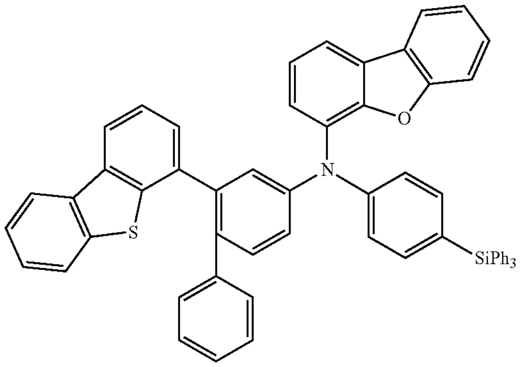
B166
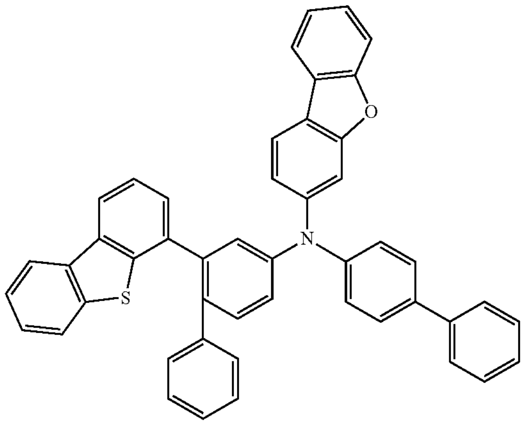
-continued
B167
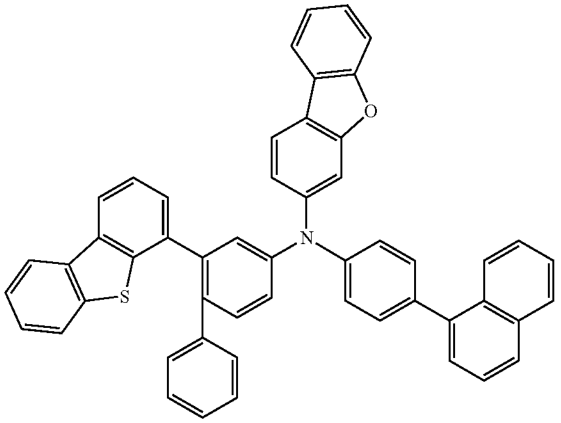
B168
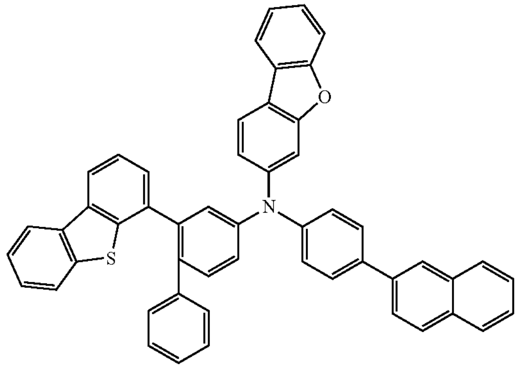
B169
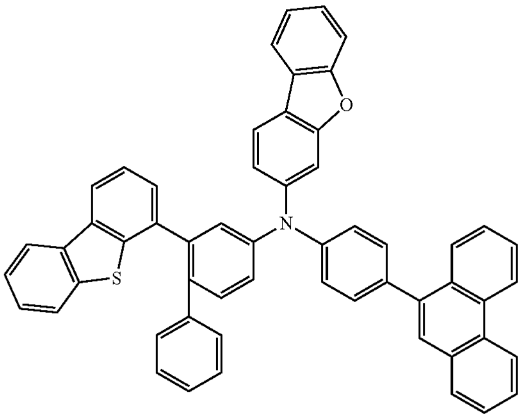

-continued
B170
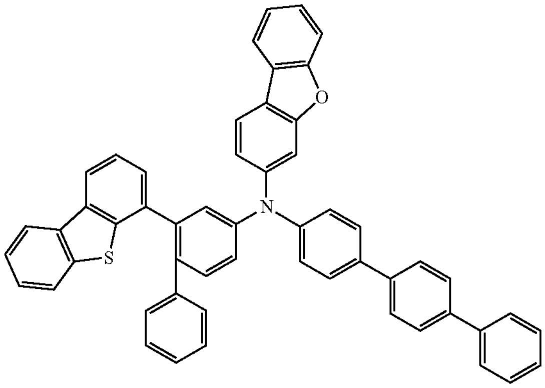
B171
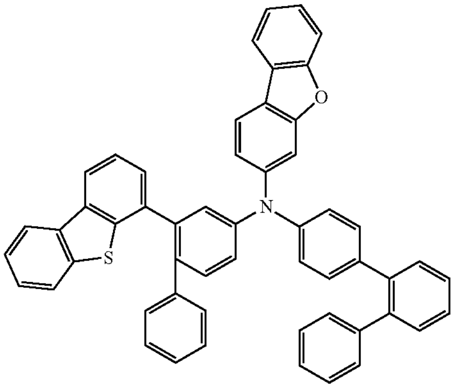
B172
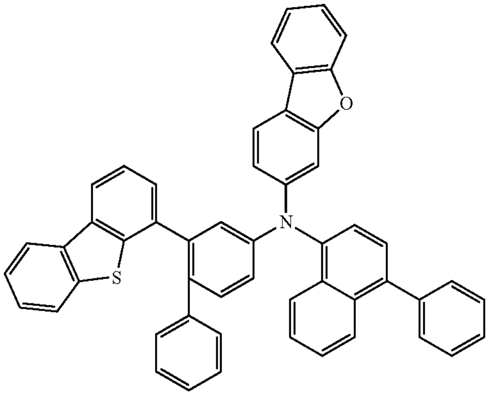
-continued
B173
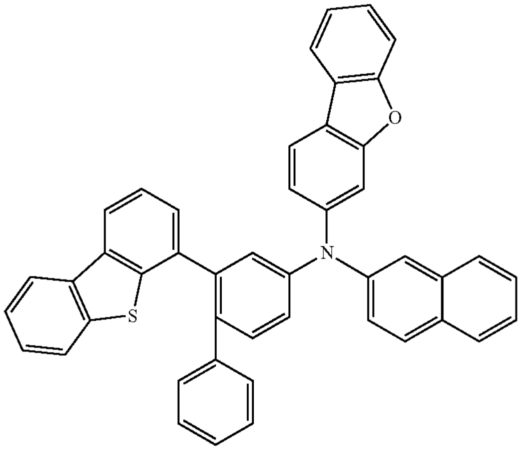
B174
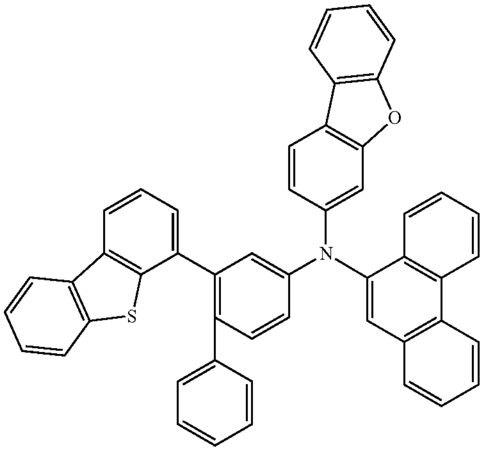
B175
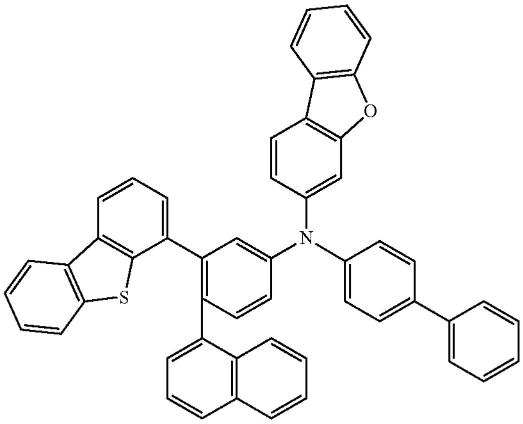

-continued
B176
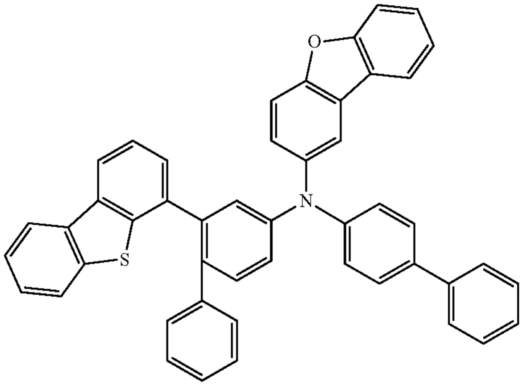
B177
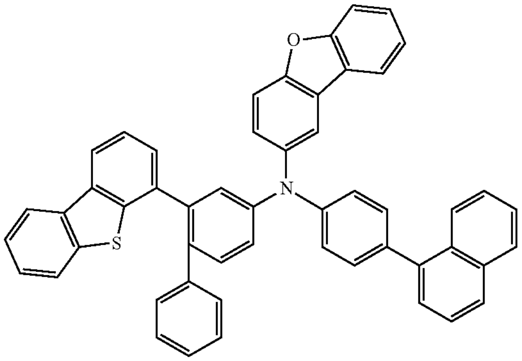
B178
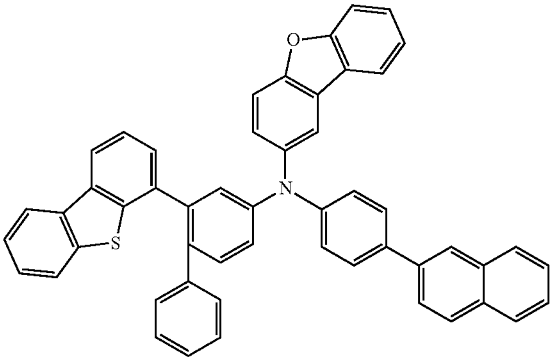
B179
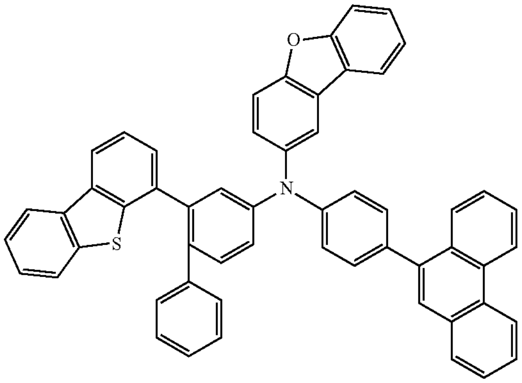
-continued
B180
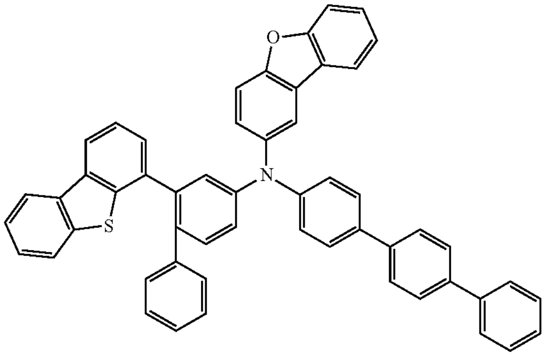
B181
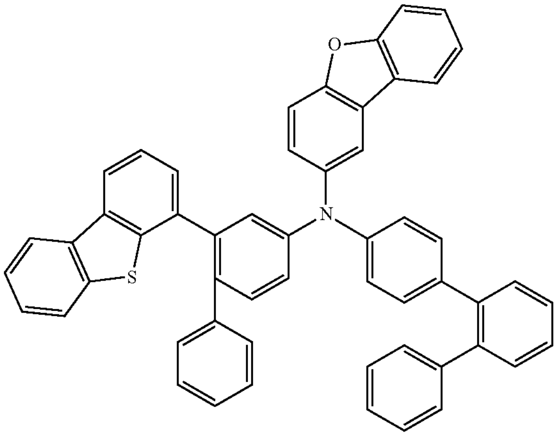
B182
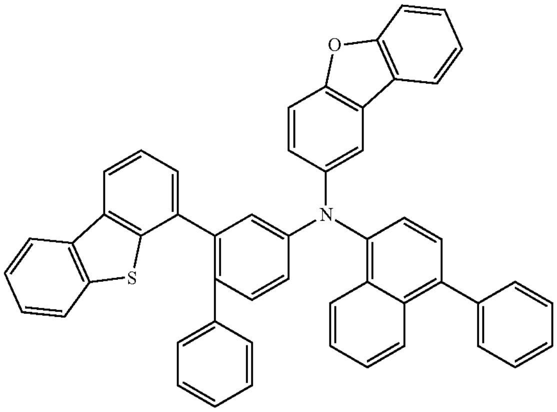

-continued
B183
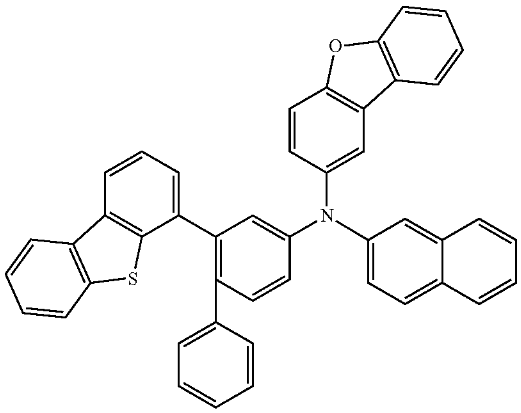
B184
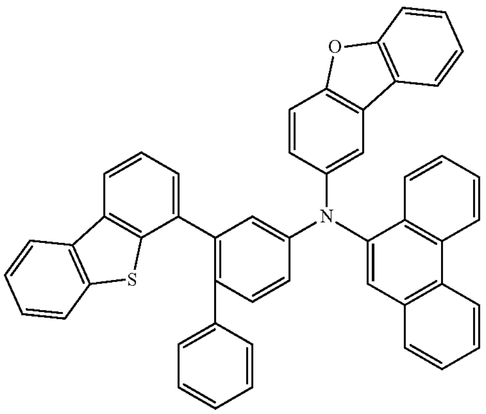
B185
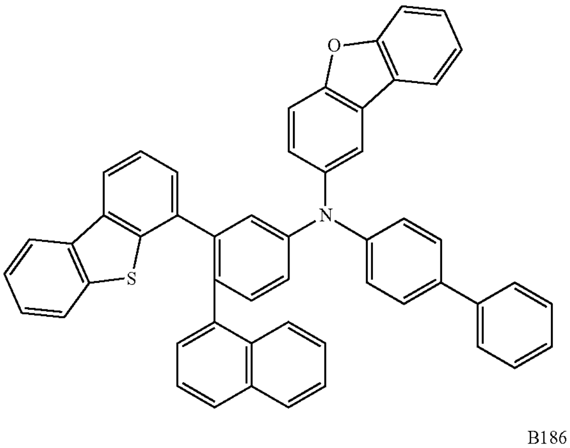
B186
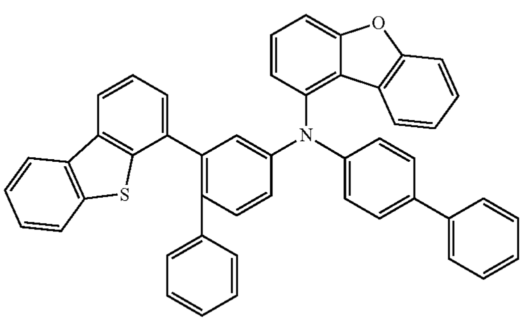
-continued
B187
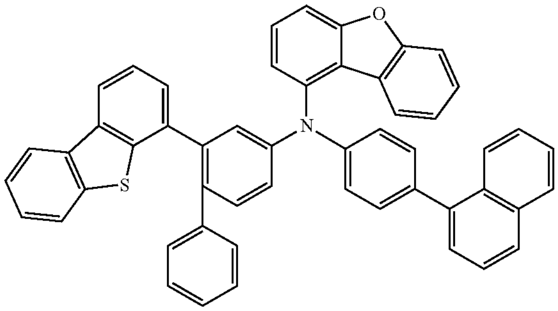
B188
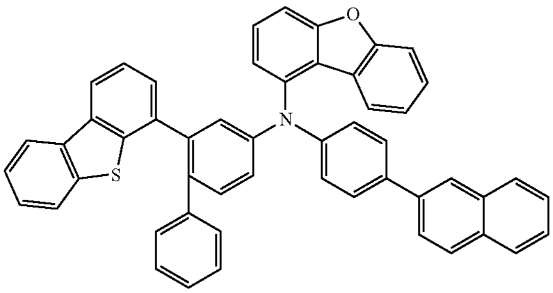
B189
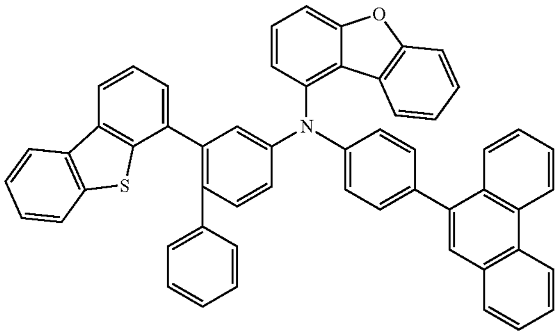
B190
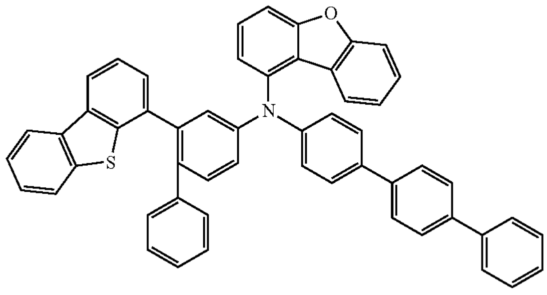

-continued
B191
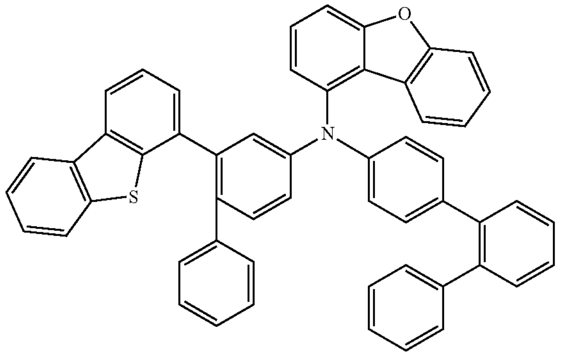
B192
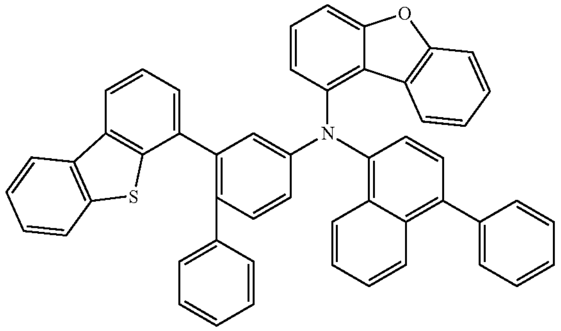
B193
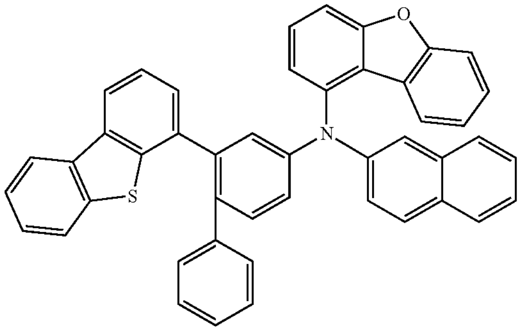
B194
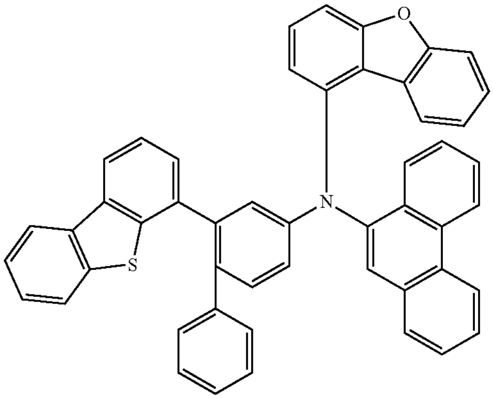
-continued
B195
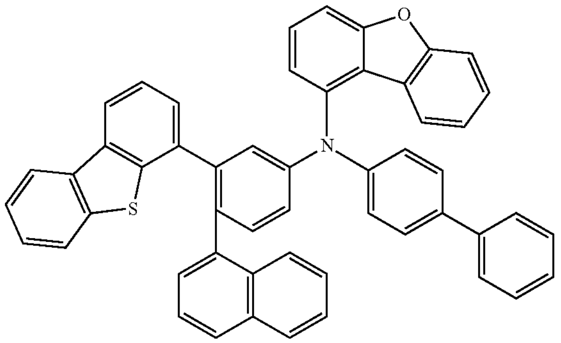
B196
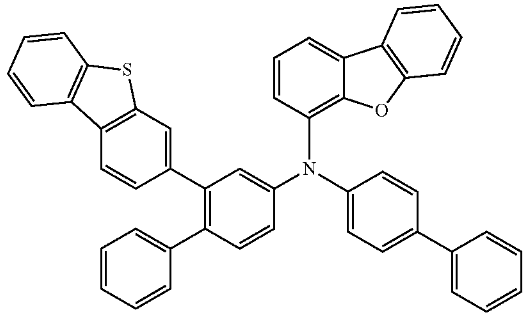
B197
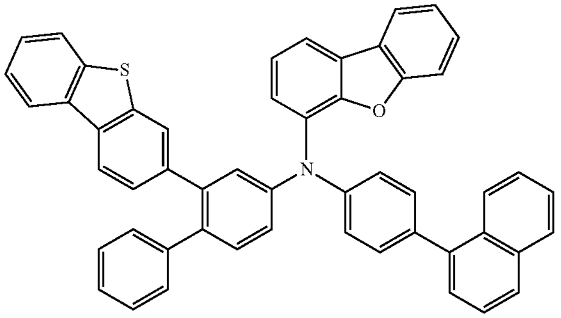
B198
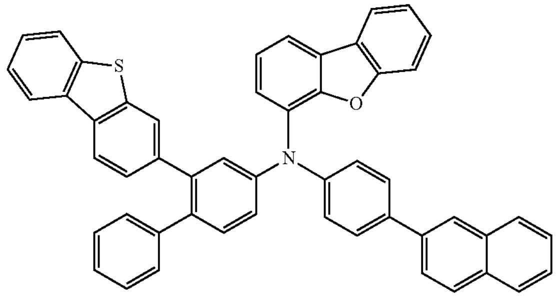

-continued
B199
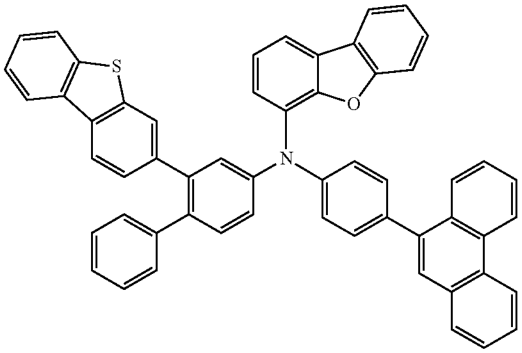
B200
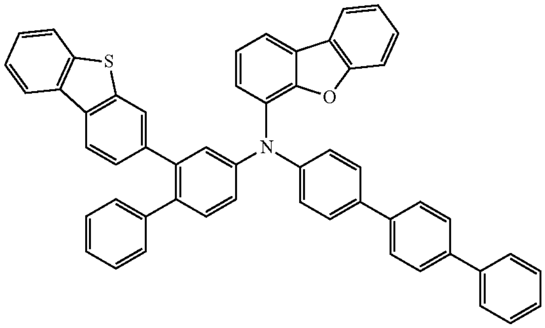
B201
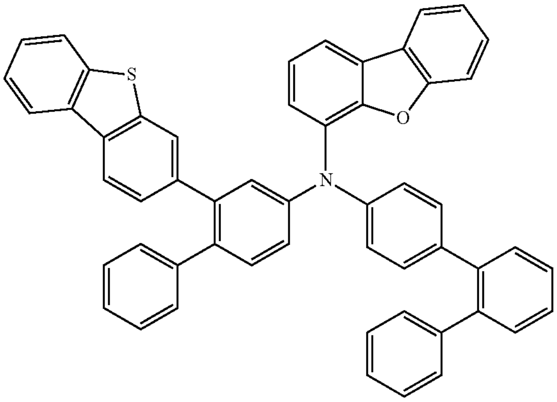
B202
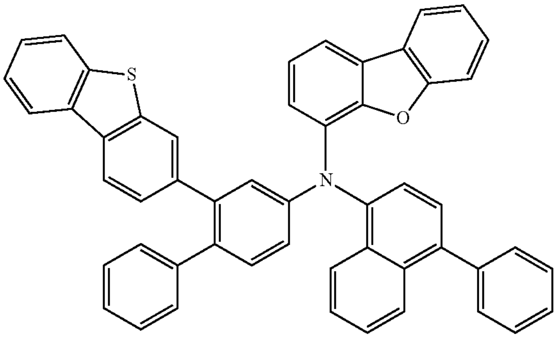
-continued
B203
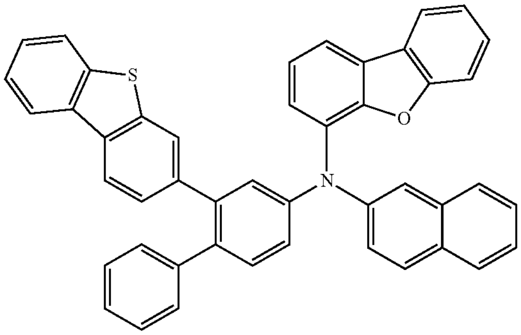
B204
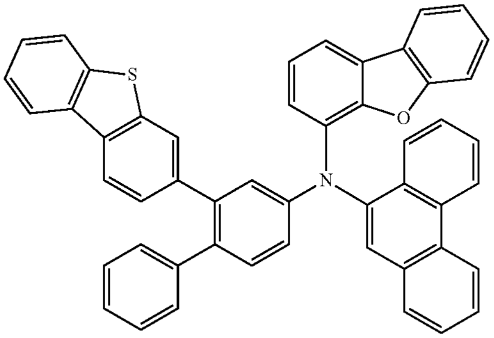
B205
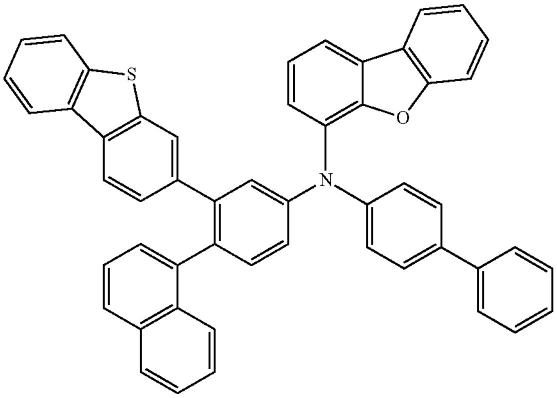
B206
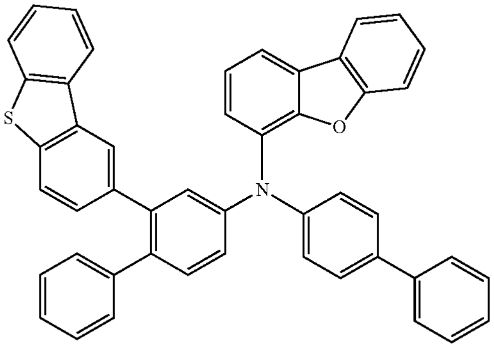

-continued
B207
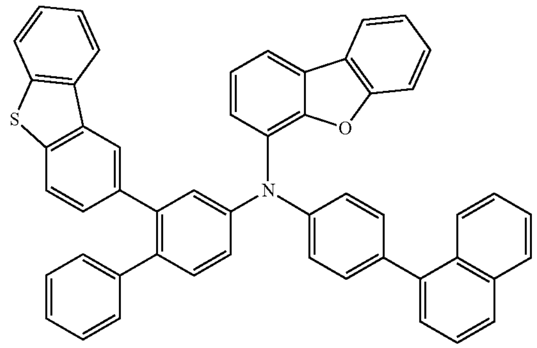
B208
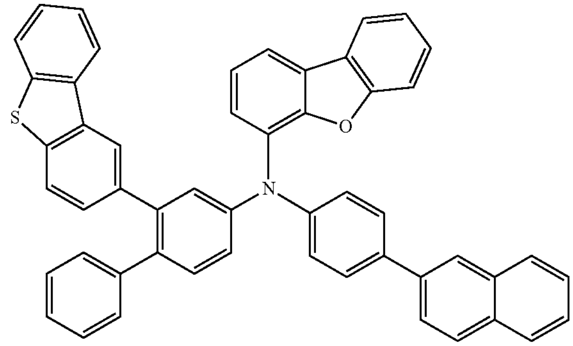
B209
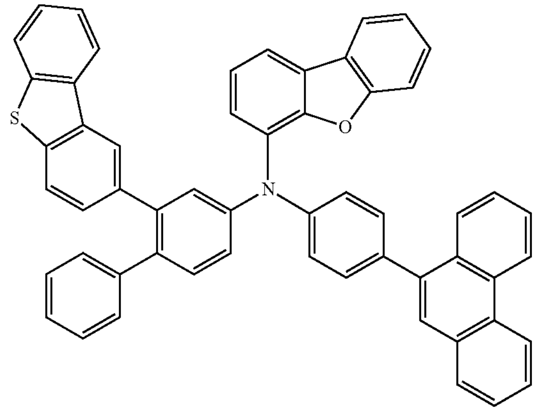
B210
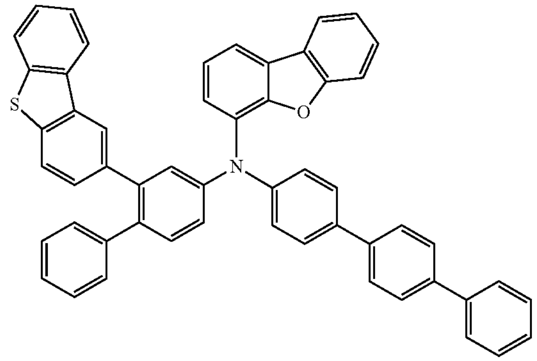
-continued
B211
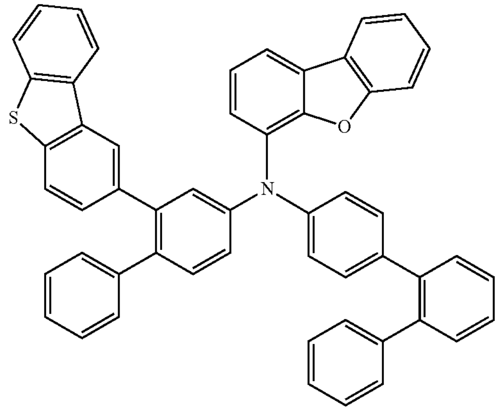
B212
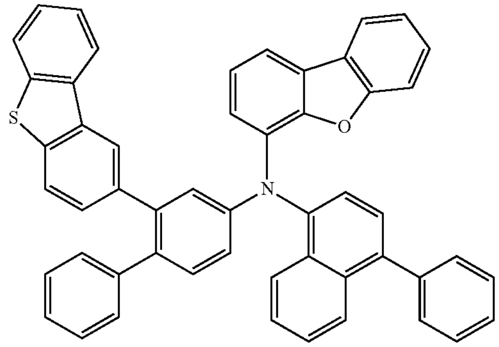
B213
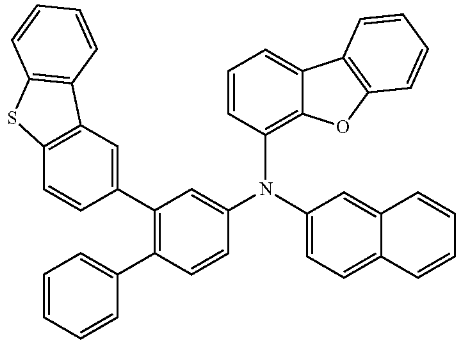
B214
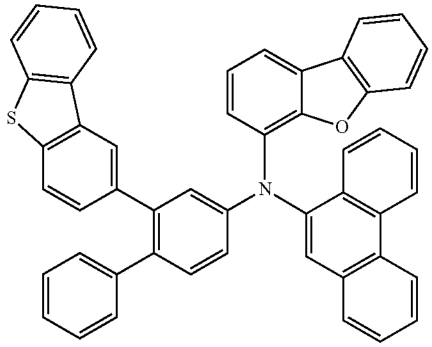

-continued
B215
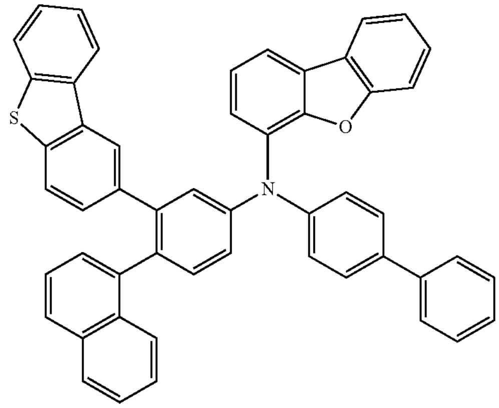
B216
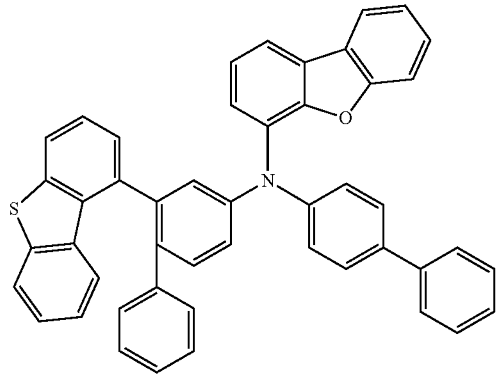
B217
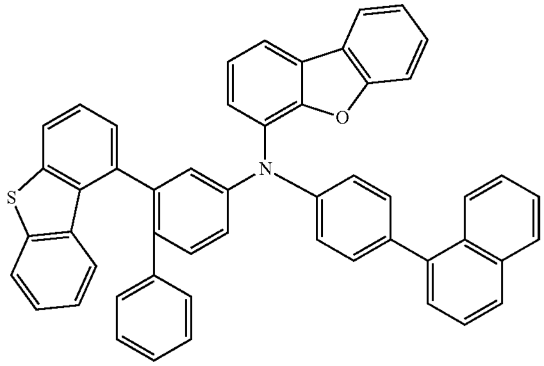
B218
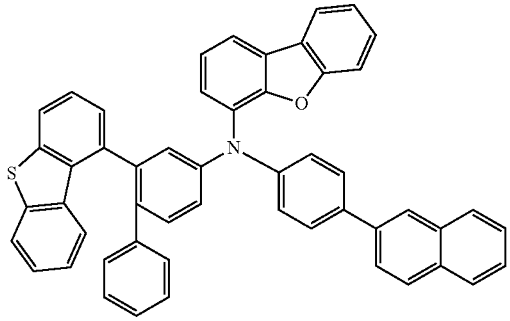
-continued
B219
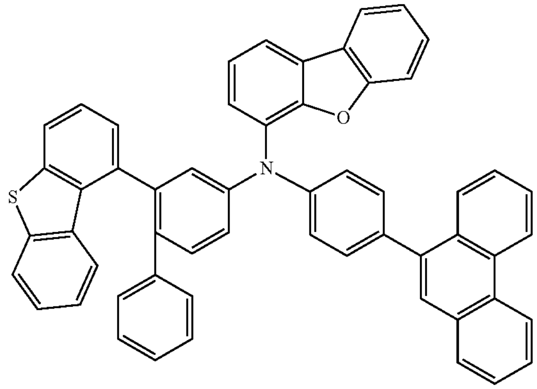
B220
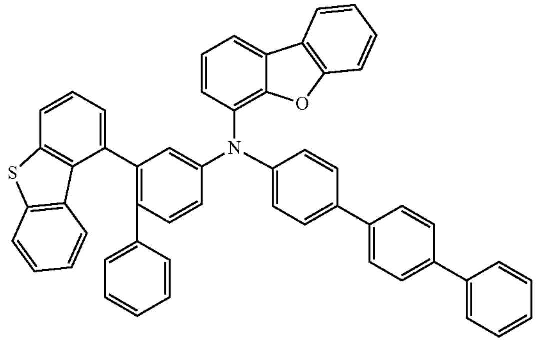
B221
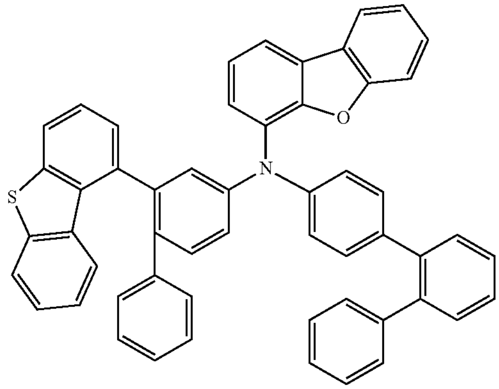
B222
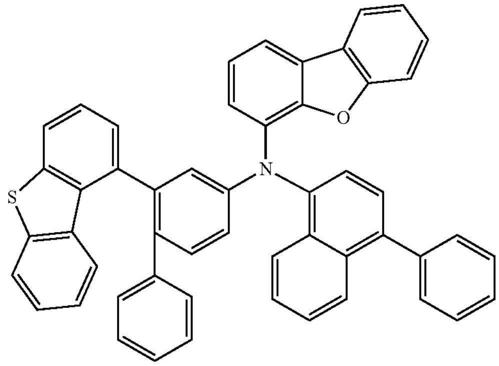

B223
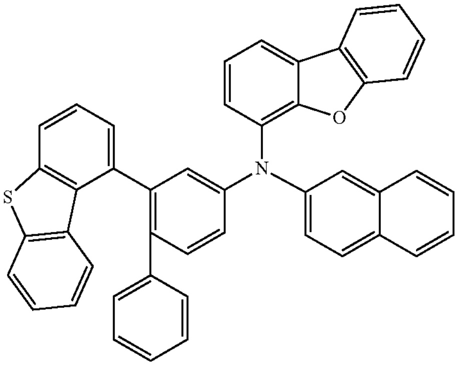
B224
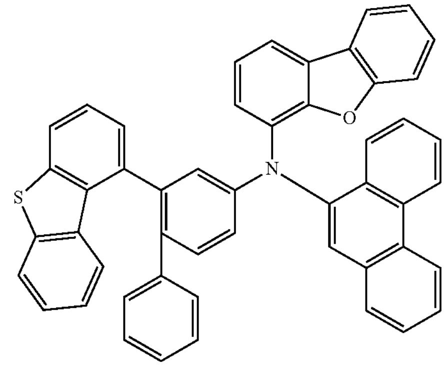
B225
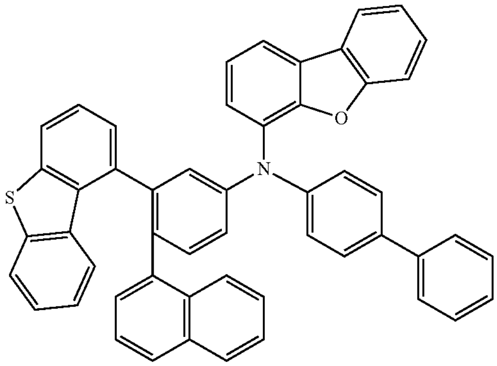
B226
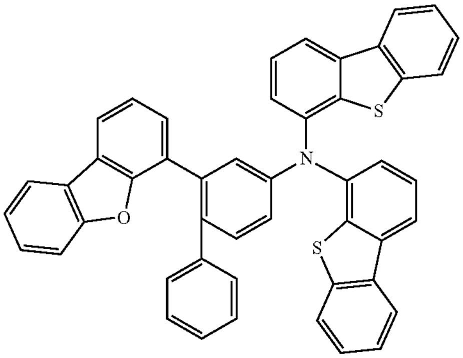
B227
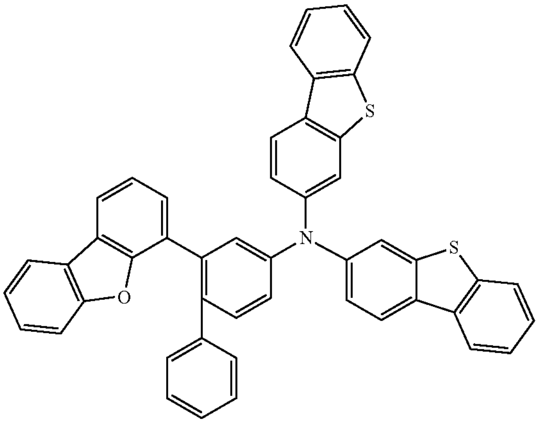
B228
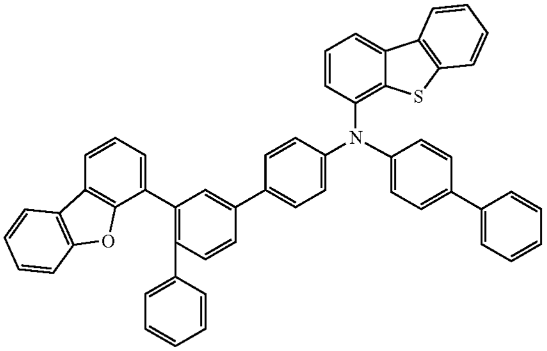
B229
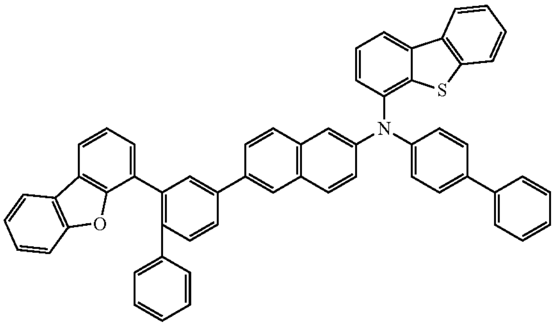
B230
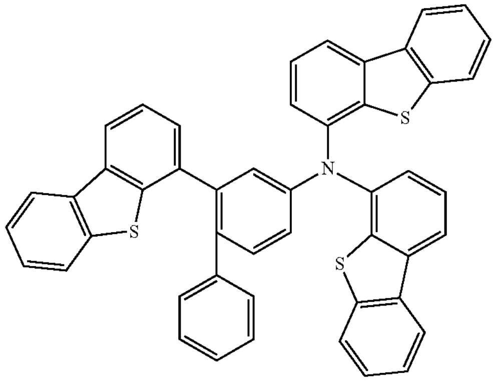

B231
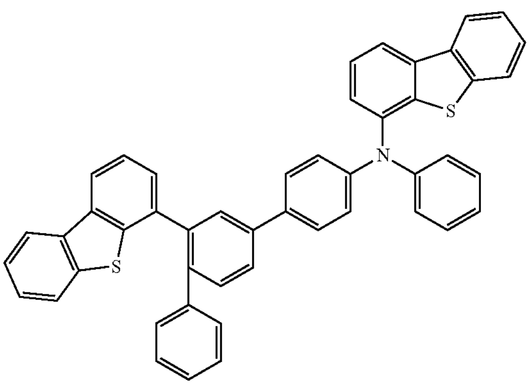
B232
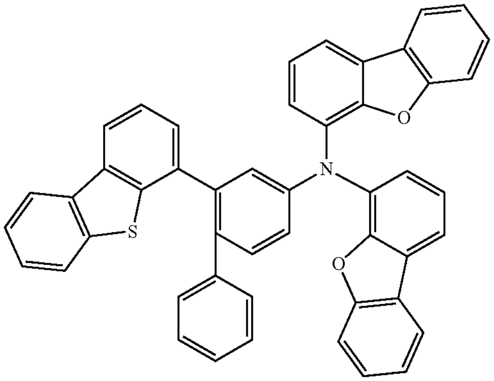
B233
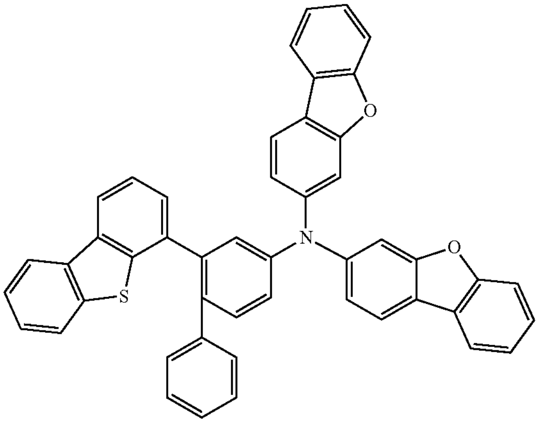
B234
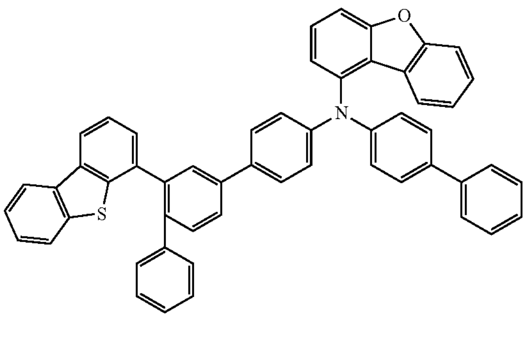
B235
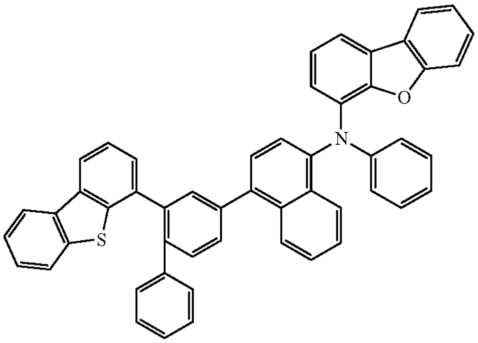
B236
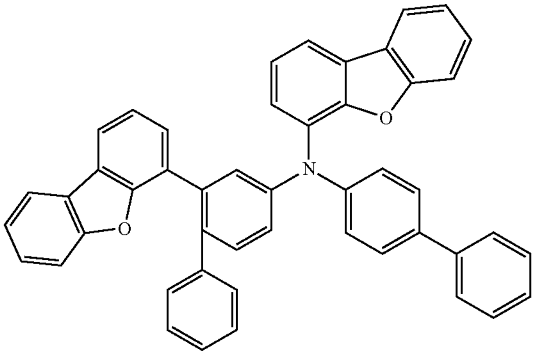
B237
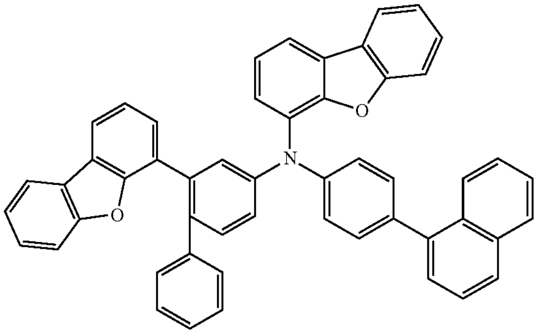
B238
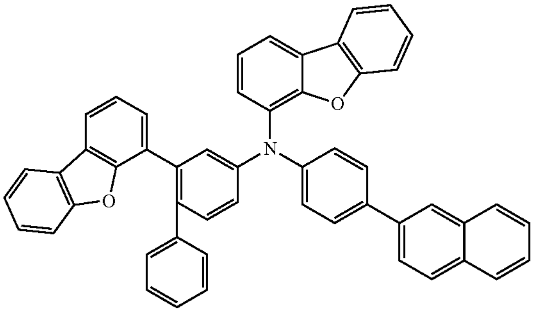

-continued
B239
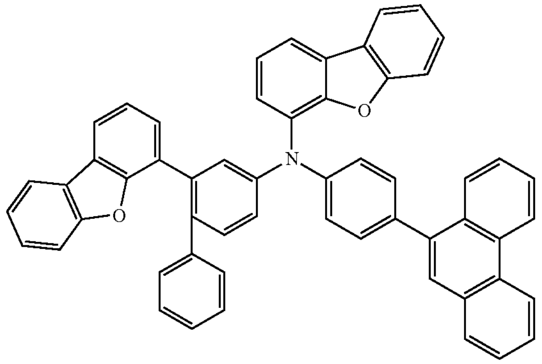
B240
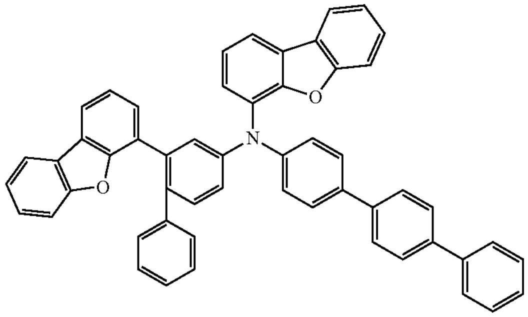
B241
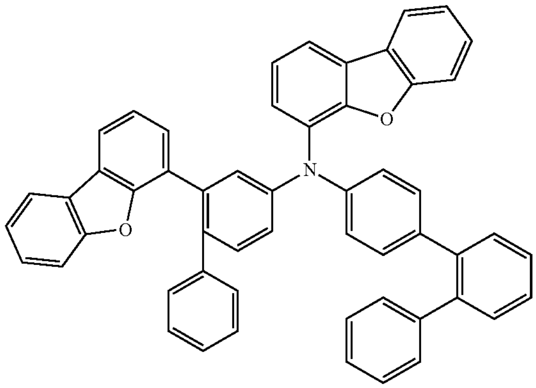
B242
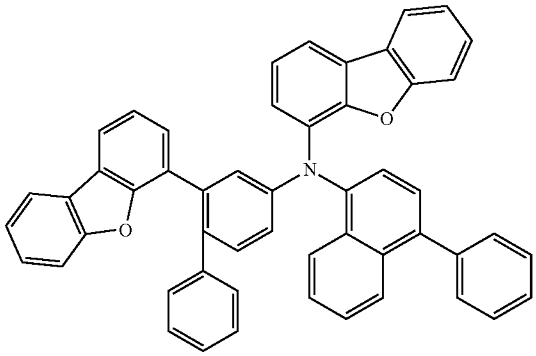
-continued
B243
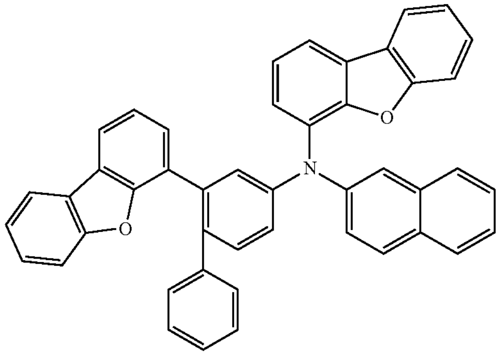
B244
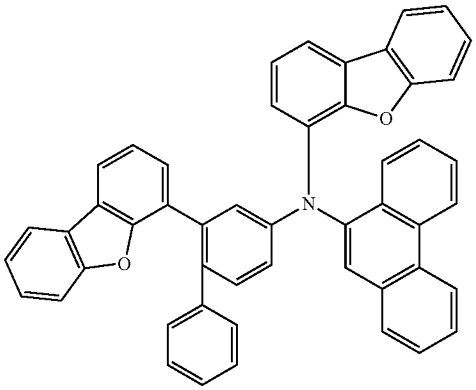
B245
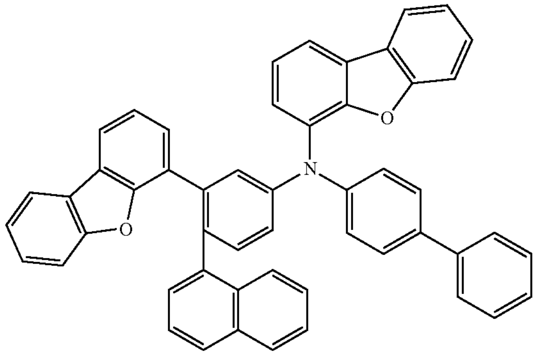

Compound Group 3
C1
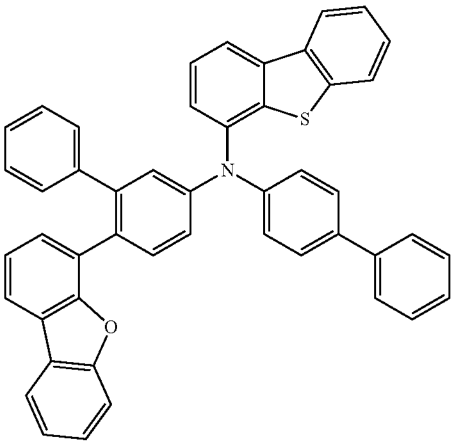
C2
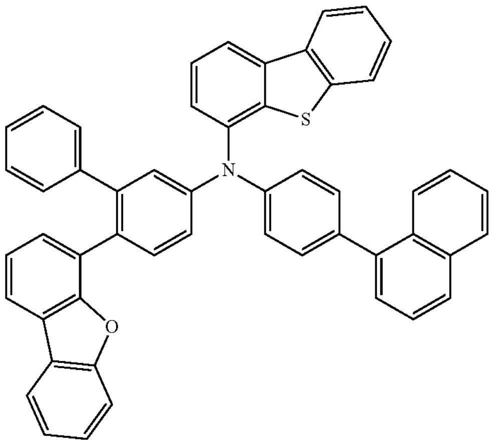
C3
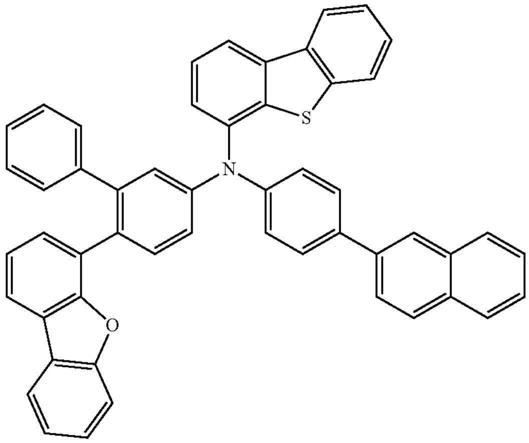
-continued
C4
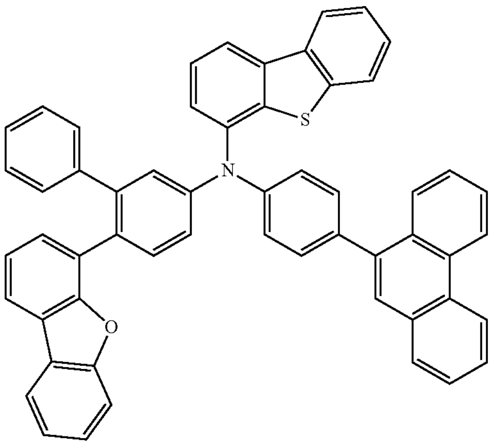
C5
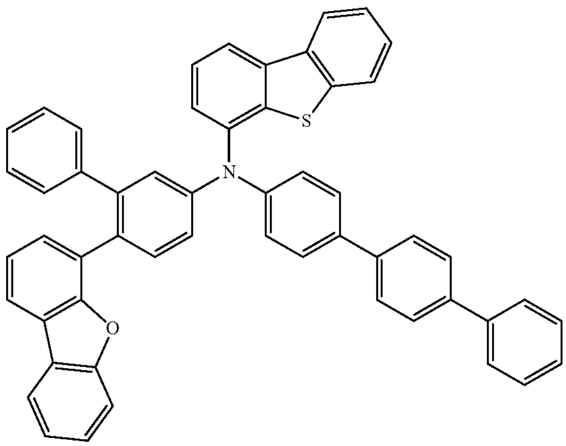
C6
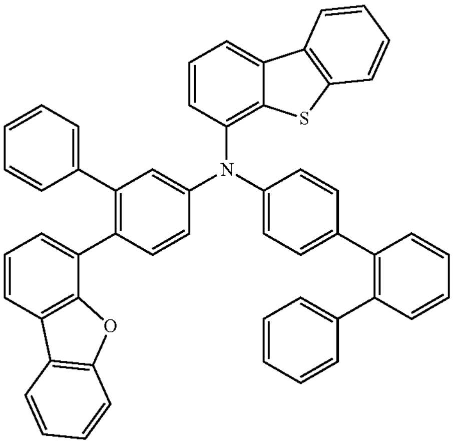

-continued
C7
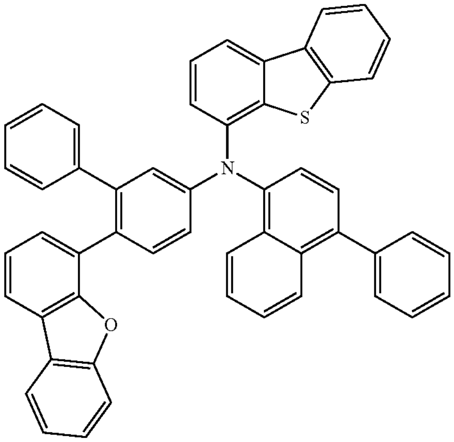
C8
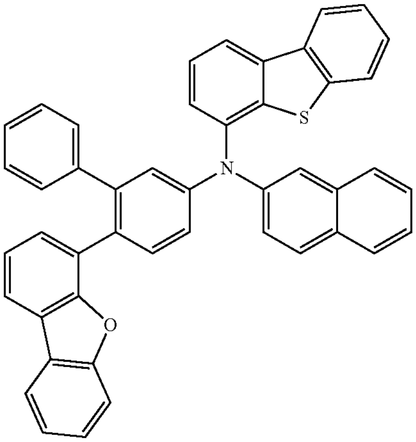
C9
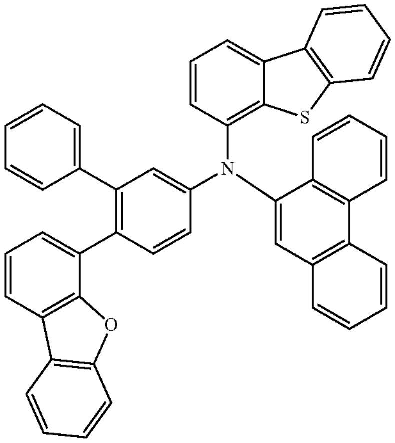
-continued
C10
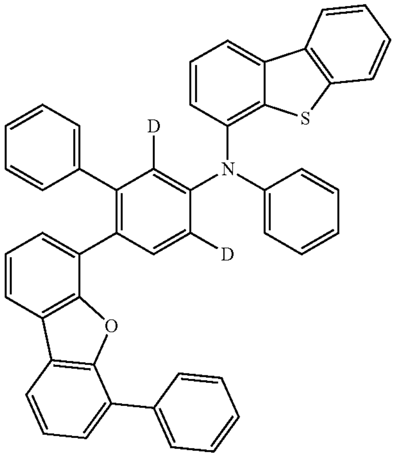
C11
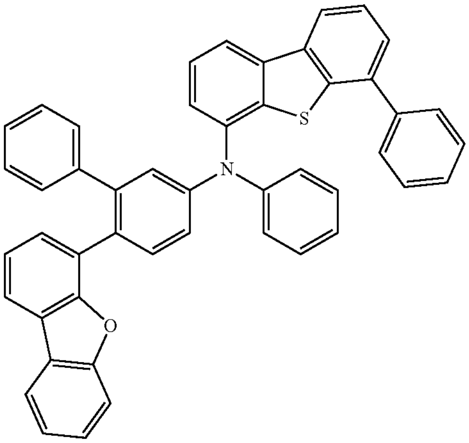
C12
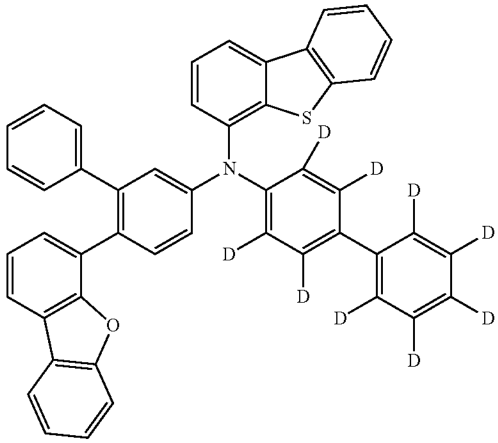

-continued
C13
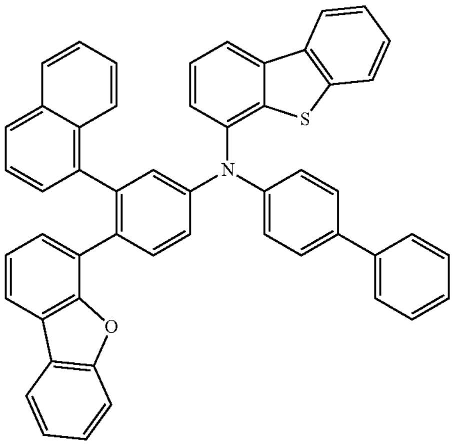
C14
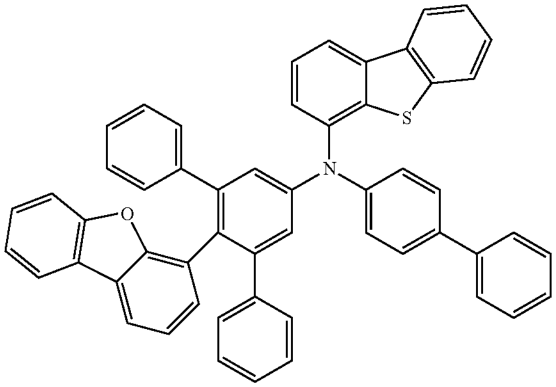
C15
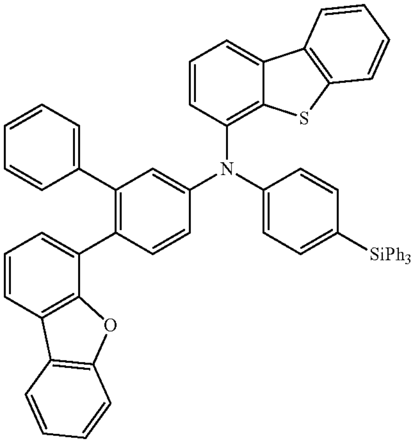
-continued
C16
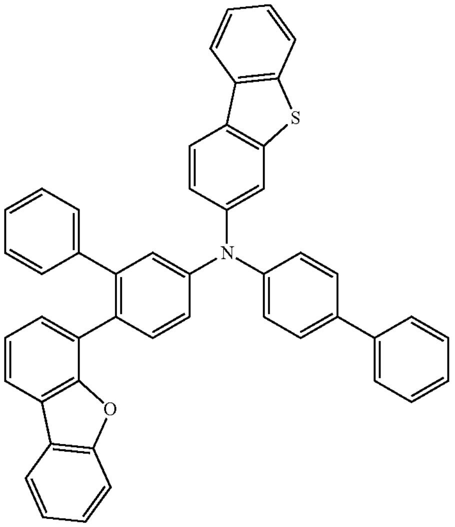
C17
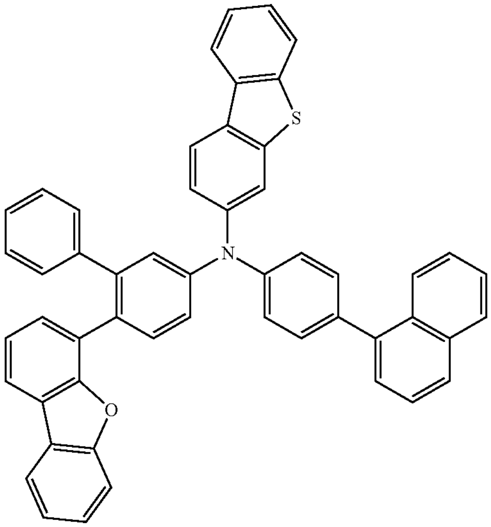
C18
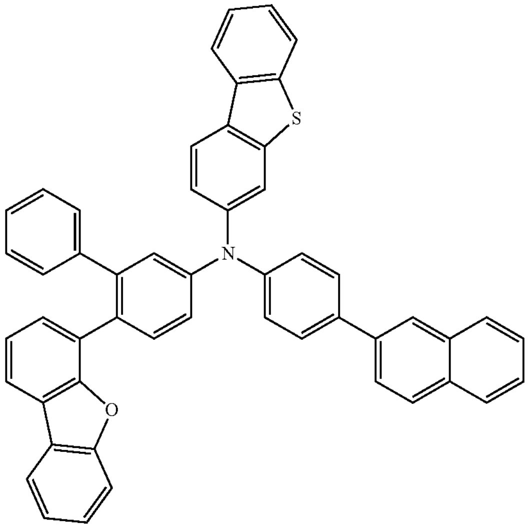

-continued
C19
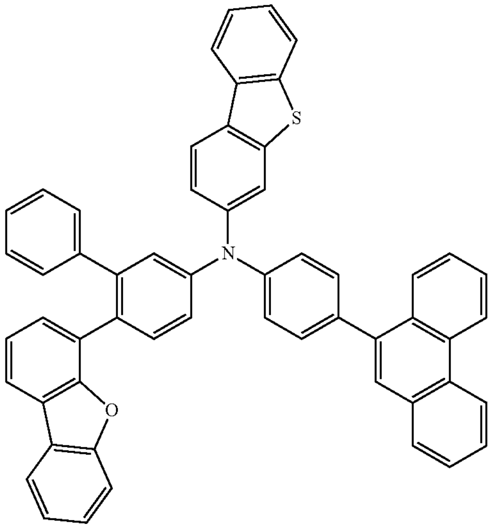
C20
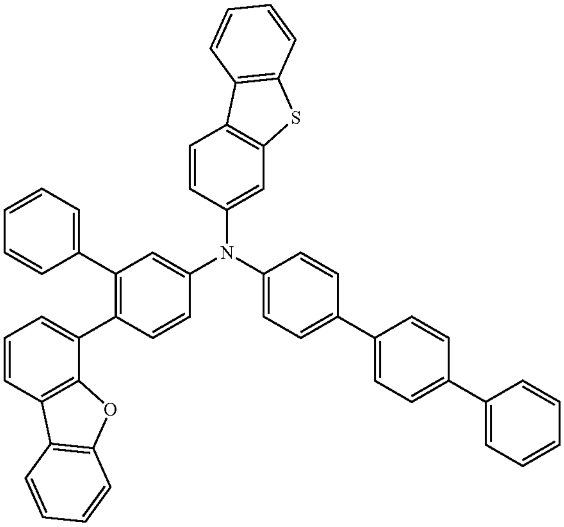
C21
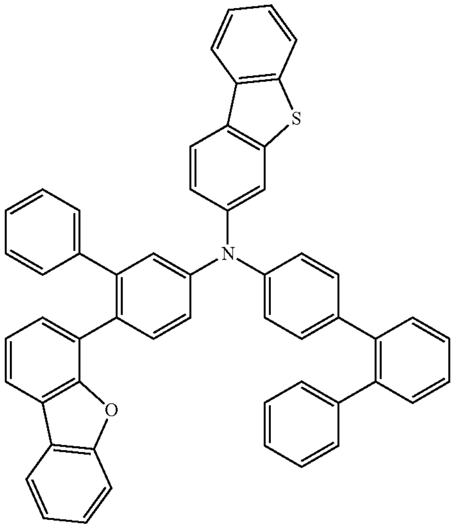
-continued
C22
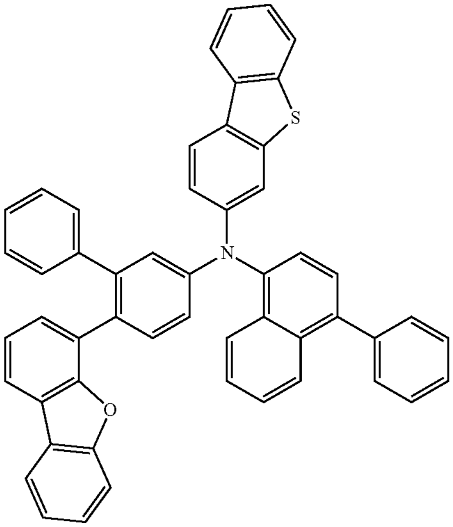
C23
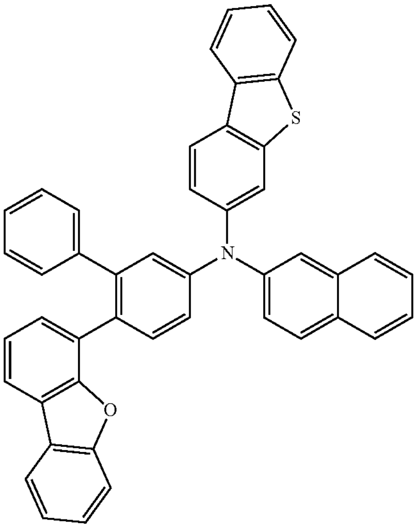
C24
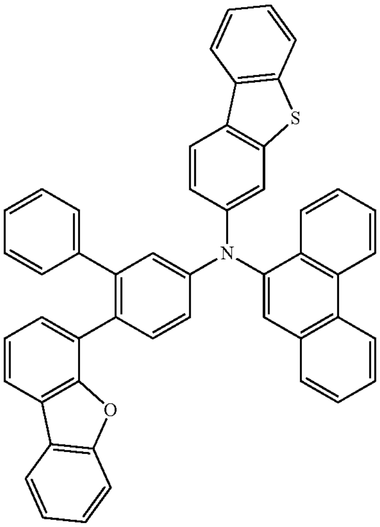

-continued
C25
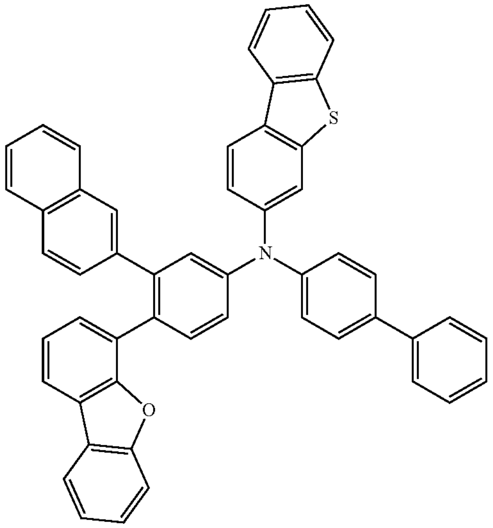
C26
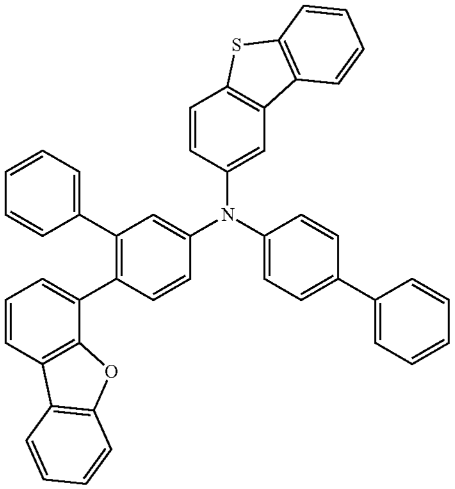
C27
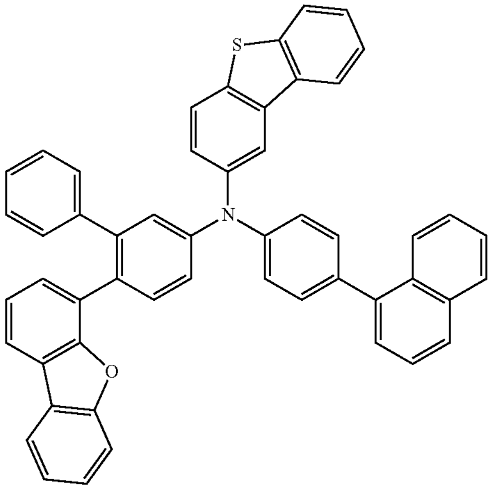
-continued
C28
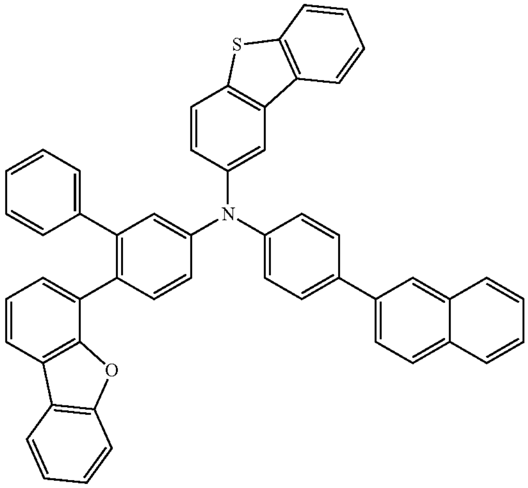
C29
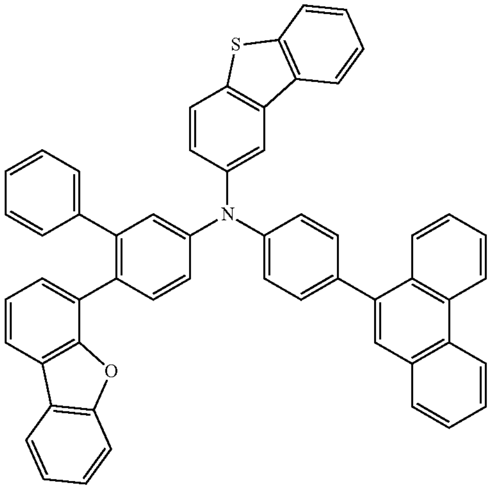
C30
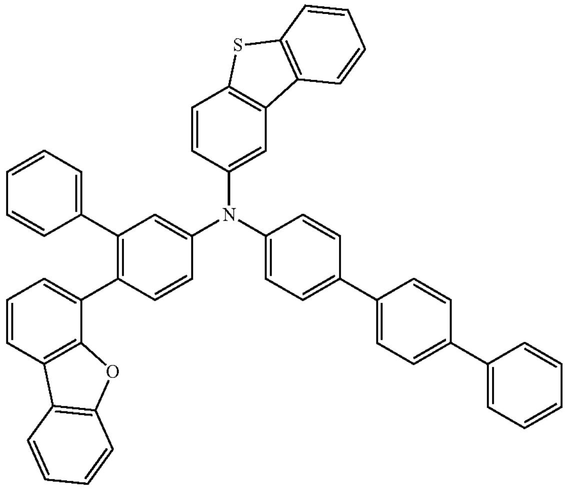

-continued
C31
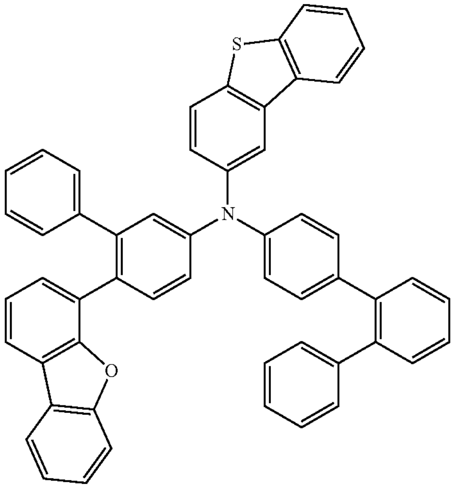
C32
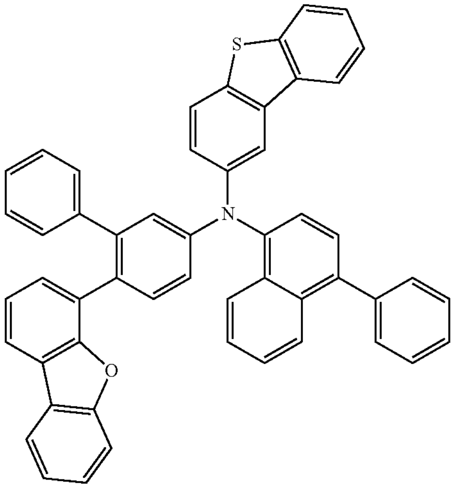
C33
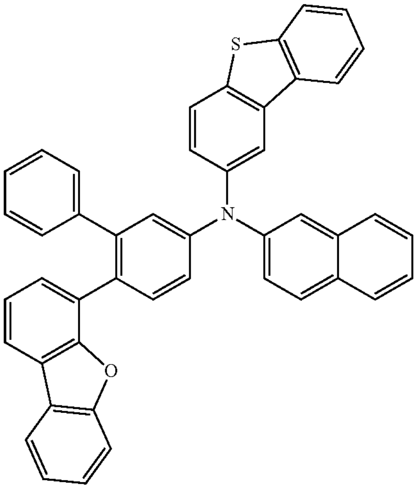
-continued
C34
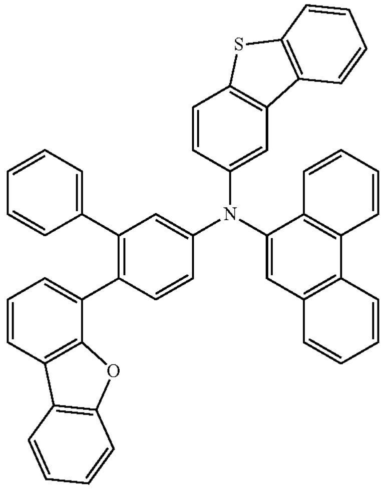
C35
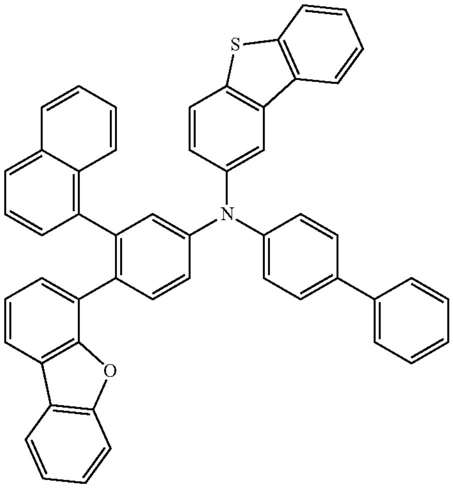
C36
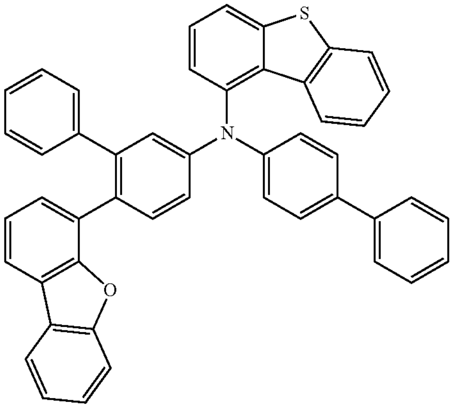

-continued
C37
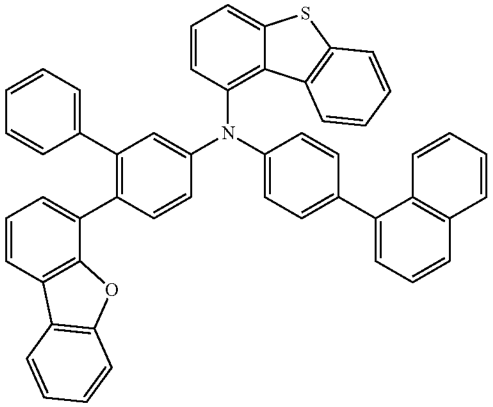
C38
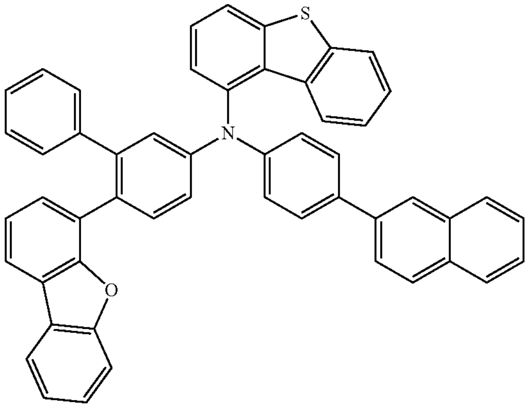
C39
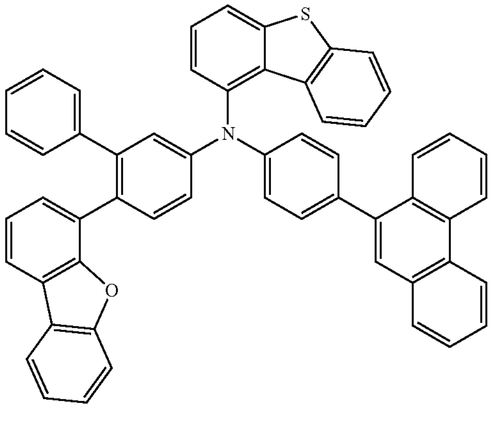
-continued
C40
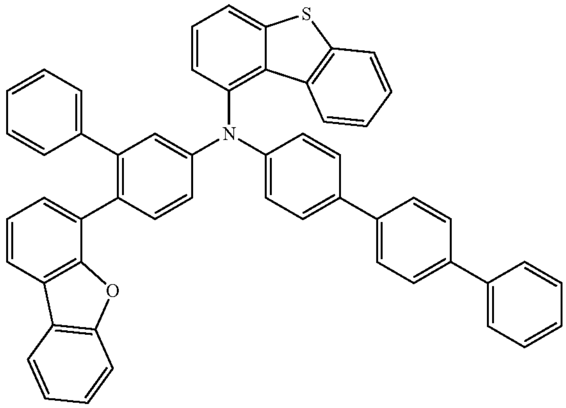
C41
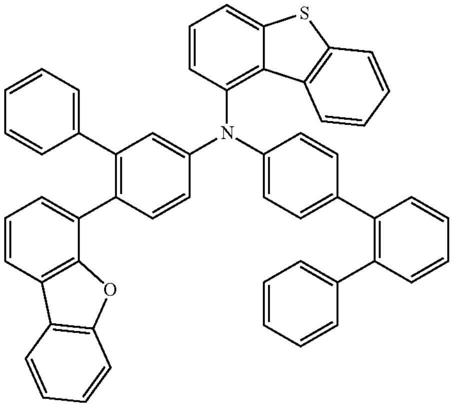
C42
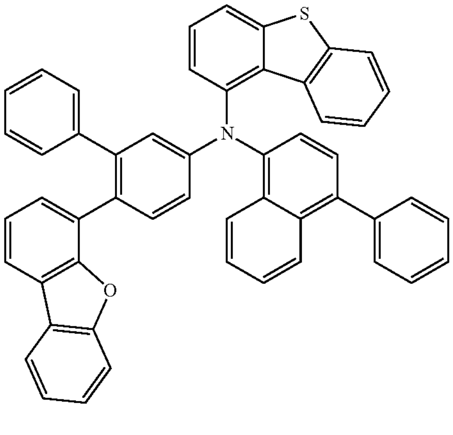

-continued
C43
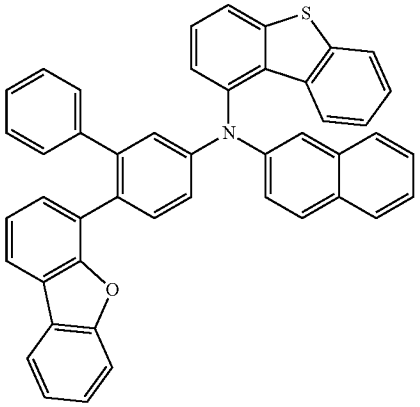
C44
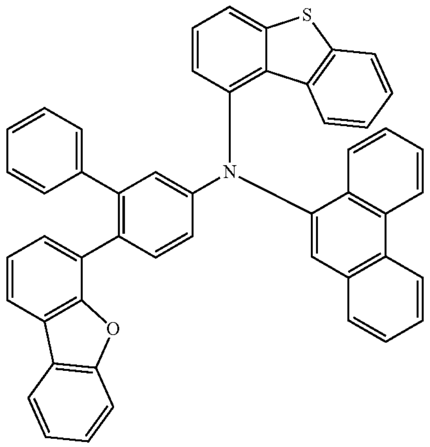
C45
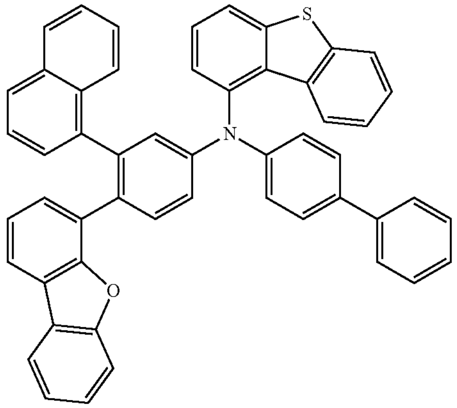
C46
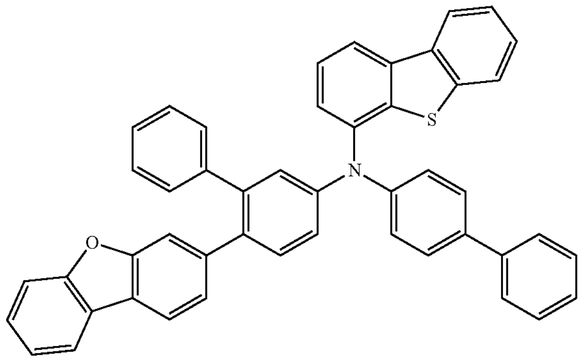
-continued
C47
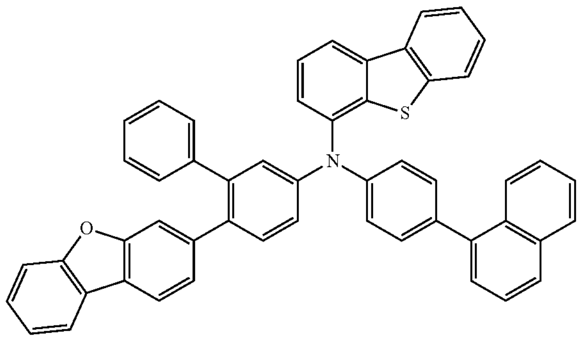
C48
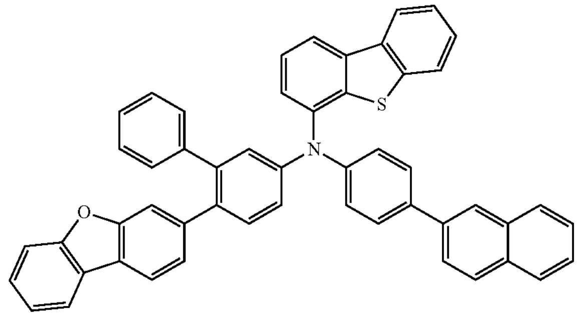
C49
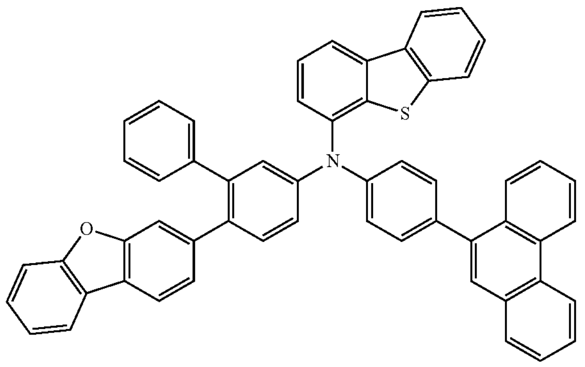
C50
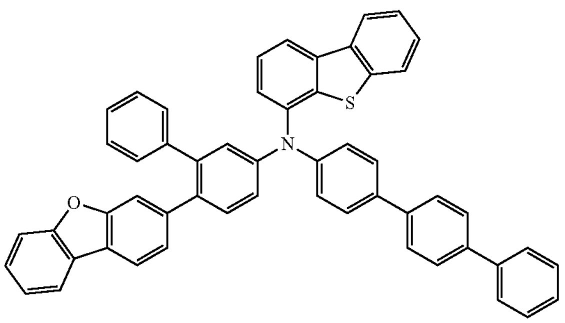

-continued
C51
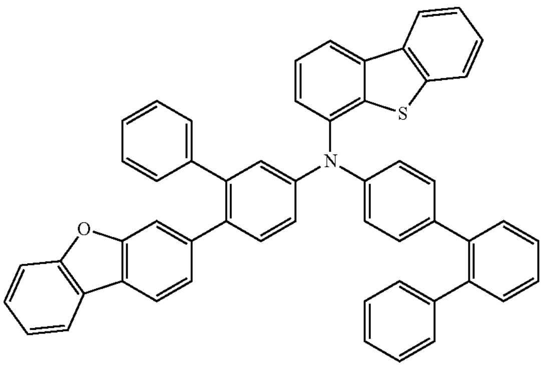
C52
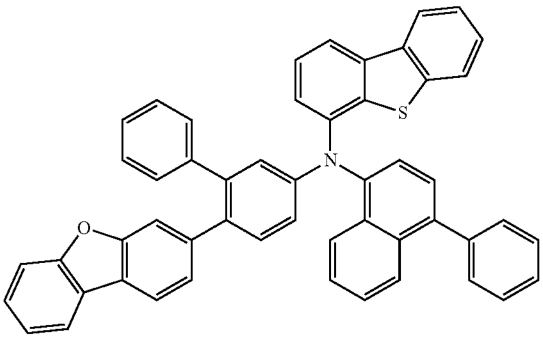
C53
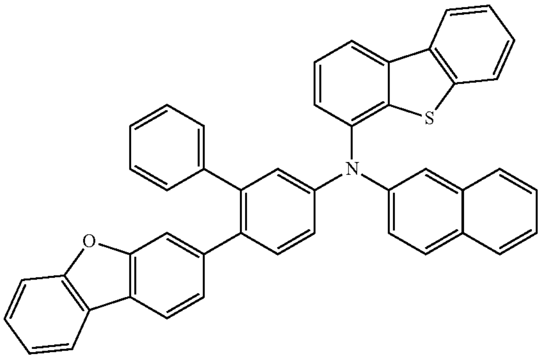
C54
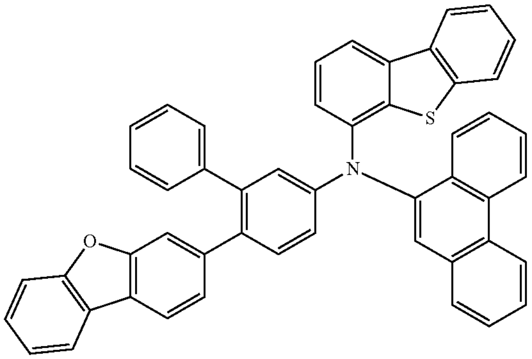
-continued
C55
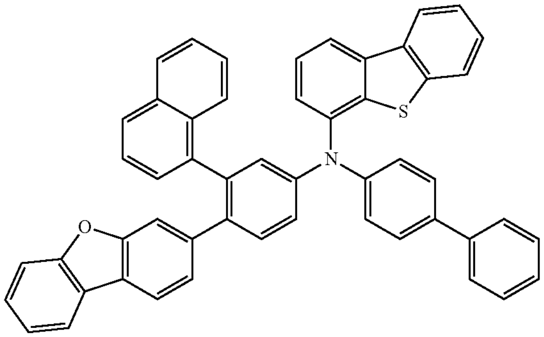
C56
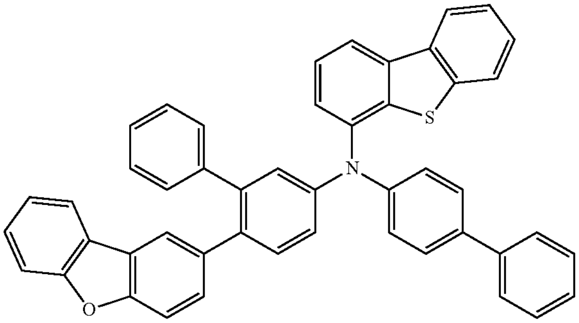
C57
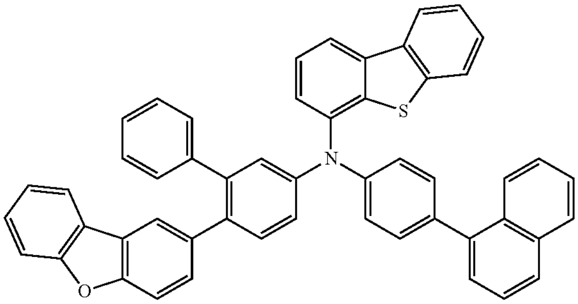
C58
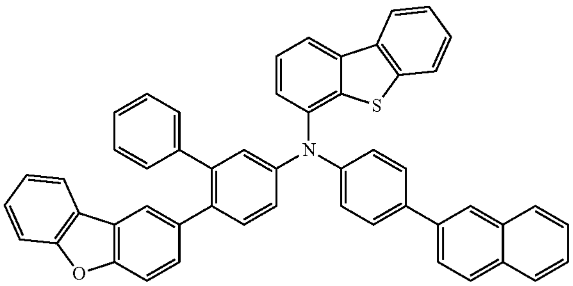

-continued
C59
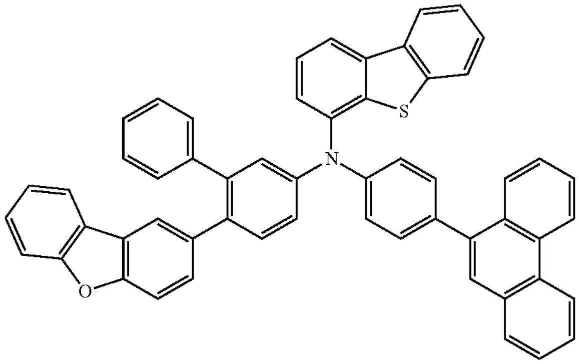
C60
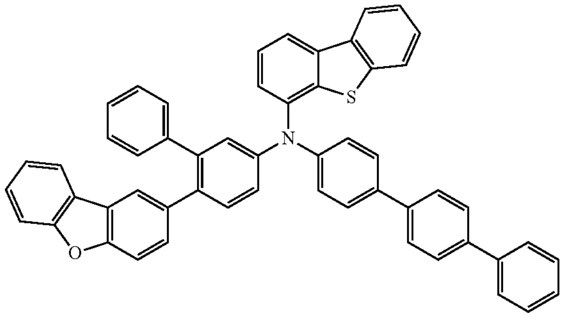
C61
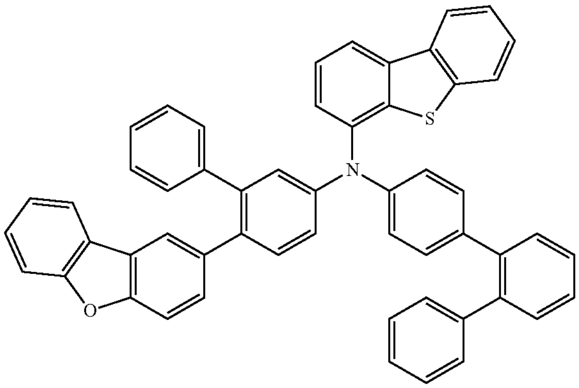
C62
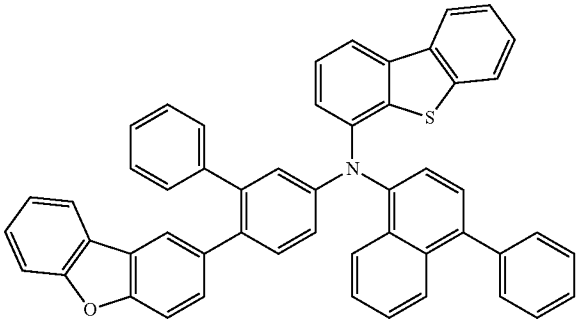
-continued
C63
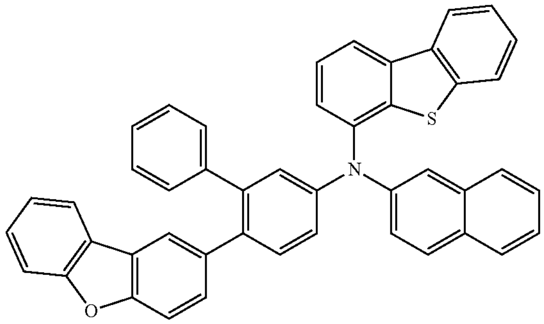
C64
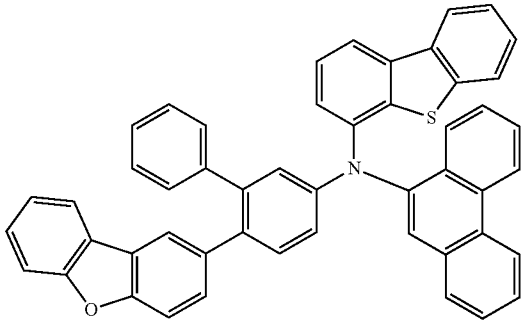
C65
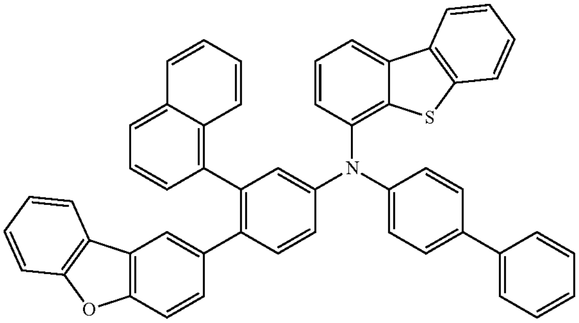
C66
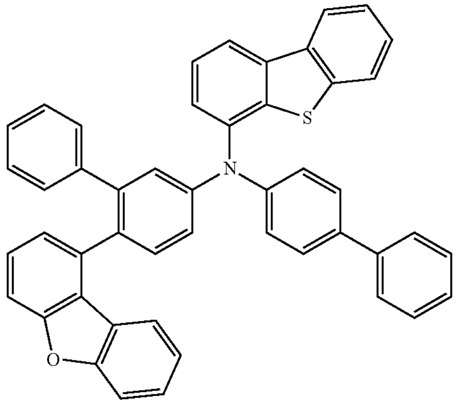

-continued
C67
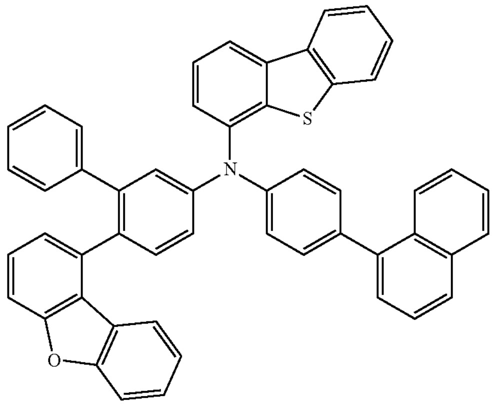
C68
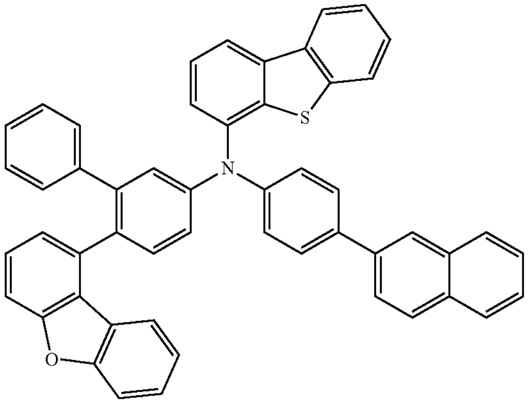
C69
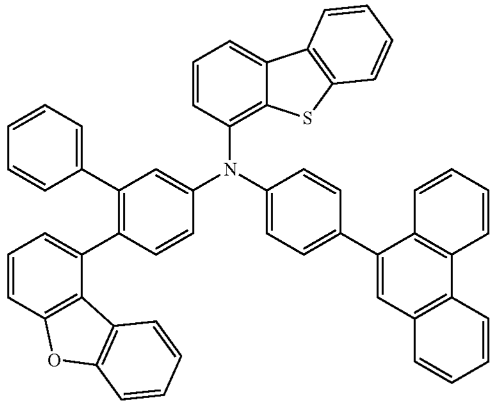
-continued
C70
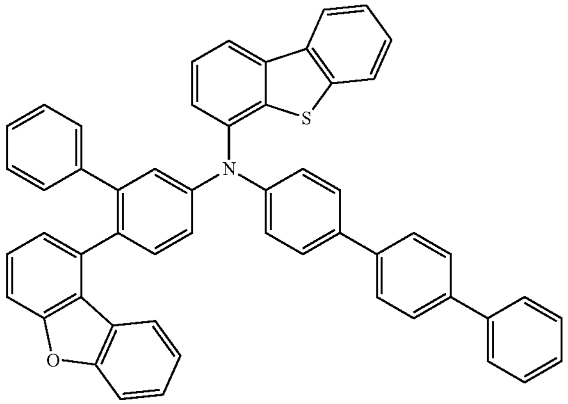
C71
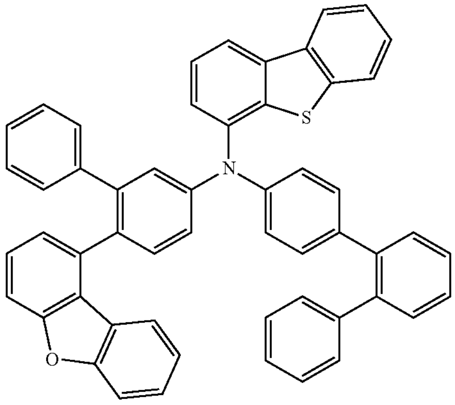
C72
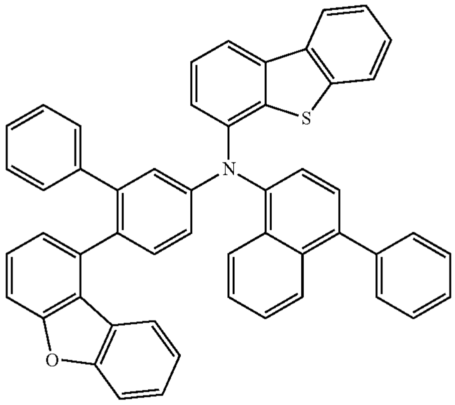
C73
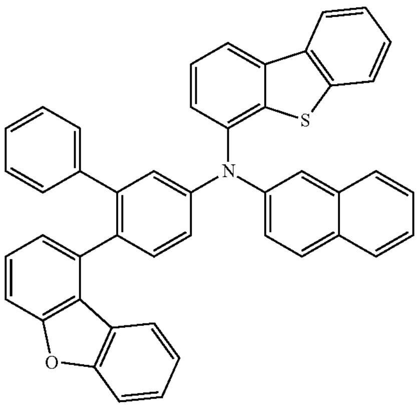

-continued
C74
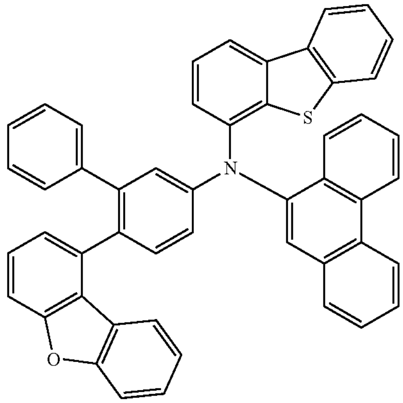
C75
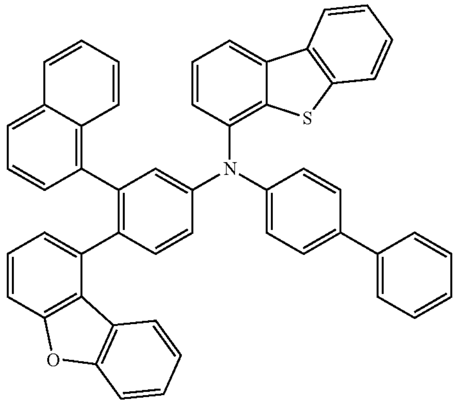
C76
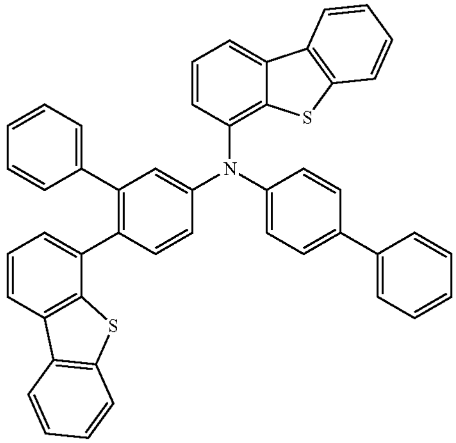
-continued
C77
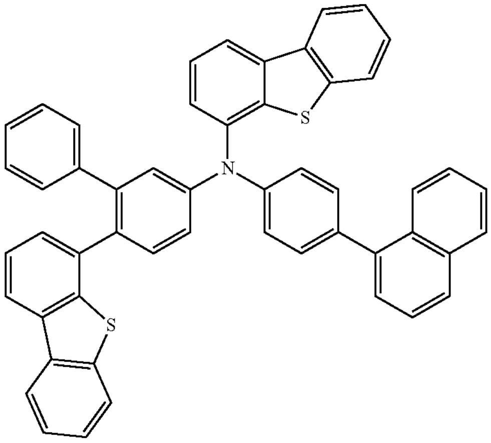
C78
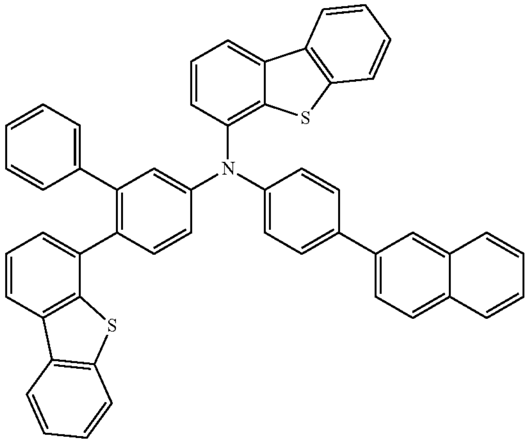
C79
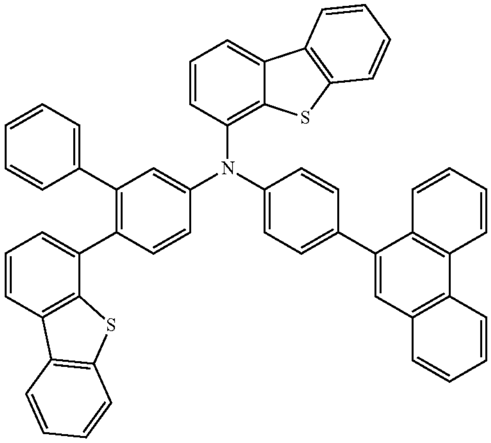

C80
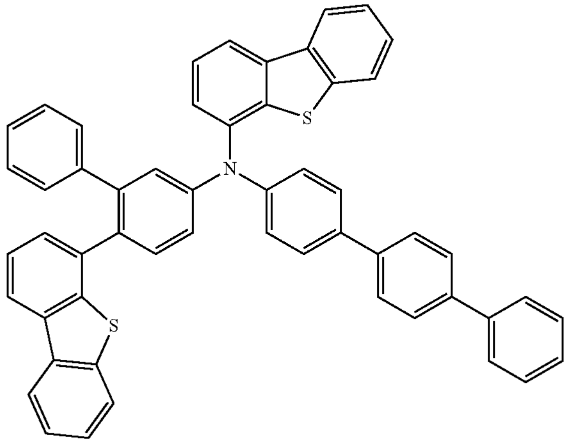
C81
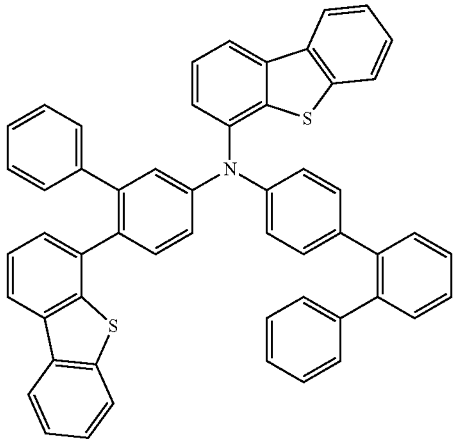
C82
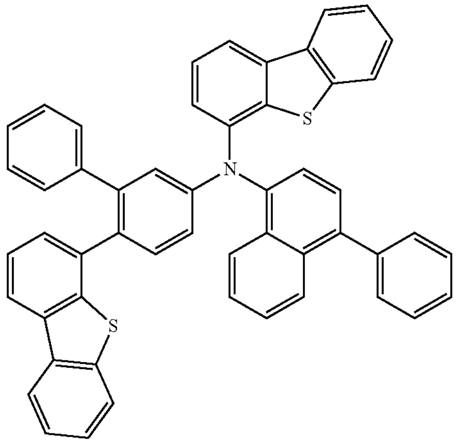
C83
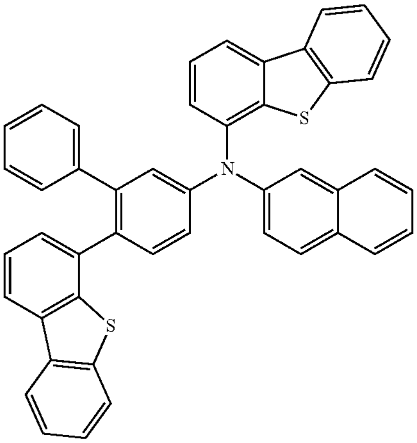
C84
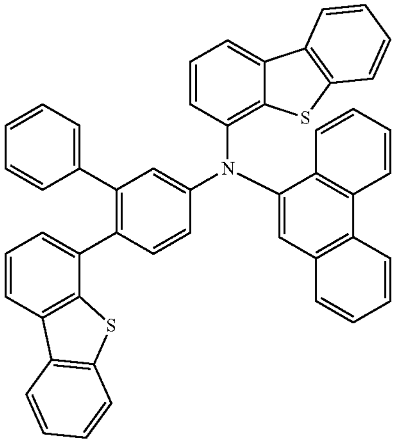
C85
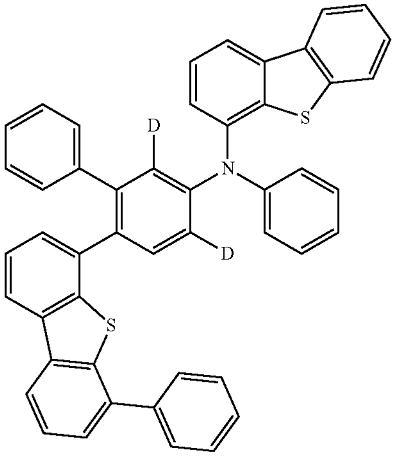

-continued
C86
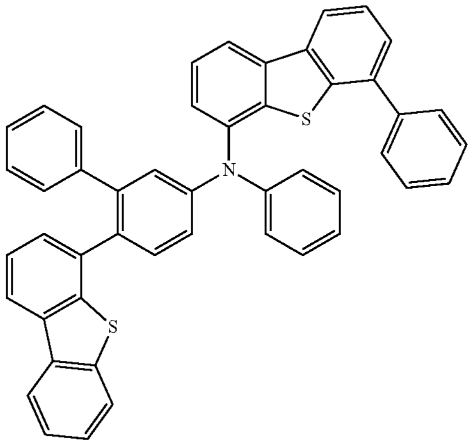
C87
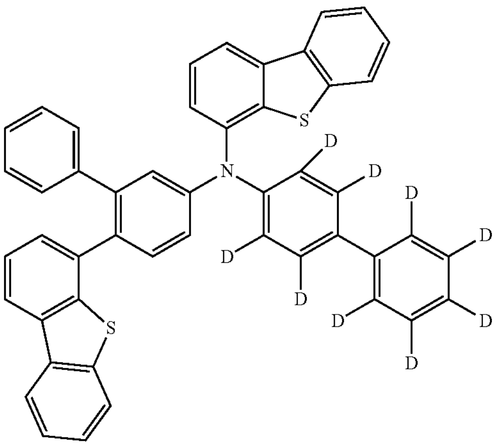
C88
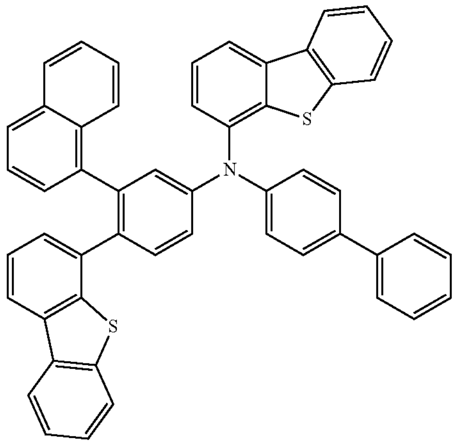
-continued
C89
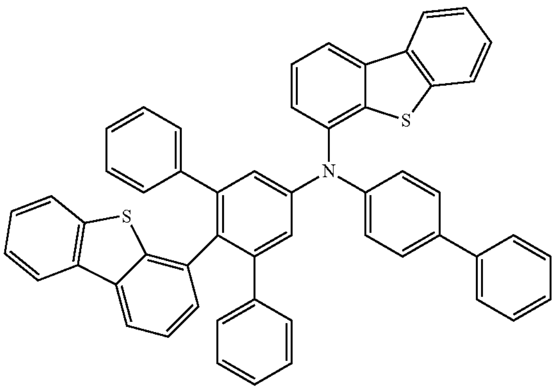
C90
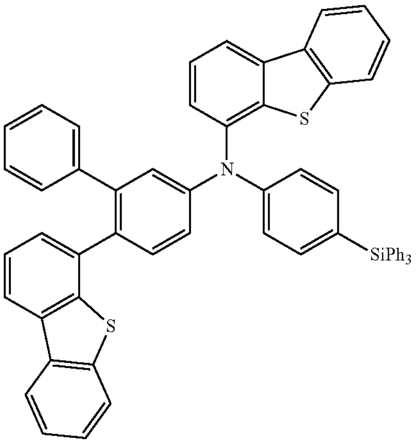
C91
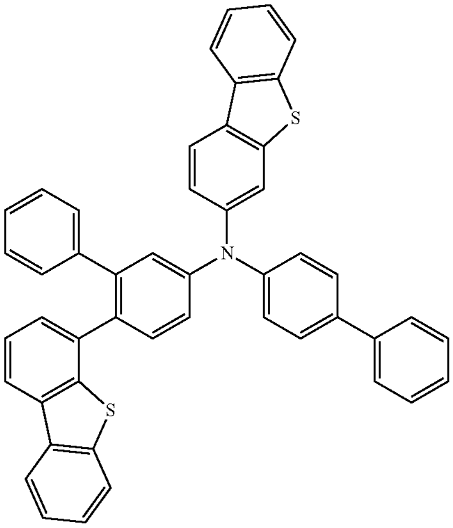

-continued
C92
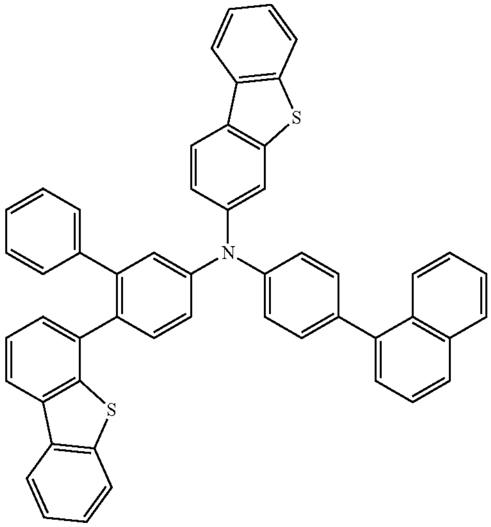
C93
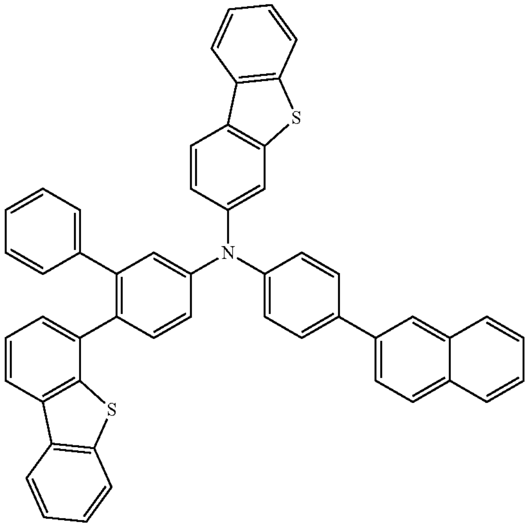
C94
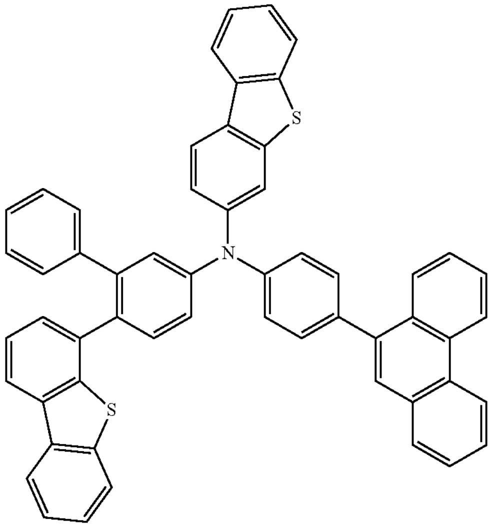
-continued
C95
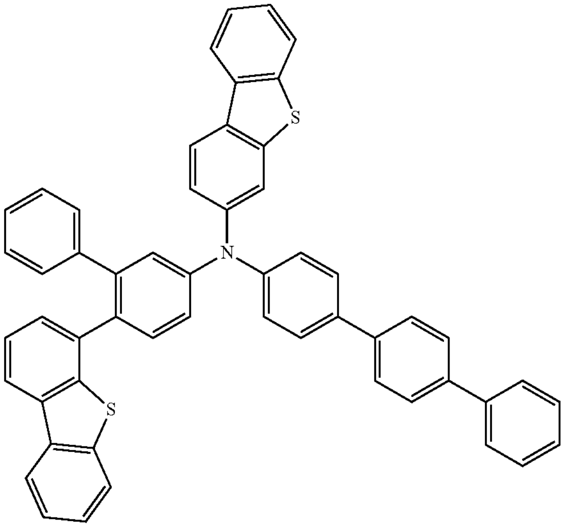
C96
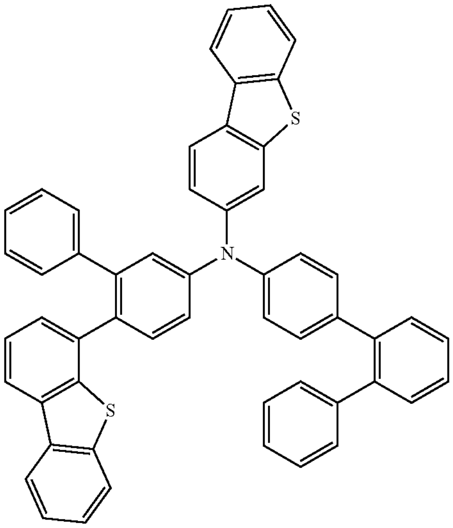
C97
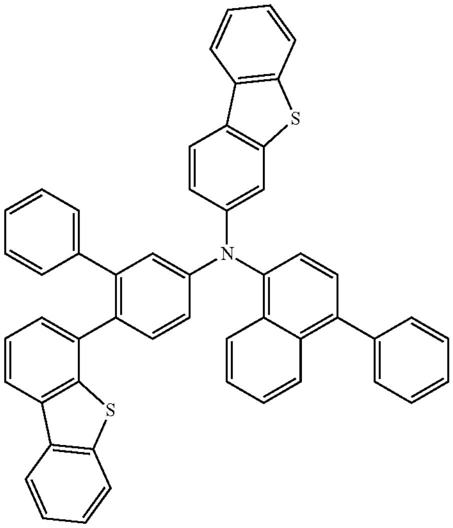

-continued
C98
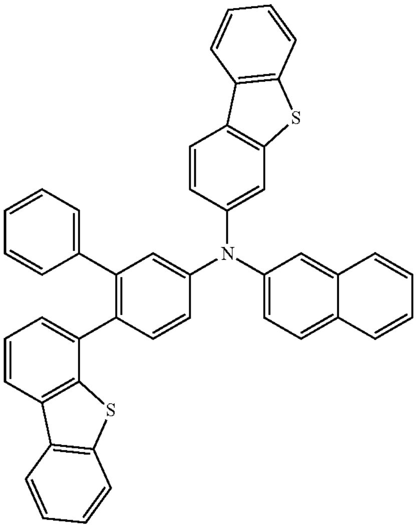
C99
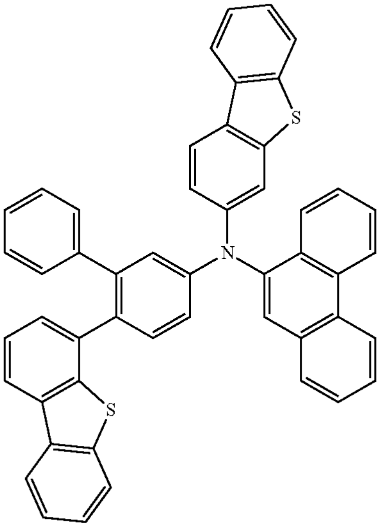
C100
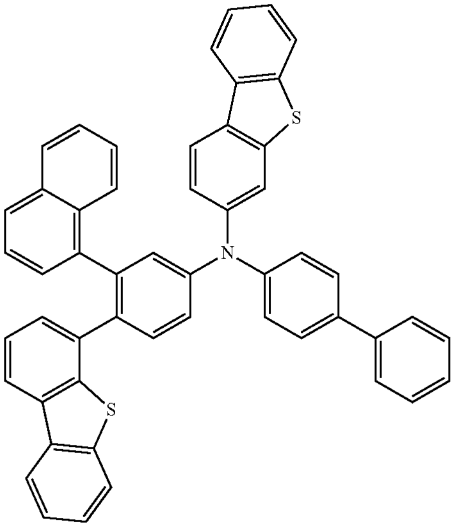
-continued
C101
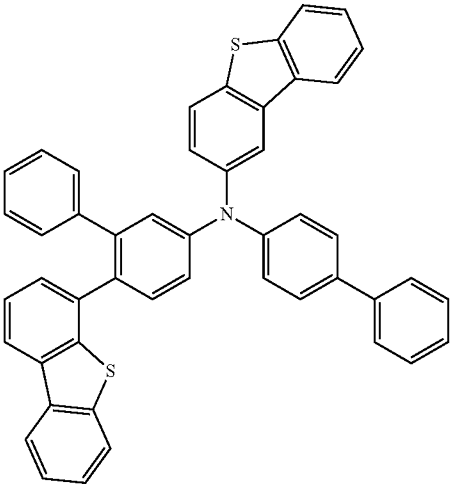
C102
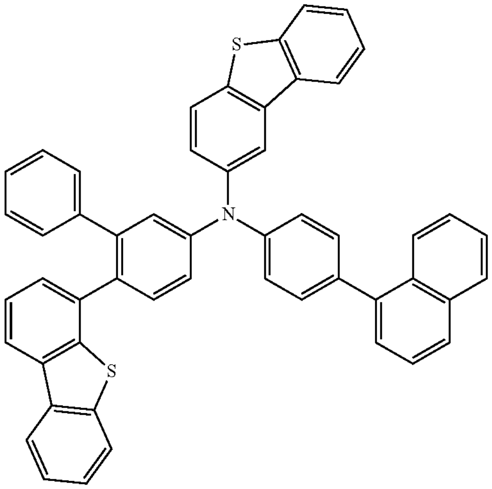
C103
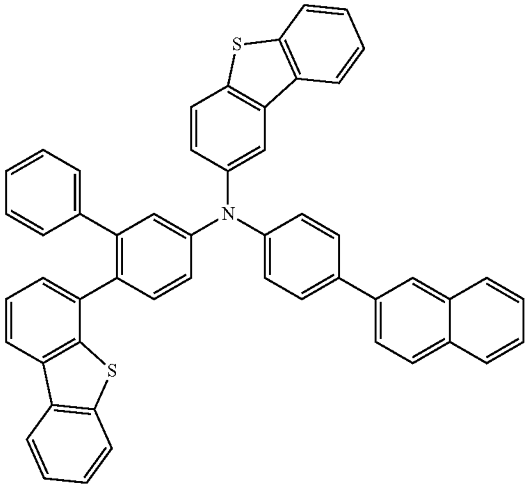

-continued
C104
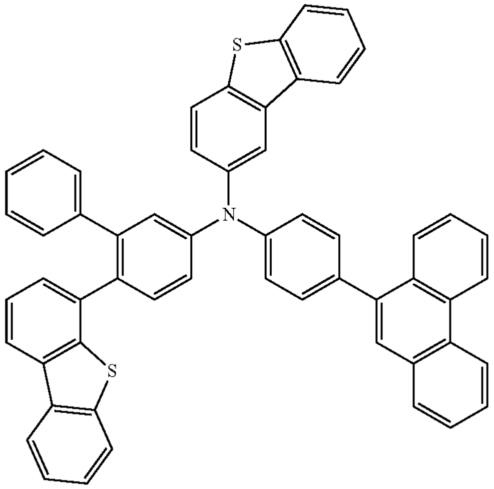
C105
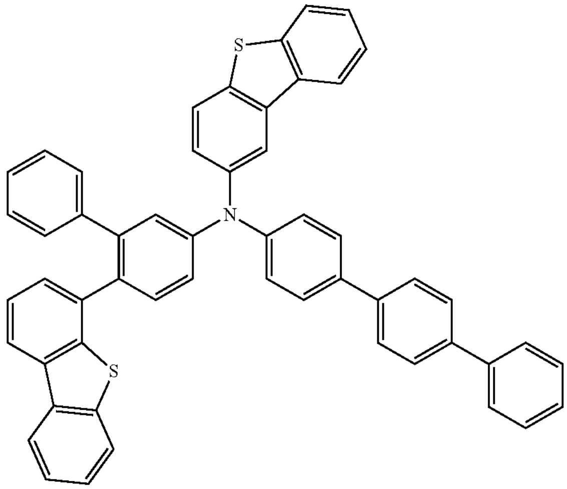
C106
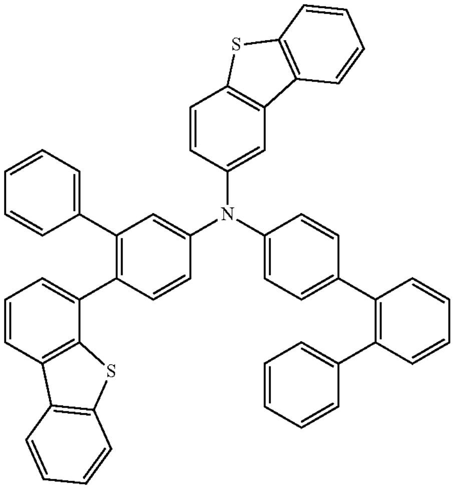
-continued
C107
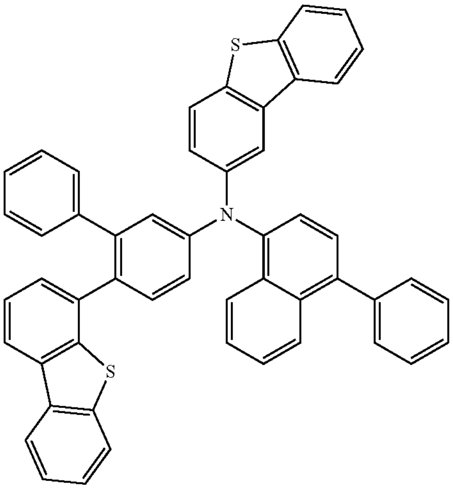
C108
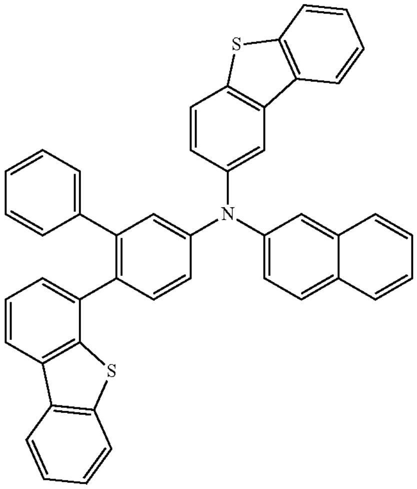
C109
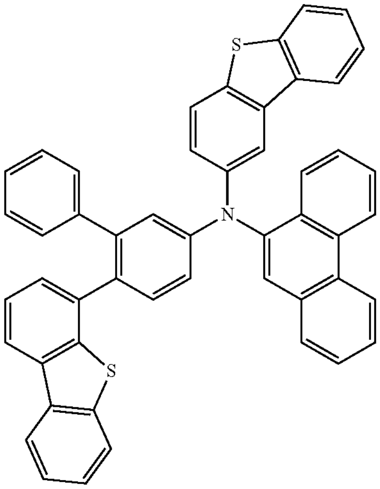

-continued
C110
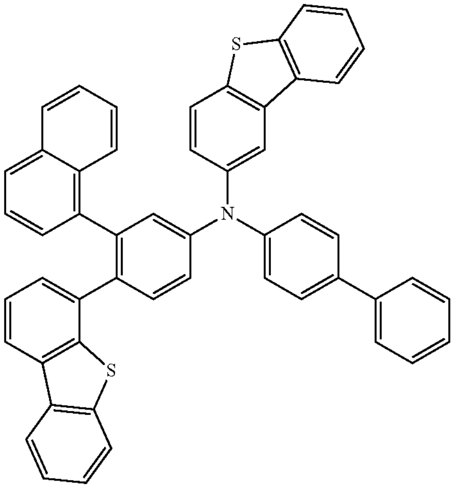
C111
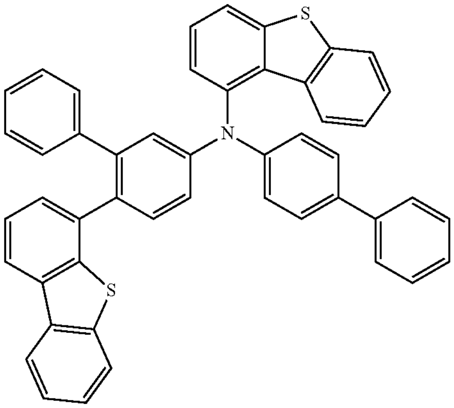
C112
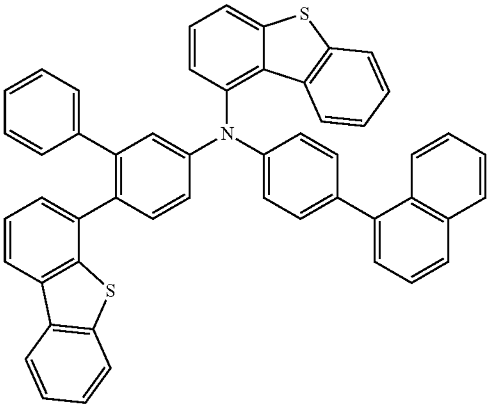
-continued
C113
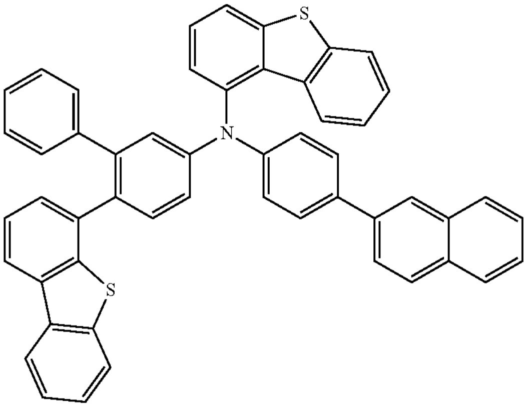
C114
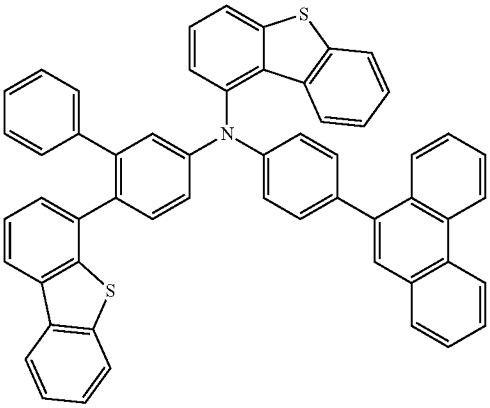
C115
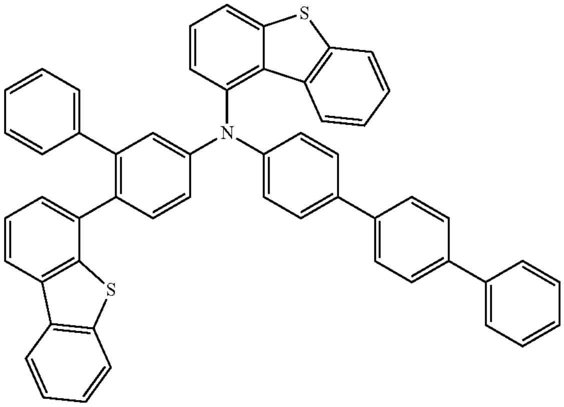

-continued
C116
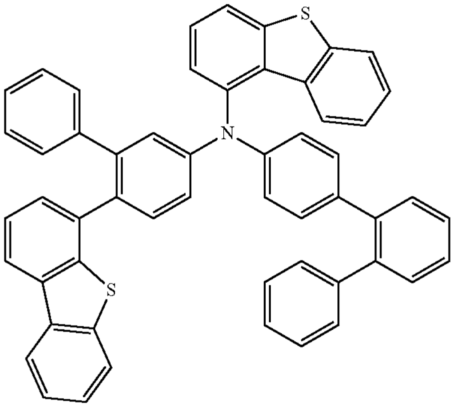
C117
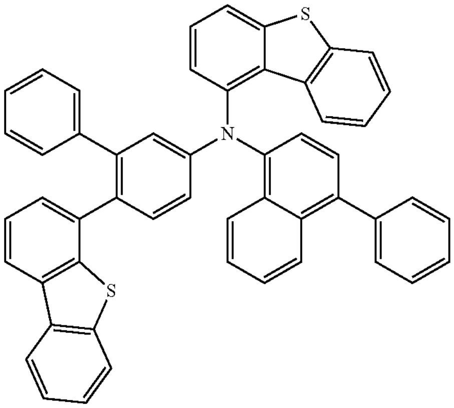
C118
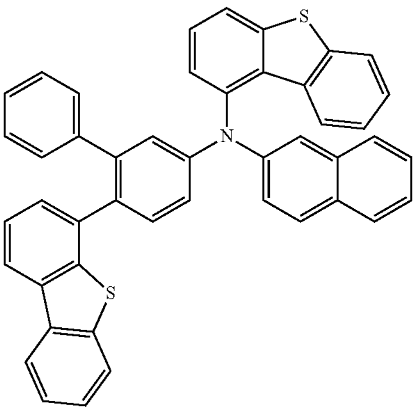
-continued
C119
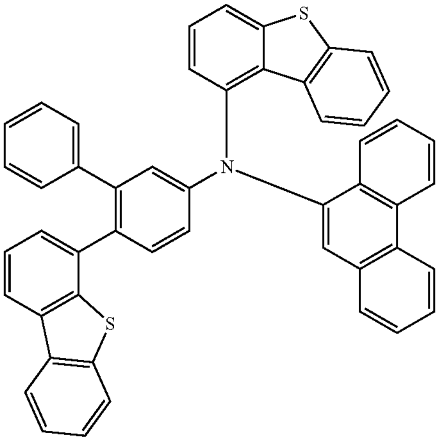
C120
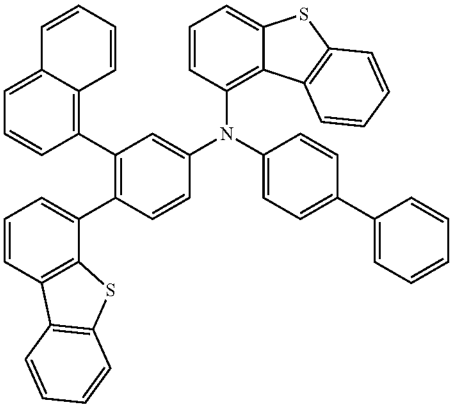
C121
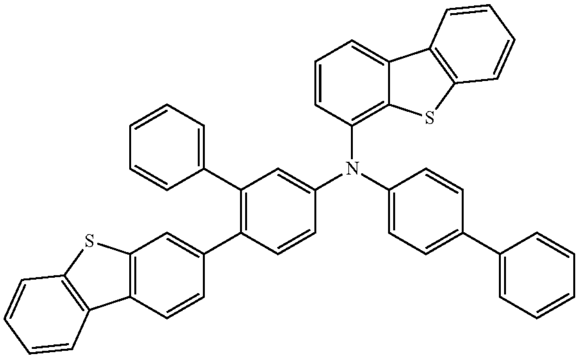
C122
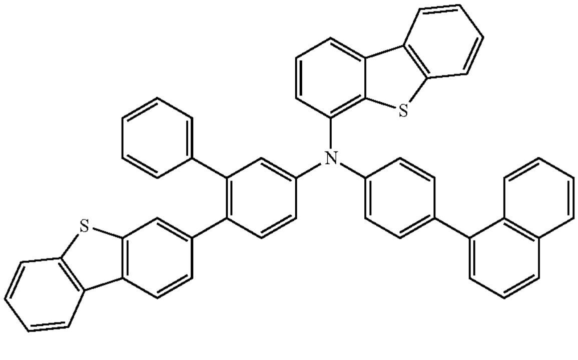

-continued
C123
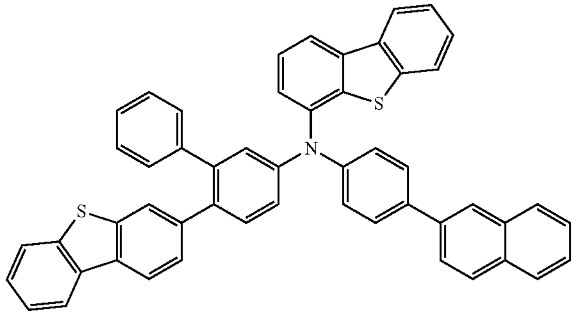
C124
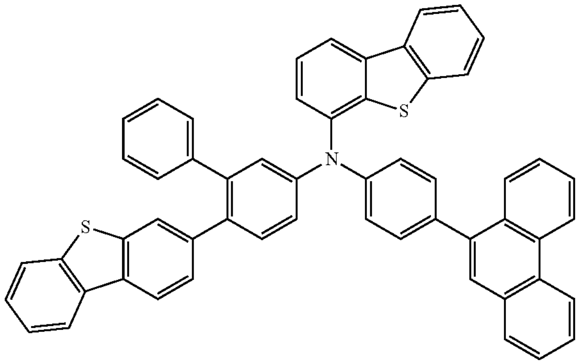
C125
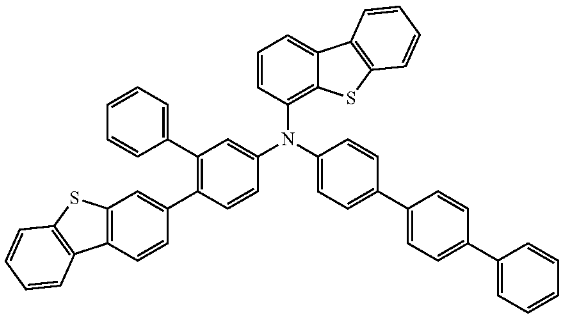
C126
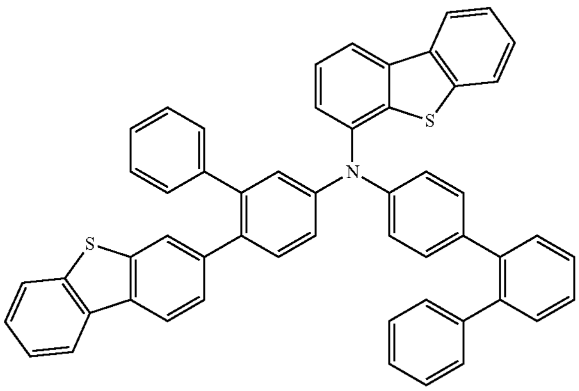
-continued
C127
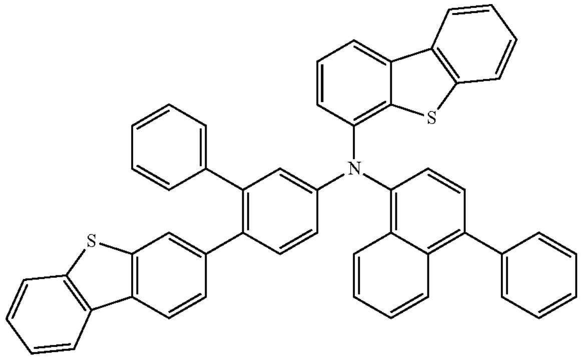
C128
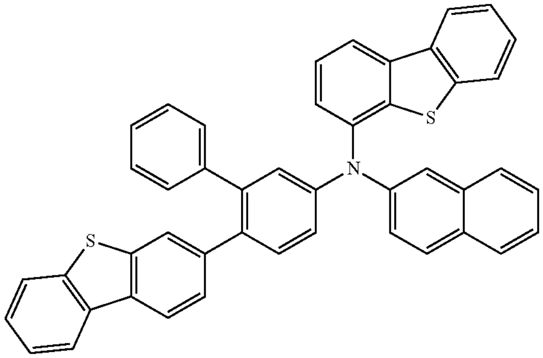
C129
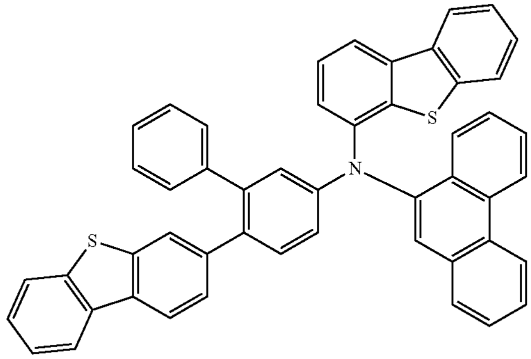
C130
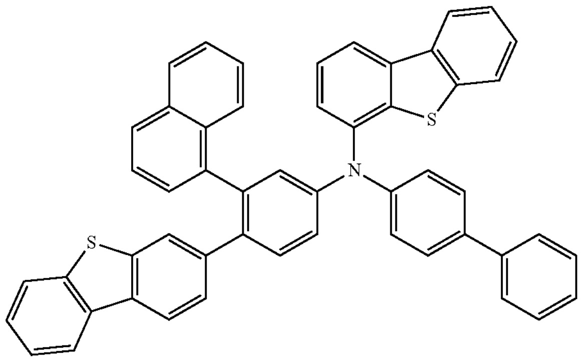

-continued
C131
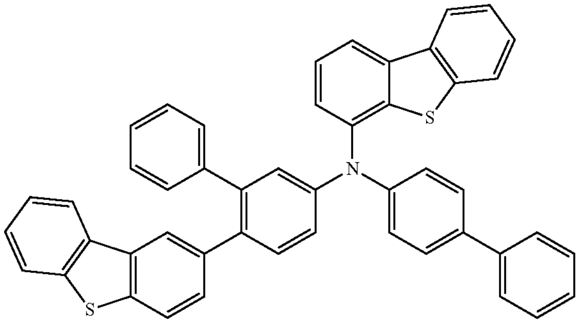
C132
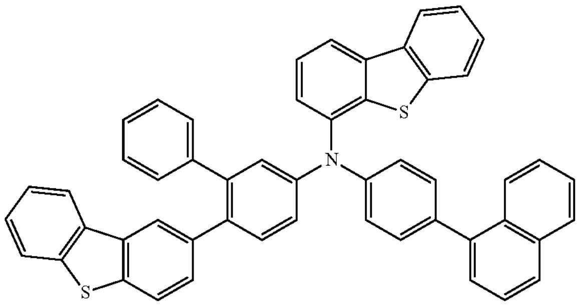
C133
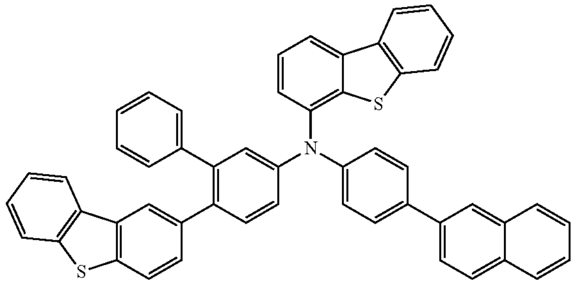
C134
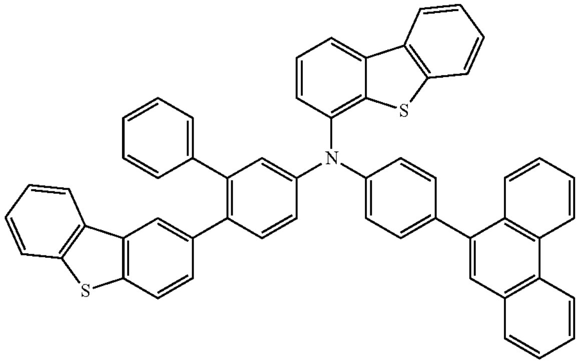
-continued
C135
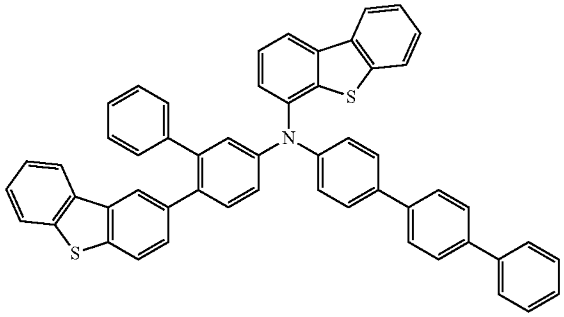
C136
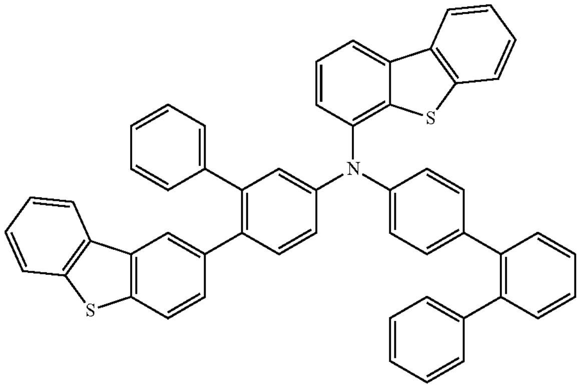
C137
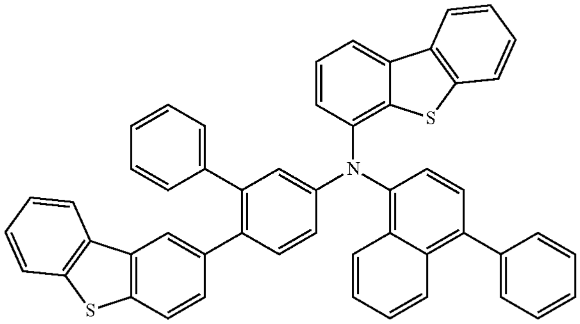
C138
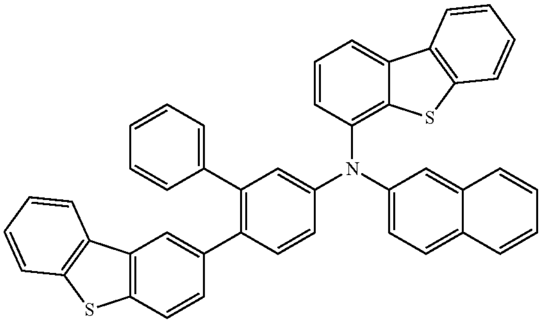

-continued
C139
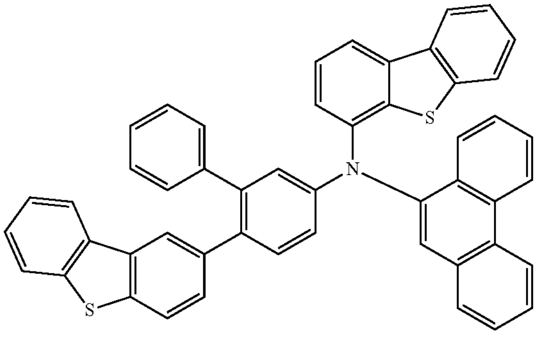
C140
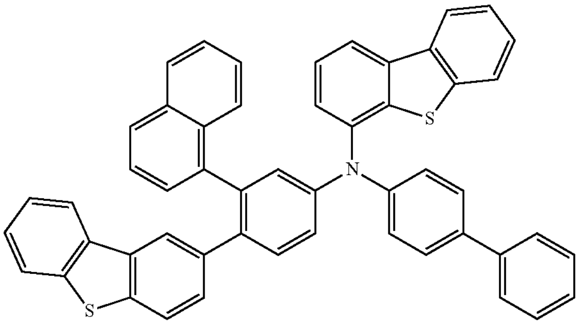
C141
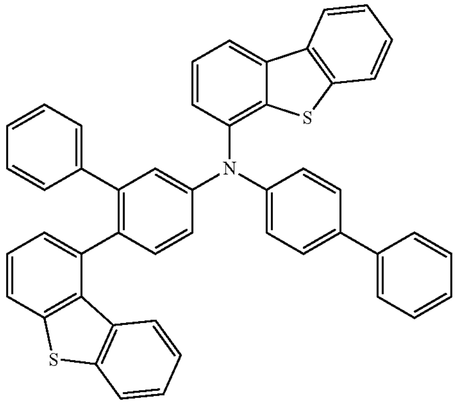
C142
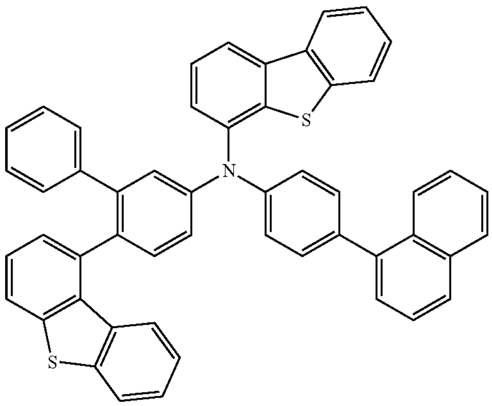
-continued
C143
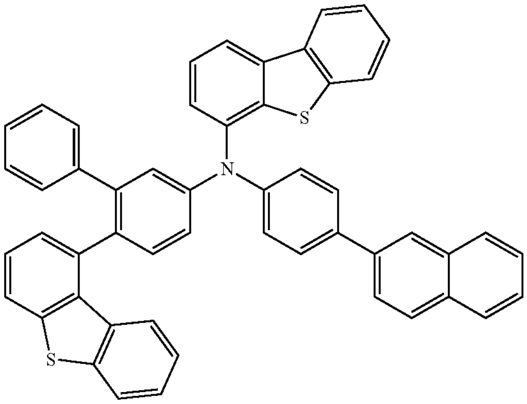
C144
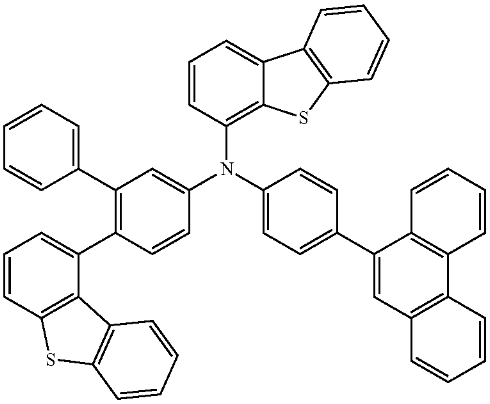
C145
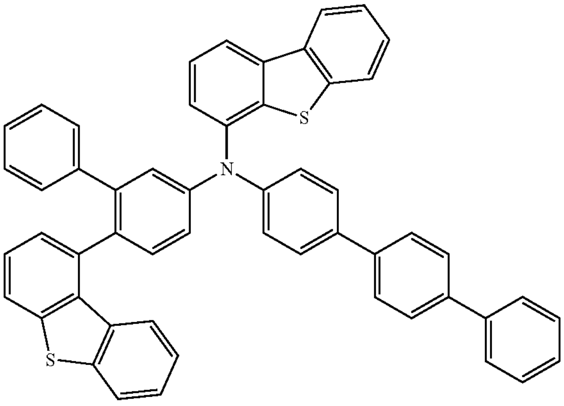

-continued
C146
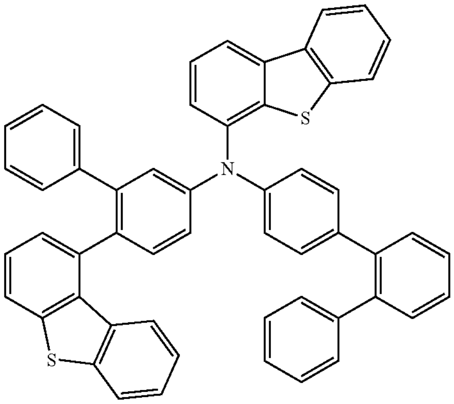
C147
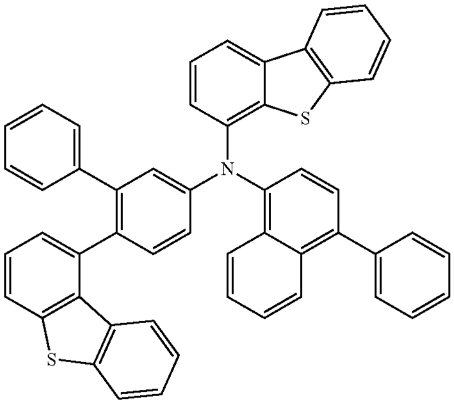
C148
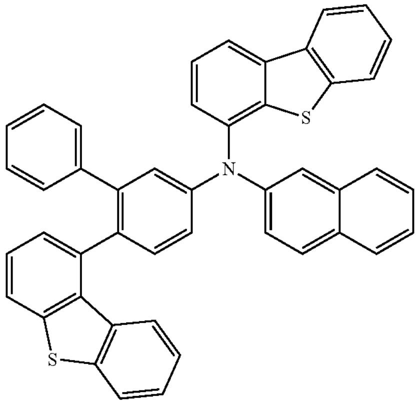
C149
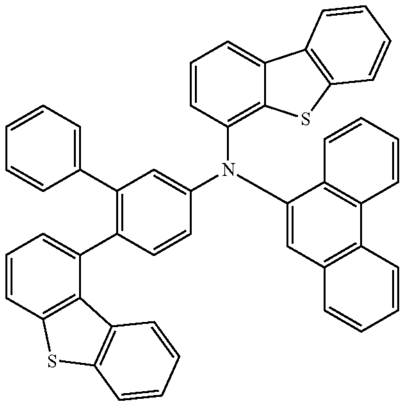
-continued
C150
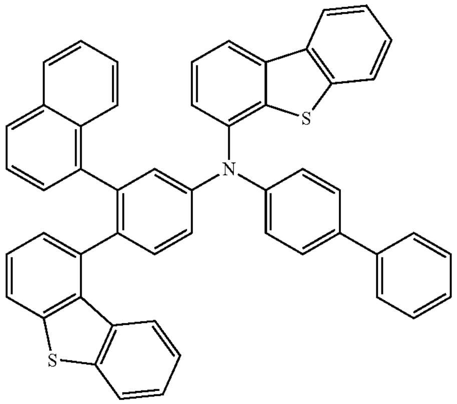
C151
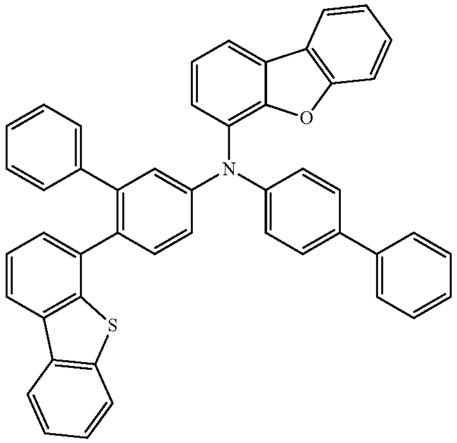
C152
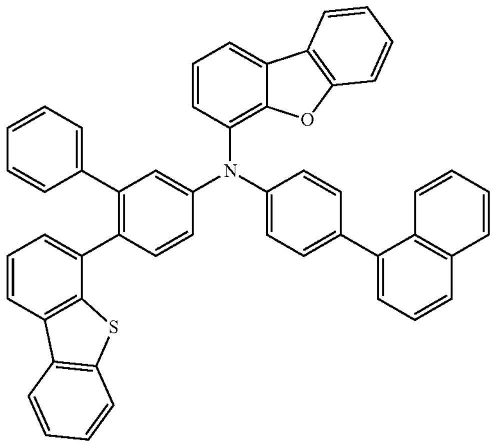

-continued
C153
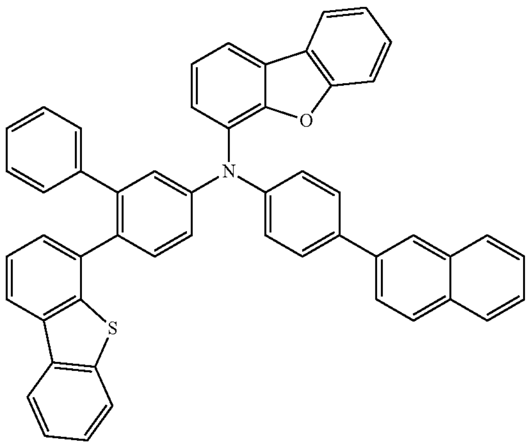
C154
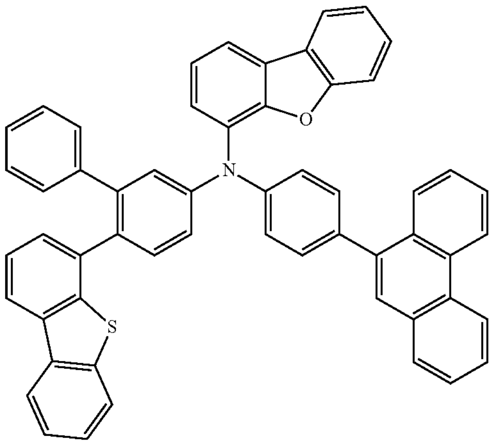
C155
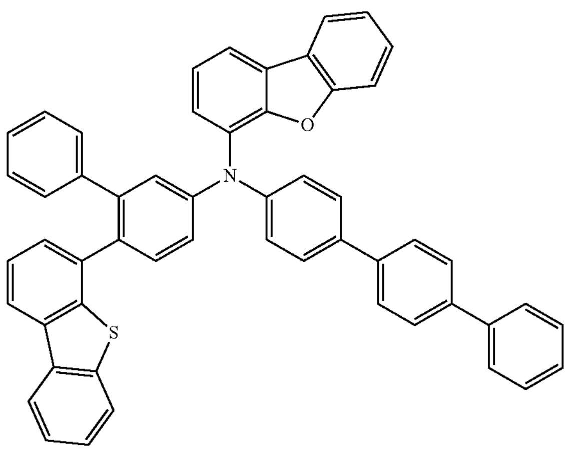
-continued
C156
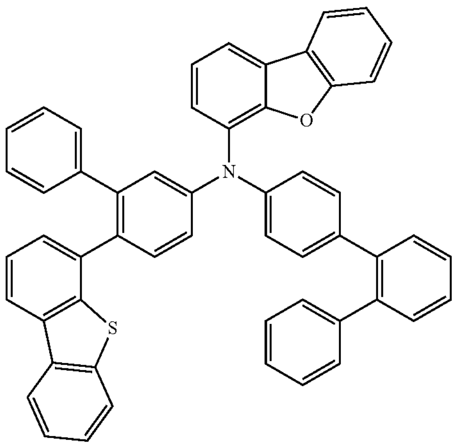
C157
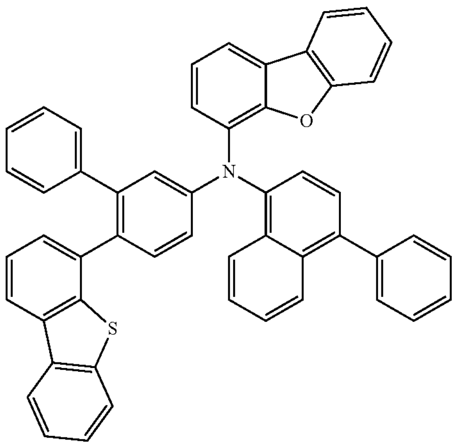
C158
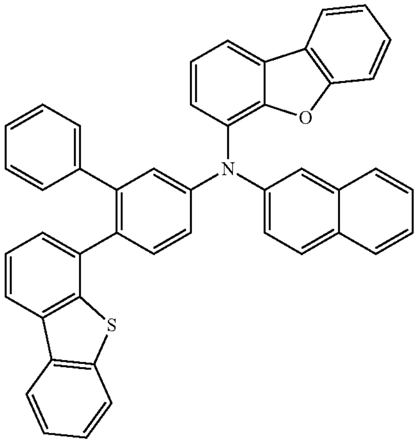

-continued
C159
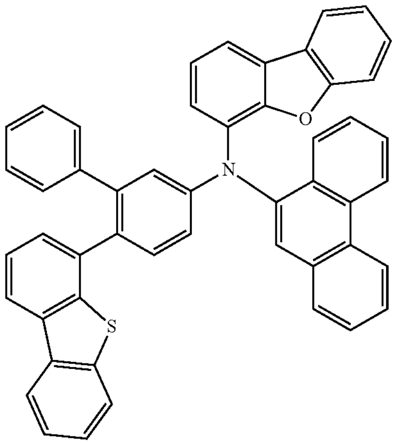
C160
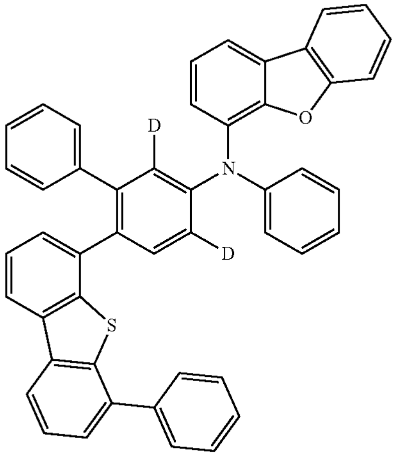
C161
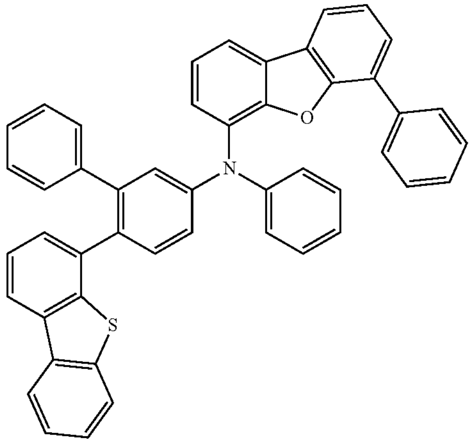
-continued
C162
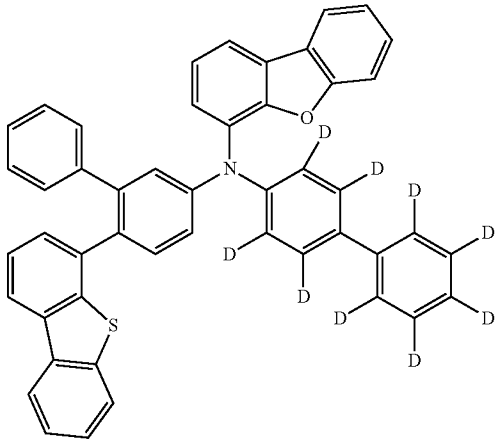
C163
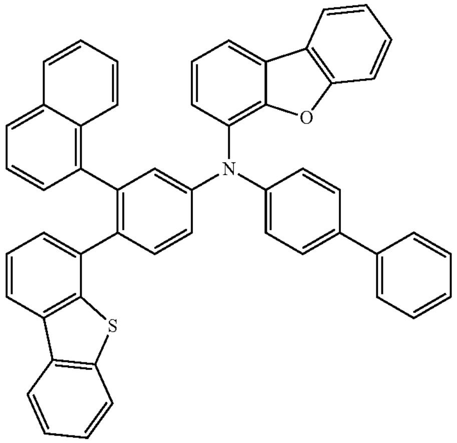
C164
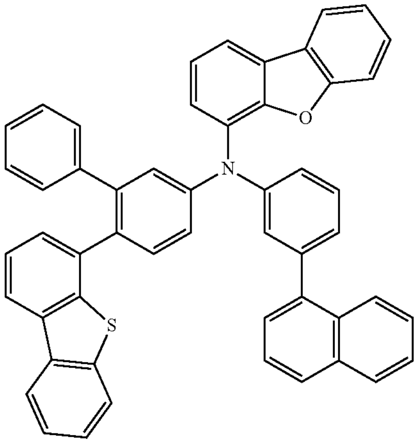

-continued
C165
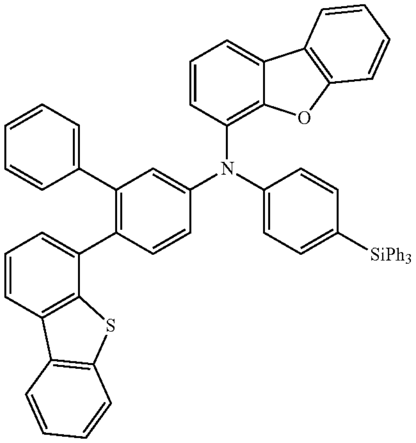
C166
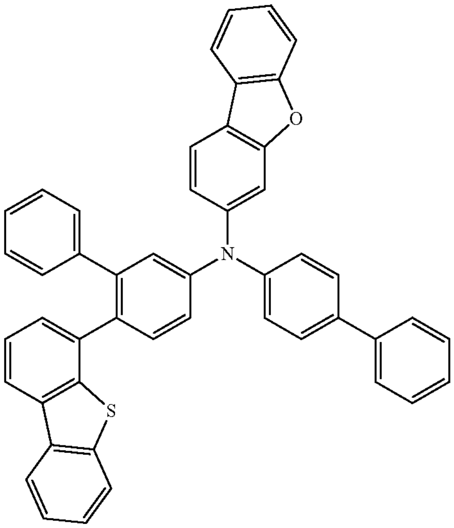
C167
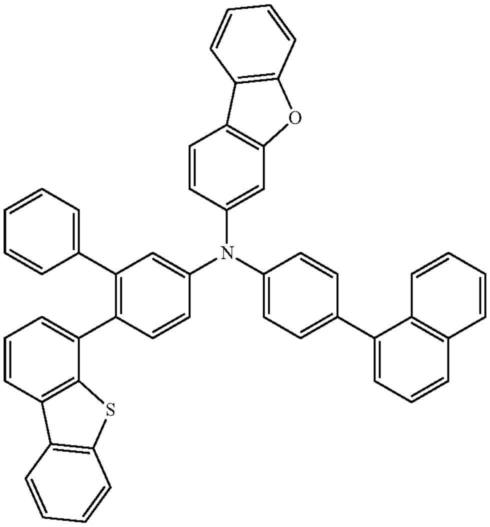
-continued
C168
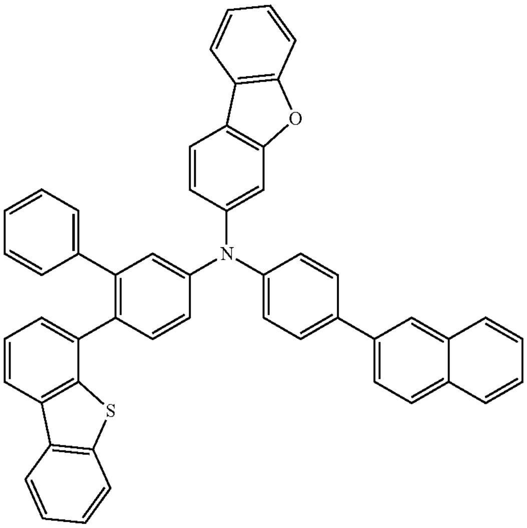
C169
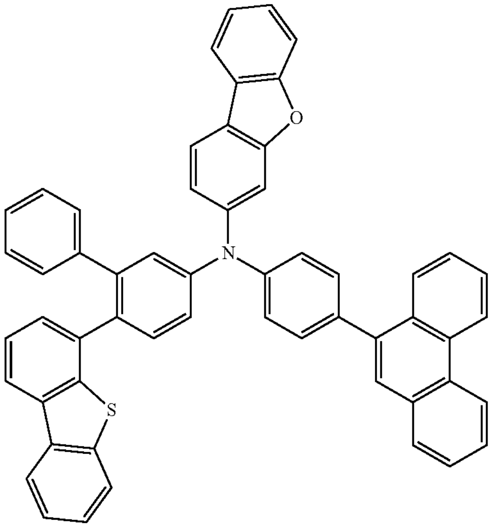
C170
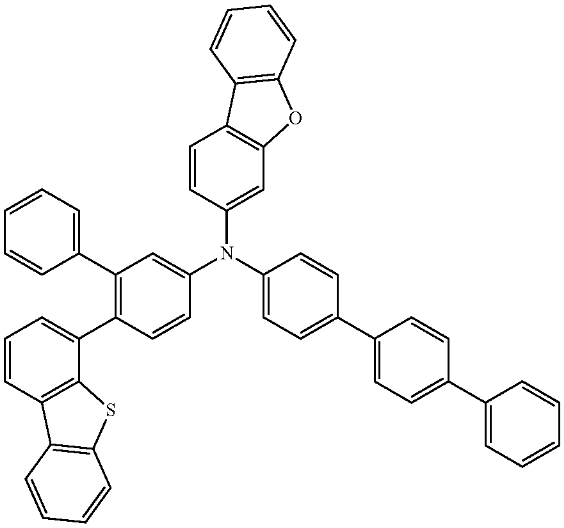

-continued
C171
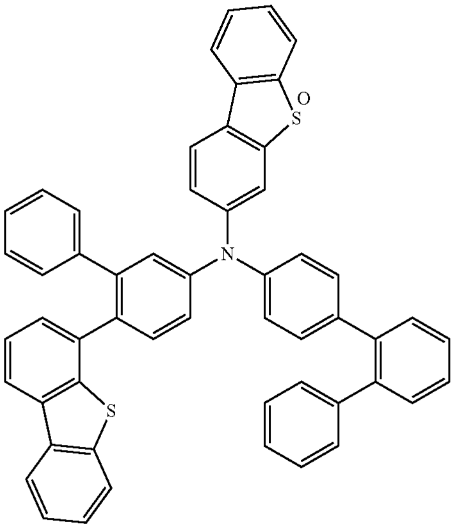
C172
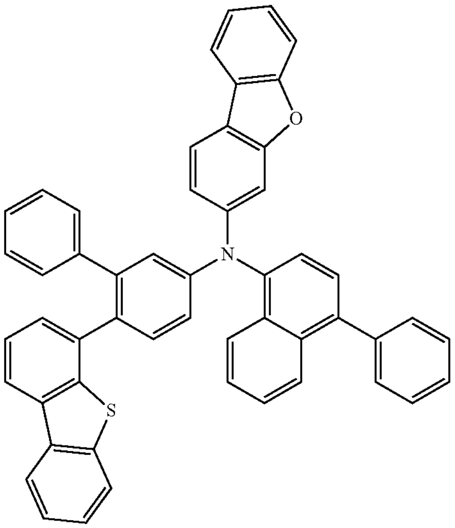
C173
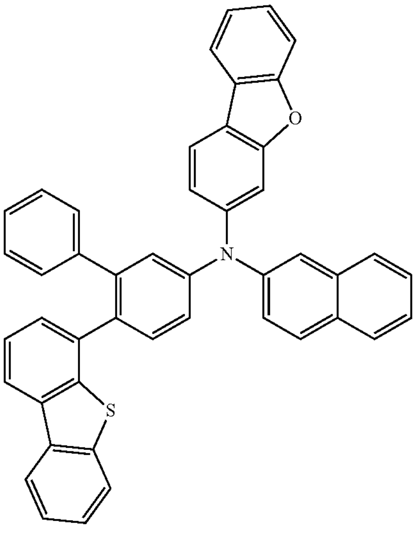
-continued
C174
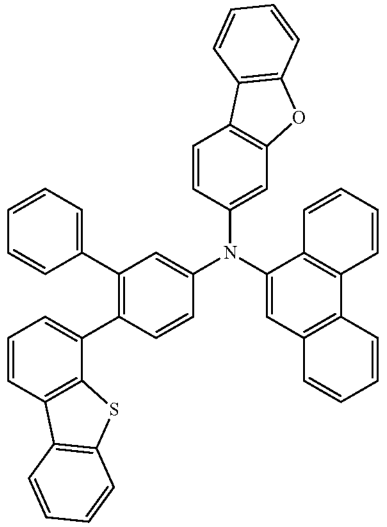
C175
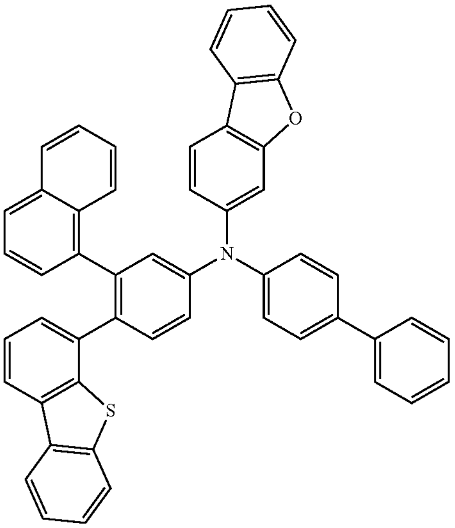
C176
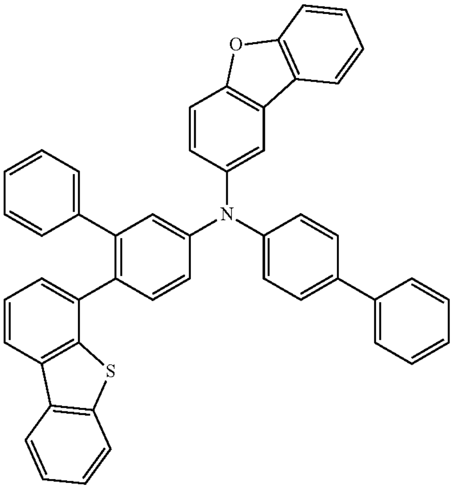

-continued
C177
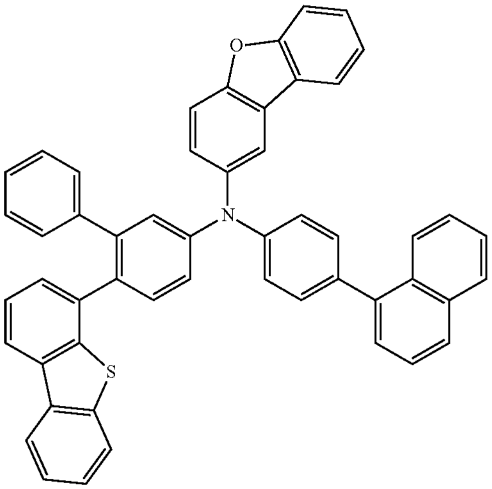
C178
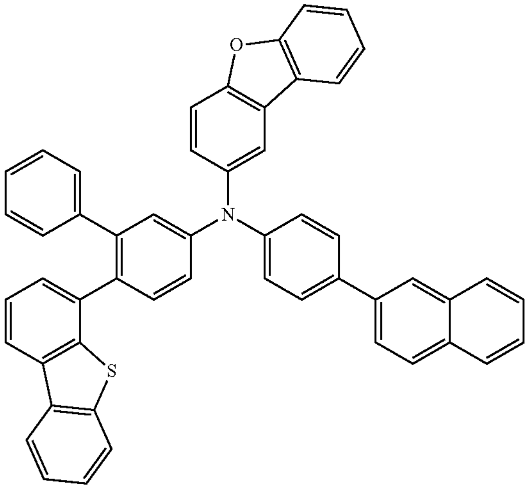
C179
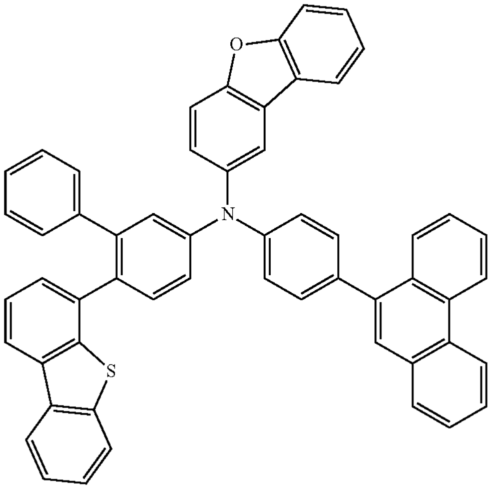
-continued
C180
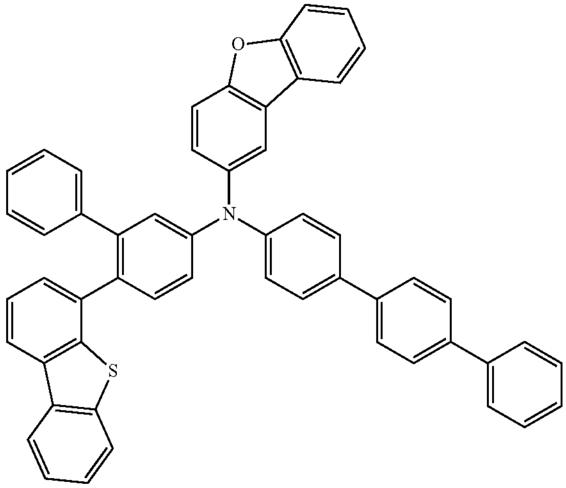
C181
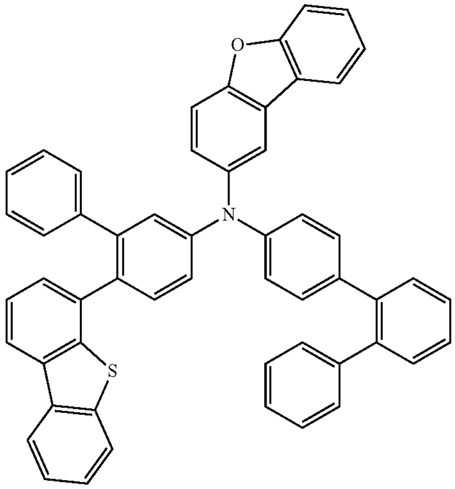
C182
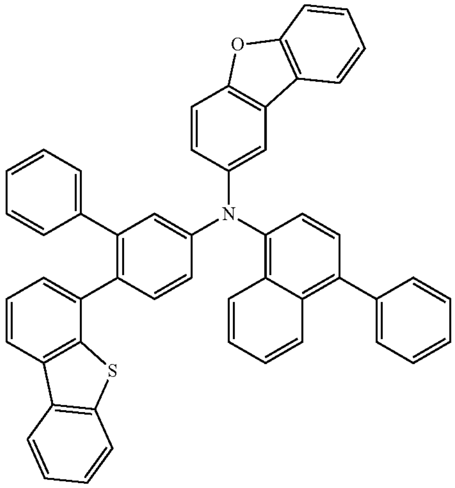

C183
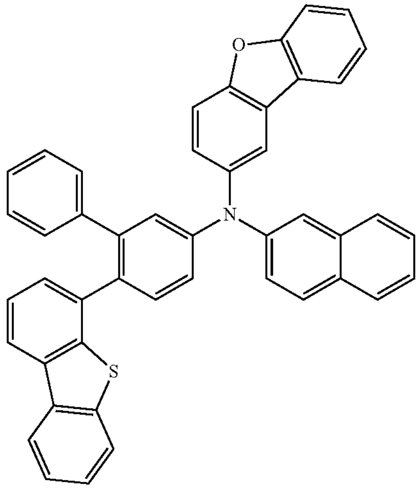
C184
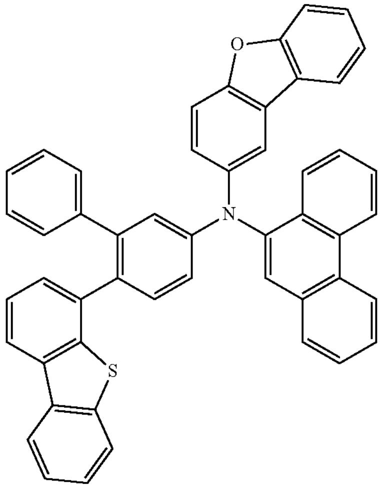
C185
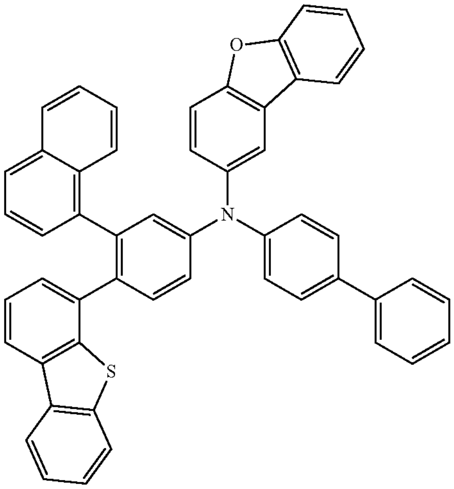
C186
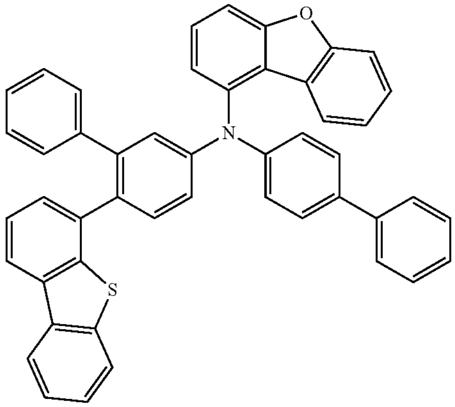
C187
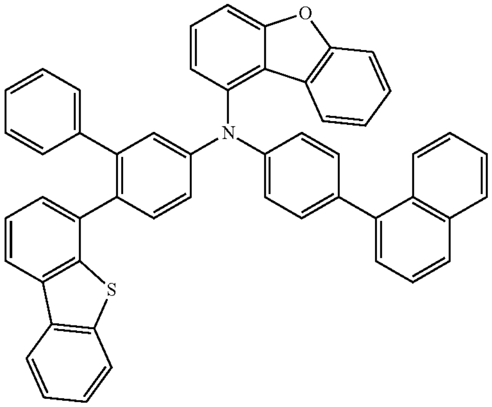
C188
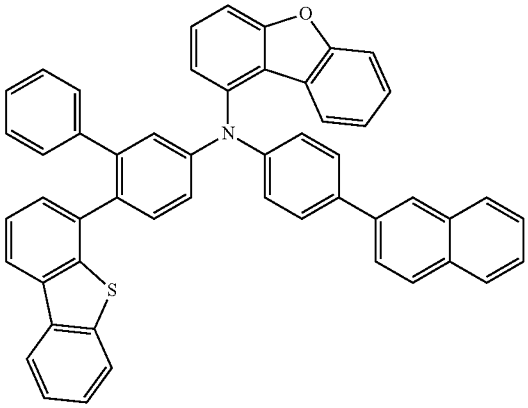

C189
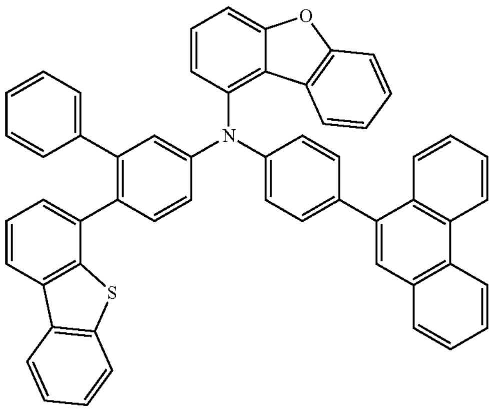
C190
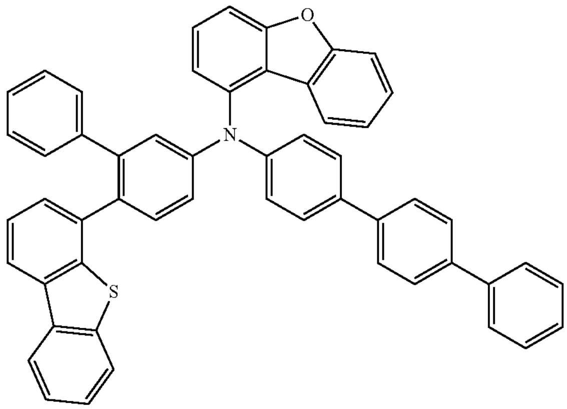
C191
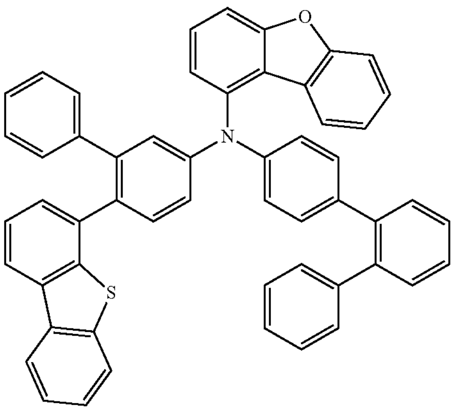
C192
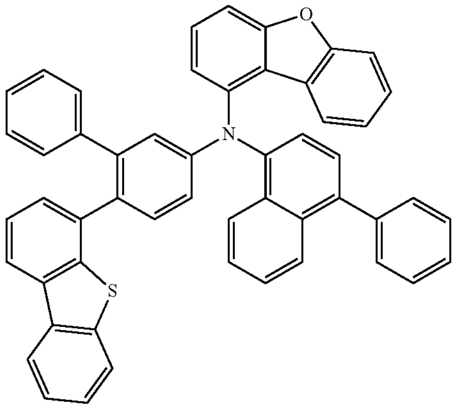
C193
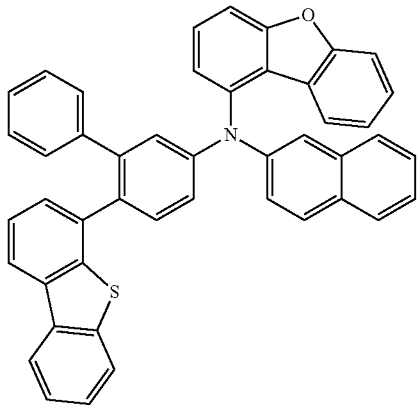
C194
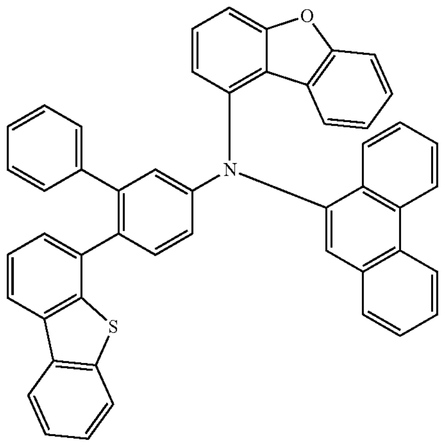

-continued
C195
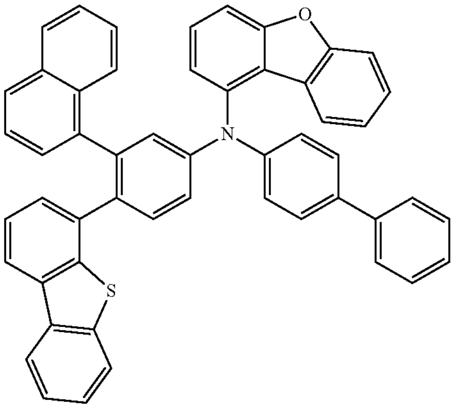
C196
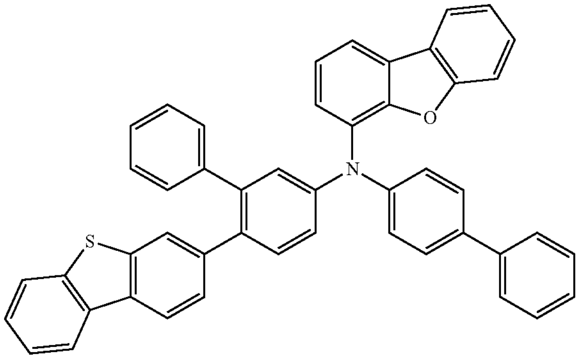
C197
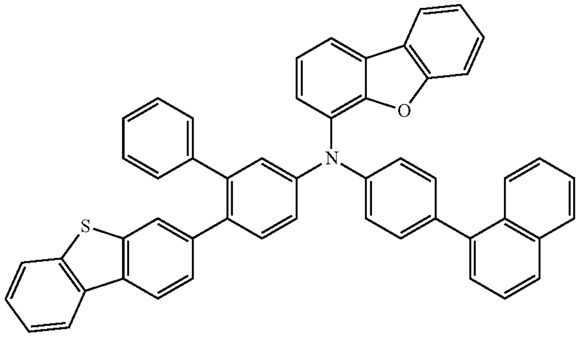
C198
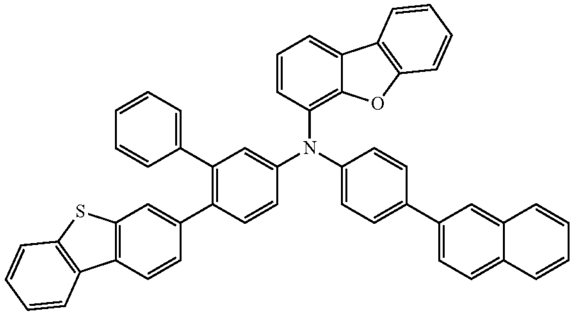
-continued
C199
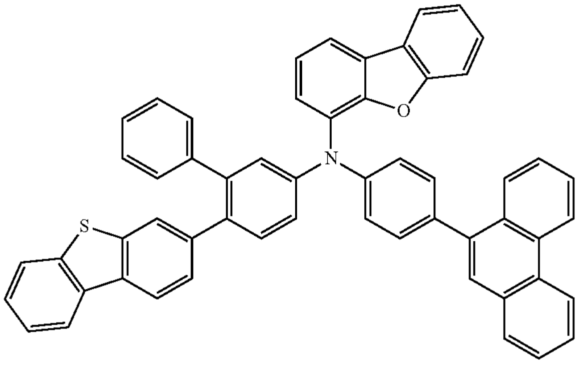
C200
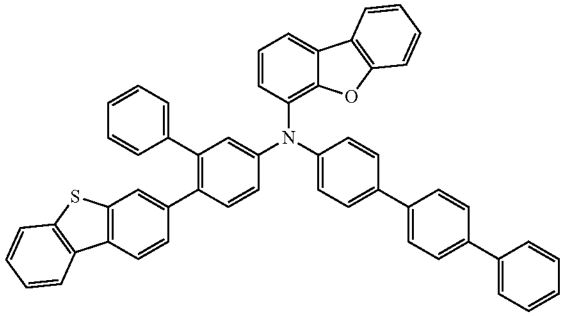
C201
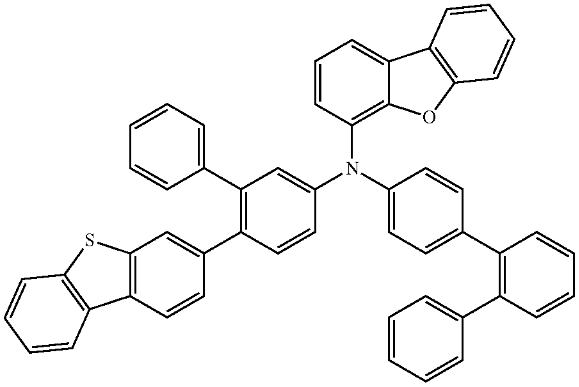
C202
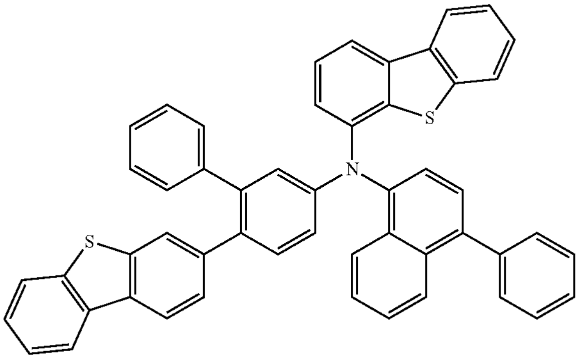

-continued
C203
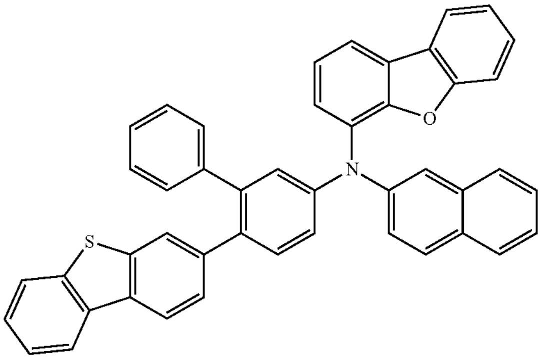
C204
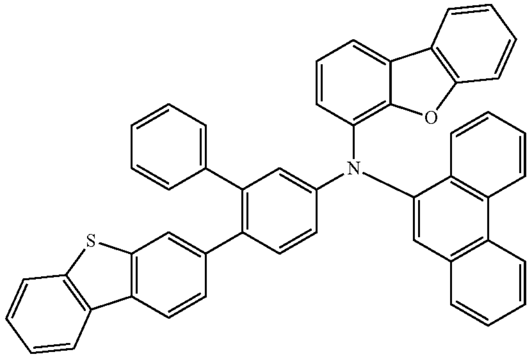
C205
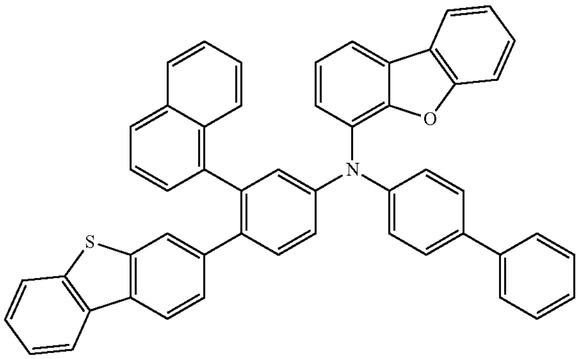
C206
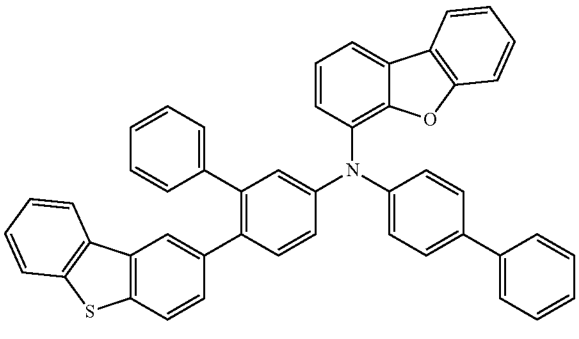
-continued
C207
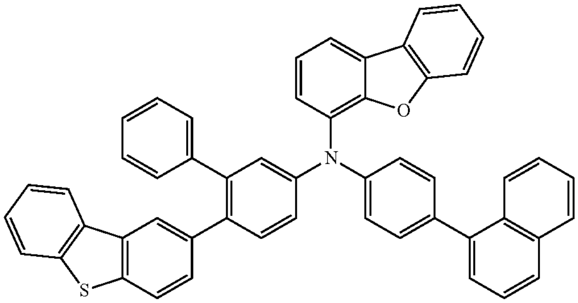
C208
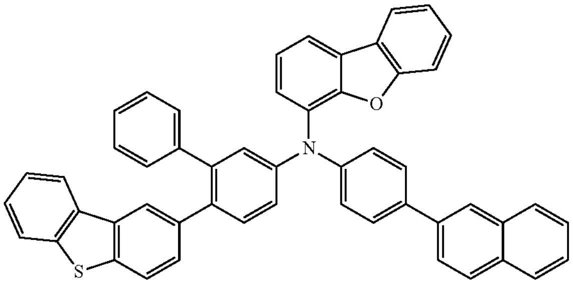
C209
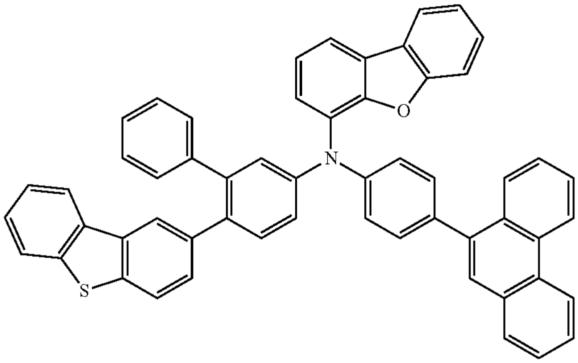
C210
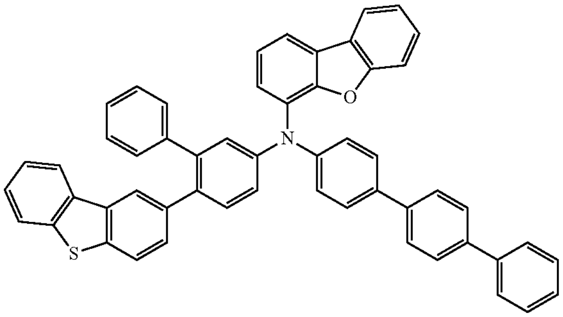

-continued
C211
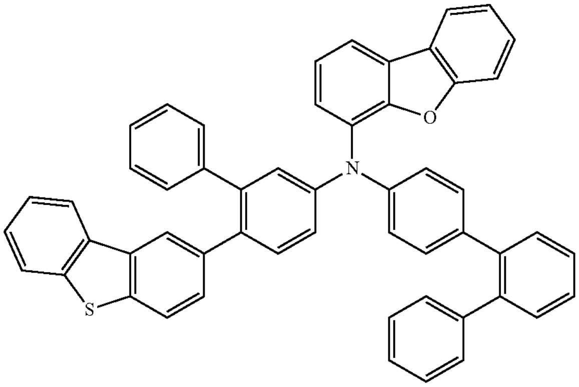
C212
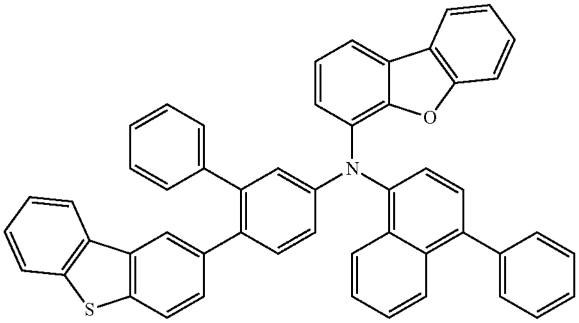
C213
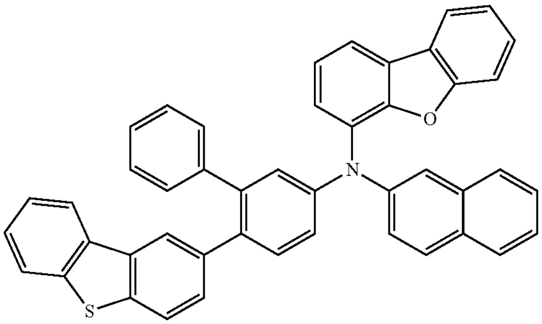
C214
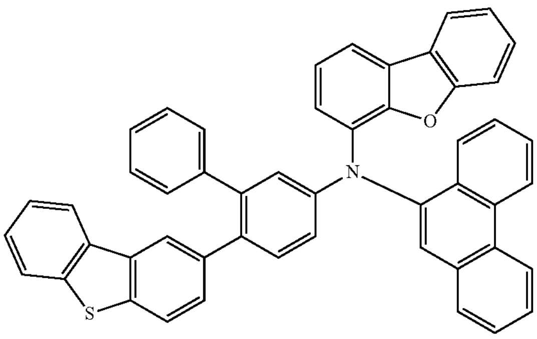
-continued
C215
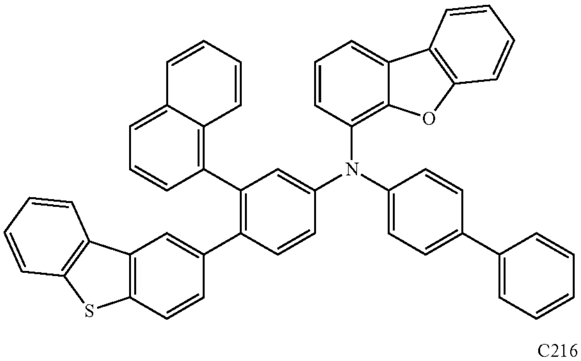
C216
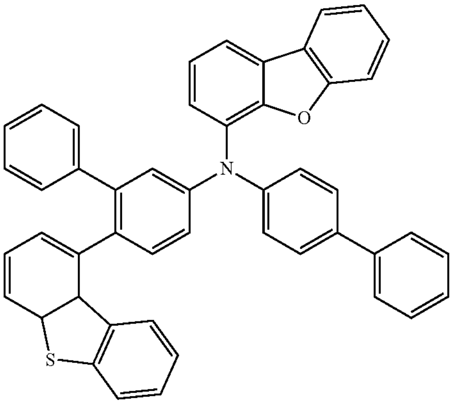
C217
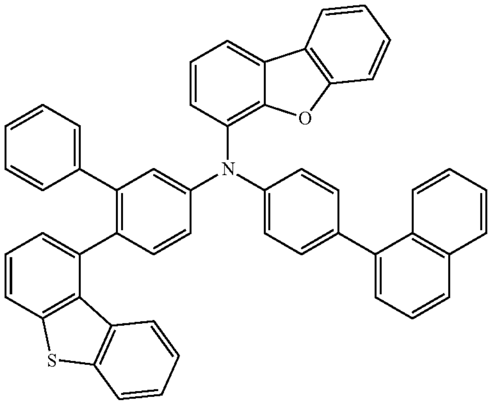
C218
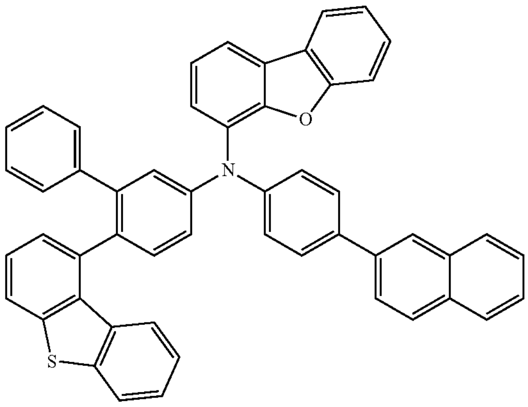

-continued
C219
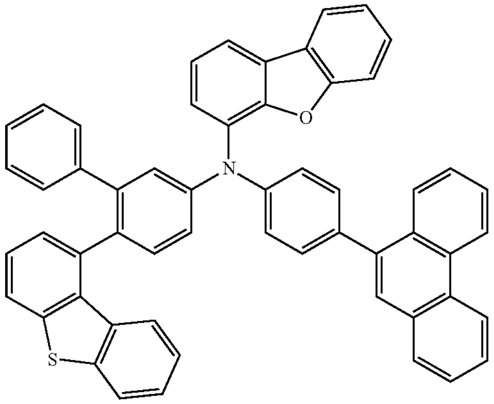
C220
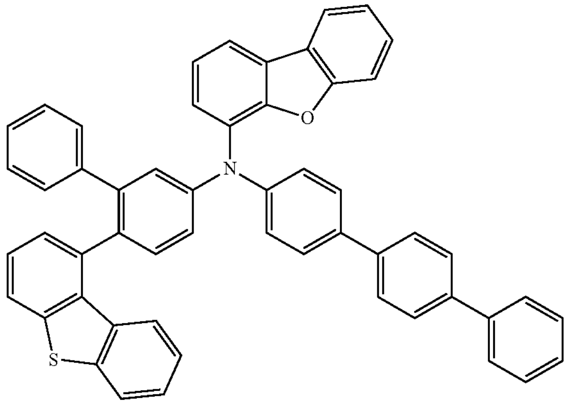
C221
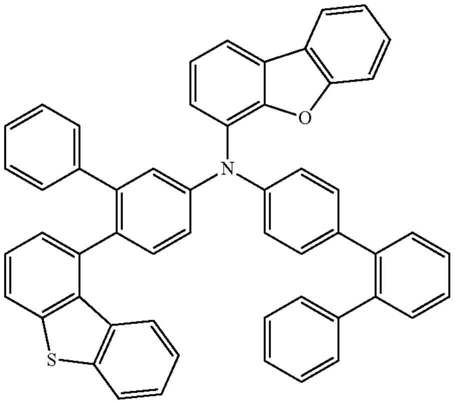
-continued
C222
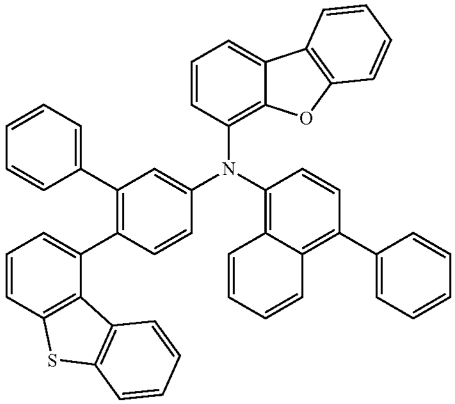
C223
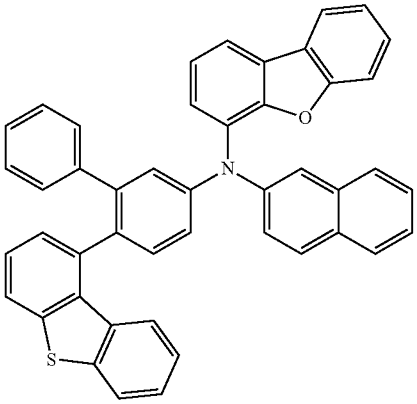
C224
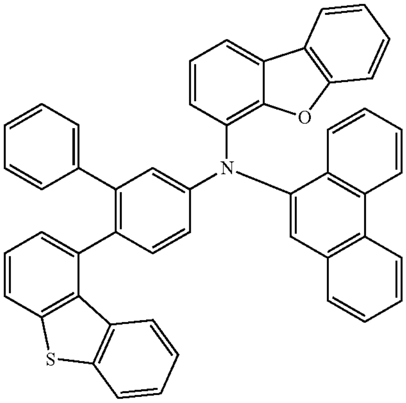
C225
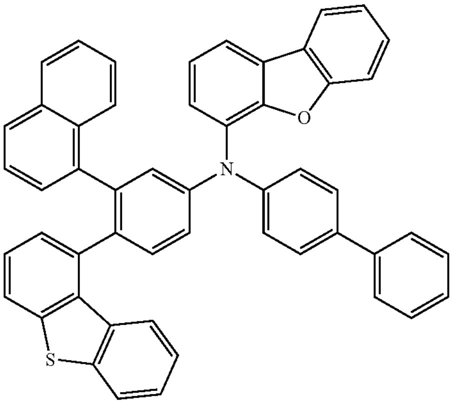

-continued
C226
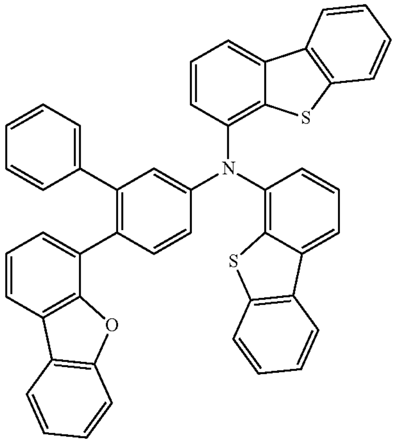
C227
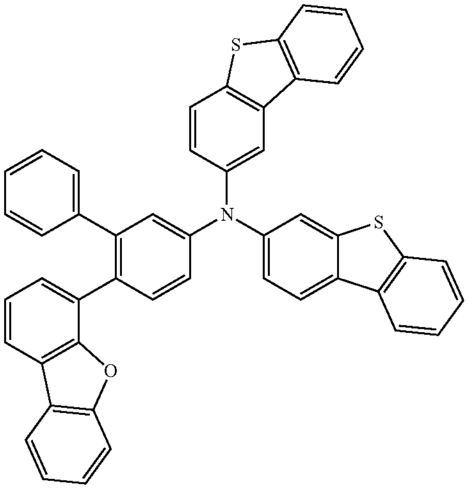
C228
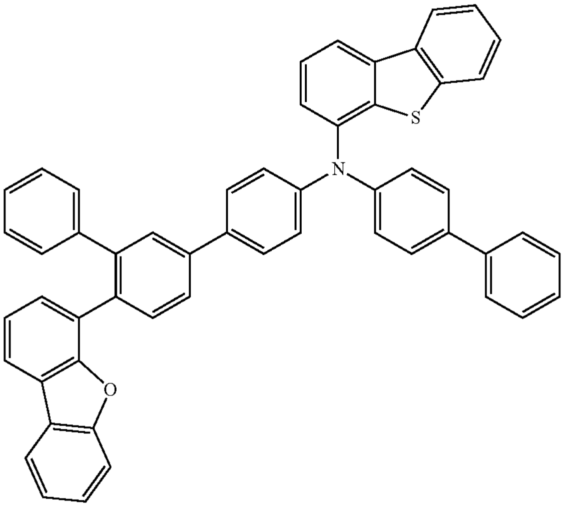
-continued
C229
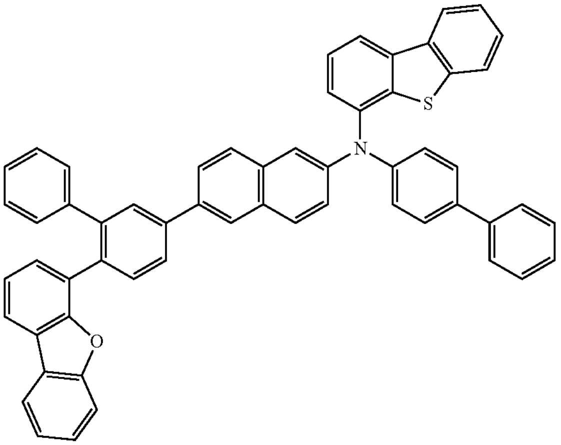
C230
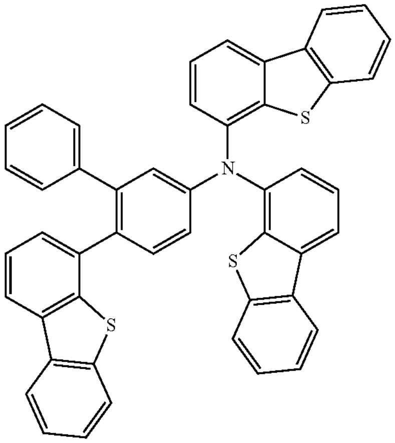
C231
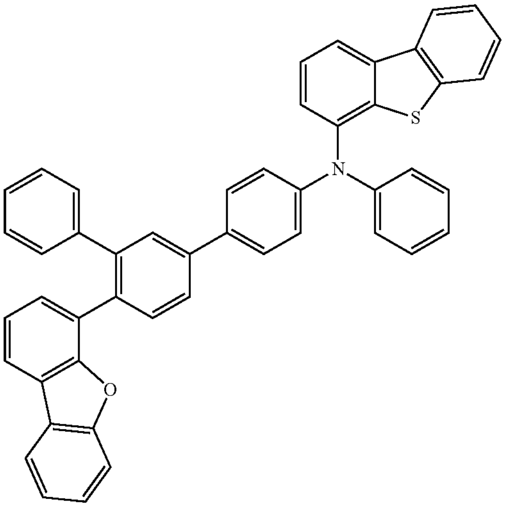

-continued
C232
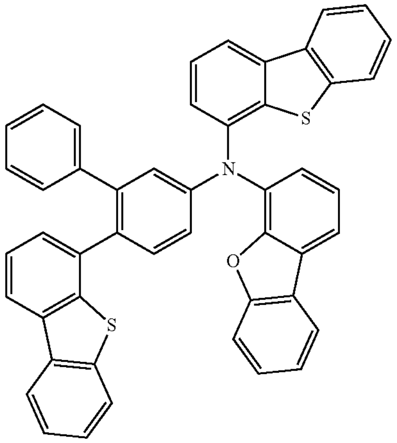
C233
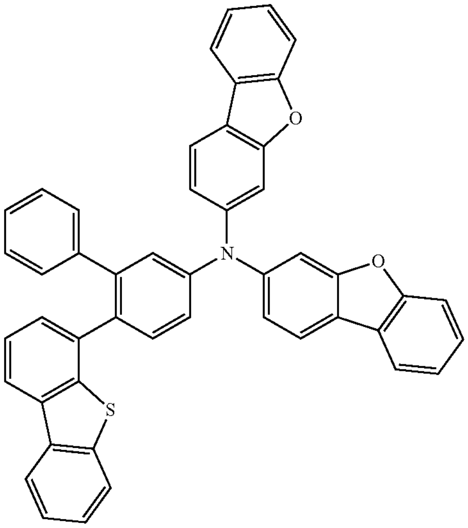
C234
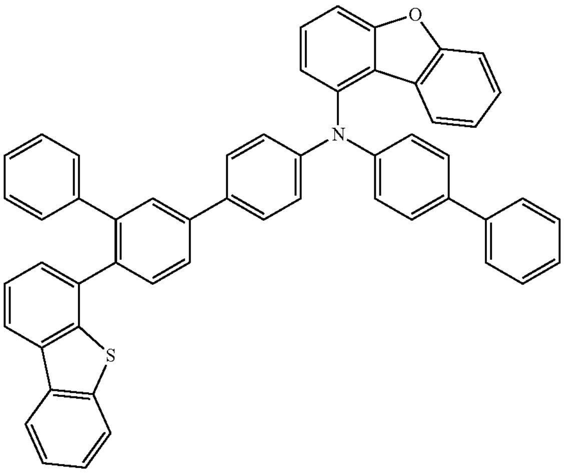
-continued
C235
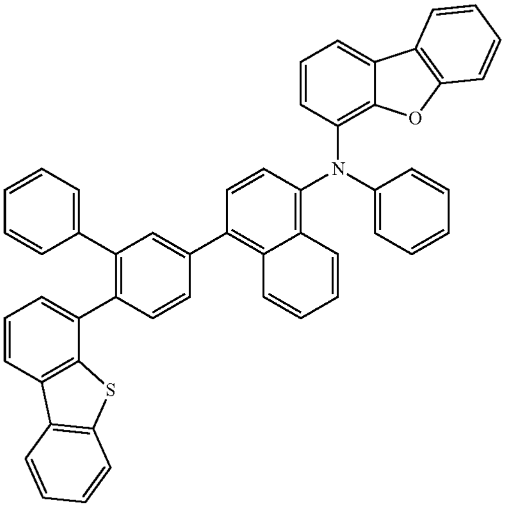
C236
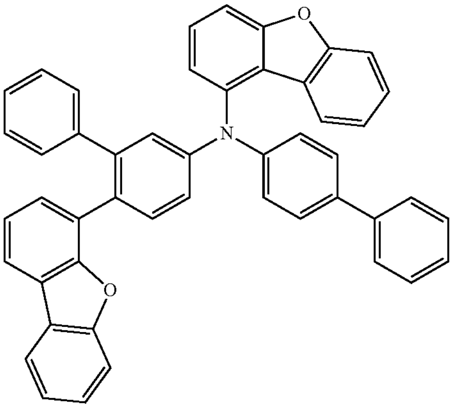
C237
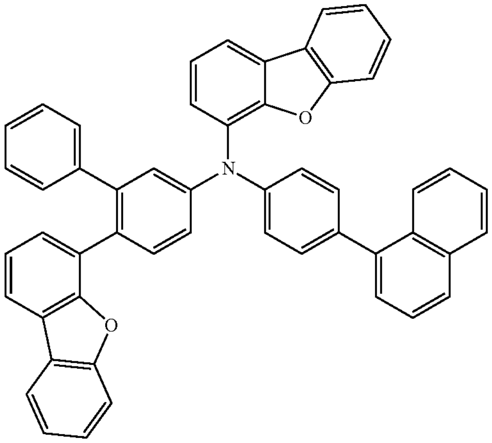

-continued
C238
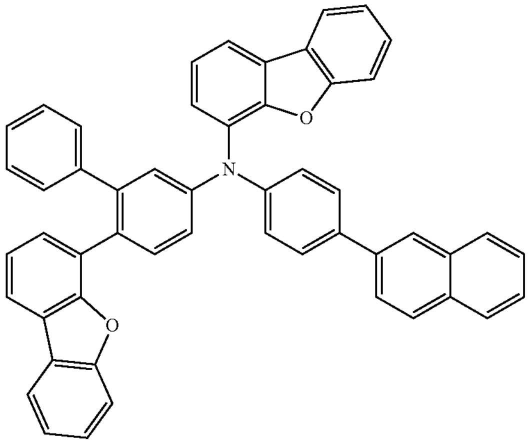
C239
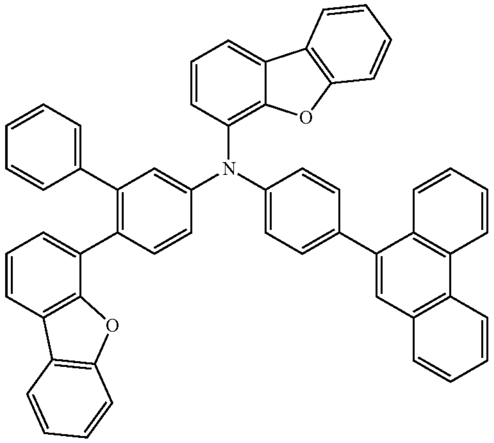
C240
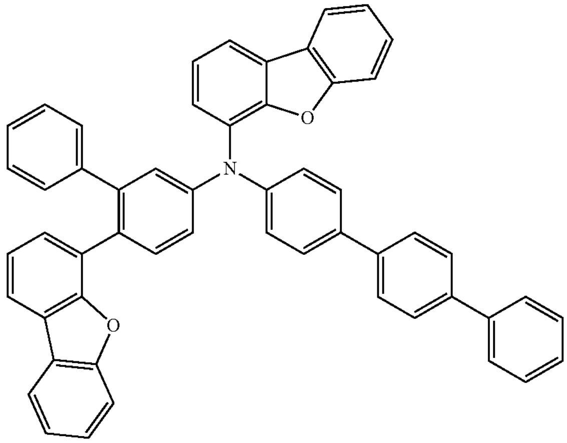
-continued
C241
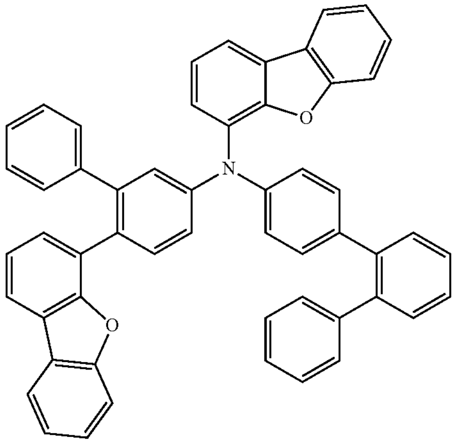
C242
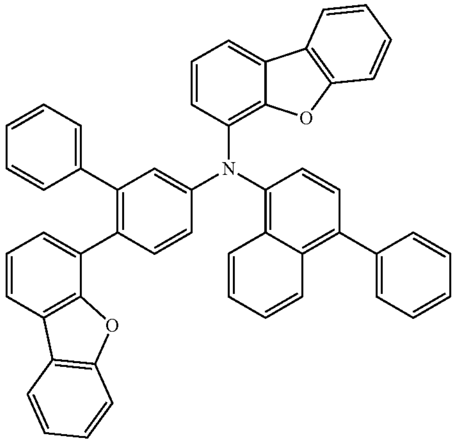
C243
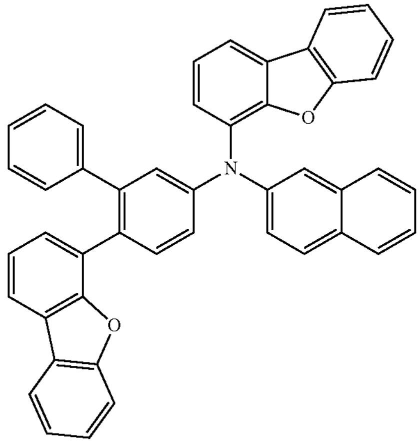

-continued

C244

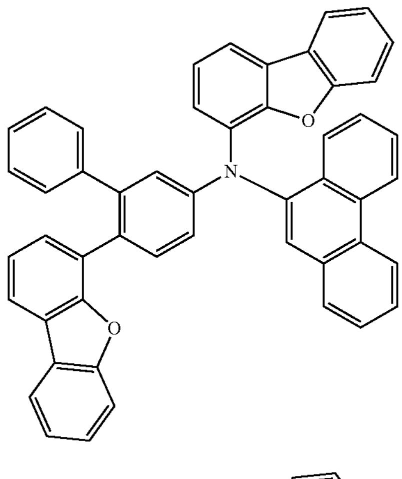

C245

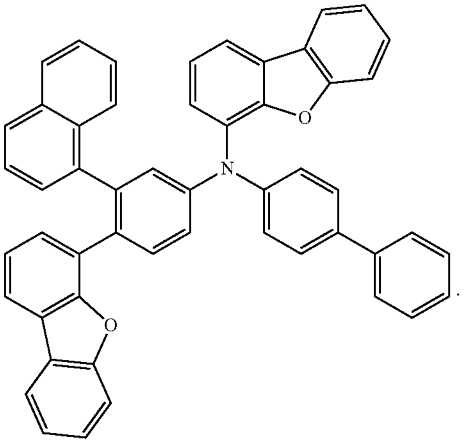

In the organic electroluminescence devices 10 of an embodiment, as shown in FIG. 1 to FIG. 4, a hole transport region HTR may include one or two or more of amine compounds represented in Compound Group 1 to Compound Group 3. In some embodiments, the hole transport region HTR may further include any suitable material, in addition to the amine compound in Compound Group 1 to Compound Group 3.

In the organic electroluminescence device 10 of an embodiment, if the hole transport region HTR includes a plurality of layers, at least one layer selected from the plurality of layers included in the hole transport region HTR may include the amine compound of an embodiment. For example, among the plurality of layers included in the hole transport region HTR, an adjacent layer to the emission layer EML may include the amine compound of an embodiment. Meanwhile, a layer not including the amine compound of an embodiment among the plurality of layers may include any suitable hole injection material, and/or any suitable hole transport material. In some embodiments, the layer including the amine compound of an embodiment may further include a suitable hole injection material, and/or a suitable hole transport material.

For example, the amine compound of an embodiment may be included in the hole injection layer HIL of the hole transport region HTR. If the hole transport layer HTL includes a plurality of functional layers, the amine compound of an embodiment may be included in an adjacent layer to the emission layer EML among the plurality of functional layers.

For example, in case where the hole transport region HTR of the organic electroluminescence device 10 of an embodiment includes the hole injection layer HIL and the hole transport layer HTL, the amine compound of an embodiment may be included in the hole transport layer HTL.

In the organic electroluminescence device 10 of an embodiment, if the hole transport layer HTL includes the amine compound of an embodiment, the hole injection layer HIL may include any suitable hole injection material. For example, the hole injection layer HIL may include a phthalocyanine compound (such as copper phthalocyanine), N,N'-diphenyl-N,N'-bis-[4-(phenyl-m-tolyl-amino)-phenyl]-phenyl-4,4'-diamine (DNTPD), 4,4',4"-[tris(3-methylphenyl)phenylamino]triphenylamine (m-MTDATA), 4,4',4"-tris(N,N-diphenylamino)triphenylamine (TDATA), 4,4',4"-tris{N,-2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPA-PEK), 4-isopropyl-4'-methyldiphenyliodonium [tetrakis(pentafluorophenyl)borate], and dipyrazino[2,3-f:2',3'-h]quinoxaline-2,3,6,7,10,11-hexacarbonitrile (HAT-CN). However, an embodiment of the present disclosure is not limited thereto.

In some embodiments, the hole transport layer HTL of the organic electroluminescence device 10 of an embodiment may further include any suitable hole transport material in addition to the amine compound of an embodiment. For example, the hole transport layer HTL may include carbazole derivatives (such as N-phenyl carbazole and/or polyvinyl carbazole), fluorene-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthalene-1-yl)-N,N'-diphenyl-benzidine (NPB), 4,4'-cyclohexylidene bis[N,N-bis(4-methylphenyl)benzeneamine (TAPC), 4,4'-bis[N,N'-(3-tolyl)amino]-3,3'-dimethylbiphenyl (HMTPD), 1,3-bis(N-carbazolyl)benzene (mCP), etc. However, an embodiment of the present disclosure is not limited thereto.

As described above, in the organic electroluminescence device 10 of an embodiment, the hole transport region HTR may further include at least one of a hole buffer layer or an electron blocking layer EBL, in addition to the hole injection layer HIL and the hole transport layer HTL. The hole buffer layer may compensate an optical resonance distance according to the wavelength of light emitted from an emission layer EML and may increase light emission efficiency. Materials which may be included in the hole transport region HTR may be used as materials included in the hole buffer layer.

If the hole transport region HTR further includes an electron blocking layer EBL between the hole transport layer HTL and the emission layer EML, the electron blocking layer EBL may play the role of preventing (or reducing) the electron injection from the electron transport region ETR to the hole transport region HTR.

In the organic electroluminescence device 10 of an embodiment, if the hole transport region HTR includes the electron blocking layer EBL, the electron blocking layer EBL may include the amine compound of an embodiment. In some embodiments, the electron blocking layer EBL may further include a suitable material, in addition to the amine compound of an embodiment. The electron blocking layer EBL may include, for example, carbazole derivatives (such as N-phenyl carbazole and/or polyvinyl carbazole), fluorene-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl) triphenylamine (TCTA)), N,N'-di(1-naphthalen-1-yl)-N,N'-diphenyl-benzidine (NPD), 4,4'-cyclohexylidene bis[N,N-bis(4-methylphenyl)benzeneamine (TAPC), 4,4'-bis[N,N'-(3-tolyl)amino]-3,3'-dimethylbiphenyl (HMTPD), mCP, etc.

In the organic electroluminescence device 10 of an embodiment, if the hole transport region HTR is a single layer, the hole transport region HTR may include the amine compound of an embodiment. In this case, the hole transport region HTR may further include any suitable hole injection material, and/or any suitable hole transport material.

The thickness of the hole transport region HTR may be from about 50 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. When the thicknesses of the hole transport region HTR, the hole injection layer HIL, the hole transport layer HTL and the electron blocking layer EBL satisfy the above-described ranges, satisfactory (or suitable) hole transport properties may be achieved without substantial increase of a driving voltage.

The hole transport region HTR may further include a charge generating material, in addition to the above-described materials, to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without limitation. For example, non-limiting examples of the p-dopant may include quinone derivatives (such as tetracyanoquinodimethane (TCNQ) and/or 2,3,5,6-tetrafluoro-7,7',8,8'-tetracyanoquinodimethane (F4-TCNQ)), and metal oxides (such as tungsten oxide and/or molybdenum oxide).

The emission layer EML is provided on the hole transport region HTR. The emission layer EML may have a thickness of, for example, about 100 Å to about 1,000 Å or about 100 Å to about 400 Å. The emission layer EML may have a single layer formed using a single material, a single layer formed using a plurality of different materials, or a multilayer structure having a plurality of layers formed using a plurality of different materials.

In the luminescence device 10 of an embodiment, the emission layer EML may include anthracene derivatives, pyrene derivatives, fluoranthene derivatives, chrysene derivatives, dihydrobenzanthracene derivatives, and/or triphenylene derivatives. For example, the emission layer EML may include one or more anthracene derivatives represented by the following Formula 2:

Formula 2

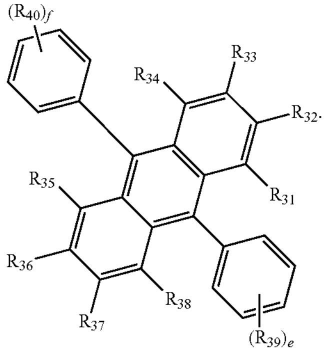

In Formula 2, $R_{31}$ to $R_{40}$ may each independently be a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 carbon atoms for forming a ring, or a substituted or unsubstituted heteroaryl group of 2 to 30 carbon atoms for forming a ring, and any of $R_{31}$ to $R_{40}$ may be combined with an adjacent group to form a ring. For example, any of $R_{31}$ to $R_{40}$ may be combined with an adjacent group to form a saturated hydrocarbon ring or an unsaturated hydrocarbon ring.

In Formula 2, "e" and "f" may each independently be an integer of 0 to 5.

Formula 2 may be represented by any one selected from the following Compound 2-1 to Compound 2-16:

2-1

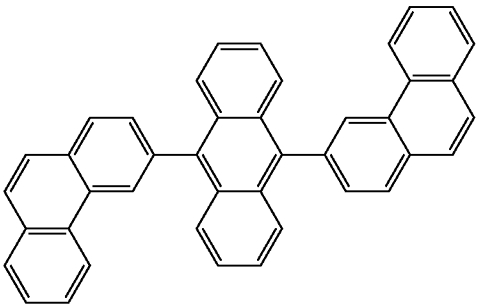

2-2

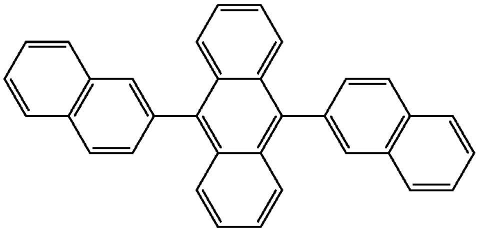

2-3

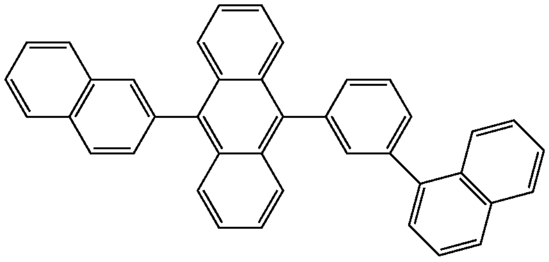

-continued
2-4
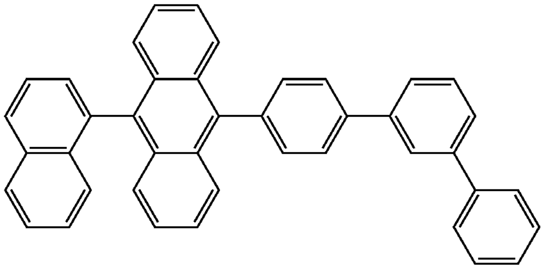
2-5
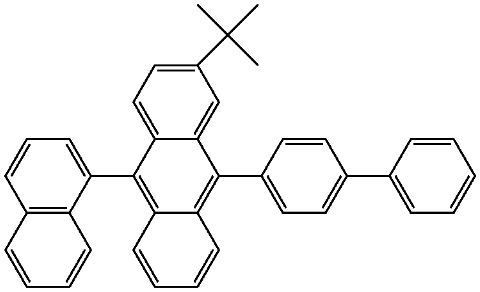
2-6
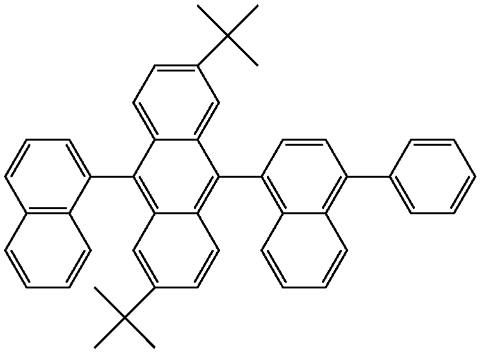
2-7
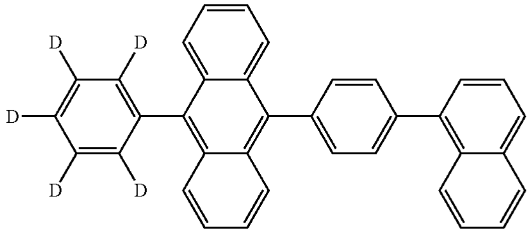
2-8
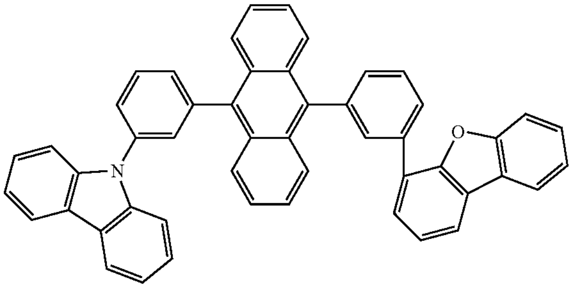
-continued
2-9
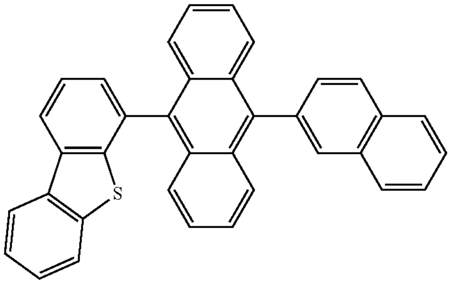
2-10
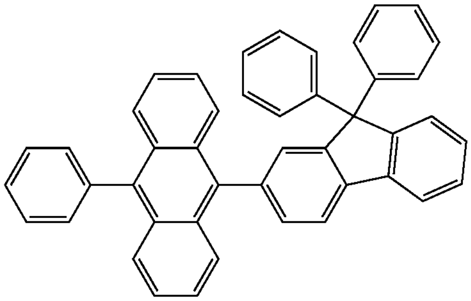
2-11
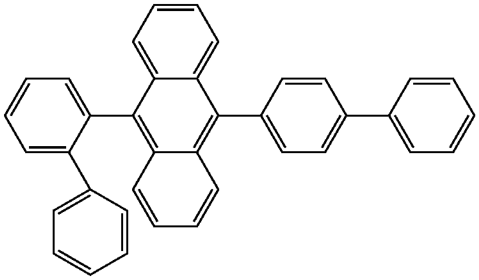
2-12
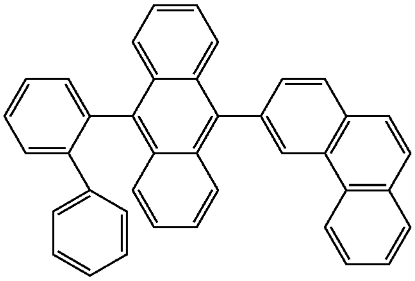
2-13
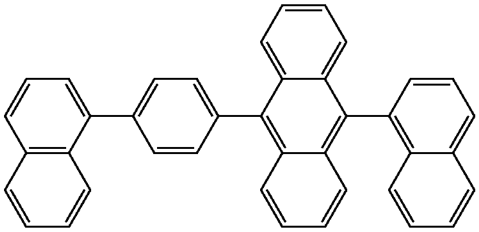

-continued 2-14

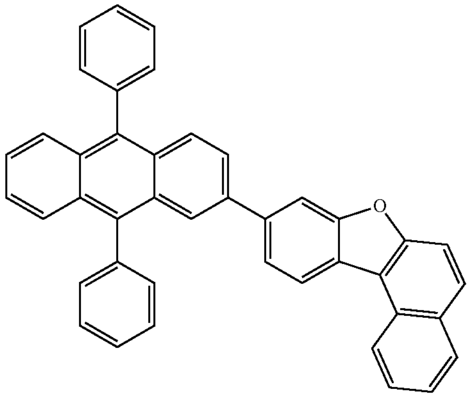

2-15

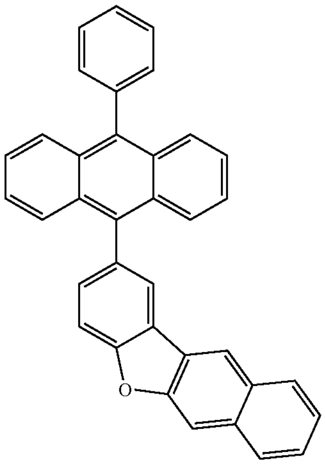

2-16

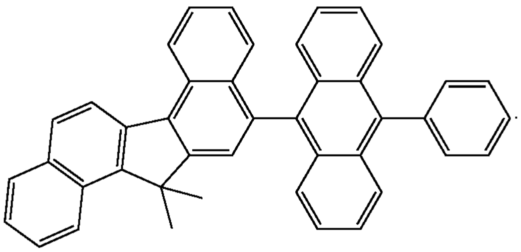

In the luminescence devices 10 of example embodiments as shown in FIG. 1 to FIG. 4, the emission layer EML may include a host and a dopant, and the emission layer EML may include the compound represented by the above-described Formula 2 as a host material.

In an embodiment, the emission layer EML may further include any suitable materials as the host material. For example, the emission layer EML may include, as the host material, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)-triphenylamine (TCTA), 1,3,5-tris(1-phenyl-1H-benzo[d]imidazol-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzo[b,d]furan (PPF), 3,3'-bis(N-carbazolyl)-1,1'-biphenyl (mCBP), 1,3-bis(N-carbazolyl)benzene (mCP), etc.

In the organic electroluminescence device 10 of an embodiment, the emission layer EML may include, as a dopant material, styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), and/or N-(4-((E)-2-(6-((E)-4-(diphenylamino)styryl)naphthalen-2-yl)vinyl)phenyl)-N-phenylbenzenamine (N-BDAVBi)), perylene and/or the derivatives thereof (for example, 2,5,8,11-tetra-t-butylperylene (TBP)), pyrene and/or the derivatives thereof (for example, 1,1-dipyrene, 1,4-dipyrenylbenzene, 1,4-bis(N,N-diphenylamino)pyrene), etc.

In case where the emission layer EML emits green light, the emission layer EML may further include, for example, a fluorescence material including tris(8-hydroxyquinolinato) aluminum ($Alq_3$). In case where the emission layer EML emits green light, the emission layer EML may include, for example, the compound of an embodiment as a host material, and as a dopant material, a metal complex or an organometallic complex (such as fac-tris(2-phenylpyridine) iridium ($Ir(ppy)_3$)), and/or coumarin and/or the derivatives thereof.

In case where the emission layer EML emits blue light, the emission layer EML may further include a fluorescence material including any one selected from the group consisting of spiro-DPVBi, spiro-6P, distyryl-benzene (DSB), distyryl-arylene (DSA), a polyfluorene (PFO)-based polymer, and a poly(p-phenylene vinylene (PPV)-based polymer. In case where the emission layer EML emits blue light, the emission layer EML may include, for example, the compound of an embodiment as a host material, and as a dopant material, a metal complex or an organometallic complex (such as (4,6-F2ppy)2Irpic), and/or perylene and/or the derivatives thereof.

In case where the emission layer EML emits red light, the emission layer EML may further include, for example, a fluorescence material including tris(dibenzoylmethanato) phenanthoroline europium (PBD: $Eu(DBM)_3(Phen)$) and/or perylene. In case where the emission layer EML emits red light, the dopant included in the emission layer EML may be selected from, for example, a metal complex or an organometallic complex (such as bis(1-phenylisoquinoline)acetylacetonate iridium (PIQIr(acac)), bis(1-phenylquinoline) acetylacetonate iridium (PQIr(acac)), tris(1-phenylquinoline)iridium (PQIr) and/or octaethylporphyrin platinum (PtOEP)), rubrene and/or the derivatives thereof, and/or 4-dicyanomethylene-2-(p-dimethylaminostyryl)-6-methyl-4H-pyrane (DCM) and/or the derivatives thereof.

In some embodiments, the organic electroluminescence device 10 of an embodiment may include a plurality of emission layers. The plurality of emission layers may be stacked one by one. For example, the organic electroluminescence device 10 including a plurality of emission layers may emit white light. The organic electroluminescence device including the plurality of emission layers may be an organic electroluminescence device having a tandem structure.

In the organic electroluminescence device 10 of an embodiment, as shown in FIGS. 1 to 4, the electron transport region ETR is provided on the emission layer EML. The electron transport region ETR may include at least one of an electron blocking layer HBL, an electron transport layer ETL, or an electron injection layer EIL. However, an embodiment of the present disclosure is not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure having a plurality of different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, from about 300 Å to about 1,500 Å.

The electron transport region ETR may be formed using one or more suitable methods such as a vacuum deposition method, a spin coating method, a cast method, a Langmuir-Blodgett (LB) method, an inkjet printing method, a laser printing method, and/or a laser induced thermal imaging (LITI) method.

If the electron transport region ETR includes an electron transport layer ETL, the electron transport region ETR may include an anthracene-based compound. The electron transport region may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-yl)phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq2), 9,10-di(naphthalen-2-yl)anthracene (ADN), 1,3-bis[3,5-di(pyridine-3-yl)phenyl]benzene (BmPyPhB)), or a mixture thereof, without limitation. The thickness of the electron transport layer ETL may be from about 100 Å to about 1,000 Å and may be, for example, from about 150 Å to about 500 Å. If the thickness of the electron transport layer ETL satisfies the above-described range, satisfactory (or suitable) electron transport properties may be obtained without substantial increase of a driving voltage.

If the electron transport region ETR includes the electron injection layer EIL, the electron transport region ETR may include metal halides (such as LiF, NaCl, CsF, RbCl, and/or RbI), a metal in lanthanoides (such as Yb), a metal oxide (such as $Li_2O$ and/or BaO), and/or lithium quinolate (Liq). However, an embodiment of the present disclosure is not limited thereto. The electron injection layer EIL also may be formed using a mixture material of an electron transport material and an insulating organo metal salt. The organo metal salt may be a material having an energy band gap of about 4 eV or more. The organo metal salt may include, for example, one or more selected from metal acetates, metal benzoates, metal acetoacetates, metal acetylacetonates, and metal stearates. The thickness of the electron injection layer EIL may be from about 1 Å to about 100 Å, and from about 3 Å to about 90 Å. If the thickness of the electron injection layer EIL satisfies the above described range, satisfactory (or suitable) electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, an embodiment of the present disclosure is not limited thereto.

The second electrode EL2 is provided on the electron transport region ETR. The second electrode EL2 may be a common electrode and/or a cathode. The second electrode EL2 may be a transmissive electrode, a transflective electrode, or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using any of the above-described materials and a transparent conductive layer formed using ITO, IZO, ZnO, ITZO, etc.

The second electrode EL2 may be connected with an auxiliary electrode. If the second electrode EL2 is connected with the auxiliary electrode, the resistance of the second electrode EL2 may decrease.

In some embodiments, on the second electrode EL2 of the organic electroluminescence device 10 of an embodiment, a capping layer CPL may be further provided. The capping layer CPL may include, for example, α-NPD, NPB, TPD, m-MTDATA, $Alq_3$, CuPc, N4,N4,N4',N4'-tetra(biphenyl-4-yl) biphenyl-4,4'-diamine (TPD15), 4,4',4"-tris(carbazol-9-yl) triphenylamine (TCTA), N,N'-bis(naphthalen-1-yl), etc.

The organic electroluminescence device 10 according to an embodiment of the present disclosure includes the amine compound of an embodiment in at least one functional layer between the first electrode EU and the second electrode EL2, thereby showing improved emission efficiency and improved life characteristics. For example, the amine compound according to an embodiment may be included in the hole transport region HTR of the organic electroluminescence device 10 of an embodiment, and the organic electroluminescence device of an embodiment may show excellent emission efficiency and long-life characteristics.

The amine compound of an embodiment includes two dibenzoheterocyclic groups, and an aryl-substituted phenylene group as a portion of a linker for connecting the two dibenzoheterocyclic groups, and may contribute to the increase of efficiency and long-life characteristics of the organic electroluminescence device.

Hereinafter, the amine compound according to an embodiment and the organic electroluminescence device of an embodiment of the present disclosure will be particularly explained referring to embodiments and comparative embodiments. However, the following embodiments are only illustrations to assist the understanding of the present disclosure, and the scope of the present disclosure is not limited thereto.

EXAMPLES

1. Synthesis of Amine Compounds

First, the synthetic method of the amine compounds according to example embodiments will be particularly explained referring to the synthetic methods of example compounds in each of Compound Group A, Compound Group B, and Compound Group C. However, the synthetic methods of the amine compounds explained below are only example embodiments, and the synthetic method of the amine compound according to an embodiment of the present disclosure is not limited thereto.

Synthesis of Compound A2

Amine Compound A2 according to an embodiment may be synthesized, for example, by the steps of the following Reaction 1:

Reaction 1

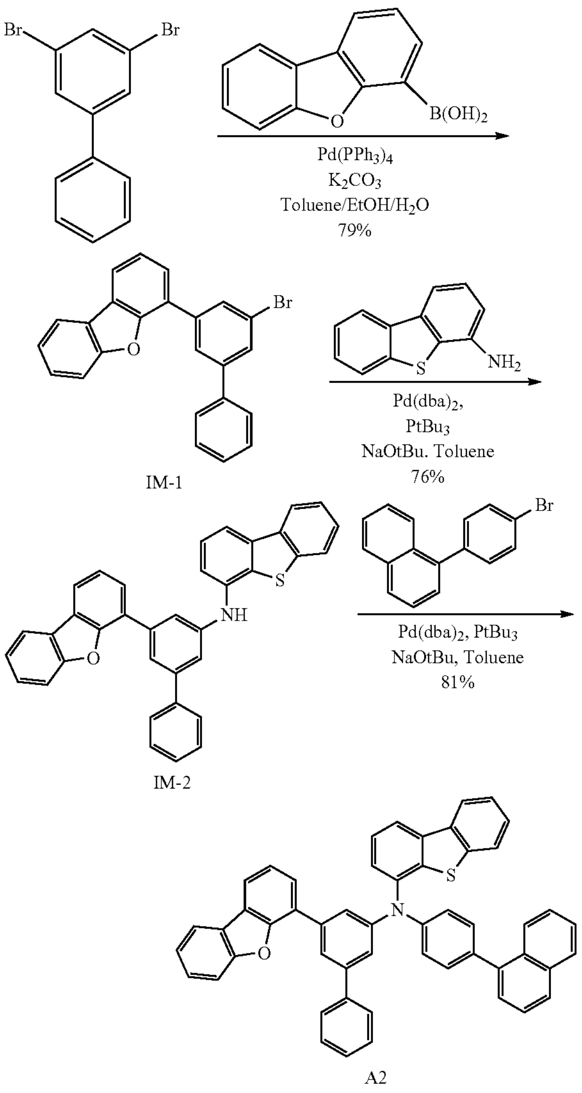

(Synthesis of Intermediate IM-1)

Under an argon (Ar) atmosphere, to a 1,000 ml, three-neck flask, 20.00 g (64.1 mmol) of 3,5-dibromo-biphenyl, 14.95 g (1.1 eq, 70.5 mmol) of 4-dibenzofuranylboronic acid, 26.58 g (3.0 eq, 192.3 mmol) of $K_2CO_3$, 3.70 g (0.05 eq, 3.2 mmol) of $Pd(PPh_3)_4$, and 448 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-1 (20.22 g, yield 79%).

By Fast Atom Bombardment-Mass Spectrometry (FAB-MS) measurement, mass number of m/z=399 was observed as a molecular ion peak, and Intermediate IM-1 was identified.

(Synthesis of Intermediate IM-2)

Under an argon atmosphere, to a 500 ml, three-neck flask, 15.00 g (37.6 mmol) of Intermediate IM-1, 0.65 g (0.03 eq, 1.1 mmol) of $Pd(dba)_2$, 3.61 g (1.0 eq, 37.6 mmol) of NaOtBu, 188 ml of toluene, 8.24 g (1.1 eq, 41.5 mmol) of 4-aminodibenzothiophene and 0.76 g (0.1 eq, 3.8 mmol) of $tBu_3P$ were added in order, followed by heating, refluxing and stirring. After cooling in the air to room temperature, water was added to the reaction solution, and an organic layer was separately taken.

Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-2 (14.78 g, yield 76%).

By FAB-MS measurement, mass number of m/z=517 was observed as a molecular ion peak, and Intermediate IM-2 was identified.

(Synthesis of Compound A2)

Under an argon atmosphere, to a 300 ml, three-neck flask, 10.00 g (19.3 mmol) of Intermediate IM-2, 0.33 g (0.03 eq, 0.6 mmol) of $Pd(dba)_2$, 3.71 g (2.0 eq, 38.6 mmol) of NaOtBu, 97 ml of toluene, 6.02 g (1.1 eq, 21.2 mmol) of 1-(4-bromophenyl)naphthalene and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound A2 (11.26 g, yield 81%) as a solid.

By FAB-MS measurement, mass number of m/z=719 was observed as a molecular ion peak, and Compound A2 was identified.

Synthesis of Compound A19

Amine Compound A19 according to an embodiment may be synthesized, for example, by the steps of the following Reaction 2:

Reaction 2

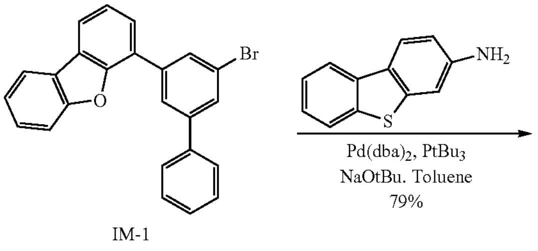

-continued

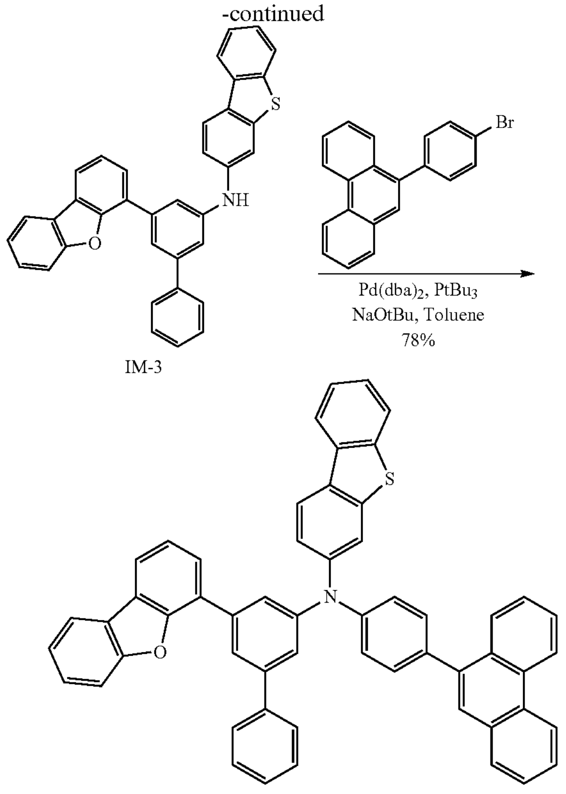

IM-3

A19

(Synthesis of Intermediate IM-3)

Under an argon atmosphere, to a 500 ml, three-neck flask, 15.00 g (37.6 mmol) of Intermediate IM-1, 0.65 g (0.03 eq, 1.1 mmol) of Pd(dba)$_2$, 3.61 g (1.0 eq, 37.6 mmol) of NaOtBu, 188 ml of toluene, 8.24 g (1.1 eq, 41.3 mmol) of 3-aminodibenzothiophene and 0.76 g (0.1 eq, 3.8 mmol) of tBu$_3$P were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-3 (15.36 g, yield 79%).

By FAB-MS measurement, mass number of m/z=517 was observed as a molecular ion peak, and Intermediate IM-3 was identified.

(Synthesis of Compound A19)

Under an argon atmosphere, to a 300 ml, three-neck flask, 10.00 g (19.3 mmol) of Intermediate IM-3, 0.33 g (0.03 eq, 0.6 mmol) of Pd(dba)$_2$, 3.71 g (2.0 eq, 38.6 mmol) of NaOtBu, 97 ml of toluene, 7.08 g (1.1 eq, 21.2 mmol) of 9-(4-bromophenyl)phenanthrene and 0.39 g (0.1 eq, 1.9 mmol) of tBu$_3$P were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound A19 (11.60 g, yield 78%) as a solid.

By FAB-MS measurement, mass number of m/z=769 was observed as a molecular ion peak, and Compound A19 was identified.

Synthesis of Compound A50

Amine Compound A50 according to an embodiment may be synthesized, for example, by the steps of the following Reaction 3:

Reaction 3

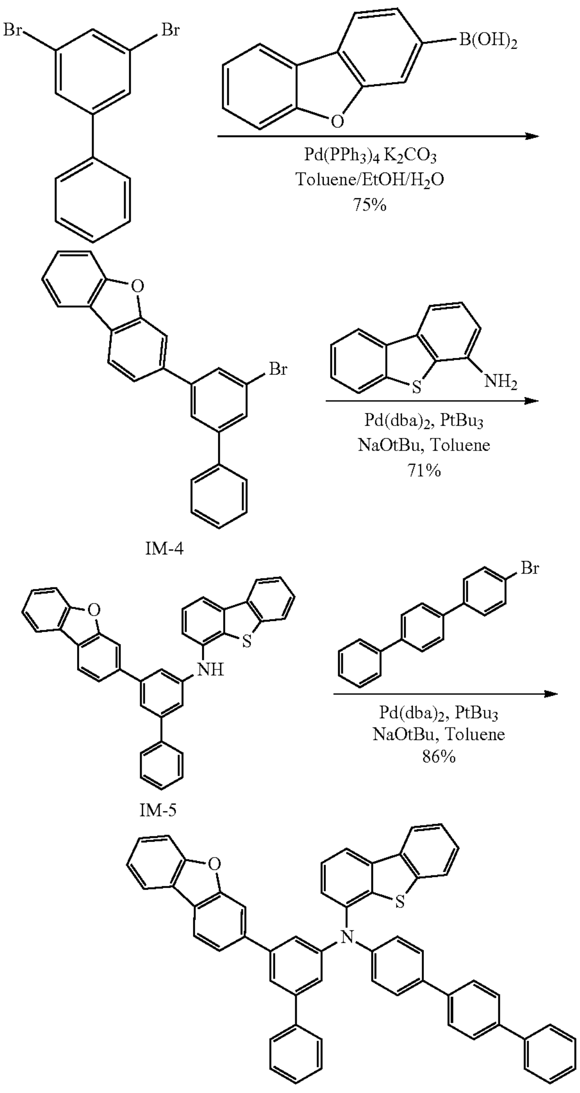

IM-4

IM-5

A50

(Synthesis of Intermediate IM-4)

Under an argon atmosphere, to a 1,000 ml, three-neck flask, 20.00 g (64.1 mmol) of 3,5-dibromo-biphenyl, 14.95 g (1.1 eq, 70.5 mmol) of 3-dibenzofuranylboronic acid, 26.58 g (3.0 eq, 192.3 mmol) of $K_2CO_3$, 3.70 g (0.05 eq, 3.2 mmol) of $Pd(PPh_3)_4$, and 448 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-4 (19.20 g, yield 75%).

By FAB-MS measurement, mass number of m/z=399 was observed as a molecular ion peak, and Intermediate IM-4 was identified.

(Synthesis of Intermediate IM-5)

Under an argon atmosphere, to a 500 ml, three-neck flask, 15.00 g (37.6 mmol) of Intermediate IM-4, 0.65 g (0.03 eq, 1.1 mmol) of $Pd(dba)_2$, 3.61 g (1.0 eq, 37.6 mmol) of NaOtBu, 188 ml of toluene, 8.24 g (1.1 eq, 41.3 mmol) of 4-aminodibenzothiophene and 0.76 g (0.1 eq, 3.8 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-5 (13.81 g, yield 71%).

By FAB-MS measurement, mass number of m/z=517 was observed as a molecular ion peak, and Intermediate IM-5 was identified.

(Synthesis of Compound A50)

Under an argon atmosphere, to a 300 ml, three-neck flask, 10.00 g (19.3 mmol) of Intermediate IM-5, 0.33 g (0.03 eq, 0.6 mmol) of $Pd(dba)_2$, 3.71 g (2.0 eq, 38.6 mmol) of NaOtBu, 97 ml of toluene, 6.57 g (1.1 eq, 21.2 mmol) of 4-bromo-p-terphenyl and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound A50 (12.39 g, yield 86%) as a solid.

By FAB-MS measurement, mass number of m/z=745 was observed as a molecular ion peak, and Compound A50 was identified.

Synthesis of Compound A86

Amine Compound A86 according to an embodiment may be synthesized, for example, by the steps of the following Reaction 4:

Reaction 4

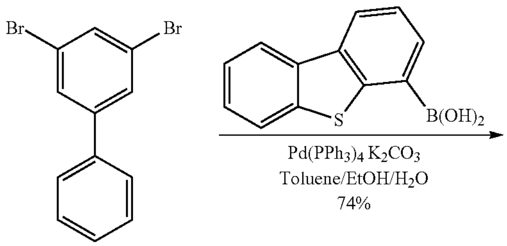

-continued

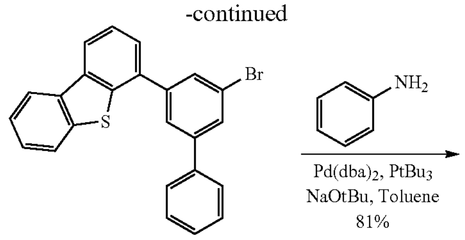

IM-6

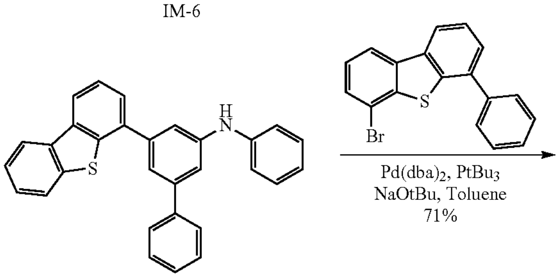

IM-7

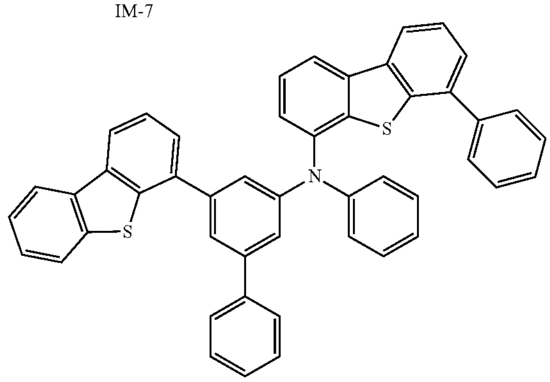

A86

(Synthesis of Intermediate IM-6)

Under an argon atmosphere, to a 1,000 ml, three-neck flask, 20.00 g (64.1 mmol) of 3,5-dibromo-biphenyl, 16.08 g (1.1 eq, 70.5 mmol) of 4-dibenzothiophenylboronic acid, 26.58 g (3.0 eq, 192.3 mmol) of $K_2CO_3$, 3.70 g (0.05 eq, 3.2 mmol) of $Pd(PPh_3)_4$, and 448 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-6 (19.70 g, yield 74%).

By FAB-MS measurement, mass number of m/z=415 was observed as a molecular ion peak, and Intermediate IM-6 was identified.

(Synthesis of Intermediate IM-7)

Under an argon atmosphere, to a 500 ml, three-neck flask, 15.00 g (36.1 mmol) of Intermediate IM-6, 0.62 g (0.03 eq, 1.1 mmol) of $Pd(dba)_2$, 3.47 g (1.0 eq, 36.1 mmol) of NaOtBu, 180 ml of toluene, 3.70 g (1.1 eq, 39.7 mmol) of aniline and 0.73 g (0.1 eq, 3.6 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-7 (12.51 g, yield 81%).

By FAB-MS measurement, mass number of m/z=427 was observed as a molecular ion peak, and Intermediate IM-7 was identified.

(Synthesis of Compound A86)

Under an argon atmosphere, to a 300 ml, three-neck flask, 10.00 g (23.4 mmol) of Intermediate IM-7, 0.40 g (0.03 eq, 0.7 mmol) of $Pd(dba)_2$, 4.50 g (2.0 eq, 46.8 mmol) of NaOtBu, 117 ml of toluene, 8.73 g (1.1 eq, 25.7 mmol) of 4-bromo-6-phenyl-dibenzothiophene and 0.47 g (0.1 eq, 2.3 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound A86 (11.39 g, yield 71%) as a solid.

By FAB-MS measurement, mass number of m/z=685 was observed as a molecular ion peak, and Compound A86 was identified.

Synthesis of Compound A103

Amine Compound A103 according to an embodiment may be synthesized, for example, by the steps of the following Reaction 5:

Reaction 5

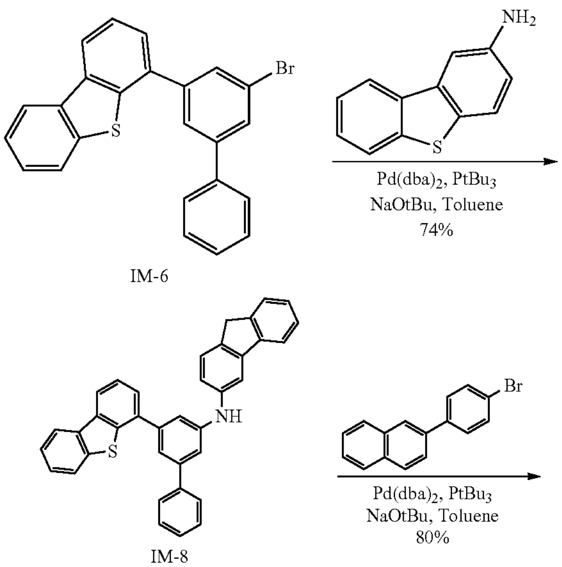

IM-6

IM-8

-continued

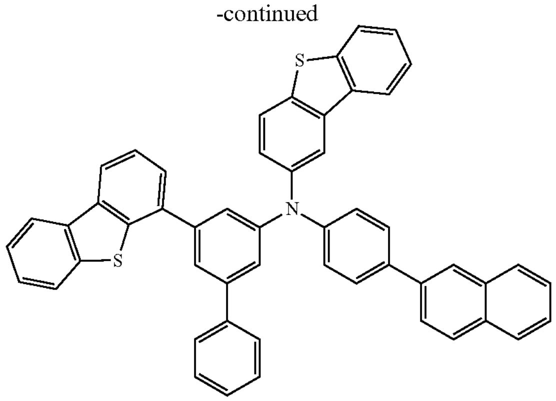

A103

(Synthesis of Intermediate IM-8)

Under an argon atmosphere, to a 500 ml, three-neck flask, 15.00 g (36.1 mmol) of Intermediate IM-6, 0.62 g (0.03 eq, 1.1 mmol) of $Pd(dba)_2$, 3.47 g (1.0 eq, 36.1 mmol) of NaOtBu, 180 ml of toluene, 7.92 g (1.1 eq, 39.7 mmol) of 2-aminodibenzothiophene and 0.73 g (0.1 eq, 3.6 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-8 (14.26 g, yield 74%).

By FAB-MS measurement, mass number of m/z=533 was observed as a molecular ion peak, and Intermediate IM-8 was identified.

(Synthesis of Compound A103)

Under an argon atmosphere, to a 300 ml, three-neck flask, 10.00 g (18.7 mmol) of Intermediate IM-8, 0.32 g (0.03 eq, 0.6 mmol) of $Pd(dba)_2$, 3.60 g (2.0 eq, 37.5 mmol) of NaOtBu, 94 ml of toluene, 5.84 g (1.1 eq, 20.6 mmol) of 2-(4-bromophenyl)naphthalene and 0.38 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound A103 (11.03 g, yield 80%) as a solid.

By FAB-MS measurement, mass number of m/z=735 was observed as a molecular ion peak, and Compound A103 was identified.

Synthesis of Compound A172

Amine Compound A172 according to an embodiment may be synthesized, for example, by the steps of the following Reaction 6:

Reaction 6

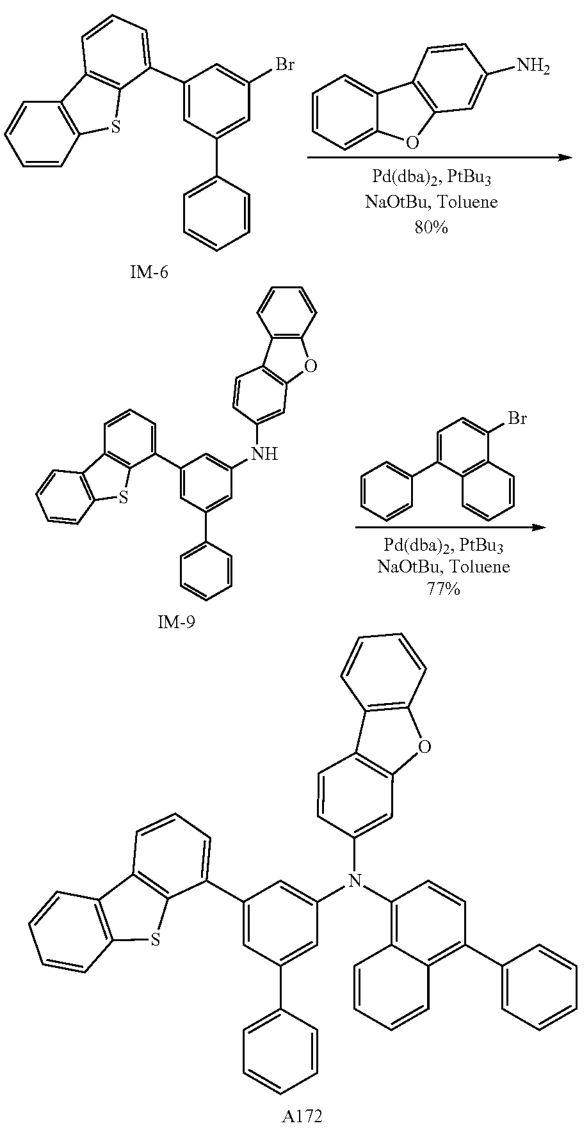

(Synthesis of Intermediate IM-9)

Under an argon atmosphere, to a 500 ml, three-neck flask, 15.00 g (36.1 mmol) of Intermediate IM-6, 0.62 g (0.03 eq, 1.1 mmol) of $Pd(dba)_2$, 3.47 g (1.0 eq, 36.1 mmol) of NaOtBu, 180 ml of toluene, 7.28 g (1.1 eq, 39.7 mmol) of 3-aminodibenzofuran and 0.73 g (0.1 eq, 3.6 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-9 (14.96 g, yield 80%).

By FAB-MS measurement, mass number of m/z=517 was observed as a molecular ion peak, and Intermediate IM-9 was identified.

(Synthesis of Compound A172)

Under an argon atmosphere, to a 300 ml, three-neck flask, 10.00 g (19.3 mmol) of Intermediate IM-9, 0.33 g (0.03 eq, 0.6 mmol) of $Pd(dba)_2$, 3.71 g (2.0 eq, 38.6 mmol) of NaOtBu, 97 ml of toluene, 6.02 g (1.1 eq, 21.2 mmol) of 1-bromo-4-phenylnaphthalene and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound A172 (10.71 g, yield 77%) as a solid.

By FAB-MS measurement, mass number of m/z=719 was observed as a molecular ion peak, and Compound A172 was identified.

Synthesis of Compound A195

Amine Compound A195 according to an embodiment may be synthesized, for example, by the steps of the following Reaction 7:

Reaction 7

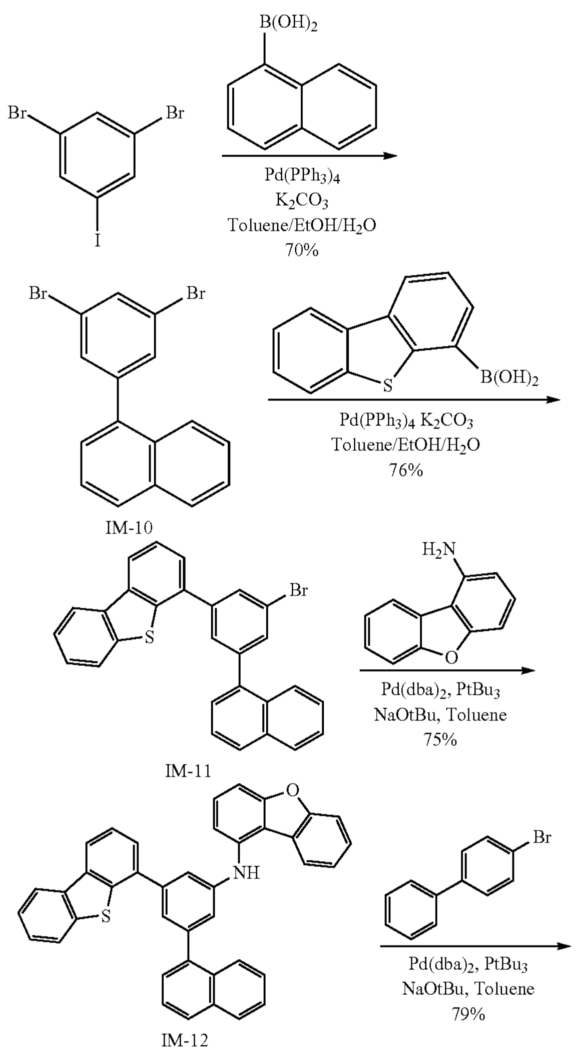

-continued

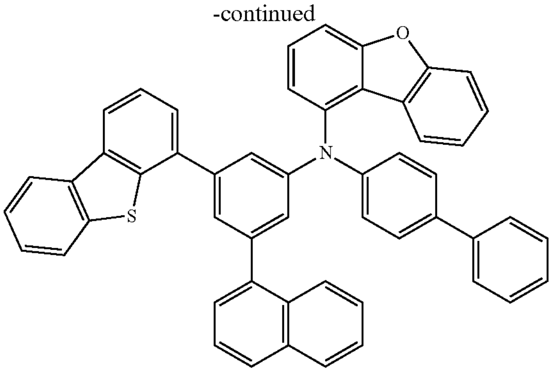

A195

(Synthesis of Intermediate IM-10)

Under an argon atmosphere, to a 1,000 ml, three-neck flask, 30.00 g (82.9 mmol) of 1,3-dibromo-1-iodobenzene, 15.69 g (1.1 eq, 91.2 mmol) of 1-naphthaleneboronic acid, 34.38 g (3.0 eq, 248.8 mmol) of $K_2CO_3$, 4.79 g (0.05 eq, 4.1 mmol) of $Pd(PPh_3)_4$, and 580 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-10 (21.02 g, yield 70%).

By FAB-MS measurement, mass number of m/z=362 was observed as a molecular ion peak, and Intermediate IM-10 was identified.

(Synthesis of Intermediate IM-11)

Under an argon atmosphere, to a 1,000 ml, three-neck flask, 20.00 g (55.2 mmol) of Intermediate IM-10, 13.86 g (1.1 eq, 60.8 mmol) of 4-dibenzothiophenylboronic acid, 22.90 g (3.0 eq, 165.7 mmol) of $K_2CO_3$, 3.19 g (0.05 eq, 2.8 mmol) of $Pd(PPh_3)_4$, and 387 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-11 (19.54 g, yield 76%).

By FAB-MS measurement, mass number of m/z=465 was observed as a molecular ion peak, and Intermediate IM-11 was identified.

(Synthesis of Intermediate IM-12)

Under an argon atmosphere, to a 500 ml, three-neck flask, 15.00 g (32.3 mmol) of Intermediate IM-11, 0.56 g (0.03 eq, 1.0 mmol) of $Pd(dba)_2$, 3.10 g (1.0 eq, 32.2 mmol) of NaOtBu, 161 ml of toluene, 6.50 g (1.1 eq, 35.5 mmol) of 1-aminodibenzofuran and 0.65 g (0.1 eq, 3.2 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-12 (13.72 g, yield 75%).

By FAB-MS measurement, mass number of m/z=567 was observed as a molecular ion peak, and Intermediate IM-12 was identified.

(Synthesis of Compound A195)

Under an argon atmosphere, to a 300 ml, three-neck flask, 10.00 g (17.6 mmol) of Intermediate IM-12, 0.30 g (0.03 eq, 0.5 mmol) of $Pd(dba)_2$, 3.39 g (2.0 eq, 35.2 mmol) of NaOtBu, 88 ml of toluene, 4.52 g (1.1 eq, 19.4 mmol) of 4-bromobiphenyl and 0.36 g (0.1 eq, 1.8 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound A195 (10.02 g, yield 79%) as a solid.

By FAB-MS measurement, mass number of m/z=719 was observed as a molecular ion peak, and Compound A195 was identified.

Synthesis of Compound A226

Amine Compound A226 according to an embodiment may be synthesized, for example, by the steps in the following Reaction 8:

Reaction 8

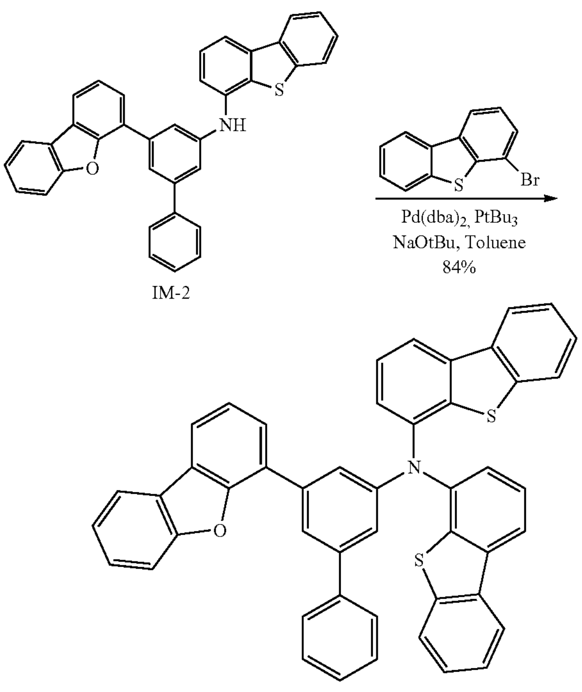

Under an argon atmosphere, to a 300 ml, three-neck flask, 10.00 g (19.3 mmol) of Intermediate IM-2, 0.33 g (0.03 eq, 0.6 mmol) of $Pd(dba)_2$, 3.71 g (2.0 eq, 38.6 mmol) of NaOtBu, 97 ml of toluene, 5.59 g (1.1 eq, 21.2 mmol) of 4-bromodibenzothiophene and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound A226 (11.36 g, yield 84%) as a solid.

By FAB-MS measurement, mass number of m/z=699 was observed as a molecular ion peak, and Compound A226 was identified.

Synthesis of Compound B1

Amine Compound B1 according to an embodiment may be synthesized, for example, by the steps of the following Reaction 9:

Reaction 9

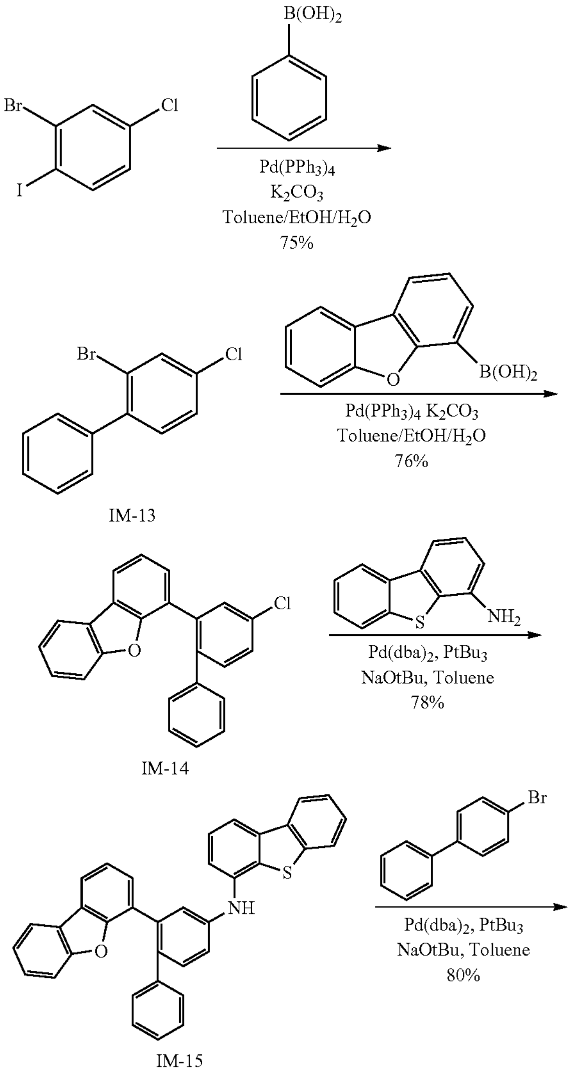

-continued

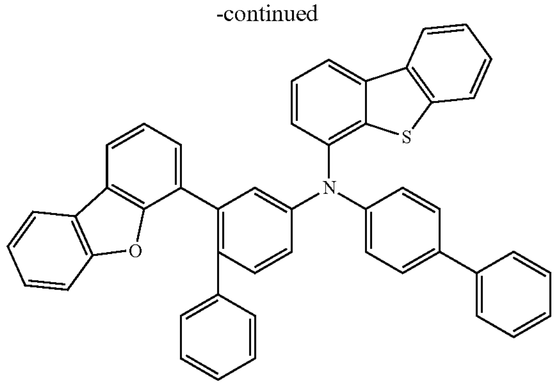

B1

(Synthesis of Intermediate IM-13)

Under an argon atmosphere, to a 1,000 ml, three-neck flask, 30.00 g (94.5 mmol) of 2-bromo-4-chloro-1-iodobenzene, 12.68 g (1.1 eq, 104.0 mmol) of phenylboronic acid, 39.20 g (3.0 eq, 283.6 mmol) of $K_2CO_3$, 5.46 g (0.05 eq, 4.7 mmol) of $Pd(PPh_3)_4$, and 662 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-13 (18.97 g, yield 75%).

By FAB-MS measurement, mass number of m/z=267 was observed as a molecular ion peak, and Intermediate IM-13 was identified.

(Synthesis of Intermediate IM-14)

Under an argon atmosphere, to a 1,000 ml, three-neck flask, 17.00 g (63.5 mmol) of Intermediate IM-13, 14.82 g (1.1 eq, 69.9 mmol) of 4-dibenzofuranylboronic acid, 26.35 g (3.0 eq, 190.6 mmol) of $K_2CO_3$, 3.67 g (0.05 eq, 3.2 mmol) of $Pd(PPh_3)_4$, and 445 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-14 (17.13 g, yield 76%).

By FAB-MS measurement, mass number of m/z=354 was observed as a molecular ion peak, and Intermediate IM-14 was identified.

(Synthesis of Intermediate IM-15)

Under an argon atmosphere, to a 500 ml, three-neck flask, 15.00 g (42.3 mmol) of Intermediate IM-14, 0.73 g (0.03 eq, 1.3 mmol) of $Pd(dba)_2$, 4.06 g (1.0 eq, 42.3 mmol) of NaOtBu, 211 ml of toluene, 9.27 g (1.1 eq, 46.5 mmol) of 4-aminodibenzothiophene and 0.86 g (0.1 eq, 4.2 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted.

Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-15 (17.07 g, yield 78%).

By FAB-MS measurement, mass number of m/z=517 was observed as a molecular ion peak, and Intermediate IM-15 was identified.

(Synthesis of Compound B1)

Under an argon atmosphere, to a 300 ml, three-neck flask, 10.00 g (19.3 mmol) of Intermediate IM-15, 0.33 g (0.03 eq, 0.6 mmol) of $Pd(dba)_2$, 3.72 g (2.0 eq, 38.6 mmol) of NaOtBu, 97 ml of toluene, 4.95 g (1.1 eq, 21.2 mmol) of 4-bromobiphenyl and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound B1 (10.35 g, yield 80%) as a solid.

By FAB-MS measurement, mass number of m/z=669 was observed as a molecular ion peak, and Compound B1 was identified.

Synthesis of Compound B18

Amine Compound B18 according to an embodiment may be synthesized, for example, by the steps of the following Reaction 10:

Reaction 10

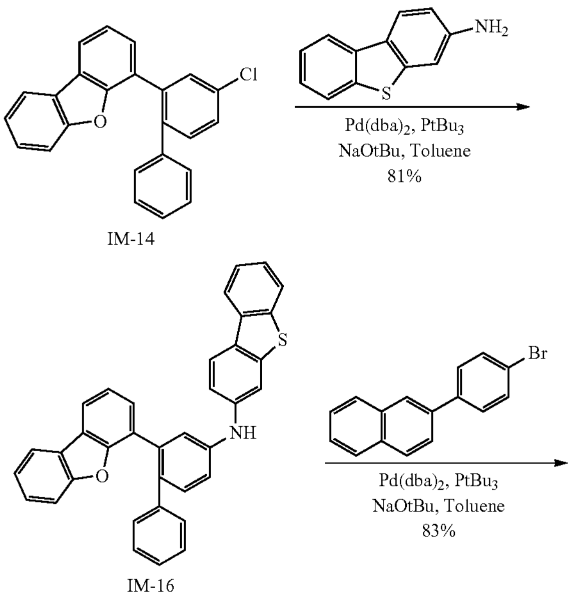

-continued

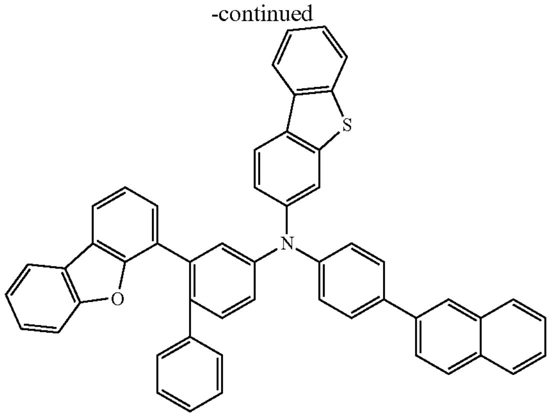

B18

(Synthesis of Intermediate IM-16)

Under an argon atmosphere, to a 500 ml, three-neck flask, 15.00 g (42.3 mmol) of Intermediate IM-14, 0.73 g (0.03 eq, 1.3 mmol) of $Pd(dba)_2$, 4.06 g (1.0 eq, 42.3 mmol) of NaOtBu, 211 ml of toluene, 9.27 g (1.1 eq, 46.5 mmol) of 3-aminodibenzothiophene and 0.86 g (0.1 eq, 4.2 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-16 (17.73 g, yield 81%).

By FAB-MS measurement, mass number of m/z=517 was observed as a molecular ion peak, and Intermediate IM-16 was identified.

(Synthesis of Compound B18)

Under an argon atmosphere, to a 300 ml, three-neck flask, 10.00 g (19.3 mmol) of Intermediate IM-16, 0.33 g (0.03 eq, 0.6 mmol) of $Pd(dba)_2$, 3.72 g (2.0 eq, 38.6 mmol) of NaOtBu, 97 ml of toluene, 6.02 g (1.1 eq, 21.2 mmol) of 2-(4-bromophenyl)naphthalene and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound B18 (11.54 g, yield 83%) as a solid.

By FAB-MS measurement, mass number of m/z=719 was observed as a molecular ion peak, and Compound B18 was identified.

Synthesis of Compound B89

Amine Compound B89 according to an embodiment may be synthesized, for example, by the steps of the following Reaction 11:

Reaction 11

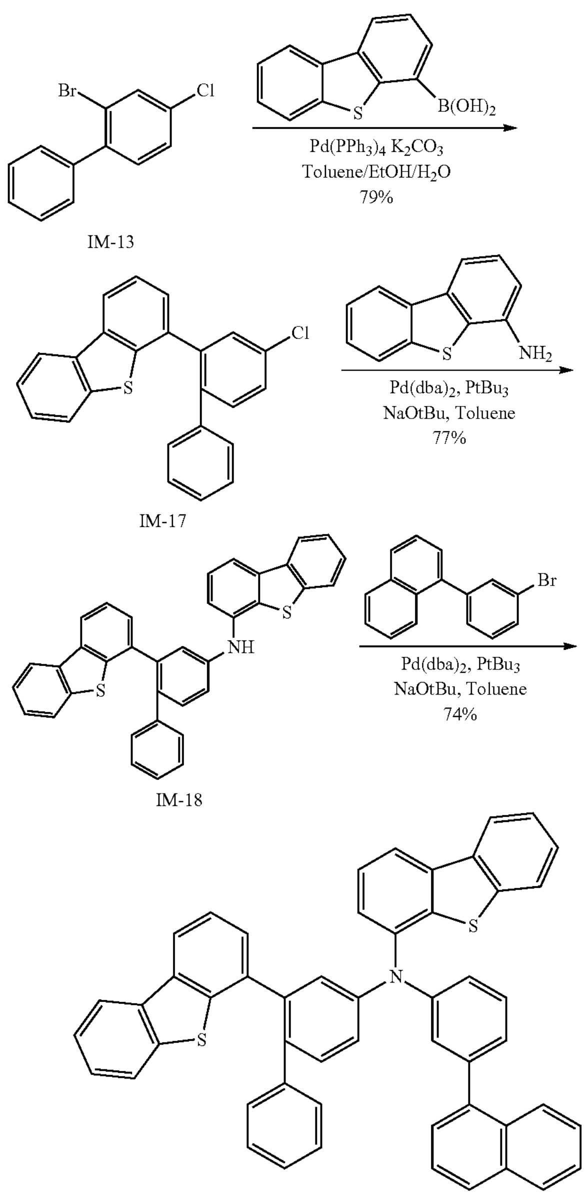

B89

(Synthesis of Intermediate IM-17)

Under an argon atmosphere, to a 1,000 ml, three-neck flask, 17.00 g (63.5 mmol) of Intermediate IM-13, 15.94 g (1.1 eq, 69.9 mmol) of 4-dibenzothiophenylboronic acid, 26.35 g (3.0 eq, 190.6 mmol) of $K_2CO_3$, 3.67 g (0.05 eq, 3.2 mmol) of $Pd(PPh_3)_4$, and 445 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-17 (18.62 g, yield 79%).

By FAB-MS measurement, mass number of m/z=370 was observed as a molecular ion peak, and Intermediate IM-17 was identified.

(Synthesis of Intermediate IM-18)

Under an argon atmosphere, to a 500 ml, three-neck flask, 15.00 g (40.4 mmol) of Intermediate IM-17, 0.70 g (0.03 eq, 1.2 mmol) of $Pd(dba)_2$, 3.89 g (1.0 eq, 40.4 mmol) of NaOtBu, 203 ml of toluene, 8.87 g (1.1 eq, 44.5 mmol) of 4-aminodibenzothiophene and 0.82 g (0.1 eq, 4.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-18 (16.62 g, yield 77%).

By FAB-MS measurement, mass number of m/z=533 was observed as a molecular ion peak, and Intermediate IM-18 was identified.

(Synthesis of Compound B89)

Under an argon atmosphere, to a 300 ml, three-neck flask, 10.00 g (18.7 mmol) of Intermediate IM-18, 0.32 g (0.03 eq, 0.6 mmol) of $Pd(dba)_2$, 3.60 g (2.0 eq, 37.5 mmol) of NaOtBu, 94 ml of toluene, 5.84 g (1.1 eq, 20.6 mmol) of 1-(3-bromophenyl)naphthalene and 0.38 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound B89 (10.20 g, yield 74%) as a solid.

By FAB-MS measurement, mass number of m/z=735 was observed as a molecular ion peak, and Compound B89 was identified.

Synthesis of Compound B91

Amine Compound B91 according to an embodiment may be synthesized, for example, by the steps of the following Reaction 12:

Reaction 12

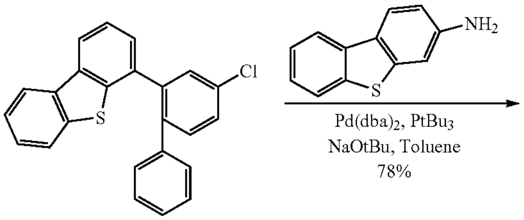

IM-17

-continued

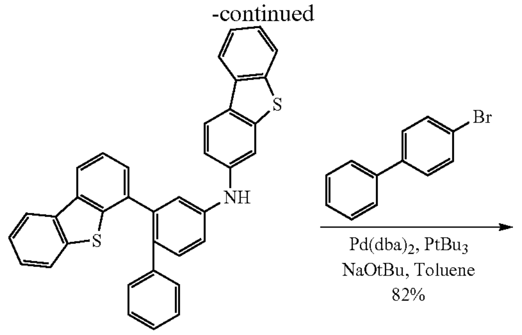

IM-19

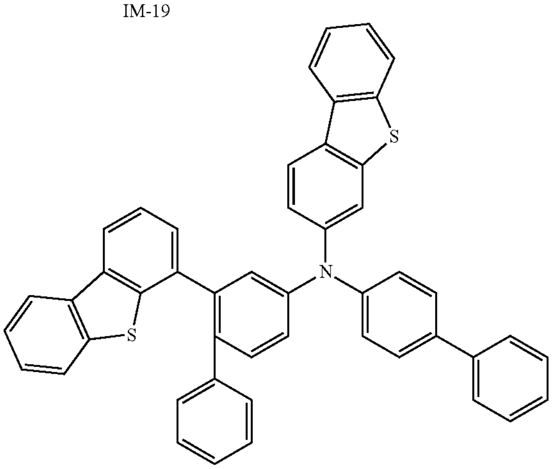

B91

(Synthesis of Intermediate IM-19)

Under an argon atmosphere, to a 500 ml, three-neck flask, 15.00 g (40.4 mmol) of Intermediate IM-17, 0.70 g (0.03 eq, 1.2 mmol) of $Pd(dba)_2$, 3.89 g (1.0 eq, 40.4 mmol) of NaOtBu, 203 ml of toluene, 8.87 g (1.1 eq, 44.5 mmol) of 3-aminodibenzothiophene and 0.82 g (0.1 eq, 4.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-19 (16.84 g, yield 78%).

By FAB-MS measurement, mass number of m/z=533 was observed as a molecular ion peak, and Intermediate IM-19 was identified.

(Synthesis of Compound B91)

Under an argon atmosphere, to a 300 ml, three-neck flask, 10.00 g (18.7 mmol) of Intermediate IM-19, 0.32 g (0.03 eq, 0.6 mmol) of $Pd(dba)_2$, 3.60 g (2.0 eq, 37.5 mmol) of NaOtBu, 94 ml of toluene, 4.80 g (1.1 eq, 20.6 mmol) of 4-bromobiphenyl and 0.38 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound B91 (10.54 g, yield 82%) as a solid.

By FAB-MS measurement, mass number of m/z=685 was observed as a molecular ion peak, and Compound B91 was identified.

Synthesis of Compound B149

Amine Compound B149 according to an embodiment may be synthesized, for example, by the steps of the following Reaction 13:

Reaction 13

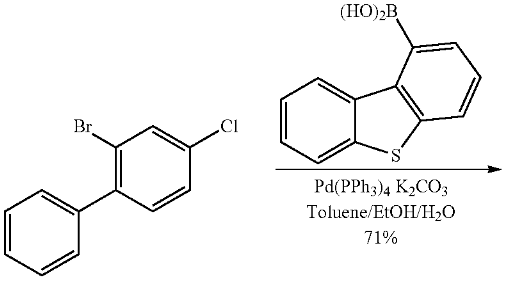

IM-13

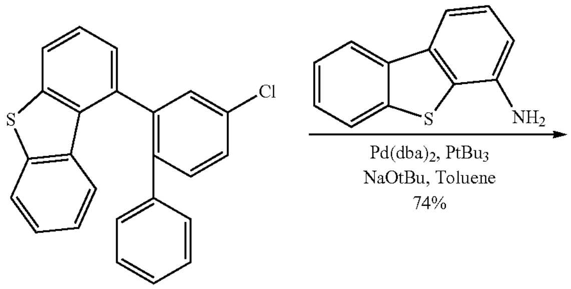

IM-20

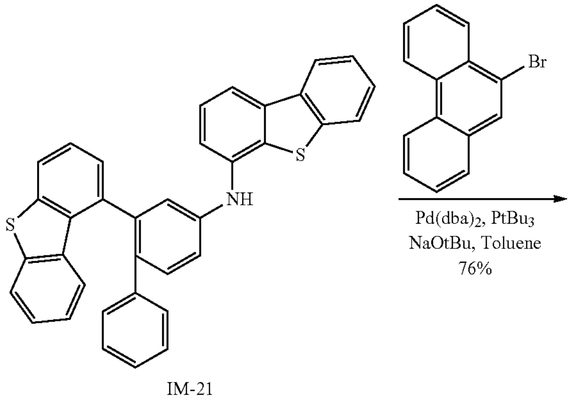

IM-21

-continued

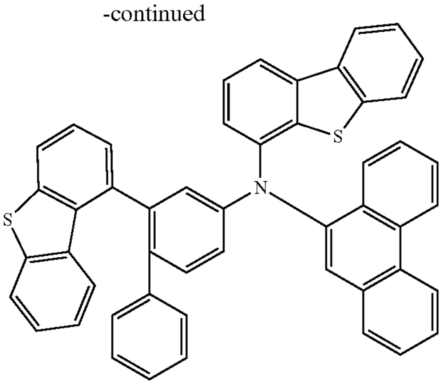

B149

(Synthesis of Intermediate IM-20)

Under an argon atmosphere, to a 1,000 ml, three-neck flask, 17.00 g (63.5 mmol) of Intermediate IM-13, 15.94 g (1.1 eq, 69.9 mmol) of 1-dibenzothiophenylboronic acid, 26.35 g (3.0 eq, 190.6 mmol) of $K_2CO_3$, 3.67 g (0.05 eq, 3.2 mmol) of $Pd(PPh_3)_4$, and 445 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-20 (16.73 g, yield 71%).

By FAB-MS measurement, mass number of m/z=370 was observed as a molecular ion peak, and Intermediate IM-20 was identified.

(Synthesis of Intermediate IM-21)

Under an argon atmosphere, to a 500 ml, three-neck flask, 15.00 g (40.4 mmol) of Intermediate IM-20, 0.70 g (0.03 eq, 1.2 mmol) of $Pd(dba)_2$, 3.89 g (1.0 eq, 40.4 mmol) of NaOtBu, 203 ml of toluene, 8.87 g (1.1 eq, 44.5 mmol) of 4-aminodibenzothiophene and 0.82 g (0.1 eq, 4.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-21 (15.92 g, yield 74%).

By FAB-MS measurement, mass number of m/z=533 was observed as a molecular ion peak, and Intermediate IM-21 was identified.

(Synthesis of Compound B149)

Under an argon atmosphere, to a 300 ml, three-neck flask, 10.00 g (18.7 mmol) of Intermediate IM-21, 0.32 g (0.03 eq, 0.6 mmol) of $Pd(dba)_2$, 3.60 g (2.0 eq, 37.5 mmol) of NaOtBu, 94 ml of toluene, 5.30 g (1.1 eq, 20.6 mmol) of 9-bromophenanthrene and 0.38 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound B149 (10.11 g, yield 76%) as a solid.

By FAB-MS measurement, mass number of m/z=709 was observed as a molecular ion peak, and Compound B149 was identified.

Synthesis of Compound B165

Amine Compound B165 according to an embodiment may be synthesized, for example, by the steps of the following Reaction 14:

Reaction 14

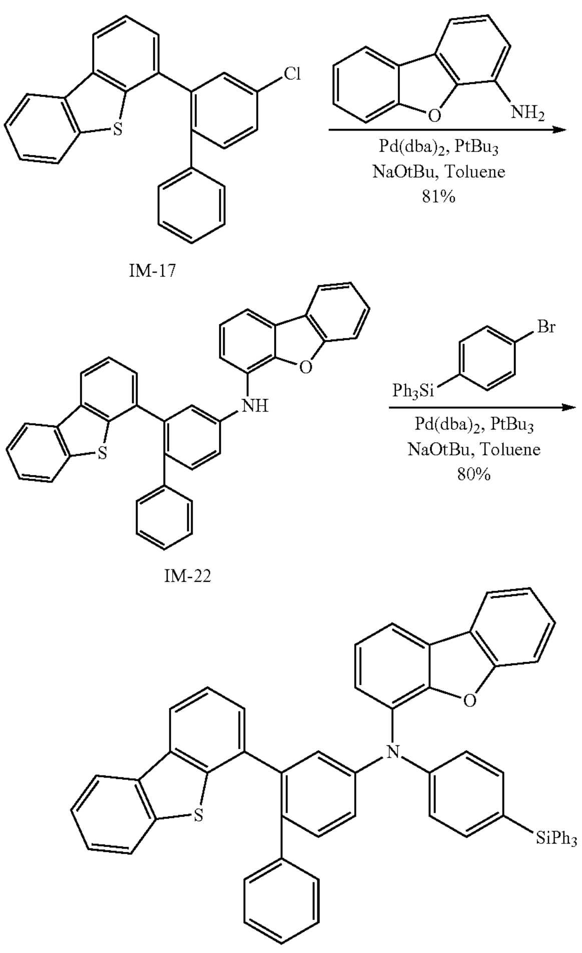

IM-17

IM-22

B165

(Synthesis of Intermediate IM-22)

Under an argon atmosphere, to a 500 ml, three-neck flask, 15.00 g (40.4 mmol) of Intermediate IM-17, 0.70 g (0.03 eq, 1.2 mmol) of $Pd(dba)_2$, 3.89 g (1.0 eq, 40.4 mmol) of NaOtBu, 203 ml of toluene, 8.15 g (1.1 eq, 44.5 mmol) of 4-aminodibenzofuran and 0.82 g (0.1 eq, 4.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted.

Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-22 (16.96 g, yield 81%).

By FAB-MS measurement, mass number of m/z=517 was observed as a molecular ion peak, and Intermediate IM-22 was identified.

(Synthesis of Compound B165)

Under an argon atmosphere, to a 300 ml, three-neck flask, 10.00 g (19.3 mmol) of Intermediate IM-22, 0.33 g (0.03 eq, 0.6 mmol) of $Pd(dba)_2$, 3.72 g (2.0 eq, 38.6 mmol) of NaOtBu, 97 ml of toluene, 8.83 g (1.1 eq, 21.2 mmol) of (4-bromophenyl)triphenylsilane and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound B165 (13.17 g, yield 80%) as a solid.

By FAB-MS measurement, mass number of m/z=852 was observed as a molecular ion peak, and Compound B165 was identified.

Synthesis of Compound B217

Amine Compound B217 according to an embodiment may be synthesized, for example, by the steps of the following Reaction 15:

Reaction 15

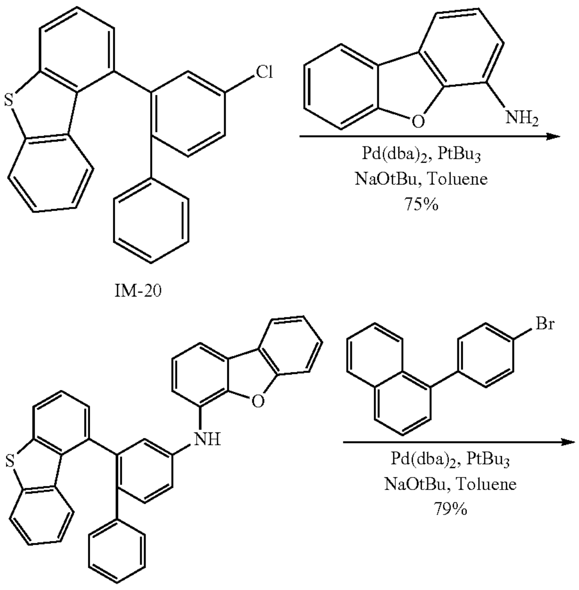

IM-20

IM-23

-continued

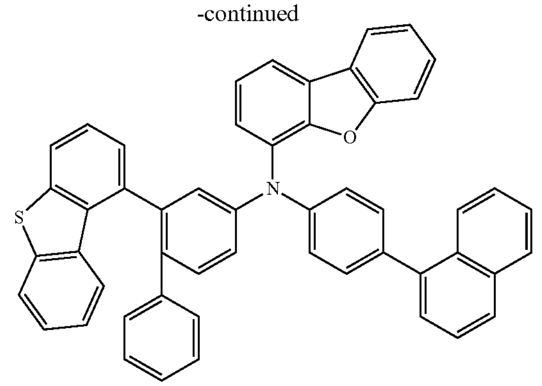

B217

(Synthesis of Intermediate IM-23)

Under an argon atmosphere, to a 500 ml, three-neck flask, 15.00 g (40.4 mmol) of Intermediate IM-20, 0.70 g (0.03 eq, 1.2 mmol) of $Pd(dba)_2$, 3.89 g (1.0 eq, 40.4 mmol) of NaOtBu, 203 ml of toluene, 8.15 g (1.1 eq, 44.5 mmol) of 4-aminodibenzofuran and 0.82 g (0.1 eq, 4.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-23 (15.70 g, yield 75%).

By FAB-MS measurement, mass number of m/z=517 was observed as a molecular ion peak, and Intermediate IM-23 was identified.

(Synthesis of Compound B217)

Under an argon atmosphere, to a 300 ml, three-neck flask, 10.00 g (19.3 mmol) of Intermediate IM-23, 0.33 g (0.03 eq, 0.6 mmol) of $Pd(dba)_2$, 3.72 g (2.0 eq, 38.6 mmol) of NaOtBu, 97 ml of toluene, 6.02 g (1.1 eq, 21.2 mmol) of 1-(4-bromophenyl)naphthalene and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound B217 (10.99 g, yield 79%) as a solid.

By FAB-MS measurement, mass number of m/z=719 was observed as a molecular ion peak, and Compound B217 was identified.

Synthesis of Compound B233

Amine Compound B233 according to an embodiment may be synthesized, for example, by the steps of the following Reaction 16:

Reaction 16

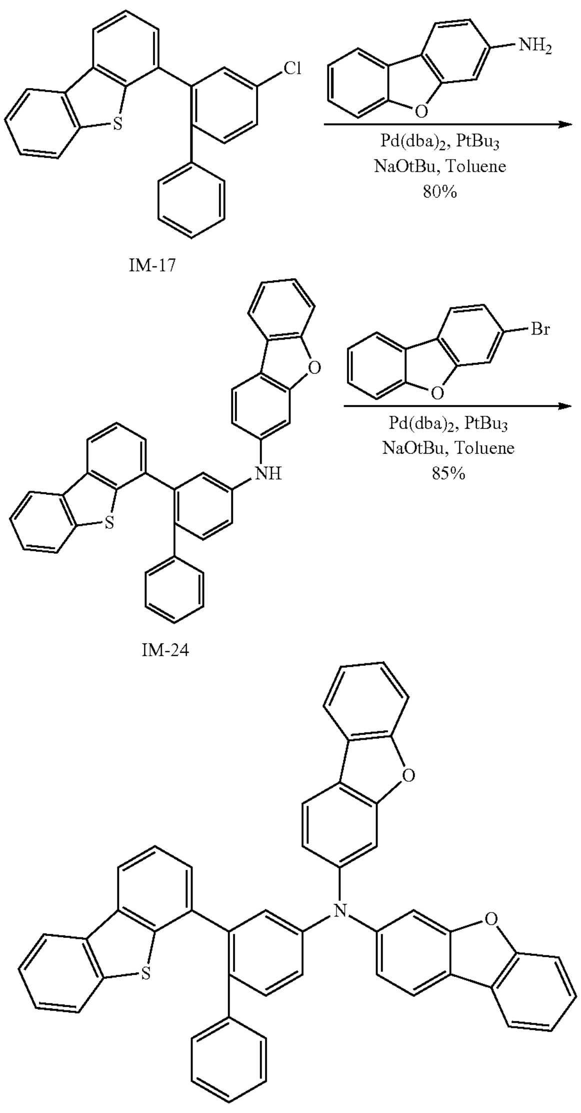

IM-17

IM-24

B233

(Synthesis of Intermediate IM-24)

Under an argon atmosphere, to a 500 ml, three-neck flask, 15.00 g (40.4 mmol) of Intermediate IM-17, 0.70 g (0.03 eq, 1.2 mmol) of Pd(dba)$_2$, 3.89 g (1.0 eq, 40.4 mmol) of NaOtBu, 203 ml of toluene, 8.15 g (1.1 eq, 44.5 mmol) of 3-aminodibenzofuran and 0.82 g (0.1 eq, 4.0 mmol) of tBu$_3$P were added in order, followed by heating, refluxing and stirring.

After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-24 (16.75 g, yield 80%).

By FAB-MS measurement, mass number of m/z=517 was observed as a molecular ion peak, and Intermediate IM-24 was identified.

(Synthesis of Compound B233)

Under an argon atmosphere, to a 300 ml, three-neck flask, 10.00 g (19.3 mmol) of Intermediate IM-24, 0.33 g (0.03 eq, 0.6 mmol) of Pd(dba)$_2$, 3.72 g (2.0 eq, 38.6 mmol) of NaOtBu, 97 ml of toluene, 5.25 g (1.1 eq, 21.2 mmol) of 3-bromodibenzofuran and 0.39 g (0.1 eq, 1.9 mmol) of tBu$_3$P were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound B233 (11.23 g, yield 85%) as a solid.

By FAB-MS measurement, mass number of m/z=683 was observed as a molecular ion peak, and Compound B233 was identified.

Synthesis of Compound C16

Amine Compound C16 according to an embodiment may be synthesized, for example, by the steps of the following Reaction 17:

Reaction 17

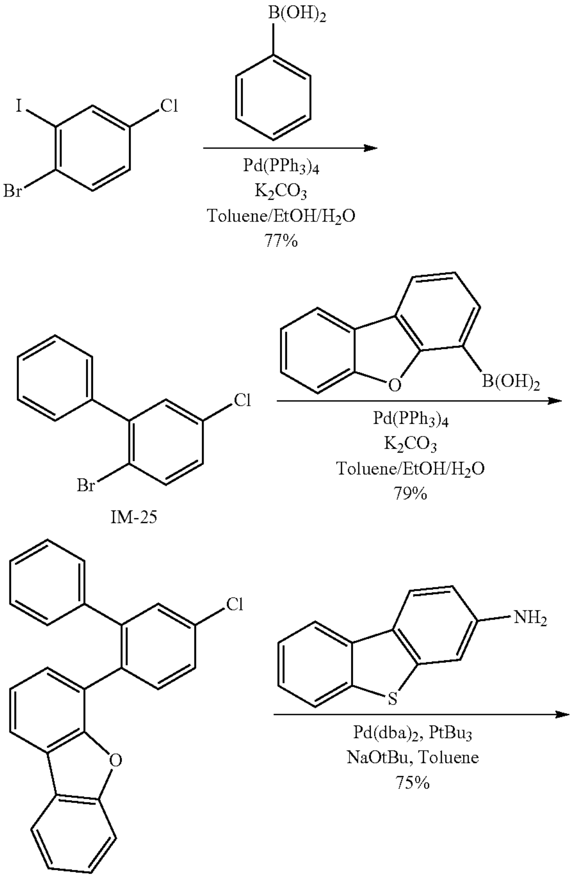

IM-25

IM-26

-continued

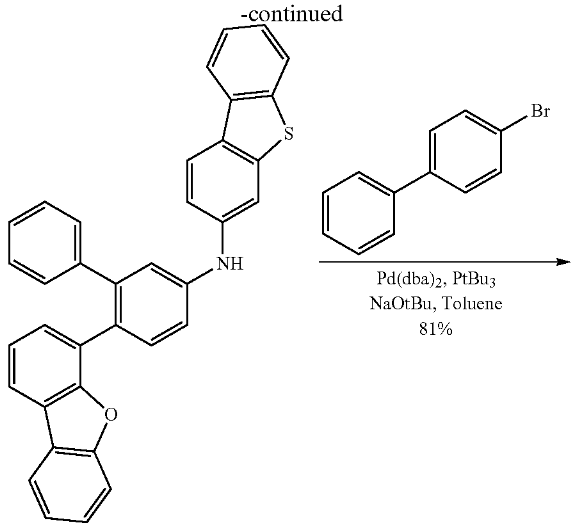

IM-27

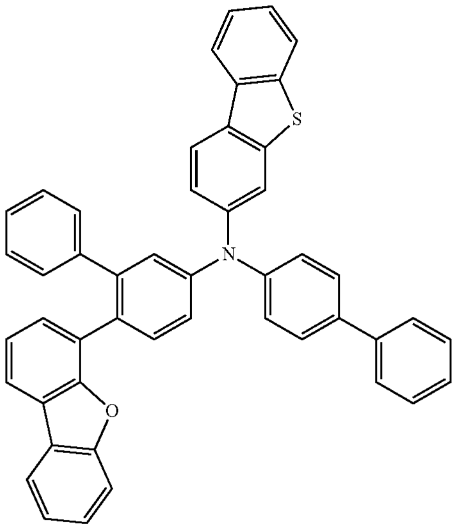

C16

(Synthesis of Intermediate IM-25)

Under an argon atmosphere, to a 1,000 ml, three-neck flask, 30.00 g (94.5 mmol) of 1-bromo-4-chloro-2-iodobenzene, 12.68 g (1.1 eq, 104.0 mmol) of phenylboronic acid, 39.20 g (3.0 eq, 283.6 mmol) of $K_2CO_3$, 5.46 g (0.05 eq, 4.7 mmol) of $Pd(PPh_3)_4$, and 662 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-25 (19.48 g, yield 77%).

By FAB-MS measurement, mass number of m/z=267 was observed as a molecular ion peak, and Intermediate IM-25 was identified.

(Synthesis of Intermediate IM-26)

Under an argon atmosphere, to a 1,000 ml, three-neck flask, 17.00 g (63.5 mmol) of Intermediate IM-25, 14.82 g (1.1 eq, 69.9 mmol) of 4-dibenzofuranylboronic acid, 26.35 g (3.0 eq, 190.6 mmol) of $K_2CO_3$, 3.67 g (0.05 eq, 3.2 mmol) of $Pd(PPh_3)_4$, and 445 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-26 (17.81 g, yield 79%).

By FAB-MS measurement, mass number of m/z=354 was observed as a molecular ion peak, and Intermediate IM-26 was identified.

(Synthesis of Intermediate IM-27)

Under an argon atmosphere, to a 500 ml, three-neck flask, 15.00 g (42.3 mmol) of Intermediate IM-26, 0.73 g (0.03 eq, 1.3 mmol) of $Pd(dba)_2$, 4.06 g (1.0 eq, 42.3 mmol) of NaOtBu, 211 ml of toluene, 9.27 g (1.1 eq, 46.5 mmol) of 3-aminodibenzothiophene and 0.86 g (0.1 eq, 4.2 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-27 (16.41 g, yield 75%).

By FAB-MS measurement, mass number of m/z=517 was observed as a molecular ion peak, and Intermediate IM-27 was identified.

(Synthesis of Compound C16)

Under an argon atmosphere, to a 300 ml, three-neck flask, 10.00 g (19.3 mmol) of Intermediate IM-27, 0.33 g (0.03 eq, 0.6 mmol) of $Pd(dba)_2$, 3.72 g (2.0 eq, 38.6 mmol) of NaOtBu, 97 ml of toluene, 4.95 g (1.1 eq, 21.2 mmol) of 4-bromobiphenyl and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C16 (10.48 g, yield 81%) as a solid.

By FAB-MS measurement, mass number of m/z=669 was observed as a molecular ion peak, and Compound C16 was identified.

Synthesis of Compound C50

Amine Compound C50 according to an embodiment may be synthesized, for example, by the steps of the following Reaction 18:

Reaction 18

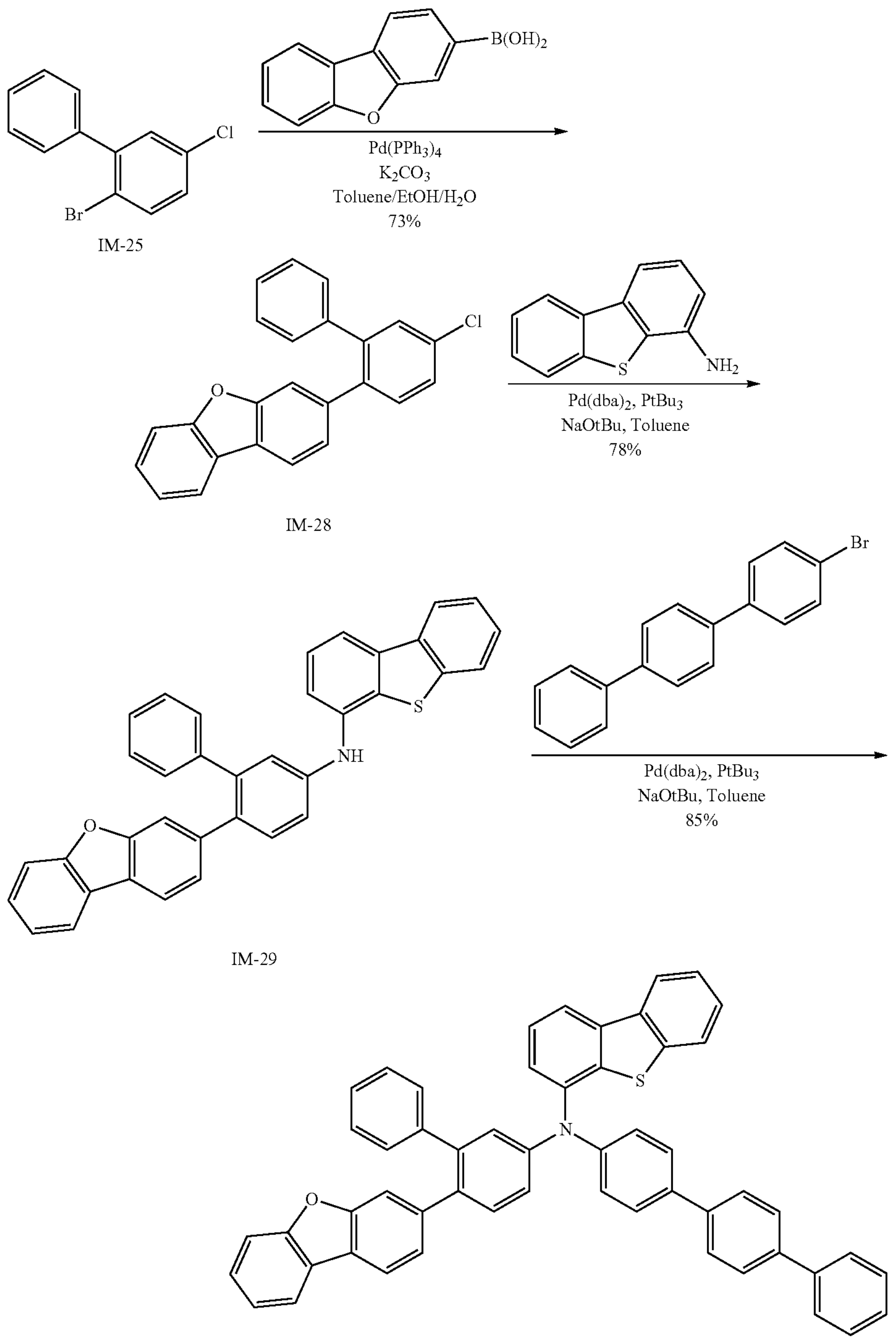

C50

(Synthesis of Intermediate IM-28)

Under an argon atmosphere, to a 1,000 ml, three-neck flask, 17.00 g (63.5 mmol) of Intermediate IM-25, 14.82 g (1.1 eq, 69.9 mmol) of 3-dibenzofuranylboronic acid, 26.35 g (3.0 eq, 190.6 mmol) of $K_2CO_3$, 3.67 g (0.05 eq, 3.2 mmol) of $Pd(PPh_3)_4$, and 445 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-28 (16.46 g, yield 73%).

By FAB-MS measurement, mass number of m/z=354 was observed as a molecular ion peak, and Intermediate IM-28 was identified.

(Synthesis of Intermediate IM-29)

Under an argon atmosphere, to a 500 ml, three-neck flask, 15.00 g (42.3 mmol) of Intermediate IM-28, 0.73 g (0.03 eq, 1.3 mmol) of $Pd(dba)_2$, 4.06 g (1.0 eq, 42.3 mmol) of NaOtBu, 211 ml of toluene, 9.27 g (1.1 eq, 46.5 mmol) of 4-aminodibenzothiophene and 0.86 g (0.1 eq, 4.2 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-29 (17.07 g, yield 78%).

By FAB-MS measurement, mass number of m/z=517 was observed as a molecular ion peak, and Intermediate IM-29 was identified.

(Synthesis of Compound C50)

Under an argon atmosphere, to a 300 ml, three-neck flask, 10.00 g (19.3 mmol) of Intermediate IM-29, 0.33 g (0.03 eq, 0.6 mmol) of $Pd(dba)_2$, 3.72 g (2.0 eq, 38.6 mmol) of NaOtBu, 97 ml of toluene, 6.57 g (1.1 eq, 21.2 mmol) of 4-bromo-terphenyl and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C50 (12.25 g, yield 85%) as a solid.

By FAB-MS measurement, mass number of m/z=745 was observed as a molecular ion peak, and Compound C50 was identified.

Synthesis of Compound C101

Amine Compound C101 according to an embodiment may be synthesized, for example, by the steps of the following Reaction 19:

Reaction 19

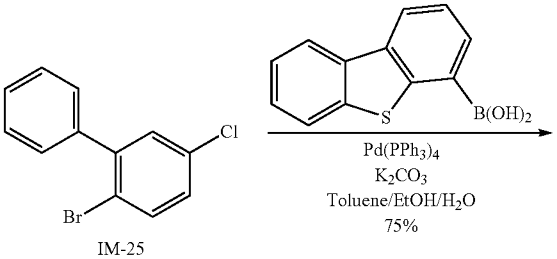

IM-25

-continued

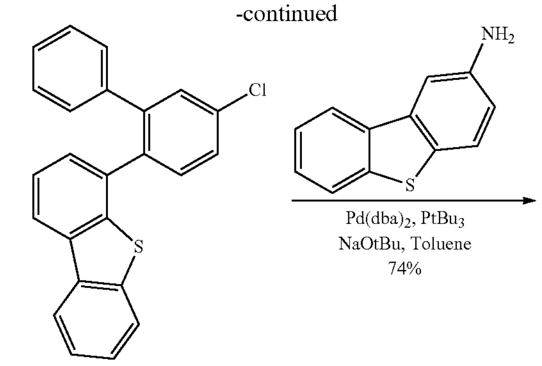

IM-30

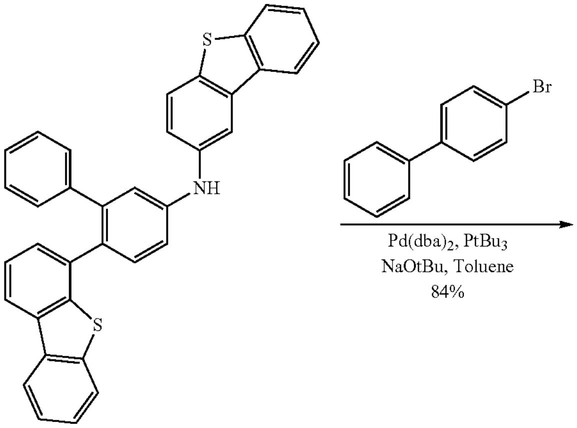

IM-31

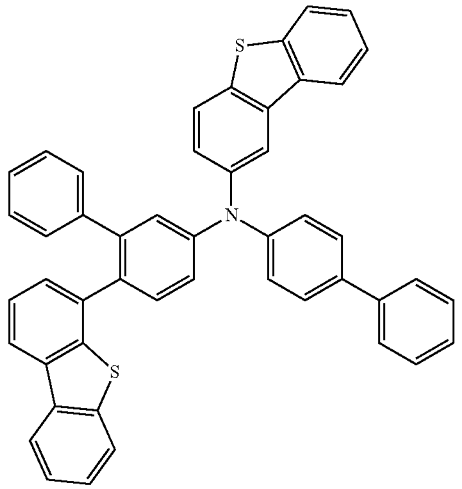

C101

(Synthesis of Intermediate IM-30)

Under an argon atmosphere, to a 1,000 ml, three-neck flask, 17.00 g (63.5 mmol) of Intermediate IM-25, 15.94 g (1.1 eq, 69.9 mmol) of 4-dibenzothiophenylboronic acid, 26.35 g (3.0 eq, 190.6 mmol) of $K_2CO_3$, 3.67 g (0.05 eq, 3.2 mmol) of $Pd(PPh_3)_4$, and 445 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-30 (17.67 g, yield 75%).

By FAB-MS measurement, mass number of m/z=370 was observed as a molecular ion peak, and Intermediate IM-30 was identified.

(Synthesis of Intermediate IM-31)

Under an argon atmosphere, to a 500 ml, three-neck flask, 15.00 g (40.4 mmol) of Intermediate IM-30, 0.70 g (0.03 eq, 1.2 mmol) of $Pd(dba)_2$, 3.89 g (1.0 eq, 40.4 mmol) of NaOtBu, 202 ml of toluene, 8.87 g (1.1 eq, 44.5 mmol) of 2-aminodibenzothiophene and 0.82 g (0.1 eq, 4.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-31 (15.97 g, yield 74%).

By FAB-MS measurement, mass number of m/z=533 was observed as a molecular ion peak, and Intermediate IM-31 was identified.

(Synthesis of Compound C101)

Under an argon atmosphere, to a 300 ml, three-neck flask, 10.00 g (18.7 mmol) of Intermediate IM-31, 0.32 g (0.03 eq, 0.6 mmol) of $Pd(dba)_2$, 3.60 g (2.0 eq, 37.5 mmol) of NaOtBu, 94 ml of toluene, 4.80 g (1.1 eq, 20.6 mmol) of 4-bromobiphenyl and 0.38 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C101 (10.80 g, yield 84%) as a solid.

By FAB-MS measurement, mass number of m/z=685 was observed as a molecular ion peak, and Compound C101 was identified.

Synthesis of Compound C113

Amine Compound C113 according to an embodiment may be synthesized, for example, by the steps of the following Reaction 20:

Reaction 20

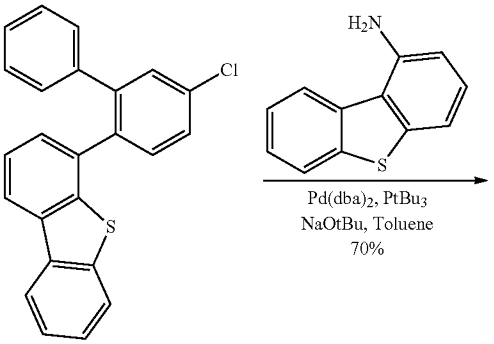

IM-30

-continued

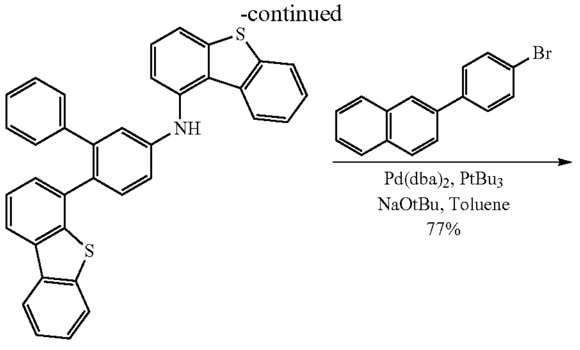

IM-32

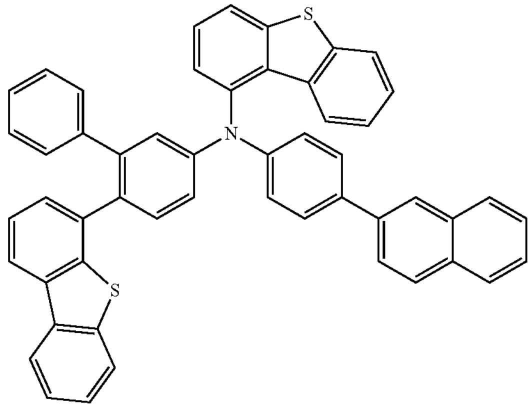

C113

(Synthesis of Intermediate IM-32)

Under an argon atmosphere, to a 500 ml, three-neck flask, 15.00 g (40.4 mmol) of Intermediate IM-30, 0.70 g (0.03 eq, 1.2 mmol) of $Pd(dba)_2$, 3.89 g (1.0 eq, 40.4 mmol) of NaOtBu, 202 ml of toluene, 8.87 g (1.1 eq, 44.5 mmol) of 1-aminodibenzothiophene and 0.82 g (0.1 eq, 4.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-32 (15.11 g, yield 70%).

By FAB-MS measurement, mass number of m/z=533 was observed as a molecular ion peak, and Intermediate IM-32 was identified.

(Synthesis of Compound C113)

Under an argon atmosphere, to a 300 ml, three-neck flask, 10.00 g (18.7 mmol) of Intermediate IM-32, 0.32 g (0.03 eq, 0.6 mmol) of $Pd(dba)_2$, 3.60 g (2.0 eq, 37.5 mmol) of NaOtBu, 94 ml of toluene, 5.84 g (1.1 eq, 20.6 mmol) of 2-(4-bromophenyl)naphthalene and 0.38 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C113 (10.62 g, yield 77%) as a solid.

By FAB-MS measurement, mass number of m/z=735 was observed as a molecular ion peak, and Compound C113 was identified.

Synthesis of Compound C132

Amine Compound C132 according to an embodiment may be synthesized, for example, by the steps of the following Reaction 21:

(Synthesis of Intermediate IM-33)

Under an argon atmosphere, to a 1,000 ml, three-neck flask, 17.00 g (63.5 mmol) of Intermediate IM-25, 15.94 g (1.1 eq, 69.9 mmol) of 2-dibenzothiophenylboronic acid, 26.35 g (3.0 eq, 190.6 mmol) of $K_2CO_3$, 3.67 g (0.05 eq, 3.2 mmol) of $Pd(PPh_3)_4$, and 445 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried Reaction 21

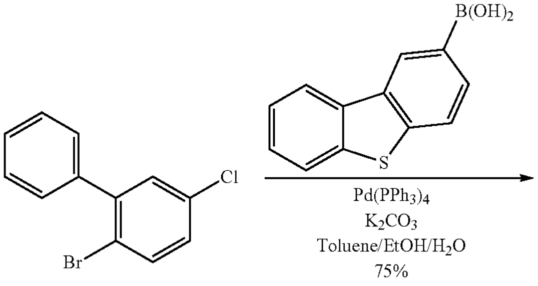

IM-25

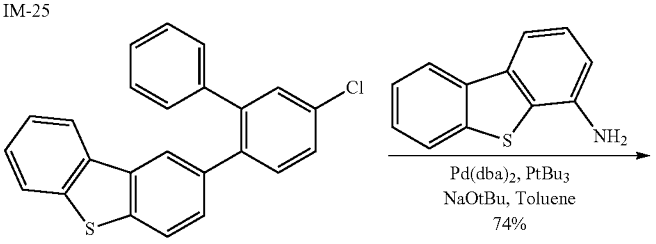

IM-33

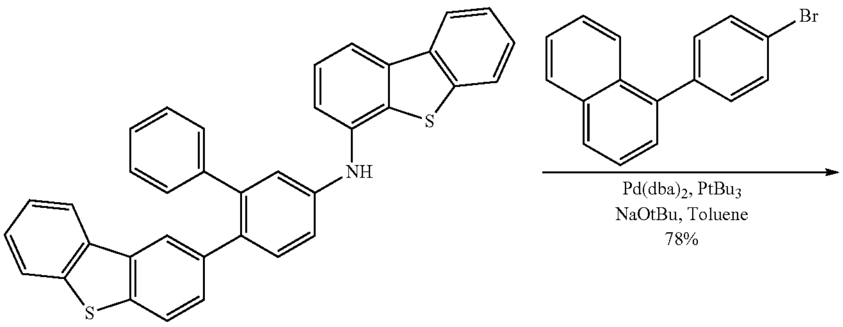

IM-34

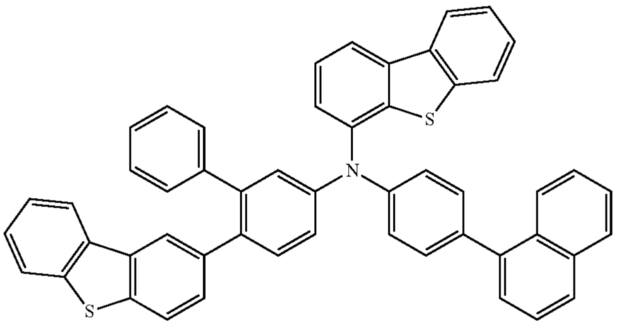

C132 with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-33 (17.67 g, yield 75%).

By FAB-MS measurement, mass number of m/z=370 was observed as a molecular ion peak, and Intermediate IM-33 was identified.

(Synthesis of Intermediate IM-34)

Under an argon atmosphere, to a 500 ml, three-neck flask, 15.00 g (40.4 mmol) of Intermediate IM-33, 0.70 g (0.03 eq, 1.2 mmol) of $Pd(dba)_2$, 3.89 g (1.0 eq, 40.4 mmol) of NaOtBu, 202 ml of toluene, 8.87 g (1.1 eq, 44.5 mmol) of 4-aminodibenzothiophene and 0.82 g (0.1 eq, 4.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-34 (15.97 g, yield 74%).

By FAB-MS measurement, mass number of m/z=533 was observed as a molecular ion peak, and Intermediate IM-34 was identified.

(Synthesis of Compound C132)

Under an argon atmosphere, to a 300 ml, three-neck flask, 10.00 g (18.7 mmol) of Intermediate IM-34, 0.32 g (0.03 eq, 0.6 mmol) of $Pd(dba)_2$, 3.60 g (2.0 eq, 37.5 mmol) of NaOtBu, 94 ml of toluene, 5.84 g (1.1 eq, 20.6 mmol) of 1-(4-bromophenyl)naphthalene and 0.38 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C132 (10.76 g, yield 78%) as a solid.

By FAB-MS measurement, mass number of m/z=735 was observed as a molecular ion peak, and Compound C132 was identified.

Synthesis of Compound C153

Amine Compound C153 according to an embodiment may be synthesized, for example, by the steps of the following Reaction 22:

Reaction 22

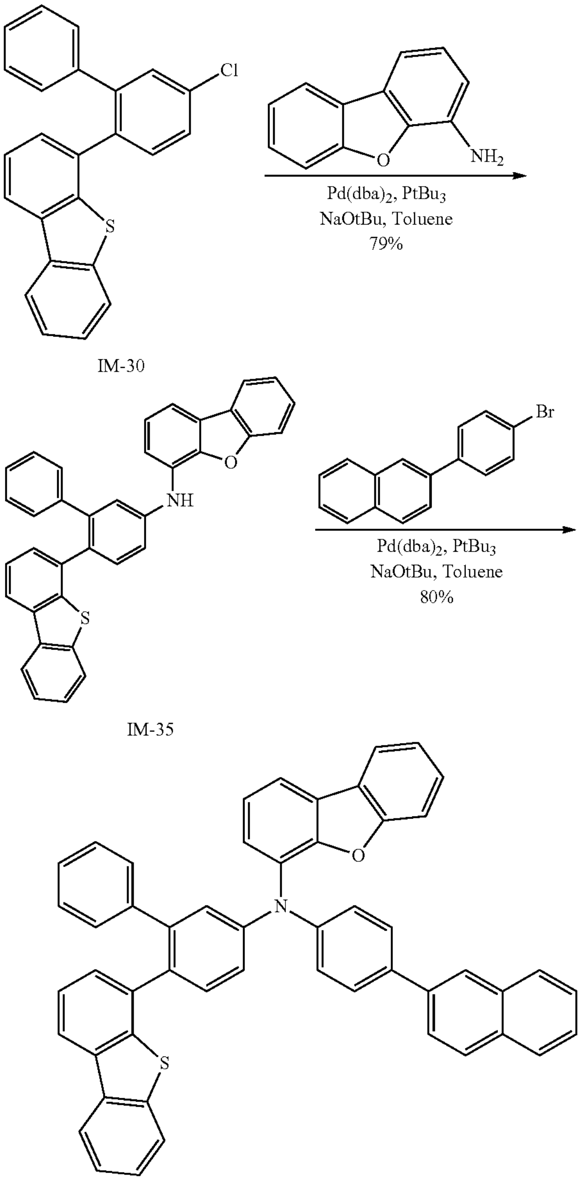

IM-30

IM-35

C153

(Synthesis of Intermediate IM-35)

Under an argon atmosphere, to a 500 ml, three-neck flask, 15.00 g (40.4 mmol) of Intermediate IM-30, 0.70 g (0.03 eq, 1.2 mmol) of $Pd(dba)_2$, 3.89 g (1.0 eq, 40.4 mmol) of NaOtBu, 202 ml of toluene, 8.15 g (1.1 eq, 44.5 mmol) of 4-aminodibenzofuran and 0.82 g (0.1 eq, 4.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-35 (16.54 g, yield 79%).

By FAB-MS measurement, mass number of m/z=517 was observed as a molecular ion peak, and Intermediate IM-35 was identified.

(Synthesis of Compound C153)

Under an argon atmosphere, to a 300 ml, three-neck flask, 10.00 g (19.3 mmol) of Intermediate IM-35, 0.33 g (0.03 eq, 0.6 mmol) of $Pd(dba)_2$, 3.72 g (2.0 eq, 38.6 mmol) of NaOtBu, 97 ml of toluene, 6.02 g (1.1 eq, 21.2 mmol) of 2-(4-bromophenyl)naphthalene and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C153 (11.13 g, yield 80%) as a solid.

By FAB-MS measurement, mass number of m/z=719 was observed as a molecular ion peak, and Compound C153 was identified.

Synthesis of Compound C221

Amine Compound C221 according to an embodiment may be synthesized, for example, by the steps of the following Reaction 23:

Reaction 23

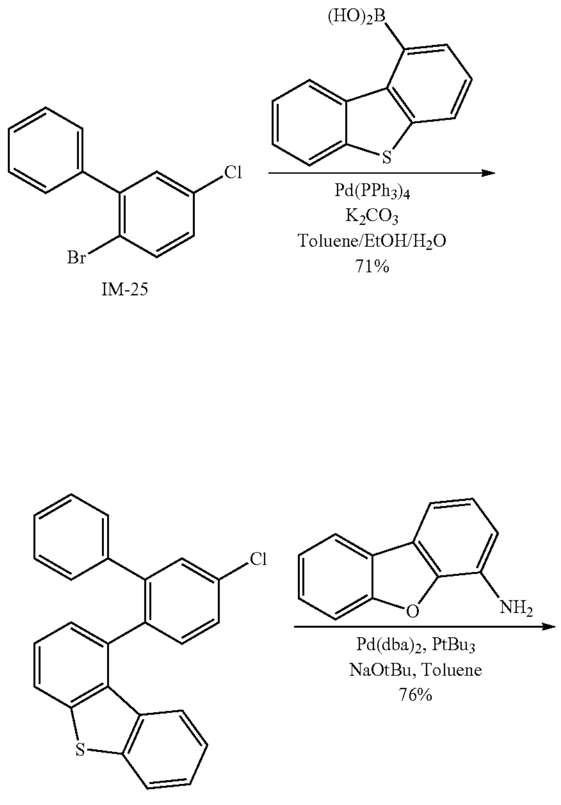

IM-25

IM-36

-continued

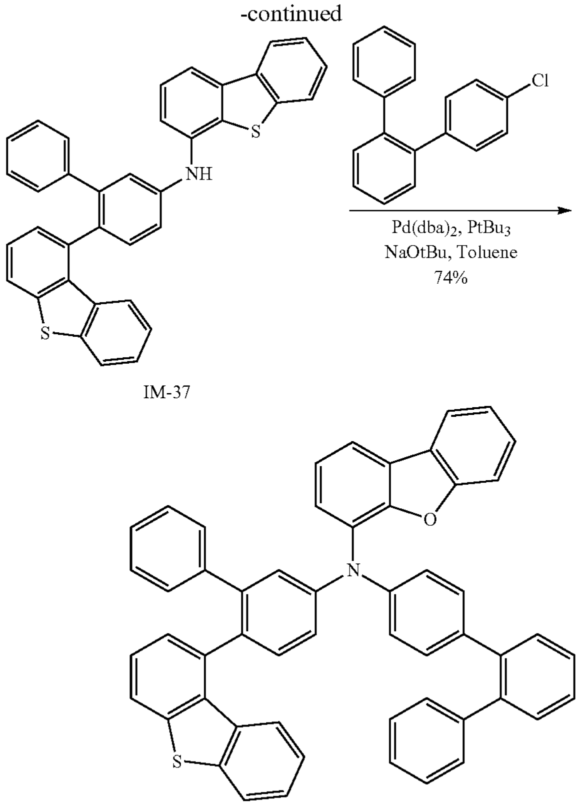

IM-37

C221

(Synthesis of Intermediate IM-36)

Under an argon atmosphere, to a 1,000 ml, three-neck flask, 17.00 g (63.5 mmol) of Intermediate IM-25, 15.94 g (1.1 eq, 69.9 mmol) of 1-dibenzothiophenylboronic acid, 26.35 g (3.0 eq, 190.6 mmol) of $K_2CO_3$, 3.67 g (0.05 eq, 3.2 mmol) of $Pd(PPh_3)_4$, and 445 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-36 (16.73 g, yield 71%).

By FAB-MS measurement, mass number of m/z=370 was observed as a molecular ion peak, and Intermediate IM-36 was identified.

(Synthesis of Intermediate IM-37)

Under an argon atmosphere, to a 500 ml, three-neck flask, 15.00 g (40.4 mmol) of Intermediate IM-36, 0.70 g (0.03 eq, 1.2 mmol) of $Pd(dba)_2$, 3.89 g (1.0 eq, 40.4 mmol) of NaOtBu, 202 ml of toluene, 8.15 g (1.1 eq, 44.5 mmol) of 4-aminodibenzofuran and 0.82 g (0.1 eq, 4.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-37 (15.91 g, yield 76%).

By FAB-MS measurement, mass number of m/z=517 was observed as a molecular ion peak, and Intermediate IM-37 was identified.

(Synthesis of Compound C221)

Under an argon atmosphere, to a 300 ml, three-neck flask, 10.00 g (19.32 mmol) of Intermediate IM-37, 0.33 g (0.03 eq, 0.6 mmol) of $Pd(dba)_2$, 3.72 g (2.0 eq, 38.6 mmol) of NaOtBu, 97 ml of toluene, 5.63 g (1.1 eq, 21.2 mmol) of 4-chloro-1,1':2',1"-terphenyl and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C221 (10.66 g, yield 74%) as a solid.

By FAB-MS measurement, mass number of m/z=745 was observed as a molecular ion peak, and Compound C221 was identified.

Synthesis of Compound C228

Amine Compound C228 according to an embodiment may be synthesized, for example, by the steps of the following Reaction 24:

Reaction 24

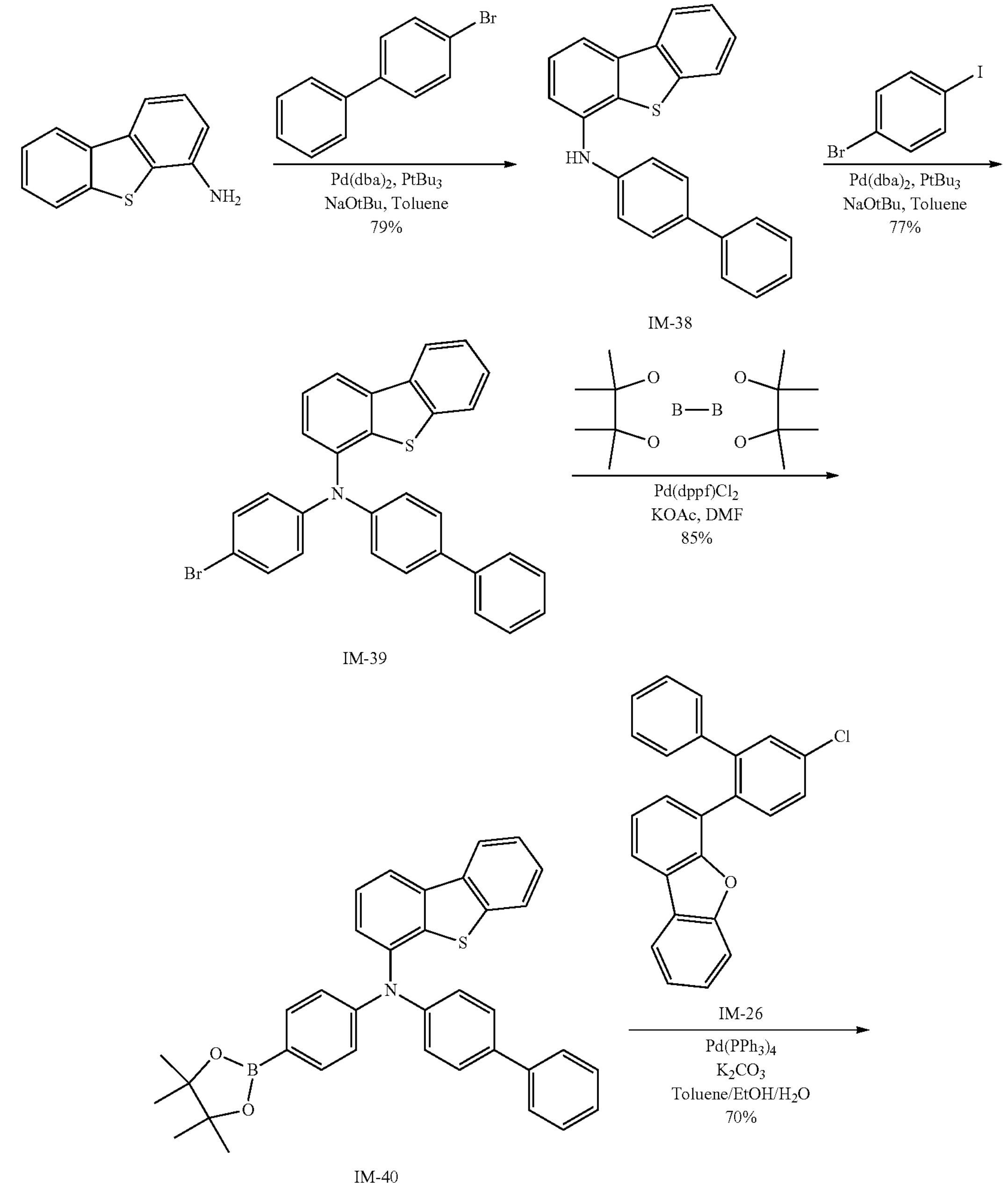

-continued

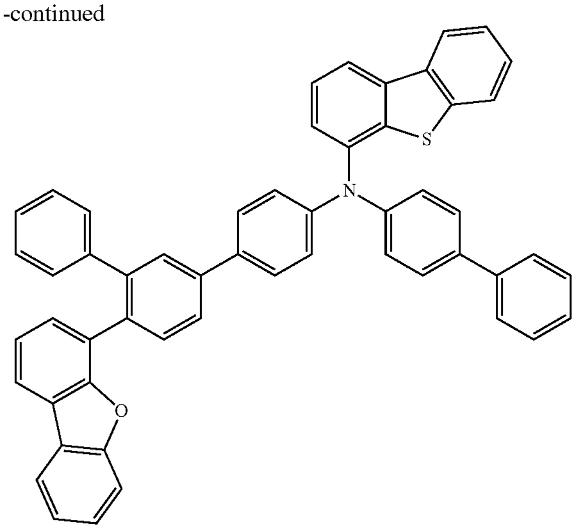

C228

(Synthesis of Intermediate IM-38)

Under an argon atmosphere, to a 1,000 ml, three-neck flask, 30.00 g (150.5 mmol) of 4-aminodibenzothiophene, 2.60 g (0.03 eq, 4.5 mmol) of $Pd(dba)_2$, 14.47 g (1.0 eq, 150.5 mmol) of NaOtBu, 752 ml of toluene, 38.60 g (1.1 eq, 165.6 mmol) of 4-bromobiphenyl and 3.05 g (0.1 eq, 15.1 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-38 (41.80 g, yield 79%).

By FAB-MS measurement, mass number of m/z=351 was observed as a molecular ion peak, and Intermediate IM-38 was identified.

(Synthesis of Intermediate IM-39)

Under an argon atmosphere, to a 500 ml, three-neck flask, 30.00 g (85.4 mmol) of Intermediate IM-38, 1.47 g (0.03 eq, 2.6 mmol) of $Pd(dba)_2$, 8.20 g (1.0 eq, 85.4 mmol) of NaOtBu, 427 ml of toluene, 26.56 g (1.1 eq, 93.9 mmol) of 1-bromo-4-iodobenzene and 1.73 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-39 (33.29 g, yield 77%).

By FAB-MS measurement, mass number of m/z=506 was observed as a molecular ion peak, and Intermediate IM-39 was identified.

(Synthesis of Intermediate IM-40)

Under an argon atmosphere, to a 500 ml, three-neck flask, 20.00 g (39.5 mmol) of Intermediate IM-39, 3.22 g (0.10 eq, 3.9 mmol) of $Pd(dppf)Cl_2$, 7.75 g (2.0 eq, 79.0 mmol) of KOAc, 427 ml of DMF, and 12.03 g (1.2 eq, 47.4 mmol) of bis(pinacolato)diboron were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-40 (18.57 g, yield 85%).

By FAB-MS measurement, mass number of m/z=553 was observed as a molecular ion peak, and Intermediate IM-40 was identified.

(Synthesis of Compound C228)

Under an argon atmosphere, to a 300 ml, three-neck flask, 10.00 g (18.1 mmol) of Intermediate IM-40, 7.05 g (1.1 eq, 19.9 mmol) of Intermediate IM-26, 7.49 g (3.0 eq, 54.2 mmol) of $K_2CO_3$, 1.04 g (0.05 eq, 0.9 mmol) of $Pd(PPh_3)_4$, and 126 ml of a mixture solution of toluene/EtOH/$H_2O$ (4/2/1) were added in order, followed by heating and stirring at about 80° C. After cooling in the air to room temperature, the reaction solution was extracted with toluene. An aqueous layer was removed, and an organic layer was washed with a saturated saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C228 (9.43 g, yield 70%) as a solid.

By FAB-MS measurement, mass number of m/z=745 was observed as a molecular ion peak, and Compound C228 was identified.

Synthesis of Compound C232

Amine Compound C232 according to an embodiment may be synthesized, for example, by the steps of the following Reaction 25:

Reaction 25

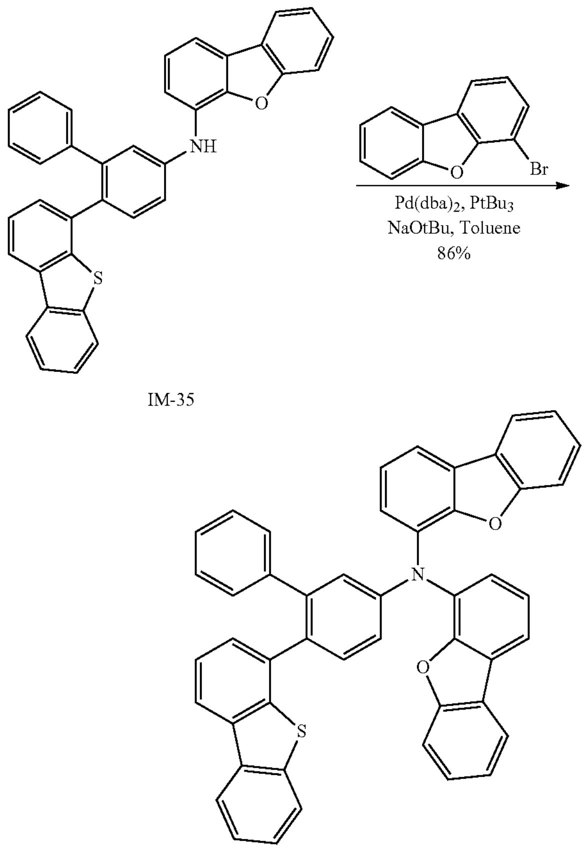

IM-35

C232

Under an argon atmosphere, to a 300 ml, three-neck flask, 10.00 g (19.3 mmol) of Intermediate IM-35, 0.33 g (0.03 eq, 0.6 mmol) of $Pd(dba)_2$, 3.72 g (2.0 eq, 38.6 mmol) of NaOtBu, 97 ml of toluene, 5.25 g (1.1 eq, 21.2 mmol) of 4-bromodibenzofuran and 0.39 g (0.1 eq, 1.9 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C232 (11.36 g, yield 86%) as a solid.

By FAB-MS measurement, mass number of m/z=683 was observed as a molecular ion peak, and Compound C232 was identified.

Synthesis of Compound C240

Amine Compound C240 according to an embodiment may be synthesized, for example, by the steps of the following Reaction 26:

Reaction 26

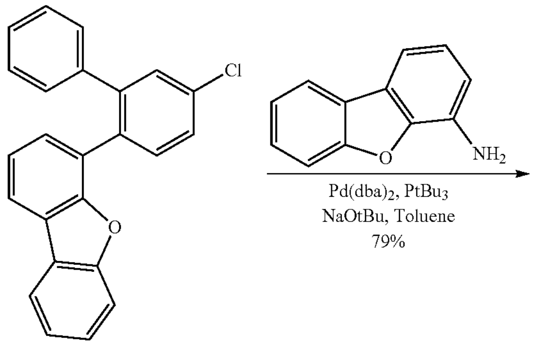

IM-26

-continued

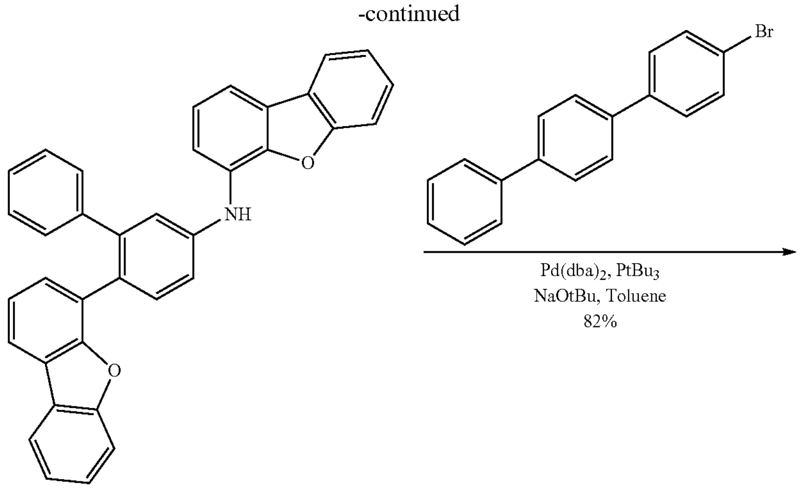

IM-41

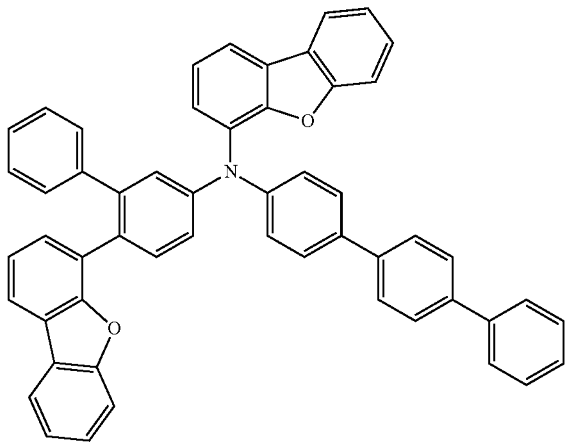

C240

(Synthesis of Intermediate IM-41)

Under an argon atmosphere, to a 500 ml, three-neck flask, 15.00 g (42.3 mmol) of Intermediate IM-26, 0.73 g (0.03 eq, 1.3 mmol) of $Pd(dba)_2$, 4.06 g (1.0 eq, 42.3 mmol) of NaOtBu, 211 ml of toluene, 8.52 g (1.1 eq, 46.5 mmol) of 4-aminodibenzofuran and 0.86 g (0.1 eq, 4.2 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Intermediate IM-41 (16.75 g, yield 79%).

By FAB-MS measurement, mass number of m/z=501 was observed as a molecular ion peak, and Intermediate IM-41 was identified.

(Synthesis of Compound C240)

Under an argon atmosphere, to a 300 ml, three-neck flask, 10.00 g (19.9 mmol) of Intermediate IM-41, 0.34 g (0.03 eq, 0.6 mmol) of $Pd(dba)_2$, 3.83 g (2.0 eq, 39.9 mmol) of NaOtBu, 100 ml of toluene, 6.78 g (1.1 eq, 21.9 mmol) of 4-bromo-terphenyl and 0.40 g (0.1 eq, 2.0 mmol) of $tBu_3P$ were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C240 (11.93 g, yield 82%) as a solid.

By FAB-MS measurement, mass number of m/z=729 was observed as a molecular ion peak, and Compound C240 was identified.

Synthesis of Compound C242

Amine Compound C242 according to an embodiment may be synthesized, for example, by the steps of the following Reaction 27:

Reaction 27

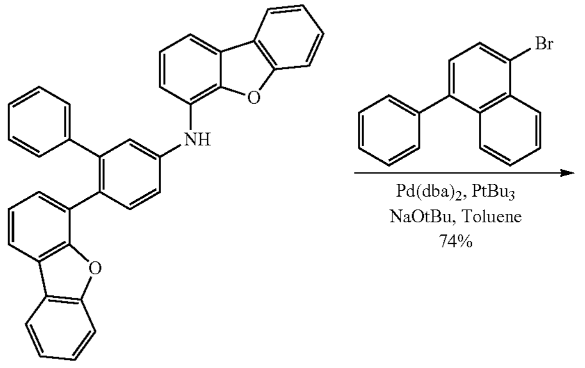

IM-41

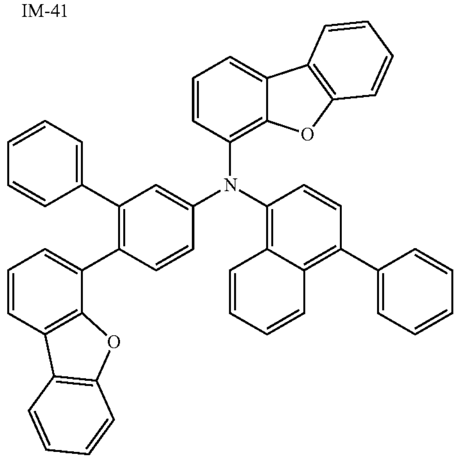

C242

Under an argon atmosphere, to a 300 ml, three-neck flask, 10.00 g (19.9 mmol) of Intermediate IM-41, 0.34 g (0.03 eq, 0.6 mmol) of Pd(dba)$_2$, 3.83 g (2.0 eq, 39.9 mmol) of NaOtBu, 100 ml of toluene, 6.21 g (1.1 eq, 21.9 mmol) of 1-bromo-4-phenylnaphthalene and 0.40 g (0.1 eq, 2.0 mmol) of tBu$_3$P were added in order, followed by heating, refluxing and stirring. After cooling in the air to room temperature, water was added to the reaction solution, and an organic layer was separately taken. Toluene was added to the aqueous layer, and organic layers were additionally extracted. Organic layers were collected, washed with a saline solution and dried with $MgSO_4$. $MgSO_4$ was filtered, and an organic layer was concentrated. The crude product thus obtained was separated by silica gel column chromatography (using a mixture solvent of hexane and toluene as an eluent) to obtain Compound C242 (10.38 g, yield 74%) as a solid.

By FAB-MS measurement, mass number of m/z=703 was observed as a molecular ion peak, and Compound C242 was identified.

2. Manufacture and Evaluation of Organic Electroluminescence Device Including Amine Compound (Manufacture of Organic Electroluminescence Device)

An organic electroluminescence device of an embodiment including the amine compound of an embodiment in a hole transport layer was manufactured by a method described below. Organic electroluminescence devices of Examples 1 to 27 were manufactured using Compounds A2, A19, A50, A86, A103, A172, A195, A226, B1, B18, B89, B91, B149, B165, B217, B233, C16, C50, C101, C113, C132, C153, C221, C228, C232, C240, and C242 as materials for a hole transport layer. The organic electroluminescence devices of Comparative Examples 1 to 11 were manufactured using Comparative Compounds R1 to R11, respectively, as materials for a hole transport layer.

The compounds used for the hole transport layer in Example 1 to Example 27, and Comparative Example 1 to Comparative Example 11 are as follows.

(Example Compounds Used for Manufacturing a Device)

A2

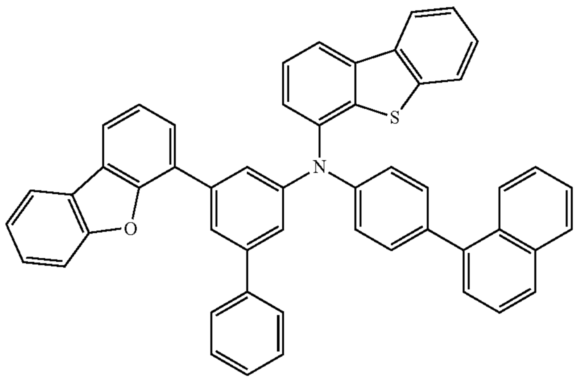

A15

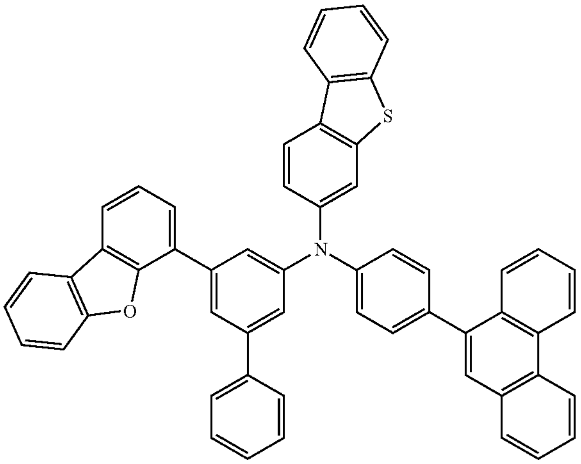

A60

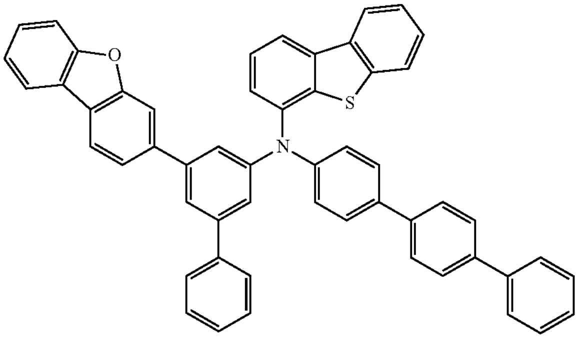

-continued
A36
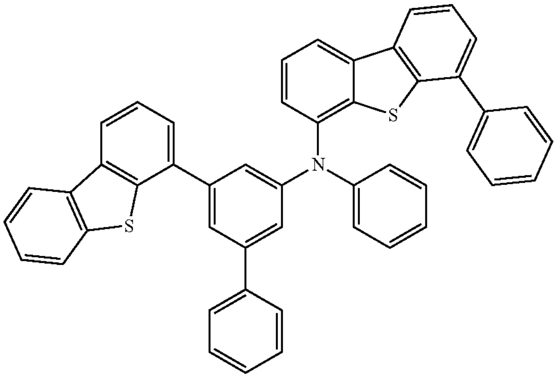
A303
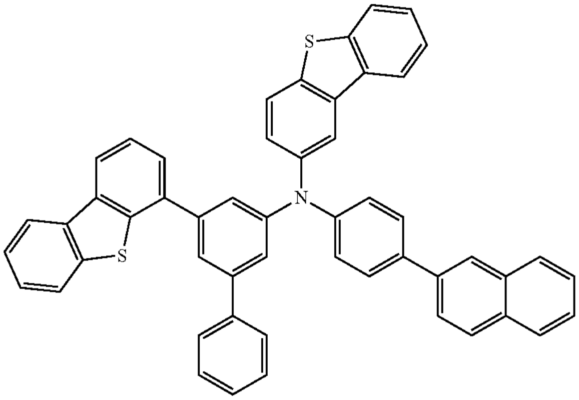
A172
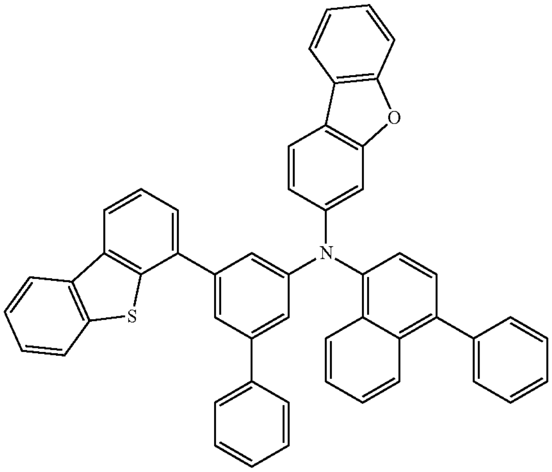
-continued
A195
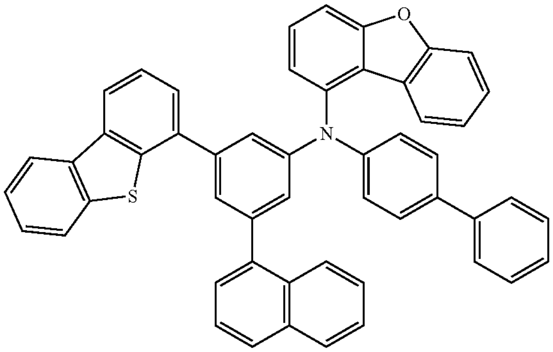
A226
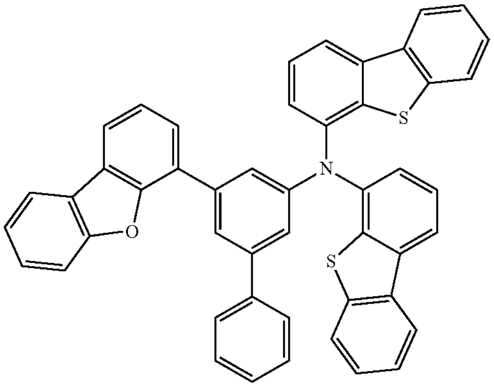
B2
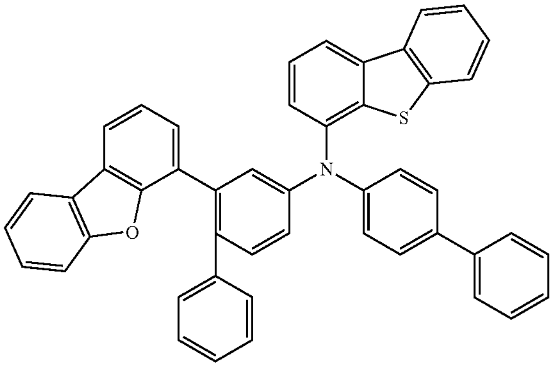
B18
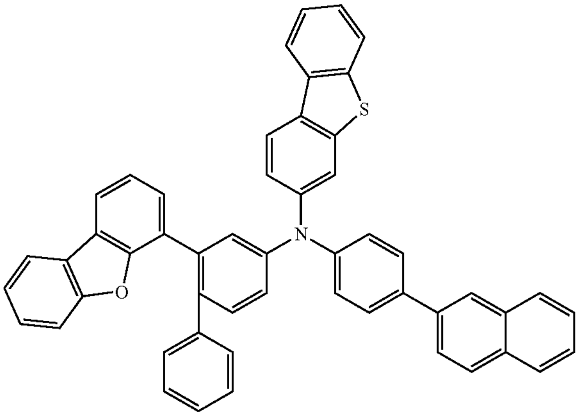

B86
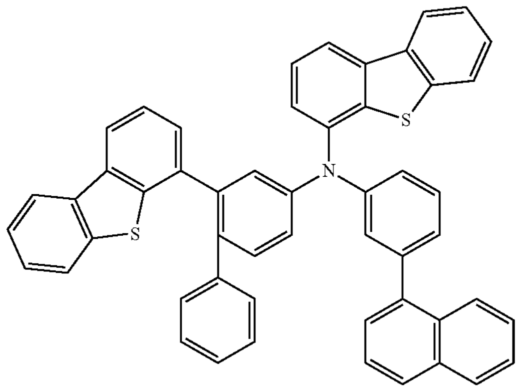
B31
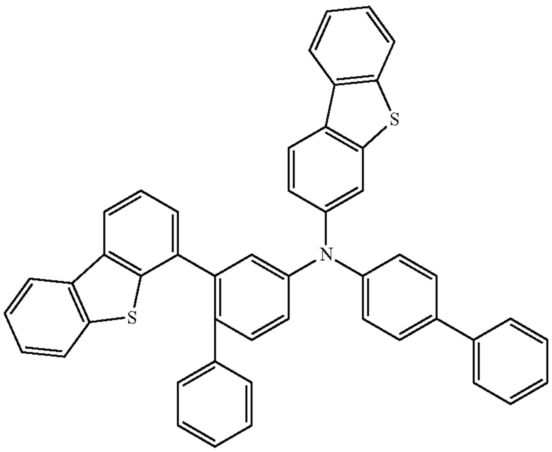
B143
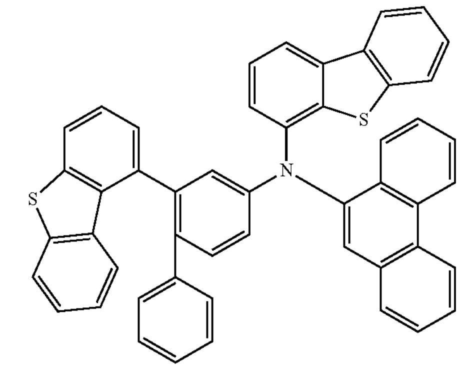
B166
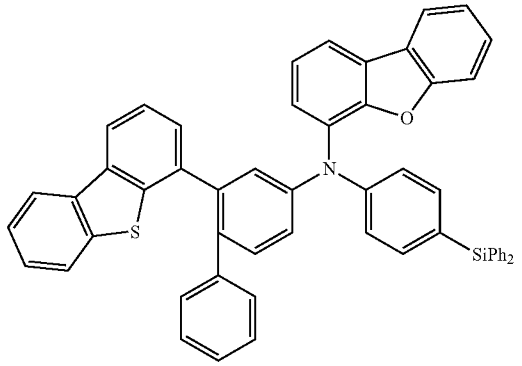
B217
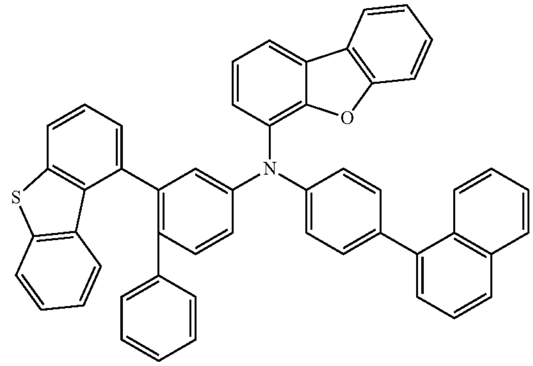
B223
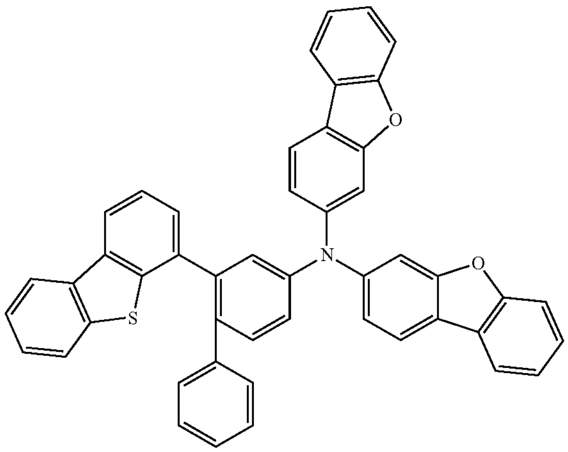
C16
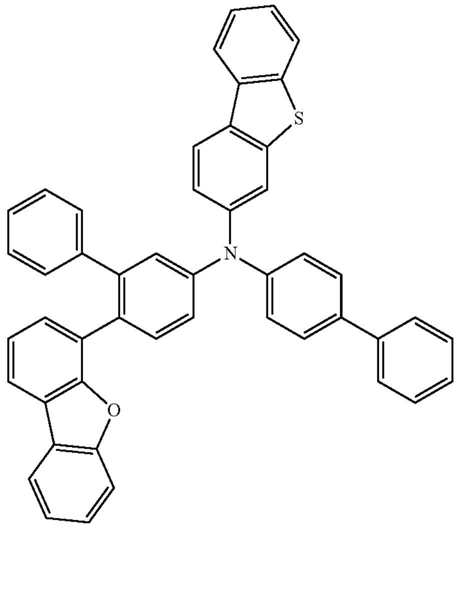

-continued
C50
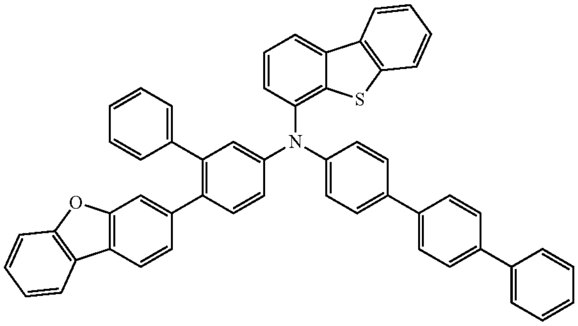
C101
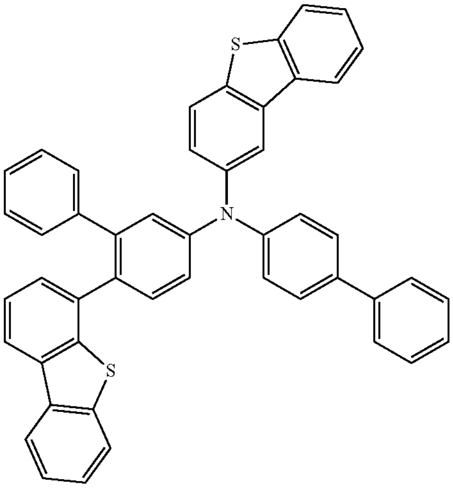
C113
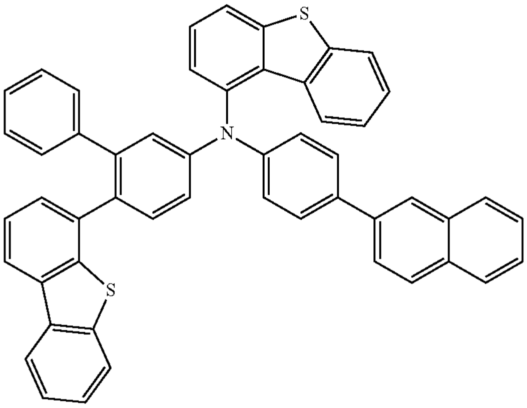
C132
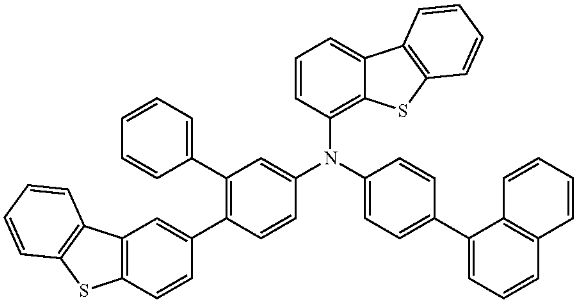
-continued
C153
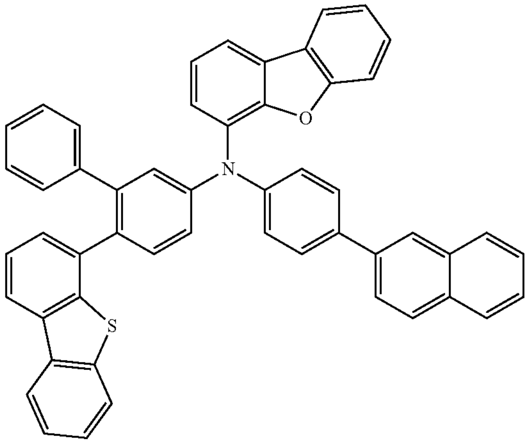
C221
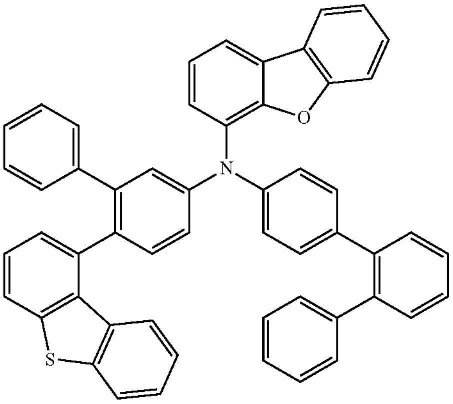
C228
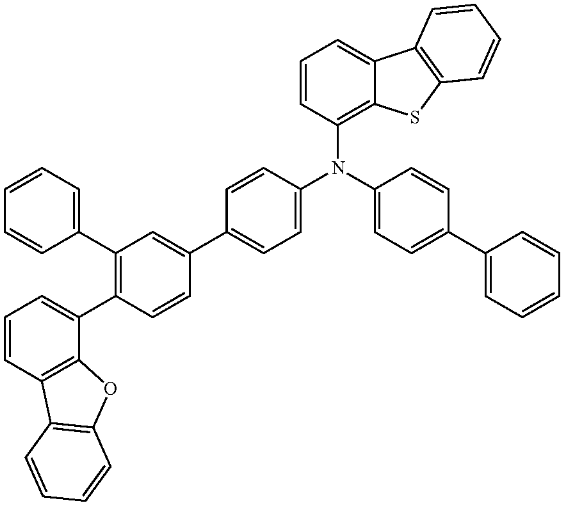

-continued
C332
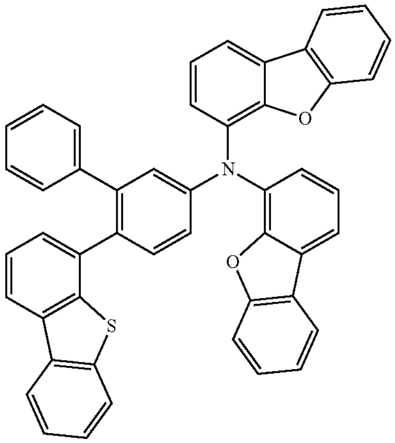
C243
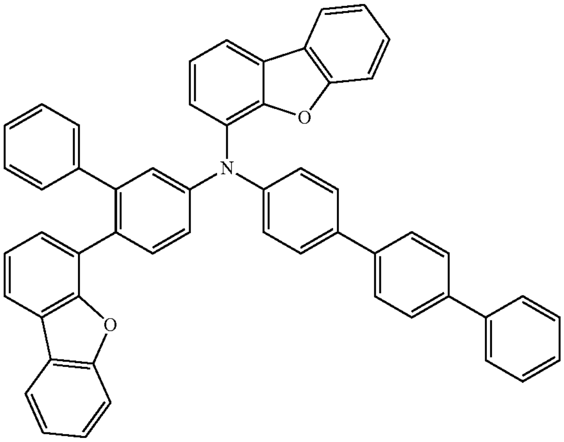
C242
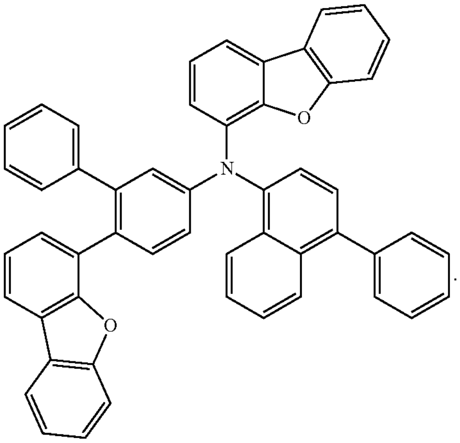
.
(Comparative Compounds Used for Manufacturing a Device)
R1
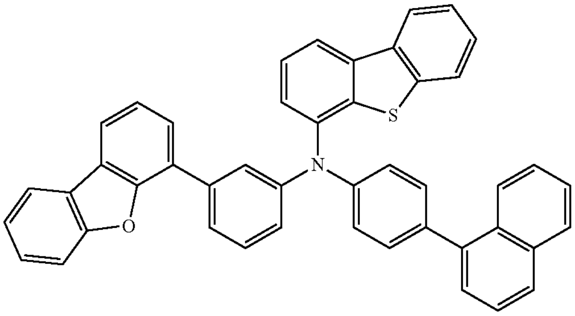
R2
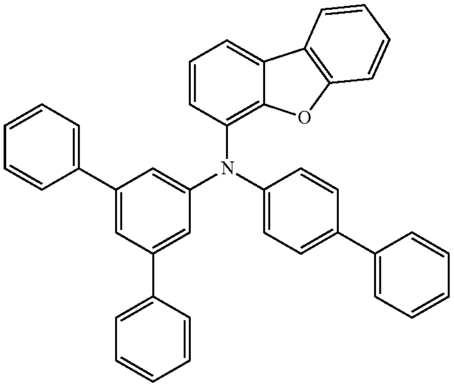
R3
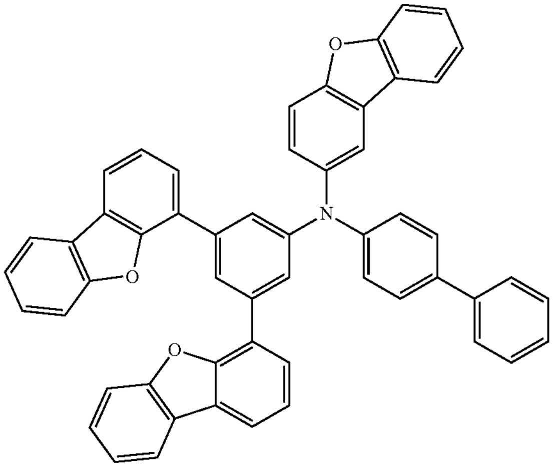

-continued
R4
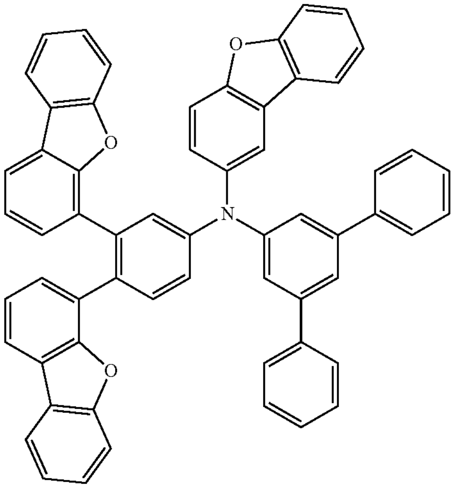
R5
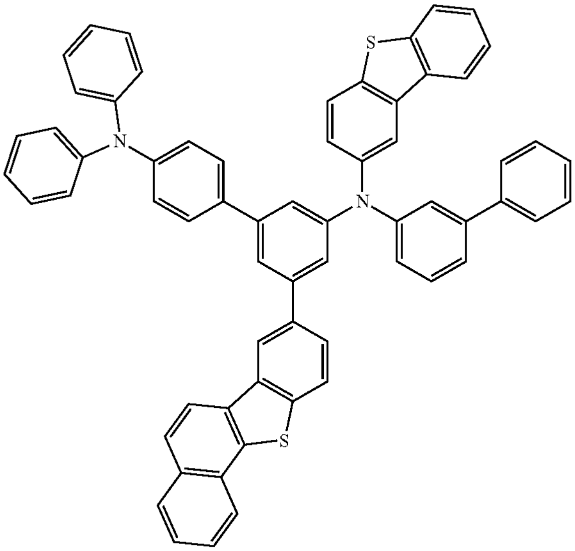
R6
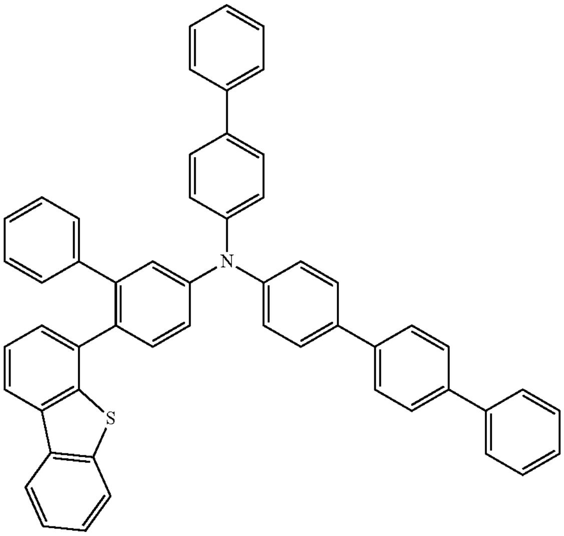
-continued
R7
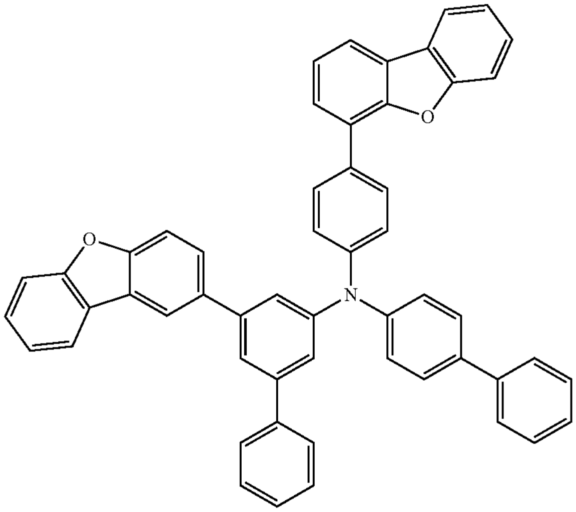
R8
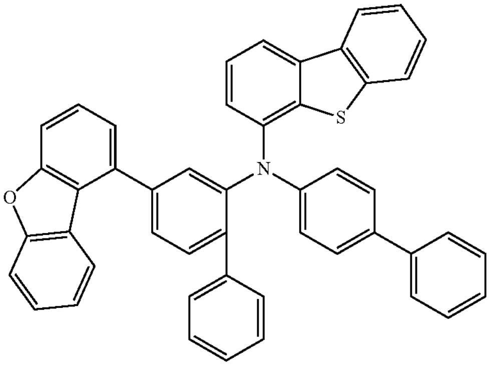
R9
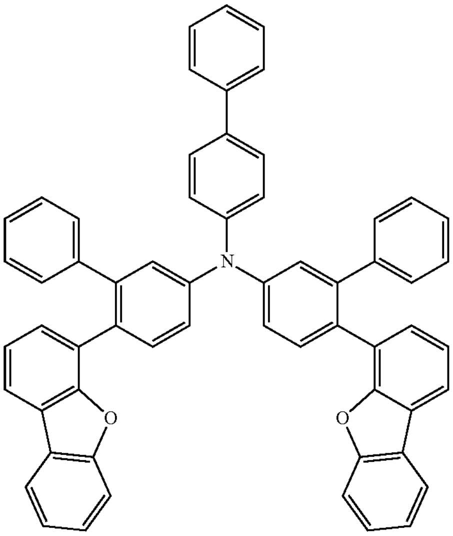

-continued

R10

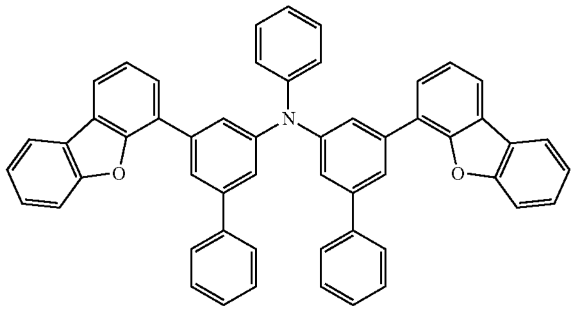

R11

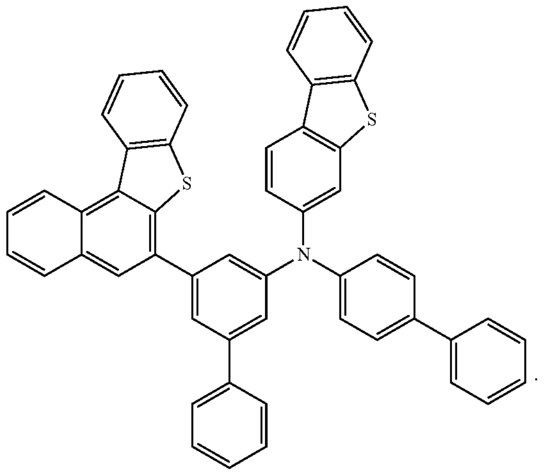

On a glass substrate, ITO with a thickness of about 1,500 Å was patterned and washed with ultra-pure water, and treated with UV-ozone for about 10 minutes. Then, 1-TNATA was deposited to a thickness of about 600 Å to form a hole injection layer. Then, the Example Compound or the Comparative Compound was deposited to a thickness of about 300 Å to form a hole transport layer.

After that, an emission layer was formed using ADN doped with 3% TBP to a thickness of about 250 Å. Then, an electron transport layer was formed by depositing $Alq_3$ to a thickness of about 250 Å, and an injection layer was formed by depositing LiF to a thickness of about 10 Å.

Then, a second electrode was formed using aluminum (Al) to a thickness of about 1,000 Å.

Here, the hole injection layer, the hole transport layer, the emission layer, the electron transport layer, the electron injection layer and the second electrode were formed using a vacuum deposition apparatus.

(Evaluation of Properties of Organic Electroluminescence Device)

In Table 1, the evaluation results on the organic electroluminescence devices of Example 1 to Example 27 and Comparative Example 1 to Comparative Example 11 are shown. In Table 1, the driving voltage, emission efficiency and device life of the organic electroluminescence devices thus manufactured are compared and shown. In the evaluation results of the properties on the Examples and the Comparative Examples, as shown in Table 1, the emission efficiency represents an efficiency value at a current density of about 10 mA/$cm^2$, and the device life represents luminance half-life at about 1.0 mA/$cm^2$.

The current density, voltage, and emission efficiency of the organic electroluminescence devices of the Examples and Comparative Examples were measured using a 2400 Series Source Meter of Keithley Instrument Co., a luminance and color meter CS-200, which is a product of Konica Minolta Co., and a PC Program LabVIEW 2.0 for measurement, which is a product of National Instrument Co., in Japan.

TABLE 1

| Device manufacturing example | Hole transport material | Voltage (V) | Emission efficiency (cd/A) | Device life [LT50] (hrs) |
|---|---|---|---|---|
| Example 1 | Example Compound A2 | 5.5 | 7.9 | 1950 |
| Example 2 | Example Compound A19 | 5.5 | 7.8 | 2000 |
| Example 3 | Example Compound A50 | 5.4 | 7.8 | 2050 |
| Example 4 | Example Compound A86 | 5.4 | 7.9 | 1900 |
| Example 5 | Example Compound A103 | 5.4 | 7.8 | 2050 |
| Example 6 | Example Compound A172 | 5.5 | 7.7 | 2000 |
| Example 7 | Example Compound A195 | 5.6 | 7.8 | 2000 |
| Example 8 | Example Compound A226 | 5.6 | 7.8 | 2050 |
| Example 9 | Example Compound B1 | 5.4 | 7.7 | 2050 |
| Example 10 | Example Compound B18 | 5.5 | 7.6 | 2100 |
| Example 11 | Example Compound B89 | 5.5 | 7.7 | 2050 |
| Example 12 | Example Compound B91 | 5.6 | 7.6 | 2150 |
| Example 13 | Example Compound B149 | 5.4 | 7.7 | 2000 |
| Example 14 | Example Compound B165 | 5.5 | 7.7 | 2050 |
| Example 15 | Example Compound B217 | 5.6 | 7.7 | 2050 |
| Example 16 | Example Compound B233 | 5.4 | 7.6 | 2150 |
| Example 17 | Example Compound C16 | 5.4 | 7.6 | 2150 |
| Example 18 | Example Compound C50 | 5.6 | 7.6 | 2200 |
| Example 19 | Example Compound C101 | 5.4 | 7.6 | 2150 |
| Example 20 | Example Compound C113 | 5.5 | 7.8 | 2100 |
| Example 21 | Example Compound C132 | 5.5 | 7.7 | 2050 |
| Example 22 | Example Compound C153 | 5.5 | 7.7 | 2100 |
| Example 23 | Example Compound C221 | 5.6 | 7.6 | 2000 |
| Example 24 | Example Compound C228 | 5.4 | 7.6 | 2200 |
| Example 25 | Example Compound C232 | 5.6 | 7.7 | 2050 |
| Example 26 | Example Compound C240 | 5.6 | 7.7 | 2150 |
| Example 27 | Example Compound C242 | 5.5 | 7.6 | 2100 |
| Comparative Example 1 | Comparative Compound R1 | 6.2 | 6.4 | 1650 |
| Comparative Example 2 | Comparative Compound R2 | 6.0 | 6.6 | 1650 |
| Comparative Example 3 | Comparative Compound R3 | 6.0 | 6.5 | 1550 |
| Comparative Example 4 | Comparative Compound R4 | 6.1 | 6.5 | 1600 |

TABLE 1-continued

| Device manufacturing example | Hole transport material | Voltage (V) | Emission efficiency (cd/A) | Device life [LT50] (hrs) |
|---|---|---|---|---|
| Comparative Example 5 | Comparative Compound R5 | 6.3 | 6.3 | 1500 |
| Comparative Example 6 | Comparative Compound R6 | 6.0 | 6.6 | 1650 |
| Comparative Example 7 | Comparative Compound R7 | 6.4 | 6.4 | 1700 |
| Comparative Example 8 | Comparative Compound R8 | 6.5 | 6.5 | 1550 |
| Comparative Example 9 | Comparative Compound R9 | 6.6 | 6.5 | 1650 |
| Comparative Example 10 | Comparative Compound R10 | 6.7 | 6.6 | 1600 |
| Comparative Example 11 | Comparative Compound R11 | 6.5 | 6.5 | 1650 |

Referring to the results of Table 1, it could be found that the organic electroluminescence devices of the Examples each using the amine compound of embodiments of the present disclosure as a material for a hole transport layer showed a low driving voltage, excellent device efficiency and improved device life characteristics.

That is, referring to Table 1, it could be confirmed that the devices of Example 1 to Example 27 showed a lower driving voltage, longer life and higher efficiency when compared with the devices of Comparative Example 1 to Comparative Example 11.

The amine compounds used in the Examples are compounds having two dibenzoheterocyclic groups, and may show the properties of a hole transport material of long life, in addition to improved properties of thermal and charge tolerance. It is believed that the amine compounds of the Examples, including a dibenzoheterocyclic group having relatively excellent (desirable) thermal and charge tolerance, may maintain hole transport properties and show high reliability, and thus, show improved results of device life.

Further, it is believed that in the amine compound of an embodiment, a heteroatom included in the dibenzoheterocyclic group improved the hole transport capacity of a whole molecule, to increase the recombination probability of holes and electrons in an emission layer, and thus the Examples showed excellent emission efficiency properties when compared with the Comparative Examples. In addition, one dibenzoheterocyclic group among the two dibenzoheterocyclic groups is bonded through a linker having a branched chain, and the symmetry of a whole molecule in a compound is degraded. Accordingly, the crystallinity of the compound may be deteriorated, layer quality may be improved, and the efficiency of the emitting devices of the Examples may be improved.

Comparative Compound R1 used in Comparative Example 1 is an amine compound in which a linker (phenylene group) bonded to a dibenzoheterocyclic group does not have a branched chain, and emission efficiency and device life characteristics were all reduced when compared with the Examples. It is believed that in case where a linker does not have a branched chain, like in Comparative Compound R1, the planarity of a whole molecule may be increased, stacking between molecules may be increased, and the deposition temperature of a material may be increased, and thus, decomposition and the decrease of layer forming properties during deposition may arise.

Comparative Compound R2 and Comparative Compound R6, used in Comparative Example 2 and Comparative Example 6, correspond to amine compounds having fewer dibenzoheterocyclic groups when compared with the Example Compounds. It is believed that in case where the number of dibenzoheterocyclic groups is decreased, as in the Comparative Compounds R2 and R6, hole transport properties and electron tolerance may be degraded, and both emission efficiency and device life characteristics may be degraded in the Comparative Examples when compared with the Examples.

In each of Comparative Compounds R3 to R5 used in Comparative Examples 3, 4 and 5, a dibenzoheterocyclic group is substituted at a linker moiety, instead of an aryl group, and carrier balance is collapsed, and both emission efficiency and device life characteristics were lower when compared with the Examples.

In each of Comparative Example 7 using Comparative Compound R7, which is an amine compound in which two dibenzoheterocyclic groups are bonded to a nitrogen atom via a linker, respectively, and Comparative Example 11 using Comparative Compound R11, which is an amine compound including a benzonaphthothiophene skeleton as a heterocyclic group, the planarity of a whole molecule may be improved, stacking between molecules may be increased, and the deposition temperature of a material may be increased, and thus, decomposition and the decrease of layer forming properties during deposition may arise. Therefore, Comparative Example 7 and Comparative Example 11 showed lower emission efficiency and device life characteristics when compared with the Examples.

Comparative Compound R8 used in Comparative Example 8 has an amine compound structure having an aryl group substituent at an ortho position with respect to the nitrogen atom of an amine group bonded to a linker, and Comparative Example 8 also showed decreased emission efficiency and device life characteristics when compared with the Examples. It is believed that the volume of a substituent substituted around the nitrogen atom was increased, a molecule became unstable, and the decomposition of a material was progressed.

Each of Comparative Compounds R9 and R10 used in Comparative Example 9 and Comparative Example 10 has an amine compound structure having two branched linkers, and the symmetry of a molecule is high and intermolecular interaction becomes strong. Accordingly, the increase of the deposition temperature was accompanied with the decomposition of a material, and both the emission efficiency and device life characteristics were low when compared with the Examples.

Referring to the results of Table 1, it could be confirmed that Example 1 to Example 27 showed improved emission efficiency and emission life at the same time, when compared with Comparative Example 1 to Comparative Example 11. That is, it could be confirmed that the Example Compounds of the present disclosure having the amine compound structure of the present embodiments, which has two dibenzoheterocyclic groups, lead to imp roved device efficiency and device life at the same time.

An amine compound of an embodiment includes two dibenzoheterocyclic groups, and a linker connecting the dibenzoheterocyclic groups has an aryl-substituted branched structure. Accordingly, the amine compound may have low molecular symmetry and improved reliability on heat and charge. In addition, the amine compound of an embodiment has improved hole transport capacity of a whole molecule, and if used in a hole transport region, the recombination probability of holes and electrons in an emission layer of an organic electroluminescence device may be increased, and the organic electroluminescence device of an embodiment may show improved emission efficiency.

The organic electroluminescence device of an embodiment includes the amine compound of an embodiment in a hole transport region and may show high efficiency and long-life characteristics.

The amine compound of an embodiment may improve the emission efficiency and device life of an organic electroluminescence device.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present disclosure have been described, it is understood that the present disclosure should not be limited to these example embodiments, but various changes and modifications can be made by one ordinary skilled in the art within the spirit and scope of the present disclosure as hereinafter claimed by the following claims and their equivalents.

What is claimed is:

1. An organic electroluminescence device, comprising:

a first electrode;

a second electrode on the first electrode;

an emission layer;

a hole transport region between the first electrode and the emission layer; and an electron transport region between the emission layer and the second electrode, wherein the hole transport region comprises an amine compound represented by Formula 1:

Formula 1

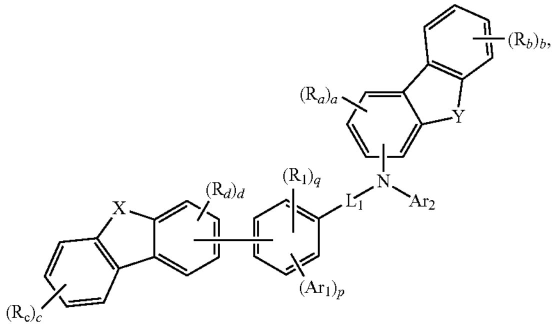

and in Formula 1,

X and Y are each independently O or S, $Ar_1$ is a substituted or unsubstituted phenyl group, or a substituted or unsubstituted naphthyl group, $Ar_2$ is selected from the following compounds:

Ar2-3

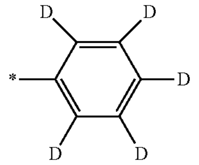

Ar2-5

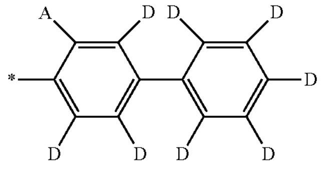

Ar2-8

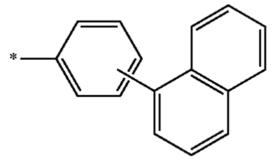

Ar2-9

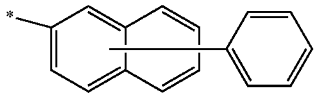

Ar2-10

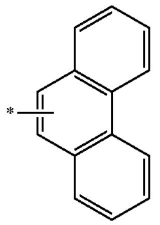

, $R_1$ is a hydrogen atom or a deuterium atom, $R_a$ to $R_d$ are each independently a hydrogen atom, a deuterium atom, a substituted or unsubstituted alkyl group of 1 to 20 carbon atoms, or a substituted or unsubstituted aryl group of 6 to 40 carbon atoms for forming a ring, $L_1$ is a direct linkage, or a substituted or unsubstituted arylene group of 6 to 30 carbon atoms for forming a ring, "a" and "d" are each independently an integer of 0 to 3, "b" and "c" are each independently an integer of 0 to 4, "p" is 1 or 2, and "q" is an integer of 0 to 3, wherein $L_1$ and $Ar_1$ or nitrogen (N) and $Ar_1$ are not bonded to adjacent carbons, wherein when Y is O and X is S or O, then a dibenzothiophene group and N, the dibenzothiophene group and $L_1$, a dibenzofuran group and N, or the dibenzofuran group and $L_1$ are unbonded to adjacent carbons, and wherein when the Formula 1 is represented by Formula 1-1, $L_1$ is direct linkage:

Formula 1-1

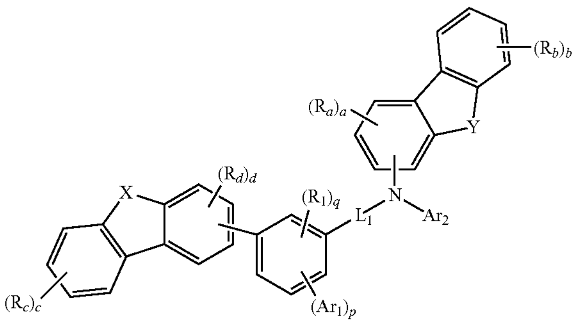

in Formula 1-1,

X, Y, $Ar_1$, $Ar_2$, $R_1$, $R_a$ to $R_d$, $L_1$, "a" to "d", "p" and "q" are the same as defined in Formula 1.

2. The organic electroluminescence device of claim 1, wherein Formula 1 is represented by Formula 1-2:

Formula 1-2

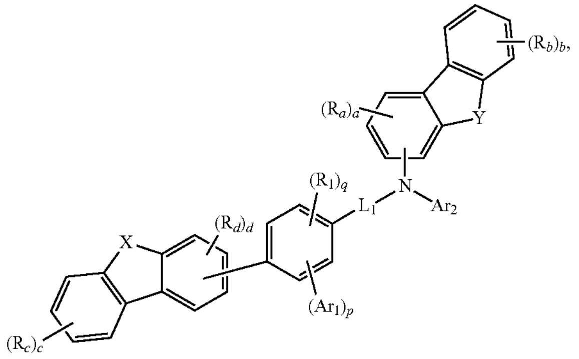

and in Formula 1-2,

X, Y, $Ar_1$, $Ar_2$, $R_1$, $R_a$ to $R_d$, $L_1$, "a" to "d", "p" and "q" are the same as defined in Formula 1.

3. The organic electroluminescence device of claim 1, wherein Formula 1-1 is represented by any one selected from Formula 1-1A to Formula 1-1C:

Formula 1-1A

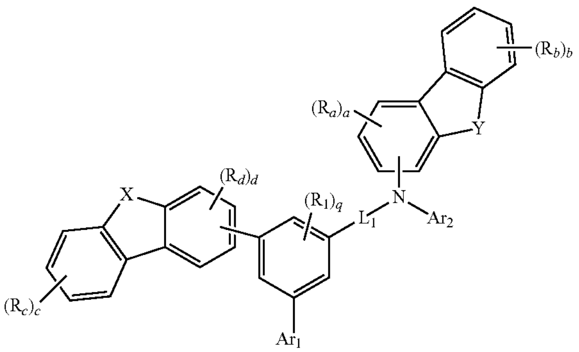

-continued

Formula 1-1B

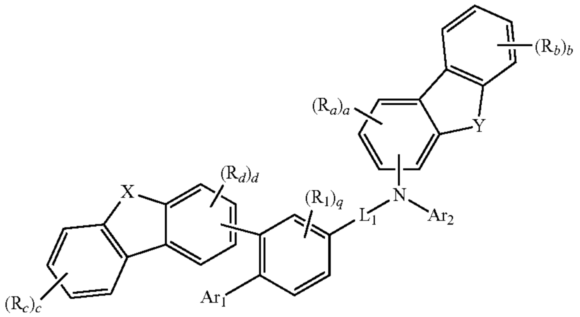

Formula 1-1C

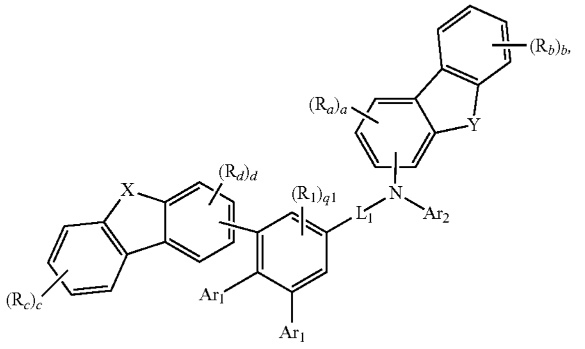

in Formula 1-1C, q1 is an integer of 0 to 2, and in Formula 1-1A to Formula 1-1C, X, Y, $Ar_1$, $Ar_2$, $R_1$, $R_a$ to $R_d$, $L_1$, "a" to "d", and "q" are the same as defined in Formula 1.

4. The organic electroluminescence device of claim 2, wherein Formula 1-2 is represented by Formula 1-2A or Formula 1-2B:

Formula 1-2A

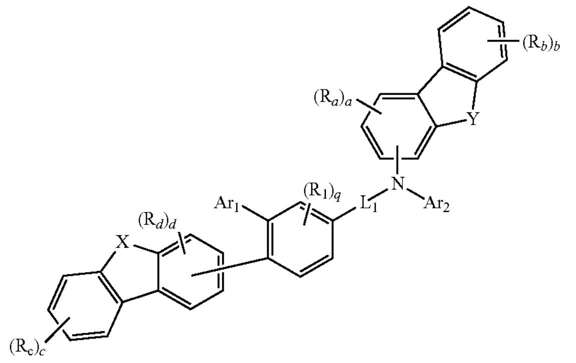

-continued

Formula 1-2B

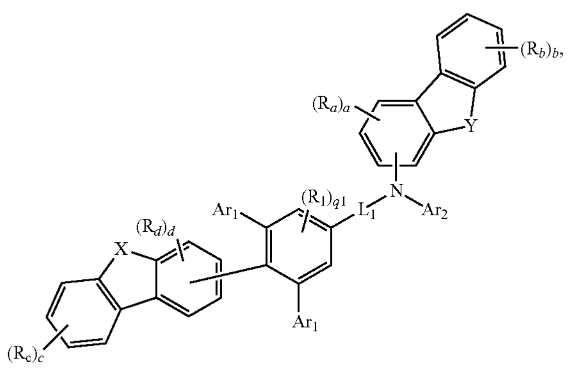

in Formula 1-2B, q1 is an integer of 0 to 2, and in Formula 1-2A and Formula 1-2B, X, Y, $Ar_1$, $Ar_2$, $R_1$, $R_a$ to $R_d$, $L_1$, "a" to "d", and "q" are the same as defined in Formula 1.

5. The organic electroluminescence device of claim 1, wherein Formula 1 is represented by any one selected from Formula 1A to Formula 1 D:

Formula 1A

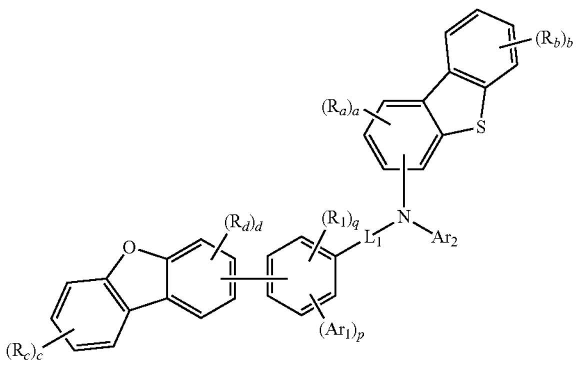

Formula 1B

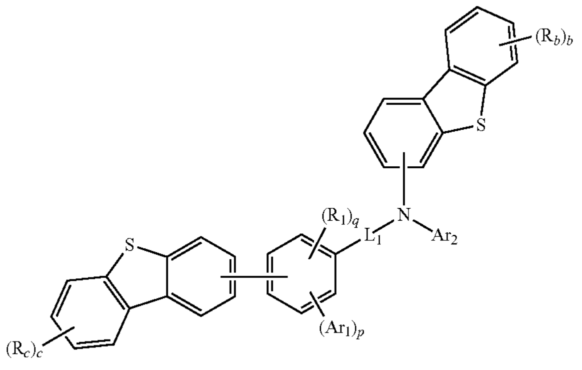

-continued

Formula 1C

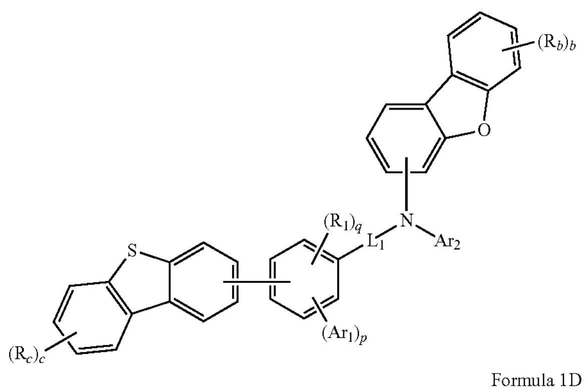

Formula 1D

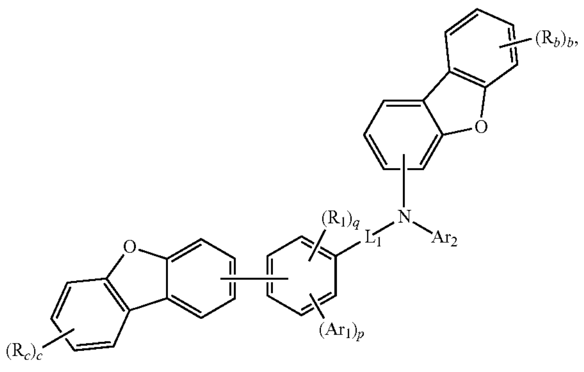

and in Formula 1A to Formula 1D, $Ar_1$, $Ar_2$, $R_1$, $R_a$ to $R_d$, $L_1$, "a" to "d", "p", and "q" are the same as defined in Formula 1.

6. The organic electroluminescence device of claim 1, wherein the emission layer comprises an anthracene derivative represented by Formula 2:

Formula 2

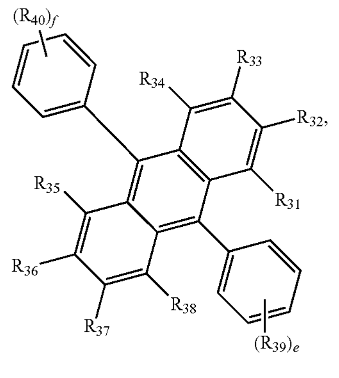

and in Formula 2, $R_{31}$ to $R_{40}$ are each independently a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 carbon atoms for forming a ring, or a substituted or unsubstituted heteroaryl group of 2 to 30 carbon atoms for forming a ring, and any of $R_{31}$ to $R_{40}$ are optionally combined with an adjacent group to form a ring, and
"e" and "f" are each independently an integer of 0 to 5.
7. The organic electroluminescence device of claim 6, wherein Formula 2 is represented by any one selected from Compound 2-1 to Compound 2-16:
2-1
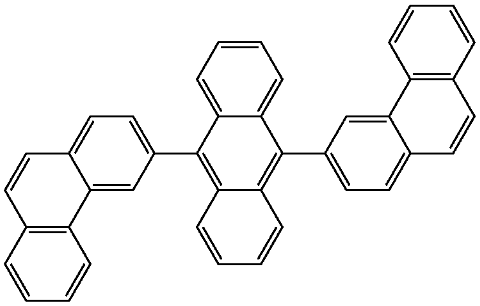
2-2
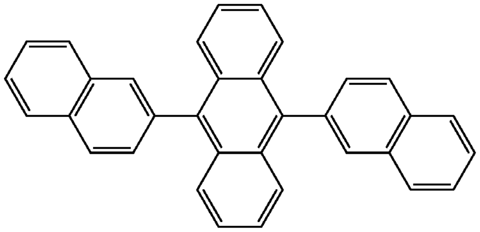
2-3
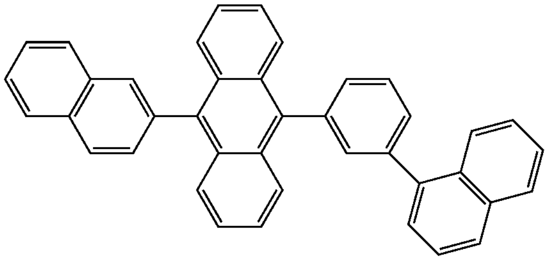
2-4
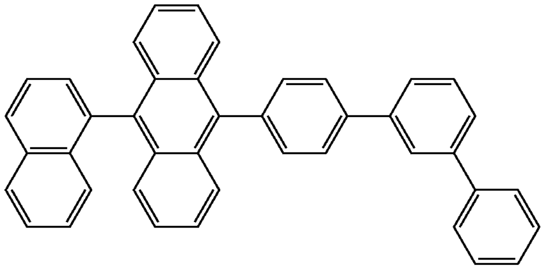
2-5
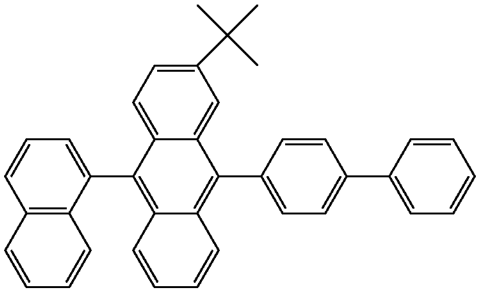
-continued
2-6
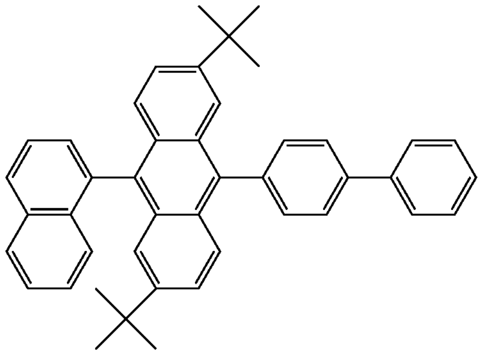
2-7
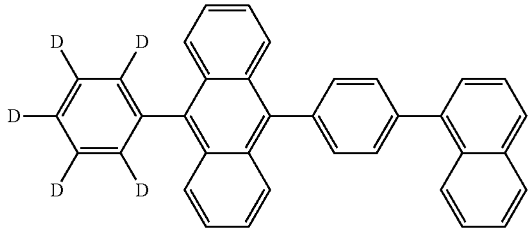
2-8
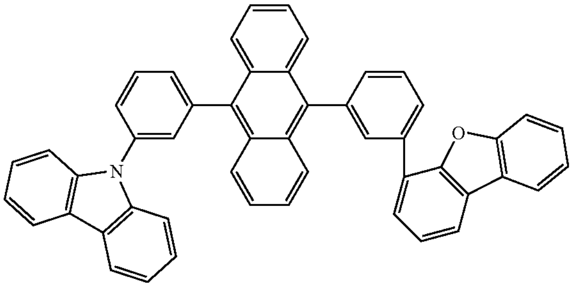
2-9
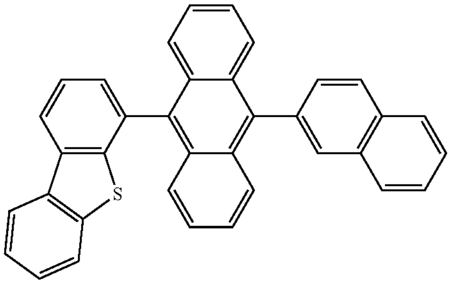
2-10
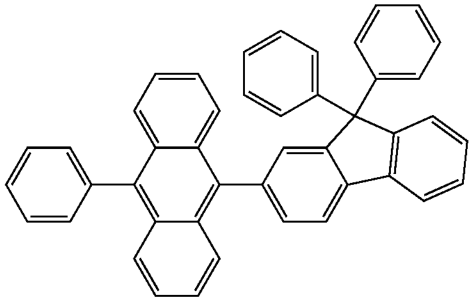

-continued 2-11

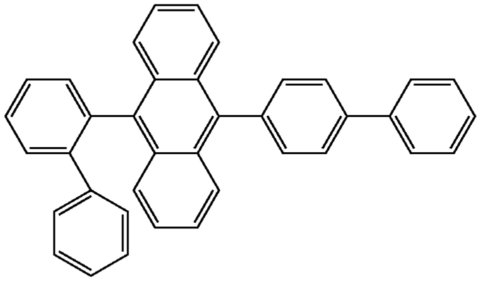

2-12

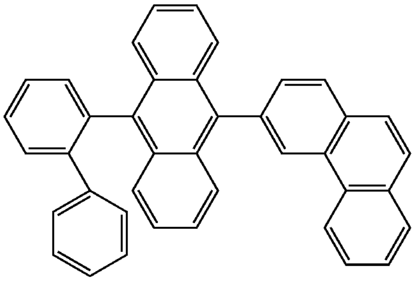

2-13

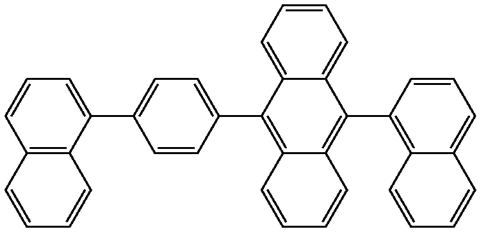

2-14

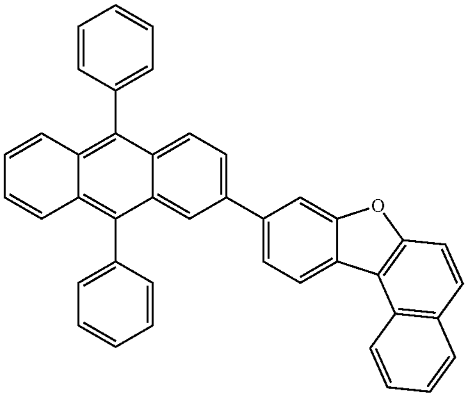

-continued 2-15

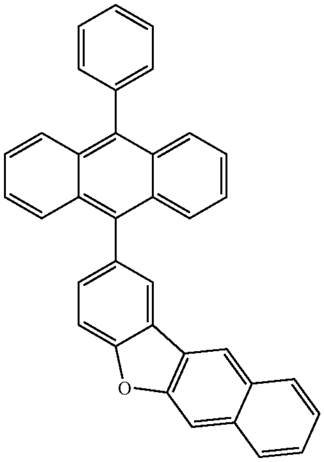

2-16

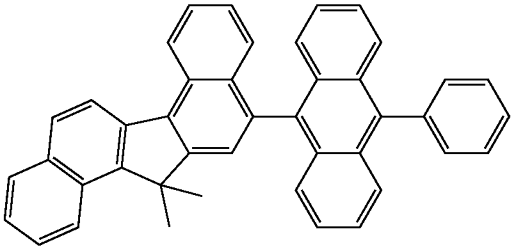

.

8. An organic electroluminescence device, comprising:

a first electrode;

a second electrode on the first electrode;

an emission layer;

a hole transport region between the first electrode and the emission layer; and an electron transport region between the emission layer and the second electrode, wherein the hole transport region comprises an amine compound any one selected from compounds in Compound Group 1 to Compound Group 3:

Compound Group 1

A2

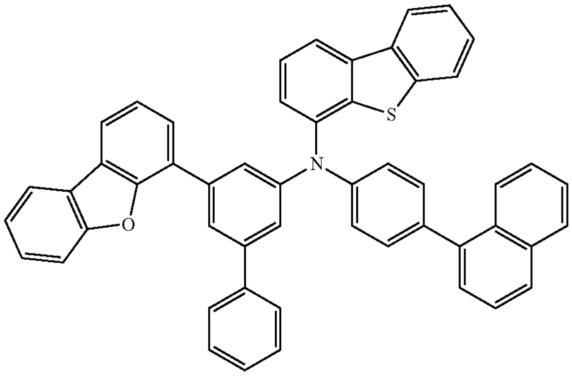

-continued
A7
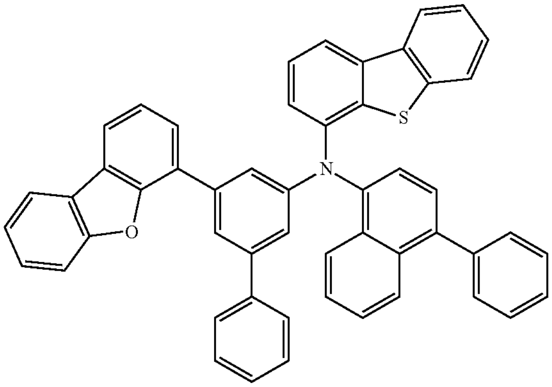
A9
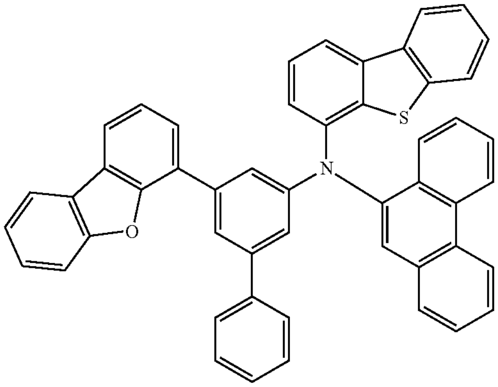
A12
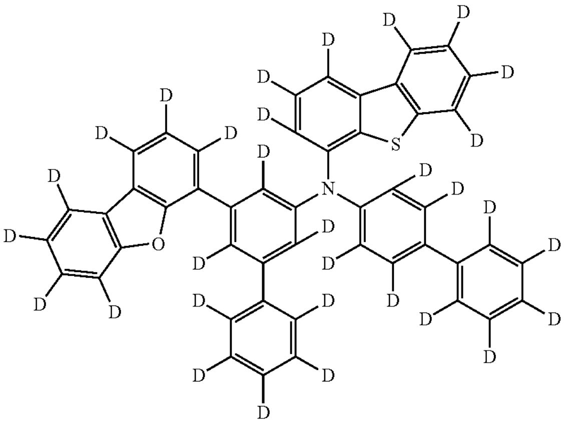
-continued
A17
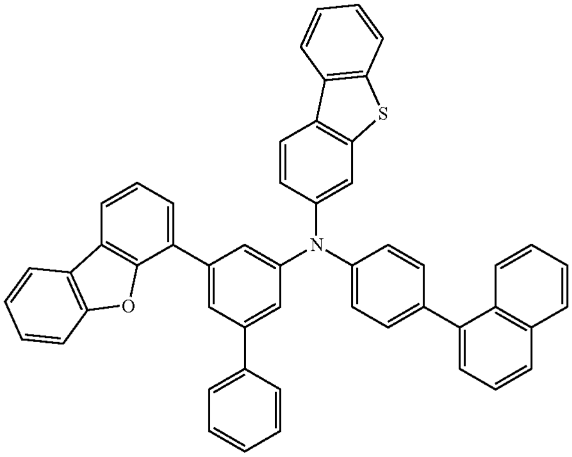
A24
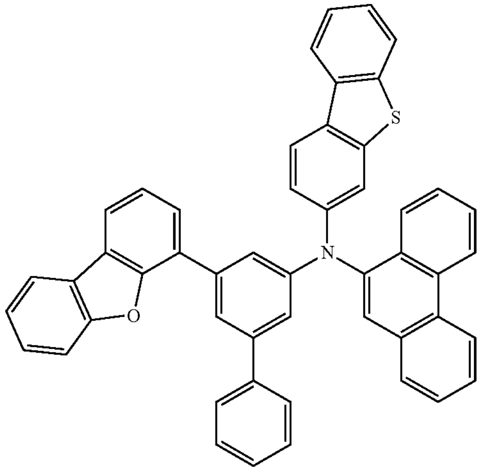
A27
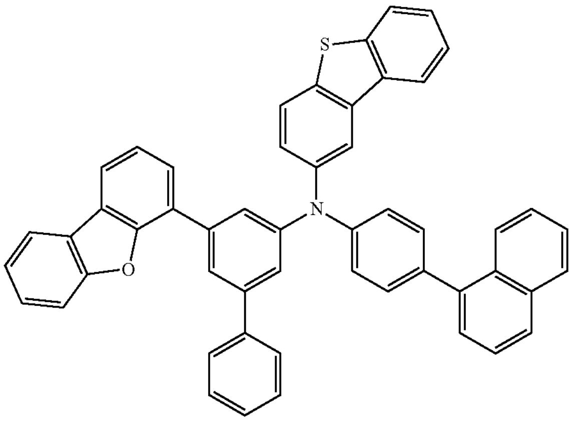

-continued
A34
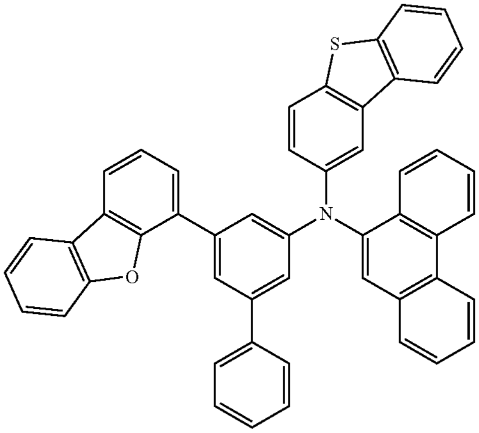
A37
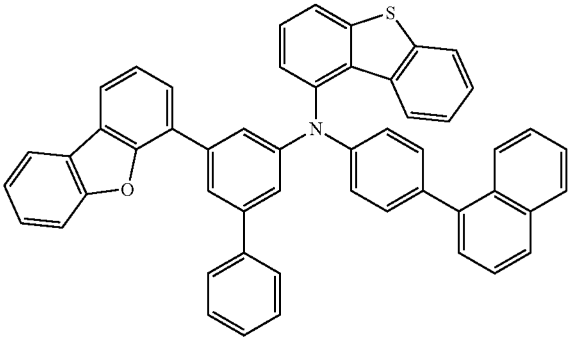
A44
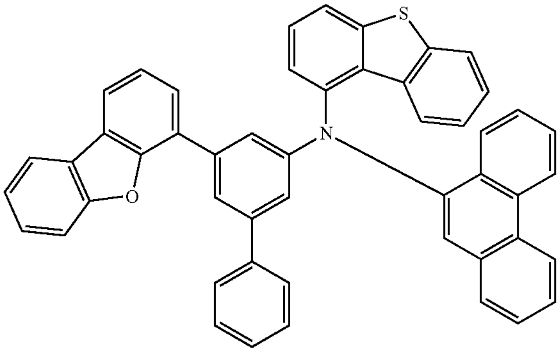
A47
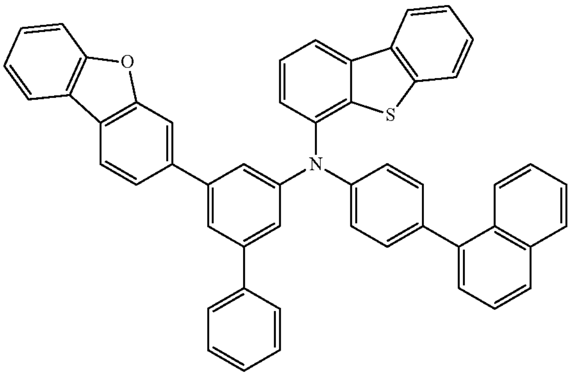
-continued
A54
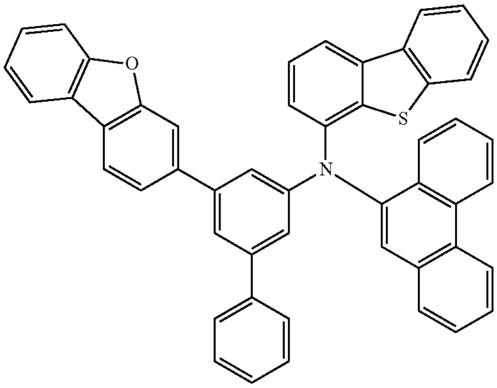
A57
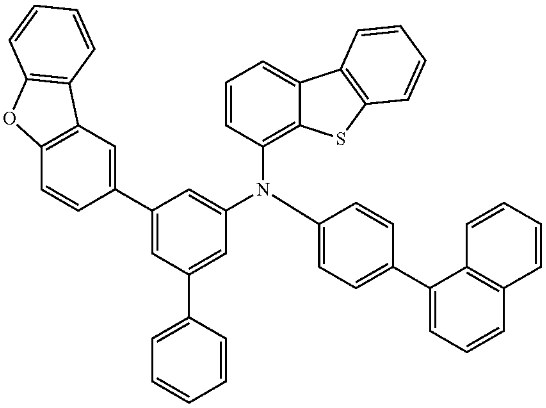
A64
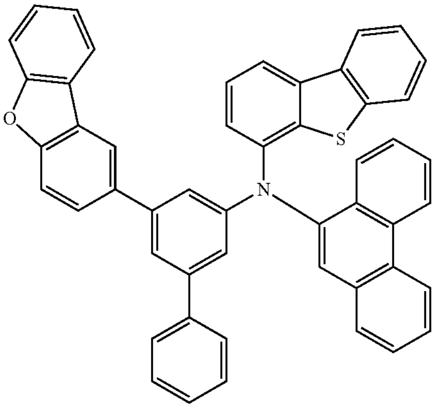
A74
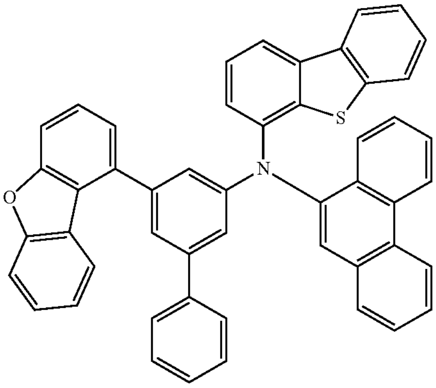

-continued
A77
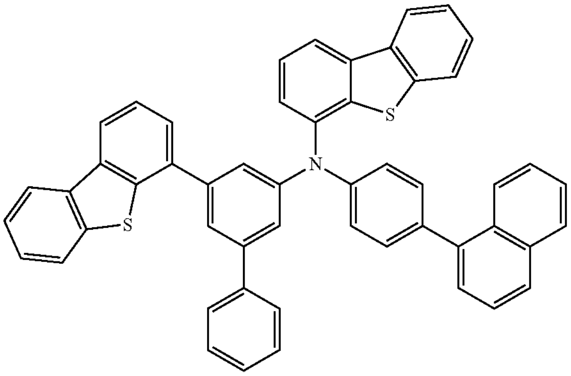
A84
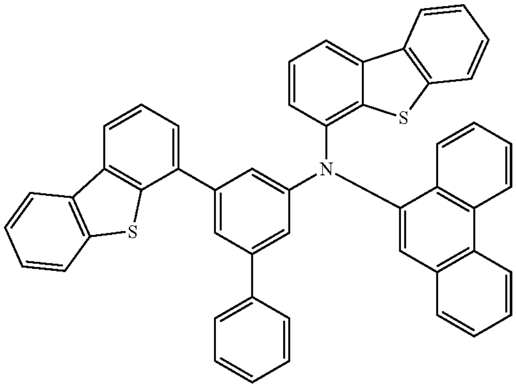
A87
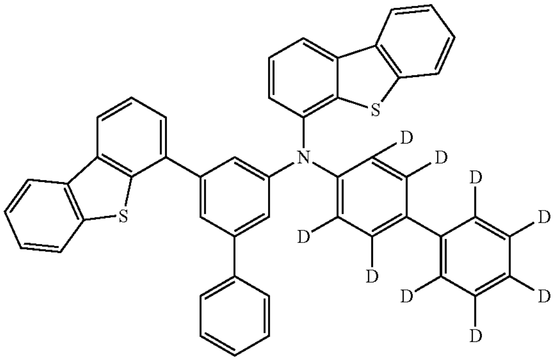
-continued
A92
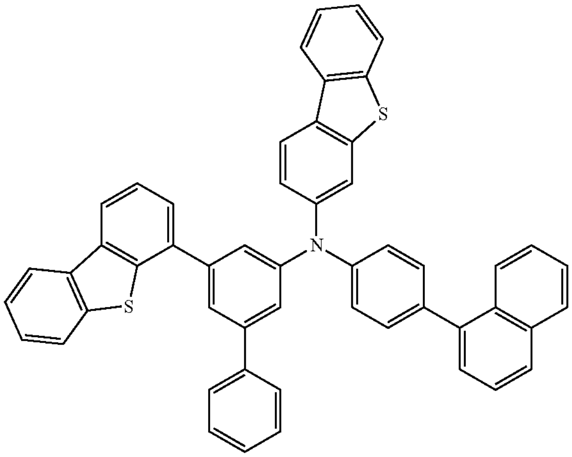
A99
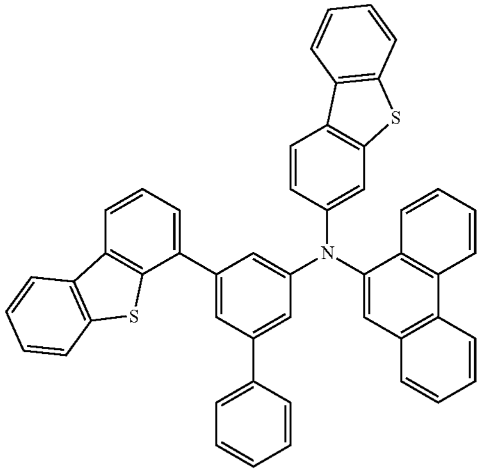
A102
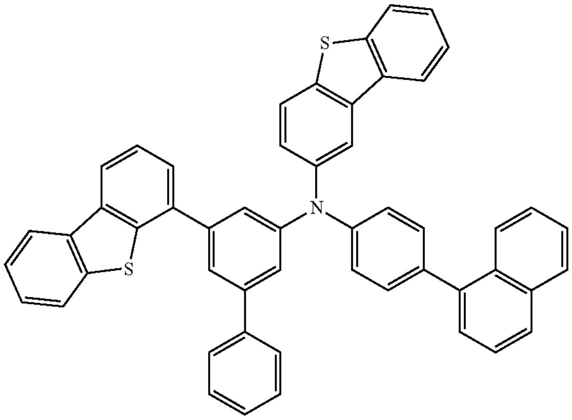

A109
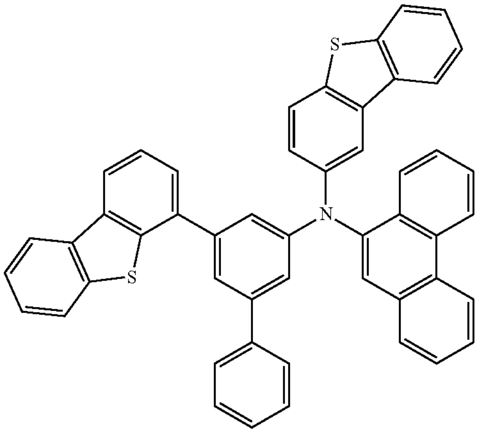
A112
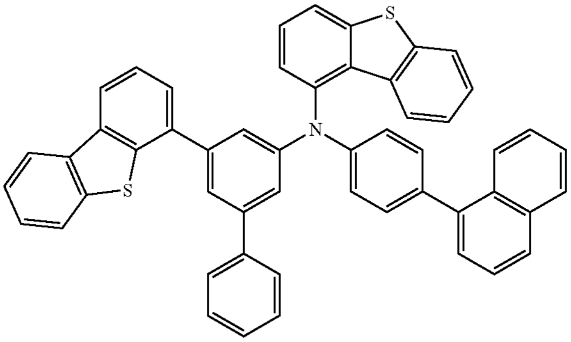
A119
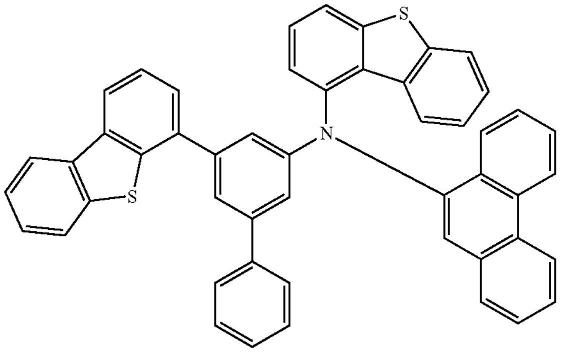
A122
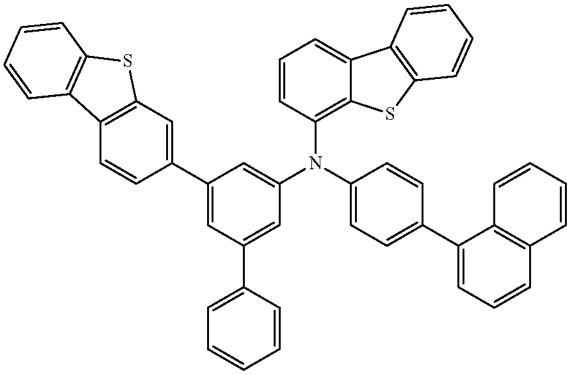
A125
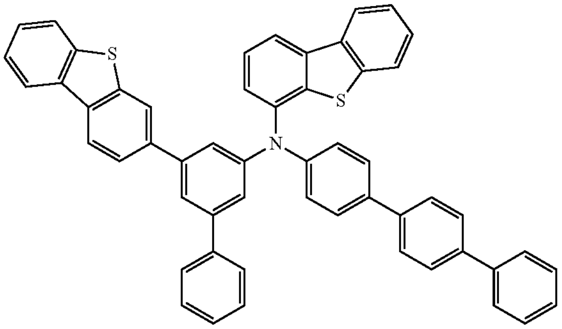
A126
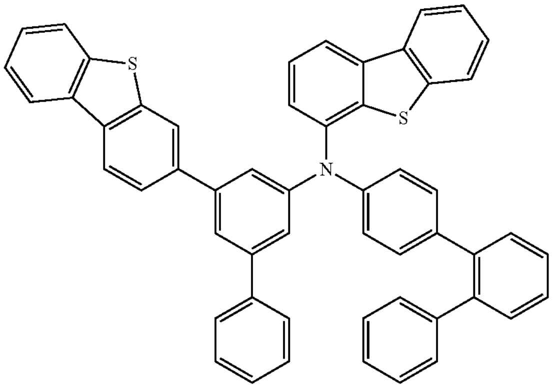
A127
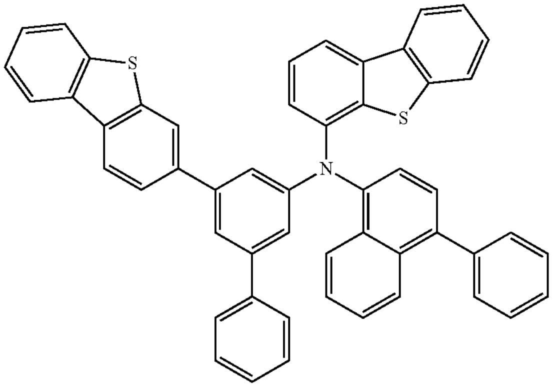
A128
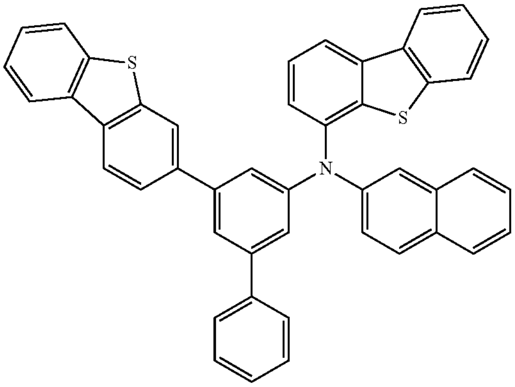

-continued
A129
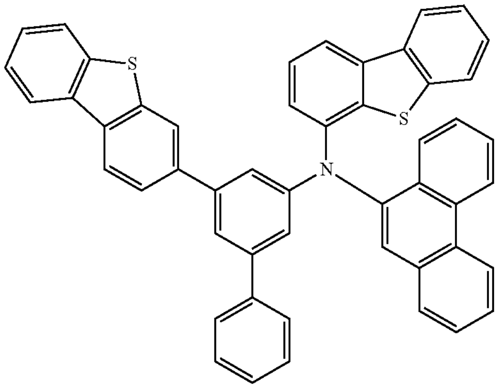
A132
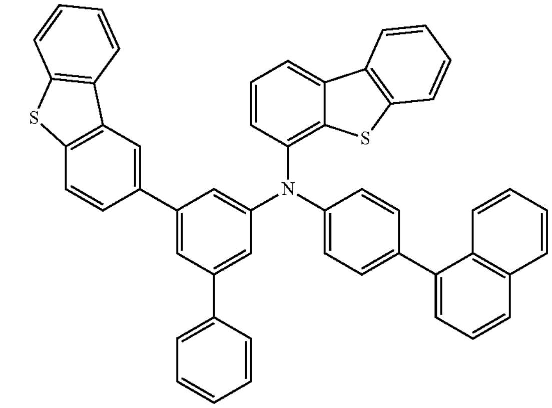
A139
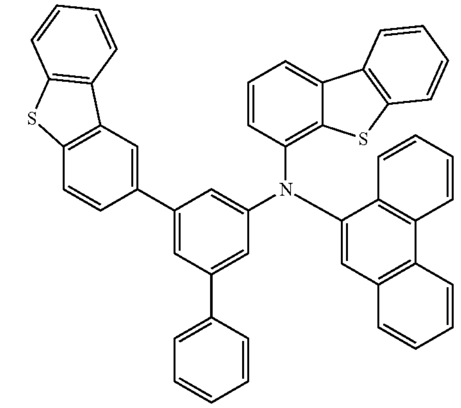
A142
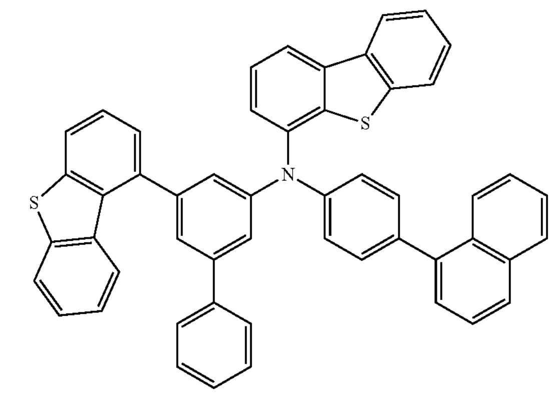
-continued
A149
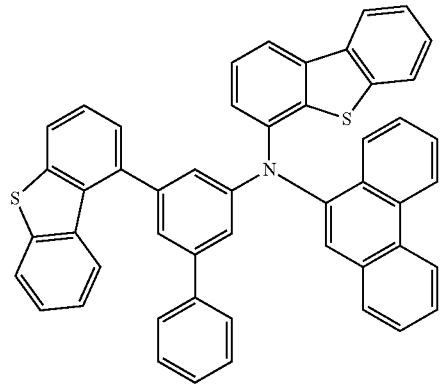
A152
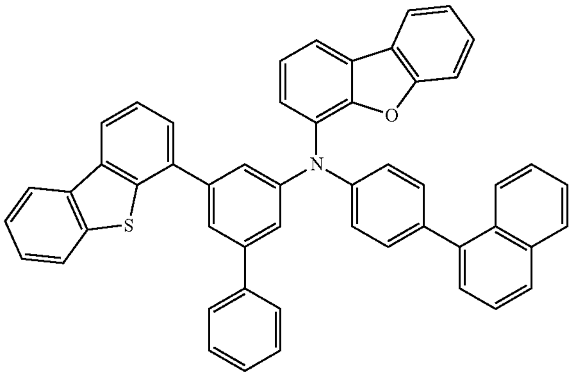
A159
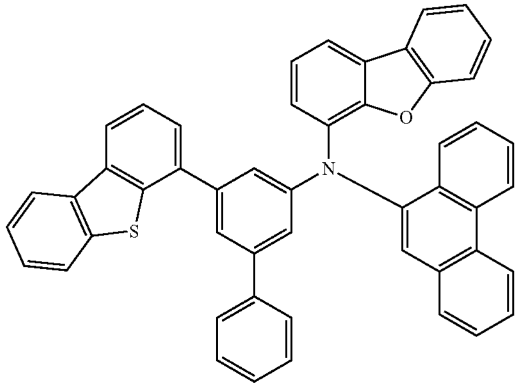
A162
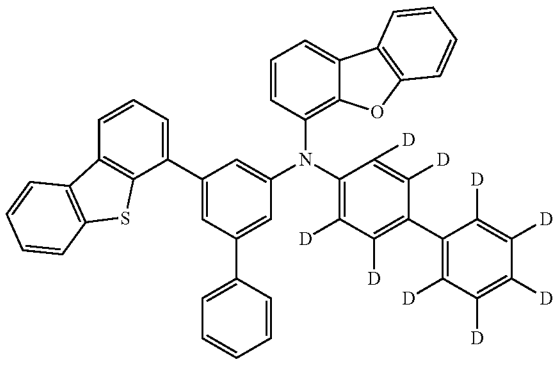

-continued
A167
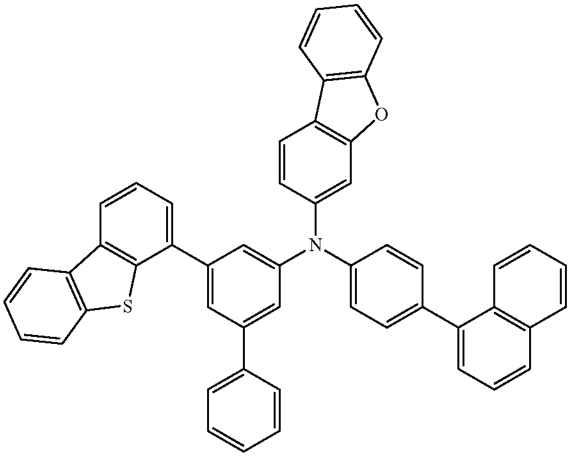
A174
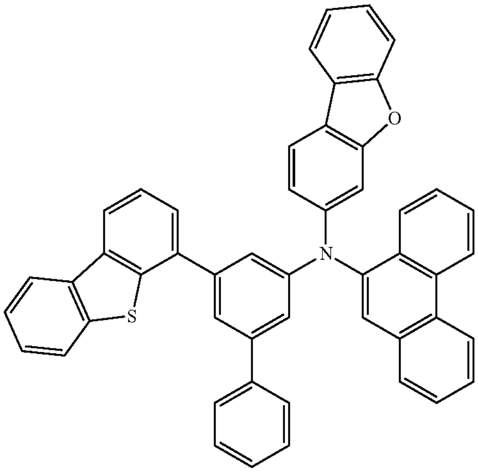
A177
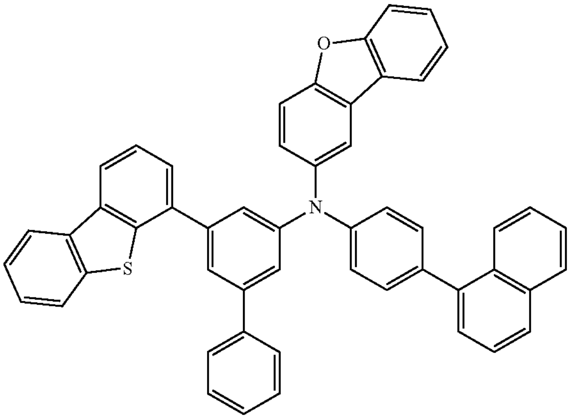
-continued
A184
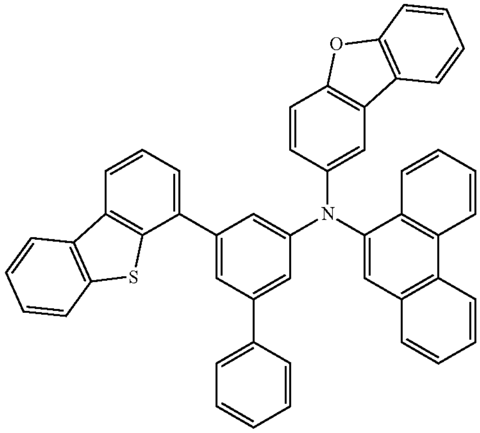
A187
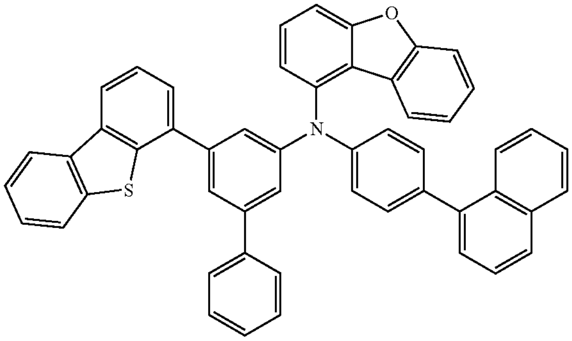
A194
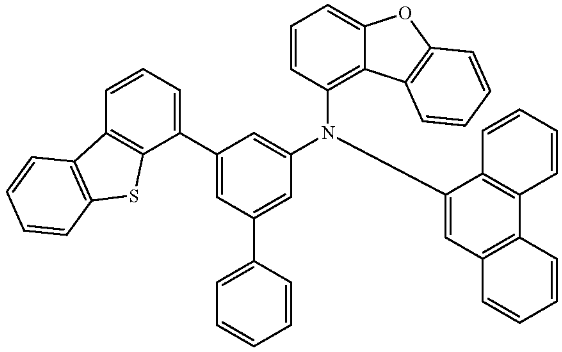
A197
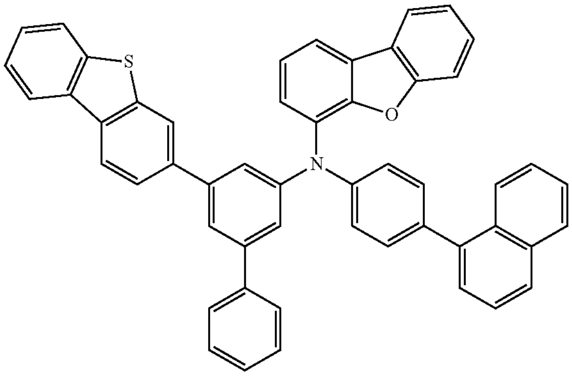

-continued
A204
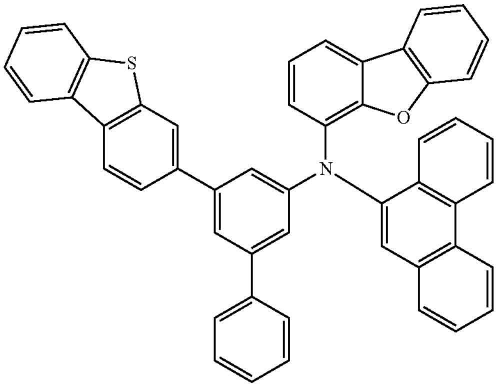
A207
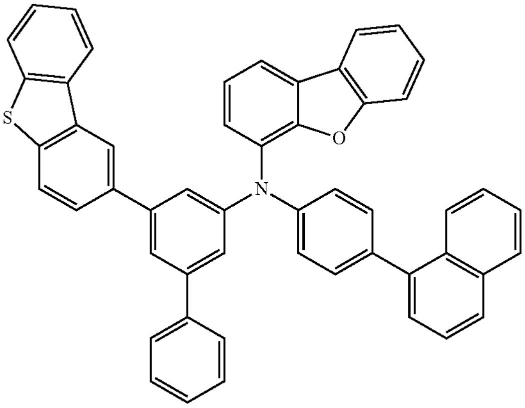
A214
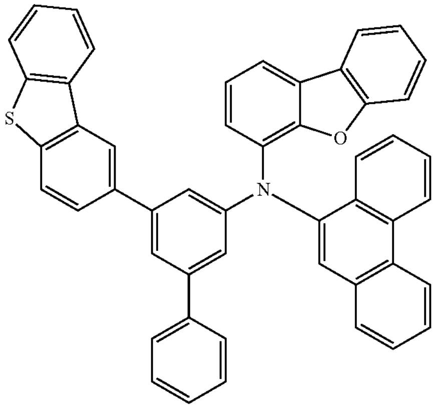
A217
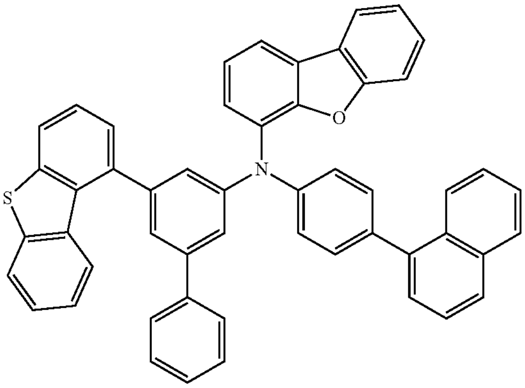
-continued
A224
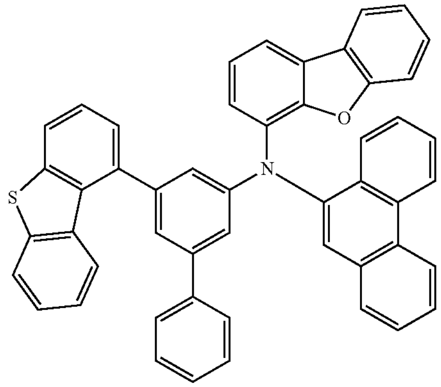
A237
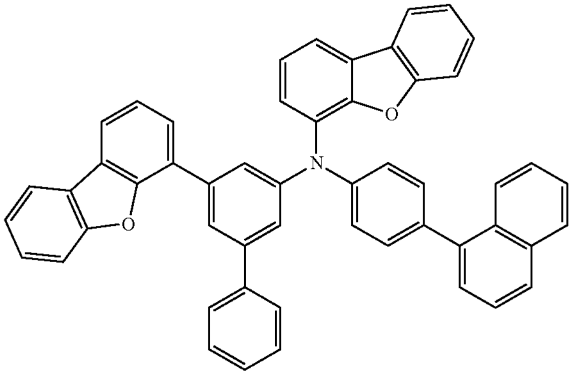
A244
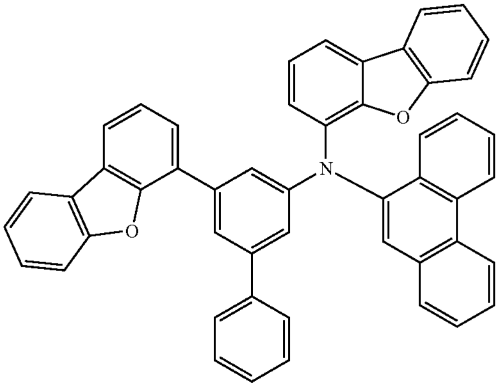
Compound Group 2
B2
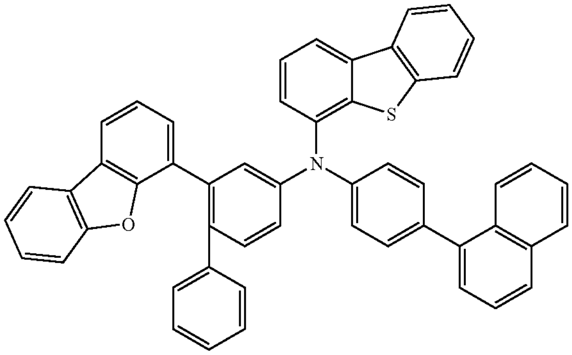

-continued
B9
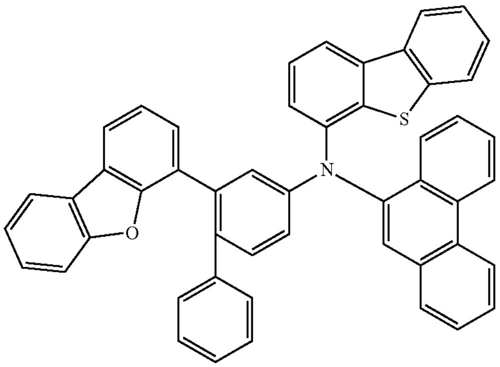
B12
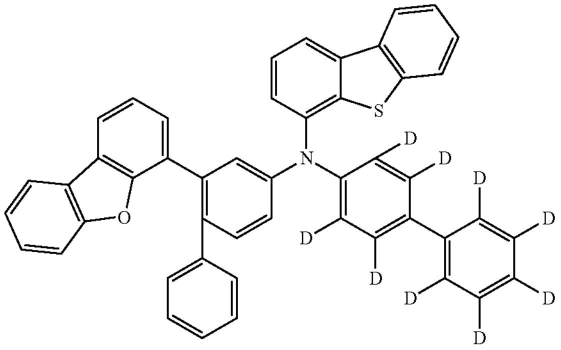
B14
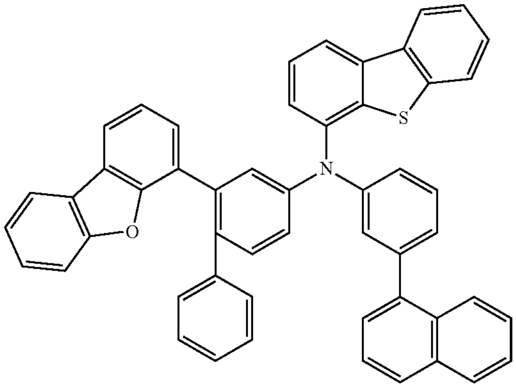
B17
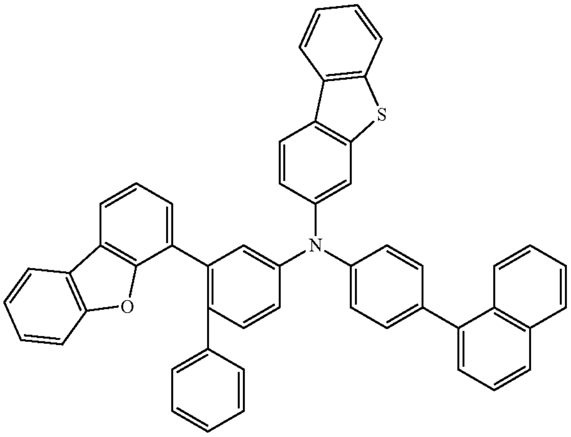
-continued
B24
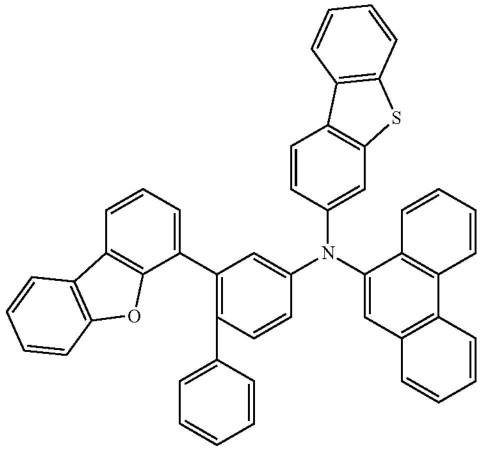
B27
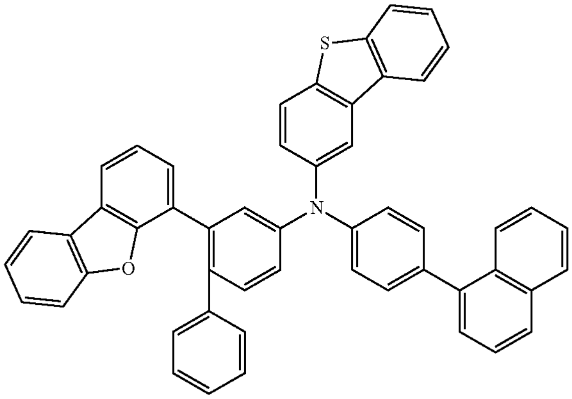
B34
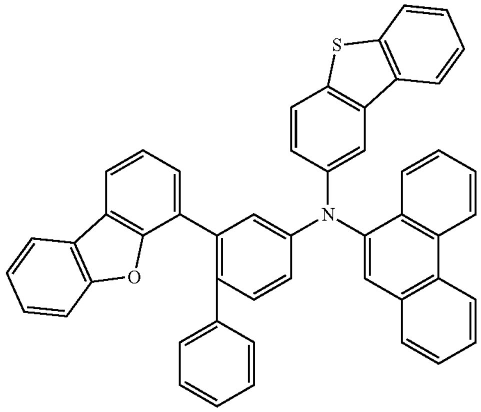
B37
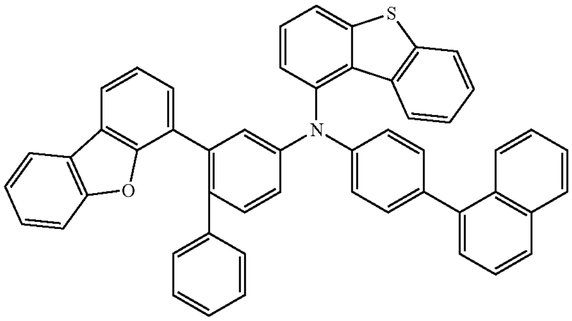

-continued
B44
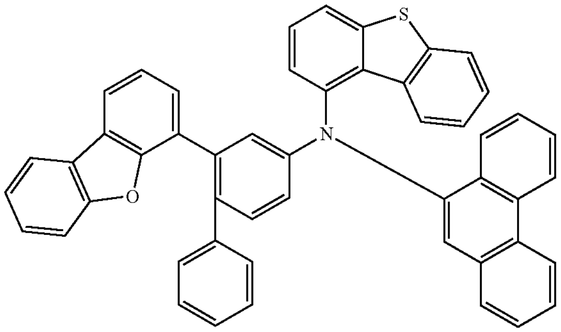
B47
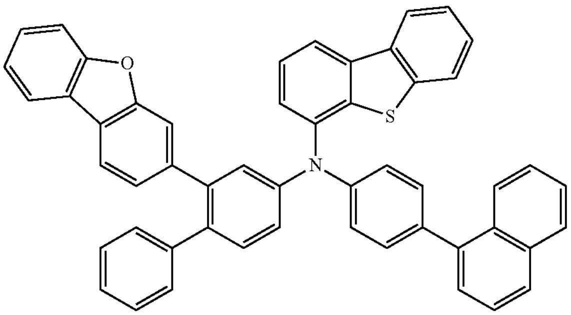
B54
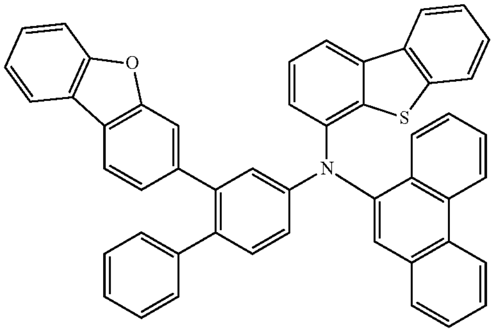
B57
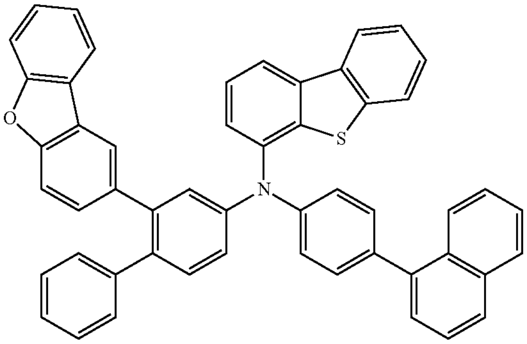
-continued
B64
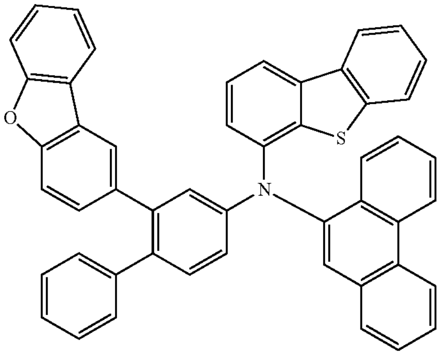
B74
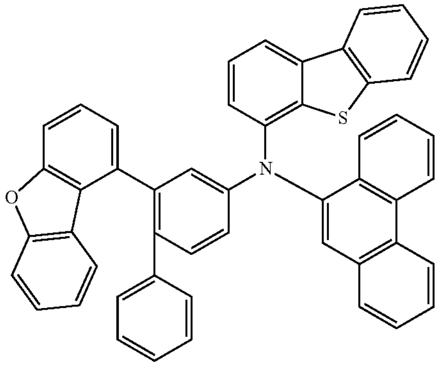
B77
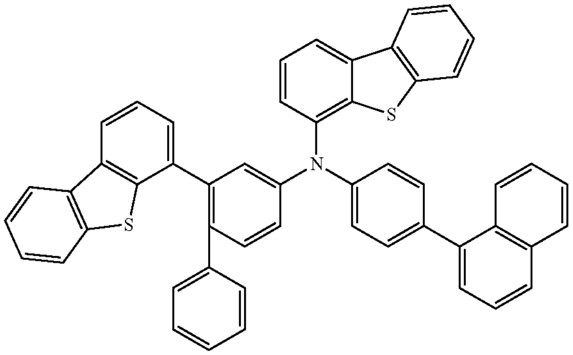
B84
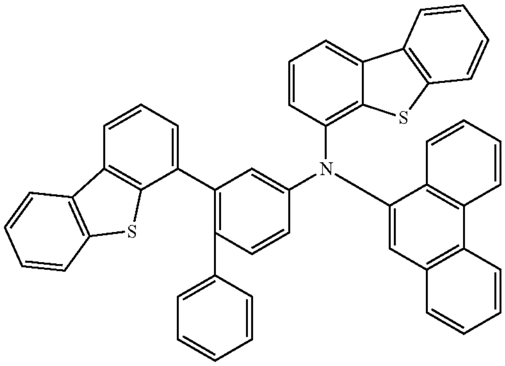

-continued
B87
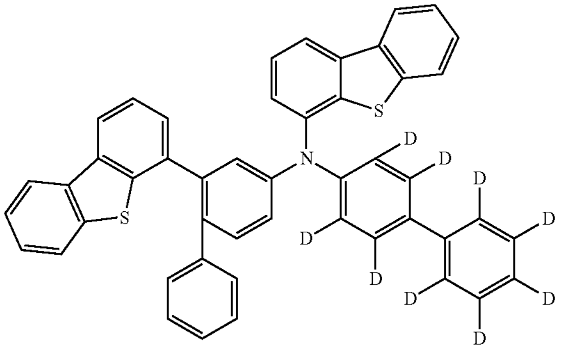
B89
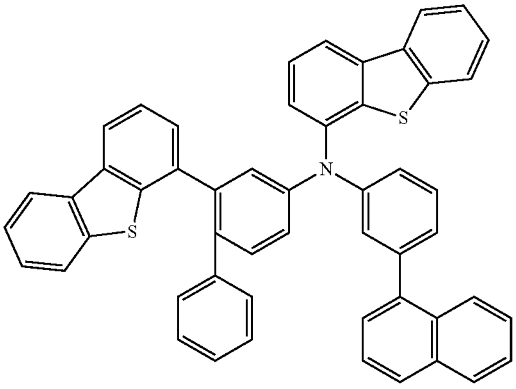
B92
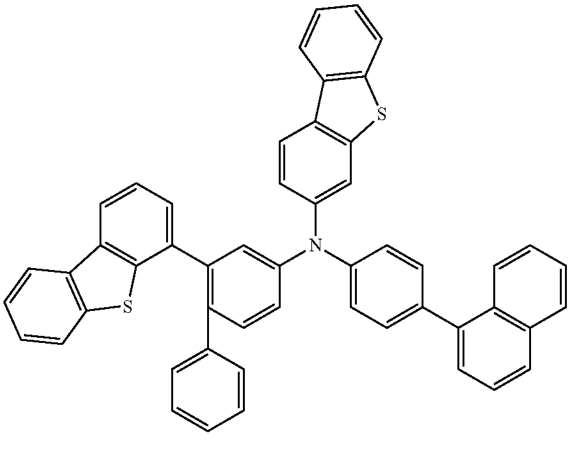
-continued
B99
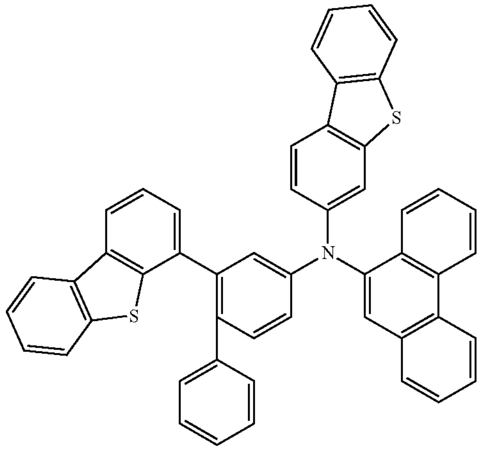
B102
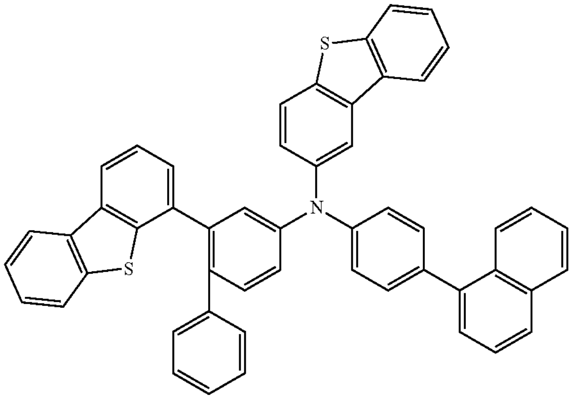
B109
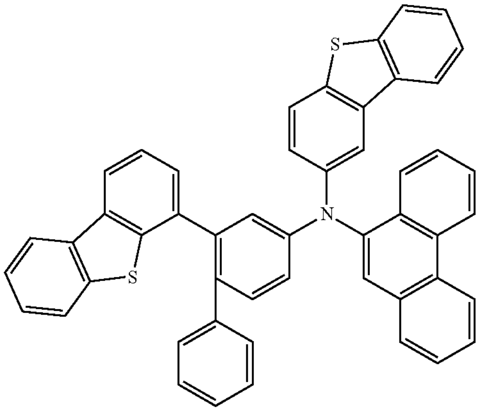
B112
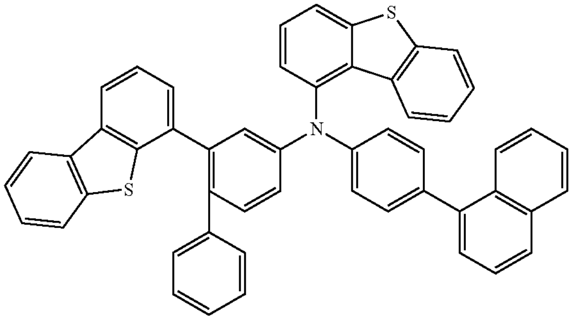

-continued
B119
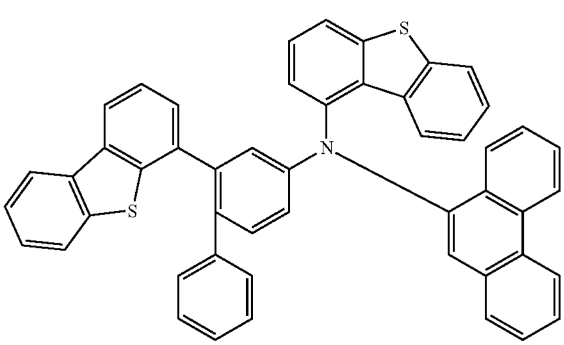
B122
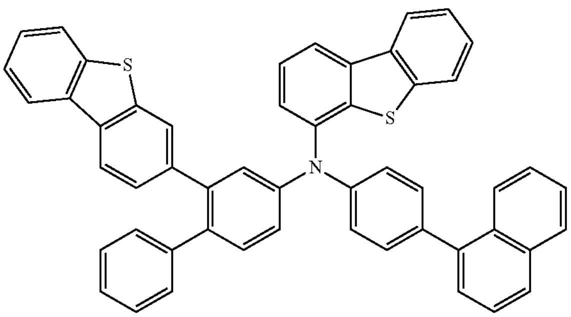
B129
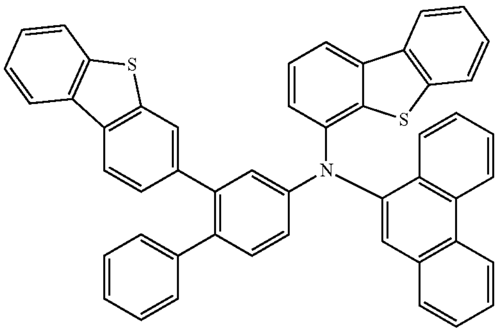
B132
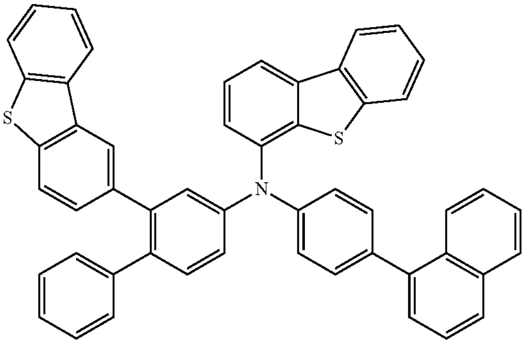
-continued
B139
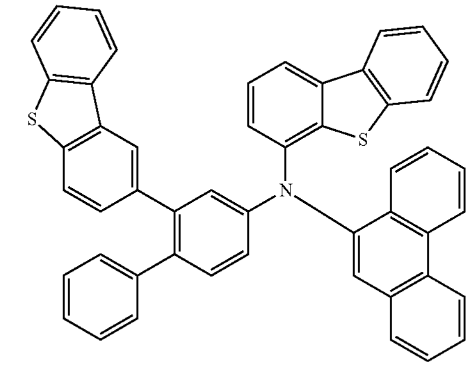
B142
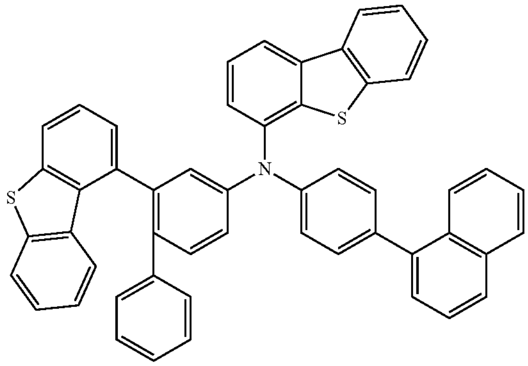
B149
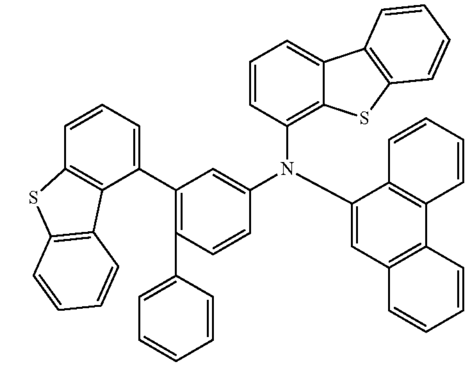
B152
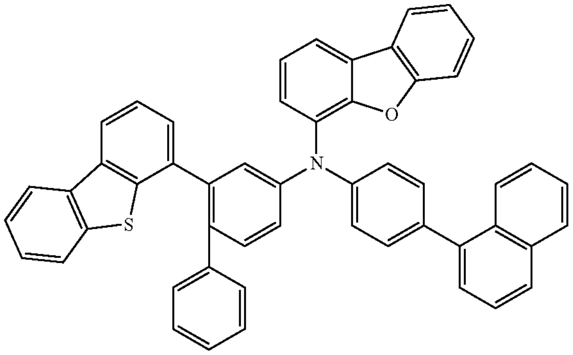

B159
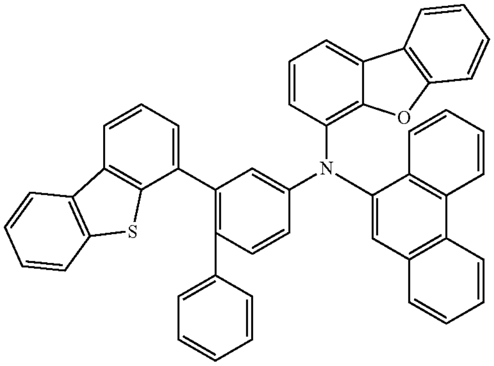
B162
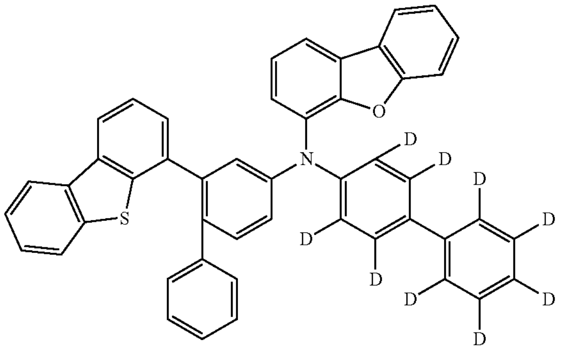
B164
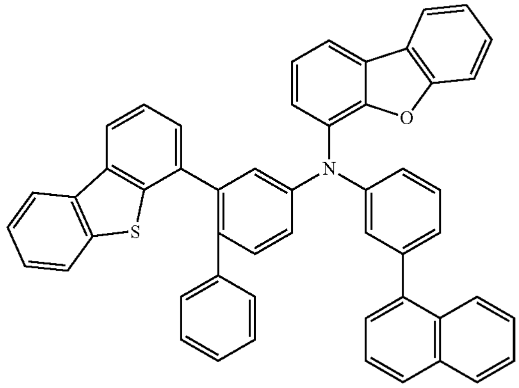
B167
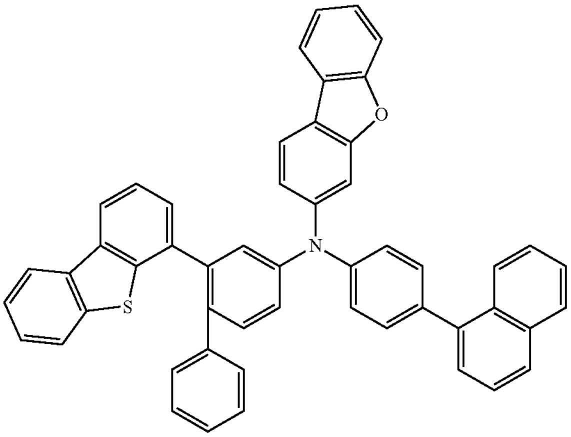
B174
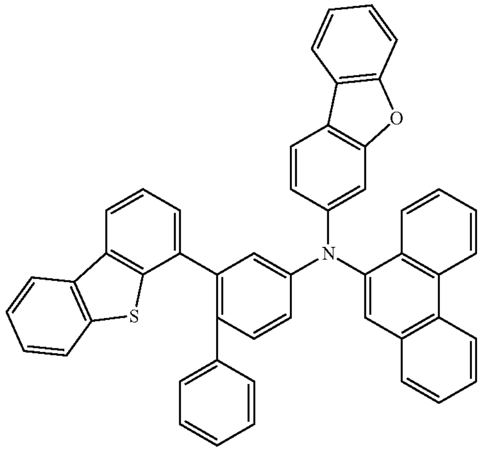
B177
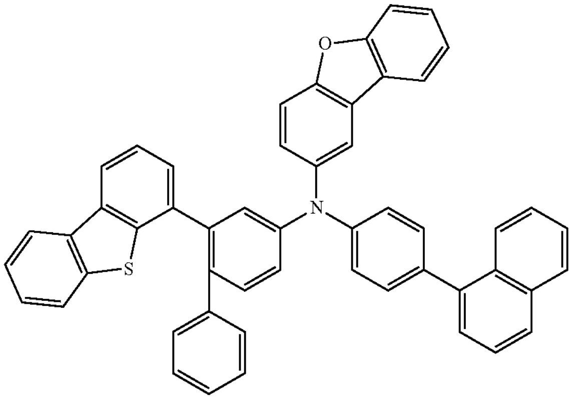
B184
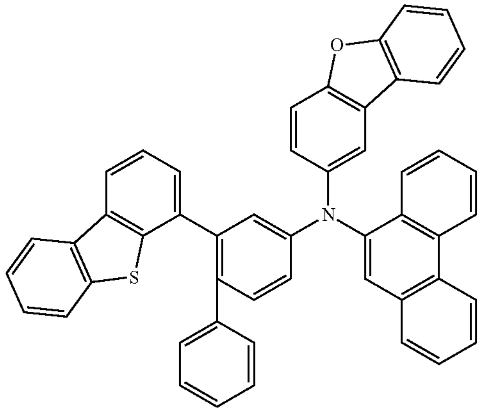
B187
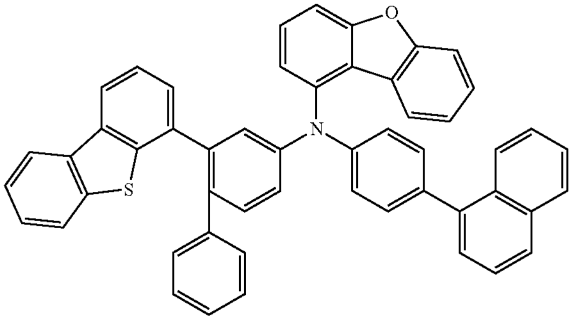

-continued
B194
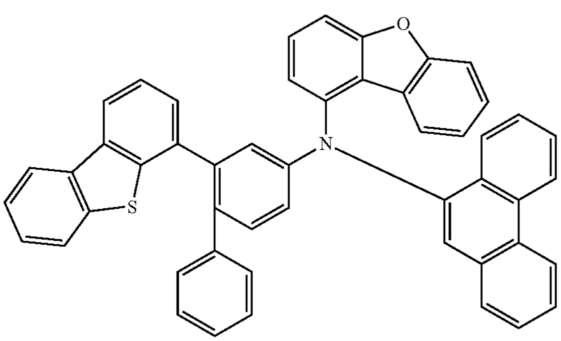
B197
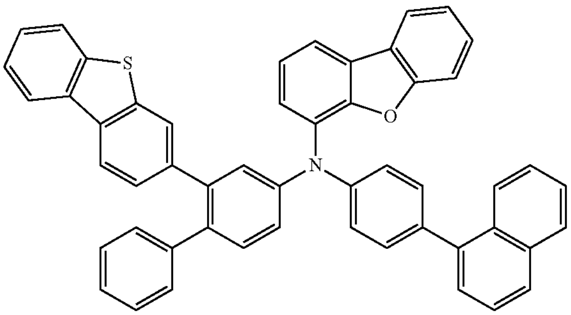
B204
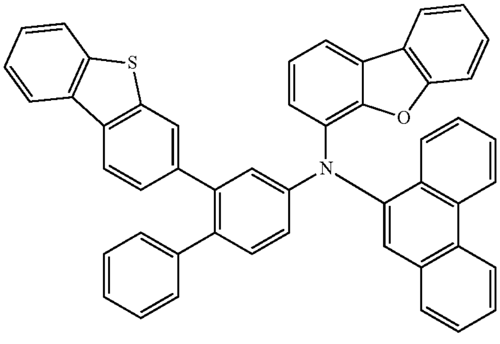
B207
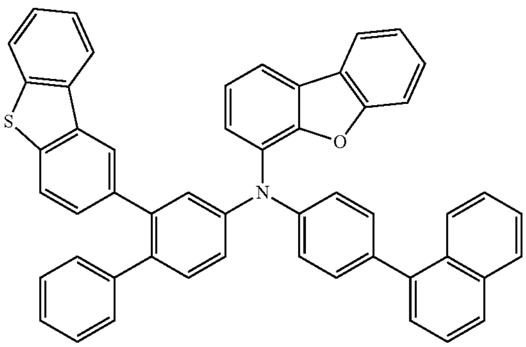
-continued
B214
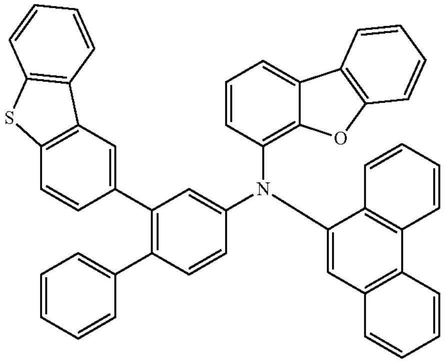
B217
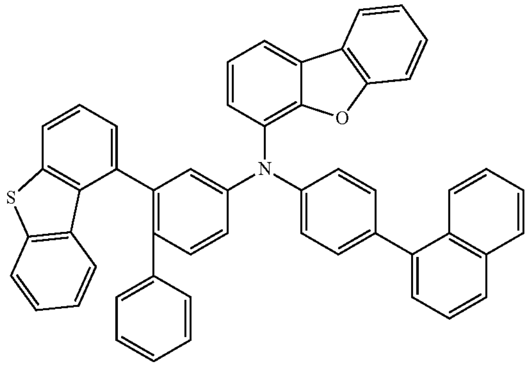
B224
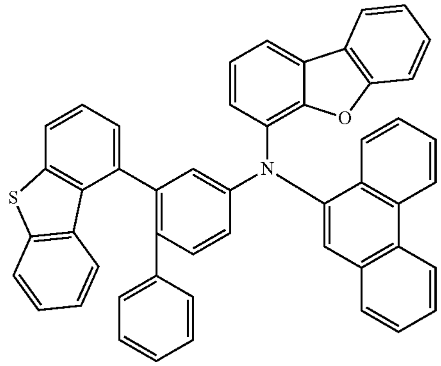
B237
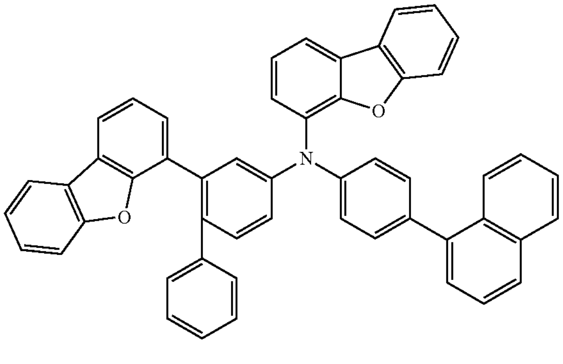

-continued
B244
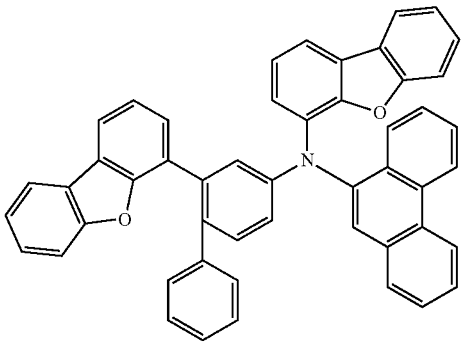
Compound Group 3
C2
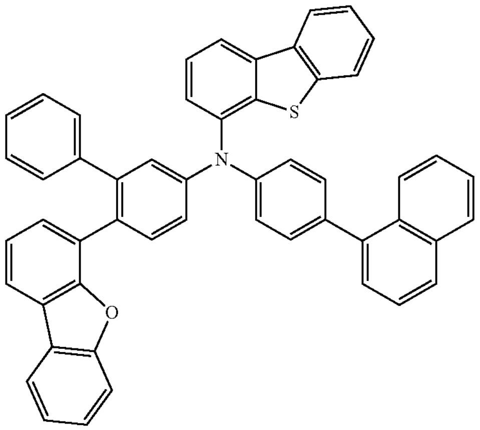
C9
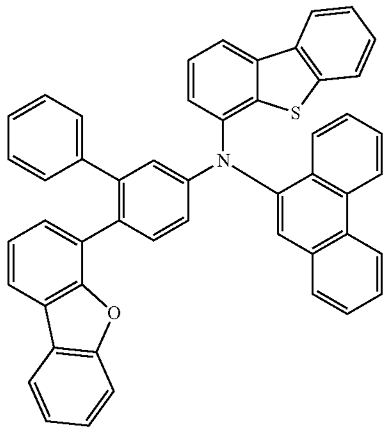
-continued
C12
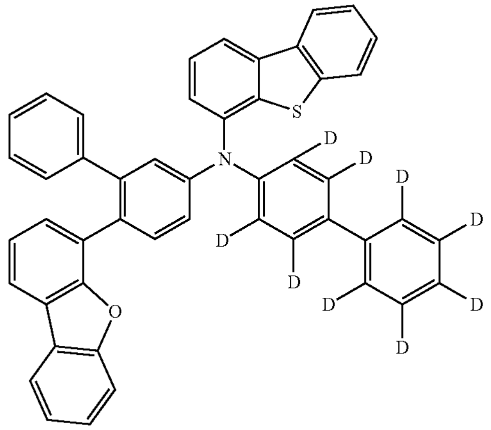
C17
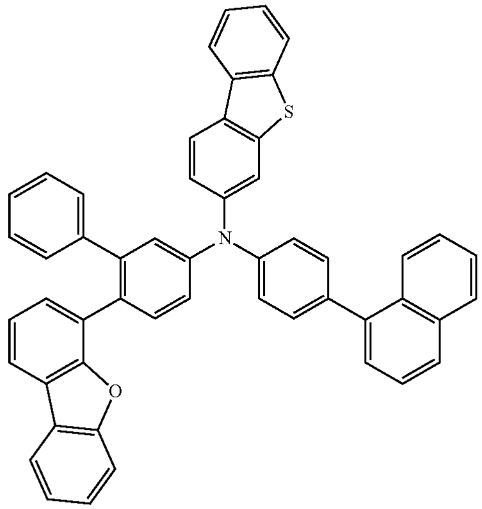
C24
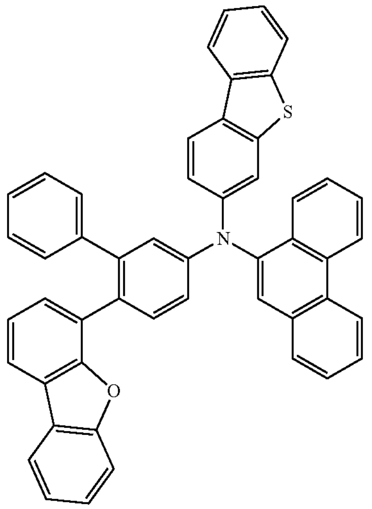

-continued
C27
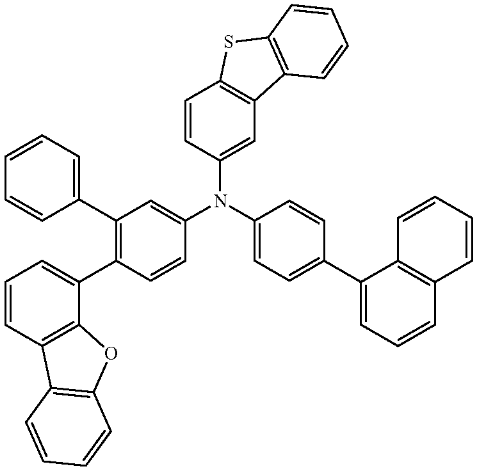
C34
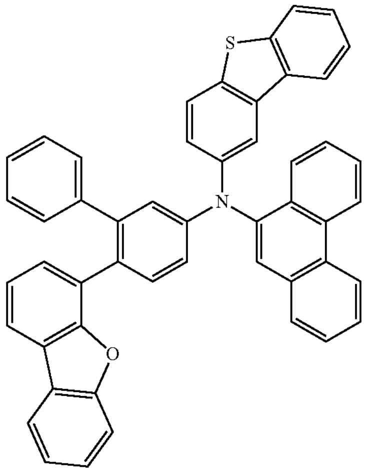
C37
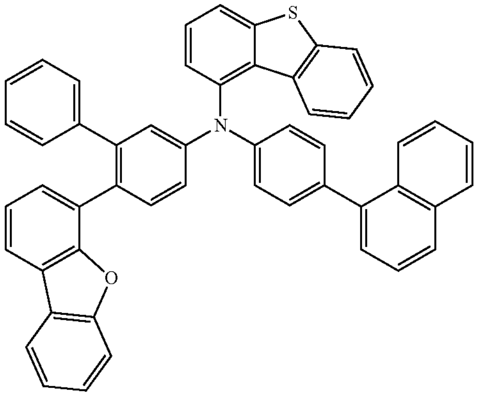
-continued
C44
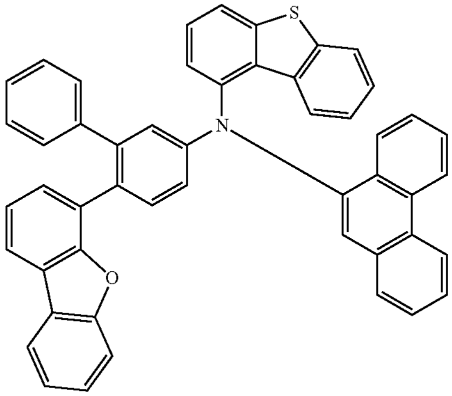
C47
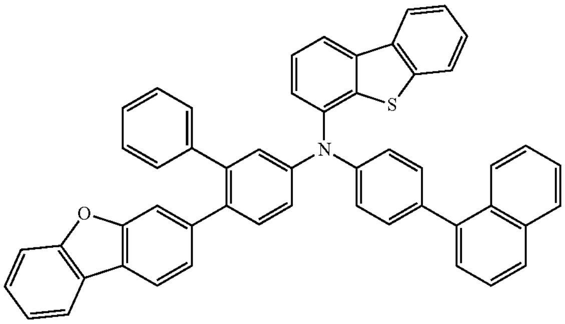
C54
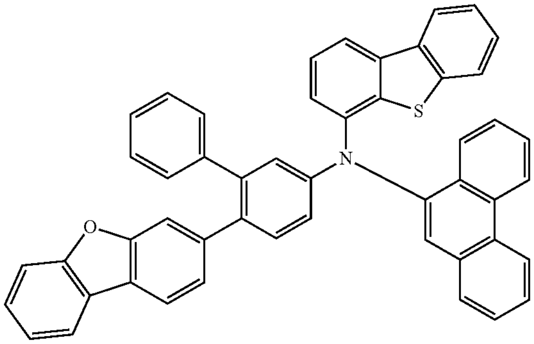
C57
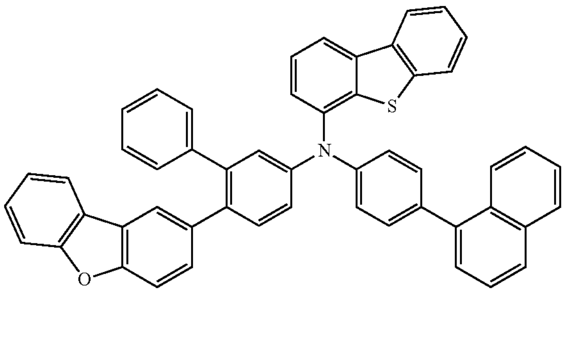

-continued
C64
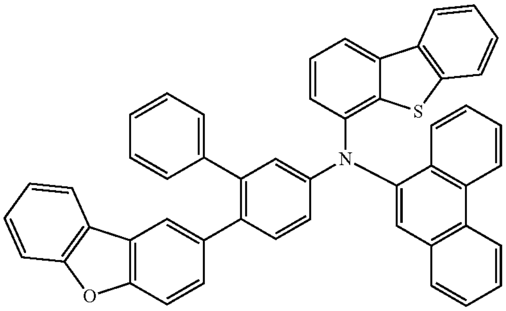
C67
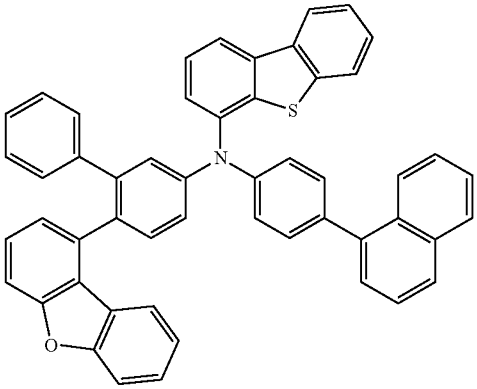
C74
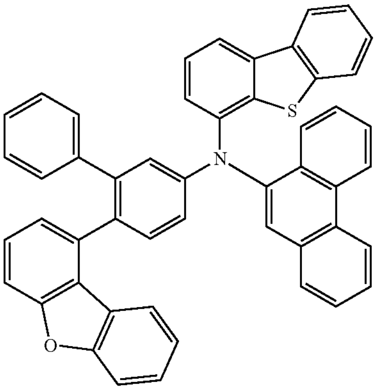
C77
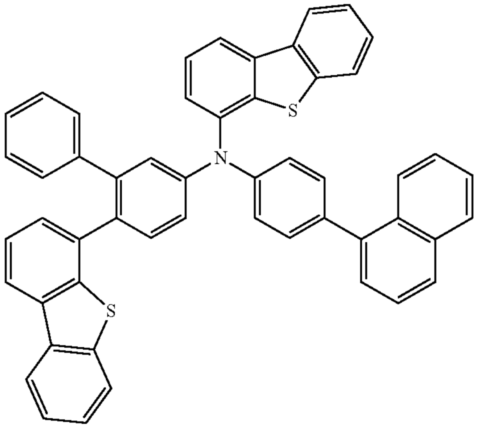
-continued
C84
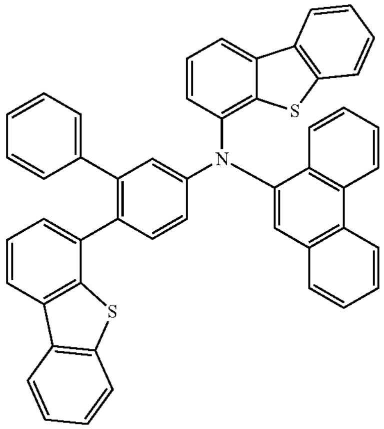
C87
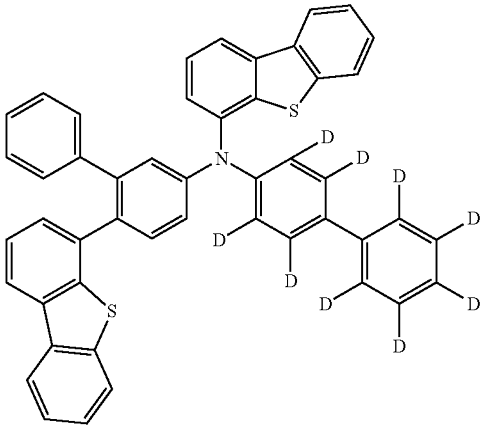
C92
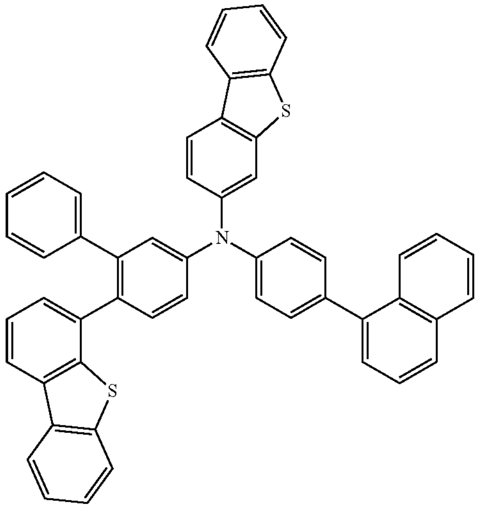

-continued
C99
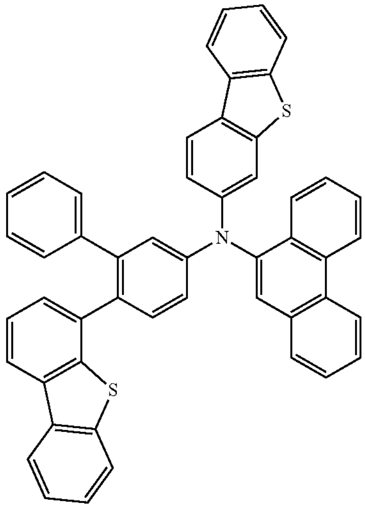
C102
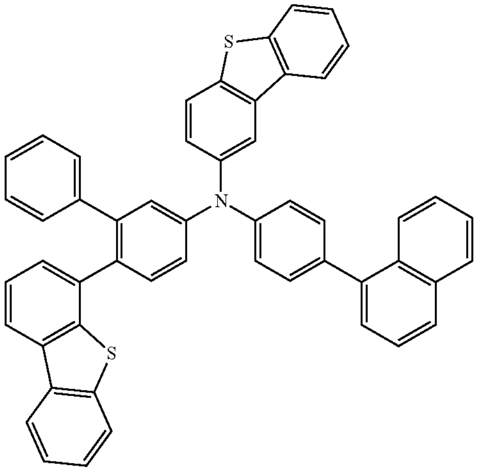
C109
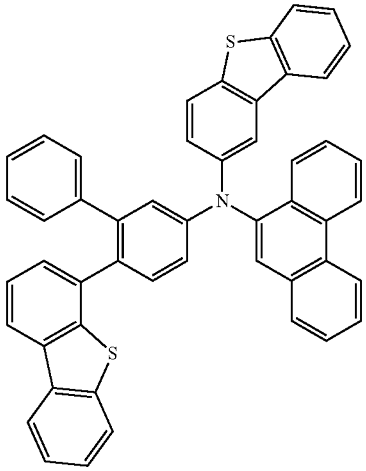
-continued
C112
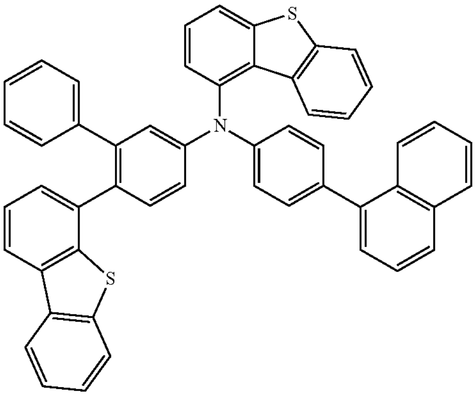
C119
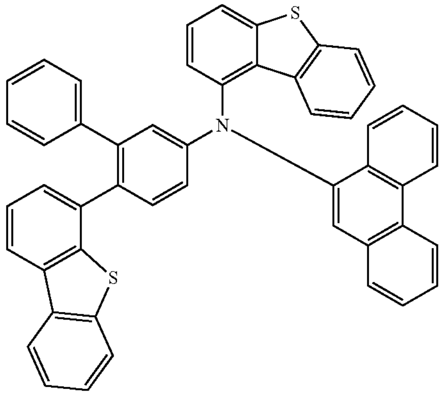
C122
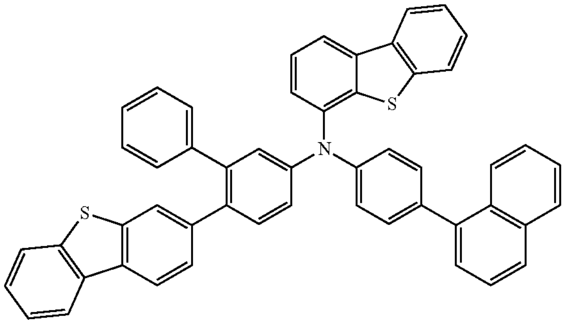
C129
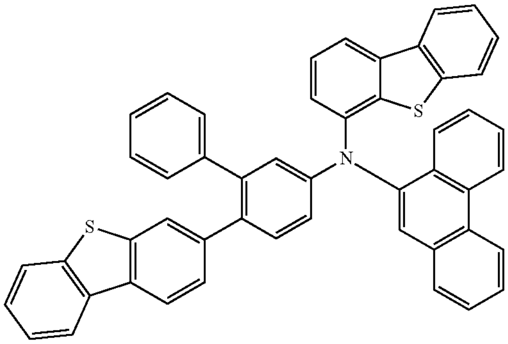

-continued
C132
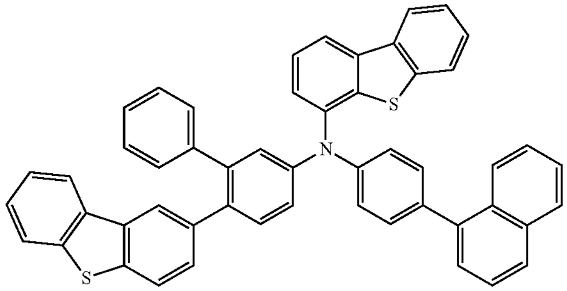
C139
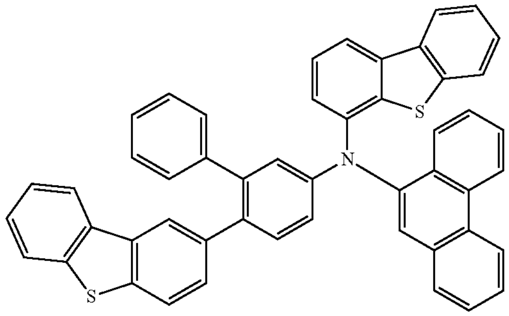
C142
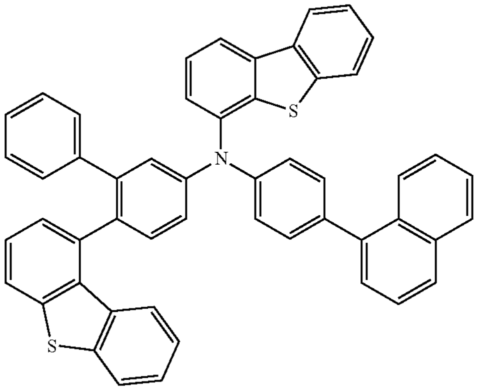
C149
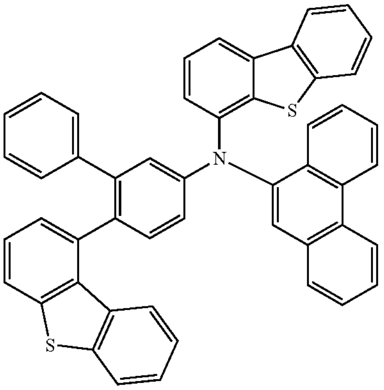
-continued
C152
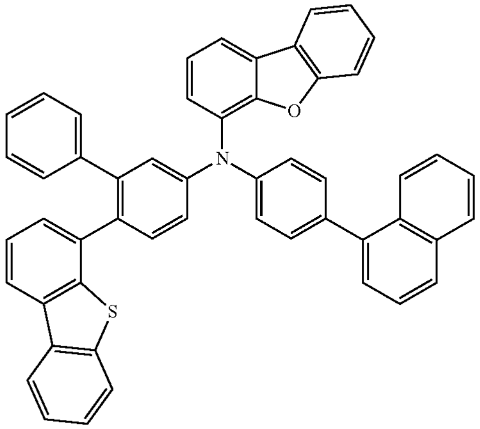
C159
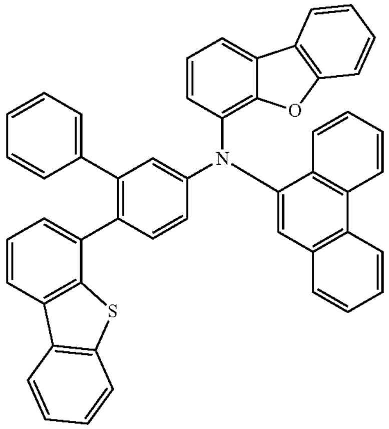
C162
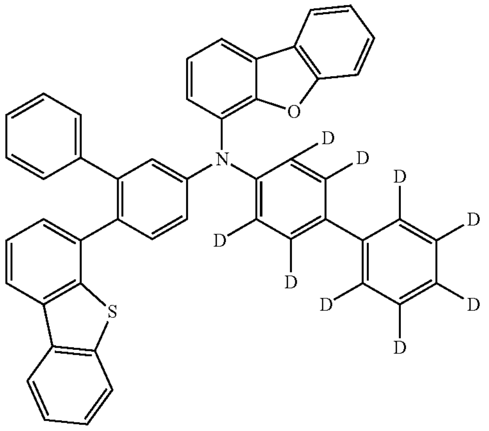

-continued
C167
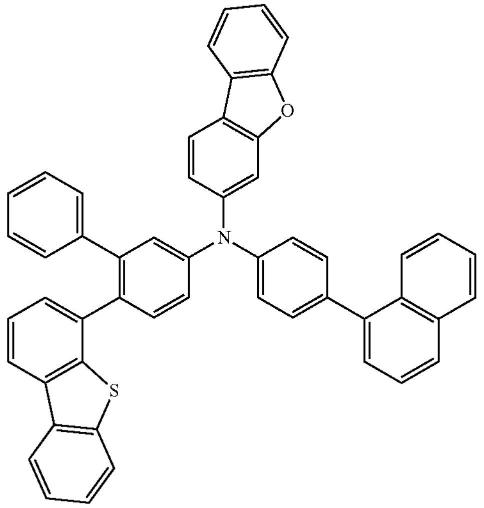
C174
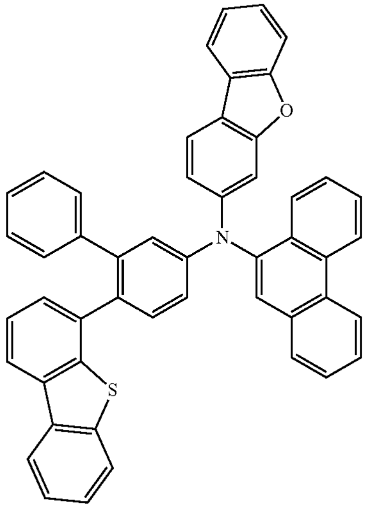
C177
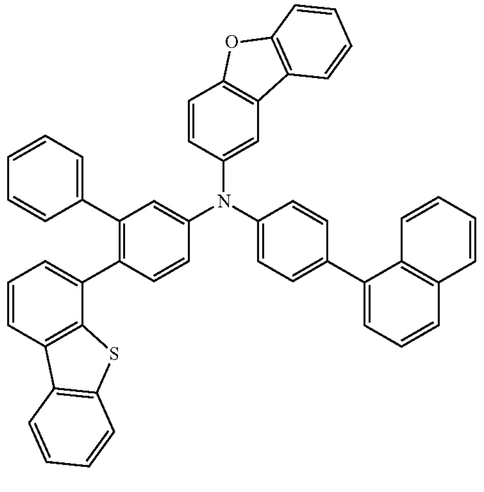
-continued
C184
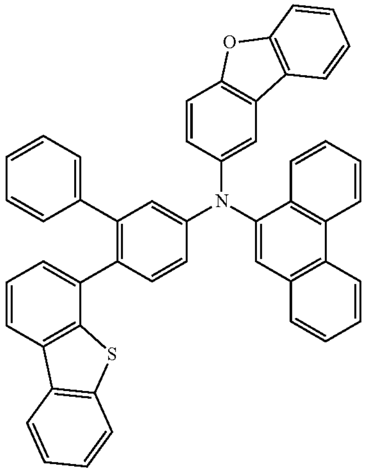
C187
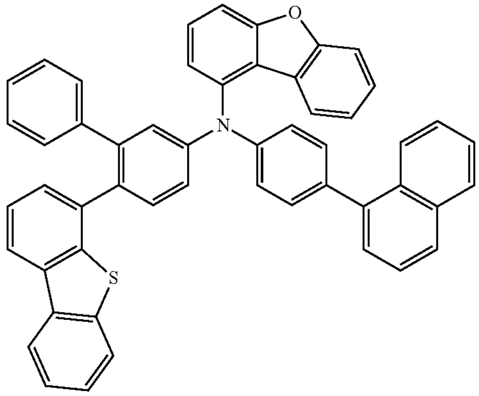
C194
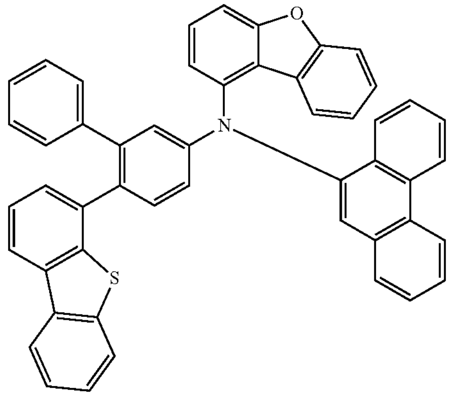
C197
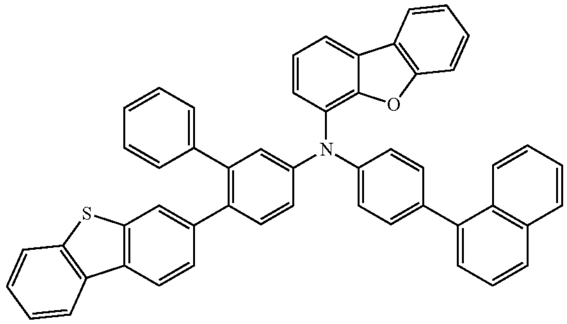

-continued
C204
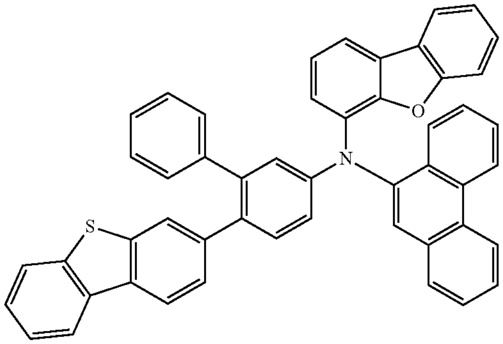
C207
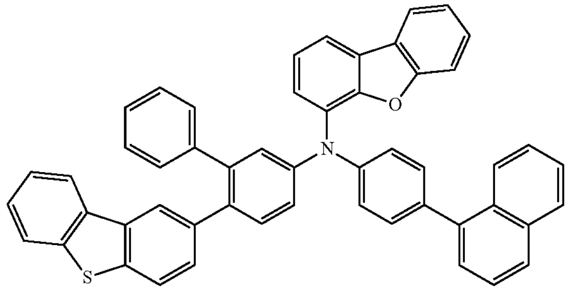
C214
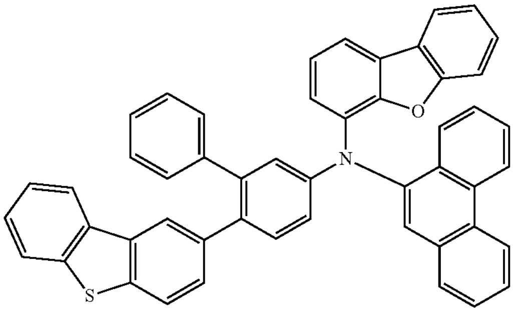
C217
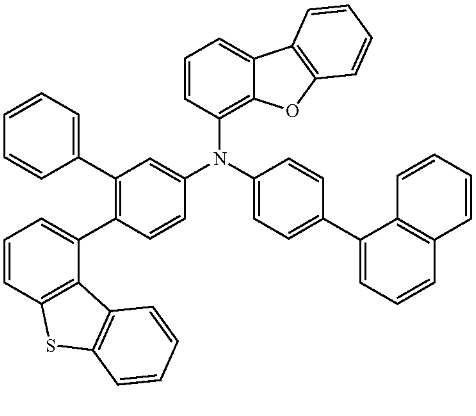
-continued
C224
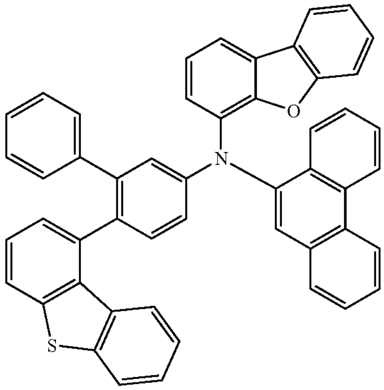
C237
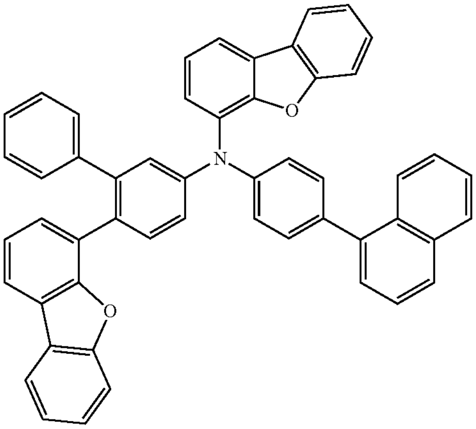
C244
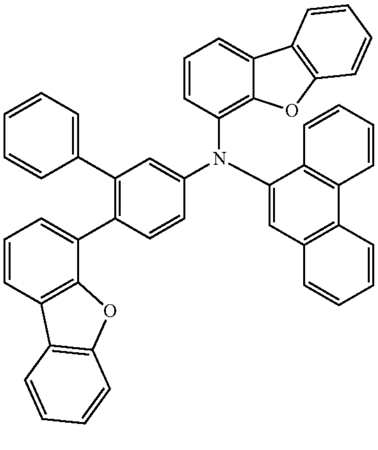
.

9. An amine compound represented by Formula 1:

Formula 1

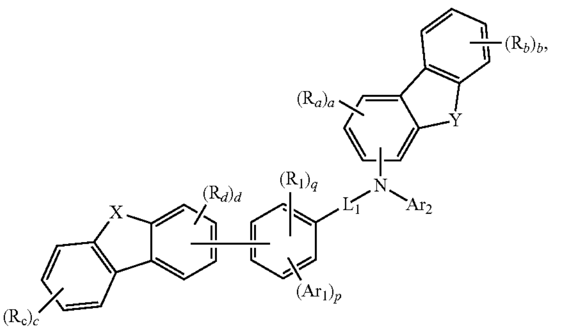

wherein in Formula 1,

X and Y are each independently O or S, $Ar_1$ is a substituted or unsubstituted aryl group of 6 to 40 carbon atoms for forming a ring, $Ar_2$ is selected from the following compounds:

Ar2-3

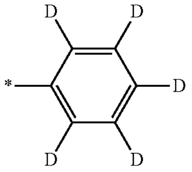

Ar2-5

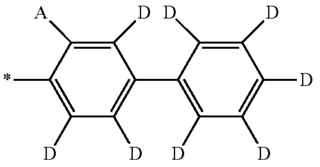

Ar2-8

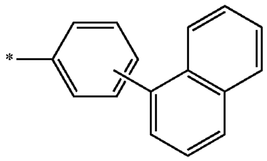

Ar2-9

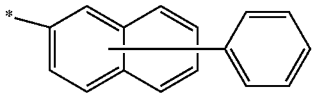

Ar2-10

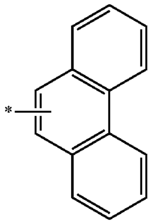

-continued

Ar2-11

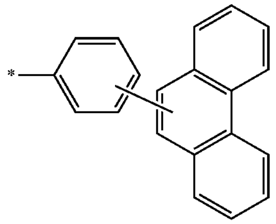

, $R_1$ is a hydrogen atom or a deuterium atom, $R_a$ to $R_d$ are each independently a hydrogen atom, a deuterium atom, a substituted or unsubstituted alkyl group of 1 to 20 carbon atoms, or a substituted or unsubstituted aryl group of 6 to 40 carbon atoms for forming a ring, $L_1$ is a direct linkage, or a substituted or unsubstituted arylene group of 6 to 30 carbon atoms for forming a ring, "a" and "d" are each independently an integer of 0 to 3, "b" and "c" are each independently an integer of 0 to 4, "p" is 1 or 2, and "q" is an integer of 0 to 3, wherein $L_1$ and $Ar_1$ or nitrogen (N) and $Ar_1$ are not bonded to adjacent carbons, wherein when Y is O and X is S or O, a dibenzothiophene group and N, the dibenzothiophene group and $L_1$, a dibenzofuran group and N, or the dibenzofuran group and $L_1$ are unbonded to adjacent carbons, wherein when Ar2 is represented by Ar2-8

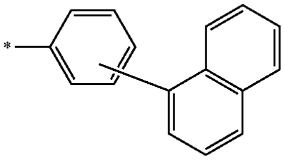

or

Ar2-11

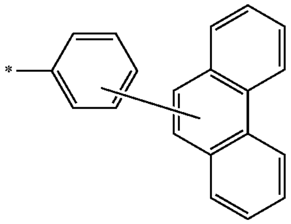

and $L_1$ is a direct linkage, then Ar1 is a substituted or unsubstituted naphthyl group, wherein when the Formula 1 is represented by Formula 1-1, $L_1$ is direct linkage:

Formula 1-1

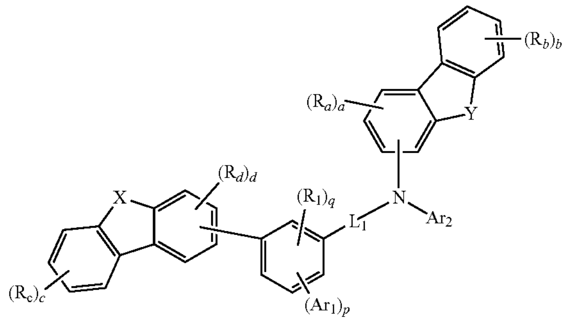

in Formula 1-1,

X, Y, $Ar_1$, $Ar_2$, $R_1$, $R_a$ to $R_d$, $L_1$, “a” to “d”, “p” and “q” are the same as defined in Formula 1.

10. The amine compound of claim 9, wherein Formula 1 is represented by Formula 1-2:

Formula 1-2

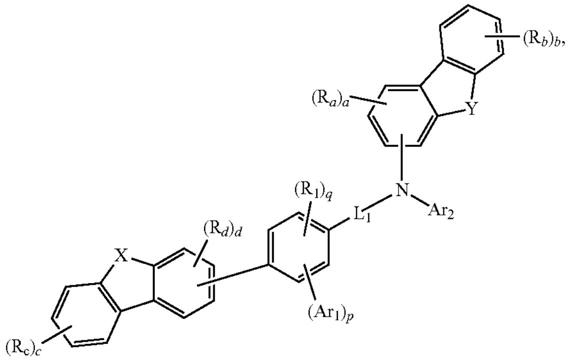

and in Formula 1-2, X, Y, $Ar_1$, $Ar_2$, $R_1$, $R_a$ to $R_d$, $L_1$, “a” to “d”, “p” and “q” are the same as defined in Formula 1.

11. The amine compound of claim 9, wherein Formula 1-1 is represented by any one selected from Formula 1-1A to Formula 1-1C:

Formula 1-1A

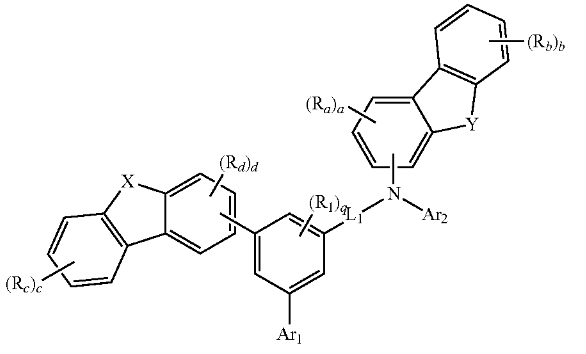

-continued

Formula 1-1B

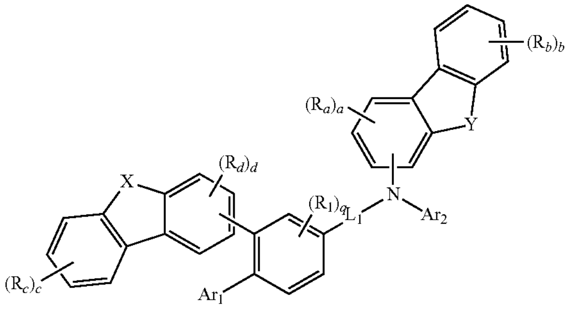

Formula 1-1C

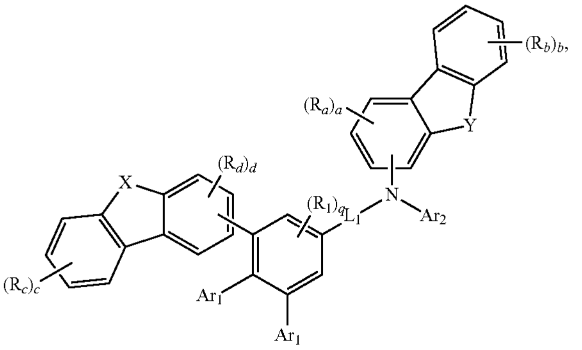

in Formula 1-1C, q1 is an integer of 0 to 2, and in Formula 1-1A to Formula 1-1C, X, Y, $Ar_1$, $Ar_2$, $R_1$, $R_a$ to $R_d$, $L_1$, “a” to “d”, and “q” are the same as defined in Formula 1.

12. The amine compound of claim 10, wherein Formula 1-2 is represented by Formula 1-2A or Formula 1-2B:

Formula 1-2A

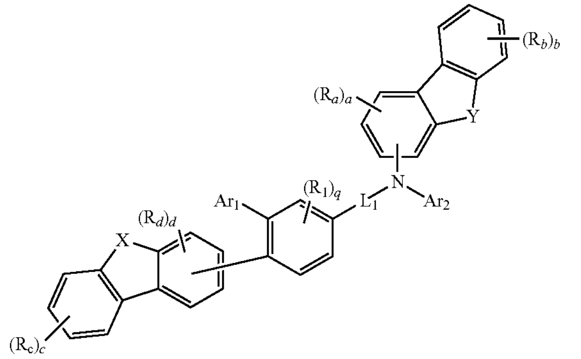

-continued

Formula 1-2B

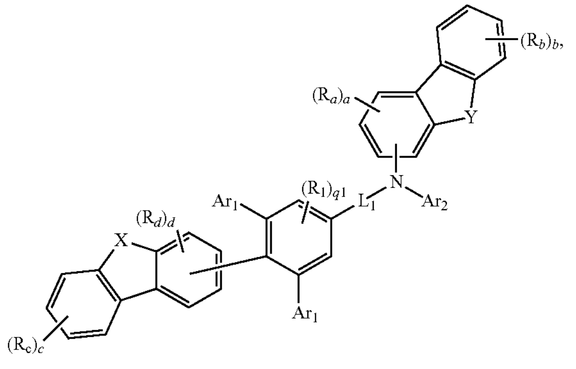

in Formula 1-2B, q1 is an integer of 0 to 2, and in Formula 1-2A and Formula 1-2B, X, Y, $Ar_1$, $Ar_2$, $R_1$, $R_a$ to $R_d$, $L_1$, "a" to "d", and "q" are the same as defined in Formula 1.

13. The amine compound of claim 9, wherein Formula 1 is represented by any one selected from Formula 1A to Formula 1D:

Formula 1A

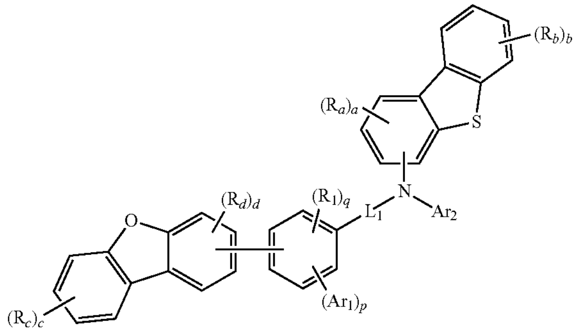

Formula 1B

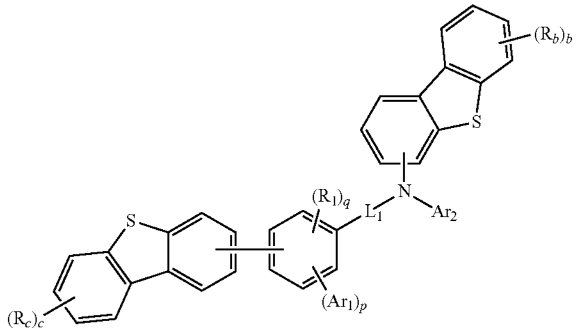

-continued

Formula 1C

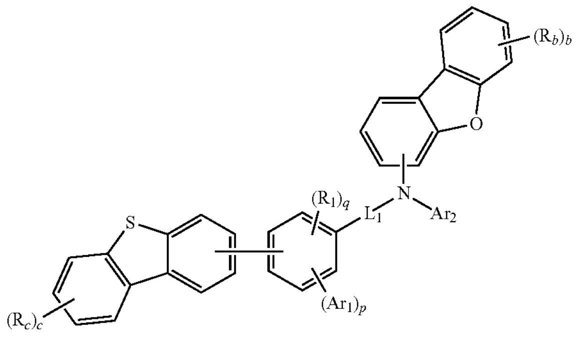

Formula 1D

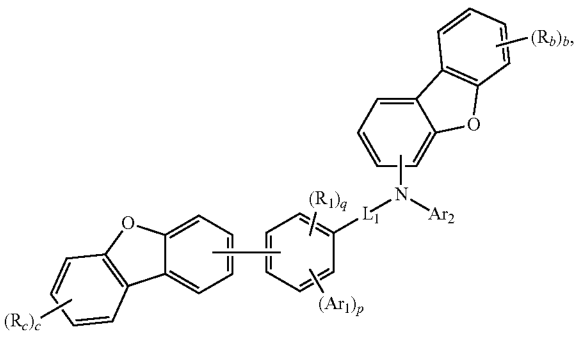

and in Formula 1A to Formula 1D, $Ar_1$, $Ar_2$, $R_1$, $R_a$ to $R_d$, $L_1$, "a" to "d", "p", and "q" are the same as defined in Formula 1.

14. The amine compound of claim 9, wherein $Ar_1$ is a substituted or unsubstituted phenyl group, or a substituted or unsubstituted naphthyl group.

15. The amine compound of claim 9, wherein $L_1$ is a direct linkage, a substituted or unsubstituted phenylene group, or a substituted or unsubstituted naphthalene group.

16. An amine compound represented by any one selected from compounds in Compound Group 1 to Compound Group 3:

Compound Group 1

A7

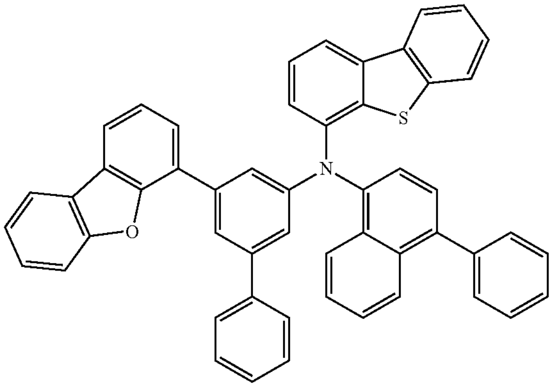

-continued
A9
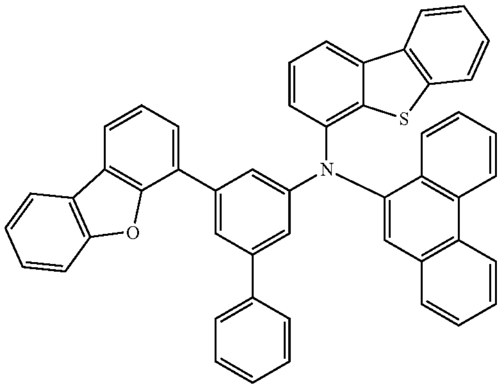
A12
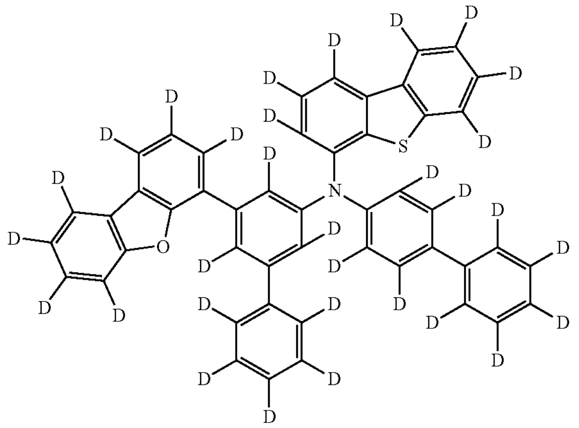
A24
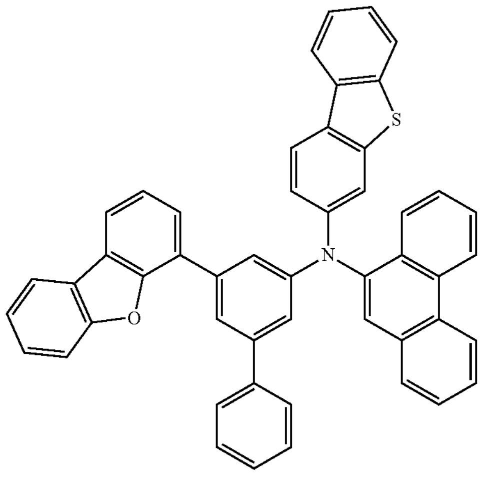
-continued
A34
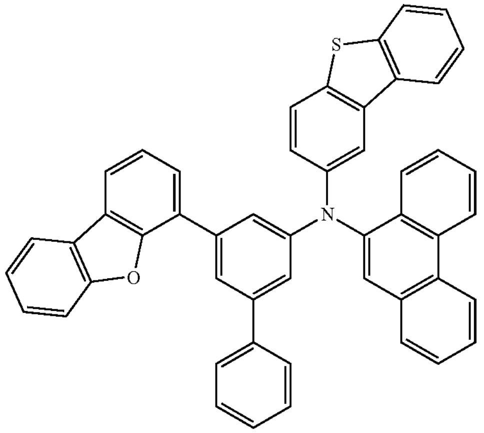
A44
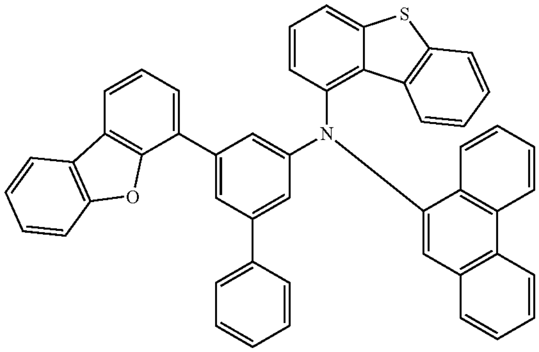
A54
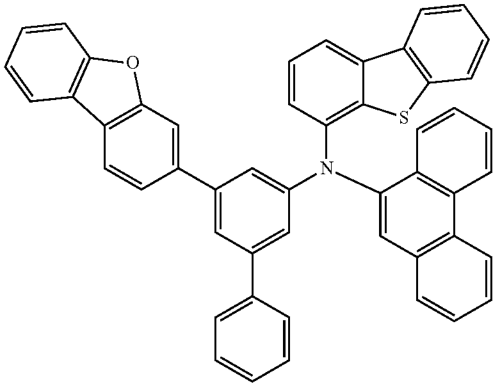
A64
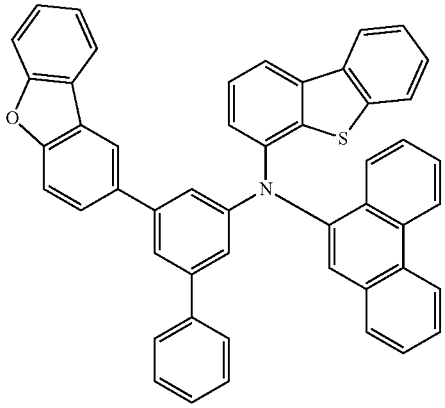

-continued
A74
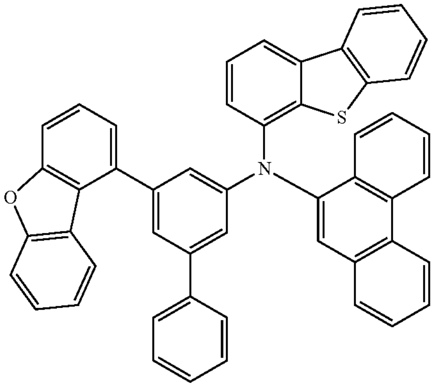
A84
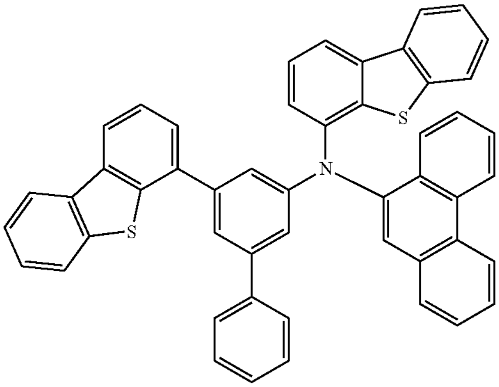
A87
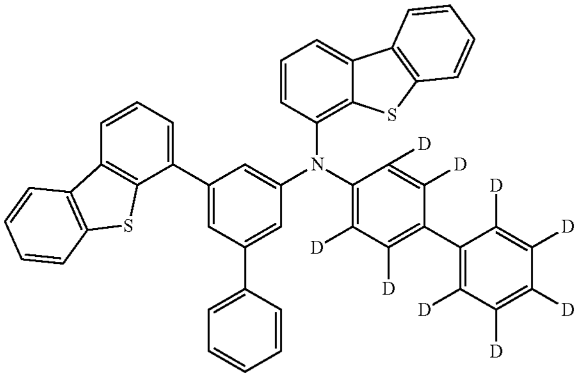
A99
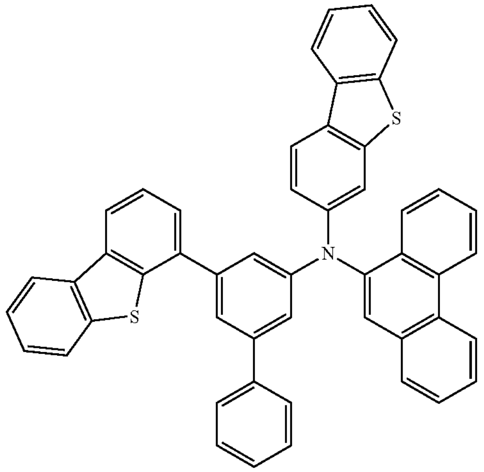
-continued
A109
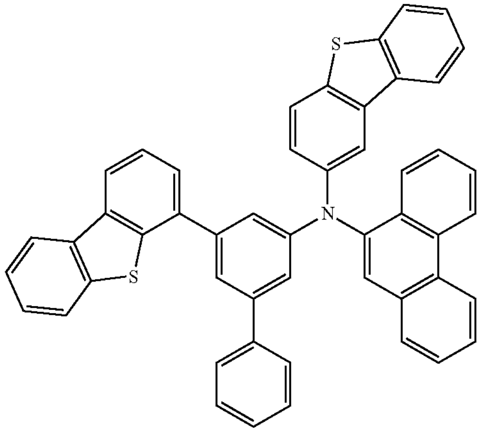
A119
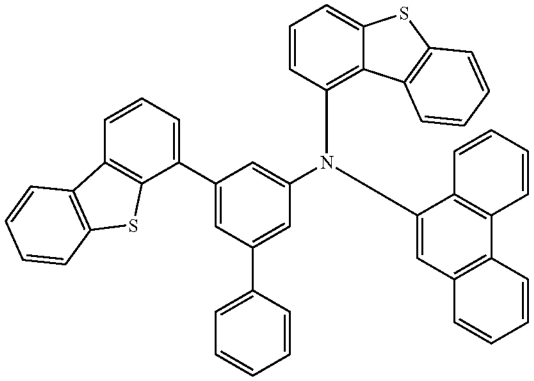
A129
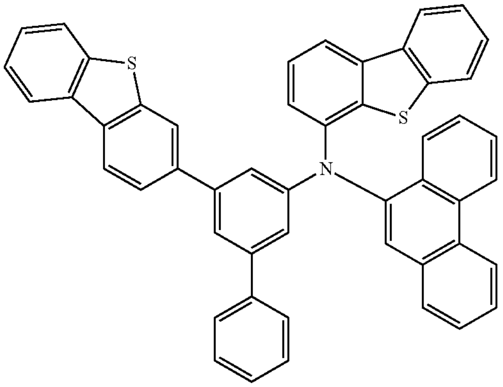
A139
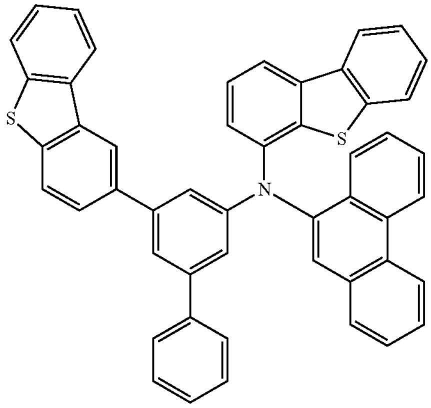

-continued
A149
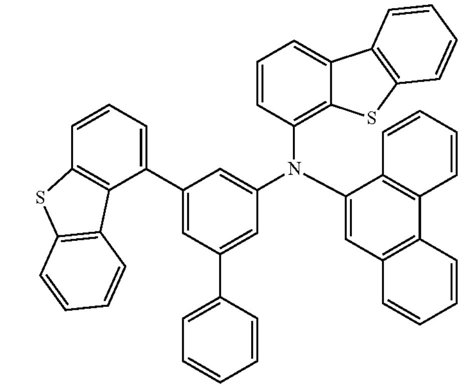
A159
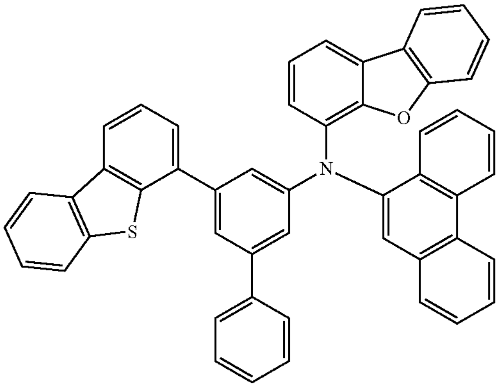
A162
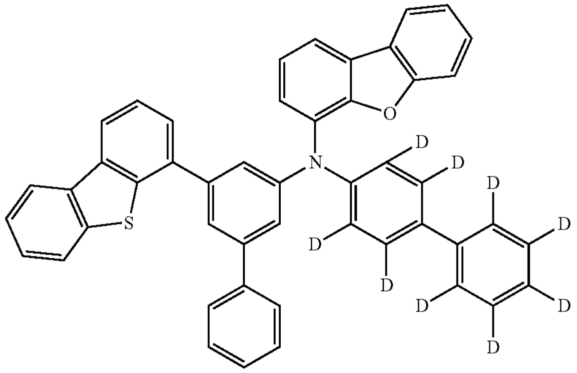
A174
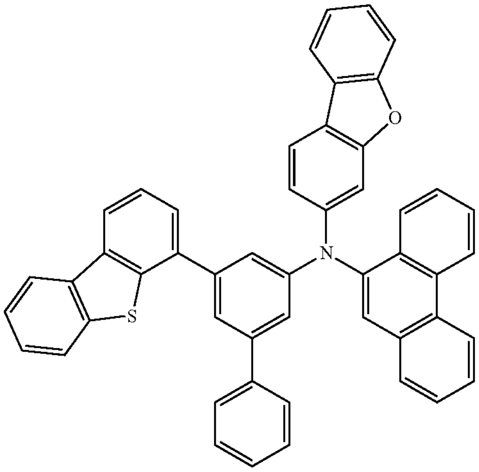
-continued
A184
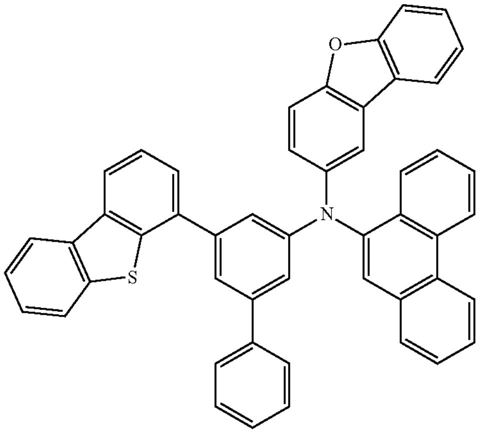
A194
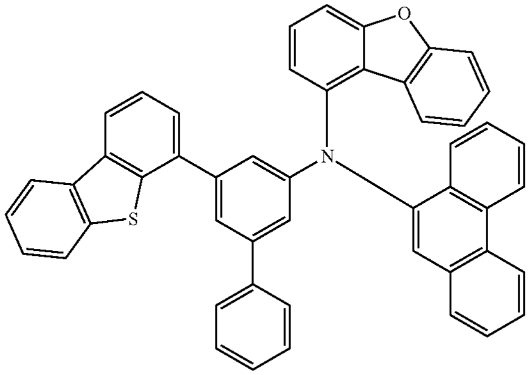
A204
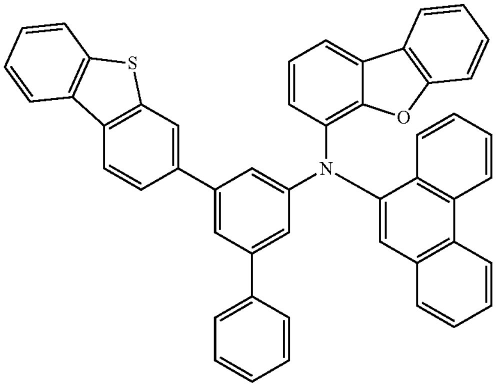
A214
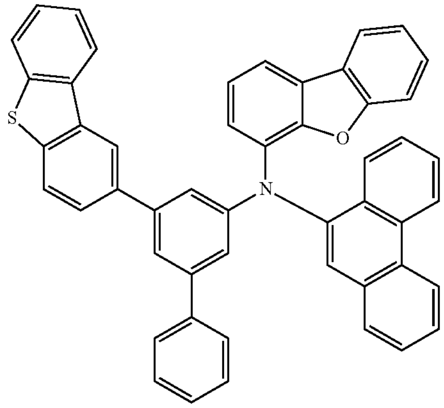

-continued
A224
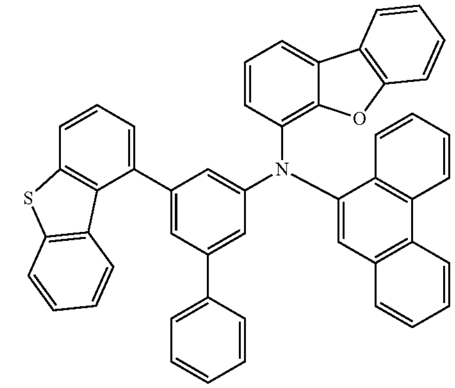
A244
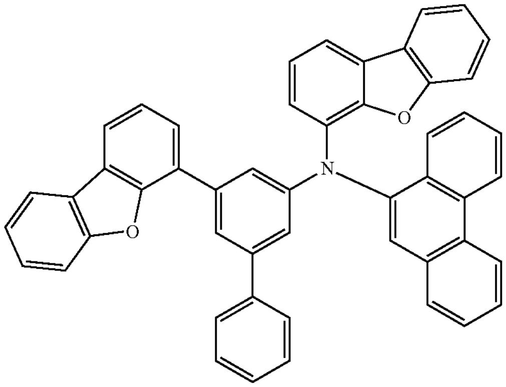
A244
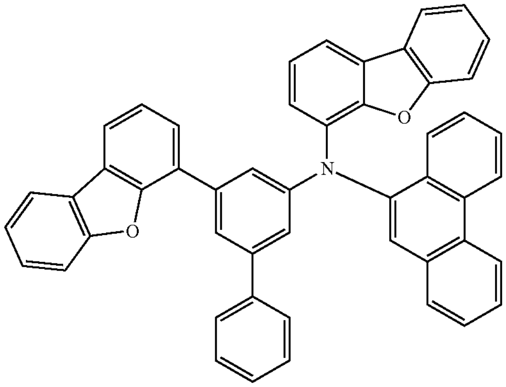
Compound Group 2
B9
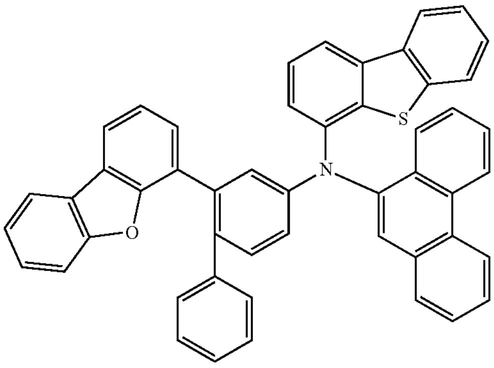
-continued
B12
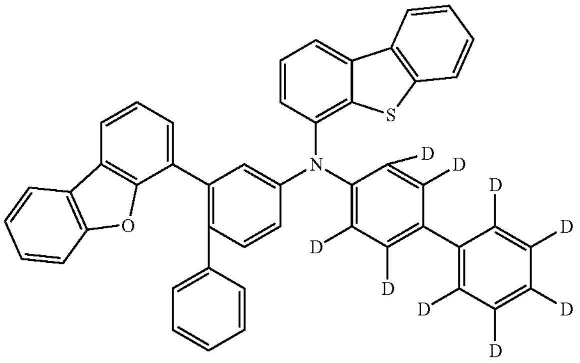
B24
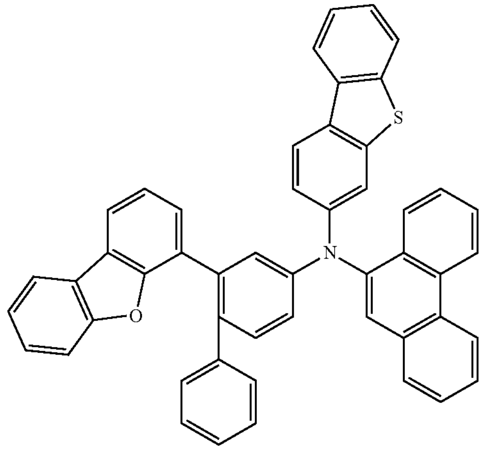
B34
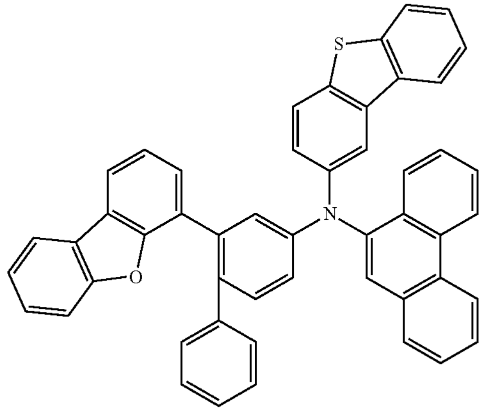
B44
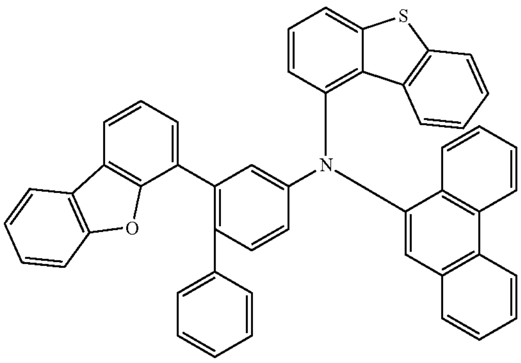

-continued
B54
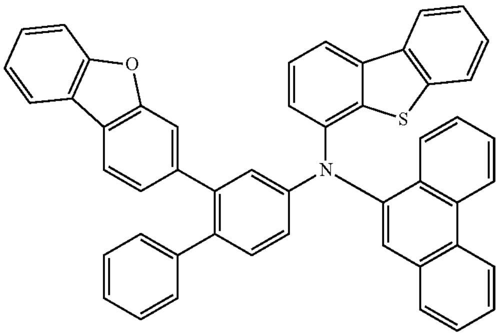
B64
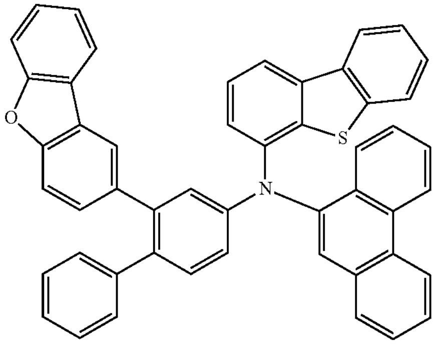
B74
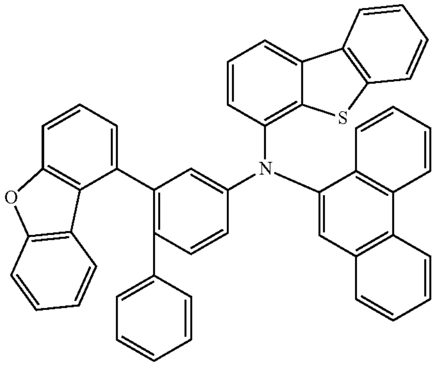
B84
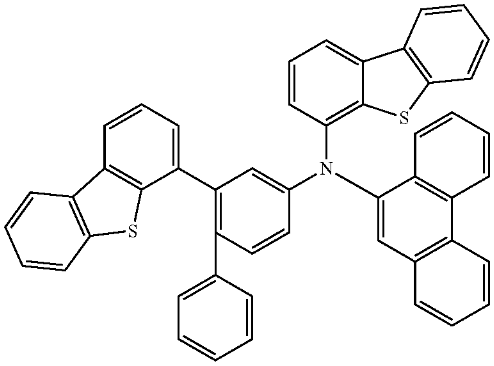
-continued
B87
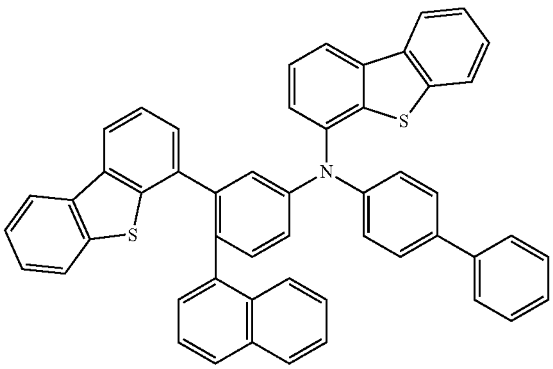
B99
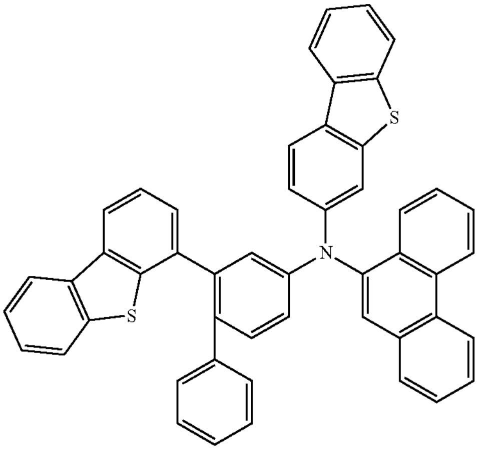
B109
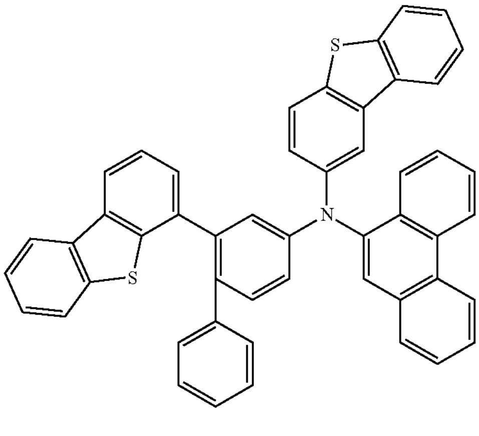
B119
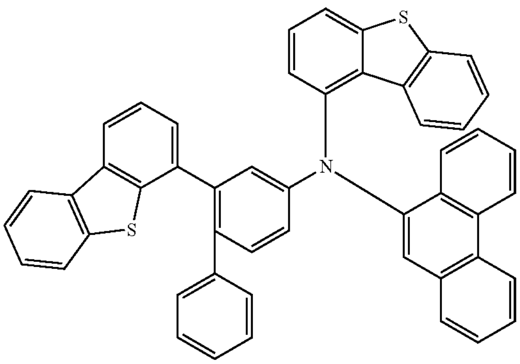

-continued
B129
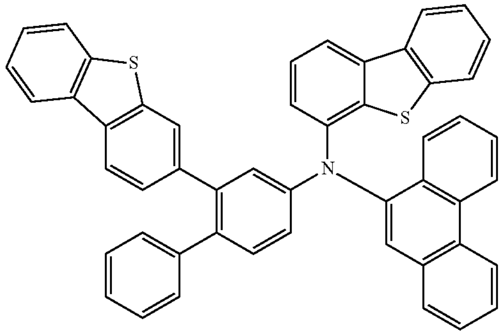
B139
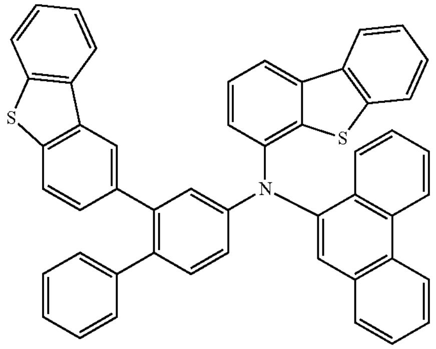
B149
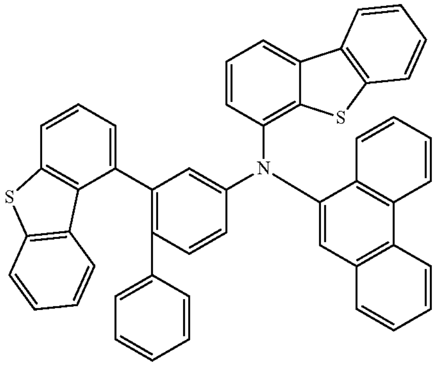
B159
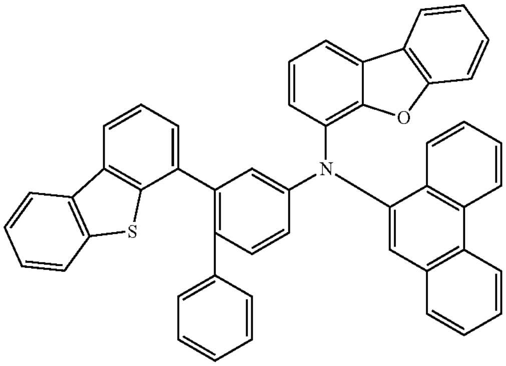
-continued
B162
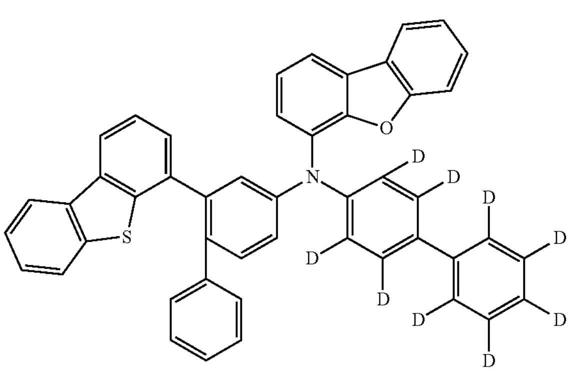
B174
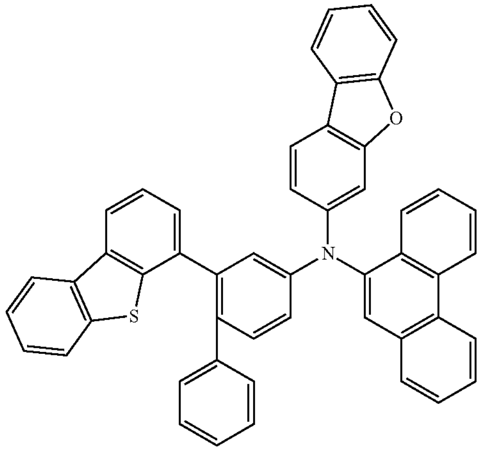
B184
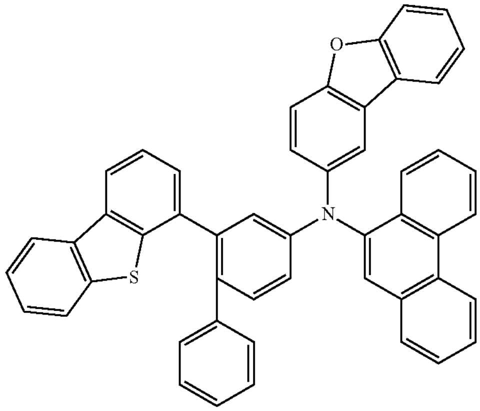
B194
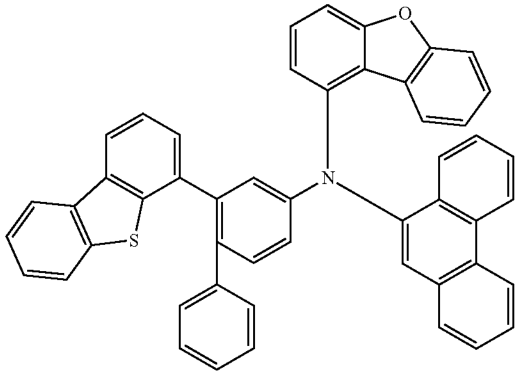

-continued
B204
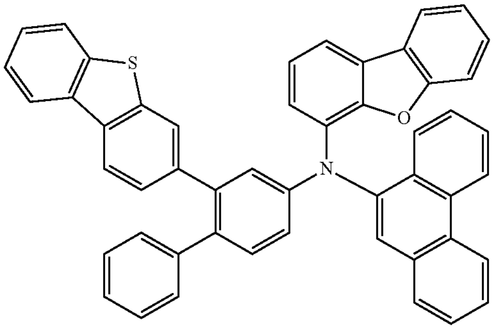
B214
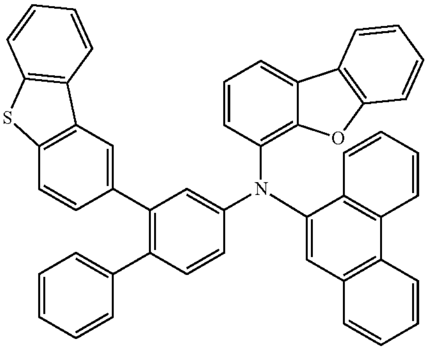
B224
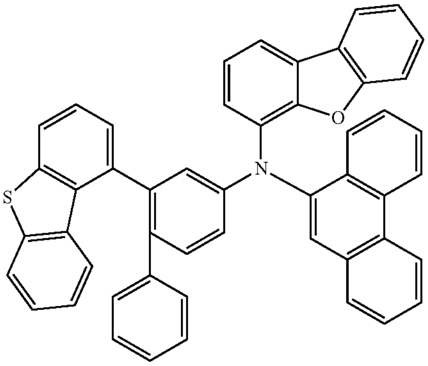
B244
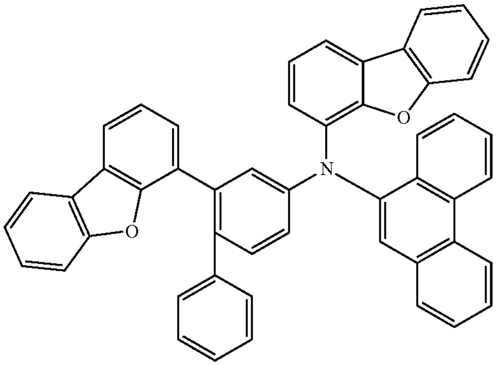
-continued
Compound Group 3
C9
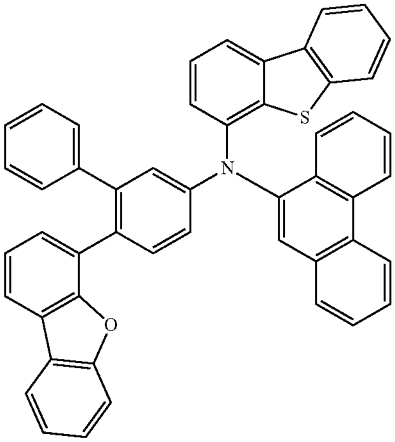
C12
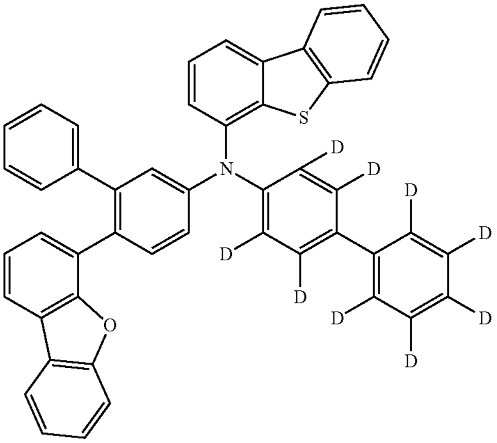
C24
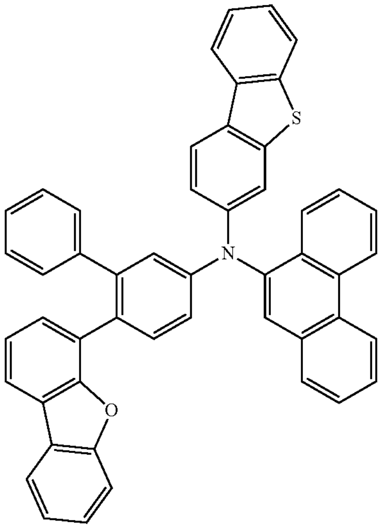

-continued
C34
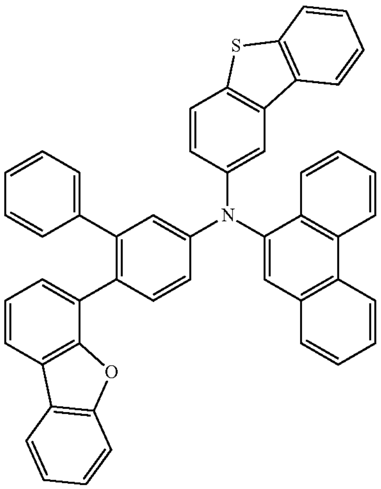
C44
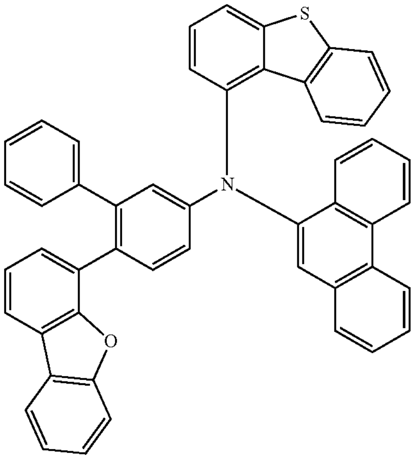
C54
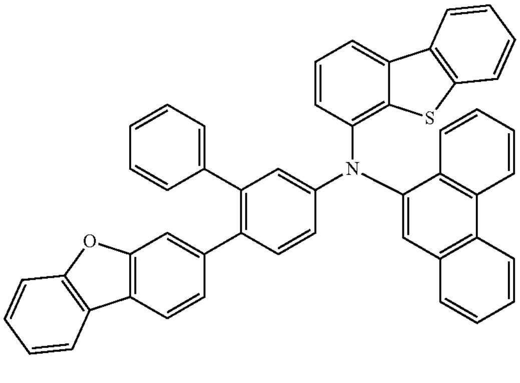
-continued
C64
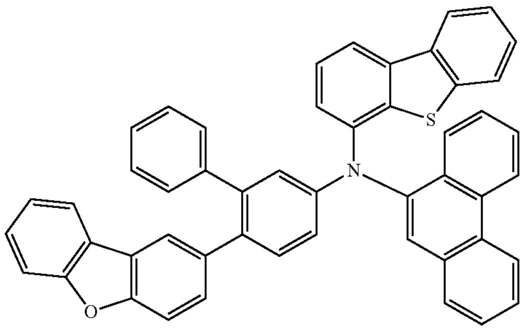
C74
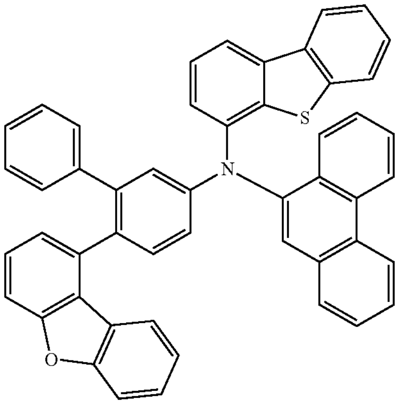
C84
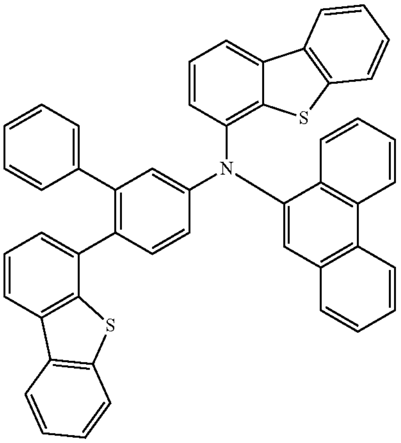
C87
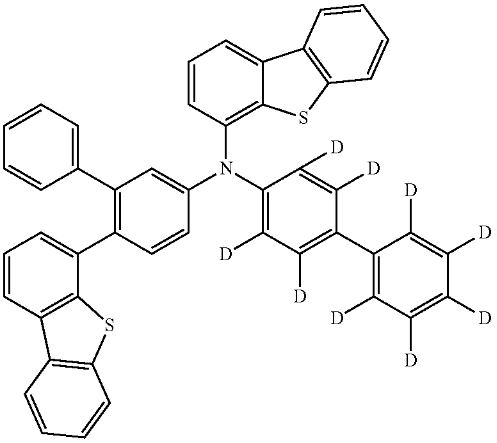

-continued
C99
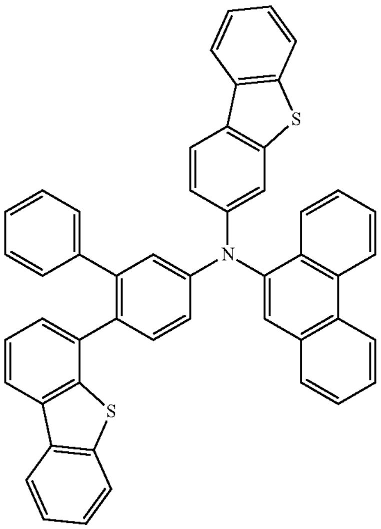
C109
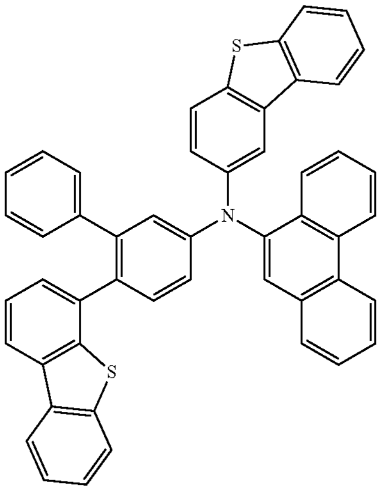
C119
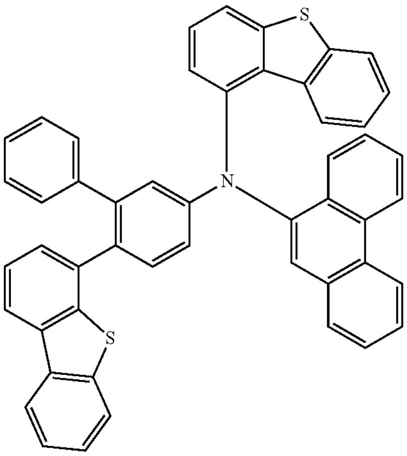
-continued
C129
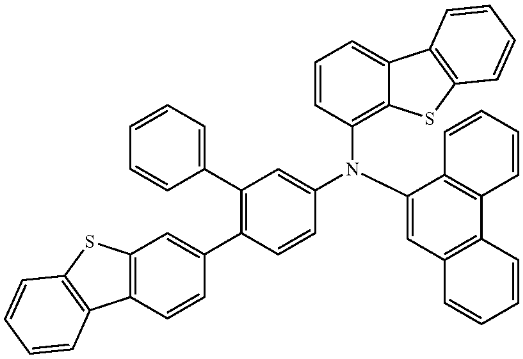
C139
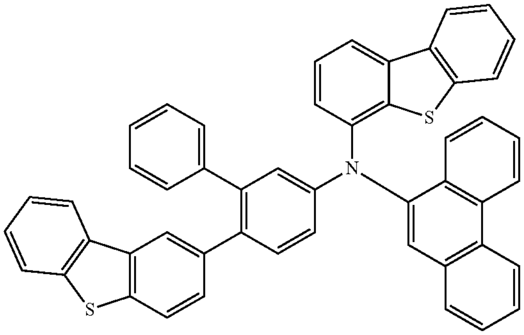
C149
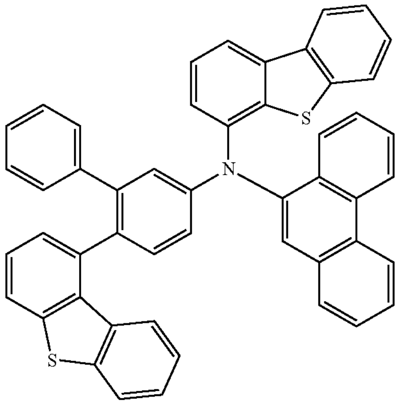
C159
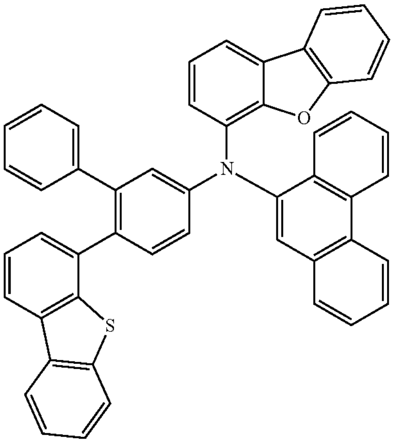

-continued
C162
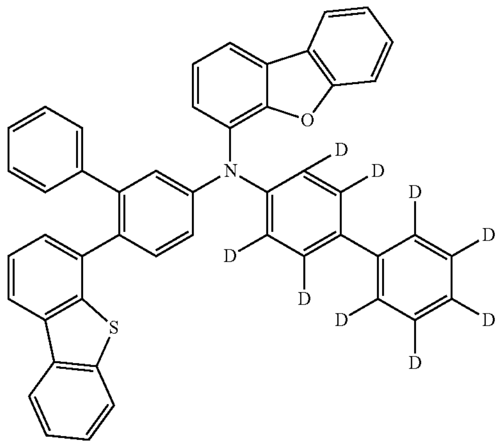
C174
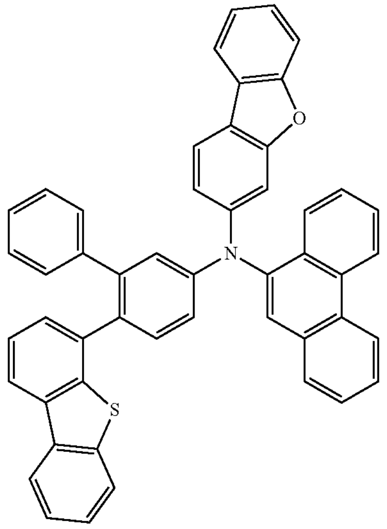
C184
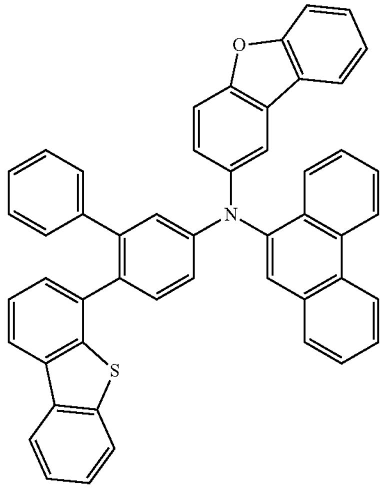
-continued
C194
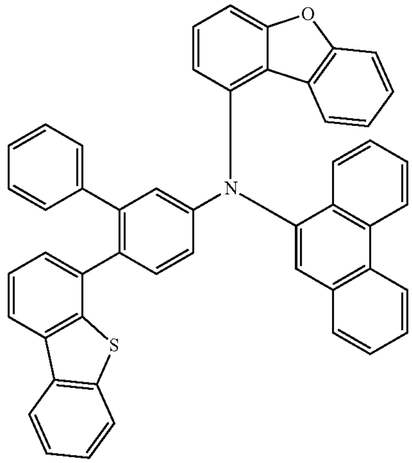
C204
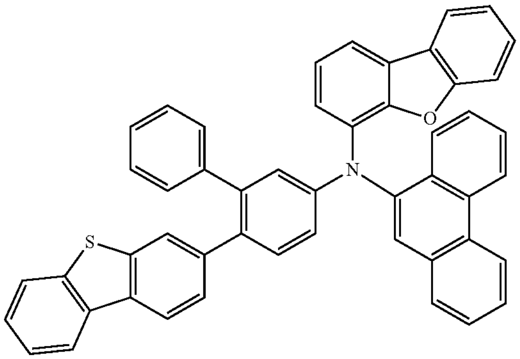
C214
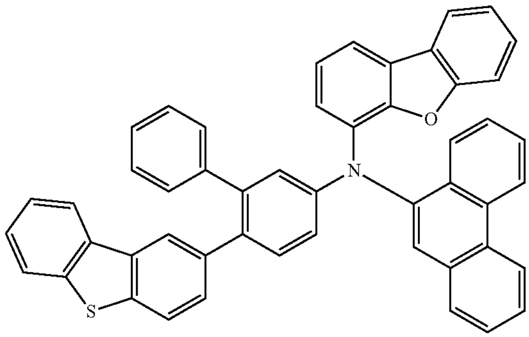
C224
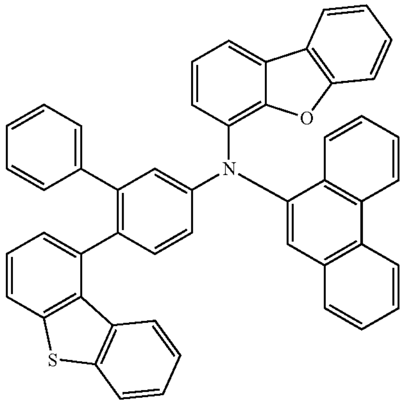

-continued
C244
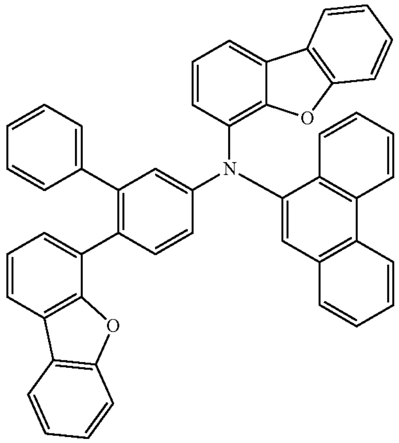
.
* * * * *